United States Patent
Park et al.

(10) Patent No.: US 12,240,836 B2
(45) Date of Patent: Mar. 4, 2025

(54) COMPOUNDS AS $GCN_2$ INHIBITORS, PHARMACEUTICAL COMPOSITIONS AND USES THEREOF

(71) Applicant: DONG-A ST CO., LTD., Seoul (KR)

(72) Inventors: Cheonhyoung Park, Seoul (KR); Kimoon Ryu, Yongin-si (KR); Tae-Hun Kim, Seoul (KR); Ha Yoon Kim, Hwaseong-si (KR); Eunhye Ju, Suwon-si (KR); Hyung Ki Lee, Hwaseong-si (KR); Youngjee Jeong, Seongnam-si (KR); Doyoung Choi, Seoul (KR); Jun Hwan Moon, Yongin-si (KR); Nayeon Park, Suwon-si (KR); Iksoo Jang, Seongnam-si (KR); Kyu Hwan Kim, Suwon-si (KR); Hyangsoo Lee, Seoul (KR); Min Jung Lee, Yongin-si (KR)

(73) Assignee: Dong-A ST Co., Ltd., Seoul (KR)

( * ) Notice: Subject to any disclaimer, the term of this patent is extended or adjusted under 35 U.S.C. 154(b) by 58 days.

(21) Appl. No.: 17/857,706

(22) Filed: Jul. 5, 2022

(65) Prior Publication Data
US 2024/0025884 A1    Jan. 25, 2024

(51) Int. Cl.

| | | |
|---|---|---|
| C07D 403/14 | (2006.01) | |
| A61K 31/506 | (2006.01) | |
| A61K 31/53 | (2006.01) | |
| A61K 31/5377 | (2006.01) | |
| A61K 31/541 | (2006.01) | |
| A61P 35/00 | (2006.01) | |
| C07D 401/14 | (2006.01) | |
| C07D 409/14 | (2006.01) | |
| C07D 413/14 | (2006.01) | |
| C07D 417/14 | (2006.01) | |
| C07D 471/04 | (2006.01) | |

(52) U.S. Cl.
CPC .......... *C07D 403/14* (2013.01); *A61K 31/506* (2013.01); *A61K 31/53* (2013.01); *A61K 31/5377* (2013.01); *A61K 31/541* (2013.01); *A61P 35/00* (2018.01); *C07D 401/14* (2013.01); *C07D 409/14* (2013.01); *C07D 413/14* (2013.01); *C07D 417/14* (2013.01); *C07D 471/04* (2013.01)

(58) Field of Classification Search
CPC ............... C07D 403/14; C07D 401/14; C07D 409/14; C07D 413/14; C07D 417/14; C07D 471/04; A61P 35/00; A61K 31/506; A61K 31/53; A61K 31/5377; A61K 31/541
See application file for complete search history.

(56) References Cited

U.S. PATENT DOCUMENTS

2023/0416237 A1    12/2023    Huang et al.

FOREIGN PATENT DOCUMENTS

| CN | 110938071 A | * | 3/2020 | ........... A61K 31/506 |
|---|---|---|---|---|
| CN | 111867581 | | 10/2020 | |
| CN | 114269736 | | 4/2022 | |
| KR | 20190104215 | | 9/2019 | |
| KR | 20220003537 | | 1/2022 | |
| WO | 2018134213 | | 7/2018 | |
| WO | 2019148136 | | 8/2019 | |
| WO | 2020211839 | | 10/2020 | |
| WO | 2021138392 | | 7/2021 | |
| WO | WO-2022111499 A1 | * | 6/2022 | ........... A61K 31/506 |

OTHER PUBLICATIONS

Paller et al. (Clin Cancer Res. 2014; 20(16): 4210-4217 (Year: 2014).*
Schafer et al Drug Discovery Today 2008;13(21/22) (Year: 2008).*
Horig et al. Journal of Translational Medicine 2004, 2:44 (Year: 2004).*
Wei, C. et al., Molecular Biology of the Cell, 2015, 26(6), 1044.
Nakagawa, T. et al., International Journal of Molecular Sciences, 2019, 20, 2761.
Wang, P. et al., Journal of Allergy and Clinical Immunology, 2019, 144, 1091.
Yuan, J. et al., Redox Biology 2022, 49, 102224.
International Search Report in counterpart Application No. PCT/IB2023/056916 dated Oct. 17, 2023, 5 pages.

* cited by examiner

*Primary Examiner* — Clinton A Brooks
*Assistant Examiner* — Jerica Katlynn Wilson
(74) *Attorney, Agent, or Firm* — NIXON & VANDERHYE, PC

(57) ABSTRACT

Provided herein are novel compounds, e.g., those of Formula (I), as GCN2 inhibitors. Also provided are pharmaceutical compositions including one or more of the novel compounds, and pharmaceutical uses thereof. Compounds provided herein can typically inhibit an activity of a GCN2 and thus can be used for treating or preventing diseases related thereto.

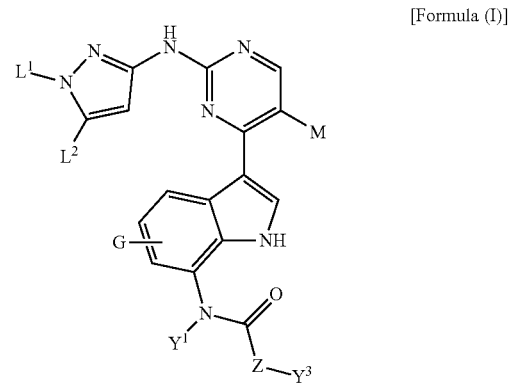

[Formula (I)]

7 Claims, No Drawings

COMPOUNDS AS GCN$_2$ INHIBITORS, PHARMACEUTICAL COMPOSITIONS AND USES THEREOF

FIELD OF THE INVENTION

The present invention relates to a novel compound as GCN2 inhibitor, a pharmaceutical composition including the same, and a pharmaceutical use thereof, which inhibits an activity of a GCN2 and thus may be used valuably in preventing or treating diseases related thereto.

BACKGROUND OF THE INVENTION

Although diverse agents currently exist as therapeutic tools for cancer, it is widely accepted that more options still need to be invented to address unmet needs in the treatment of patients with cancer. Several studies have showed that modulating essential components in the tumor microenvironment could be a promising therapeutic option for cancer therapy. Cancer cells are generally in the tumor microenvironment with deprivations of several nutrients, e.g. glucose, oxygen and amino acids. The integrated stress response (ISR) is one pathway by which tumor cells adapt to nutrient deficiencies. General control nonderepressible kinase 2 (GCN2) (encoded by EIF2AK4 in humans) is one of the cytoplasmic serine/threonine protein kinase that mediates nutrient stress pathway in the tumor microenvironment. In response to amino acid deficiency, GCN2 phosphorylates the eukaryotic initiation factor 2 alpha (eIF2a) to activate the ISR, which leads to initiation of a transcriptional program through the activating transcription factor-4 (ATF4). ATF4 functions as a crucial ISR transcription factor promoting stress remediation by inducing expression of significant subset of genes related to amino acid import and metabolism. Under the ATF4-mediated ISR pathway, GCN2 plays as a pivotal component in response to recovery from nutrient deprivation. Also, in various human tumors, elevated expression level of GCN2 has been observed compared to normal tissues. GCN2 was highly expressed in various cancers (e.g. thyroid cancer, melanoma, testis cancer, endometrial cancer, lung cancer, head and neck cancer, pancreatic cancer, glioma, stomach cancer, urothelial cancer, skin cancer, breast cancer, colorectal cancer or renal cancer, etc.) at both protein and mRNA levels. In addition, GCN2 function is closely related to induction of T cell anergy under tryptophan depletion condition caused by indoleamine 2,3-dioxygenase (IDO). Inhibition of GCN2 has been reported as a therapeutic approach for cancer therapy (see, e.g., Wei, C. et al. in Mol. Biol. Cell. 2015, 26(6), 1044). Thus, inhibition of GCN2 activity may provide a beneficial therapeutic option for cancer patients. Furthermore, several GCN2 inhibitors resulting in the downregulation of eIF2a phosphorylation and ATF expression show the potential to treat neurodegenerative disease such as Alzheimer's disease, Parkinson's Disease, Huntington's Disease, amyotrophic lateral sclerosis, and spinocerebellar ataxia as well as doxorubicin-induced cardiotoxicity (Nakagawa, T. et al. Int. J. Mol. Sci. 2019, 20, 2761). Recent studies have shown that GCN2 inhibitors might be potential drug for inflammation disease (Wang, P. et al. in J. Allergy Clin. Immunol. 2019, 144, p. 1091) and hepatic steatosis (Yuan, J. et al. in Redox Biology 2022, 49, 102224).

SUMMARY OF THE INVENTION

An objective of the present invention is to provide a novel compound showing general control nonderepressible kinase 2 (GCN2) inhibitory activity, a stereoisomer thereof, a pharmaceutically acceptable salt thereof, or a solvate thereof.

An objective of the present invention is to provide a method for preparing the compound of the present invention, the stereoisomer thereof, the pharmaceutically acceptable salt thereof, or the solvate thereof.

An objective of the present invention is to provide a pharmaceutical composition for treating or preventing GCN2 activation-related diseases, comprising the compound of the present invention, the stereoisomer thereof, the pharmaceutically acceptable salt thereof, or the solvate thereof as an active ingredient.

An objective of the present invention is to provide a method for preventing or treating GCN2 activation-related diseases, including administering a therapeutically effective amount of the compound of the present invention, the stereoisomer thereof, the pharmaceutically acceptable salt thereof, or the solvate thereof into a subject.

An objective of the present invention is to provide a use of the compound of the present invention, the stereoisomer thereof, the pharmaceutically acceptable salt thereof, or the solvate thereof in preparation of a medicament for preventing or treating GCN2 activation-related diseases.

A objective of the present invention is to provide a use of the compound of the present invention, the stereoisomer thereof, the pharmaceutically acceptable salt thereof, or the solvate thereof for preventing or treating GCN2 activation-related diseases.

An objective of the present invention is to provide a method for inhibiting GCN2 activity, including administering a therapeutically effective amount of the compound of the present invention, the stereoisomer thereof, the pharmaceutically acceptable salt thereof, or the solvate thereof into a subject.

DETAILED DESCRIPTION OF THE INVENTION

GCN2 Inhibitor Compound

The present invention provides a compound represented by a following formula (I), a stereoisomer thereof, a pharmaceutically acceptable salt thereof, or a solvate thereof:

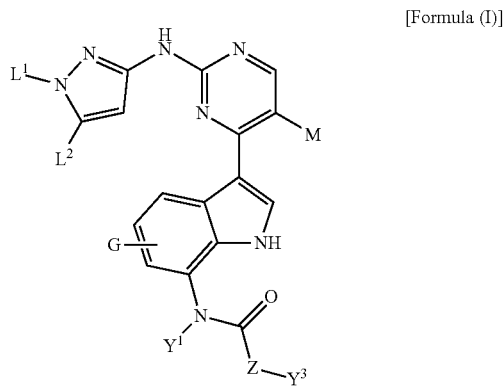

[Formula (I)]

wherein, $L^1$ and $L^2$ each independently represent H; ($C_{1-5}$)alkyl; or $L^1$ and $L^2$ may be connected to form a 5 to 6-membered ring, M represents H; halogen; ($C_{1-5}$)alkyl; ($C_{3-7}$)cycloalkyl; or ($C_{1-5}$)alkoxy, G represents H; halogen; $(C_{1-5})$alkyl; $(C_{1-5})$alkoxy; or —NH$_2$, wherein at least one H of —NH$_2$ optionally substituted with $(C_{1-5})$alkyl, $Y^1$ represents H; or $(C_{1-5})$alkyl, Z represents —C(=O)—; or —CH$_2$— optionally substituted with one or more $(C_{1-5})$alkyl; and/or Z may be connected to $Y^1$ to form a 5- to 6-membered ring, $Y^3$ represents 4- to 6-membered heterocycloalkyl which is optionally substituted with $W^1$ and $W^2$; or $Y^3$ may be connected to Z to form an aryl or a heteroaryl in case that Z is connected to $Y^1$ to form the 5- to 6-membered ring, $W_1$ and $W_2$ each independently represent H; halogen; —OH; $(C_{1-5})$alkyl optionally substituted with —OH or —CN; 5- to 7-membered heterocycloalkyl optionally substituted with $(C_{1-5})$alkyl; a heteroaryl optionally substituted with $(C_{1-5})$alkyl; —COR$^1$; —OR$^2$ or —NH$_2$, wherein at least one H of —NH$_2$ optionally substituted with a heteroaryl, $R^1$ represents $(C_{1-5})$alkoxy; —OH; 5-7 membered heterocycloalkyl optionally substituted with $(C_{1-5})$alkyl; or —NH$_2$, wherein at least one H of —NH$_2$ optionally substituted with $(C_{3-7})$cycloalkyl, $R^2$ represents $(C_{1-5})$alkyl optionally substituted with a heteroaryl; an aryl; or a heteroaryl, wherein the aryl or the heteroaryl is optionally substituted with one or more $R^{2a}$, $R^{2a}$ independently represents halogen; $(C_{1-5})$alkyl optionally substituted with an aryl or 5- to 7-membered heterocycloalkyl substituted with $(C_{1-5})$alkyl; $(C_{5-6})$cycloalkenyl optionally substituted with $(C_{1-5})$alkyl; 5- to 7-membered heterocycloalkyl substituted with $(C_{1-5})$alkyl or —OH; —CF$_3$; $(C_{1-5})$alkoxy optionally substituted with an aryl; an aryl; a heteroaryl optionally substituted with $(C_{1-5})$alkyl; thio($C_{1-5}$)alkyl; —COR$^1$; or NR$^3$R$^4$, $R^3$ and $R^4$ each independently represent H; halogen; $(C_{1-5})$alkyl optionally substituted with halogen, —CF$_3$, —OH, $(C_{1-5})$alkoxy, $(C_{1-5})$alkyl-N—$(C_{1-5})$alkyl, an aryl or $(C_{3-7})$cycloalkyl; $(C_{3-7})$cycloalkyl; $(C_{1-5})$alkoxy; an aryl; or —C(=O)($C_{1-5}$)alkyl.

According to another specific embodiment of the present invention, it may be provided that $Y^3$ represents azetidinyl; pyrrolidinyl; piperidinyl; tetrahydropyridinyl; or oxopyrrolidinyl, which is optionally substituted with $W^1$ and $W^2$, $W_1$ and $W_2$ each independently represent H; halogen; —OH; $(C_1$—O)alkyl optionally substituted with —OH or —CN; methylpiperazinyl; morpholinyl; pyridinyl; methylpyrazolyl; —COR$^1$; —OR$^2$; —NH$_2$; —NH(pyridinyl) or —NH(pyrimidinyl), $R^1$ represents $(C_{1-5})$alkoxy; —OH; —NH$_2$; —NH—$(C_{3-7})$cycloalkyl; oxopiperazinyl; morpholinyl; thiomorpholinyl; methylpiperazinyl; or tetrahydropyridinyl, $R^2$ represents $(C_{1-5})$alkyl optionally substituted with pyridinyl; halophenyl; dihalophenyl; (amino)halophenyl; (methylpiperazinyl)(methyl)phenyl; (dimehtylamino)phenyl; aminophenyl; biphenyl; (phenylpropanyl)phenyl; (cyclopropylamino)pyrimidinyl; (trifluoroethylamino)pyrimidinyl; pyridinyl; pyrimidinyl; cyclopropyl(isoxazole)carboxamide; (dimethyl)pyrimidinyl; pyrazinyl; aminopyridinyl; halopyridinyl; aminopyrazinyl; halopyrimidinyl; (methyl)halopyrimidinyl; (amino)(methyl)pyrimidinyl; (amino)halopyrimidinyl; dihalopyrimidinyl; amino(dihalophenyl)pyrimidinyl; (amino)(trifluoromethyl)pyrimidinyl; pentylpyrimidinyl; methylpyrazolyl; methyl(benzothiophene)carboxylate; methyl(thiophene)carboxylate; (thiophene)carboxylic acid; (thiophene)carboxamide; methyl(thiophene)carboxamide; cyclopropyl(thiophene)carboxamide; methylisoxazolyl; benzoisoxazolyl; isothiazolyl; methylthiophenyl; pyrazolyl; (methyl)(trifluoromethyl)pyrazolyl; isoxazolyl; aminopyrazolyl; methyl(pyrrole)carboxylate; ethyl(isoxazole)carboxylate; (isoxazole)carboxamide; methyl(isoxazole)carboxamide; cyclopropyl(isoxazole)carboxamide; dimethyl(isoxazole)carboxamide; cyclopropyl(oxazole)carboxamide; (pyrimidine)carboxylic acid; (pyrimidine)carboxamide; methyl(pyrimidine)carboxamide; dimethyl(pyrimidine)carboxamide; (pyrazine)carboxamide; methyl(pyrazine)carboxamide; aminotriazinyl; (methylamino)triazinyl; (dimethylamino)triazinyl; (cyclopropylamino)triazinyl; diaminotriazinyl; (amino)(pyrrolidinyl)triazinyl; aminopyrimidinyl; (methylamino)pyrimidinyl; (ethylamino)pyrimidinyl; (propylamino)pyrimidinyl; (butylamino)pyrimidinyl; (hydroxyethylamino)pyrimidinyl; (hydroxypropylamino)pyrimidinyl; (methoxyethylamino)pyrimidinyl; (((dimethylamino)propyl)amino)pyrimidinyl; (benzylamino)pyrimidinyl; (phenethylamino)pyrimidinyl; (cyclohexylamino)pyrimidinyl; (dimethylamino)pyrimidinyl; (ethylmethylamino)pyrimidinyl; (diethylamino)pyrimidinyl; (ethylpropylamino)pyrimidinyl; (butylethylamino)pyrimidinyl; pyrrolidinylpyrimidinyl; (hydroxypyrrolidinyl)pyrimidinyl; piperidinylpyrimidinyl; (hydroxypiperidinyl)pyrimidinyl; morpholinopyrimidinyl; (methylpiperazinyl)pyrimidinyl; (amino)(methylamino)pyrimidinyl; (amino)(pyrrolidinyl)pyrimidinyl; (methylamino)halopyrimidinyl; (ethylamino)halopyrimidinyl; (cyclopropylamino)halopyrimidinyl; (cyclohexylamino)halopyrimidinyl; (dimethylamino)halopyrimidinyl; (ethylmethylamino)halopyrimidinyl; (diethylamino)halopyrimidinyl; (methylphenylamino)halopyrimidinyl; (benzylmethylamino)halopyrimidinyl; (pyrrolidinyl)halopyrimidinyl; (piperidinyl)halopyrimidinyl; (morpholino)halopyrimidinyl; (thiomorpholino)halopyrimidinyl; (methylpiperazinyl)halopyrimidinyl; (cyclopropylamino)methylpyrimidinyl; (amino)pyrimidinyl; (methylthio)pyrimidinyl; (methoxy)pyrimidinyl; (benzyloxy)pyrimidinyl; acetamidopyrimidinyl; (difluoropropylamino)pyrimidinyl; (difluoroethylamino)pyrimidinyl; (trifluoropropylamino)pyrimidinyl; (fluoroethylamino)pyrimidinyl; (cyclobutylamino)pyrimidinyl; (cyclopentylamino)pyrimidinyl; (isopropylamino)pyrimidinyl; (sec-butylamino)pyrimidinyl; ((cyclopropylmethyl)amino)pyrimidinyl; (((dimethylamino)ethyl)amino)pyrimidinyl; (((dimethylamino)propyl)amino)pyrimidinyl; (methoxyamino)pyrimidinyl; (benzylmethylamino)pyrimidinyl; (cyclohexylamino)halopyrimidinyl; (cyclopropylmethylamino)halopyrimidinyl; (benzylamino)halopyrimidinyl; (cyclopropylamino)halopyrimidinyl; (cyclopropylamino)methylpyrimidinyl; (cyclopropylamino)(trifluoromethyl)pyrimidinyl; (cyclopropylamino)(methoxy)pyrimidinyl; (cyclopropylamino)pyrazinyl; (ethylamino)pyrazinyl; (propylamino)pyrazinyl; (hydroxyethylamino)pyrazinyl; (((dimethylamino)ethyl)amino)pyrazinyl; phenylpyrimidinyl; (methylpyrazolyl)pyrimidinyl; (dimethylcyclohexenyl)pyrimidinyl; dihydropyranylpyrimidinyl; or pyridinylpyrimidinyl.

According to another specific embodiment of the present invention, it may be provided that the compound represented by formula (I) above is a compound represented by a following formula (Ib):

[Formula (Ib)]

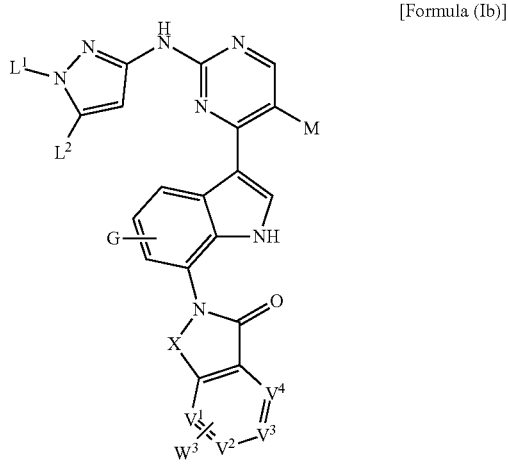

X represents —CH$_2$—; or —C(=O)—,

V$^1$, V$^2$, V$^3$ and V$^4$ each independently represent CH or N, wherein V$^1$, V$^2$, V$^3$ and V$^4$ each independently be substituted with W$^3$ in case that V$^1$, V$^2$, V$^3$ and/or V$^4$ are(is) CH, W$^3$ independently represents H, halogen; (C$_{1-5}$)alkyl; (C$_{1-5}$)alkoxy; —OH; —NO$_2$; —NR$^5$R$^6$; —CH=CR$^7$R$^8$; —C≡C—R$^9$; (C$_{5-6}$)cycloalkenyl; 5- to 7-membered heterocycloalkyl optionally substituted with (C$_{1-5}$)alkyl, —C(=O)O(C$_{1-5}$)alkyl, —S(=O)$_2$(C$_{1-5}$)alkyl, —C(=O)(C$_{1-5}$)alkyl or —C(=O)(NH$_2$); an aryl; or a heteroaryl, wherein the aryl or the heteroaryl may be optionally substituted with one or more R$^{10}$, R$^5$ and R$^6$ each independently represent H; (C$_{1-5}$)alkyl optionally substituted with (C$_{3-7}$)cycloalkyl or an aryl; 5- to 7-membered heterocycloalkyl optionally substituted with (C$_{1-5}$)alkyl; an aryl; —C(=O)R$^{11}$; or —S(=O)$_2$R$^{12}$, R$^7$ represents (C$_{1-5}$)alkyl optionally substituted with —OH; an aryl optionally substituted with halogen; or —C(=O)R$^{13}$, R$^8$ represents H; or (C$_{1-5}$)alkyl, R$^9$ represents an aryl optionally substituted with —NH$_2$, R$^{10}$ independently represents H; halogen; —CN; —CF$_3$; —OH; —OCF$_3$; (C$_{1-5}$)alkyl optionally substituted with (C$_{3-7}$)cycloalkyl, 5- to 7-membered heterocycloalkyl, or —OH; (C$_{1-5}$)alkoxy; —NH$_2$ optionally substituted with one or more (C$_{1-5}$)alkyl; 5- to 7-membered heterocycloalkyl optionally substituted with (C$_{1-5}$)alkyl; —C(=O)R$^{14}$; —S(=O)$_2$-(5- to 7-membered heterocycloalkyl); or an aryl, wherein R$^{10}$ is optionally connected to each other to form 5 to 6-membered ring, R$^{11}$ represents (C$_{1-5}$)alkyl optionally substituted with —N(CH$_3$)$_2$, an aryl, or a hydroxyaryl; (C$_{3-7}$)cycloalkyl optionally comprising C(=O); (C$_{3-7}$)cycloalkyl optionally substituted with (C$_{1-5}$)alkyl; (C$_{3-7}$)cycloalkyl fused with an aryl; (C$_{5-6}$)cycloalkenyl optionally substituted with (C$_{1-5}$)alkyl; 5- to 7-membered heterocycloalkyl optionally substituted with (C$_{1-5}$)alkyl or —NH$_2$; an aryl; or a heteroaryl optionally substituted with (C$_{1-5}$)alkyl or —OH, R$^{12}$ represents (C$_{1-5}$)alkyl; or an aryl optionally substituted with (C$_{1-5}$)alkyl and/or halogen, R$^{13}$ represents (C$_{1-5}$)alkyl; (C$_{1-5}$)alkoxy; —OH; —NH$_2$, wherein at least one H of —NH$_2$ optionally substituted with (C$_{1-5}$)alkyl; (C$_{3-7}$)cycloalkyl; hydroxy(C$_{1-5}$)alkyl; (C$_{1-5}$)alkoxy(C$_{1-5}$)alkyl; —NH$_2$, R$^{14}$ represents 5- to 7-membered heterocycloalkyl; —NH$_2$; or —OH, L$^1$, L$^2$, M, and G are as defined above.

According to another specific embodiment of the present invention, it may be provided that W$^3$ independently represents H, halogen; (C$_{1-5}$)alkyl; (C$_{1-5}$)alkoxy; —OH; —NO$_2$; —NR$^5$R$^6$; —CH=CR$^7$R$^8$; —C≡C—R$^9$; (C$_{5-6}$)cycloalkenyl; morpholinyl; tetrahydropyridinyl; dihydropyranyl; tert-butyl(tetrahydropyridine)carboxylate; dihydrothiopyranyl; methyltetrahydropyridinyl; (methylsulfonyl)tetrahydropyridinyl; acetyltetrahydropyridinyl; (tetrahydropyridine) carboxamide; 1,1-dioxide-dihydrothiopyranyl; phenyl; (trifluoromethoxy)phenyl; aminophenyl; tert-butyl(phenyl) carbamate; (pyrrolidinylsulfonyl)phenyl; oxopiperidine(carbonyl)phenyl; (methylpiperazinyl)phenyl; isoindolyl; cyanophenyl; cyanohalophenyl; (trifluoromethyl)phenyl; (dimethylamino)phenyl; hydroxybenzylphenyl; methoxyphenyl; biphenyl; methylphenyl; hydroxyphenyl; dihydroindenyl; benzoic acid; methylbenzoate; pyridinyl; pyrazolyl; methylpyrazolyl; furanyl; aminopyridinyl; halopyridinyl; hydroxypyridinyl; (methoxy)halopyridinyl; methoxypyridinyl; (methyl)halopyridinyl; piperazinylpyridinyl; pyrrolopyridinyl; (dimethylamino)pyrimidinyl; (cyclopropylmethyl)pyrazolyl; (morpholinoethyl)pyrazolyl; pyrimidinyl; aminopyrimidinyl; (methylpiperazinyl)pyridinyl; piperazinylpyridinyl; morpholinopyridinyl; dihalopyridinyl; methylpyridinyl; pyrrolyl; tert-butyl(pyrrole)carboxylate; dimethylisoxazolyl; isoquinolinyl; methylindazolyl; methylthiophenyl; indazolyl; thiophenyl; cyanopyridinyl; (hydroxymethyl)pyridinyl; picolinamide; (dimethylamino) pyridinyl; (methylamino)pyridinyl; dimethylpyridinyl; or (methylamino)pyridinyl, R$^5$ and R$^6$ each independently represent H; (C$_{1-5}$)alkyl optionally substituted with (C$_{3-7}$)cycloalkyl or phenyl; morpholinyl, or piperazinyl optionally substituted with (C$_{1-5}$)alkyl; phenyl; —C(=O)R$^{11}$; or —S(=O)$_2$R$^{12}$, R$^7$ represents methyl optionally substituted with —OH; phenyl optionally substituted with halogen; or —C(=O)R$^{13}$, R$^9$ represents phenyl optionally substituted with —NH$_2$, R$^{11}$ represents (C$_{1-5}$)alkyl optionally substituted with —N(CH$_3$)$_2$, phenyl, or hydroxyphenyl; (C$_{3-7}$)cycloalkyl optionally comprising C(=O); (C$_{3-7}$)cycloalkyl substituted with (C$_{1-5}$)alkyl; (C$_{3-7}$)cycloalkyl fused with phenyl; (C$_{5-6}$)cycloalkenyl optionally substituted with (C$_{1-5}$)alkyl; morpholinyl; methylpiperidinyl; oxopyrrolidinyl; oxoimidazolidinyl; pyrrolidinyl; piperidinyl; tetrahydrofuranyl; tetrahydropyranyl; methyltetrahydropyranyl; aminopyrrolidinyl; methylpyrrolidinyl; phenyl; pyridinyl; oxazolyl; pyridazinyl; methylisoxazolyl; methyloxazolyl; isoxazolyl; methylpyridinyl; furanyl; or hydroxypyrimidinyl, R$^{12}$ represents (C$_{1-5}$)alkyl; phenyl; methylphenyl; or (methyl)halophenyl, R$^{14}$ represents oxopiperidinyl; —NH$_2$; or —OH.

Throughout the present specification, the concepts defined as follows are used when defining the compounds of Formula (I) and Formula (Ib). The following definitions are also applied to the terms used either individually or as a part of a larger group thereof throughout the present specification, unless otherwise particularly indicated.

The term "alkyl" means a linear or branched or cyclic hydrocarbon radical respectively, each carbon atom may be arbitrarily substituted with at least one of cyano, hydroxy, alkoxy, oxo, halogen, carbonyl, sulfonyl, cyanyl, and the like, but is not limited thereto.

The term "cycloalkyl" means a saturated monocyclic hydrocarbon ring, and may be arbitrarily fused with an aryl. For example, cyclopropyl, cyclobutyl, cyclopentyl, cyclohexyl and the like, but is not limited thereto.

The term "alkoxy" refers to —O-alkyl, wherein alkyl is as defined above. An examples of such groups include methoxy, ethoxy, n-propoxy, iso-propoxy, n-butoxy, 2-butoxy, n-pentoxy, t-butoxy and the like, but is not limited thereto.

The term "n-membered ring" means a n-membered saturated or unsaturated carbon ring in which one or more than carbon atom may be optionally replaced with heteroatom (such as N, O, S); the n-membered saturated or unsaturated carbon ring may optionally comprise one or more C(=O) (n may be 4 to 6). For example, pyrrolidine, 1H-pyrrole-2,5-dione, 1,5-dihydro-2H-pyrrol-2-one, and the like, but is not limited thereto.

The term "heterocycloalkyl" means a form which includes 1 to 4 heteroatoms selected from N, O and S; "heterocycloalkyl" is saturated or partially saturated (partially unsaturated) or aromatic; "heterocycloalkyl" may arbitrarily comprise one or more —C(=O)— or —S(=O)$_2$—. An appropriate heterocycloalkyl may include, for example azetidinyl; pyrrolidinyl; piperidinyl; tetrahydropyridinyl; oxopyrrolidinyl; oxopiperazinyl; morpholinyl; thiomorpholinyl; piperazinyl; dihydropyranyl; dihydrothiopyranyl; 1,1-dihydrothiopyran-1,1-dioxide; isoindolyl; dihydroindenyl; pyridinyl; pyrazolyl; pyrimidinyl; pyrrolyl; isoquinolinyl; indazolyl; thiophenyl; oxoimidazolidinyl; tetrahydrofuranyl; tetrahydropyranyl; oxazolyl; pyridazinyl; isoxazolyl; oxopiperidinyl and the like, but is not limited thereto.

The term "halo(gen)" means a substituent selected from fluoro (F), chloro (Cl), bromo (Br) and iodo (I).

The term "aryl" means an aromatic group including phenyl, naphthyl, etc., but is not limited thereto; and is arbitrarily fused with cycloalkyl or heterocycloalkyl.

The term "heteroaryl" refers to a 5- to 7-membered aromatic, monocyclic ring, which includes at least one heteroatom, for example, 1 to 4, or in some exemplary embodiments 1 to 3 heteroatoms selected from N, O and S, and in which remaining ring atoms are carbons; a 8- to 12-membered bicyclic ring, which includes at least one heteroatom, for example, 1 to 4, or in some exemplary embodiments 1 to 3 heteroatoms selected from N, O and S, and in which remaining ring atoms are carbons, at least one ring is aromatic; For example of a heteroaryl group includes pyridinyl, pyrimidinyl, pyridazinyl, pyrazinyl, triazinyl, imidazolyl, isoxazolyl, oxazolyl, thiazolyl, thiadiazolyl, tetrazolyl, thienyl, benzothienyl, furyl, benzofuryl, benzoimidazolyl, indolyl, indolinyl, pyrrolyl, thiophenyl, pyridizinyl, triazolyl, quinolinyl, pyrazolyl, pyrrolopyridinyl, pyrazolopyridinyl, benzoxazolyl, benzothiazolyl, indazolyl and 5,6,7,8-tetrahydroisoquinoline, and the like, but is not limited thereto.

The term "amino" as used herein refers to the group —NH$_2$.

Other terms and abbreviations used in the present specification have their original meanings, unless otherwise defined.

In the present invention, representative examples of the compound represented by the formula 1 above are as follows.

| | |
|---|---|
| 1) | (S)-2-(3-((2-(cyclopropylamino)pyrimidin-4-yl)oxy)pyrrolidin-1-yl)-N-(3-(2-((1,5-dimethyl-1H-pyrazol-3-yl)amino)-5-methylpyrimidin-4-yl)-6-fluoro-1H-indol-7-yl)acetamide |
| 2) | (S)-N-(5-amino-3-(2-((1,5-dimethyl-1H-pyrazol-3-yl)amino)-5-methylpyrimidin-4-yl)-1H-indol-7-yl)-2-(3-((2-(cyclopropylamino)pyrimidin-4-yl)oxy)pyrrolidin-1-yl)acetamide |
| 3) | (S)-2-(3-((2-(cyclopropylamino)pyrimidin-4-yl)oxy)pyrrolidin-1-yl)-N-(3-(2-((1,5-dimethyl-1H-pyrazol-3-yl)amino)-5-methylpyrimidin-4-yl)-6-(dimethylamino)-1H-indol-7-yl)acetamide |
| 4) | (S)-2-(3-((2-(cyclopropylamino)pyrimidin-4-yl)oxy)pyrrolidin-1-yl)-N-(3-(2-((1,5-dimethyl-1H-pyrazol-3-yl)amino)-5-methylpyrimidin-4-yl)-6-methoxy-1H-indol-7-yl)acetamide |
| 5) | (S)-N-(3-(2-((1,5-dimethyl-1H-pyrazol-3-yl)amino)-5-methylpyrimidin-4-yl)-6-(dimethylamino)-1H-inden-7-yl)-2-(3-((2-((2,2,2-trifluoroethyl)amino)pyrimidin-4-yl)oxy)pyrrolidin-1-yl)acetamide |
| 6) | (S)-N-(3-(2-((1,5-dimethyl-1H-pyrazol-3-yl)amino)-5-methylpyrimidin-4-yl)-6-methoxy-1H-indol-7-yl)-2-(3-((2-((2,2,2-trifluoroethyl)amino)pyrimidin-4-yl)oxy)pyrrolidin-1-yl)acetamide |
| 7) | (S)-2-(3-((6-(cyclopropylamino)pyrimidin-4-yl)oxy)pyrrolidin-1-yl)-N-(3-(2-((1,5-dimethyl-1H-pyrazol-3-yl)amino)pyrimidin-4-yl)-1H-indol-7-yl)acetamide |
| 8) | (S)-N-(3-(2-((1,5-dimethyl-1H-pyrazol-3-yl)amino)-5-fluoropyrimidin-4-yl)-1H-indol-7-yl)-2-(3-(pyridin-4-yloxy)pyrrolidin-1-yl)acetamide |
| 9) | (S)-N-(3-(5-chloro-2-((1,5-dimethyl-1H-pyrazol-3-yl)amino)pyrimidin-4-yl)-1H-indol-7-yl)-2-(3-(pyridin-4-yloxy)pyrrolidin-1-yl)acetamide |
| 10) | (3-(5-chloro-2-((1,5-dimethyl-1H-pyrazol-3-yl)amino)pyrimidin-4-yl)-1H-indol-7-yl)-2-(3-((2-(cyclopropylamino)pyrimidin-4-yl)oxy)pyrrolidin-1-yl)acetamide |
| 11) | (3-((2-(cyclopropylamino)pyrimidin-4-yl)oxy)pyrrolidin-1-yl)-N-(3-(2-((1,5-dimethyl-1H-pyrazol-3-yl)amino)-5-ethylpyrimidin-4-yl)-1H-indol-7-yl)acetamide |
| 12) | (S)-N-(3-(5-cyclopropyl-2-((1,5-dimethyl-1H-pyrazol-3-yl)amino)pyrimidin-4-yl)-1H-indol-7-yl)-2-(3-((2-(cyclopropylamino)pyrimidin-4-yl)oxy)pyrrolidin-1-yl)acetamide |
| 13) | (S)-2-(3-((2-(cyclopropylamino)pyrimidin-4-yl)oxy)pyrrolidin-1-yl)-N-(3-(2-((1,5-dimethyl-1H-pyrazol-3-yl)amino)-5-methoxypyrimidin-4-yl)-1H-indol-7-yl)acetamide |

-continued 14) (S)-2-(3-((3-(cyclopropylamino)-1,2,4-triazin-5-yl)oxy)pyrrolidin-1-yl)-N-(3-(2-((1,5-dimethyl-1H-pyrazol-3-yl)amino)-5-methoxypyrimidin-4-yl)-1H-indol-7-yl)acetamide
15) (S)-N-(3-(2-((5,6-dihydro-4H-pyrrolo[1,2-b]pyrazol-2-yl)amino)-5-methylpyrimidin-4-yl)-1H-indol-7-yl)-2-(3-(pyrimidin-4-yloxy)pyrrolidin-1-yl)acetamide
16) (S)-2-(3-((2-(cyclopropylamino)pyrimidin-4-yl)oxy)pyrrolidin-1-yl)-N-(3-(2-((5,6-dihydro-4H-pyrrolo[1,2-b]pyrazol-2-yl)amino)-5-methylpyrimidin-4-yl)-1H-indol-7-yl)acetamide
17) (S)-2-(3-((2-(cyclopropylamino)pyrimidin-4-yl)oxy)pyrrolidin-1-yl)-N-(3-(5-methyl-2-((5-methyl-1-(2-morpholinoethyl)-1H-pyrazol-3-yl)amino)pyrimidin-4-yl)-1H-indol-7-yl)acetamide
18) (S)-N-(3-(2-((1,5-dimethyl-1H-pyrazol-3-yl)amino)-5-methylpyrimidin-4-yl)-1H-indol-7-yl)-2-oxo-2-(3-(pyridin-4-yloxy)pyrrolidin-1-yl)acetamide
19) N-(3-(2-((1,5-dimethyl-1H-pyrazol-3-yl)amino)-5-methylpyrimidin-4-yl)-1H-indol-7-yl)-2-oxo-2-(3-(pyridin-3-yloxy)pyrrolidin-1-yl)acetamide
20) (S)-2-(3-((2-(cyclopropylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)-2-oxoacetamide
21) (S)-N-(3-(2-((1,5-dimethyl-1H-pyrazol-3-yl)amino)-5-methylpyrimidin-4-yl)-1H-indol-7-yl)-N-methyl-2-(3-(pyrimidin-4-yloxy)pyrrolidin-1-yl)acetamide
22) N-(3-(2-((1,5-dimethyl-1H-pyrazol-3-yl)amino)-5-methylpyrimidin-4-yl)-1H-indol-7-yl)-2-(pyrrolidin-1-yl)propenamide
23) N-(3-(2-((1,5-dimethyl-1H-pyrazol-3-yl)amino)-5-methylpyrimidin-4-yl)-1H-indol-7-yl)-2-((S)-3-(pyridin-4-yloxy)pyrrolidin-1-yl)propenamide
24) N-(3-(2-((1,5-dimethyl-1H-pyrazol-3-yl)amino)-5-methylpyrimidin-4-yl)-1H-indol-7-yl)-2-methyl-2-(pyrrolidin-1-yl)propenamide
25) (S)-N-(3-(2-((1,5-dimethyl-1H-pyrazol-3-yl)amino)-5-methylpyrimidin-4-yl)-1H-indol-7-yl)-2-methyl-2-(3-(pyridin-4-yloxy)pyrrolidin-1-yl)propenamide
26) N-(3-(2-((1,5-dimethyl-1H-pyrazol-3-yl)amino)-5-methylpyrimidin-4-yl)-1H-indol-7-yl)-2-(3-hydroxyazetidin-1-yl)acetamide
27) N-(3-(2-((1,5-dimethyl-1H-pyrazol-3-yl)amino)-5-methylpyrimidin-4-yl)-1H-indol-7-yl)-2-(3-(pyridin-4-ylmethoxy)azetidin-1-yl)acetamide
28) N-(3-(2-((1,5-dimethyl-1H-pyrazol-3-yl)amino)-5-methylpyrimidin-4-yl)-1H-indol-7-yl)-2-(3-(pyridin-4-yloxy)azetidin-1-yl)acetamide
29) N-(3-(2-((1,5-dimethyl-1H-pyrazol-3-yl)amino)-5-methylpyrimidin-4-yl)-1H-indol-7-yl)-2-(3-(pyrimidin-4-yloxy)azetidin-1-yl)acetamide
30) N-(3-(2-((1,5-dimethyl-1H-pyrazol-3-yl)amino)-5-methylpyrimidin-4-yl)-1H-indol-7-yl)-2-(3-(pyridin-3-yloxy)azetidin-1-yl)acetamide
31) methyl 1-(2-((3-(2-((1,5-dimethyl-1H-pyrazol-3-yl)amino)-5-methylpyrimidin-4-yl)-1H-indol-7-yl)amino)-2-oxoethyl)azetidine-3-carboxylate
32) 1-(2-((3-(2-((1,5-dimethyl-1H-pyrazol-3-yl)amino)-5-methylpyrimidin-4-yl)-1H-indol-7-yl)amino)-2-oxoethyl)azetidine-3-carboxylic acid
33) N-cyclopropyl-3-((1-(2-((3-(2-((1,5-dimethyl-1H-pyrazol-3-yl)amino)-5-methylpyrimidin-4-yl)-1H-indol-7-yl)amino)-2-oxoethyl)azetidin-3-yl)oxy)isoxazole-5-carboxamide
34) 2-(3,6-dihydro-[4,4'-bipyridin]-1(2H)-yl)-N-(3-(2-((1,5-dimethyl-1H-pyrazol-3-yl)amino)-5-methylpyrimidin-4-yl)-1H-indol-7-yl)acetamide
35) N-(3-(2-((1,5-dimethyl-1H-pyrazol-3-yl)amino)-5-methylpyrimidin-4-yl)-1H-indol-7-yl)-2-(4-(1-methyl-1H-pyrazol-4-yl)-3,6-dihydropyridin-1(2H)-yl)acetamide
36) N-(3-(2-((1,5-dimethyl-1H-pyrazol-3-yl)amino)-5-methylpyrimidin-4-yl)-1H-indol-7-yl)-2-(4-(4-methylpiperazin-1-yl)piperidin-1-yl)acetamide
37) N-(3-(2-((1,5-dimethyl-1H-pyrazol-3-yl)amino)-5-methylpyrimidin-4-yl)-1H-indol-7-yl)-2-(4-morpholinopiperidin-1-yl)acetamide
38) N-(3-(2-((1,5-dimethyl-1H-pyrazol-3-yl)amino)-5-methylpyrimidin-4-yl)-1H-indol-7-yl)-2-(4-(pyridin-3-yloxy)piperidin-1-yl)acetamide
39) N-(3-(2-((1,5-dimethyl-1H-pyrazol-3-yl)amino)-5-methylpyrimidin-4-yl)-1H-indol-7-yl)-2-(4-(pyridin-2-yloxy)piperidin-1-yl)acetamide
40) N-(3-(2-((1,5-dimethyl-1H-pyrazol-3-yl)amino)-5-methylpyrimidin-4-yl)-1H-indol-7-yl)-2-(4-(pyridin-4-yloxy)piperidin-1-yl)acetamide
41) N-(3-(2-((1,5-dimethyl-1H-pyrazol-3-yl)amino)-5-methylpyrimidin-4-yl)-1H-indol-7-yl)-2-(4-(pyrimidin-2-yloxy)piperidin-1-yl)acetamide
42) N-(3-(2-((1,5-dimethyl-1H-pyrazol-3-yl)amino)-5-methylpyrimidin-4-yl)-1H-indol-7-yl)-2-(4-((4,6-dimethylpyrimidin-2-yl)oxy)piperidin-1-yl)acetamide
43) N-cyclopropyl-3-((1-(2-((3-(2-((1,5-dimethyl-1H-pyrazol-3-yl)amino)-5-methylpyrimidin-4-yl)-1H-indol-7-yl)amino)-2-oxoethyl)piperidin-4-yl)oxy)isoxazole-5-carboxamide
44) N-cyclopropyl-3-((1-(2-((3-(2-((1,5-dimethyl-1H-pyrazol-3-yl)amino)-5-methylpyrimidin-4-yl)-1H-indol-7-yl)amino)-2-oxoethyl)piperidin-3-yl)oxy)isoxazole-5-carboxamide -continued

| | |
|---|---|
| 45) | 2-(3-(cyanomethyl)pyrrolidin-1-yl)-N-(3-(2-((1,5-dimethyl-1H-pyrazol-3-yl)amino)-5-methylpyrimidin-4-yl)-1H-indol-7-yl)acetamide |
| 46) | (R)-2-(3-(cyanomethyl)pyrrolidin-1-yl)-N-(3-(2-((1,5-dimethyl-1H-pyrazol-3-yl)amino)-5-methylpyrimidin-4-yl)-1H-indol-7-yl)acetamide |
| 47) | (S)-N-(3-(2-((1,5-dimethyl-1H-pyrazol-3-yl)amino)-5-methylpyrimidin-4-yl)-1H-indol-7-yl)-2-(3-(pyrimidin-4-ylamino)pyrrolidin-1-yl)acetamide |
| 48) | (R)-N-(3-(2-((1,5-dimethyl-1H-pyrazol-3-yl)amino)-5-methylpyrimidin-4-yl)-1H-indol-7-yl)-2-(3-(pyrimidin-4-ylamino)pyrrolidin-1-yl)acetamide |
| 49) | (R)-N-(3-(2-((1,5-dimethyl-1H-pyrazol-3-yl)amino)-5-methylpyrimidin-4-yl)-1H-indol-7-yl)-2-(3-(pyridin-4-ylamino)pyrrolidin-1-yl)acetamide |
| 50) | N-(3-(2-((1,5-dimethyl-1H-pyrazol-3-yl)amino)-5-methylpyrimidin-4-yl)-1H-indol-7-yl)-2-((3R,4S)-3-fluoro-4-hydroxypyrrolidin-1-yl)acetamide |
| 51) | N-(3-(2-((1,5-dimethyl-1H-pyrazol-3-yl)amino)-5-methylpyrimidin-4-yl)-1H-indol-7-yl)-2-((3R,4R)-3-fluoro-4-(pyridin-4-yloxy)pyrrolidin-1-yl)acetamide |
| 52) | 2-((3R,4S)-3-((2-(cyclopropylamino)pyrimidin-4-yl)oxy)-4-fluoropyrrolidin-1-yl)-N-(3-(2-((1,5-dimethyl-1H-pyrazol-3-yl)amino)-5-methylpyrimidin-4-yl)-1H-indol-7-yl)acetamide |
| 53) | 2-((3R,4R)-3-((2-(cyclopropylamino)pyrimidin-4-yl)oxy)-4-fluoropyrrolidin-1-yl)-N-(3-(2-((1,5-dimethyl-1H-pyrazol-3-yl)amino)-5-methylpyrimidin-4-yl)-1H-indol-7-yl)acetamide |
| 54) | 2-((3S,4R)-3-((2-(cyclopropylamino)pyrimidin-4-yl)oxy)-4-fluoropyrrolidin-1-yl)-N-(3-(2-((1,5-dimethyl-1H-pyrazol-3-yl)amino)-5-methylpyrimidin-4-yl)-1H-indol-7-yl)acetamide |
| 55) | methyl (2S,4S)-4-((2-(cyclopropylamino)pyrimidin-4-yl)oxy)-1-(2-((3-(2-((1,5-dimethyl-1H-pyrazol-3-yl)amino)-5-methylpyrimidin-4-yl)-1H-indol-7-yl)amino)-2-oxoethyl)pyrrolidine-2-carboxylate |
| 56) | (2S,4S)-4-((2-(cyclopropylamino)pyrimidin-4-yl)oxy)-1-(2-((3-(2-((1,5-dimethyl-1H-pyrazol-3-yl)amino)-5-methylpyrimidin-4-yl)-1H-indol-7-yl)amino)-2-oxoethyl)pyrrolidine-2-carboxylic acid |
| 57) | 2-((2S,4S)-4-((2-(cyclopropylamino)pyrimidin-4-yl)oxy)-2-(hydroxymethyl)pyrrolidin-1-yl)-N-(3-(2-((1,5-dimethyl-1H-pyrazol-3-yl)amino)-5-methylpyrimidin-4-yl)-1H-indol-7-yl)acetamide |
| 58) | (2S,4S)-4-((2-(cyclopropylamino)pyrimidin-4-yl)oxy)-1-(2-((3-(2-((1,5-dimethyl-1H-pyrazol-3-yl)amino)-5-methylpyrimidin-4-yl)-1H-indol-7-yl)amino)-2-oxoethyl)pyrrolidine-2-carboxamide |
| 59) | 2-((2S,4S)-2-(aminomethyl)-4-((2-(cyclopropylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 60) | (S)-2-(3-((2-(cyclopropylamino)pyrimidin-4-yl)oxy)-2-oxopyrrolidin-1-yl)-N-(3-(2-((1,5-dimethyl-1H-pyrazol-3-yl)amino)-5-methylpyrimidin-4-yl)-1H-indol-7-yl)acetamide |
| 61) | (S)-2-(4-((2-(cyclopropylamino)pyrimidin-4-yl)oxy)-2-oxopyrrolidin-1-yl)-N-(3-(2-((1,5-dimethyl-1H-pyrazol-3-yl)amino)-5-methylpyrimidin-4-yl)-1H-indol-7-yl)acetamide |
| 62) | (S)-N-(3-(2-((1,5-dimethyl-1H-pyrazol-3-yl)amino)-5-methylpyrimidin-4-yl)-1H-indol-7-yl)-2-(3-(3-oxopiperazine-1-carbonyl)pyrrolidin-1-yl)acetamide |
| 63) | (S)-N-(3-(2-((1,5-dimethyl-1H-pyrazol-3-yl)amino)-5-methylpyrimidin-4-yl)-1H-indol-7-yl)-2-(3-(morpholine-4-carbonyl)pyrrolidin-1-yl)acetamide |
| 64) | (S)-N-(3-(2-((1,5-dimethyl-1H-pyrazol-3-yl)amino)-5-methylpyrimidin-4-yl)-1H-indol-7-yl)-2-(3-(thiomorpholine-4-carbonyl)pyrrolidin-1-yl)acetamide |
| 65) | (R)-N-(3-(2-((1,5-dimethyl-1H-pyrazol-3-yl)amino)-5-methylpyrimidin-4-yl)-1H-indol-7-yl)-2-(3-(4-methylpiperazine-1-carbonyl)pyrrolidin-1-yl)acetamide |
| 66) | (R)-N-(3-(2-((1,5-dimethyl-1H-pyrazol-3-yl)amino)-5-methylpyrimidin-4-yl)-1H-indol-7-yl)-2-(3-(3-oxopiperazine-1-carbonyl)pyrrolidin-1-yl)acetamide |
| 67) | (R)-N-(3-(2-((1,5-dimethyl-1H-pyrazol-3-yl)amino)-5-methylpyrimidin-4-yl)-1H-indol-7-yl)-2-(3-(morpholine-4-carbonyl)pyrrolidin-1-yl)acetamide |
| 68) | (R)-N-(3-(2-((1,5-dimethyl-1H-pyrazol-3-yl)amino)-5-methylpyrimidin-4-yl)-1H-indol-7-yl)-2-(3-(thiomorpholine-4-carbonyl)pyrrolidin-1-yl)acetamide |
| 69) | (S)-N-(3-(2-((1,5-dimethyl-1H-pyrazol-3-yl)amino)-5-methylpyrimidin-4-yl)-1H-indol-7-yl)-2-(3-(1,2,3,6-tetrahydropyridine-1-carbonyl)pyrrolidin-1-yl)acetamide |
| 70) | N-(3-(2-((1,5-dimethyl-1H-pyrazol-3-yl)amino)-5-methylpyrimidin-4-yl)-1H-indol-7-yl)-2-(3-hydroxypyrrolidin-1-yl)acetamide |
| 71) | (R)-N-(3-(2-((1,5-dimethyl-1H-pyrazol-3-yl)amino)-5-methylpyrimidin-4-yl)-1H-indol-7-yl)-2-(3-hydroxypyrrolidin-1-yl)acetamide |
| 72) | (S)-N-(3-(2-((1,5-dimethyl-1H-pyrazol-3-yl)amino)-5-methylpyrimidin-4-yl)-1H-indol-7-yl)-2-(3-hydroxypyrrolidin-1-yl)acetamide |

-continued 73) (S)-N-(3-(2-((1,5-dimethyl-1H-pyrazol-3-yl)amino)-5-methylpyrimidin-4-yl)-1H-indol-7-yl)-2-(3-(pyridin-2-yloxy)pyrrolidin-1-yl)acetamide
74) (S)-N-(3-(2-((1,5-dimethyl-1H-pyrazol-3-yl)amino)-5-methylpyrimidin-4-yl)-1H-indol-7-yl)-2-(3-(pyridin-3-yloxy)pyrrolidin-1-yl)acetamide
75) (S)-N-(3-(2-((1,5-dimethyl-1H-pyrazol-3-yl)amino)-5-methylpyrimidin-4-yl)-1H-indol-7-yl)-2-(3-(pyridin-4-yloxy)pyrrolidin-1-yl)acetamide
76) N-(3-(2-((1,5-dimethyl-1H-pyrazol-3-yl)amino)-5-methylpyrimidin-4-yl)-1H-indol-7-yl)-2-(3-(pyridin-4-yloxy)pyrrolidin-1-yl)acetamide
77) (R)-N-(3-(2-((1,5-dimethyl-1H-pyrazol-3-yl)amino)-5-methylpyrimidin-4-yl)-1H-indol-7-yl)-2-(3-(pyridin-4-yloxy)pyrrolidin-1-yl)acetamide
78) (S)-N-(3-(2-((1,5-dimethyl-1H-pyrazol-3-yl)amino)-5-methylpyrimidin-4-yl)-1H-indol-7-yl)-2-(3-(pyrimidin-4-yloxy)pyrrolidin-1-yl)acetamide
79) (S)-N-(3-(2-((1,5-dimethyl-1H-pyrazol-3-yl)amino)-5-methylpyrimidin-4-yl)-1H-indol-7-yl)-2-(3-(pyrazin-2-yloxy)pyrrolidin-1-yl)acetamide
80) (S)-N-(3-(2-((1,5-dimethyl-1H-pyrazol-3-yl)amino)-5-methylpyrimidin-4-yl)-1H-indol-7-yl)-2-(3-(4-fluorophenoxy)pyrrolidin-1-yl)acetamide
81) (S)-N-(3-(2-((1,5-dimethyl-1H-pyrazol-3-yl)amino)-5-methylpyrimidin-4-yl)-1H-indol-7-yl)-2-(3-(3-fluorophenoxy)pyrrolidin-1-yl)acetamide
82) (S)-2-(3-(4-chlorophenoxy)pyrrolidin-1-yl)-N-(3-(2-((1,5-dimethyl-1H-pyrazol-3-yl)amino)-5-methylpyrimidin-4-yl)-1H-indol-7-yl)acetamide
83) (S)-2-(3-(2,4-difluorophenoxy)pyrrolidin-1-yl)-N-(3-(2-((1,5-dimethyl-1H-pyrazol-3-yl)amino)-5-methylpyrimidin-4-yl)-1H-indol-7-yl)acetamide
84) (S)-2-(3-(3,4-difluorophenoxy)pyrrolidin-1-yl)-N-(3-(2-((1,5-dimethyl-1H-pyrazol-3-yl)amino)-5-methylpyrimidin-4-yl)-1H-indol-7-yl)acetamide
85) (S)-2-(3-(3,5-difluorophenoxy)pyrrolidin-1-yl)-N-(3-(2-((1,5-dimethyl-1H-pyrazol-3-yl)amino)-5-methylpyrimidin-4-yl)-1H-indol-7-yl)acetamide
86) (S)-2-(3-(2-chloro-4-fluorophenoxy)pyrrolidin-1-yl)-N-(3-(2-((1,5-dimethyl-1H-pyrazol-3-yl)amino)-5-methylpyrimidin-4-yl)-1H-indol-7-yl)acetamide
87) (S)-2-(3-(3-amino-4-fluorophenoxy)pyrrolidin-1-yl)-N-(3-(2-((1,5-dimethyl-1H-pyrazol-3-yl)amino)-5-methylpyrimidin-4-yl)-1H-indol-7-yl)acetamide
88) (S)-2-(3-(3-aminophenoxy)pyrrolidin-1-yl)-N-(3-(2-((1,5-dimethyl-1H-pyrazol-3-yl)amino)-5-methylpyrimidin-4-yl)-1H-indol-7-yl)acetamide
89) (S)-2-(3-(3-(diethylamino)phenoxy)pyrrolidin-1-yl)-N-(3-(2-((1,5-dimethyl-1H-pyrazol-3-yl)amino)-5-methylpyrimidin-4-yl)-1H-indol-7-yl)acetamide
90) (S)-2-(3-((2-chloropyridin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide
91) (S)-2-(3-((2-aminopyridin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide
92) (S)-N-(3-(2-((1,5-dimethyl-1H-pyrazol-3-yl)amino)-5-methylpyrimidin-4-yl)-1H-indol-7-yl)-2-(3-((5-fluoropyrimidin-2-yl)oxy)pyrrolidin-1-yl)acetamide
93) (S)-2-(3-((6-aminopyrazin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide
94) (S)-2-(3-((6-chloro-5-methylpyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide
95) (S)-2-(3-((2-amino-6-methylpyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide
96) (S)-2-(3-((5-amino-2-chloropyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide
97) (S)-2-(3-((5-bromo-2-methylpyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide
98) (S)-2-(3-((2-amino-6-(5-chloro-2-fluorophenyl)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide
99) (S)-2-(3-((2-amino-6-(trifluoromethyl)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide
100) (S)-2-(3-([1,1'-biphenyl]-4-yloxy)pyrrolidin-1-yl)-N-(3-(2-((1,5-dimethyl-1H-pyrazol-3-yl)amino)-5-methylpyrimidin-4-yl)-1H-indol-7-yl)acetamide
101) (S)-N-(3-(2-((1,5-dimethyl-1H-pyrazol-3-yl)amino)-5-methylpyrimidin-4-yl)-1H-indol-7-yl)-2-(3-(4-(2-phenylpropan-2-yl)phenoxy)pyrrolidin-1-yl)acetamide
102) (S)-N-(3-(2-((1,5-dimethyl-1H-pyrazol-3-yl)amino)-5-methylpyrimidin-4-yl)-1H-indol-7-yl)-2-(3-((5-pentylpyrimidin-2-yl)oxy)pyrrolidin-1-yl)acetamide

| | |
|---|---|
| 103) | (S)-N-(3-(2-((1,5-dimethyl-1H-pyrazol-3-yl)amino)-5-methylpyrimidin-4-yl)-1H-indol-7-yl)-2-(3-(4-((4-methylpiperazin-1-yl)methyl)phenoxy)pyrrolidin-1-yl)acetamide |
| 104) | (S)-N-(3-(2-((1,5-dimethyl-1H-pyrazol-3-yl)amino)-5-methylpyrimidin-4-yl)-1H-indol-7-yl)-2-(3-((1-methyl-1H-pyrazol-5-yl)oxy)pyrrolidin-1-yl)acetamide |
| 105) | (S)-N-(3-(2-((1,5-dimethyl-1H-pyrazol-3-yl)amino)-5-methylpyrimidin-4-yl)-1H-indol-7-yl)-2-(3-((1-methyl-1H-pyrazol-3-yl)oxy)pyrrolidin-1-yl)acetamide |
| 106) | methyl (S)-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)benzo[b]thiophene-2-carboxylate |
| 107) | methyl (S)-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)thiophene-2-carboxylate |
| 108) | (S)-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)thiophene-2-carboxylic acid |
| 109) | (S)-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)thiophene-2-carboxamide |
| 110) | (S)-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)-N-methylthiophene-2- |
| 111) | (S)-N-cyclopropyl-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)thiophene-2- |
| 112) | S)-N-(3-(2-((1,5-dimethyl-1H-pyrazol-3-yl)amino)-5-methylpyrimidin-4-yl)-1H-indol-7-yl)-2-(3-((5-methylisoxazol-3-yl)oxy)pyrrolidin-1-yl)acetamide |
| 113) | (S)-2-(3-(benzo[d]isoxazol-3-yloxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 114) | (S)-N-(3-(2-((1,5-dimethyl-1H-pyrazol-3-yl)amino)-5-methylpyrimidin-4-yl)-1H-indol-7-yl)-2-(3-(isothiazol-3-yloxy)pyrrolidin-1-yl)acetamide |
| 115) | (S)-N-(3-(2-((1,5-dimethyl-1H-pyrazol-3-yl)amino)-5-methylpyrimidin-4-yl)-1H-indol-7-yl)-2-(3-((2-methylthiophen-3-yl)oxy)pyrrolidin-1-yl)acetamide |
| 116) | (S)-2-(3-((1H-pyrazol-3-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 117) | (R)-N-(3-(2-((1,5-dimethyl-1H-pyrazol-3-yl)amino)-5-methylpyrimidin-4-yl)-1H-indol-7-yl)-2-(3-((1-methyl-5-(trifluoromethyl)-1H-pyrazol-3-yl)oxy)pyrrolidin-1-yl)acetamide |
| 118) | (S)-N-(3-(2-((1,5-dimethyl-1H-pyrazol-3-yl)amino)-5-methylpyrimidin-4-yl)-1H-indol-7-yl)-2-(3-(isoxazol-3-yloxy)pyrrolidin-1-yl)acetamide |
| 119) | (S)-2-(3-((5-amino-1H-pyrazol-3-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 120) | methyl (S)-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)-1H-pyrrole-2-carboxylate |
| 121) | ethyl (S)-5-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)isoxazole-4-carboxylate |
| 122) | (S)-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)isoxazole-5-carboxamide |
| 123) | (S)-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)-N-methylisoxazole-5-carboxamide |
| 124) | (S)-N-cyclopropyl-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)isoxazole-5-carboxamide |
| 125) | (S)-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)-N,N-dimethylisoxazole-5-carboxamide |
| 126) | (S)-N-cyclopropyl-2-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)oxazole-5-carboxamide |
| 127) | (S)-N-cyclopropyl-2-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)oxazole-4-carboxamide |
| 128) | (S)-2-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)pyrimidine-4-carboxylic acid |
| 129) | (S)-2-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)pyrimidine-4-carboxamide |

| | |
|---|---|
| 130) | (S)-2-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)-N-methylpyrimidine-4-carboxamide |
| 131) | (S)-2-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)-N,N-dimethylpyrimidine-4-carboxamide |
| 132) | (S)-6-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)pyrazine-2-carboxamide |
| 133) | (S)-6-(1-(2-((3-(2-(1,5-dimethyl-1H-pyrazol-3-yl)amino)-5-methylpyrimidin-4-yl)-1H-indol-7-yl)amino)-2-oxoethyl)pyrrolidin-3-yl)oxy)-N-methylpyrazine-2-carboxamide |
| 134) | (S)-2-(3-((4-amino-1,3,5-triazin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 135) | (S)-N-(3-(2-((1,5-dimethyl-1H-pyrazol-3-yl)amino)-5-methylpyrimidin-4-yl)-1H-indol-7-yl)-2-(3-((4-(methylamino)-1,3,5-triazin-2-yl)oxy)pyrrolidin-1-yl)acetamide |
| 136) | (S)-N-(3-(2-((1,5-dimethyl-1H-pyrazol-3-yl)amino)-5-methylpyrimidin-4-yl)-1H-indol-7-yl)-2-(3-((4-(dimethylamino)-1,3,5-triazin-2-yl)oxy)pyrrolidin-1-yl)acetamide |
| 137) | (S)-2-(3-((4-(cyclopropylamino)-1,3,5-triazin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 138) | (S)-2-(3-((4,6-diamino-1,3,5-triazin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 139) | (S)-2-(3-((4-amino-6-(pyrrolidin-1-yl)-1,3,5-triazin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 140) | (S)-2-(3-((6-aminopyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 141) | (S)-N-(3-(2-((1,5-dimethyl-1H-pyrazol-3-yl)amino)-5-methylpyrimidin-4-yl)-1H-indol-7-yl)-2-(3-((6-(methylamino)pyrimidin-4-yl)oxy)pyrrolidin-1-yl)acetamide |
| 142) | (S)-N-(3-(2-((1,5-dimethyl-1H-pyrazol-3-yl)amino)-5-methylpyrimidin-4-yl)-1H-indol-7-yl)-2-(3-((6-(ethylamino)pyrimidin-4-yl)oxy)pyrrolidin-1-yl)acetamide |
| 143) | (S)-N-(3-(2-((1,5-dimethyl-1H-pyrazol-3-yl)amino)-5-methylpyrimidin-4-yl)-1H-indol-7-yl)-2-(3-((6-(propylamino)pyrimidin-4-yl)oxy)pyrrolidin-1-yl)acetamide |
| 144) | (S)-2-(3-((6-(butylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 145) | (S)-N-(3-(2-((1,5-dimethyl-1H-pyrazol-3-yl)amino)-5-methylpyrimidin-4-yl)-1H-indol-7-yl)-2-(3-((6-((2-hydroxyethyl)amino)pyrimidin-4-yl)oxy)pyrrolidin-1-yl)acetamide |
| 146) | (S)-N-(3-(2-((1,5-dimethyl-1H-pyrazol-3-yl)amino)-5-methylpyrimidin-4-yl)-1H-indol-7-yl)-2-(3-((6-((3-hydroxypropyl)amino)pyrimidin-4-yl)oxy)pyrrolidin-1-yl)acetamide |
| 147) | (S)-N-(3-(2-((1,5-dimethyl-1H-pyrazol-3-yl)amino)-5-methylpyrimidin-4-yl)-1H-indol-7-yl)-2-(3-((6-((2-methoxyethyl)amino)pyrimidin-4-yl)oxy)pyrrolidin-1-yl)acetamide |
| 148) | (S)-N-(3-(2-((1,5-dimethyl-1H-pyrazol-3-yl)amino)-5-methylpyrimidin-4-yl)-1H-indol-7-yl)-2-(3-((6-((3-(dimethylamino)propyl)amino)pyrimidin-4-yl)oxy)pyrrolidin-1-yl)acetamide |
| 149) | (S)-2-(3-((6-(benzylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 150) | (S)-N-(3-(2-((1,5-dimethyl-1H-pyrazol-3-yl)amino)-5-methylpyrimidin-4-yl)-1H-indol-7-yl)-2-(3-((6-(phenethylamino)pyrimidin-4-yl)oxy)pyrrolidin-1-yl)acetamide |
| 151) | (S)-2-(3-((6-(cyclopropylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 152) | (S)-2-(3-((6-(cyclohexylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 153) | (S)-N-(3-(2-((1,5-dimethyl-1H-pyrazol-3-yl)amino)-5-methylpyrimidin-4-yl)-1H-indol-7-yl)-2-(3-((6-(dimethylamino)pyrimidin-4-yl)oxy)pyrrolidin-1-yl)acetamide |
| 154) | (S)-N-(3-(2-((1,5-dimethyl-1H-pyrazol-3-yl)amino)-5-methylpyrimidin-4-yl)-1H-indol-7-yl)-2-(3-((6-(ethyl(methyl)amino)pyrimidin-4-yl)oxy)pyrrolidin-1-yl)acetamide |
| 155) | (S)-2-(3-((6-(diethylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |

| | |
|---|---|
| 156) | (S)-N-(3-(2-((1,5-dimethyl-1H-pyrazol-3-yl)amino)-5-methylpyrimidin-4-yl)-1H-indol-7-yl)-2-(3-((6-(ethyl(propyl)amino)pyrimidin-4-yl)oxy)pyrrolidin-1-yl)acetamide |
| 157) | (S)-2-(3-((6-(butyl(ethyl)amino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 158) | (S)-N-(3-(2-((1,5-dimethyl-1H-pyrazol-3-yl)amino)-5-methylpyrimidin-4-yl)-1H-indol-7-yl)-2-(3-((6-(pyrrolidin-1-yl)pyrimidin-4-yl)oxy)pyrrolidin-1-yl)acetamide |
| 159) | N-(3-(2-((1,5-dimethyl-1H-pyrazol-3-yl)amino)-5-methylpyrimidin-4-yl)-1H-indol-7-yl)-2-((3S)-3-((6-(3-hydroxypyrrolidin-1-yl)pyrimidin-4-yl)oxy)pyrrolidin-1-yl)acetamide |
| 160) | N-(3-(2-((1,5-dimethyl-1H-pyrazol-3-yl)amino)-5-methylpyrimidin-4-yl)-1H-indol-7-yl)-2-((S)-3-((6-((R)-3-hydroxypyrrolidin-1-yl)pyrimidin-4-yl)oxy)pyrrolidin-1-yl)acetamide |
| 161) | N-(3-(2-((1,5-dimethyl-1H-pyrazol-3-yl)amino)-5-methylpyrimidin-4-yl)-1H-indol-7-yl)-2-((S)-3-((6-((S)-3-hydroxypyrrolidin-1-yl)pyrimidin-4-yl)oxy)pyrrolidin-1-yl)acetamide |
| 162) | (S)-N-(3-(2-((1,5-dimethyl-1H-pyrazol-3-yl)amino)-5-methylpyrimidin-4-yl)-1H-indol-7-yl)-2-(3-((6-(piperidin-1-yl)pyrimidin-4-yl)oxy)pyrrolidin-1-yl)acetamide |
| 163) | (S)-N-(3-(2-((1,5-dimethyl-1H-pyrazol-3-yl)amino)-5-methylpyrimidin-4-yl)-1H-indol-7-yl)-2-(3-((6-(4-hydroxypiperidin-1-yl)pyrimidin-4-yl)oxy)pyrrolidin-1-yl)acetamide |
| 164) | (S)-N-(3-(2-((1,5-dimethyl-1H-pyrazol-3-yl)amino)-5-methylpyrimidin-4-yl)-1H-indol-7-yl)-2-(3-((6-morpholinopyrimidin-4-yl)oxy)pyrrolidin-1-yl)acetamide |
| 165) | (S)-N-(3-(2-((1,5-dimethyl-1H-pyrazol-3-yl)amino)-5-methylpyrimidin-4-yl)-1H-indol-7-yl)-2-(3-((6-(4-methylpiperazin-1-yl)pyrimidin-4-yl)oxy)pyrrolidin-1-yl)acetamide |
| 166) | (S)-2-(3-((2-amino-6-(methylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 167) | (S)-2-(3-((2-amino-6-(pyrrolidin-1-yl)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 168) | (S)-2-(3-((4-aminopyrimidin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 169) | (S)-N-(3-(2-((1,5-dimethyl-1H-pyrazol-3-yl)amino)-5-methylpyrimidin-4-yl)-1H-indol-7-yl)-2-(3-((4-(methylamino)pyrimidin-2-yl)oxy)pyrrolidin-1-yl)acetamide |
| 170) | (S)-N-(3-(2-((1,5-dimethyl-1H-pyrazol-3-yl)amino)-5-methylpyrimidin-4-yl)-1H-indol-7-yl)-2-(3-((4-(dimethylamino)pyrimidin-2-yl)oxy)pyrrolidin-1-yl)acetamide |
| 171) | (S)-N-(3-(2-((1,5-dimethyl-1H-pyrazol-3-yl)amino)-5-methylpyrimidin-4-yl)-1H-indol-7-yl)-2-(3-((4-(ethyl(methyl)amino)pyrimidin-2-yl)oxy)pyrrolidin-1-yl)acetamide |
| 172) | (S)-2-(3-((4-(diethylamino)pyrimidin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 173) | (S)-N-(3-(2-((1,5-dimethyl-1H-pyrazol-3-yl)amino)-5-methylpyrimidin-4-yl)-1H-indol-7-yl)-2-(3-((4-(pyrrolidin-1-yl)pyrimidin-2-yl)oxy)pyrrolidin-1-yl)acetamide |
| 174) | (S)-N-(3-(2-((1,5-dimethyl-1H-pyrazol-3-yl)amino)-5-methylpyrimidin-4-yl)-1H-indol-7-yl)-2-(3-((4-(piperidin-1-yl)pyrimidin-2-yl)oxy)pyrrolidin-1-yl)acetamide |
| 175) | (S)-2-(3-((4-(cyclopropylamino)pyrimidin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 176) | (S)-2-(3-((4-amino-5-fluoropyrimidin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 177) | (S)-N-(3-(2-((1,5-dimethyl-1H-pyrazol-3-yl)amino)-5-methylpyrimidin-4-yl)-1H-indol-7-yl)-2-(3-((5-fluoro-4-(methylamino)pyrimidin-2-yl)oxy)pyrrolidin-1-yl)acetamide |
| 178) | (S)-N-(3-(2-((1,5-dimethyl-1H-pyrazol-3-yl)amino)-5-methylpyrimidin-4-yl)-1H-indol-7-yl)-2-(3-((4-(ethylamino)-5-fluoropyrimidin-2-yl)oxy)pyrrolidin-1-yl)acetamide |
| 179) | (S)-2-(3-((4-(cyclopropylamino)-5-fluoropyrimidin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 180) | (S)-2-(3-((4-(cyclohexylamino)-5-fluoropyrimidin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 181) | (S)-N-(3-(2-((1,5-dimethyl-1H-pyrazol-3-yl)amino)-5-methylpyrimidin-4-yl)-1H-indol-7-yl)-2-(3-((4-(dimethylamino)-5-fluoropyrimidin-2-yl)oxy)pyrrolidin-1-yl)acetamide |

| | |
|---|---|
| 182) | (S)-N-(3-(2-((1,5-dimethyl-1H-pyrazol-3-yl)amino)-5-methylpyrimidin-4-yl)-1H-indol-7-yl)-2-(3-((4-(ethyl(methyl)amino)-5-fluoropyrimidin-2-yl)oxy)pyrrolidin-1-yl)acetamide |
| 183) | (S)-2-(3-((4-(diethylamino)-5-fluoropyrimidin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 184) | (S)-N-(3-(2-((1,5-dimethyl-1H-pyrazol-3-yl)amino)-5-methylpyrimidin-4-yl)-1H-indol-7-yl)-2-(3-((5-fluoro-4-(methyl(phenyl)amino)pyrimidin-2-yl)oxy)pyrrolidin-1-yl)acetamide |
| 185) | (S)-2-(3-((4-(benzyl(methyl)amino)-5-fluoropyrimidin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 186) | (S)-N-(3-(2-((1,5-dimethyl-1H-pyrazol-3-yl)amino)-5-methylpyrimidin-4-yl)-1H-indol-7-yl)-2-(3-((5-fluoro-4-(pyrrolidin-1-yl)pyrimidin-2-yl)oxy)pyrrolidin-1-yl)acetamide |
| 187) | (S)-N-(3-(2-((1,5-dimethyl-1H-pyrazol-3-yl)amino)-5-methylpyrimidin-4-yl)-1H-indol-7-yl)-2-(3-((5-fluoro-4-(piperidin-1-yl)pyrimidin-2-yl)oxy)pyrrolidin-1-yl)acetamide |
| 188) | (S)-N-(3-(2-((1,5-dimethyl-1H-pyrazol-3-yl)amino)-5-methylpyrimidin-4-yl)-1H-indol-7-yl)-2-(3-((5-fluoro-4-morpholinopyrimidin-2-yl)oxy)pyrrolidin-1-yl)acetamide |
| 189) | (S)-N-(3-(2-((1,5-dimethyl-1H-pyrazol-3-yl)amino)-5-methylpyrimidin-4-yl)-1H-indol-7-yl)-2-(3-((5-fluoro-4-thiomorpholinopyrimidin-2-yl)oxy)pyrrolidin-1-yl)acetamide |
| 190) | (S)-N-(3-(2-((1,5-dimethyl-1H-pyrazol-3-yl)amino)-5-methylpyrimidin-4-yl)-1H-indol-7-yl)-2-(3-((5-fluoro-4-(4-methylpiperazin-1-yl)pyrimidin-2-yl)oxy)pyrrolidin-1-yl)acetamide |
| 191) | (S)-2-(3-((4-(cyclopropylamino)-5-methylpyrimidin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 192) | (S)-2-(3-((2-aminopyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 193) | (S)-N-(3-(2-((1,5-dimethyl-1H-pyrazol-3-yl)amino)-5-methylpyrimidin-4-yl)-1H-indol-7-yl)-2-(3-((2-(methylthio)pyrimidin-4-yl)oxy)pyrrolidin-1-yl)acetamide |
| 194) | (S)-N-(3-(2-((1,5-dimethyl-1H-pyrazol-3-yl)amino)-5-methylpyrimidin-4-yl)-1H-indol-7-yl)-2-(3-((2-methoxypyrimidin-4-yl)oxy)pyrrolidin-1-yl)acetamide |
| 195) | (S)-2-(3-((2-(benzyloxy)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 196) | (S)-2-(3-((2-acetamidopyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 197) | (S)-N-(3-(2-((1,5-dimethyl-1H-pyrazol-3-yl)amino)-5-methylpyrimidin-4-yl)-1H-indol-7-yl)-2-(3-((2-(methylamino)pyrimidin-4-yl)oxy)pyrrolidin-1-yl)acetamide |
| 198) | (S)-N-(3-(2-((1,5-dimethyl-1H-pyrazol-3-yl)amino)-5-methylpyrimidin-4-yl)-1H-indol-7-yl)-2-(3-((2-((2,2,2-trifluoroethyl)amino)pyrimidin-4-yl)oxy)pyrrolidin-1-yl)acetamide |
| 199) | (S)-2-(3-((2-((2,2-difluoropropyl)amino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 200) | (S)-2-(3-((2-((2,2-difluoroethyl)amino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 201) | N-(3-(2-((1,5-dimethyl-1H-pyrazol-3-yl)amino)-5-methylpyrimidin-4-yl)-1H-indol-7-yl)-2-((3S)-3-((2-((1,1,1-trifluoropropan-2-yl)amino)pyrimidin-4-yl)oxy)pyrrolidin-1-yl)acetamide |
| 202) | (S)-N-(3-(2-((1,5-dimethyl-1H-pyrazol-3-yl)amino)-5-methylpyrimidin-4-yl)-1H-indol-7-yl)-2-(3-((2-((2-fluoroethyl)amino)pyrimidin-4-yl)oxy)pyrrolidin-1-yl)acetamide |
| 203) | (S)-N-(3-(2-((1,5-dimethyl-1H-pyrazol-3-yl)amino)-5-methylpyrimidin-4-yl)-1H-indol-7-yl)-2-(3-((2-(ethylamino)pyrimidin-4-yl)oxy)pyrrolidin-1-yl)acetamide |
| 204) | (S)-N-(3-(2-((1,5-dimethyl-1H-pyrazol-3-yl)amino)-5-methylpyrimidin-4-yl)-1H-indol-7-yl)-2-(3-((2-(propylamino)pyrimidin-4-yl)oxy)pyrrolidin-1-yl)acetamide |
| 205) | (S)-2-(3-((2-(butylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 206) | (S)-N-(3-(2-((1,5-dimethyl-1H-pyrazol-3-yl)amino)-5-methylpyrimidin-4-yl)-1H-indol-7-yl)-2-(3-((2-((3-hydroxypropyl)amino)pyrimidin-4-yl)oxy)pyrrolidin-1-yl)acetamide |
| 207) | (S)-2-(3-((2-(cyclopropylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |

-continued

| | |
|---|---|
| 208) | (S)-2-(3-((2-(cyclobutylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 209) | (S)-2-(3-((2-(cyclopentylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 210) | (S)-2-(3-((2-(cyclohexylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 211) | (S)-N-(3-(2-((1,5-dimethyl-1H-pyrazol-3-yl)amino)-5-methylpyrimidin-4-yl)-1H-indol-7-yl)-2-(3-((2-(isopropylamino)pyrimidin-4-yl)oxy)pyrrolidin-1-yl)acetamide |
| 212) | 2-((3S)-3-((2-(sec-butylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 213) | (S)-2-(3-((2-((cyclopropylmethyl)amino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 214) | (S)-2-(3-((2-(benzylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 215) | (S)-N-(3-(2-((1,5-dimethyl-1H-pyrazol-3-yl)amino)-5-methylpyrimidin-4-yl)-1H-indol-7-yl)-2-(3-((2-((2-hydroxyethyl)amino)pyrimidin-4-yl)oxy)pyrrolidin-1-yl)acetamide |
| 216) | (S)-N-(3-(2-((1,5-dimethyl-1H-pyrazol-3-yl)amino)-5-methylpyrimidin-4-yl)-1H-indol-7-yl)-2-(3-((2-((2-methoxyethyl)amino)pyrimidin-4-yl)oxy)pyrrolidin-1-yl)acetamide |
| 217) | (S)-N-(3-(2-((1,5-dimethyl-1H-pyrazol-3-yl)amino)-5-methylpyrimidin-4-yl)-1H-indol-7-yl)-2-(3-((2-((2-(dimethylamino)ethyl)amino)pyrimidin-4-yl)oxy)pyrrolidin-1-yl)acetamide |
| 218) | (S)-N-(3-(2-((1,5-dimethyl-1H-pyrazol-3-yl)amino)-5-methylpyrimidin-4-yl)-1H-indol-7-yl)-2-(3-((2-((3-(dimethylamino)propyl)amino)pyrimidin-4-yl)oxy)pyrrolidin-1-yl)acetamide |
| 219) | (S)-N-(3-(2-((1,5-dimethyl-1H-pyrazol-3-yl)amino)-5-methylpyrimidin-4-yl)-1H-indol-7-yl)-2-(3-((2-(methoxyamino)pyrimidin-4-yl)oxy)pyrrolidin-1-yl)acetamide |
| 220) | (S)-N-(3-(2-((1,5-dimethyl-1H-pyrazol-3-yl)amino)-5-methylpyrimidin-4-yl)-1H-indol-7-yl)-2-(3-((2-(dimethylamino)pyrimidin-4-yl)oxy)pyrrolidin-1-yl)acetamide |
| 221) | (S)-2-(3-((2-(benzyl(methyl)amino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 222) | (S)-N-(3-(2-((1,5-dimethyl-1H-pyrazol-3-yl)amino)-5-methylpyrimidin-4-yl)-1H-indol-7-yl)-2-(3-((2-(pyrrolidin-1-yl)pyrimidin-4-yl)oxy)pyrrolidin-1-yl)acetamide |
| 223) | (S)-N-(3-(2-((1,5-dimethyl-1H-pyrazol-3-yl)amino)-5-methylpyrimidin-4-yl)-1H-indol-7-yl)-2-(3-((2-(piperidin-1-yl)pyrimidin-4-yl)oxy)pyrrolidin-1-yl)acetamide. |
| 224) | (S)-N-(3-(2-((1,5-dimethyl-1H-pyrazol-3-yl)amino)-5-methylpyrimidin-4-yl)-1H-indol-7-yl)-2-(3-((2-morpholinopyrimidin-4-yl)oxy)pyrrolidin-1-yl)acetamide |
| 225) | (S)-N-(3-(2-((1,5-dimethyl-1H-pyrazol-3-yl)amino)-5-methylpyrimidin-4-yl)-1H-indol-7-yl)-2-(3-((2-(4-methylpiperazin-1-yl)pyrimidin-4-yl)oxy)pyrrolidin-1-yl)acetamide |
| 226) | (S)-2-(3-((2-amino-5-fluoropyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 227) | (S)-2-(3-((2-(cyclopropylamino)-5-fluoropyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 228) | (S)-2-(3-((2-(cyclohexylamino)-5-fluoropyrimidin-4-yl)oxy)pyrrolidine-1-yl)-N-(3-(2-((1,5-dimethyl-1H-pyrazol-3-yl)amino)-5-methylpyrimidin-4-yl)-1H-indol-7-yl)acetamide |
| 229) | (S)-2-(3-((2-((cyclopropylmethyl)amino)-5-fluoropyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 230) | (S)-2-(3-((2-(benzylamino)-5-fluoropyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 231) | (S)-N-(3-(2-((1,5-dimethyl-1H-pyrazol-3-yl)amino)-5-methylpyrimidin-4-yl)-1H-indol-7-yl)-2-(3-((2-(dimethylamino)-5-fluoropyrimidin-4-yl)oxy)pyrrolidin-1-yl)acetamide |
| 232) | (S)-N-(3-(2-((1,5-dimethyl-1H-pyrazol-3-yl)amino)-5-methylpyrimidin-4-yl)-1H-indol-7-yl)-2-(3-((5-fluoro-2-morpholinopyrimidin-4-yl)oxy)pyrrolidin-1-yl)acetamide |

| | |
|---|---|
| 233) | (S)-N-(3-(2-((1,5-dimethyl-1HI-pyrazol-3-yl)amino)-5-methylpyrimidin-4-yl)-1H-indol-7-yl)-2-(3-((5-fluoro-2-(4-methylpiperazin-1-yl)pyrimidin-4-yl)oxy)pyrrolidin-1-yl)acetamide |
| 234) | (S)-2-(3-((2-(cyclopropylamino)-6-fluoropyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 235) | (S)-2-(3-((2-(cyclopropylamino)-5-methylpyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 236) | (S)-2-(3-((2-(cyclopropylamino)-6-methylpyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 237) | (S)-2-(3-((2-(cyclopropylamino)-6-(trifluoromethyl)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 238) | (S)-2-(3-((2-(cyclopropylamino)-6-methoxypyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 239) | (S)-N-(3-(2-((1,5-dimethyl-1H-pyrazol-3-yl)amino)-5-methylpyrimidin-4-yl)-1H-indol-7-yl)-2-(3-((2-((2-(dimethylamino)ethyl)amino)pyrimidin-5-yl)oxy)pyrrolidin-1-yl)acetamide |
| 240) | (S)-N-(3-(2-((1,5-dimethyl-1H-pyrazol-3-yl)amino)-5-methylpyrimidin-4-yl)-1H-indol-7-yl)-2-(3-((2-(dimethylamino)pyrimidin-5-yl)oxy)pyrrolidin-1-yl)acetamide |
| 241) | (S)-N-(3-(2-((1,5-dimethyl-1H-pyrazol-3-yl)amino)-5-methylpyrimidin-4-yl)-1H-indol-7-yl)-2-(3-((2-morpholinopyrimidin-5-yl)oxy)pyrrolidin-1-yl)acetamide |
| 242) | (S)-N-(3-(2-((1,5-dimethyl-1H-pyrazol-3-yl)amino)-5-methylpyrimidin-4-yl)-1H-indol-7-yl)-2-(3-((2-(4-methylpiperazin-1-yl)pyrimidin-5-yl)oxy)pyrrolidin-1-yl)acetamide |
| 243) | (S)-2-(3-((6-(cyclopropylamino)pyrazin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 244) | (S)-N-(3-(2-((1,5-dimethyl-1H-pyrazol-3-yl)amino)-5-methylpyrimidin-4-yl)-1H-indol-7-yl)-2-(3-((6-(ethylamino)pyrazin-2-yl)oxy)pyrrolidin-1-yl)acetamide |
| 245) | (S)-N-(3-(2-((1,5-dimethyl-1H-pyrazol-3-yl)amino)-5-methylpyrimidin-4-yl)-1H-indol-7-yl)-2-(3-((6-(propylamino)pyrazin-2-yl)oxy)pyrrolidin-1-yl)acetamide |
| 246) | (S)-N-(3-(2-((1,5-dimethyl-1H-pyrazol-3-yl)amino)-5-methylpyrimidin-4-yl)-1H-indol-7-yl)-2-(3-((6-((2-hydroxyethyl)amino)pyrazin-2-yl)oxy)pyrrolidin-1-yl)acetamide |
| 247) | (S)-N-(3-(2-((1,5-dimethyl-1H-pyrazol-3-yl)amino)-5-methylpyrimidin-4-yl)-1H-indol-7-yl)-2-(3-((6-((2-(dimethylamino)ethyl)amino)pyrazin-2-yl)oxy)pyrrolidin-1-yl)acetamide |
| 248) | (S)-N-(3-(2-((1,5-dimethyl-1H-pyrazol-3-yl)amino)-5-methylpyrimidin-4-yl)-1H-indol-7-yl)-2-(3-((6-phenylpyrimidin-4-yl)oxy)pyrrolidin-1-yl)acetamide |
| 249) | S)-N-(3-(2-((1,5-dimethyl-1H-pyrazol-3-yl)amino)-5-methylpyrimidin-4-yl)-1H-indol-7-yl)-2-(3-((6-(1-methyl-1H-pyrazol-4-yl)pyrimidin-4-yl)oxy)pyrrolidin-1-yl)acetamide |
| 250) | (S)-2-(3-((6-(3,6-dihydro-2H-pyran-4-yl)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 251) | (S)-2-(3-((6-(3,6-dihydro-2H-pyran-4-yl)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 252) | (S)-N-(3-(2-((1,5-dimethyl-1H-pyrazol-3-yl)amino)-5-methylpyrimidin-4-yl)-1H-indol-7-yl)-2-(3-((4-(4,4-dimethylcyclohex-1-en-1-yl)pyrimidin-2-yl)oxy)pyrrolidin-1-yl)acetamide |
| 253) | (S)-2-(3-((4-(3,6-dihydro-2H-pyran-4-yl)pyrimidin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 254) | (S)-N-(3-(2-((1,5-dimethyl-1H-pyrazol-3-yl)amino)-5-methylpyrimidin-4-yl)-1H-indol-7-yl)-2-(3-((4-phenylpyrimidin-2-yl)oxy)pyrrolidin-1-yl)acetamide |
| 255) | (S)-N-(3-(2-((1,5-dimethyl-1H-pyrazol-3-yl)amino)-5-methylpyrimidin-4-yl)-1H-indol-7-yl)-2-(3-((5-(pyridin-3-yl)pyrimidin-2-yl)oxy)pyrrolidin-1-yl)acetamide |
| 256) | (S)-N-(3-(2-((1,5-dimethyl-1H-pyrazol-3-yl)amino)-5-methylpyrimidin-4-yl)-1H-indol-7-yl)-2-(3-((5-(pyridin-4-yl)pyrimidin-2-yl)oxy)pyrrolidin-1-yl)acetamide |
| 257) | N-(3-(2-((1,5-dimethyl-1H-pyrazol-3-yl)amino)-5-methylpyrimidin-4-yl)-1H-indol-7-yl)-2-(3-((2-phenylpyrimidin-5-yl)oxy)pyrrolidin-1-yl)acetamide |
| 258) | (S)-N-(3-(2-((1,5-dimethyl-1H-pyrazol-3-yl)amino)-5-methylpyrimidin-4-yl)-1H-indol-7-yl)-2-(3-((2-(pyridin-3-yl)pyrimidin-5-yl)oxy)pyrrolidin-1-yl)acetamide |

| | |
|---|---|
| 259) | (S)-N-(3-(2-((1,5-dimethyl-1H-pyrazol-3-yl)amino)-5-methylpyrimidin-4-yl)-1H-indol-7-yl)-2-(3-((2-(pyridin-4-yl)pyrimidin-5-yl)oxy)pyrrolidin-1-yl)acetamide |
| 260) | 2-(3-(2-((1,5-dimethyl-1H-pyrazol-3-yl)amino)-5-methylpyrimidin-4-yl)-1H-indol-7-yl)isoindoline-1,3-dione |
| 261) | 2-(3-(2-((1,5-dimethyl-1H-pyrazol-3-yl)amino)-5-methylpyrimidin-4-yl)-1H-indol-7-yl)-4-fluoroisoindoline-1,3-dione |
| 262) | 4-bromo-2-(3-(2-((1,5-dimethyl-1H-pyrazol-3-yl)amino)-5-methylpyrimidin-4-yl)-1H-indol-7-yl)isoindoline-1,3-dione |
| 263) | 2-(3-(2-((1,5-dimethyl-1H-pyrazol-3-yl)amino)-5-methylpyrimidin-4-yl)-1H-indol-7-yl)-4-hydroxyisoindoline-1,3-dione |
| 264) | 2-(3-(2-((1,5-dimethyl-1H-pyrazol-3-yl)amino)-5-methylpyrimidin-4-yl)-1H-indol-7-yl)-5-nitroisoindoline-1,3-dione |
| 265) | 6-(3-(2-((1,5-dimethyl-1H-pyrazol-3-yl)amino)-5-methylpyrimidin-4-yl)-1H-indol-7-yl)-5H-pyrrolo[3,4-b]pyridine-5,7(6H)-dione |
| 266) | 4-bromo-2-(3-(2-((1,5-dimethyl-1H-pyrazol-3-yl)amino)-5-methylpyrimidin-4-yl)-1H-indol-7-yl)isoindolin-1-one |
| 267) | 2-(3-(2-((1,5-dimethyl-1H-pyrazol-3-yl)amino)-5-methylpyrimidin-4-yl)-1H-indol-7-yl)isoindolin-1-one |
| 268) | 2-(3-(2-((1,5-dimethyl-1H-pyrazol-3-yl)amino)-5-methylpyrimidin-4-yl)-1H-indol-7-yl)-6-nitroisoindolin-1-one |
| 269) | 6-amino-2-(3-(2-((1,5-dimethyl-1H-pyrazol-3-yl)amino)-5-methylpyrimidin-4-yl)-1H-indol-7-yl)isoindolin-1-one |
| 270) | 5-bromo-2-(3-(2-((1,5-dimethyl-1H-pyrazol-3-yl)amino)-5-methylpyrimidin-4-yl)-1H-indol-7-yl)isoindolin-1-one |
| 271) | 2-(3-(2-((1,5-dimethyl-1H-pyrazol-3-yl)amino)-5-methylpyrimidin-4-yl)-1H-indol-7-yl)-4-nitroisoindolin-1-one |
| 272) | 4-amino-2-(3-(2-((1,5-dimethyl-1H-pyrazol-3-yl)amino)-5-methylpyrimidin-4-yl)-1H-indol-7-yl)isoindolin-1-one |
| 273) | 7-chloro-2-(3-(2-((1,5-dimethyl-1H-pyrazol-3-yl)amino)-5-methylpyrimidin-4-yl)-1H-indol-7-yl)isoindolin-1-one |
| 274) | 2-(3-(2-((1,5-dimethyl-1H-pyrazol-3-yl)amino)-5-methylpyrimidin-4-yl)-1H-indol-7-yl)-7-nitroisoindolin-1-one |
| 275) | 2-(3-(2-((1,5-dimethyl-1H-pyrazol-3-yl)amino)-5-methylpyrimidin-4-yl)-1H-indol-7-yl)-7-iodoisoindolin-1-one |
| 276) | 7-amino-2-(3-(2-((1,5-dimethyl-1H-pyrazol-3-yl)amino)-5-methylpyrimidin-4-yl)-1H-indol-7-yl)isoindolin-1-one |
| 277) | 7-bromo-2-(3-(2-((1,5-dimethyl-1H-pyrazol-3-yl)amino)-5-methylpyrimidin-4-yl)-1H-indol-7-yl)isoindolin-1-one |
| 278) | 2-(3-(2-((1,5-dimethyl-1H-pyrazol-3-yl)amino)-5-methylpyrimidin-4-yl)-1H-indol-7-yl)-4-iodoisoindolin-1-one |
| 279) | 2-(3-(2-((1,5-dimethyl-1H-pyrazol-3-yl)amino)-5-methylpyrimidin-4-yl)-1H-indol-7-yl)-6-methoxyisoindolin-1-one |
| 280) | 2-(3-(2-((1,5-dimethyl-1H-pyrazol-3-yl)amino)-5-methylpyrimidin-4-yl)-1H-indol-7-yl)-4,6-dimethoxyisoindolin-1-one |
| 281) | 2-(3-(2-((1,5-dimethyl-1H-pyrazol-3-yl)amino)-5-methylpyrimidin-4-yl)-1H-indol-7-yl)-4-hydroxyisoindolin-1-one |
| 282) | 2-(3-(2-((1,5-dimethyl-1H-pyrazol-3-yl)amino)-5-methylpyrimidin-4-yl)-1H-indol-7-yl)-7-fluoroisoindolin-1-one |
| 283) | 4-bromo-2-(3-(2-((1,5-dimethyl-1H-pyrazol-3-yl)amino)-5-methylpyrimidin-4-yl)-1H-indol-7-yl)-7-fluoroisoindolin-1-one |
| 284) | 6-bromo-2-(3-(2-((1,5-dimethyl-1H-pyrazol-3-yl)amino)-5-methylpyrimidin-4-yl)-1H-indol-7-yl)isoindolin-1-one |
| 285) | 3-bromo-6-(3-(2-((1,5-dimethyl-1H-pyrazol-3-yl)amino)-5-methylpyrimidin-4-yl)-1H-indol-7-yl)-5,6-dihydro-7H-pyrrolo[3,4-b]pyridin-7-one |
| 286) | 4-bromo-6-(3-(2-((1,5-dimethyl-1H-pyrazol-3-yl)amino)-5-methylpyrimidin-4-yl)-1H-indol-7-yl)-5,6-dihydro-7H-pyrrolo[3,4-b]pyridin-7-one |
| 287) | 6-(3-(2-((1,5-dimethyl-1H-pyrazol-3-yl)amino)-5-methylpyrimidin-4-yl)-1H-indol-7-yl)-3-methyl-5,6-dihydro-7H-pyrrolo[3,4-b]pyridin-7-one |
| 288) | 6-(3-(2-((1,5-dimethyl-1H-pyrazol-3-yl)amino)-5-methylpyrimidin-4-yl)-1H-indol-7-yl)-5,6-dihydro-7H-pyrrolo[3,4-b]pyridin-7-one |
| 289) | 7-bromo-2-(3-(2-((1,5-dimethyl-1H-pyrazol-3-yl)amino)-5-methylpyrimidin-4-yl)-1H-indol-7-yl)-1,2-dihydro-3H-pyrrolo[3,4-c]pyridin-3-one |
| 290) | 4-bromo-2-(3-(2-((1,5-dimethyl-1H-pyrazol-3-yl)amino)-5-methylpyrimidin-4-yl)-1H-indol-7-yl)-2,3-dihydro-1H-pyrrolo[3,4-c]pyridin-1-one |
| 291) | N-(2-(3-(2-((1,5-dimethyl-1H-pyrazol-3-yl)amino)-5-methylpyrimidin-4-yl)-1H-indol-7-yl)-3-oxoisoindolin-5-yl)cyclopropanecarboxamide |
| 292) | N-(2-(3-(2-((1,5-dimethyl-1H-pyrazol-3-yl)amino)-5-methylpyrimidin-4-yl)-1H-indol-7-yl)-3-oxoisoindolin-4-yl)cyclohexanecarboxamide |
| 293) | N-(2-(3-(2-((1,5-dimethyl-1H-pyrazol-3-yl)amino)-5-methylpyrimidin-4-yl)-1H-indol-7-yl)-3-oxoisoindolin-4-yl)benzamide |
| 294) | N-(2-(3-(2-((1,5-dimethyl-1H-pyrazol-3-yl)amino)-5-methylpyrimidin-4-yl)-1H-indol-7-yl)-1-oxoisoindolin-4-yl)benzamide |

| | |
|---|---|
| 295) | N-(2-(3-(2-((1,5-dimethyl-1H-pyrazol-3-yl)amino)-5-methylpyrimidin-4-yl)-1H-indol-7-yl)-1-oxoisoindolin-4-yl)cyclohexanecarboxamide |
| 296) | N-(2-(3-(2-((1,5-dimethyl-1H-pyrazol-3-yl)amino)-5-methylpyrimidin-4-yl)-1H-indol-7-yl)-1-oxoisoindolin-4-yl)morpholine-4-carboxamide |
| 297) | N-(2-(3-(2-((1,5-dimethyl-1H-pyrazol-3-yl)amino)-5-methylpyrimidin-4-yl)-1H-indol-7-yl)-1-oxoisoindolin-4-yl)picolinamide |
| 298) | N-(2-(3-(2-((1,5-dimethyl-1H-pyrazol-3-yl)amino)-5-methylpyrimidin-4-yl)-1H-indol-7-yl)-1-oxoisoindolin-4-yl)nicotinamide |
| 299) | N-(2-(3-(2-((1,5-dimethyl-1H-pyrazol-3-yl)amino)-5-methylpyrimidin-4-yl)-1H-indol-7-yl)-1-oxoisoindolin-4-yl)oxazole-4-carboxamide |
| 300) | N-(2-(3-(2-((1,5-dimethyl-1H-pyrazol-3-yl)amino)-5-methylpyrimidin-4-yl)-1H-indol-7-yl)-1-oxoisoindolin-4-yl)cyclopropanecarboxamide |
| 301) | N-(2-(3-(2-((1,5-dimethyl-1H-pyrazol-3-yl)amino)-5-methylpyrimidin-4-yl)-1H-indol-7-yl)-1-oxoisoindolin-4-yl)isonicotinamide |
| 302) | N-(2-(3-(2-((1,5-dimethyl-1H-pyrazol-3-yl)amino)-5-methylpyrimidin-4-yl)-1H-indol-7-yl)-1-oxoisoindolin-4-yl)pyridazine-4-carboxamide |
| 303) | N-(2-(3-(2-((1,5-dimethyl-1H-pyrazol-3-yl)amino)-5-methylpyrimidin-4-yl)-1H-indol-7-yl)-1-oxoisoindolin-4-yl)-4-methylcyclohexane-1-carboxamide |
| 304) | N-(2-(3-(2-((1,5-dimethyl-1H-pyrazol-3-yl)amino)-5-methylpyrimidin-4-yl)-1H-indol-7-yl)-1-oxoisoindolin-4-yl)-2-(3-hydroxyphenyl)acetamide |
| 305) | N-(2-(3-(2-((1,5-dimethyl-1H-pyrazol-3-yl)amino)-5-methylpyrimidin-4-yl)-1H-indol-7-yl)-1-oxoisoindolin-4-yl)-2-phenylacetamide |
| 306) | N-(2-(3-(2-((1,5-dimethyl-1H-pyrazol-3-yl)amino)-5-methylpyrimidin-4-yl)-1H-indol-7-yl)-1-oxoisoindolin-4-yl)-1-methylpiperidine-4-carboxamide |
| 307) | N-(2-(3-(2-((1,5-dimethyl-1H-pyrazol-3-yl)amino)-5-methylpyrimidin-4-yl)-1H-indol-7-yl)-1-oxoisoindolin-4-yl)-1-methylpiperidine-3-carboxamide |
| 308) | N-(2-(3-(2-((1,5-dimethyl-1H-pyrazol-3-yl)amino)-5-methylpyrimidin-4-yl)-1H-indol-7-yl)-1-oxoisoindolin-4-yl)-5-oxopyrrolidine-2-carboxamide |
| 309) | N-(2-(3-(2-((1,5-dimethyl-1H-pyrazol-3-yl)amino)-5-methylpyrimidin-4-yl)-1H-indol-7-yl)-1-oxoisoindolin-4-yl)cyclohex-3-ene-1-carboxamide |
| 310) | N-(2-(3-(2-((1,5-dimethyl-1H-pyrazol-3-yl)amino)-5-methylpyrimidin-4-yl)-1H-indol-7-yl)-1-oxoisoindolin-4-yl)cyclopent-3-ene-1-carboxamide |
| 311) | N-(2-(3-(2-((1,5-dimethyl-1H-pyrazol-3-yl)amino)-5-methylpyrimidin-4-yl)-1H-indol-7-yl)-1-oxoisoindolin-4-yl)-1-methylcyclopent-3-ene-1-carboxamide |
| 312) | N-(2-(3-(2-((1,5-dimethyl-1H-pyrazol-3-yl)amino)-5-methylpyrimidin-4-yl)-1H-indol-7-yl)-1-oxoisoindolin-4-yl)cycloheptanecarboxamide |
| 313) | N-(2-(3-(2-((1,5-dimethyl-1H-pyrazol-3-yl)amino)-5-methylpyrimidin-4-yl)-1H-indol-7-yl)-1-oxoisoindolin-4-yl)-2-oxoimidazolidine-1-carboxamide |
| 314) | N-(2-(3-(2-((1,5-dimethyl-1H-pyrazol-3-yl)amino)-5-methylpyrimidin-4-yl)-1H-indol-7-yl)-1-oxoisoindolin-4-yl)-2,3-dihydro-1H-indene-2-carboxamide |
| 315) | (R)-N-(2-(3-(2-((1,5-dimethyl-1H-pyrazol-3-yl)amino)-5-methylpyrimidin-4-yl)-1H-indol-7-yl)-1-oxoisoindolin-4-yl)pyrrolidine-3-carboxamide |
| 316) | (S)-N-(2-(3-(2-((1,5-dimethyl-1H-pyrazol-3-yl)amino)-5-methylpyrimidin-4-yl)-1H-indol-7-yl)-1-oxoisoindolin-4-yl)pyrrolidine-3-carboxamide |
| 317) | (S)-N-(2-(3-(2-((1,5-dimethyl-1H-pyrazol-3-yl)amino)-5-methylpyrimidin-4-yl)-1H-indol-7-yl)-1-oxoisoindolin-4-yl)-5-oxopyrrolidine-2-carboxamide |
| 318) | (R)-N-(2-(3-(2-((1,5-dimethyl-1H-pyrazol-3-yl)amino)-5-methylpyrimidin-4-yl)-1H-indol-7-yl)-1-oxoisoindolin-4-yl)-5-oxopyrrolidine-2-carboxamide |
| 319) | N-(2-(3-(2-((1,5-dimethyl-1H-pyrazol-3-yl)amino)-5-methylpyrimidin-4-yl)-1H-indol-7-yl)-1-oxoisoindolin-4-yl)piperidine-3-carboxamide |
| 320) | N-(2-(3-(2-((1,5-dimethyl-1H-pyrazol-3-yl)amino)-5-methylpyrimidin-4-yl)-1H-indol-7-yl)-1-oxoisoindolin-4-yl)-4-oxocyclohexane-1-carboxamide |
| 321) | N-(2-(3-(2-((1,5-dimethyl-1H-pyrazol-3-yl)amino)-5-methylpyrimidin-4-yl)-1H-indol-7-yl)-1-oxoisoindolin-4-yl)-5-methylisoxazole-4-carboxamide |
| 322) | N-(2-(3-(2-((1,5-dimethyl-1H-pyrazol-3-yl)amino)-5-methylpyrimidin-4-yl)-1H-indol-7-yl)-1-oxoisoindolin-4-yl)-2-methyloxazole-4-carboxamide |
| 323) | N-(2-(3-(2-((1,5-dimethyl-1H-pyrazol-3-yl)amino)-5-methylpyrimidin-4-yl)-1H-indol-7-yl)-1-oxoisoindolin-4-yl)oxazole-5-carboxamide |
| 324) | N-(2-(3-(2-((1,5-dimethyl-1H-pyrazol-3-yl)amino)-5-methylpyrimidin-4-yl)-1H-indol-7-yl)-1-oxoisoindolin-4-yl)isoxazole-3-carboxamide |
| 325) | N-(2-(3-(2-((1,5-dimethyl-1H-pyrazol-3-yl)amino)-5-methylpyrimidin-4-yl)-1H-indol-7-yl)-1-oxoisoindolin-4-yl)-5-methylisoxazole-3-carboxamide |

| | |
|---|---|
| 326) | N-(2-(3-(2-((1,5-dimethyl-1H-pyrazol-3-yl)amino)-5-methylpyrimidin-4-yl)-1H-indol-7-yl)-1-oxoisoindolin-4-yl)tetrahydrofuran-3-carboxamide |
| 327) | N-(2-(3-(2-((1,5-dimethyl-1H-pyrazol-3-yl)amino)-5-methylpyrimidin-4-yl)-1H-indol-7-yl)-1-oxoisoindolin-4-yl)tetrahydro-2H-pyran-3-carboxamide |
| 328) | N-(2-(3-(2-((1,5-dimethyl-1H-pyrazol-3-yl)amino)-5-methylpyrimidin-4-yl)-1H-indol-7-yl)-1-oxoisoindolin-4-yl)-4-methyltetrahydro-2H-pyran-4-carboxamide |
| 329) | N-(2-(3-(2-((1,5-dimethyl-1H-pyrazol-3-yl)amino)-5-methylpyrimidin-4-yl)-1H-indol-7-yl)-1-oxoisoindolin-4-yl)-3-methylcyclohexane-1-carboxamide |
| 330) | N-(2-(3-(2-((1,5-dimethyl-1H-pyrazol-3-yl)amino)-5-methylpyrimidin-4-yl)-1H-indol-7-yl)-1-oxoisoindolin-4-yl)-4-methylcyclohex-3-ene-1-carboxamide |
| 331) | (2R,4S)-4-amino-N-(2-(3-(2-((1,5-dimethyl-1H-pyrazol-3-yl)amino)-5-methylpyrimidin-4-yl)-1H-indol-7-yl)-1-oxoisoindolin-4-yl)pyrrolidine-2-carboxamide |
| 332) | N-(2-(3-(2-((1,5-dimethyl-1H-pyrazol-3-yl)amino)-5-methylpyrimidin-4-yl)-1H-indol-7-yl)-1-oxoisoindolin-4-yl)-3-methylpiperidine-3-carboxamide |
| 333) | (R)-N-(2-(3-(2-((1,5-dimethyl-1H-pyrazol-3-yl)amino)-5-methylpyrimidin-4-yl)-1H-indol-7-yl)-1-oxoisoindolin-4-yl)-1-methylpyrrolidine-3-carboxamide |
| 334) | N-(2-(3-(2-((1,5-dimethyl-1H-pyrazol-3-yl)amino)-5-methylpyrimidin-4-yl)-1H-indol-7-yl)-1-oxoisoindolin-4-yl)-5-methylnicotinamide |
| 335) | N-(2-(3-(2-((1,5-dimethyl-1H-pyrazol-3-yl)amino)-5-methylpyrimidin-4-yl)-1H-indol-7-yl)-1-oxoisoindolin-4-yl)-2-(dimethylamino)acetamide |
| 336) | N-(2-(3-(2-((1,5-dimethyl-1H-pyrazol-3-yl)amino)-5-methylpyrimidin-4-yl)-1H-indol-7-yl)-1-oxoisoindolin-4-yl)cyclopentanecarboxamide |
| 337) | N-(2-(3-(2-((1,5-dimethyl-1H-pyrazol-3-yl)amino)-5-methylpyrimidin-4-yl)-1H-indol-7-yl)-1-oxoisoindolin-4-yl)tetrahydro-2H-pyran-4-carboxamide |
| 338) | N-(2-(3-(2-((1,5-dimethyl-1H-pyrazol-3-yl)amino)-5-methylpyrimidin-4-yl)-1H-indol-7-yl)-1-oxoisoindolin-4-yl)furan-3-carboxamide |
| 339) | N-(2-(3-(2-((1,5-dimethyl-1H-pyrazol-3-yl)amino)-5-methylpyrimidin-4-yl)-1H-indol-7-yl)-1-oxoisoindolin-4-yl)-6-hydroxypyrimidine-4-carboxamide |
| 340) | N-(2-(3-(2-((1,5-dimethyl-1H-pyrazol-3-yl)amino)-5-methylpyrimidin-4-yl)-1H-indol-7-yl)-3-oxoisoindolin-4-yl)benzenesulfonamide |
| 341) | N-(2-(3-(2-((1,5-dimethyl-1H-pyrazol-3-yl)amino)-5-methylpyrimidin-4-yl)-1H-indol-7-yl)-1-oxoisoindolin-4-yl)benzenesulfonamide |
| 342) | N-(2-(3-(2-((1,5-dimethyl-1H-pyrazol-3-yl)amino)-5-methylpyrimidin-4-yl)-1H-indol-7-yl)-1-oxoisoindolin-4-yl)methanesulfonamide |
| 343) | N-(2-(3-(2-((1,5-dimethyl-1H-pyrazol-3-yl)amino)-5-methylpyrimidin-4-yl)-1H-indol-7-yl)-1-oxoisoindolin-4-yl)-4-methylbenzenesulfonamide |
| 344) | N-(2-(3-(2-((1,5-dimethyl-1H-pyrazol-3-yl)amino)-5-methylpyrimidin-4-yl)-1H-indol-7-yl)-1-oxoisoindolin-4-yl)propane-2-sulfonamide |
| 345) | N-(2-(3-(2-((1,5-dimethyl-1H-pyrazol-3-yl)amino)-5-methylpyrimidin-4-yl)-1H-indol-7-yl)-1-oxoisoindolin-4-yl)-4-fluoro-3-methylbenzenesulfonamide |
| 346) | 2-(3-(2-((1,5-dimethyl-1H-pyrazol-3-yl)amino)-5-methylpyrimidin-4-yl)-1H-indol-7-yl)-7-(phenylamino)isoindolin-1-one |
| 347) | 2-(3-(2-((1,5-dimethyl-1H-pyrazol-3-yl)amino)-5-methylpyrimidin-4-yl)-1H-indol-7-yl)-7-morpholinoisoindolin-1-one |
| 348) | 2-(3-(2-((1,5-dimethyl-1H-pyrazol-3-yl)amino)-5-methylpyrimidin-4-yl)-1H-indol-7-yl)-7-(4-methylpiperazin-1-yl)isoindolin-1-one |
| 349) | 2-(3-(2-((1,5-dimethyl-1H-pyrazol-3-yl)amino)-5-methylpyrimidin-4-yl)-1H-indol-7-yl)-7-(dimethylamino)isoindolin-1-one |
| 350) | 7-(benzylamino)-2-(3-(2-((1,5-dimethyl-1H-pyrazol-3-yl)amino)-5-methylpyrimidin-4-yl)-1H-indol-7-yl)isoindolin-1-one |
| 351) | 7-((cyclopropylmethyl)amino)-2-(3-(2-((1,5-dimethyl-1H-pyrazol-3-yl)amino)-5-methylpyrimidin-4-yl)-1H-indol-7-yl)isoindolin-1-one |
| 352) | 2-(3-(2-((1,5-dimethyl-1H-pyrazol-3-yl)amino)-5-methylpyrimidin-4-yl)-1H-indol-7-yl)-4-morpholinoisoindolin-1-one |
| 353) | 4-((cyclopropylmethyl)amino)-2-(3-(2-((1,5-dimethyl-1H-pyrazol-3-yl)amino)-5-methylpyrimidin-4-yl)-1H-indol-7-yl)isoindolin-1-one |
| 354) | 4-(benzylamino)-2-(3-(2-((1,5-dimethyl-1H-pyrazol-3-yl)amino)-5-methylpyrimidin-4-yl)-1H-indol-7-yl)isoindolin-1-one |
| 355) | 2-(3-(2-((1,5-dimethyl-1H-pyrazol-3-yl)amino)-5-methylpyrimidin-4-yl)-1H-indol-7-yl)-7-(phenylamino)isoindolin-1-one |
| 356) | 2-(3-(2-((1,5-dimethyl-1H-pyrazol-3-yl)amino)-5-methylpyrimidin-4-yl)-1H-indol-7-yl)-4-(phenylethynyl)isoindolin-1-one |
| 357) | 4-((4-aminophenyl)ethynyl)-2-(3-(2-((1,5-dimethyl-1H-pyrazol-3-yl)amino)-5-methylpyrimidin-4-yl)-1H-indol-7-yl)isoindolin-1-one |
| 358) | (E)-3-(2-(3-(2-((1,5-dimethyl-1H-pyrazol-3-yl)amino)-5-methylpyrimidin-4-yl)-1H-indol-7-yl)-1-oxoisoindolin-4-yl)acrylamide |

| | |
|---|---|
| 359) | (E)-3-(2-(3-(2-((1,5-dimethyl-1HI-pyrazol-3-yl)amino)-5-methylpyrimidin-4-yl)-1H-indol-7-yl)-7-fluoro-1-oxoisoindolin-4-yl)-N,N-dimethylacrylamide |
| 360) | (E)-3-(2-(3-(2-((1,5-dimethyl-1H-pyrazol-3-yl)amino)-5-methylpyrimidin-4-yl)-1H-indol-7-yl)-1-oxoisoindolin-4-yl)-N,N-dimethylacrylamide |
| 361) | (E)-3-(2-(3-(2-((1,5-dimethyl-1H-pyrazol-3-yl)amino)-5-methylpyrimidin-4-yl)-1H-indol-7-yl)-1-oxoisoindolin-4-yl)-2-methylacrylamide |
| 362) | (E)-2-(3-(2-((1,5-dimethyl-1H-pyrazol-3-yl)amino)-5-methylpyrimidin-4-yl)-1H-indol-7-yl)-4-(3-oxobut-1-en-1-yl)isoindolin-1-one |
| 363) | (E)-3-(2-(3-(2-((1,5-dimethyl-1H-pyrazol-3-yl)amino)-5-methylpyrimidin-4-yl)-1H-indol-7-yl)-1-oxoisoindolin-4-yl)-N-methylacrylamide |
| 364) | (E)-3-(2-(3-(2-((1,5-dimethyl-1H-pyrazol-3-yl)amino)-5-methylpyrimidin-4-yl)-1H-indol-7-yl)-1-oxoisoindolin-4-yl)-N-ethylacrylamide |
| 365) | (E)-N-cyclopropyl-3-(2-(3-(2-((1,5-dimethyl-1H-pyrazol-3-yl)amino)-5-methylpyrimidin-4-yl)-1H-indol-7-yl)-1-oxoisoindolin-4-yl)acrylamide |
| 366) | (E)-3-(2-(3-(2-((1,5-dimethyl-1H-pyrazol-3-yl)amino)-5-methylpyrimidin-4-yl)-1H-indol-7-yl)-1-oxoisoindolin-4-yl)acrylohydrazide |
| 367) | (E)-3-(2-(3-(2-((1,5-dimethyl-1H-pyrazol-3-yl)amino)-5-methylpyrimidin-4-yl)-1H-indol-7-yl)-1-oxoisoindolin-4-yl)acrylic acid |
| 368) | (E)-3-(2-(3-(2-((1,5-dimethyl-1H-pyrazol-3-yl)amino)-5-methylpyrimidin-4-yl)-1H-indol-7-yl)-1-oxoisoindolin-4-yl)-N,N-diethylacrylamide |
| 369) | (E)-N,N-dibutyl-3-(2-(3-(2-((1,5-dimethyl-1H-pyrazol-3-yl)amino)-5-methylpyrimidin-4-yl)-1H-indol-7-yl)-1-oxoisoindolin-4-yl)acrylamide |
| 370) | (E)-3-(2-(3-(2-((1,5-dimethyl-1H-pyrazol-3-yl)amino)-5-methylpyrimidin-4-yl)-1H-indol-7-yl)-1-oxoisoindolin-4-yl)-N-isopropylacrylamide |
| 371) | (E)-N-(tert-butyl)-3-(2-(3-(2-((1,5-dimethyl-1H-pyrazol-3-yl)amino)-5-methylpyrimidin-4-yl)-1H-indol-7-yl)-1-oxoisoindolin-4-yl)acrylamide |
| 372) | (E)-3-(2-(3-(2-((1,5-dimethyl-1H-pyrazol-3-yl)amino)-5-methylpyrimidin-4-yl)-1H-indol-7-yl)-1-oxoisoindolin-4-yl)-N-(2-hydroxyethyl)acrylamide |
| 373) | (E)-3-(2-(3-(2-((1,5-dimethyl-1H-pyrazol-3-yl)amino)-5-methylpyrimidin-4-yl)-1H-indol-7-yl)-1-oxoisoindolin-4-yl)-N-propylacrylamide |
| 374) | (E)-3-(2-(3-(2-((1,5-dimethyl-1H-pyrazol-3-yl)amino)-5-methylpyrimidin-4-yl)-1H-indol-7-yl)-1-oxoisoindolin-4-yl)-N-(2-methoxyethyl)acrylamide |
| 375) | (E)-2-(3-(2-((1,5-dimethyl-1H-pyrazol-3-yl)amino)-5-methylpyrimidin-4-yl)-1H-indol-7-yl)-4-(3-hydroxyprop-1-en-1-yl)isoindolin-1-one |
| 376) | (E)-3-(2-(3-(2-((1,5-dimethyl-1H-pyrazol-3-yl)amino)-5-methylpyrimidin-4-yl)-1H-indol-7-yl)-1-oxoisoindolin-4-yl)-N-ethyl-2-methylacrylamide |
| 377) | 2-(3-(2-((1,5-dimethyl-1H-pyrazol-3-yl)amino)-5-methylpyrimidin-4-yl)-1H-indol-7-yl)-4-phenylisoindolin-1-one |
| 378) | 2-(3-(2-((1,5-dimethyl-1H-pyrazol-3-yl)amino)-5-methylpyrimidin-4-yl)-1H-indol-7-yl)-5-phenylisoindolin-1-one |
| 379) | 2-(3-(2-((1,5-dimethyl-1H-pyrazol-3-yl)amino)-5-methylpyrimidin-4-yl)-1H-indol-7-yl)-6-phenylisoindolin-1-one |
| 380) | 2-(3-(2-((1,5-dimethyl-1H-pyrazol-3-yl)amino)-5-methylpyrimidin-4-yl)-1H-indol-7-yl)-6-(pyridin-4-yl)isoindolin-1-one |
| 381) | 2-(3-(2-((1,5-dimethyl-1H-pyrazol-3-yl)amino)-5-methylpyrimidin-4-yl)-1H-indol-7-yl)-6-(1,2,3,6-tetrahydropyridin-4-yl)isoindolin-1-one |
| 382) | 2-(3-(2-((1,5-dimethyl-1H-pyrazol-3-yl)amino)-5-methylpyrimidin-4-yl)-1H-indol-7-yl)-7-phenylisoindolin-1-one |
| 383) | 2-(3-(2-((1,5-dimethyl-1H-pyrazol-3-yl)amino)-5-methylpyrimidin-4-yl)-1H-indol-7-yl)-7-(pyridin-4-yl)isoindolin-1-one |
| 384) | 7-(cyclohex-1-en-1-yl)-2-(3-(2-((1,5-dimethyl-1H-pyrazol-3-yl)amino)-5-methylpyrimidin-4-yl)-1H-indol-7-yl)isoindolin-1-one |
| 385) | 7-(3,6-dihydro-2H-pyran-4-yl)-2-(3-(2-((1,5-dimethyl-1H-pyrazol-3-yl)amino)-5-methylpyrimidin-4-yl)-1H-indol-7-yl)isoindolin-1-one |
| 386) | 2-(3-(2-((1,5-dimethyl-1H-pyrazol-3-yl)amino)-5-methylpyrimidin-4-yl)-1H-indol-7-yl)-7-(1H-pyrazol-4-yl)isoindolin-1-one |
| 387) | 2-(3-(2-((1,5-dimethyl-1H-pyrazol-3-yl)amino)-5-methylpyrimidin-4-yl)-1H-indol-7-yl)-4-(pyridin-4-yl)isoindolin-1-one |
| 388) | 2-(3-(2-((1,5-dimethyl-1H-pyrazol-3-yl)amino)-5-methylpyrimidin-4-yl)-1H-indol-7-yl)-4-(pyridin-3-yl)isoindolin-1-one |
| 389) | 2-(3-(2-((1,5-dimethyl-1H-pyrazol-3-yl)amino)-5-methylpyrimidin-4-yl)-1H-indol-7-yl)-4-(1-methyl-1H-pyrazol-4-yl)isoindolin-1-one |
| 390) | 2-(3-(2-((1,5-dimethyl-1H-pyrazol-3-yl)amino)-5-methylpyrimidin-4-yl)-1H-indol-7-yl)-4-(1H-pyrazol-4-yl)isoindolin-1-one |
| 391) | 4-(cyclohex-1-en-1-yl)-2-(3-(2-((1,5-dimethyl-1H-pyrazol-3-yl)amino)-5-methylpyrimidin-4-yl)-1H-indol-7-yl)isoindolin-1-one |

| | |
|---|---|
| 392) | 4-(3,6-dihydro-2H-pyran-4-yl)-2-(3-(2-((1,5-dimethyl-1H-pyrazol-3-yl)amino)-5-methylpyrimidin-4-yl)-1H-indol-7-yl)isoindolin-1-one |
| 393) | 2-(3-(2-((1,5-dimethyl-1H-pyrazol-3-yl)amino)-5-methylpyrimidin-4-yl)-1H-indol-7-yl)-4-(furan-3-yl)isoindolin-1-one |
| 394) | 2-(3-(2-((1,5-dimethyl-1H-pyrazol-3-yl)amino)-5-methylpyrimidin-4-yl)-1H-indol-7-yl)-4-(1,2,3,6-tetrahydropyridin-4-yl)isoindolin-1-one |
| 395) | 2-(3-(2-((1,5-dimethyl-1H-pyrazol-3-yl)amino)-5-methylpyrimidin-4-yl)-1H-indol-7-yl)-4-(4-(trifluoromethoxy)phenyl)isoindolin-1-one |
| 396) | 4-(4-aminophenyl)-2-(3-(2-((1,5-dimethyl-1H-pyrazol-3-yl)amino)-5-methylpyrimidin-4-yl)-1H-indol-7-yl)isoindolin-1-one |
| 397) | tert-butyl 4-(2-(3-(2-((1,5-dimethyl-1H-pyrazol-3-yl)amino)-5-methylpyrimidin-4-yl)-1H-indol-7-yl)-1-oxoisoindolin-4-yl)-3,6-dihydropyridine-1(2H)-carboxylate |
| 398) | tert-butyl (4-(2-(3-(2-((1,5-dimethyl-1H-pyrazol-3-yl)amino)-5-methylpyrimidin-4-yl)-1H-indol-7-yl)-1-oxoisoindolin-4-yl)phenyl)carbamate |
| 399) | 4-(2-aminopyridin-4-yl)-2-(3-(2-((1,5-dimethyl-1H-pyrazol-3-yl)amino)-5-methylpyrimidin-4-yl)-1H-indol-7-yl)isoindolin-1-one |
| 400) | 2-(3-(2-((1,5-dimethyl-1H-pyrazol-3-yl)amino)-5-methylpyrimidin-4-yl)-1H-indol-7-yl)-4-(3-fluoropyridin-4-yl)isoindolin-1-one |
| 401) | 2-(3-(2-((1,5-dimethyl-1H-pyrazol-3-yl)amino)-5-methylpyrimidin-4-yl)-1H-indol-7-yl)-4-(6-hydroxypyridin-3-yl)isoindolin-1-one |
| 402) | 4-(2-chloropyridin-4-yl)-2-(3-(2-((1,5-dimethyl-1H-pyrazol-3-yl)amino)-5-methylpyrimidin-4-yl)-1H-indol-7-yl)isoindolin-1-one |
| 403) | 2-(3-(2-((1,5-dimethyl-1H-pyrazol-3-yl)amino)-5-methylpyrimidin-4-yl)-1H-indol-7-yl)-4-(5-fluoro-2-methoxypyridin-4-yl)isoindolin-1-one |
| 404) | 2-(3-(2-((1,5-dimethyl-1H-pyrazol-3-yl)amino)-5-methylpyrimidin-4-yl)-1H-indol-7-yl)-4-(2-fluoropyridin-4-yl)isoindolin-1-one |
| 405) | 4-(6-chloropyridin-3-yl)-2-(3-(2-((1,5-dimethyl-1H-pyrazol-3-yl)amino)-5-methylpyrimidin-4-yl)-1H-indol-7-yl)isoindolin-1-one |
| 406) | 2-(3-(2-((1,5-dimethyl-1H-pyrazol-3-yl)amino)-5-methylpyrimidin-4-yl)-1H-indol-7-yl)-4-(6-methoxypyridin-3-yl)isoindolin-1-one |
| 407) | 2-(3-(2-((1,5-dimethyl-1H-pyrazol-3-yl)amino)-5-methylpyrimidin-4-yl)-1H-indol-7-yl)-4-(6-fluoro-5-methylpyridin-3-yl)isoindolin-1-one |
| 408) | 2-(3-(2-((1,5-dimethyl-1H-pyrazol-3-yl)amino)-5-methylpyrimidin-4-yl)-1H-indol-7-yl)-4-(2-(piperazin-1-yl)pyridin-4-yl)isoindolin-1-one |
| 409) | 2-(3-(2-((1,5-dimethyl-1H-pyrazol-3-yl)amino)-5-methylpyrimidin-4-yl)-1H-indol-7-yl)-4-(4-(pyrrolidin-1-ylsulfonyl)phenyl)isoindolin-1-one |
| 410) | (E)-2-(3-(2-((1,5-dimethyl-1H-pyrazol-3-yl)amino)-5-methylpyrimidin-4-yl)-1H-indol-7-yl)-4-(3-fluorostyryl)isoindolin-1-one |
| 411) | 2-(3-(2-((1,5-dimethyl-1H-pyrazol-3-yl)amino)-5-methylpyrimidin-4-yl)-1H-indol-7-yl)-4-(1H-pyrrolo[2,3-b]pyridin-4-yl)isoindolin-1-one |
| 412) | 2-(3-(2-((1,5-dimethyl-1H-pyrazol-3-yl)amino)-5-methylpyrimidin-4-yl)-1H-indol-7-yl)-4-(4-(4-oxopiperidine-1-carbonyl)phenyl)isoindolin-1-one |
| 413) | 4-(3,6-dihydro-2H-thiopyran-4-yl)-2-(3-(2-((1,5-dimethyl-1H-pyrazol-3-yl)amino)-5-methylpyrimidin-4-yl)-1H-indol-7-yl)isoindolin-1-one |
| 414) | 2-(3-(2-((1,5-dimethyl-1H-pyrazol-3-yl)amino)-5-methylpyrimidin-4-yl)-1H-indol-7-yl)-4-(2-(dimethylamino)pyrimidin-5-yl)isoindolin-1-one |
| 415) | 4-(1-(cyclopropylmethyl)-1H-pyrazol-4-yl)-2-(3-(2-((1,5-dimethyl-1H-pyrazol-3-yl)amino)-5-methylpyrimidin-4-yl)-1H-indol-7-yl)isoindolin-1-one |
| 416) | 2-(3-(2-((1,5-dimethyl-1H-pyrazol-3-yl)amino)-5-methylpyrimidin-4-yl)-1H-indol-7-yl)-4-(1-(2-morpholinoethyl)-1H-pyrazol-4-yl)isoindolin-1-one |
| 417) | 2-(3-(2-((1,5-dimethyl-1H-pyrazol-3-yl)amino)-5-methylpyrimidin-4-yl)-1H-indol-7-yl)-4-(pyrimidin-5-yl)isoindolin-1-one |
| 418) | 4-(2-aminopyrimidin-5-yl)-2-(3-(2-((1,5-dimethyl-1H-pyrazol-3-yl)amino)-5-methylpyrimidin-4-yl)-1H-indol-7-yl)isoindolin-1-one |
| 419) | 4-(5-aminopyridin-3-yl)-2-(3-(2-((1,5-dimethyl-1H-pyrazol-3-yl)amino)-5-methylpyrimidin-4-yl)-1H-indol-7-yl)isoindolin-1-one |
| 420) | 4-(6-aminopyridin-3-yl)-2-(3-(2-((1,5-dimethyl-1H-pyrazol-3-yl)amino)-5-methylpyrimidin-4-yl)-1H-indol-7-yl)isoindolin-1-one |
| 421) | 2-(3-(2-((1,5-dimethyl-1H-pyrazol-3-yl)amino)-5-methylpyrimidin-4-yl)-1H-indol-7-yl)-4-(pyrimidin-4-yl)isoindolin-1-one |
| 422) | 4-(2-aminopyrimidin-4-yl)-2-(3-(2-((1,5-dimethyl-1H-pyrazol-3-yl)amino)-5-methylpyrimidin-4-yl)-1H-indol-7-yl)isoindolin-1-one |
| 423) | 2-(3-(2-((1,5-dimethyl-1H-pyrazol-3-yl)amino)-5-methylpyrimidin-4-yl)-1H-indol-7-yl)-4-(4-(4-methylpiperazin-1-yl)pyridin-2-yl)isoindolin-1-one |
| 424) | 2-(3-(2-((1,5-dimethyl-1H-pyrazol-3-yl)amino)-5-methylpyrimidin-4-yl)-1H-indol-7-yl)-4-(2-(piperazin-1-yl)pyrimidin-5-yl)isoindolin-1-one |
| 425) | 2-(3-(2-((1,5-dimethyl-1H-pyrazol-3-yl)amino)-5-methylpyrimidin-4-yl)-1H-indol-7-yl)-4-(6-morpholinopyridin-3-yl)isoindolin-1-one |
| 426) | 2-(3-(2-((1,5-dimethyl-1H-pyrazol-3-yl)amino)-5-methylpyrimidin-4-yl)-1H-indol-7-yl)-4-(4-(4-methylpiperazin-1-yl)phenyl)isoindolin-1-one |
| 427) | 4-(2,6-difluoropyridin-4-yl)-2-(3-(2-((1,5-dimethyl-1H-pyrazol-3-yl)amino)-5-methylpyrimidin-4-yl)-1H-indol-7-yl)isoindolin-1-one |

| | |
|---|---|
| 428) | 4-(3,5-difluoropyridin-4-yl)-2-(3-(2-((1,5-dimethyl-1H-pyrazol-3-yl)amino)-5-methylpyrimidin-4-yl)-1H-indol-7-yl)isoindolin-1-one |
| 429) | 2-(3-(2-((1,5-dimethyl-1H-pyrazol-3-yl)amino)-5-methylpyrimidin-4-yl)-1H-indol-7-yl)-4-(2-methylpyridin-4-yl)isoindolin-1-one |
| 430) | 2-(3-(2-((1,5-dimethyl-1H-pyrazol-3-yl)amino)-5-methylpyrimidin-4-yl)-1H-indol-7-yl)-[4,5'-biisoindolin]-1-one |
| 431) | 2-(3-(2-((1,5-dimethyl-1H-pyrazol-3-yl)amino)-5-methylpyrimidin-4-yl)-1H-indol-7-yl)-4-(2-fluoropyridin-3-yl)isoindolin-1-one |
| 432) | 4-(2-(3-(2-((1,5-dimethyl-1H-pyrazol-3-yl)amino)-5-methylpyrimidin-4-yl)-1H-indol-7-yl)-1-oxoisoindolin-4-yl)benzonitrile |
| 433) | 4-(2-(3-(2-((1,5-dimethyl-1H-pyrazol-3-yl)amino)-5-methylpyrimidin-4-yl)-1H-indol-7-yl)-1-oxoisoindolin-4-yl)-3-fluorobenzonitrile |
| 434) | 2-(3-(2-((1,5-dimethyl-1H-pyrazol-3-yl)amino)-5-methylpyrimidin-4-yl)-1H-indol-7-yl)-4-(2-(trifluoromethyl)phenyl)isoindolin-1-one |
| 435) | 2-(3-(2-((1,5-dimethyl-1H-pyrazol-3-yl)amino)-5-methylpyrimidin-4-yl)-1H-indol-7-yl)-4-(2-methoxypyridin-3-yl)isoindolin-1-one |
| 436) | 2-(3-(2-((1,5-dimethyl-1H-pyrazol-3-yl)amino)-5-methylpyrimidin-4-yl)-1H-indol-7-yl)-4-(4-(dimethylamino)phenyl)isoindolin-1-one |
| 437) | 2-(3-(2-((1,5-dimethyl-1H-pyrazol-3-yl)amino)-5-methylpyrimidin-4-yl)-1H-indol-7-yl)-4-(2-(hydroxymethyl)phenyl)isoindolin-1-one |
| 438) | 2-(3-(2-((1,5-dimethyl-1H-pyrazol-3-yl)amino)-5-methylpyrimidin-4-yl)-1H-indol-7-yl)-4-(2-methoxyphenyl)isoindolin-1-one |
| 439) | 4-([1,1'-biphenyl]-2-yl)-2-(3-(2-((1,5-dimethyl-1H-pyrazol-3-yl)amino)-5-methylpyrimidin-4-yl)-1H-indol-7-yl)isoindolin-1-one |
| 440) | 2-(3-(2-((1,5-dimethyl-1H-pyrazol-3-yl)amino)-5-methylpyrimidin-4-yl)-1H-indol-7-yl)-4-(o-tolyl)isoindolin-1-one |
| 441) | 2-(3-(2-((1,5-dimethyl-1H-pyrazol-3-yl)amino)-5-methylpyrimidin-4-yl)-1H-indol-7-yl)-4-(2-hydroxyphenyl)isoindolin-1-one |
| 442) | 2-(3-(2-((1,5-dimethyl-1H-pyrazol-3-yl)amino)-5-methylpyrimidin-4-yl)-1H-indol-7-yl)-4-(1H-pyrrol-2-yl)isoindolin-1-one |
| 443) | tert-butyl 2-(2-(3-(2-((1,5-dimethyl-1H-pyrazol-3-yl)amino)-5-methylpyrimidin-4-yl)-1H-indol-7-yl)-1-oxoisoindolin-4-yl)-1H-pyrrole-1-carboxylate |
| 444) | 2-(3-(2-((1,5-dimethyl-1H-pyrazol-3-yl)amino)-5-methylpyrimidin-4-yl)-1H-indol-7-yl)-4-(3,5-dimethylisoxazol-4-yl)isoindolin-1-one |
| 445) | 2-(3-(2-((1,5-dimethyl-1H-pyrazol-3-yl)amino)-5-methylpyrimidin-4-yl)-1H-indol-7-yl)-4-(2-methoxypyridin-4-yl)isoindolin-1-one |
| 446) | 2-(3-(2-((1,5-dimethyl-1H-pyrazol-3-yl)amino)-5-methylpyrimidin-4-yl)-1H-indol-7-yl)-4-(2-hydroxypyridin-4-yl)isoindolin-1-one |
| 447) | 4-(3-aminopyridin-4-yl)-2-(3-(2-((1,5-dimethyl-1H-pyrazol-3-yl)amino)-5-methylpyrimidin-4-yl)-1H-indol-7-yl)isoindolin-1-one |
| 448) | 2-(3-(2-((1,5-dimethyl-1H-pyrazol-3-yl)amino)-5-methylpyrimidin-4-yl)-1H-indol-7-yl)-4-(isoquinolin-7-yl)isoindolin-1-one |
| 449) | 2-(3-(2-((1,5-dimethyl-1H-pyrazol-3-yl)amino)-5-methylpyrimidin-4-yl)-1H-indol-7-yl)-4-(1-methyl-1H-indazol-5-yl)isoindolin-1-one |
| 450) | 2-(3-(2-((1,5-dimethyl-1H-pyrazol-3-yl)amino)-5-methylpyrimidin-4-yl)-1H-indol-7-yl)-4-(1-methyl-1H-indazol-6-yl)isoindolin-1-one |
| 451) | 2-(3-(2-((1,5-dimethyl-1H-pyrazol-3-yl)amino)-5-methylpyrimidin-4-yl)-1H-indol-7-yl)-4-(5-methylthiophen-2-yl)isoindolin-1-one |
| 452) | 4-(2,3-dihydro-1H-inden-5-yl)-2-(3-(2-((1,5-dimethyl-1H-pyrazol-3-yl)amino)-5-methylpyrimidin-4-yl)-1H-indol-7-yl)isoindolin-1-one |
| 453) | 2-(3-(2-((1,5-dimethyl-1H-pyrazol-3-yl)amino)-5-methylpyrimidin-4-yl)-1H-indol-7-yl)-4-(4-methylthiophen-3-yl)isoindolin-1-one |
| 454) | 2-(3-(2-((1,5-dimethyl-1H-pyrazol-3-yl)amino)-5-methylpyrimidin-4-yl)-1H-indol-7-yl)-7-fluoro-4-(2-methylpyridin-4-yl)isoindolin-1-one |
| 455) | 2-(3-(2-((1,5-dimethyl-1H-pyrazol-3-yl)amino)-5-methylpyrimidin-4-yl)-1H-indol-7-yl)-4-(3-methylpyridin-4-yl)isoindolin-1-one |
| 456) | 4-(6-aminopyrimidin-4-yl)-2-(3-(2-((1,5-dimethyl-1H-pyrazol-3-yl)amino)-5-methylpyrimidin-4-yl)-1H-indol-7-yl)isoindolin-1-one |
| 457) | 2-(3-(2-((1,5-dimethyl-1H-pyrazol-3-yl)amino)-5-methylpyrimidin-4-yl)-1H-indol-7-yl)-4-(1H-indazol-4-yl)isoindolin-1-one |
| 458) | 2-(2-(3-(2-((1,5-dimethyl-1H-pyrazol-3-yl)amino)-5-methylpyrimidin-4-yl)-1H-indol-7-yl)-1-oxoisoindolin-4-yl)benzoic acid |
| 459) | 2-(3-(2-((1,5-dimethyl-1H-pyrazol-3-yl)amino)-5-methylpyrimidin-4-yl)-1H-indol-7-yl)-4-(2-(hydroxymethyl)phenyl)isoindolin-1-one |
| 460) | 2-(3-(2-((1,5-dimethyl-1H-pyrazol-3-yl)amino)-5-methylpyrimidin-4-yl)-1H-indol-7-yl)-4-(4-(hydroxymethyl)phenyl)isoindolin-1-one |
| 461) | 2-(3-(2-((1,5-dimethyl-1H-pyrazol-3-yl)amino)-5-methylpyrimidin-4-yl)-1H-indol-7-yl)-4-(thiophen-3-yl)isoindolin-1-one |
| 462) | 4-(2-aminophenyl)-2-(3-(2-((1,5-dimethyl-1H-pyrazol-3-yl)amino)-5-methylpyrimidin-4-yl)-1H-indol-7-yl)isoindolin-1-one |
| 463) | methyl 2-(2-(3-(2-((1,5-dimethyl-1H-pyrazol-3-yl)amino)-5-methylpyrimidin-4-yl)-1H-indol-7-yl)-1-oxoisoindolin-4-yl)benzoate |
| 464) | 2-(3-(2-((1,5-dimethyl-1H-pyrazol-3-yl)amino)-5-methylpyrimidin-4-yl)-1H-indol-7-yl)-4-(1-methyl-1,2,3,6-tetrahydropyridin-4-yl)isoindolin-1-one |
| 465) | 2-(3-(2-((1,5-dimethyl-1H-pyrazol-3-yl)amino)-5-methylpyrimidin-4-yl)-1H-indol-7-yl)-4-(1-(methylsulfonyl)-1,2,3,6-tetrahydropyridin-4-yl)isoindolin-1-one |

-continued

| | |
|---|---|
| 466) | 4-(1-acetyl-1,2,3,6-tetrahydropyridin-4-yl)-2-(3-(2-((1,5-dimethyl-1H-pyrazol-3-yl)amino)-5-methylpyrimidin-4-yl)-1H-indol-7-yl)isoindolin-1-one |
| 467) | 4-(2-(3-(2-((1,5-dimethyl-1H-pyrazol-3-yl)amino)-5-methylpyrimidin-4-yl)-1H-indol-7-yl)-1-oxoisoindolin-4-yl)-3,6-dihydropyridine-1(2H)-carboxamide |
| 468) | 2-(3-(2-((1,5-dimethyl-1H-pyrazol-3-yl)amino)-5-methylpyrimidin-4-yl)-1H-indol-7-yl)-4-(1,1-dioxido-3,6-dihydro-2H-thiopyran-4-yl)isoindolin-1-one |
| 469) | 4-(2-(3-(2-((1,5-dimethyl-1H-pyrazol-3-yl)amino)-5-methylpyrimidin-4-yl)-1H-indol-7-yl)-1-oxoisoindolin-4-yl)picolinonitrile |
| 470) | 5-(2-(3-(2-((1,5-dimethyl-1H-pyrazol-3-yl)amino)-5-methylpyrimidin-4-yl)-1H-indol-7-yl)-1-oxoisoindolin-4-yl)picolinonitrile |
| 471) | 2-(3-(2-((1,5-dimethyl-1H-pyrazol-3-yl)amino)-5-methylpyrimidin-4-yl)-1H-indol-7-yl)-4-(3-(hydroxymethyl)pyridin-4-yl)isoindolin-1-one |
| 472) | 2-(3-(2-((1,5-dimethyl-1H-pyrazol-3-yl)amino)-5-methylpyrimidin-4-yl)-1H-indol-7-yl)-4-(2-(hydroxymethyl)pyridin-4-yl)isoindolin-1-one |
| 473) | 4-(2-(3-(2-((1,5-dimethyl-1H-pyrazol-3-yl)amino)-5-methylpyrimidin-4-yl)-1H-indol-7-yl)-1-oxoisoindolin-4-yl)picolinamide |
| 474) | 5-(2-(3-(2-((1,5-dimethyl-1H-pyrazol-3-yl)amino)-5-methylpyrimidin-4-yl)-1H-indol-7-yl)-1-oxoisoindolin-4-yl)picolinamide |
| 475) | 2-(3-(2-((1,5-dimethyl-1H-pyrazol-3-yl)amino)-5-methylpyrimidin-4-yl)-1H-indol-7-yl)-4-(2-(dimethylamino)pyridin-4-yl)isoindolin-1-one |
| 476) | 2-(3-(2-((1,5-dimethyl-1H-pyrazol-3-yl)amino)-5-methylpyrimidin-4-yl)-1H-indol-7-yl)-4-(2-(methylamino)pyridin-4-yl)isoindolin-1-one |
| 477) | 2-(3-(2-((1,5-dimethyl-1H-pyrazol-3-yl)amino)-5-methylpyrimidin-4-yl)-1H-indol-7-yl)-4-(5-methylpyridin-3-yl)isoindolin-1-one |
| 478) | 2-(3-(2-((1,5-dimethyl-1H-pyrazol-3-yl)amino)-5-methylpyrimidin-4-yl)-1H-indol-7-yl)-4-(5-fluoropyridin-3-yl)isoindolin-1-one |
| 479) | 2-(3-(2-((1,5-dimethyl-1H-pyrazol-3-yl)amino)-5-methylpyrimidin-4-yl)-1H-indol-7-yl)-4-(2,6-dimethylpyridin-4-yl)isoindolin-1-one |
| 480) | 2-(3-(2-((1,5-dimethyl-1H-pyrazol-3-yl)amino)-5-methylpyrimidin-4-yl)-1H-indol-7-yl)-7-fluoro-4-(pyridin-4-yl)isoindolin-1-one |
| 481) | 2-(3-(2-((1,5-dimethyl-1H-pyrazol-3-yl)amino)-5-methylpyrimidin-4-yl)-1H-indol-7-yl)-7-fluoro-4-(2-methoxypyridin-4-yl)isoindolin-1-one |
| 482) | 2-(3-(2-((1,5-dimethyl-1H-pyrazol-3-yl)amino)-5-methylpyrimidin-4-yl)-1H-indol-7-yl)-7-fluoro-4-(2-(methylamino)pyridin-4-yl)isoindolin-1-one |
| 483) | 2-(3-(2-((1,5-dimethyl-1H-pyrazol-3-yl)amino)-5-methylpyrimidin-4-yl)-1H-indol-7-yl)-4-(2-(dimethylamino)pyridin-4-yl)-7-fluoroisoindolin-1-one |
| 484) | 2-(3-(2-((1,5-dimethyl-1H-pyrazol-3-yl)amino)-5-methylpyrimidin-4-yl)-1H-indol-7-yl)-7-fluoro-4-(5-fluoropyridin-3-yl)isoindolin-1-one |
| 485) | 2-(3-(2-((1,5-dimethyl-1H-pyrazol-3-yl)amino)-5-methylpyrimidin-4-yl)-1H-indol-7-yl)-7-fluoro-4-(2-fluoropyridin-4-yl)isoindolin-1-one |
| 486) | 2-(3-(2-((1,5-dimethyl-1H-pyrazol-3-yl)amino)-5-methylpyrimidin-4-yl)-1H-indol-7-yl)-7-fluoro-4-(5-methylpyridin-3-yl)isoindolin-1-one |
| 487) | 2-(3-(2-((1,5-dimethyl-1H-pyrazol-3-yl)amino)-5-methylpyrimidin-4-yl)-1H-indol-7-yl)-7-fluoro-4-(3-methylpyridin-4-yl)isoindolin-1-one |
| 488) | 2-(3-(2-((1,5-dimethyl-1H-pyrazol-3-yl)amino)-5-methylpyrimidin-4-yl)-1H-indol-7-yl)-4-(2,6-dimethylpyridin-4-yl)-7-fluoroisoindolin-1-one |
| 489) | 2-(3-(2-((1,5-dimethyl-1H-pyrazol-3-yl)amino)-5-methylpyrimidin-4-yl)-1H-indol-7-yl)-7-nitro-4-(pyridin-4-yl)isoindolin-1-one |
| 490) | 2-(3-(2-((1,5-dimethyl-1H-pyrazol-3-yl)amino)-5-methylpyrimidin-4-yl)-1H-indol-7-yl)-7-(dimethylamino)-4-(pyridin-4-yl)isoindolin-1-one |
| 491) | 2-(3-(2-((1,5-dimethyl-1H-pyrazol-3-yl)amino)-5-methylpyrimidin-4-yl)-1H-indol-7-yl)-7-(methylamino)-4-(pyridin-4-yl)isoindolin-1-one |
| 492) | 2-(3-(2-((1,5-dimethyl-1H-pyrazol-3-yl)amino)-5-methylpyrimidin-4-yl)-1H-indol-7-yl)-7-iodo-4-phenylisoindolin-1-one |
| 493) | 6-(3-(2-((1,5-dimethyl-1H-pyrazol-3-yl)amino)-5-methylpyrimidin-4-yl)-1H-indol-7-yl)-4-phenyl-5,6-dihydro-7H-pyrrolo[3,4-b]pyridin-7-one |
| 494) | 6-(3-(2-((1,5-dimethyl-1H-pyrazol-3-yl)amino)-5-methylpyrimidin-4-yl)-1H-indol-7-yl)-4-(pyridin-4-yl)-5,6-dihydro-7H-pyrrolo[3,4-b]pyridin-7-one |
| 495) | 6-(3-(2-((1,5-dimethyl-1H-pyrazol-3-yl)amino)-5-methylpyrimidin-4-yl)-1H-indol-7-yl)-4-(pyridin-3-yl)-5,6-dihydro-7H-pyrrolo[3,4-b]pyridin-7-one |
| 496) | 6-(3-(2-((1,5-dimethyl-1H-pyrazol-3-yl)amino)-5-methylpyrimidin-4-yl)-1H-indol-7-yl)-4-(1,2,3,6-tetrahydropyridin-4-yl)-5,6-dihydro-7H-pyrrolo[3,4-b]pyridin-7-one |
| 497) | 6-(3-(2-((1,5-dimethyl-1H-pyrazol-3-yl)amino)-5-methylpyrimidin-4-yl)-1H-indol-7-yl)-3-(pyridin-4-yl)-5,6-dihydro-7H-pyrrolo[3,4-b]pyridin-7-one |
| 498) | 6-(3-(2-((1,5-dimethyl-1H-pyrazol-3-yl)amino)-5-methylpyrimidin-4-yl)-1H-indol-7-yl)-3-(1,2,3,6-tetrahydropyridin-4-yl)-5,6-dihydro-7H-pyrrolo[3,4-b]pyridin-7-one |

| | |
|---|---|
| 499) | 2-(3-(2-((1,5-dimethyl-1H-pyrazol-3-yl)amino)-5-methylpyrimidin-4-yl)-1H-indol-7-yl)-7-(1,2,3,6-tetrahydropyridin-4-yl)-1,2-dihydro-3H-pyrrolo[3,4-c]pyridin-3-one |
| 500) | 2-(3-(2-((1,5-dimethyl-1H-pyrazol-3-yl)amino)-5-methylpyrimidin-4-yl)-1H-indol-7-yl)-7-(pyridin-4-yl)-1,2-dihydro-3H-pyrrolo [3,4-c]pyridin-3-one |
| 501) | 2-(3-(2-((1,5-dimethyl-1H-pyrazol-3-yl)amino)-5-methylpyrimidin-4-yl)-1H-indol-7-yl)-4-(pyridin-4-yl)-2,3-dihydro-1H-pyrrolo[3,4-c]pyridin-1-one |
| 502) | 2-(3-(2-((1,5-dimethyl-1H-pyrazol-3-yl)amino)-5-methylpyrimidin-4-yl)-1H-indol-7-yl)-4-(2-methylpyridin-4-yl)-2,3-dihydro-1H-pyrrolo[3,4-c]pyridin-1-one |
| 503) | 2-(3-(2-((1,5-dimethyl-1H-pyrazol-3-yl)amino)-5-methylpyrimidin-4-yl)-1H-indol-7-yl)-4-(5-fluoropyridin-3-yl)-2,3-dihydro-1H-pyrrolo[3,4-c]pyridin-1-one |
| 504) | 2-(3-(2-((1,5-dimethyl-1H-pyrazol-3-yl)amino)-5-methylpyrimidin-4-yl)-1H-indol-7-yl)-4-(2-fluoropyridin-4-yl)-2,3-dihydro-1H-pyrrolo[3,4-c]pyridin-1-one |
| 505) | 2-(3-(2-((1,5-dimethyl-1H-pyrazol-3-yl)amino)-5-methylpyrimidin-4-yl)-1H-indol-7-yl)-4-(5-methylpyridin-3-yl)-2,3-dihydro-1H-pyrrolo[3,4-c]pyridin-1-one |
| 506) | 2-(3-(2-((1,5-dimethyl-1H-pyrazol-3-yl)amino)-5-methylpyrimidin-4-yl)-1H-indol-7-yl)-4-(3-methylpyridin-4-yl)-2,3-dihydro-1H-pyrrolo[3,4-c]pyridin-1-one |

Method for Preparing GCN2 Inhibitor Compound

Hereinafter, a method for preparing the compound represented by Formula (I) or Formula (Ib), is described on the basis of an exemplary reaction formula for better understanding of the present invention. However, it should be interpreted by those skilled in the art, to which the present invention pertains, that the compound of Formula (I) or Formula (Ib) may be prepared by means of various methods based on a structure of Formula (I) and Formula (Ib), and such methods are all included in the scope of the present invention. In other words, it should be appreciated that the compound according to the present invention may be prepared by arbitrarily combining various synthesis methods which are described in the present specification or disclosed in the prior art and this belongs to the scope of the present invention. In the following reaction formulas, all the substituents are the same as defined above, unless indicated otherwise.

A synthesis method for the compound of the Formula (I) above according to the present invention may be indicated as an example such as a following a reaction formula 1:

[Reaction Formula 1]

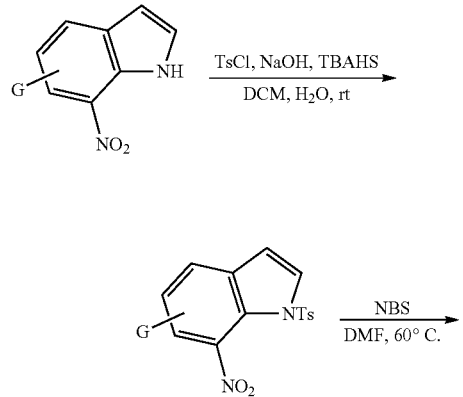

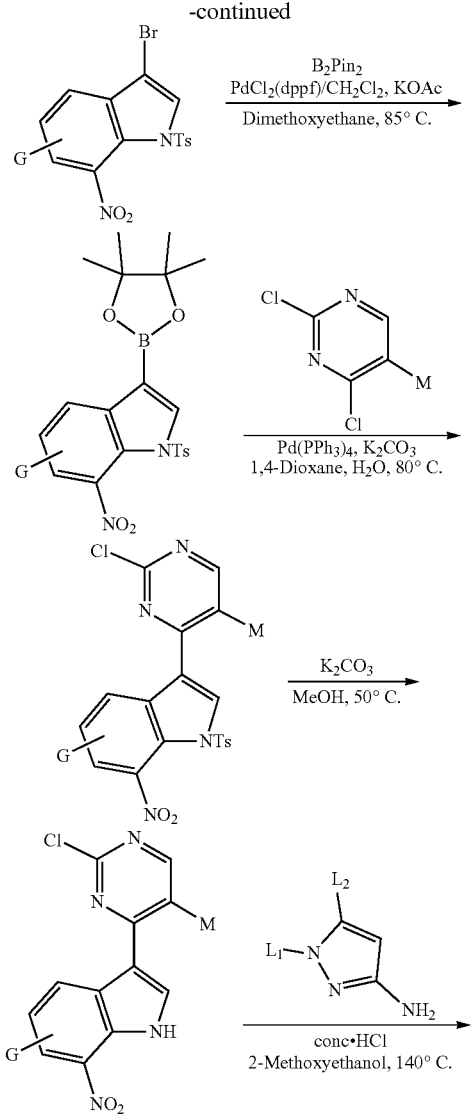

-continued

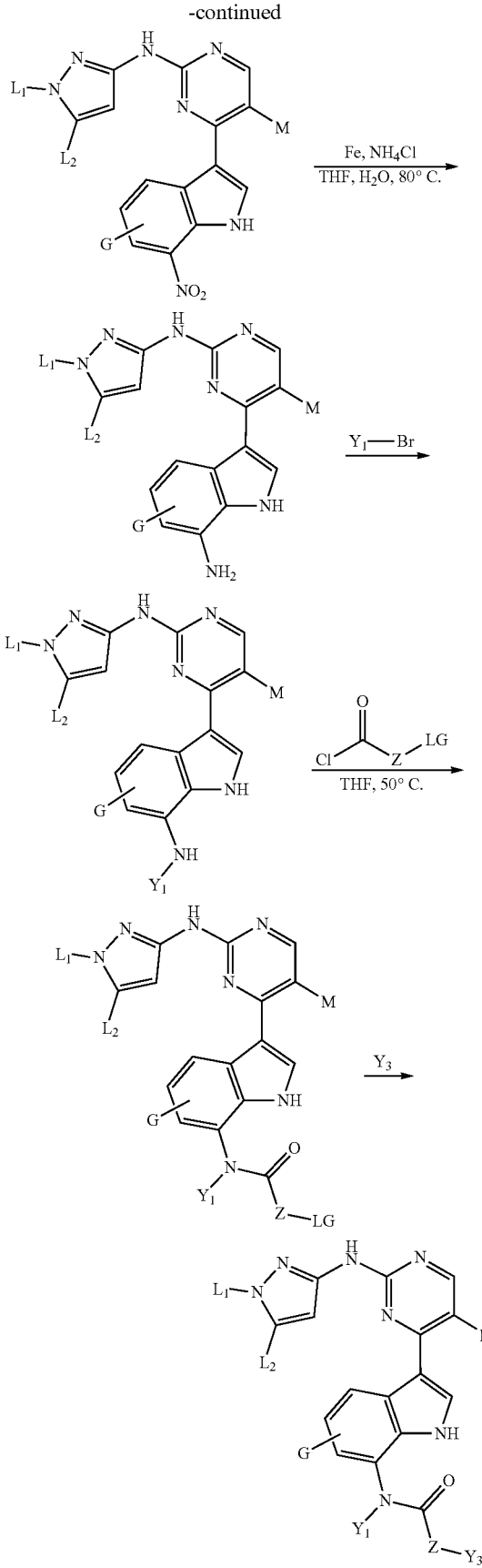

wherein, G, M, $L_1$, $L_2$, $Y_1$, Z, $Y_3$, $W_1$ and $R_2$ are as defined in the Formula (I); LG represents —Cl or —OH.

In the Reaction Formula 1 above, an intermediate compound $Y_3$ may be synthesized through methods of following reaction formulas 1-1, 1-2, or 1-3:

[Reaction formula 1-1]

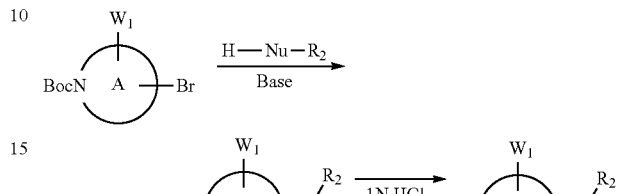

[Reaction Formula 1-2]

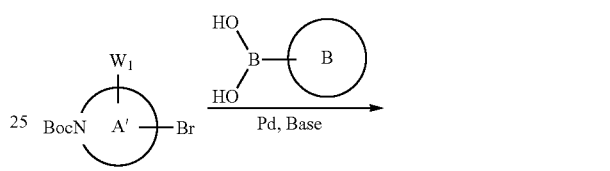

[Reaction Formula 1-3]

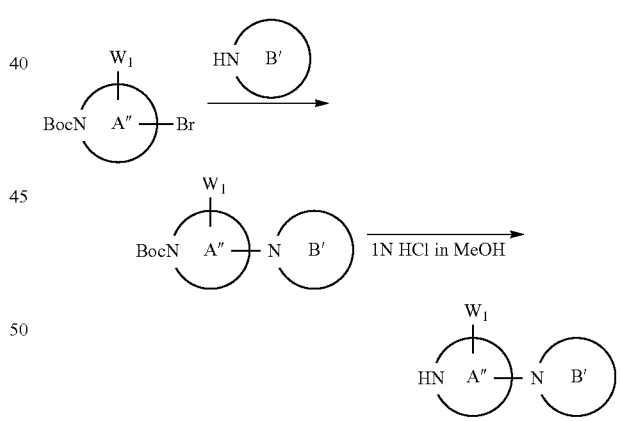

wherein, Nu represents —NH— or —O—;

A represents azetidinyl, pyrrolidinyl, piperidinyl or oxopyrrolidinyl;

A' represents tetrahydropyridinyl;

A" represents piperidinyl;

B represents pyridinyl or methylpyrazolyl;

B' represents methylpiperazinyl or morpholinyl.

A synthesis method for the compound of the Formula (Ib) above according to the present invention may be indicated as an example such as a following a reaction formula 2:

[Reaction Formula 2]
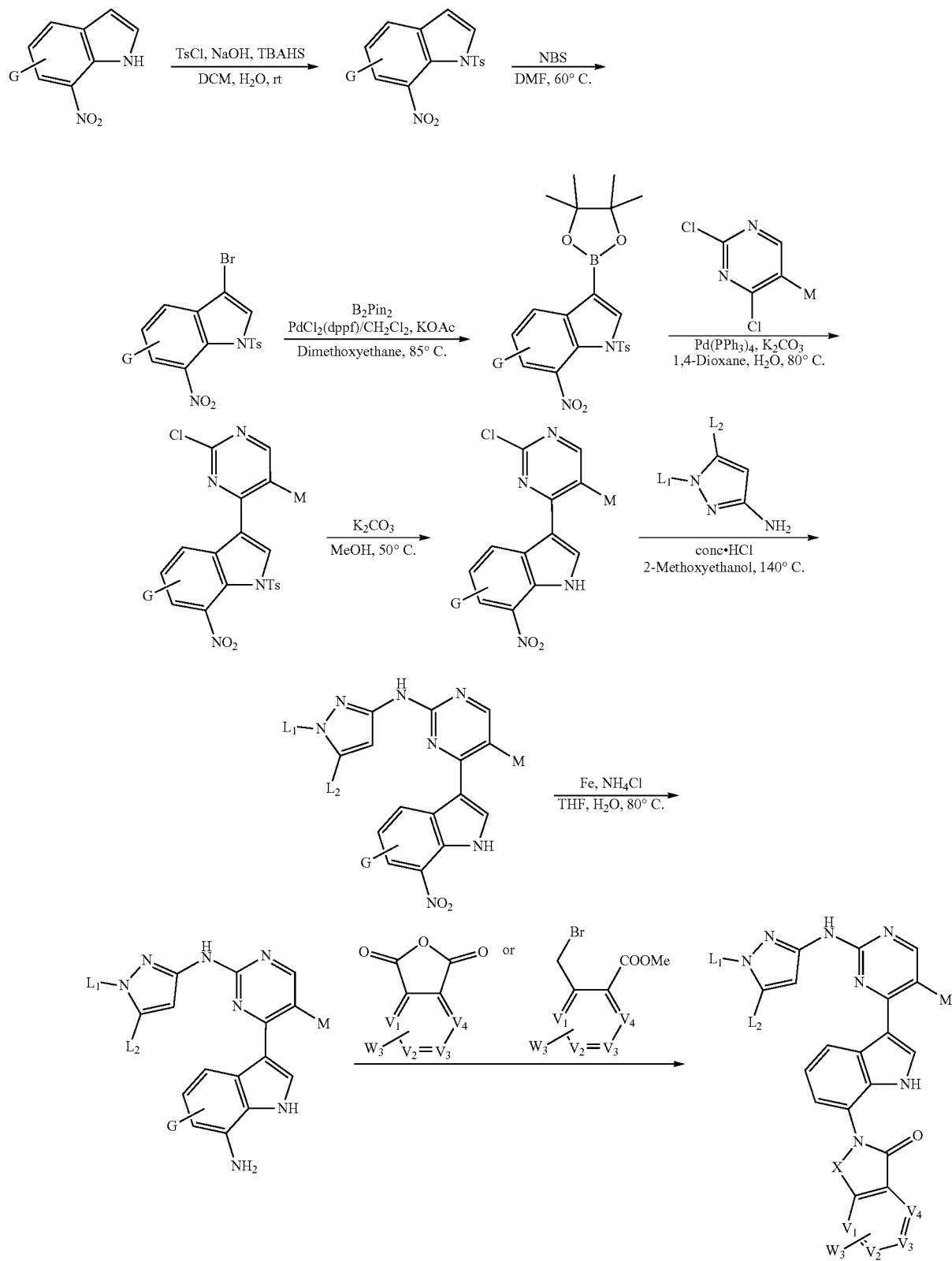
wherein, G, M, $L_1$, $L_2$, $V_1$, $V_2$, $V_3$, $V_4$, $W_3$ and X are as defined in the Formula (Ib).

In the Reaction Formula 2 above, an intermediate compound

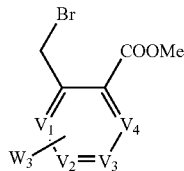

may be

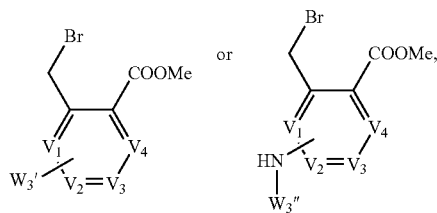

which may be synthesized through methods of following Reaction Formulas 2-1 or 2-2:

[Reaction Formula 2-1]

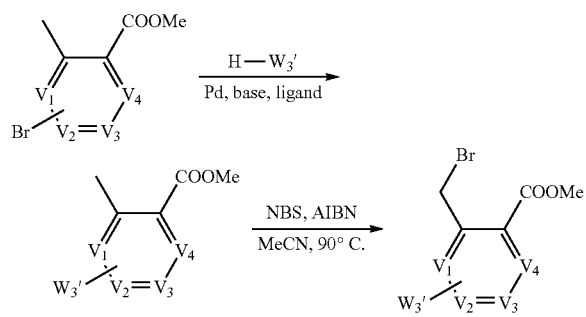

[Reaction Formula 2-2]

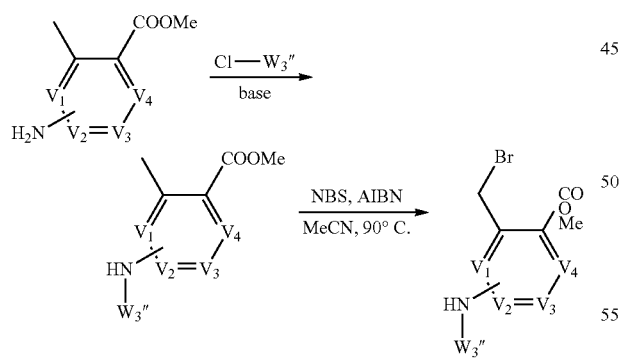

wherein, $W_3'$ represents $-NR_5R^{6'}$; $-CH=CR_7R^{8'}$; $-C\equiv C-R_9'$; ($C_{5-6}$)cycloalkenyl, ($C_{1-5}$)alkyl, $-C(=O)O(C_{1-5})$alkyl, $-S(=O)_2(C_{1-5})$alkyl, $-C(=O)(C_{1-5})$alkyl or $-C(=O)(NH_2)$; an aryl; or a heteroaryl, wherein the aryl or the heteroaryl may be optionally substituted with one or more $R^{10'}$, $W_3''$ represents $-C(=O)R^{11'}$; or $-S(=O)_2R^{12'}$, $R^{5'}$ and $R^{6'}$ each independently represent H; ($C_{1-5}$)alkyl optionally substituted with ($C_{3-7}$)cycloalkyl or an aryl; 5- to 7-membered heterocycloalkyl optionally substituted with ($C_{1-5}$)alkyl or an aryl, $R^{7'}$ represents ($C_{1-5}$)alkyl optionally substituted with $-OH$; an aryl optionally substituted with halogen; or $-C(=O)R^{13'}$, $R^{8'}$ represents H; or ($C_{1-5}$)alkyl, $R^{9'}$ represents an aryl optionally substituted with $-NH_2$, $R^{10'}$ independently represents H; halogen; $-CN$; $-CF_3$; $-OH$; $-OCF_3$; ($C_{1-5}$)alkyl optionally substituted with ($C_{3-7}$)cycloalkyl, 5- to 7-membered heterocycloalkyl, or $-OH$; ($C_{1-5}$)alkoxy; $-NH_2$ optionally substituted with one or more ($C_{1-5}$)alkyl; 5- to 7-membered heterocycloalkyl optionally substituted with ($C_{1-5}$)alkyl; $-C(=O)R^{14'}$; $-S(=O)_2$-(5- to 7-membered heterocycloalkyl); or an aryl, wherein $R^{10}$ is optionally connected to each other to form 5 to 6-membered ring, $R^{11'}$ represents ($C_{1-5}$)alkyl optionally substituted with $-N(CH_3)_2$, an aryl, or a hydroxyaryl; ($C_{3-7}$)cycloalkyl optionally comprising C(=O); ($C_{3-7}$)cycloalkyl optionally substituted with ($C_{1-5}$)alkyl; ($C_{3-7}$)cycloalkyl fused with an aryl; ($C_{5-6}$)cycloalkenyl optionally substituted with ($C_{1-5}$)alkyl; 5- to 7-membered heterocycloalkyl optionally substituted with ($C_{1-5}$)alkyl or $-NH_2$; an aryl; or a heteroaryl optionally substituted with ($C_{1-5}$)alkyl or $-OH$, $R^{12'}$ represents ($C_{1-5}$)alkyl; or an aryl optionally substituted with ($C_{1-5}$)alkyl and/or halogen, $R^{13'}$ represents ($C_{1-5}$)alkyl; ($C_{1-5}$)alkoxy; $-OH$; $-NH_2$, wherein at least one H of $-NH_2$ optionally substituted with ($C_{1-5}$)alkyl; ($C_{3-7}$)cycloalkyl; hydroxy($C_{1-5}$)alkyl; ($C_{1-5}$)alkoxy($C_{1-5}$)alkyl; $-NH_2$, $R^{14'}$ represents 5- to 7-membered heterocycloalkyl; $-NH_2$; or $-OH$.

The compound of the Formula (I) and Formula (Ib) according to the present invention may be separated or purified from products of the reaction formulas 1 and 2 above by means of several methods such as crystallization, silica gel column chromatography, etc. In this way, the compound according to the present invention, as well as an initiation, an intermediate, etc., for preparing the same may be synthesized by means of various methods, and it should be understood that such methods are included in the scope of the present invention with regard to a preparation for the compound of the Formula (I) and Formula (Ib).

Composition Containing GCN2 Inhibitor Compound, and Use Thereof

The present invention provides a pharmaceutical composition and a use of treating or preventing GCN2 activation-related diseases, the composition including a compound represented by the following Formula (I), a stereoisomer thereof, a pharmaceutically acceptable salt thereof or a solvate thereof as an active ingredient:

[Formula (I)]

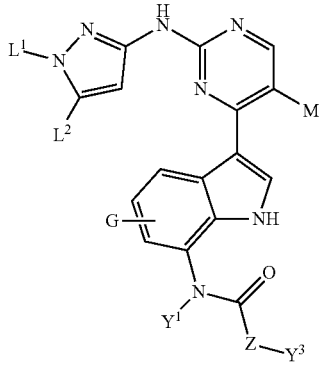

Formula (I) is the same as defined above.

The compound represented by formula (I) above may be a compound represented by a following formula (Ib):

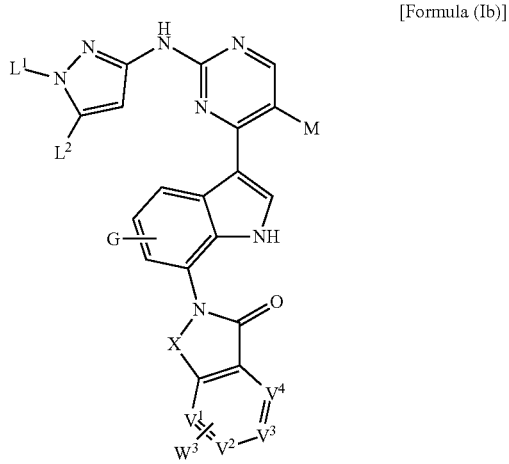

[Formula (Ib)]

Formula (Ib) is the same as defined above.

The compound of Formula (I) or (Ib), the stereoisomer thereof, the pharmaceutically acceptable salt thereof or the solvate thereof has a remarkable effect on preventing or treating GCN2 activation-related diseases by showing GCN2 inhibitory activity. Thus, achieving a remarkable effect of preventing or treating GCN2 activation-related diseases.

In the present invention, the said GCN2 activation-related diseases means diseases associated with enhanced activity of GCN2 and comprise a cancer, a neurodegenerative disease, a chronic infection, a metabolic disease such as hepatic steatosis, and the cancer comprises thyroid cancer, melanoma, prostate cancer, endometrial cancer, lung cancer, head and neck cancer, pancreatic cancer, glioma, stomach cancer, urothelial cancer, skin cancer, breast cancer, colorectal cancer, renal cancer, fibrosarcoma, bone sarcoma, connective tissue sarcoma, giant cell carcinoma, squamous cell carcinoma, leukemia, skin cancer, soft tissue cancer, liver cancer, adenocarcinoma, hepatocellular carcinoma, multiple myeloma, myelodysplastic syndrome, myeloproliferative neoplasm, malignant glioma, non-Hodgkin's lymphoma, Hodgkin's lymphoma, Burkitt's lymphoma, chronic lymphocytic leukemia, chronic myeloid leukemia, hairy cell leukemia, plasmacytoma, lymphoplasmacytic lymphoma, acute lymphoblastic leukemia, acute myeloid leukemia, chronic myelomonocytic leukemia, juvenile myelomonocytic leukemia, large granular lymphocytic leukemia, B-cell prolymphocytic leukemia, T-cell prolymphocytic leukemia, small cell lung cancer, pediatric neuroblastoma or symptoms related thereto.

In the present invention, pharmaceutically acceptable salt mean the salt conventionally used in a pharmaceutical industry, for example, acid salt prepared from 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, L-ascorbic acid, L-aspartic acid, benzenesulfonic acid, benzoic acid, (+)-camphoric acid, (+)-camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, D-glucoheptonic acid, D-gluconic acid, D-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, L-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, L-pyroglutamic acid, salicylic acid, sebacic acid, stearic acid, succinic acid, sulfuric acid, L-tartaric acid, thiocyanic acid, toluenesulfonic acid, undecylenic acid or other compounds that can be used as acids, and the like.

For its administration, the pharmaceutical composition of the present invention may further contain at least one type of a pharmaceutically acceptable carrier, in addition to the compound represented by Formula (I) or (Ib), the stereoisomer thereof, the pharmaceutically acceptable salt thereof or solvate thereof, and may be also used with the addition of other conventional additives such as antioxidants, buffer solutions, bacteriostatic agents, etc., if needed. Also, such pharmaceutical composition may be formulated such a way that diluents, dispersing agents, surfactants, binders and lubricants are additionally added thereto.

The composition of the present invention may be orally or parenterally administered (for example, applied intravenously, hypodermically, intraperitoneally or locally) according to an intended method, in which a dosage thereof varies in a range thereof depending on a patient's weight, age, gender, health condition and diet, an administration time, an administration method, an excretion rate, a severity of a disease and the like. A daily dosage of the compound represented by the formula (I) or (Ib) is about 0.001 to 1000 mg/kg and may be administered once a day or divided into several times.

In addition to the compound represented by Formula (I) or (Ib), the stereoisomer thereof, the pharmaceutically acceptable salt thereof or solvate thereof, said pharmaceutical composition of the present invention may further contain at least one therapeutic agent as an active ingredient which show a medicinal effect the same thereto or similar thereto. Therapeutic agents may selected from the group consisting of chemotherapy agent, radiotherapy agent, immunotherapy agent and tumor microenvironment modulating agent.

According to the present invention, the compound represented by Formula (I) or (Ib), the stereoisomer thereof, the pharmaceutically acceptable salt thereof or solvate thereof show GCN2 inhibition activity, thus achieving a remarkable effect of preventing or treating GCN2 activation-related diseases.

According to one specific embodiment of the present invention, the present invention provides a method for preventing or treating GCN2 activation-related diseases, including administering a therapeutically effective amount of the compound represented by Formula (I) or (Ib), the stereoisomers thereof, the pharmaceutically acceptable salt thereof or solvate thereof into a subject. The method for preventing or treating GCN2 activation-related diseases according to the present invention includes not only dealing with the cancer themselves before expression of their symptoms, but also inhibiting or avoiding such symptoms by administering the compound represented by Formula (I) or (Ib), the stereoisomer thereof, the pharmaceutically acceptable salt thereof or solvate thereof.

According to one specific embodiment of the present invention, the present invention provides a use of the compound represented by the formula (I) or (Ib), the stereoisomer thereof, the pharmaceutically acceptable salt thereof or the solvate thereof in preparation of a medicament for treating GCN2 activation-related diseases.

For preparing a medicament, the compound represented by Formula (I) or (Ib), the stereoisomer thereof, the pharmaceutically acceptable salt thereof or solvate thereof may be combined with acceptable adjuvants, diluents, carriers, etc., and may be prepared into a complex preparation together with other active agents (therapeutic agents) and thus have a synergy action of active components.

According to one specific embodiment of the present invention, the present invention also provides a method for inhibiting GCN2 activity, wherein the method comprises administering a therapeutically effective dose of the formula (I) or (Ib), the stereoisomer thereof, the pharmaceutically acceptable salt thereof or the solvate thereof into a subject.

As used herein, the "subject" means mammals including humans, and the "administration" means providing a predetermined material to a patient by means of any appropriate method.

As used herein, the term "therapeutically effective amount" refers to an amount of the compound represented by Formula (I) or (Ib), the stereoisomer thereof, the pharmaceutically acceptable salt thereof or solvate thereof, which are effective in preventing or treating GCN2 activation-related diseases.

(1) The present invention provides a compound represented by a following Formula (I), a stereoisomer thereof, a pharmaceutically acceptable salt thereof, or a solvate thereof:

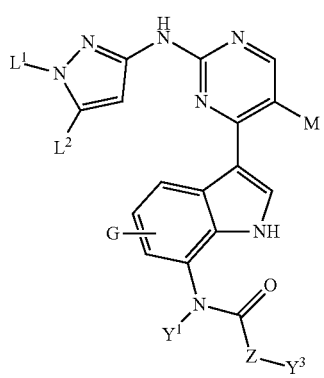

[Formula (I)]

Wherein, $L^1$ and $L^2$ each independently represent H; $(C_{1-5})$alkyl; or $L^1$ and $L^2$ may be connected to form a 5 to 6-membered ring, M represents H; halogen; $(C_{1-5})$alkyl; $(C_{3-7})$cycloalkyl; or $(C_{1-5})$alkoxy, G represents H; halogen; $(C_{1-5})$alkyl; $(C_{1-5})$alkoxy; or $-NH_2$, wherein at least one H of $-NH_2$ optionally substituted with $(C_{1-5})$alkyl, $Y^1$ represents H; or $(C_{1-5})$alkyl, Z represents $-C(=O)-$; or $-CH_2-$ optionally substituted with one or more $(C_{1-5})$alkyl; and/or Z may be connected to $Y^1$ to form a 5- to 6-membered ring, $Y^3$ represents 4- to 6-membered heterocycloalkyl which is optionally substituted with $W^1$ and $W^2$; or $Y^3$ may be connected to Z to form an aryl or a heteroaryl in case that Z is connected to $Y^1$ to form the 5- to 6-membered ring, $W_1$ and $W_2$ each independently represent H; halogen; $-OH$; $(C_{1-5})$alkyl optionally substituted with $-OH$ or $-CN$; 5- to 7-membered heterocycloalkyl optionally substituted with $(C_{1-5})$alkyl; a heteroaryl optionally substituted with $(C_{1-5})$alkyl; $-COR^1$; $-OR^2$ or $-NH_2$, wherein at least one H of $-NH_2$ optionally substituted with a heteroaryl, $R^1$ represents $(C_{1-5})$alkoxy; $-OH$; 5-7 membered heterocycloalkyl optionally substituted with $(C_{1-5})$alkyl; or $-NH_2$, wherein at least one H of $-NH_2$ optionally substituted with $(C_{3-7})$cycloalkyl, $R^2$ represents $(C_{1-5})$alkyl optionally substituted with a heteroaryl; an aryl; or a heteroaryl, wherein the aryl or the heteroaryl is optionally substituted with one or more $R^{2a}$, $R^{2a}$ independently represents halogen; $(C_{1-5})$alkyl optionally substituted with an aryl or 5- to 7-membered heterocycloalkyl substituted with $(C_{1-5})$alkyl; $(C_{5-6})$cycloalkenyl optionally substituted with $(C_{1-5})$alkyl; 5- to 7-membered heterocycloalkyl substituted with $(C_{1-5})$alkyl or $-OH$; $-CF_3$; $(C_{1-5})$alkoxy optionally substituted with an aryl; an aryl; a heteroaryl optionally substituted with $(C_{1-5})$alkyl; thio$(C_{1-5})$alkyl; $-COR^1$; or $NR^3R^4$, $R^3$ and $R^4$ each independently represent H; halogen; $(C_{1-5})$alkyl optionally substituted with halogen, $-CF_3$, $-OH$, $(C_{1-5})$alkoxy, $(C_{1-5})$alkyl-N—$(C_{1-5})$alkyl, an aryl or $(C_{3-7})$cycloalkyl; $(C_{3-7})$cycloalkyl; $(C_{1-5})$alkoxy; an aryl; or $-C(=O)(C_{1-5})$alkyl.

(2) The compound, the stereoisomer thereof, the pharmaceutically acceptable salt thereof or the solvate thereof according to (1), wherein:

$Y^3$ represents azetidinyl; pyrrolidinyl; piperidinyl; tetrahydropyridinyl; or oxopyrrolidinyl, which is optionally substituted with $W^1$ and $W^2$, $W_1$ and $W_2$ each independently represent H; halogen; $-OH$; $(C_{1-5})$alkyl optionally substituted with $-OH$ or $-CN$; methylpiperazinyl; morpholinyl; pyridinyl; methylpyrazolyl; $-COR^1$; $-OR^2$; $-NH_2$; $-NH$(pyridinyl) or $-NH$(pyrimidinyl), $R^1$ represents $(C_{1-5})$alkoxy; $-OH$; $-NH_2$; $-NH-$$(C_{3-7})$cycloalkyl; oxopiperazinyl; morpholinyl; thiomorpholinyl; methylpiperazinyl; or tetrahydropyridinyl, $R^2$ represents $(C_{1-5})$alkyl optionally substituted with pyridinyl; halophenyl; dihalophenyl; (amino)halophenyl; (methylpiperazinyl)(methyl)phenyl; (dimehtylamino)phenyl; aminophenyl; biphenyl; (phenylpropanyl) phenyl; (cyclopropylamino)pyrimidinyl; (trifluoroethylamino)pyrimidinyl; pyridinyl; pyrimidinyl; cyclopropyl(isoxazole)carboxamide; (dimethyl) pyrimidinyl; pyrazinyl; aminopyridinyl; halopyridinyl; aminopyrazinyl; halopyrimidinyl; (methyl)halopyrimidinyl; (amino)(methyl)pyrimidinyl; (amino)halopyrimidinyl; dihalopyrimidinyl; amino(dihalophenyl)pyrimidinyl; (amino)(trifluoromethyl)pyrimidinyl; pentylpyrimidinyl; methylpyrazolyl; methyl(benzothiophene)carboxylate; methyl(thiophene)carboxylate; (thiophene)carboxylic acid; (thiophene)carboxamide; methyl(thiophene)carboxamide; cyclopropyl(thiophene)carboxamide; methylisoxazolyl; benzoisoxazolyl; isothiazolyl; methylthiophenyl; pyrazolyl; (methyl)(trifluoromethyl)pyrazolyl; isoxazolyl; aminopyrazolyl;

methyl(pyrrole)carboxylate; ethyl(isoxazole)carboxylate; (isoxazole)carboxamide; methyl(isoxazole)carboxamide; cyclopropyl(isoxazole)carboxamide; dimethyl(isoxazole)carboxamide; cyclopropyl(oxazole)carboxamide; (pyrimidine)carboxylic acid; (pyrimidine)carboxamide; methyl(pyrimidine)carboxamide; dimethyl(pyrimidine)carboxamide; (pyrazine)carboxamide; methyl(pyrazine)carboxamide; aminotriazinyl; (methylamino)triazinyl; (dimethylamino)triazinyl; (cyclopropylamino)triazinyl; diaminotriazinyl; (amino)(pyrrolidinyl)triazinyl; aminopyrimidinyl; (methylamino)pyrimidinyl; (ethylamino)pyrimidinyl; (propylamino)pyrimidinyl; (butylamino)pyrimidinyl; (hydroxyethylamino)pyrimidinyl; (hydroxypropylamino)pyrimidinyl; (methoxyethylamino)pyrimidinyl; (((dimethylamino)propyl)amino)pyrimidinyl; (benzylamino)pyrimidinyl; (phenethylamino)pyrimidinyl; (cyclohexylamino)pyrimidinyl; (dimethylamino)pyrimidinyl; (ethylmethylamino)pyrimidinyl; (diethylamino)pyrimidinyl; (ethylpropylamino)pyrimidinyl; (butylethylamino)pyrimidinyl; pyrrolidinylpyrimidinyl; (hydroxypyrrolidinyl)pyrimidinyl; piperidinylpyrimidinyl; (hydroxypiperidinyl)pyrimidinyl; morpholinopyrimidinyl; (methylpiperazinyl)pyrimidinyl; (amino)(methylamino)pyrimidinyl; (amino)(pyrrolidinyl)pyrimidinyl; (methylamino)halopyrimidinyl; (ethylamino)halopyrimidinyl; (cyclopropylamino)halopyrimidinyl; (cyclohexylamino)halopyrimidinyl; (dimethylamino)halopyrimidinyl; (ethylmethylamino)halopyrimidinyl; (diethylamino)halopyrimidinyl; (methylphenylamino)halopyrimidinyl; (benzylmethylamino)halopyrimidinyl; (pyrrolidinyl)halopyrimidinyl; (piperidinyl)halopyrimidinyl; (morpholino)halopyrimidinyl; (thiomorpholino)halopyrimidinyl; (methylpiperazinyl)halopyrimidinyl; (cyclopropylamino)methylpyrimidinyl; (amino)pyrimidinyl; (methylthio)pyrimidinyl; (methoxy)pyrimidinyl; (benzyloxy)pyrimidinyl; acetamidopyrimidinyl; (difluoropropylamino)pyrimidinyl; (difluoroethylamino)pyrimidinyl; (trifluoropropylamino)pyrimidinyl; (fluoroethylamino)pyrimidinyl; (cyclobutylamino)pyrimidinyl; (cyclopentylamino)pyrimidinyl; (isopropylamino)pyrimidinyl; (sec-butylamino)pyrimidinyl; ((cyclopropylmethyl)amino)pyrimidinyl; (((dimethylamino)ethyl)amino)pyrimidinyl; (((dimethylamino)propyl)amino)pyrimidinyl; (methoxyamino)pyrimidinyl; (benzylmethylamino)pyrimidinyl; (cyclohexylamino)halopyrimidinyl; (cyclopropylmethylamino)halopyrimidinyl; (benzylamino)halopyrimidinyl; (cyclopropylamino)halopyrimidinyl; (cyclopropylamino)methylpyrimidinyl; (cyclopropylamino)(trifluoromethyl)pyrimidinyl; (cyclopropylamino)(methoxy)pyrimidinyl; (cyclopropylamino)pyrazinyl; (ethylamino)pyrazinyl; (propylamino)pyrazinyl; (hydroxyethylamino)pyrazinyl; (((dimethylamino)ethyl)amino)pyrazinyl; phenylpyrimidinyl; (methylpyrazolyl)pyrimidinyl; (dimethylcyclohexenyl)pyrimidinyl; dihydropyranylpyrimidinyl; or pyridinylpyrimidinyl.

(3) The compound, the stereoisomer thereof, the pharmaceutically acceptable salt thereof, or the solvate thereof according to (1) or (2), wherein the compound represented by formula (I) above is a compound represented by a following Formula (Ib):

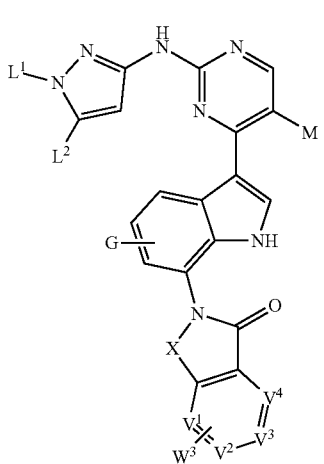

[Formula (Ib)]

X represents —$CH_2$—; or —C(=O)—, $V^1$, $V^2$, $V^3$ and $V^4$ each independently represent CH or N, wherein $V^1$, $V^2$, $V^3$ and $V^4$ each independently be substituted with $W^3$ in case that $V^1$, $V^2$, $V^3$ and/or $V^4$ are(is) CH, $W^3$ independently represents H, halogen; ($C_{1-5}$)alkyl; ($C_{1-5}$)alkoxy; —OH; —$NO_2$; —$NR^5R^6$; —CH=$CR^7R^8$; —C≡C—$R^9$; ($C_{5-6}$)cycloalkenyl; 5- to 7-membered heterocycloalkyl optionally substituted with ($C_{1-5}$)alkyl, —C(=O)O($C_{1-5}$)alkyl, —S(=O)$_2$($C_{1-5}$)alkyl, —C(=O)($C_{1-5}$)alkyl or —C(=O)($NH_2$); an aryl; or a heteroaryl, wherein the aryl or the heteroaryl may be optionally substituted with one or more $R^{10}$, $R^5$ and $R^6$ each independently represent H; ($C_{1-5}$)alkyl optionally substituted with ($C_{3-7}$)cycloalkyl or an aryl; 5- to 7-membered heterocycloalkyl optionally substituted with ($C_{1-5}$)alkyl; an aryl; —C(=O)$R^{11}$; or —S(=O)$_2R^{12}$, $R^7$ represents ($C_{1-5}$)alkyl optionally substituted with —OH; an aryl optionally substituted with halogen; or —C(=O)$R^1$3, $R^8$ represents H; or ($C_{1-5}$)alkyl, $R^9$ represents an aryl optionally substituted with —$NH_2$, $R^{10}$ independently represents H; halogen; —CN; —$CF_3$; —OH; —$OCF_3$; ($C_{1-5}$)alkyl optionally substituted with ($C_{3-7}$)cycloalkyl, 5- to 7-membered heterocycloalkyl, or —OH; ($C_{1-5}$)alkoxy; —$NH_2$ optionally substituted with one or more ($C_{1-5}$)alkyl; 5- to 7-membered heterocycloalkyl optionally substituted with ($C_{1-5}$)alkyl; —C(=O)$R^{14}$; —S(=O)$_2$-(5- to 7-membered heterocycloalkyl); or an aryl, wherein $R^{10}$ is optionally connected to each other to form 5 to 6-membered ring, $R^{11}$ represents ($C_{1-5}$)alkyl optionally substituted with —N($CH_3$)$_2$, an aryl, or a hydroxyaryl; ($C_{3-7}$)cycloalkyl optionally comprising C(=O); ($C_{3-7}$)cycloalkyl optionally substituted with ($C_{1-5}$)alkyl; ($C_{3-7}$)cycloalkyl fused with an aryl; ($C_{5-6}$)cycloalkenyl optionally substituted with ($C_{1-5}$)alkyl; 5- to 7-membered heterocycloalkyl optionally substituted with ($C_{1-5}$)alkyl or —$NH_2$; an aryl; or a heteroaryl optionally substituted with ($C_{1-5}$)alkyl or —OH, $R^{12}$ represents ($C_{1-5}$)alkyl; or an aryl optionally substituted with ($C_{1-5}$)alkyl and/or halogen, $R^{13}$ represents ($C_{1-5}$)alkyl; ($C_{1-5}$)alkoxy; —OH; —$NH_2$, wherein at least one H of —$NH_2$ optionally substituted with ($C_{1-5}$)alkyl; ($C_{3-7}$)cycloalkyl; hydroxy($C_{1-5}$)alkyl; ($C_{1-5}$)alkoxy($C_{1-5}$)alkyl; —$NH_2$, $R^{14}$ represents 5- to 7-membered heterocycloalkyl; —$NH_2$; or —OH, $L^1$, $L^2$, M, and G are as defined in (1).

(4) The compound, the stereoisomer thereof, the pharmaceutically acceptable salt thereof, or the solvate thereof according to (1), (2) or (3), $W^3$ independently represents H; halogen; $(C_{1-5})$alkyl; $(C_{1-5})$alkoxy; —OH; —$NO_2$; —$NR^5R^6$; —CH=$CR^7R^8$; —C≡C—$R^9$; $(C_{5-6})$cycloalkenyl; morpholinyl; tetrahydropyridinyl; dihydropyranyl; tert-butyl(tetrahydropyridine)carboxylate; dihydrothiopyranyl; methyltetrahydropyridinyl; (methylsulfonyl)tetrahydropyridinyl; acetyltetrahydropyridinyl; (tetrahydropyridine)carboxamide; 1,1-dioxide-dihydrothiopyranyl; phenyl; (trifluoromethoxy)phenyl; aminophenyl; tert-butyl(phenyl)carbamate; (pyrrolidinylsulfonyl)phenyl; oxopiperidine(carbonyl)phenyl; (methylpiperazinyl)phenyl; isoindolyl; cyanophenyl; cyanohalophenyl; (trifluoromethyl)phenyl; (dimethylamino)phenyl; hydroxybenzyl; methoxyphenyl; biphenyl; methylphenyl; hydroxyphenyl; dihydroindenyl; benzoic acid; methylbenzoate; pyridinyl; pyrazolyl; methylpyrazolyl; furanyl; aminopyridinyl; halopyridinyl; hydroxypyridinyl; (methoxy)halopyridinyl; methoxypyridinyl; (methyl)halopyridinyl; piperazinylpyridinyl; pyrrolopyridinyl; (dimethylamino)pyrimidinyl; (cyclopropylmethyl)pyrazolyl; (morpholinoethyl)pyrazolyl; pyrimidinyl; aminopyrimidinyl; (methylpiperazinyl)pyridinyl; piperazinylpyridinyl; morpholinopyridinyl; dihalopyridinyl; methylpyridinyl; pyrrolyl; tert-butyl(pyrrole)carboxylate; dimethylisoxazolyl; isoquinolinyl; methylindazolyl; methylthiophenyl; indazolyl; thiophenyl; cyanopyridinyl; (hydroxymethyl)pyridinyl; picolinamide; (dimethylamino)pyridinyl; (methylamino)pyridinyl; dimethylpyridinyl; or (methylamino)pyridinyl, $R^5$ and $R^6$ each independently represent H; $(C_{1-5})$alkyl optionally substituted with $(C_{3-7})$cycloalkyl or phenyl; morpholinyl, or piperazinyl optionally substituted with $(C_{1-5})$alkyl; phenyl; —C(=O)$R^{11}$; or —S(=O)$_2R^{12}$, $R^7$ represents methyl optionally substituted with —OH; phenyl optionally substituted with halogen; or —C(=O)$R^{13}$, $R^9$ represents phenyl optionally substituted with —$NH_2$, $R^{11}$ represents $(C_{1-5})$alkyl optionally substituted with —N(CH$_3$)$_2$, phenyl, or hydroxyphenyl; $(C_{3-7})$cycloalkyl optionally comprising C(=O); $(C_{3-7})$cycloalkyl substituted with $(C_{1-5})$alkyl; $(C_{3-7})$cycloalkyl fused with phenyl; $(C_{5-6})$cycloalkenyl optionally substituted with $(C_{1-5})$alkyl; morpholinyl; methylpiperidinyl; oxopyrrolidinyl; oxoimidazolidinyl; pyrrolidinyl; piperidinyl; tetrahydrofuranyl; tetrahydropyranyl; methyltetrahydropyranyl; aminopyrrolidinyl; methylpyrrolidinyl; phenyl; pyridinyl; oxazolyl; pyridazinyl; methylisoxazolyl; methyloxazolyl; isoxazolyl; methylpyridinyl; furanyl; or hydroxypyrimidinyl, $R^{12}$ represents $(C_{1-5})$alkyl; phenyl; methylphenyl; or (methyl)halophenyl, $R^{14}$ represents oxopiperidinyl; —$NH_2$; or —OH, and halo and halogen are each independently F, Cl, Br or I.

(5) The compound, the stereoisomer thereof, the pharmaceutically acceptable salt thereof, or the solvate thereof according to (1), (2), (3) or (4), wherein the compound is one selected from the group consisting of the following compounds:

1) (S)-2-(3-((2-(cyclopropylamino)pyrimidin-4-yl)oxy)pyrrolidin-1-yl)-N-(3-(2-((1,5-dimethyl-1H-pyrazol-3-yl)amino)-5-methylpyrimidin-4-yl)-6-fluoro-1H-indol-7-yl)acetamide
2) (S)-N-(5-amino-3-(2-((1,5-dimethyl-1H-pyrazol-3-yl)amino)-5-methylpyrimidin-4-yl)-1H-indol-7-yl)-2-(3-((2-(cyclopropylamino)pyrimidin-4-yl)oxy)pyrrolidin-1-yl)acetamide
3) (S)-2-(3-((2-(cyclopropylamino)pyrimidin-4-yl)oxy)pyrrolidin-1-yl)-N-(3-(2-((1,5-dimethyl-1H-pyrazol-3-yl)amino)-5-methylpyrimidin-4-yl)-6-(dimethylamino)-1H-indol-7-yl)acetamide
4) (S)-2-(3-((2-(cyclopropylamino)pyrimidin-4-yl)oxy)pyrrolidin-1-yl)-N-(3-(2-((1,5-dimethyl-1H-pyrazol-3-yl)amino)-5-methylpyrimidin-4-yl)-6-methoxy-1H-indol-7-yl)acetamide
5) (S)-N-(3-(2-((1,5-dimethyl-1H-pyrazol-3-yl)amino)-5-methylpyrimidin-4-yl)-6-(dimethylamino)-1H-inden-7-yl)-2-(3-((2-((2,2,2-trifluoroethyl)amino)pyrimidin-4-yl)oxy)pyrrolidin-1-yl)acetamide
6) (S)-N-(3-(2-((1,5-dimethyl-1H-pyrazol-3-yl)amino)-5-methylpyrimidin-4-yl)-6-methoxy-1H-indol-7-yl)-2-(3-((2-((2,2,2-trifluoroethyl)amino)pyrimidin-4-yl)oxy)pyrrolidin-1-yl)acetamide
7) (S)-2-(3-((6-(cyclopropylamino)pyrimidin-4-yl)oxy)pyrrolidin-1-yl)-N-(3-(2-((1,5-dimethyl-1H-pyrazol-3-yl)amino)pyrimidin-4-yl)-1H-indol-7-yl)acetamide
8) (S)-N-(3-(2-((1,5-dimethyl-1H-pyrazol-3-yl)amino)-5-fluoropyrimidin-4-yl)-1H-indol-7-yl)-2-(3-(pyridin-4-yloxy)pyrrolidin-1-yl)acetamide
9) (S)-N-(3-(5-chloro-2-((1,5-dimethyl-1H-pyrazol-3-yl)amino)pyrimidin-4-yl)-1H-indol-7-yl)-2-(3-(pyridin-4-yloxy)pyrrolidin-1-yl)acetamide
10) (3-(5-chloro-2-((1,5-dimethyl-1H-pyrazol-3-yl)amino)pyrimidin-4-yl)-1H-indol-7-yl)-2-(3-((2-(cyclopropylamino)pyrimidin-4-yl)oxy)pyrrolidin-1-yl)acetamide
11) (3-((2-(cyclopropylamino)pyrimidin-4-yl)oxy)pyrrolidin-1-yl)-N-(3-(2-((1,5-dimethyl-1H-pyrazol-3-yl)amino)-5-ethylpyrimidin-4-yl)-1H-indol-7-yl)acetamide
12) (S)-N-(3-(5-cyclopropyl-2-((1,5-dimethyl-1H-pyrazol-3-yl)amino)pyrimidin-4-yl)-1H-indol-7-yl)-2-(3-((2-(cyclopropylamino)pyrimidin-4-yl)oxy)pyrrolidin-1-yl)acetamide
13) (S)-2-(3-((2-(cyclopropylamino)pyrimidin-4-yl)oxy)pyrrolidin-1-yl)-N-(3-(2-((1,5-dimethyl-1H-pyrazol-3-yl)amino)-5-methoxypyrimidin-4-yl)-1H-indol-7-yl)acetamide

| | |
|---|---|
| 14) | (S)-2-(3-((3-(cyclopropylamino)-1,2,4-triazin-5-yl)oxy)pyrrolidin-1-yl)-N-(3-(2-((1,5-dimethyl-1H-pyrazol-3-yl)amino)-5-methoxypyrimidin-4-yl)-1H-indol-7-yl)acetamide |
| 15) | (S)-N-(3-(2-((5,6-dihydro-4H-pyrrolo[1,2-b]pyrazol-2-yl)amino)-5-methylpyrimidin-4-yl)-1H-indol-7-yl)-2-(3-(pyrimidin-4-yloxy)pyrrolidin-1-yl)acetamide |
| 16) | (S)-2-(3-((2-(cyclopropylamino)pyrimidin-4-yl)oxy)pyrrolidin-1-yl)-N-(3-(2-((5,6-dihydro-4H-pyrrolo[1,2-b]pyrazol-2-yl)amino)-5-methylpyrimidin-4-yl)-1H-indol-7-yl)acetamide |
| 17) | (S)-2-(3-((2-(cyclopropylamino)pyrimidin-4-yl)oxy)pyrrolidin-1-yl)-N-(3-(5-methyl-2-((5-methyl-1-(2-morpholinoethyl)-1H-pyrazol-3-yl)amino)pyrimidin-4-yl)-1H-indol-7-yl)acetamide |
| 18) | (S)-N-(3-(2-((1,5-dimethyl-1H-pyrazol-3-yl)amino)-5-methylpyrimidin-4-yl)-1H-indol-7-yl)-2-ox0-2-(3-(pyridin-4-yloxy)pyrrolidin-1-yl)acetamide |
| 19) | N-(3-(2-((1,5-dimethyl-1H-pyrazol-3-yl)amino)-5-methylpyrimidin-4-yl)-1H-indol-7-yl)-2-0x0-2-(3-(pyridin-3-yloxy)pyrrolidin-1-yl)acetamide |
| 20) | (S)-2-(3-((2-(cyclopropylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)-2-oxoacetamide |
| 21) | (S)-N-(3-(2-((1,5-dimethyl-1H-pyrazol-3-yl)amino)-5-methylpyrimidin-4-yl)-1H-indol-7-yl)-N-methyl-2-(3-(pyrimidin-4-yloxy)pyrrolidin-1-yl)acetamide |
| 22) | N-(3-(2-((1,5-dimethyl-1H-pyrazol-3-yl)amino)-5-methylpyrimidin-4-yl)-1H-indol-7-yl)-2-(pyrrolidin-1-yl)propenamide |
| 23) | N-(3-(2-((1,5-dimethyl-1H-pyrazol-3-yl)amino)-5-methylpyrimidin-4-yl)-1H-indol-7-yl)-2-((S)-3-(pyridin-4-yloxy)pyrrolidin-1-yl)propenamide |
| 24) | N-(3-(2-((1,5-dimethyl-1H-pyrazol-3-yl)amino)-5-methylpyrimidin-4-yl)-1H-indol-7-yl)-2-methyl-2-(pyrrolidin-1-yl)propenamide |
| 25) | (S)-N-(3-(2-((1,5-dimethyl-1H-pyrazol-3-yl)amino)-5-methylpyrimidin-4-yl)-1H-indol-7-yl)-2-methyl-2-(3-(pyridin-4-yloxy)pyrrolidin-1-yl)propenamide |
| 26) | N-(3-(2-((1,5-dimethyl-1H-pyrazol-3-yl)amino)-5-methylpyrimidin-4-yl)-1H-indol-7-yl)-2-(3-hydroxyazetidin-1-yl)acetamide |
| 27) | N-(3-(2-((1,5-dimethyl-1H-pyrazol-3-yl)amino)-5-methylpyrimidin-4-yl)-1H-indol-7-yl)-2-(3-(pyridin-4-ylmethoxy)azetidin-1-yl)acetamide |
| 28) | N-(3-(2-((1,5-dimethyl-1H-pyrazol-3-yl)amino)-5-methylpyrimidin-4-yl)-1H-indol-7-yl)-2-(3-(pyridin-4-yloxy)azetidin-1-yl)acetamide |
| 29) | N-(3-(2-((1,5-dimethyl-1H-pyrazol-3-yl)amino)-5-methylpyrimidin-4-yl)-1H-indol-7-yl)-2-(3-(pyrimidin-4-yloxy)azetidin-1-yl)acetamide |
| 30) | N-(3-(2-((1,5-dimethyl-1H-pyrazol-3-yl)amino)-5-methylpyrimidin-4-yl)-1H-indol-7-yl)-2-(3-(pyridin-3-yloxy)azetidin-1-yl)acetamide |
| 31) | methyl 1-(2-((3-(2-((1,5-dimethyl-1H-pyrazol-3-yl)amino)-5-methylpyrimidin-4-yl)-1H-indol-7-yl)amino)-2-oxoethyl)azetidine-3-carboxylate |
| 32) | 1-(2-((3-(2-((1,5-dimethyl-1H-pyrazol-3-yl)amino)-5-methylpyrimidin-4-yl)-1H-indol-7-yl)amino)-2-oxoethyl)azetidine-3-carboxylic acid |
| 33) | N-cyclopropyl-3-((1-(2-((3-(2-((1,5-dimethyl-1H-pyrazol-3-yl)amino)-5-methylpyrimidin-4-yl)-1H-indol-7-yl)amino)-2-oxoethyl)azetidin-3-yl)oxy)isoxazole-5-carboxamide |
| 34) | 2-(3,6-dihydro-[4,4'-bipyridin]-1(2H)-yl)-N-(3-(2-((1,5-dimethyl-1H-pyrazol-3-yl)amino)-5-methylpyrimidin-4-yl)-1H-indol-7-yl)acetamide |
| 35) | N-(3-(2-((1,5-dimethyl-1H-pyrazol-3-yl)amino)-5-methylpyrimidin-4-yl)-1H-indol-7-yl)-2-(4-(1-methyl-1H-pyrazol-4-yl)-3,6-dihydropyridin-1(2H)-yl)acetamide |
| 36) | N-(3-(2-((1,5-dimethyl-1H-pyrazol-3-yl)amino)-5-methylpyrimidin-4-yl)-1H-indol-7-yl)-2-(4-(4-methylpiperazin-1-yl)piperidin-1-yl)acetamide |
| 37) | N-(3-(2-((1,5-dimethyl-1H-pyrazol-3-yl)amino)-5-methylpyrimidin-4-yl)-1H-indol-7-yl)-2-(4-morpholinopiperidin-1-yl)acetamide |
| 38) | N-(3-(2-((1,5-dimethyl-1H-pyrazol-3-yl)amino)-5-methylpyrimidin-4-yl)-1H-indol-7-yl)-2-(4-(pyridin-3-yloxy)piperidin-1-yl)acetamide |
| 39) | N-(3-(2-((1,5-dimethyl-1H-pyrazol-3-yl)amino)-5-methylpyrimidin-4-yl)-1H-indol-7-yl)-2-(4-(pyridin-2-yloxy)piperidin-1-yl)acetamide |
| 40) | N-(3-(2-((1,5-dimethyl-1H-pyrazol-3-yl)amino)-5-methylpyrimidin-4-yl)-1H-indol-7-yl)-2-(4-(pyridin-4-yloxy)piperidin-1-yl)acetamide |
| 41) | N-(3-(2-((1,5-dimethyl-1H-pyrazol-3-yl)amino)-5-methylpyrimidin-4-yl)-1H-indol-7-yl)-2-(4-(pyrimidin-2-yloxy)piperidin-1-yl)acetamide |
| 42) | N-(3-(2-((1,5-dimethyl-1H-pyrazol-3-yl)amino)-5-methylpyrimidin-4-yl)-1H-indol-7-yl)-2-(4-((4,6-dimethylpyrimidin-2-yl)oxy)piperidin-1-yl)acetamide |
| 43) | N-cyclopropyl-3-((1-(2-((3-(2-((1,5-dimethyl-1H-pyrazol-3-yl)amino)-5-methylpyrimidin-4-yl)-1H-indol-7-yl)amino)-2-oxoethyl)piperidin-4-yl)oxy)isoxazole-5-carboxamide |
| 44) | N-cyclopropyl-3-((1-(2-((3-(2-((1,5-dimethyl-1H-pyrazol-3-yl)amino)-5-methylpyrimidin-4-yl)-1H-indol-7-yl)amino)-2-oxoethyl)piperidin-3-yl)oxy)isoxazole-5-carboxamide |
| 45) | 2-(3-(cyanomethyl)pyrrolidin-1-yl)-N-(3-(2-((1,5-dimethyl-1H-pyrazol-3-yl)amino)-5-methylpyrimidin-4-yl)-1H-indol-7-yl)acetamide |
| 46) | (R)-2-(3-(cyanomethyl)pyrrolidin-1-yl)-N-(3-(2-((1,5-dimethyl-1H-pyrazol-3-yl)amino)-5-methylpyrimidin-4-yl)-1H-indol-7-yl)acetamide |
| 47) | (S)-N-(3-(2-((1,5-dimethyl-1H-pyrazol-3-yl)amino)-5-methylpyrimidin-4-yl)-1H-indol-7-yl)-2-(3-(pyrimidin-4-ylamino)pyrrolidin-1-yl)acetamide |
| 48) | (R)-N-(3-(2-((1,5-dimethyl-1H-pyrazol-3-yl)amino)-5-methylpyrimidin-4-yl)-1H-indol-7-yl)-2-(3-(pyrimidin-4-ylamino)pyrrolidin-1-yl)acetamide |

| | |
|---|---|
| 49) | (R)-N-(3-(2-((1,5-dimethyl-1H-pyrazol-3-yl)amino)-5-methylpyrimidin-4-yl)-1H-indol-7-yl)-2-(3-(pyridin-4-ylamino)pyrrolidin-1-yl)acetamide |
| 50) | N-(3-(2-((1,5-dimethyl-1H-pyrazol-3-yl)amino)-5-methylpyrimidin-4-yl)-1H-indol-7-yl)-2-((3R,4S)-3-fluoro-4-hydroxypyrrolidin-1-yl)acetamide |
| 51) | N-(3-(2-((1,5-dimethyl-1H-pyrazol-3-yl)amino)-5-methylpyrimidin-4-yl)-1H-indol-7-yl)-2-((3R,4R)-3-fluoro-4-(pyridin-4-yloxy)pyrrolidin-1-yl)acetamide |
| 52) | 2-((3R,4S)-3-((2-(cyclopropylamino)pyrimidin-4-yl)oxy)-4-fluoropyrrolidin-1-yl)-N-(3-(2-((1,5-dimethyl-1H-pyrazol-3-yl)amino)-5-methylpyrimidin-4-yl)-1H-indol-7-yl)acetamide |
| 53) | 2-((3R,4R)-3-((2-(cyclopropylamino)pyrimidin-4-yl)oxy)-4-fluoropyrrolidin-1-yl)-N-(3-(2-((1,5-dimethyl-1H-pyrazol-3-yl)amino)-5-methylpyrimidin-4-yl)-1H-indol-7-yl)acetamide |
| 54) | 2-((3S,4R)-3-((2-(cyclopropylamino)pyrimidin-4-yl)oxy)-4-fluoropyrrolidin-1-yl)-N-(3-(2-((1,5-dimethyl-1H-pyrazol-3-yl)amino)-5-methylpyrimidin-4-yl)-1H-indol-7-yl)acetamide |
| 55) | methyl (2S,4S)-4-((2-(cyclopropylamino)pyrimidin-4-yl)oxy)-1-(2-((3-(2-((1,5-dimethyl-1H-pyrazol-3-yl)amino)-5-methylpyrimidin-4-yl)-1H-indol-7-yl)amino)-2-oxoethyl)pyrrolidine-2-carboxylate |
| 56) | (2S,4S)-4-((2-(cyclopropylamino)pyrimidin-4-yl)oxy)-1-(2-((3-(2-((1,5-dimethyl-1H-pyrazol-3-yl)amino)-5-methylpyrimidin-4-yl)-1H-indol-7-yl)amino)-2-oxoethyl)pyrrolidine-2-carboxylic acid |
| 57) | 2-((2S,4S)-4-((2-(cyclopropylamino)pyrimidin-4-yl)oxy)-2-(hydroxymethyl)pyrrolidin-1-yl)-N-(3-(2-((1,5-dimethyl-1H-pyrazol-3-yl)amino)-5-methylpyrimidin-4-yl)-1H-indol-7-yl)acetamide |
| 58) | (2S,4S)-4-((2-(cyclopropylamino)pyrimidin-4-yl)oxy)-1-(2-((3-(2-((1,5-dimethyl-1H-pyrazol-3-yl)amino)-5-methylpyrimidin-4-yl)-1H-indol-7-yl)amino)-2-oxoethyl)pyrrolidine-2-carboxamide |
| 59) | 2-((2S,4S)-2-(aminomethyl)-4-((2-(cyclopropylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 60) | (S)-2-(3-((2-(cyclopropylamino)pyrimidin-4-yl)oxy)-2-oxopyrrolidin-1-yl)-N-(3-(2-((1,5-dimethyl-1H-pyrazol-3-yl)amino)-5-methylpyrimidin-4-yl)-1H-indol-7-yl)acetamide |
| 61) | (S)-2-(4-((2-(cyclopropylamino)pyrimidin-4-yl)oxy)-2-oxopyrrolidin-1-yl)-N-(3-(2-((1,5-dimethyl-1H-pyrazol-3-yl)amino)-5-methylpyrimidin-4-yl)-1H-indol-7-yl)acetamide |
| 62) | (S)-N-(3-(2-((1,5-dimethyl-1H-pyrazol-3-yl)amino)-5-methylpyrimidin-4-yl)-1H-indol-7-yl)-2-(3-(3-oxopiperazine-1-carbonyl)pyrrolidin-1-yl)acetamide |
| 63) | (S)-N-(3-(2-((1,5-dimethyl-1H-pyrazol-3-yl)amino)-5-methylpyrimidin-4-yl)-1H-indol-7-yl)-2-(3-(morpholine-4-carbonyl)pyrrolidin-1-yl)acetamide |
| 64) | (S)-N-(3-(2-((1,5-dimethyl-1H-pyrazol-3-yl)amino)-5-methylpyrimidin-4-yl)-1H-indol-7-yl)-2-(3-(thiomorpholine-4-carbonyl)pyrrolidin-1-yl)acetamide |
| 65) | (R)-N-(3-(2-((1,5-dimethyl-1H-pyrazol-3-yl)amino)-5-methylpyrimidin-4-yl)-1H-indol-7-yl)-2-(3-(4-methylpiperazine-1-carbonyl)pyrrolidin-1-yl)acetamide |
| 66) | (R)-N-(3-(2-((1,5-dimethyl-1H-pyrazol-3-yl)amino)-5-methylpyrimidin-4-yl)-1H-indol-7-yl)-2-(3-(3-oxopiperazine-1-carbonyl)pyrrolidin-1-yl)acetamide |
| 67) | (R)-N-(3-(2-((1,5-dimethyl-1H-pyrazol-3-yl)amino)-5-methylpyrimidin-4-yl)-1H-indol-7-yl)-2-(3-(morpholine-4-carbonyl)pyrrolidin-1-yl)acetamide |
| 68) | (R)-N-(3-(2-((1,5-dimethyl-1H-pyrazol-3-yl)amino)-5-methylpyrimidin-4-yl)-1H-indol-7-yl)-2-(3-(thiomorpholine-4-carbonyl)pyrrolidin-1-yl)acetamide |
| 69) | (S)-N-(3-(2-((1,5-dimethyl-1H-pyrazol-3-yl)amino)-5-methylpyrimidin-4-yl)-1H-indol-7-yl)-2-(3-(1,2,3,6-tetrahydropyridine-1-carbonyl)pyrrolidin-1-yl)acetamide |
| 70) | N-(3-(2-((1,5-dimethyl-1H-pyrazol-3-yl)amino)-5-methylpyrimidin-4-yl)-1H-indol-7-yl)-2-(3-hydroxypyrrolidin-1-yl)acetamide |
| 71) | (R)-N-(3-(2-((1,5-dimethyl-1H-pyrazol-3-yl)amino)-5-methylpyrimidin-4-yl)-1H-indol-7-yl)-2-(3-hydroxypyrrolidin-1-yl)acetamide |
| 72) | (S)-N-(3-(2-((1,5-dimethyl-1H-pyrazol-3-yl)amino)-5-methylpyrimidin-4-yl)-1H-indol-7-yl)-2-(3-hydroxypyrrolidin-1-yl)acetamide |
| 73) | (S)-N-(3-(2-((1,5-dimethyl-1H-pyrazol-3-yl)amino)-5-methylpyrimidin-4-yl)-1H-indol-7-yl)-2-(3-(pyridin-2-yloxy)pyrrolidin-1-yl)acetamide |
| 74) | (S)-N-(3-(2-((1,5-dimethyl-1H-pyrazol-3-yl)amino)-5-methylpyrimidin-4-yl)-1H-indol-7-yl)-2-(3-(pyridin-3-yloxy)pyrrolidin-1-yl)acetamide |
| 75) | (S)-N-(3-(2-((1,5-dimethyl-1H-pyrazol-3-yl)amino)-5-methylpyrimidin-4-yl)-1H-indol-7-yl)-2-(3-(pyridin-4-yloxy)pyrrolidin-1-yl)acetamide |
| 76) | N-(3-(2-((1,5-dimethyl-1H-pyrazol-3-yl)amino)-5-methylpyrimidin-4-yl)-1H-indol-7-yl)-2-(3-(pyridin-4-yloxy)pyrrolidin-1-yl)acetamide |
| 77) | (R)-N-(3-(2-((1,5-dimethyl-1H-pyrazol-3-yl)amino)-5-methylpyrimidin-4-yl)-1H-indol-7-yl)-2-(3-(pyridin-4-yloxy)pyrrolidin-1-yl)acetamide |
| 78) | (S)-N-(3-(2-((1,5-dimethyl-1H-pyrazol-3-yl)amino)-5-methylpyrimidin-4-yl)-1H-indol-7-yl)-2-(3-(pyrimidin-4-yloxy)pyrrolidin-1-yl)acetamide |
| 79) | (S)-N-(3-(2-((1,5-dimethyl-1H-pyrazol-3-yl)amino)-5-methylpyrimidin-4-yl)-1H-indol-7-yl)-2-(3-(pyrazin-2-yloxy)pyrrolidin-1-yl)acetamide |
| 80) | (S)-N-(3-(2-((1,5-dimethyl-1H-pyrazol-3-yl)amino)-5-methylpyrimidin-4-yl)-1H-indol-7-yl)-2-(3-(4-fluorophenoxy)pyrrolidin-1-yl)acetamide |
| 81) | (S)-N-(3-(2-((1,5-dimethyl-1H-pyrazol-3-yl)amino)-5-methylpyrimidin-4-yl)-1H-indol-7-yl)-2-(3-(3-fluorophenoxy)pyrrolidin-1-yl)acetamide |
| 82) | (S)-2-(3-(4-chlorophenoxy)pyrrolidin-1-yl)-N-(3-(2-((1,5-dimethyl-1H-pyrazol-3-yl)amino)-5-methylpyrimidin-4-yl)-1H-indol-7-yl)acetamide |

-continued

| | |
|---|---|
| 83) | (S)-2-(3-(2,4-difluorophenoxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 84) | (S)-2-(3-(3,4-difluorophenoxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 85) | (S)-2-(3-(3,5-difluorophenoxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 86) | (S)-2-(3-(2-chloro-4-fluorophenoxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 87) | (S)-2-(3-(3-amino-4-fluorophenoxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 88) | (S)-2-(3-(3-aminophenoxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 89) | (S)-2-(3-(3-(diethylamino)phenoxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 90) | (S)-2-(3-((2-chloropyridin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 91) | (S)-2-(3-((2-aminopyridin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 92) | (S)-N-(3-(2-((1,5-dimethyl-1H-pyrazol-3-yl)amino)-5-methylpyrimidin-4-yl)-1H-indol-7-yl)-2-(3-((5-fluoropyrimidin-2-yl)oxy)pyrrolidin-1-yl)acetamide |
| 93) | (S)-2-(3-((6-aminopyrazin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 94) | (S)-2-(3-((6-chloro-5-methylpyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 95) | (S)-2-(3-((2-amino-6-methylpyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 96) | (S)-2-(3-((5-amino-2-chloropyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 97) | (S)-2-(3-((5-bromo-2-methylpyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 98) | (S)-2-(3-((2-amino-6-(5-chloro-2-fluorophenyl)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 99) | (S)-2-(3-((2-amino-6-(trifluoromethyl)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 100) | (S)-2-(3-(([1,1'-biphenyl]-4-yloxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 101) | (S)-N-(3-(2-((1,5-dimethyl-1H-pyrazol-3-yl)amino)-5-methylpyrimidin-4-yl)-1H-indol-7-yl)-2-(3-(4-(2-phenylpropan-2-yl)phenoxy)pyrrolidin-1-yl)acetamide |
| 102) | (S)-N-(3-(2-((1,5-dimethyl-1H-pyrazol-3-yl)amino)-5-methylpyrimidin-4-yl)-1H-indol-7-yl)-2-(3-((5-pentylpyrimidin-2-yl)oxy)pyrrolidin-1-yl)acetamide |
| 103) | (S)-N-(3-(2-((1,5-dimethyl-1H-pyrazol-3-yl)amino)-5-methylpyrimidin-4-yl)-1H-indol-7-yl)-2-(3-(4-((4-methylpiperazin-1-yl)methyl)phenoxy)pyrrolidin-1-yl)acetamide |
| 104) | (S)-N-(3-(2-((1,5-dimethyl-1H-pyrazol-3-yl)amino)-5-methylpyrimidin-4-yl)-1H-indol-7-yl)-2-(3-((1-methyl-1H-pyrazol-5-yl)oxy)pyrrolidin-1-yl)acetamide |
| 105) | (S)-N-(3-(2-((1,5-dimethyl-1H-pyrazol-3-yl)amino)-5-methylpyrimidin-4-yl)-1H-indol-7-yl)-2-(3-((1-methyl-1H-pyrazol-3-yl)oxy)pyrrolidin-1-yl)acetamide |
| 106) | methyl (S)-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)benzo[b]thiophene-2-carboxylate |
| 107) | methyl (S)-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)thiophene-2-carboxylate |
| 108) | (S)-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)thiophene-2-carboxylic acid |
| 109) | (S)-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)thiophene-2-carboxamide |
| 110) | (S)-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)-N-methylthiophene-2- |
| 111) | (S)-N-cyclopropyl-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)thiophene-2- |
| 112) | S)-N-(3-(2-((1,5-dimethyl-1H-pyrazol-3-yl)amino)-5-methylpyrimidin-4-yl)-1H-indol-7-yl)-2-(3-((5-methylisoxazol-3-yl)oxy)pyrrolidin-1-yl)acetamide |
| 113) | (S)-2-(3-(benzo[d]isoxazol-3-yloxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 114) | (S)-N-(3-(2-((1,5-dimethyl-1H-pyrazol-3-yl)amino)-5-methylpyrimidin-4-yl)-1H-indol-7-yl)-2-(3-(isothiazol-3-yloxy)pyrrolidin-1-yl)acetamide |

| | |
|---|---|
| 115) | (S)-N-(3-(2-((1,5-dimethyl-1H-pyrazol-3-yl)amino)-5-methylpyrimidin-4-yl)-1H-indol-7-yl)-2-(3-((2-methylthiophen-3-yl)oxy)pyrrolidin-1-yl)acetamide |
| 116) | (S)-2-(3-((1H-pyrazol-3-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 117) | (R)-N-(3-(2-((1,5-dimethyl-1H-pyrazol-3-yl)amino)-5-methylpyrimidin-4-yl)-1H-indol-7-yl)-2-(3-((1-methyl-5-(trifluoromethyl)-1H-pyrazol-3-yl)oxy)pyrrolidin-1-yl)acetamide |
| 118) | (S)-N-(3-(2-((1,5-dimethyl-1H-pyrazol-3-yl)amino)-5-methylpyrimidin-4-yl)-1H-indol-7-yl)-2-(3-(isoxazol-3-yloxy)pyrrolidin-1-yl)acetamide |
| 119) | (S)-2-(3-((5-amino-1H-pyrazol-3-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 120) | methyl (S)-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)-1H-pyrrole-2-carboxylate |
| 121) | ethyl (S)-5-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)isoxazole-4-carboxylate |
| 122) | (S)-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)isoxazole-5-carboxamide |
| 123) | (S)-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)-N-methylisoxazole-5-carboxamide |
| 124) | (S)-N-cyclopropyl-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)isoxazole-5-carboxamide |
| 125) | (S)-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)-N,N-dimethylisoxazole-5-carboxamide |
| 126) | (S)-N-cyclopropyl-2-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)oxazole-5-carboxamide |
| 127) | (S)-N-cyclopropyl-2-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)oxazole-4-carboxamide |
| 128) | (S)-2-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)pyrimidine-4-carboxylic acid |
| 129) | (S)-2-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)pyrimidine-4-carboxamide |
| 130) | (S)-2-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)-N-methylpyrimidine-4-carboxamide |
| 131) | (S)-2-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)-N,N-dimethylpyrimidine-4-carboxamide |
| 132) | (S)-6-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)pyrazine-2-carboxamide |
| 133) | (S)-6-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)-N-methylpyrazine-2-carboxamide |
| 134) | (S)-2-(3-((4-amino-1,3,5-triazin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 135) | (S)-N-(3-(2-((1,5-dimethyl-1H-pyrazol-3-yl)amino)-5-methylpyrimidin-4-yl)-1H-indol-7-yl)-2-(3-((4-(methylamino)-1,3,5-triazin-2-yl)oxy)pyrrolidin-1-yl)acetamide |
| 136) | (S)-N-(3-(2-((1,5-dimethyl-1H-pyrazol-3-yl)amino)-5-methylpyrimidin-4-yl)-1H-indol-7-yl)-2-(3-((4-(dimethylamino)-1,3,5-triazin-2-yl)oxy)pyrrolidin-1-yl)acetamide |
| 137) | (S)-2-(3-((4-(cyclopropylamino)-1,3,5-triazin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 138) | (S)-2-(3-((4,6-diamino-1,3,5-triazin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 139) | (S)-2-(3-((4-amino-6-(pyrrolidin-1-yl)-1,3,5-triazin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 140) | (S)-2-(3-((6-aminopyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 141) | (S)-N-(3-(2-((1,5-dimethyl-1H-pyrazol-3-yl)amino)-5-methylpyrimidin-4-yl)-1H-indol-7-yl)-2-(3-((6-(methylamino)pyrimidin-4-yl)oxy)pyrrolidin-1-yl)acetamide |
| 142) | (S)-N-(3-(2-((1,5-dimethyl-1H-pyrazol-3-yl)amino)-5-methylpyrimidin-4-yl)-1H-indol-7-yl)-2-(3-((6-(ethylamino)pyrimidin-4-yl)oxy)pyrrolidin-1-yl)acetamide |

| | |
|---|---|
| 143) | (S)-N-(3-(2-((1,5-dimethyl-1H-pyrazol-3-yl)amino)-5-methylpyrimidin-4-yl)-1H-indol-7-yl)-2-(3-((6-(propylamino)pyrimidin-4-yl)oxy)pyrrolidin-1-yl)acetamide |
| 144) | (S)-2-(3-((6-(butylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 145) | (S)-N-(3-(2-((1,5-dimethyl-1H-pyrazol-3-yl)amino)-5-methylpyrimidin-4-yl)-1H-indol-7-yl)-2-(3-((6-((2-hydroxyethyl)amino)pyrimidin-4-yl)oxy)pyrrolidin-1-yl)acetamide |
| 146) | (S)-N-(3-(2-((1,5-dimethyl-1H-pyrazol-3-yl)amino)-5-methylpyrimidin-4-yl)-1H-indol-7-yl)-2-(3-((6-((3-hydroxypropyl)amino)pyrimidin-4-yl)oxy)pyrrolidin-1-yl)acetamide |
| 147) | (S)-N-(3-(2-((1,5-dimethyl-1H-pyrazol-3-yl)amino)-5-methylpyrimidin-4-yl)-1H-indol-7-yl)-2-(3-((6-((2-methoxyethyl)amino)pyrimidin-4-yl)oxy)pyrrolidin-1-yl)acetamide |
| 148) | (S)-N-(3-(2-((1,5-dimethyl-1H-pyrazol-3-yl)amino)-5-methylpyrimidin-4-yl)-1H-indol-7-yl)-2-(3-((6-((3-(dimethylamino)propyl)amino)pyrimidin-4-yl)oxy)pyrrolidin-1-yl)acetamide |
| 149) | (S)-2-(3-((6-(benzylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 150) | (S)-N-(3-(2-((1,5-dimethyl-1H-pyrazol-3-yl)amino)-5-methylpyrimidin-4-yl)-1H-indol-7-yl)-2-(3-((6-(phenethylamino)pyrimidin-4-yl)oxy)pyrrolidin-1-yl)acetamide |
| 151) | (S)-2-(3-((6-(cyclopropylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 152) | (S)-2-(3-((6-(cyclohexylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 153) | (S)-N-(3-(2-((1,5-dimethyl-1H-pyrazol-3-yl)amino)-5-methylpyrimidin-4-yl)-1H-indol-7-yl)-2-(3-((6-(dimethylamino)pyrimidin-4-yl)oxy)pyrrolidin-1-yl)acetamide |
| 154) | (S)-N-(3-(2-((1,5-dimethyl-1H-pyrazol-3-yl)amino)-5-methylpyrimidin-4-yl)-1H-indol-7-yl)-2-(3-((6-(ethyl(methyl)amino)pyrimidin-4-yl)oxy)pyrrolidin-1-yl)acetamide |
| 155) | (S)-2-(3-((6-(diethylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 156) | (S)-N-(3-(2-((1,5-dimethyl-1H-pyrazol-3-yl)amino)-5-methylpyrimidin-4-yl)-1H-indol-7-yl)-2-(3-((6-(ethyl(propyl)amino)pyrimidin-4-yl)oxy)pyrrolidin-1-yl)acetamide |
| 157) | (S)-2-(3-((6-(butyl(ethyl)amino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 158) | (S)-N-(3-(2-((1,5-dimethyl-1H-pyrazol-3-yl)amino)-5-methylpyrimidin-4-yl)-1H-indol-7-yl)-2-(3-((6-(pyrrolidin-1-yl)pyrimidin-4-yl)oxy)pyrrolidin-1-yl)acetamide |
| 159) | N-(3-(2-((1,5-dimethyl-1H-pyrazol-3-yl)amino)-5-methylpyrimidin-4-yl)-1H-indol-7-yl)-2-((3S)-3-((6-(3-hydroxypyrrolidin-1-yl)pyrimidin-4-yl)oxy)pyrrolidin-1-yl)acetamide |
| 160) | N-(3-(2-((1,5-dimethyl-1H-pyrazol-3-yl)amino)-5-methylpyrimidin-4-yl)-1H-indol-7-yl)-2-((S)-3-((6-((R)-3-hydroxypyrrolidin-1-yl)pyrimidin-4-yl)oxy)pyrrolidin-1-yl)acetamide |
| 161) | N-(3-(2-((1,5-dimethyl-1H-pyrazol-3-yl)amino)-5-methylpyrimidin-4-yl)-1H-indol-7-yl)-2-((S)-3-((6-((S)-3-hydroxypyrrolidin-1-yl)pyrimidin-4-yl)oxy)pyrrolidin-1-yl)acetamide |
| 162) | (S)-N-(3-(2-((1,5-dimethyl-1H-pyrazol-3-yl)amino)-5-methylpyrimidin-4-yl)-1H-indol-7-yl)-2-(3-((6-(piperidin-1-yl)pyrimidin-4-yl)oxy)pyrrolidin-1-yl)acetamide |
| 163) | (S)-N-(3-(2-((1,5-dimethyl-1H-pyrazol-3-yl)amino)-5-methylpyrimidin-4-yl)-1H-indol-7-yl)-2-(3-((6-(4-hydroxypiperidin-1-yl)pyrimidin-4-yl)oxy)pyrrolidin-1-yl)acetamide |
| 164) | (S)-N-(3-(2-((1,5-dimethyl-1H-pyrazol-3-yl)amino)-5-methylpyrimidin-4-yl)-1H-indol-7-yl)-2-(3-((6-morpholinopyrimidin-4-yl)oxy)pyrrolidin-1-yl)acetamide |
| 165) | (S)-N-(3-(2-((1,5-dimethyl-1H-pyrazol-3-yl)amino)-5-methylpyrimidin-4-yl)-1H-indol-7-yl)-2-(3-((6-(4-methylpiperazin-1-yl)pyrimidin-4-yl)oxy)pyrrolidin-1-yl)acetamide |
| 166) | (S)-2-(3-((2-amino-6-(methylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 167) | (S)-2-(3-((2-amino-6-(pyrrolidin-1-yl)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 168) | (S)-2-(3-((4-aminopyrimidin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |

-continued

| | |
|---|---|
| 169) | (S)-N-(3-(2-((1,5-dimethyl-1H-pyrazol-3-yl)amino)-5-methylpyrimidin-4-yl)-1H-indol-7-yl)-2-(3-((4-(methylamino)pyrimidin-2-yl)oxy)pyrrolidin-1-yl)acetamide |
| 170) | (S)-N-(3-(2-((1,5-dimethyl-1H-pyrazol-3-yl)amino)-5-methylpyrimidin-4-yl)-1H-indol-7-yl)-2-(3-((4-(dimethylamino)pyrimidin-2-yl)oxy)pyrrolidin-1-yl)acetamide |
| 171) | (S)-N-(3-(2-((1,5-dimethyl-1H-pyrazol-3-yl)amino)-5-methylpyrimidin-4-yl)-1H-indol-7-yl)-2-(3-((4-(ethyl(methyl)amino)pyrimidin-2-yl)oxy)pyrrolidin-1-yl)acetamide |
| 172) | (S)-2-(3-((4-(diethylamino)pyrimidin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 173) | (S)-N-(3-(2-((1,5-dimethyl-1H-pyrazol-3-yl)amino)-5-methylpyrimidin-4-yl)-1H-indol-7-yl)-2-(3-((4-(pyrrolidin-1-yl)pyrimidin-2-yl)oxy)pyrrolidin-1-yl)acetamide |
| 174) | (S)-N-(3-(2-((1,5-dimethyl-1H-pyrazol-3-yl)amino)-5-methylpyrimidin-4-yl)-1H-indol-7-yl)-2-(3-((4-(piperidin-1-yl)pyrimidin-2-yl)oxy)pyrrolidin-1-yl)acetamide |
| 175) | (S)-2-(3-((4-(cyclopropylamino)pyrimidin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 176) | (S)-2-(3-((4-amino-5-fluoropyrimidin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 177) | (S)-N-(3-(2-((1,5-dimethyl-1H-pyrazol-3-yl)amino)-5-methylpyrimidin-4-yl)-1H-indol-7-yl)-2-(3-((5-fluoro-4-(methylamino)pyrimidin-2-yl)oxy)pyrrolidin-1-yl)acetamide |
| 178) | (S)-N-(3-(2-((1,5-dimethyl-1H-pyrazol-3-yl)amino)-5-methylpyrimidin-4-yl)-1H-indol-7-yl)-2-(3-((4-(ethylamino)-5-fluoropyrimidin-2-yl)oxy)pyrrolidin-1-yl)acetamide |
| 179) | (S)-2-(3-((4-(cyclopropylamino)-5-fluoropyrimidin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 180) | (S)-2-(3-((4-(cyclohexylamino)-5-fluoropyrimidin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 181) | (S)-N-(3-(2-((1,5-dimethyl-1H-pyrazol-3-yl)amino)-5-methylpyrimidin-4-yl)-1H-indol-7-yl)-2-(3-((4-(dimethylamino)-5-fluoropyrimidin-2-yl)oxy)pyrrolidin-1-yl)acetamide |
| 182) | (S)-N-(3-(2-((1,5-dimethyl-1H-pyrazol-3-yl)amino)-5-methylpyrimidin-4-yl)-1H-indol-7-yl)-2-(3-((4-(ethyl(methyl)amino)-5-fluoropyrimidin-2-yl)oxy)pyrrolidin-1-yl)acetamide |
| 183) | (S)-2-(3-((4-(diethylamino)-5-fluoropyrimidin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 184) | (S)-N-(3-(2-((1,5-dimethyl-1H-pyrazol-3-yl)amino)-5-methylpyrimidin-4-yl)-1H-indol-7-yl)-2-(3-((5-fluoro-4-(methyl(phenyl)amino)pyrimidin-2-yl)oxy)pyrrolidin-1-yl)acetamide |
| 185) | (S)-2-(3-((4-(benzyl(methyl)amino)-5-fluoropyrimidin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 186) | (S)-N-(3-(2-((1,5-dimethyl-1H-pyrazol-3-yl)amino)-5-methylpyrimidin-4-yl)-1H-indol-7-yl)-2-(3-((5-fluoro-4-(pyrrolidin-1-yl)pyrimidin-2-yl)oxy)pyrrolidin-1-yl)acetamide |
| 187) | (S)-N-(3-(2-((1,5-dimethyl-1H-pyrazol-3-yl)amino)-5-methylpyrimidin-4-yl)-1H-indol-7-yl)-2-(3-((5-fluoro-4-(piperidin-1-yl)pyrimidin-2-yl)oxy)pyrrolidin-1-yl)acetamide |
| 188) | (S)-N-(3-(2-((1,5-dimethyl-1H-pyrazol-3-yl)amino)-5-methylpyrimidin-4-yl)-1H-indol-7-yl)-2-(3-((5-fluoro-4-morpholinopyrimidin-2-yl)oxy)pyrrolidin-1-yl)acetamide |
| 189) | (S)-N-(3-(2-((1,5-dimethyl-1H-pyrazol-3-yl)amino)-5-methylpyrimidin-4-yl)-1H-indol-7-yl)-2-(3-((5-fluoro-4-thiomorpholinopyrimidin-2-yl)oxy)pyrrolidin-1-yl)acetamide |
| 190) | (S)-N-(3-(2-((1,5-dimethyl-1H-pyrazol-3-yl)amino)-5-methylpyrimidin-4-yl)-1H-indol-7-yl)-2-(3-((5-fluoro-4-(4-methylpiperazin-1-yl)pyrimidin-2-yl)oxy)pyrrolidin-1-yl)acetamide |
| 191) | (S)-2-(3-((4-(cyclopropylamino)-5-methylpyrimidin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 192) | (S)-2-(3-((2-aminopyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 193) | (S)-N-(3-(2-((1,5-dimethyl-1H-pyrazol-3-yl)amino)-5-methylpyrimidin-4-yl)-1H-indol-7-yl)-2-(3-((2-(methylthio)pyrimidin-4-yl)oxy)pyrrolidin-1-yl)acetamide |
| 194) | (S)-N-(3-(2-((1,5-dimethyl-1H-pyrazol-3-yl)amino)-5-methylpyrimidin-4-yl)-1H-indol-7-yl)-2-(3-((2-methoxypyrimidin-4-yl)oxy)pyrrolidin-1-yl)acetamide |
| 195) | (S)-2-(3-((2-(benzyloxy)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |

| | |
|---|---|
| 196) | (S)-2-(3-((2-acetamidopyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 197) | (S)-N-(3-(2-((1,5-dimethyl-1H-pyrazol-3-yl)amino)-5-methylpyrimidin-4-yl)-1H-indol-7-yl)-2-(3-((2-(methylamino)pyrimidin-4-yl)oxy)pyrrolidin-1-yl)acetamide |
| 198) | (S)-N-(3-(2-((1,5-dimethyl-1H-pyrazol-3-yl)amino)-5-methylpyrimidin-4-yl)-1H-indol-7-yl)-2-(3-((2-((2,2,2-trifluoroethyl)amino)pyrimidin-4-yl)oxy)pyrrolidin-1-yl)acetamide |
| 199) | (S)-2-(3-((2-((2,2-difluoropropyl)amino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 200) | (S)-2-(3-((2-((2,2-difluoroethyl)amino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 201) | N-(3-(2-((1,5-dimethyl-1H-pyrazol-3-yl)amino)-5-methylpyrimidin-4-yl)-1H-indol-7-yl)-2-((3S)-3-((2-((1,1,1-trifluoropropan-2-yl)amino)pyrimidin-4-yl)oxy)pyrrolidin-1-yl)acetamide |
| 202) | (S)-N-(3-(2-((1,5-dimethyl-1H-pyrazol-3-yl)amino)-5-methylpyrimidin-4-yl)-1H-indol-7-yl)-2-(3-((2-((2-fluoroethyl)amino)pyrimidin-4-yl)oxy)pyrrolidin-1-yl)acetamide |
| 203) | (S)-N-(3-(2-((1,5-dimethyl-1H-pyrazol-3-yl)amino)-5-methylpyrimidin-4-yl)-1H-indol-7-yl)-2-(3-((2-(ethylamino)pyrimidin-4-yl)oxy)pyrrolidin-1-yl)acetamide |
| 204) | (S)-N-(3-(2-((1,5-dimethyl-1H-pyrazol-3-yl)amino)-5-methylpyrimidin-4-yl)-1H-indol-7-yl)-2-(3-((2-(propylamino)pyrimidin-4-yl)oxy)pyrrolidin-1-yl)acetamide |
| 205) | (S)-2-(3-((2-(butylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 206) | (S)-N-(3-(2-((1,5-dimethyl-1H-pyrazol-3-yl)amino)-5-methylpyrimidin-4-yl)-1H-indol-7-yl)-2-(3-((2-((3-hydroxypropyl)amino)pyrimidin-4-yl)oxy)pyrrolidin-1-yl)acetamide |
| 207) | (S)-2-(3-((2-(cyclopropylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 208) | (S)-2-(3-((2-(cyclobutylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 209) | (S)-2-(3-((2-(cyclopentylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 210) | (S)-2-(3-((2-(cyclohexylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 211) | (S)-N-(3-(2-((1,5-dimethyl-1H-pyrazol-3-yl)amino)-5-methylpyrimidin-4-yl)-1H-indol-7-yl)-2-(3-((2-(isopropylamino)pyrimidin-4-yl)oxy)pyrrolidin-1-yl)acetamide |
| 212) | 2-((3S)-3-((2-(sec-butylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 213) | (S)-2-(3-((2-((cyclopropylmethyl)amino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 214) | (S)-2-(3-((2-(benzylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 215) | (S)-N-(3-(2-((1,5-dimethyl-1H-pyrazol-3-yl)amino)-5-methylpyrimidin-4-yl)-1H-indol-7-yl)-2-(3-((2-((2-hydroxyethyl)amino)pyrimidin-4-yl)oxy)pyrrolidin-1-yl)acetamide |
| 216) | (S)-N-(3-(2-((1,5-dimethyl-1H-pyrazol-3-yl)amino)-5-methylpyrimidin-4-yl)-1H-indol-7-yl)-2-(3-((2-((2-methoxyethyl)amino)pyrimidin-4-yl)oxy)pyrrolidin-1-yl)acetamide |
| 217) | (S)-N-(3-(2-((1,5-dimethyl-1H-pyrazol-3-yl)amino)-5-methylpyrimidin-4-yl)-1H-indol-7-yl)-2-(3-((2-((2-(dimethylamino)ethyl)amino)pyrimidin-4-yl)oxy)pyrrolidin-1-yl)acetamide |
| 218) | (S)-N-(3-(2-((1,5-dimethyl-1H-pyrazol-3-yl)amino)-5-methylpyrimidin-4-yl)-1H-indol-7-yl)-2-(3-((2-((3-(dimethylamino)propyl)amino)pyrimidin-4-yl)oxy)pyrrolidin-1-yl)acetamide |
| 219) | (S)-N-(3-(2-((1,5-dimethyl-1H-pyrazol-3-yl)amino)-5-methylpyrimidin-4-yl)-1H-indol-7-yl)-2-(3-((2-(methoxyamino)pyrimidin-4-yl)oxy)pyrrolidin-1-yl)acetamide |
| 220) | (S)-N-(3-(2-((1,5-dimethyl-1H-pyrazol-3-yl)amino)-5-methylpyrimidin-4-yl)-1H-indol-7-yl)-2-(3-((2-(dimethylamino)pyrimidin-4-yl)oxy)pyrrolidin-1-yl)acetamide |
| 221) | (S)-2-(3-((2-(benzyl(methyl)amino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |

-continued

| | |
|---|---|
| 222) | (S)-N-(3-(2-((1,5-dimethyl-1H-pyrazol-3-yl)amino)-5-methylpyrimidin-4-yl)-1H-indol-7-yl)-2-(3-((2-(pyrrolidin-1-yl)pyrimidin-4-yl)oxy)pyrrolidin-1-yl)acetamide |
| 223) | (S)-N-(3-(2-((1,5-dimethyl-1H-pyrazol-3-yl)amino)-5-methylpyrimidin-4-yl)-1H-indol-7-yl)-2-(3-((2-(piperidin-1-yl)pyrimidin-4-yl)oxy)pyrrolidin-1-yl)acetamide. |
| 224) | (S)-N-(3-(2-((1,5-dimethyl-1H-pyrazol-3-yl)amino)-5-methylpyrimidin-4-yl)-1H-indol-7-yl)-2-(3-((2-morpholinopyrimidin-4-yl)oxy)pyrrolidin-1-yl)acetamide |
| 225) | (S)-N-(3-(2-((1,5-dimethyl-1H-pyrazol-3-yl)amino)-5-methylpyrimidin-4-yl)-1H-indol-7-yl)-2-(3-((2-(4-methylpiperazin-1-yl)pyrimidin-4-yl)oxy)pyrrolidin-1-yl)acetamide |
| 226) | (S)-2-(3-((2-amino-5-fluoropyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 227) | (S)-2-(3-((2-(cyclopropylamino)-5-fluoropyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 228) | (S)-2-(3-((2-(cyclohexylamino)-5-fluoropyrimidin-4-yl)oxy)pyrrolidine-1-yl)-N-(3-(2-((1,5-dimethyl-1H-pyrazol-3-yl)amino)-5-methylpyrimidin-4-yl)-1H-indol-7-yl)acetamide |
| 229) | (S)-2-(3-((2-((cyclopropylmethyl)amino)-5-fluoropyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 230) | (S)-2-(3-((2-(benzylamino)-5-fluoropyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 231) | (S)-N-(3-(2-((1,5-dimethyl-1H-pyrazol-3-yl)amino)-5-methylpyrimidin-4-yl)-1H-indol-7-yl)-2-(3-((2-(dimethylamino)-5-fluoropyrimidin-4-yl)oxy)pyrrolidin-1-yl)acetamide |
| 232) | (S)-N-(3-(2-((1,5-dimethyl-1H-pyrazol-3-yl)amino)-5-methylpyrimidin-4-yl)-1H-indol-7-yl)-2-(3-((5-fluoro-2-morpholinopyrimidin-4-yl)oxy)pyrrolidin-1-yl)acetamide |
| 233) | (S)-N-(3-(2-((1,5-dimethyl-1H-pyrazol-3-yl)amino)-5-methylpyrimidin-4-yl)-1H-indol-7-yl)-2-(3-((5-fluoro-2-(4-methylpiperazin-1-yl)pyrimidin-4-yl)oxy)pyrrolidin-1-yl)acetamide |
| 234) | (S)-2-(3-((2-(cyclopropylamino)-6-fluoropyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 235) | (S)-2-(3-((2-(cyclopropylamino)-5-methylpyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 236) | (S)-2-(3-((2-(cyclopropylamino)-6-methylpyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 237) | (S)-2-(3-((2-(cyclopropylamino)-6-(trifluoromethyl)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 238) | (S)-2-(3-((2-(cyclopropylamino)-6-methoxypyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 239) | (S)-N-(3-(2-((1,5-dimethyl-1H-pyrazol-3-yl)amino)-5-methylpyrimidin-4-yl)-1H-indol-7-yl)-2-(3-((2-((2-(dimethylamino)ethyl)amino)pyrimidin-5-yl)oxy)pyrrolidin-1-yl)acetamide |
| 240) | (S)-N-(3-(2-((1,5-dimethyl-1H-pyrazol-3-yl)amino)-5-methylpyrimidin-4-yl)-1H-indol-7-yl)-2-(3-((2-(dimethylamino)pyrimidin-5-yl)oxy)pyrrolidin-1-yl)acetamide |
| 241) | (S)-N-(3-(2-((1,5-dimethyl-1H-pyrazol-3-yl)amino)-5-methylpyrimidin-4-yl)-1H-indol-7-yl)-2-(3-((2-morpholinopyrimidin-5-yl)oxy)pyrrolidin-1-yl)acetamide |
| 242) | (S)-N-(3-(2-((1,5-dimethyl-1H-pyrazol-3-yl)amino)-5-methylpyrimidin-4-yl)-1H-indol-7-yl)-2-(3-((2-(4-methylpiperazin-1-yl)pyrimidin-5-yl)oxy)pyrrolidin-1-yl)acetamide |
| 243) | (S)-2-(3-((6-(cyclopropylamino)pyrazin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 244) | (S)-N-(3-(2-((1,5-dimethyl-1H-pyrazol-3-yl)amino)-5-methylpyrimidin-4-yl)-1H-indol-7-yl)-2-(3-((6-(ethylamino)pyrazin-2-yl)oxy)pyrrolidin-1-yl)acetamide |
| 245) | (S)-N-(3-(2-((1,5-dimethyl-1H-pyrazol-3-yl)amino)-5-methylpyrimidin-4-yl)-1H-indol-7-yl)-2-(3-((6-(propylamino)pyrazin-2-yl)oxy)pyrrolidin-1-yl)acetamide |
| 246) | (S)-N-(3-(2-((1,5-dimethyl-1H-pyrazol-3-yl)amino)-5-methylpyrimidin-4-yl)-1H-indol-7-yl)-2-(3-((6-((2-hydroxyethyl)amino)pyrazin-2-yl)oxy)pyrrolidin-1-yl)acetamide |
| 247) | (S)-N-(3-(2-((1,5-dimethyl-1H-pyrazol-3-yl)amino)-5-methylpyrimidin-4-yl)-1H-indol-7-yl)-2-(3-((6-((2-(dimethylamino)ethyl)amino)pyrazin-2-yl)oxy)pyrrolidin-1-yl)acetamide |

| | |
|---|---|
| 248) | (S)-N-(3-(2-((1,5-dimethyl-1H-pyrazol-3-yl)amino)-5-methylpyrimidin-4-yl)-1H-indol-7-yl)-2-(3-((6-phenylpyrimidin-4-yl)oxy)pyrrolidin-1-yl)acetamide |
| 249) | S)-N-(3-(2-((1,5-dimethyl-1H-pyrazol-3-yl)amino)-5-methylpyrimidin-4-yl)-1H-indol-7-yl)-2-(3-((6-(1-methyl-1H-pyrazol-4-yl)pyrimidin-4-yl)oxy)pyrrolidin-1-yl)acetamide |
| 250) | (S)-2-(3-((6-(3,6-dihydro-2H-pyran-4-yl)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 251) | (S)-2-(3-((6-(3,6-dihydro-2H-pyran-4-yl)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 252) | (S)-N-(3-(2-((1,5-dimethyl-1H-pyrazol-3-yl)amino)-5-methylpyrimidin-4-yl)-1H-indol-7-yl)-2-(3-((4-(4,4-dimethylcyclohex-1-en-1-yl)pyrimidin-2-yl)oxy)pyrrolidin-1-yl)acetamide |
| 253) | (S)-2-(3-((4-(3,6-dihydro-2H-pyran-4-yl)pyrimidin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 254) | (S)-N-(3-(2-((1,5-dimethyl-1H-pyrazol-3-yl)amino)-5-methylpyrimidin-4-yl)-1H-indol-7-yl)-2-(3-((4-phenylpyrimidin-2-yl)oxy)pyrrolidin-1-yl)acetamide |
| 255) | (S)-N-(3-(2-((1,5-dimethyl-1H-pyrazol-3-yl)amino)-5-methylpyrimidin-4-yl)-1H-indol-7-yl)-2-(3-((5-(pyridin-3-yl)pyrimidin-2-yl)oxy)pyrrolidin-1-yl)acetamide |
| 256) | (S)-N-(3-(2-((1,5-dimethyl-1H-pyrazol-3-yl)amino)-5-methylpyrimidin-4-yl)-1H-indol-7-yl)-2-(3-((5-(pyridin-4-yl)pyrimidin-2-yl)oxy)pyrrolidin-1-yl)acetamide |
| 257) | N-(3-(2-((1,5-dimethyl-1H-pyrazol-3-yl)amino)-5-methylpyrimidin-4-yl)-1H-indol-7-yl)-2-(3-((2-phenylpyrimidin-5-yl)oxy)pyrrolidin-1-yl)acetamide |
| 258) | (S)-N-(3-(2-((1,5-dimethyl-1H-pyrazol-3-yl)amino)-5-methylpyrimidin-4-yl)-1H-indol-7-yl)-2-(3-((2-(pyridin-3-yl)pyrimidin-5-yl)oxy)pyrrolidin-1-yl)acetamide |
| 259) | (S)-N-(3-(2-((1,5-dimethyl-1H-pyrazol-3-yl)amino)-5-methylpyrimidin-4-yl)-1H-indol-7-yl)-2-(3-((2-(pyridin-4-yl)pyrimidin-5-yl)oxy)pyrrolidin-1-yl)acetamide |
| 260) | 2-(3-(2-((1,5-dimethyl-1H-pyrazol-3-yl)amino)-5-methylpyrimidin-4-yl)-1H-indol-7-yl)isoindoline-1,3-dione |
| 261) | 2-(3-(2-((1,5-dimethyl-1H-pyrazol-3-yl)amino)-5-methylpyrimidin-4-yl)-1H-indol-7-yl)-4-fluoroisoindoline-1,3-dione |
| 262) | 4-bromo-2-(3-(2-((1,5-dimethyl-1H-pyrazol-3-yl)amino)-5-methylpyrimidin-4-yl)-1H-indol-7-yl)isoindoline-1,3-dione |
| 263) | 2-(3-(2-((1,5-dimethyl-1H-pyrazol-3-yl)amino)-5-methylpyrimidin-4-yl)-1H-indol-7-yl)-4-hydroxyisoindoline-1,3-dione |
| 264) | 2-(3-(2-((1,5-dimethyl-1H-pyrazol-3-yl)amino)-5-methylpyrimidin-4-yl)-1H-indol-7-yl)-5-nitroisoindoline-1,3-dione |
| 265) | 6-(3-(2-((1,5-dimethyl-1H-pyrazol-3-yl)amino)-5-methylpyrimidin-4-yl)-1H-indol-7-yl)-5H-pyrrolo[3,4-b]pyridine-5,7(6H)-dione |
| 266) | 4-bromo-2-(3-(2-((1,5-dimethyl-1H-pyrazol-3-yl)amino)-5-methylpyrimidin-4-yl)-1H-indol-7-yl)isoindolin-1-one |
| 267) | 2-(3-(2-((1,5-dimethyl-1H-pyrazol-3-yl)amino)-5-methylpyrimidin-4-yl)-1H-indol-7-yl)isoindolin-1-one |
| 268) | 2-(3-(2-((1,5-dimethyl-1H-pyrazol-3-yl)amino)-5-methylpyrimidin-4-yl)-1H-indol-7-yl)-6-nitroisoindolin-1-one |
| 269) | 6-amino-2-(3-(2-((1,5-dimethyl-1H-pyrazol-3-yl)amino)-5-methylpyrimidin-4-yl)-1H-indol-7-yl)isoindolin-1-one |
| 270) | 5-bromo-2-(3-(2-((1,5-dimethyl-1H-pyrazol-3-yl)amino)-5-methylpyrimidin-4-yl)-1H-indol-7-yl)isoindolin-1-one |
| 271) | 2-(3-(2-((1,5-dimethyl-1H-pyrazol-3-yl)amino)-5-methylpyrimidin-4-yl)-1H-indol-7-yl)-4-nitroisoindolin-1-one |
| 272) | 4-amino-2-(3-(2-((1,5-dimethyl-1H-pyrazol-3-yl)amino)-5-methylpyrimidin-4-yl)-1H-indol-7-yl)isoindolin-1-one |
| 273) | 7-chloro-2-(3-(2-((1,5-dimethyl-1H-pyrazol-3-yl)amino)-5-methylpyrimidin-4-yl)-1H-indol-7-yl)isoindolin-1-one |
| 274) | 2-(3-(2-((1,5-dimethyl-1H-pyrazol-3-yl)amino)-5-methylpyrimidin-4-yl)-1H-indol-7-yl)-7-nitroisoindolin-1-one |
| 275) | 2-(3-(2-((1,5-dimethyl-1H-pyrazol-3-yl)amino)-5-methylpyrimidin-4-yl)-1H-indol-7-yl)-7-iodoisoindolin-1-one |
| 276) | 7-amino-2-(3-(2-((1,5-dimethyl-1H-pyrazol-3-yl)amino)-5-methylpyrimidin-4-yl)-1H-indol-7-yl)isoindolin-1-one |
| 277) | 7-bromo-2-(3-(2-((1,5-dimethyl-1H-pyrazol-3-yl)amino)-5-methylpyrimidin-4-yl)-1H-indol-7-yl)isoindolin-1-one |
| 278) | 2-(3-(2-((1,5-dimethyl-1H-pyrazol-3-yl)amino)-5-methylpyrimidin-4-yl)-1H-indol-7-yl)-4-iodoisoindolin-1-one |
| 279) | 2-(3-(2-((1,5-dimethyl-1H-pyrazol-3-yl)amino)-5-methylpyrimidin-4-yl)-1H-indol-7-yl)-6-methoxyisoindolin-1-one |
| 280) | 2-(3-(2-((1,5-dimethyl-1H-pyrazol-3-yl)amino)-5-methylpyrimidin-4-yl)-1H-indol-7-yl)-4,6-dimethoxyisoindolin-1-one |
| 281) | 2-(3-(2-((1,5-dimethyl-1H-pyrazol-3-yl)amino)-5-methylpyrimidin-4-yl)-1H-indol-7-yl)-4-hydroxyisoindolin-1-one |
| 282) | 2-(3-(2-((1,5-dimethyl-1H-pyrazol-3-yl)amino)-5-methylpyrimidin-4-yl)-1H-indol-7-yl)-7-fluoroisoindolin-1-one |

| | |
|---|---|
| 283) | 4-bromo-2-(3-(2-((1,5-dimethyl-1H-pyrazol-3-yl)amino)-5-methylpyrimidin-4-yl)-1H-indol-7-yl)-7-fluoroisoindolin-1-one |
| 284) | 6-bromo-2-(3-(2-((1,5-dimethyl-1H-pyrazol-3-yl)amino)-5-methylpyrimidin-4-yl)-1H-indol-7-yl)isoindolin-1-one |
| 285) | 3-bromo-6-(3-(2-((1,5-dimethyl-1H-pyrazol-3-yl)amino)-5-methylpyrimidin-4-yl)-1H-indol-7-yl)-5,6-dihydro-7H-pyrrolo[3,4-b]pyridin-7-one |
| 286) | 4-bromo-6-(3-(2-((1,5-dimethyl-1H-pyrazol-3-yl)amino)-5-methylpyrimidin-4-yl)-1H-indol-7-yl)-5,6-dihydro-7H-pyrrolo[3,4-b]pyridin-7-one |
| 287) | 6-(3-(2-((1,5-dimethyl-1H-pyrazol-3-yl)amino)-5-methylpyrimidin-4-yl)-1H-indol-7-yl)-3-methyl-5,6-dihydro-7H-pyrrolo[3,4-b]pyridin-7-one |
| 288) | 6-(3-(2-((1,5-dimethyl-1H-pyrazol-3-yl)amino)-5-methylpyrimidin-4-yl)-1H-indol-7-yl)-5,6-dihydro-7H-pyrrolo[3,4-b]pyridin-7-one |
| 289) | 7-bromo-2-(3-(2-((1,5-dimethyl-1H-pyrazol-3-yl)amino)-5-methylpyrimidin-4-yl)-1H-indol-7-yl)-1,2-dihydro-3H-pyrrolo[3,4-c]pyridin-3-one |
| 290) | 4-bromo-2-(3-(2-((1,5-dimethyl-1H-pyrazol-3-yl)amino)-5-methylpyrimidin-4-yl)-1H-indol-7-yl)-2,3-dihydro-1H-pyrrolo[3,4-c]pyridin-1-one |
| 291) | N-(2-(3-(2-((1,5-dimethyl-1H-pyrazol-3-yl)amino)-5-methylpyrimidin-4-yl)-1H-indol-7-yl)-3-oxoisoindolin-5-yl)cyclopropanecarboxamide |
| 292) | N-(2-(3-(2-((1,5-dimethyl-1H-pyrazol-3-yl)amino)-5-methylpyrimidin-4-yl)-1H-indol-7-yl)-3-oxoisoindolin-4-yl)cyclohexanecarboxamide |
| 293) | N-(2-(3-(2-((1,5-dimethyl-1H-pyrazol-3-yl)amino)-5-methylpyrimidin-4-yl)-1H-indol-7-yl)-3-oxoisoindolin-4-yl)benzamide |
| 294) | N-(2-(3-(2-((1,5-dimethyl-1H-pyrazol-3-yl)amino)-5-methylpyrimidin-4-yl)-1H-indol-7-yl)-1-oxoisoindolin-4-yl)benzamide |
| 295) | N-(2-(3-(2-((1,5-dimethyl-1H-pyrazol-3-yl)amino)-5-methylpyrimidin-4-yl)-1H-indol-7-yl)-1-oxoisoindolin-4-yl)cyclohexanecarboxamide |
| 296) | N-(2-(3-(2-((1,5-dimethyl-1H-pyrazol-3-yl)amino)-5-methylpyrimidin-4-yl)-1H-indol-7-yl)-1-oxoisoindolin-4-yl)morpholine-4-carboxamide |
| 297) | N-(2-(3-(2-((1,5-dimethyl-1H-pyrazol-3-yl)amino)-5-methylpyrimidin-4-yl)-1H-indol-7-yl)-1-oxoisoindolin-4-yl)picolinamide |
| 298) | N-(2-(3-(2-((1,5-dimethyl-1H-pyrazol-3-yl)amino)-5-methylpyrimidin-4-yl)-1H-indol-7-yl)-1-oxoisoindolin-4-yl)nicotinamide |
| 299) | N-(2-(3-(2-((1,5-dimethyl-1H-pyrazol-3-yl)amino)-5-methylpyrimidin-4-yl)-1H-indol-7-yl)-1-oxoisoindolin-4-yl)oxazole-4-carboxamide |
| 300) | N-(2-(3-(2-((1,5-dimethyl-1H-pyrazol-3-yl)amino)-5-methylpyrimidin-4-yl)-1H-indol-7-yl)-1-oxoisoindolin-4-yl)cyclopropanecarboxamide |
| 301) | N-(2-(3-(2-((1,5-dimethyl-1H-pyrazol-3-yl)amino)-5-methylpyrimidin-4-yl)-1H-indol-7-yl)-1-oxoisoindolin-4-yl)isonicotinamide |
| 302) | N-(2-(3-(2-((1,5-dimethyl-1H-pyrazol-3-yl)amino)-5-methylpyrimidin-4-yl)-1H-indol-7-yl)-1-oxoisoindolin-4-yl)pyridazine-4-carboxamide |
| 303) | N-(2-(3-(2-((1,5-dimethyl-1H-pyrazol-3-yl)amino)-5-methylpyrimidin-4-yl)-1H-indol-7-yl)-1-oxoisoindolin-4-yl)-4-methylcyclohexane-1-carboxamide |
| 304) | N-(2-(3-(2-((1,5-dimethyl-1H-pyrazol-3-yl)amino)-5-methylpyrimidin-4-yl)-1H-indol-7-yl)-1-oxoisoindolin-4-yl)-2-(3-hydroxyphenyl)acetamide |
| 305) | N-(2-(3-(2-((1,5-dimethyl-1H-pyrazol-3-yl)amino)-5-methylpyrimidin-4-yl)-1H-indol-7-yl)-1-oxoisoindolin-4-yl)-2-phenylacetamide |
| 306) | N-(2-(3-(2-((1,5-dimethyl-1H-pyrazol-3-yl)amino)-5-methylpyrimidin-4-yl)-1H-indol-7-yl)-1-oxoisoindolin-4-yl)-1-methylpiperidine-4-carboxamide |
| 307) | N-(2-(3-(2-((1,5-dimethyl-1H-pyrazol-3-yl)amino)-5-methylpyrimidin-4-yl)-1H-indol-7-yl)-1-oxoisoindolin-4-yl)-1-methylpiperidine-3-carboxamide |
| 308) | N-(2-(3-(2-((1,5-dimethyl-1H-pyrazol-3-yl)amino)-5-methylpyrimidin-4-yl)-1H-indol-7-yl)-1-oxoisoindolin-4-yl)-5-oxopyrrolidine-2-carboxamide |
| 309) | N-(2-(3-(2-((1,5-dimethyl-1H-pyrazol-3-yl)amino)-5-methylpyrimidin-4-yl)-1H-indol-7-yl)-1-oxoisoindolin-4-yl)cyclohex-3-ene-1-carboxamide |
| 310) | N-(2-(3-(2-((1,5-dimethyl-1H-pyrazol-3-yl)amino)-5-methylpyrimidin-4-yl)-1H-indol-7-yl)-1-oxoisoindolin-4-yl)cyclopent-3-ene-1-carboxamide |
| 311) | N-(2-(3-(2-((1,5-dimethyl-1H-pyrazol-3-yl)amino)-5-methylpyrimidin-4-yl)-1H-indol-7-yl)-1-oxoisoindolin-4-yl)-1-methylcyclopent-3-ene-1-carboxamide |
| 312) | N-(2-(3-(2-((1,5-dimethyl-1H-pyrazol-3-yl)amino)-5-methylpyrimidin-4-yl)-1H-indol-7-yl)-1-oxoisoindolin-4-yl)cycloheptanecarboxamide |
| 313) | N-(2-(3-(2-((1,5-dimethyl-1H-pyrazol-3-yl)amino)-5-methylpyrimidin-4-yl)-1H-indol-7-yl)-1-oxoisoindolin-4-yl)-2-oxoimidazolidine-1-carboxamide |
| 314) | N-(2-(3-(2-((1,5-dimethyl-1H-pyrazol-3-yl)amino)-5-methylpyrimidin-4-yl)-1H-indol-7-yl)-1-oxoisoindolin-4-yl)-2,3-dihydro-1H-indene-2-carboxamide |
| 315) | (R)-N-(2-(3-(2-((1,5-dimethyl-1H-pyrazol-3-yl)amino)-5-methylpyrimidin-4-yl)-1H-indol-7-yl)-1-oxoisoindolin-4-yl)pyrrolidine-3-carboxamide |
| 316) | (S)-N-(2-(3-(2-((1,5-dimethyl-1H-pyrazol-3-yl)amino)-5-methylpyrimidin-4-yl)-1H-indol-7-yl)-1-oxoisoindolin-4-yl)pyrrolidine-3-carboxamide |
| 317) | (S)-N-(2-(3-(2-((1,5-dimethyl-1H-pyrazol-3-yl)amino)-5-methylpyrimidin-4-yl)-1H-indol-7-yl)-1-oxoisoindolin-4-yl)-5-oxopyrrolidine-2-carboxamide |
| 318) | (R)-N-(2-(3-(2-((1,5-dimethyl-1H-pyrazol-3-yl)amino)-5-methylpyrimidin-4-yl)-1H-indol-7-yl)-1-oxoisoindolin-4-yl)-5-oxopyrrolidine-2-carboxamide |
| 319) | N-(2-(3-(2-((1,5-dimethyl-1H-pyrazol-3-yl)amino)-5-methylpyrimidin-4-yl)-1H-indol-7-yl)-1-oxoisoindolin-4-yl)piperidine-3-carboxamide |
| 320) | N-(2-(3-(2-((1,5-dimethyl-1H-pyrazol-3-yl)amino)-5-methylpyrimidin-4-yl)-1H-indol-7-yl)-1-oxoisoindolin-4-yl)-4-oxocyclohexane-1-carboxamide |
| 321) | N-(2-(3-(2-((1,5-dimethyl-1H-pyrazol-3-yl)amino)-5-methylpyrimidin-4-yl)-1H-indol-7-yl)-1-oxoisoindolin-4-yl)-5-methylisoxazole-4-carboxamide |

| | |
|---|---|
| 322) | N-(2-(3-(2-((1,5-dimethyl-1H-pyrazol-3-yl)amino)-5-methylpyrimidin-4-yl)-1H-indol-7-yl)-1-oxoisoindolin-4-yl)-2-methyloxazole-4-carboxamide |
| 323) | N-(2-(3-(2-((1,5-dimethyl-1H-pyrazol-3-yl)amino)-5-methylpyrimidin-4-yl)-1H-indol-7-yl)-1-oxoisoindolin-4-yl)oxazole-5-carboxamide |
| 324) | N-(2-(3-(2-((1,5-dimethyl-1H-pyrazol-3-yl)amino)-5-methylpyrimidin-4-yl)-1H-indol-7-yl)-1-oxoisoindolin-4-yl)isoxazole-3-carboxamide |
| 325) | N-(2-(3-(2-((1,5-dimethyl-1H-pyrazol-3-yl)amino)-5-methylpyrimidin-4-yl)-1H-indol-7-yl)-1-oxoisoindolin-4-yl)-5-methylisoxazole-3-carboxamide |
| 326) | N-(2-(3-(2-((1,5-dimethyl-1H-pyrazol-3-yl)amino)-5-methylpyrimidin-4-yl)-1H-indol-7-yl)-1-oxoisoindolin-4-yl)tetrahydrofuran-3-carboxamide |
| 327) | N-(2-(3-(2-((1,5-dimethyl-1H-pyrazol-3-yl)amino)-5-methylpyrimidin-4-yl)-1H-indol-7-yl)-1-oxoisoindolin-4-yl)tetrahydro-2H-pyran-3-carboxamide |
| 328) | N-(2-(3-(2-((1,5-dimethyl-1H-pyrazol-3-yl)amino)-5-methylpyrimidin-4-yl)-1H-indol-7-yl)-1-oxoisoindolin-4-yl)-4-methyltetrahydro-2H-pyran-4-carboxamide |
| 329) | N-(2-(3-(2-((1,5-dimethyl-1H-pyrazol-3-yl)amino)-5-methylpyrimidin-4-yl)-1H-indol-7-yl)-1-oxoisoindolin-4-yl)-3-methylcyclohexane-1-carboxamide |
| 330) | N-(2-(3-(2-((1,5-dimethyl-1H-pyrazol-3-yl)amino)-5-methylpyrimidin-4-yl)-1H-indol-7-yl)-1-oxoisoindolin-4-yl)-4-methylcyclohex-3-ene-1-carboxamide |
| 331) | (2R,4S)-4-amino-N-(2-(3-(2-((1,5-dimethyl-1H-pyrazol-3-yl)amino)-5-methylpyrimidin-4-yl)-1H-indol-7-yl)-1-oxoisoindolin-4-yl)pyrrolidine-2-carboxamide |
| 332) | N-(2-(3-(2-((1,5-dimethyl-1H-pyrazol-3-yl)amino)-5-methylpyrimidin-4-yl)-1H-indol-7-yl)-1-oxoisoindolin-4-yl)-3-methylpiperidine-3-carboxamide |
| 333) | (R)-N-(2-(3-(2-((1,5-dimethyl-1H-pyrazol-3-yl)amino)-5-methylpyrimidin-4-yl)-1H-indol-7-yl)-1-oxoisoindolin-4-yl)-1-methylpyrrolidine-3-carboxamide |
| 334) | N-(2-(3-(2-((1,5-dimethyl-1H-pyrazol-3-yl)amino)-5-methylpyrimidin-4-yl)-1H-indol-7-yl)-1-oxoisoindolin-4-yl)-5-methylnicotinamide |
| 335) | N-(2-(3-(2-((1,5-dimethyl-1H-pyrazol-3-yl)amino)-5-methylpyrimidin-4-yl)-1H-indol-7-yl)-1-oxoisoindolin-4-yl)-2-(dimethylamino)acetamide |
| 336) | N-(2-(3-(2-((1,5-dimethyl-1H-pyrazol-3-yl)amino)-5-methylpyrimidin-4-yl)-1H-indol-7-yl)-1-oxoisoindolin-4-yl)cyclopentanecarboxamide |
| 337) | N-(2-(3-(2-((1,5-dimethyl-1H-pyrazol-3-yl)amino)-5-methylpyrimidin-4-yl)-1H-indol-7-yl)-1-oxoisoindolin-4-yl)tetrahydro-2H-pyran-4-carboxamide |
| 338) | N-(2-(3-(2-((1,5-dimethyl-1H-pyrazol-3-yl)amino)-5-methylpyrimidin-4-yl)-1H-indol-7-yl)-1-oxoisoindolin-4-yl)furan-3-carboxamide |
| 339) | N-(2-(3-(2-((1,5-dimethyl-1H-pyrazol-3-yl)amino)-5-methylpyrimidin-4-yl)-1H-indol-7-yl)-1-oxoisoindolin-4-yl)-6-hydroxypyrimidine-4-carboxamide |
| 340) | N-(2-(3-(2-((1,5-dimethyl-1H-pyrazol-3-yl)amino)-5-methylpyrimidin-4-yl)-1H-indol-7-yl)-3-oxoisoindolin-4-yl)benzenesulfonamide |
| 341) | N-(2-(3-(2-((1,5-dimethyl-1H-pyrazol-3-yl)amino)-5-methylpyrimidin-4-yl)-1H-indol-7-yl)-1-oxoisoindolin-4-yl)benzenesulfonamide |
| 342) | N-(2-(3-(2-((1,5-dimethyl-1H-pyrazol-3-yl)amino)-5-methylpyrimidin-4-yl)-1H-indol-7-yl)-1-oxoisoindolin-4-yl)methanesulfonamide |
| 343) | N-(2-(3-(2-((1,5-dimethyl-1H-pyrazol-3-yl)amino)-5-methylpyrimidin-4-yl)-1H-indol-7-yl)-1-oxoisoindolin-4-yl)-4-methylbenzenesulfonamide |
| 344) | N-(2-(3-(2-((1,5-dimethyl-1H-pyrazol-3-yl)amino)-5-methylpyrimidin-4-yl)-1H-indol-7-yl)-1-oxoisoindolin-4-yl)propane-2-sulfonamide |
| 345) | N-(2-(3-(2-((1,5-dimethyl-1H-pyrazol-3-yl)amino)-5-methylpyrimidin-4-yl)-1H-indol-7-yl)-1-oxoisoindolin-4-yl)-4-fluoro-3-methylbenzenesulfonamide |
| 346) | 2-(3-(2-((1,5-dimethyl-1H-pyrazol-3-yl)amino)-5-methylpyrimidin-4-yl)-1H-indol-7-yl)-7-(phenylamino)isoindolin-1-one |
| 347) | 2-(3-(2-((1,5-dimethyl-1H-pyrazol-3-yl)amino)-5-methylpyrimidin-4-yl)-1H-indol-7-yl)-7-morpholinoisoindolin-1-one |
| 348) | 2-(3-(2-((1,5-dimethyl-1H-pyrazol-3-yl)amino)-5-methylpyrimidin-4-yl)-1H-indol-7-yl)-7-(4-methylpiperazin-1-yl)isoindolin-1-one |
| 349) | 2-(3-(2-((1,5-dimethyl-1H-pyrazol-3-yl)amino)-5-methylpyrimidin-4-yl)-1H-indol-7-yl)-7-(dimethylamino)isoindolin-1-one |
| 350) | 7-(benzylamino)-2-(3-(2-((1,5-dimethyl-1H-pyrazol-3-yl)amino)-5-methylpyrimidin-4-yl)-1H-indol-7-yl)isoindolin-1-one |
| 351) | 7-((cyclopropylmethyl)amino)-2-(3-(2-((1,5-dimethyl-1H-pyrazol-3-yl)amino)-5-methylpyrimidin-4-yl)-1H-indol-7-yl)isoindolin-1-one |
| 352) | 2-(3-(2-((1,5-dimethyl-1H-pyrazol-3-yl)amino)-5-methylpyrimidin-4-yl)-1H-indol-7-yl)-4-morpholinoisoindolin-1-one |
| 353) | 4-((cyclopropylmethyl)amino)-2-(3-(2-((1,5-dimethyl-1H-pyrazol-3-yl)amino)-5-methylpyrimidin-4-yl)-1H-indol-7-yl)isoindolin-1-one |
| 354) | 4-(benzylamino)-2-(3-(2-((1,5-dimethyl-1H-pyrazol-3-yl)amino)-5-methylpyrimidin-4-yl)-1H-indol-7-yl)isoindolin-1-one |
| 355) | 2-(3-(2-((1,5-dimethyl-1H-pyrazol-3-yl)amino)-5-methylpyrimidin-4-yl)-1H-indol-7-yl)-7-(phenylamino)isoindolin-1-one |
| 356) | 2-(3-(2-((1,5-dimethyl-1H-pyrazol-3-yl)amino)-5-methylpyrimidin-4-yl)-1H-indol-7-yl)-4-(phenylethynyl)isoindolin-1-one |
| 357) | 4-((4-aminophenyl)ethynyl)-2-(3-(2-((1,5-dimethyl-1H-pyrazol-3-yl)amino)-5-methylpyrimidin-4-yl)-1H-indol-7-yl)isoindolin-1-one |
| 358) | (E)-3-(2-(3-(2-((1,5-dimethyl-1H-pyrazol-3-yl)amino)-5-methylpyrimidin-4-yl)-1H-indol-7-yl)-1-oxoisoindolin-4-yl)acrylamide |
| 359) | (E)-3-(2-(3-(2-((1,5-dimethyl-1H-pyrazol-3-yl)amino)-5-methylpyrimidin-4-yl)-1H-indol-7-yl)-7-fluoro-1-oxoisoindolin-4-yl)-N,N-dimethylacrylamide |

| | |
|---|---|
| 360) | (E)-3-(2-(3-(2-((1,5-dimethyl-1H-pyrazol-3-yl)amino)-5-methylpyrimidin-4-yl)-1H-indol-7-yl)-1-oxoisoindolin-4-yl)-N,N-dimethylacrylamide |
| 361) | (E)-3-(2-(3-(2-((1,5-dimethyl-1H-pyrazol-3-yl)amino)-5-methylpyrimidin-4-yl)-1H-indol-7-yl)-1-oxoisoindolin-4-yl)-2-methylacrylamide |
| 362) | (E)-2-(3-(2-((1,5-dimethyl-1H-pyrazol-3-yl)amino)-5-methylpyrimidin-4-yl)-1H-indol-7-yl)-4-(3-oxobut-1-en-1-yl)isoindolin-1-one |
| 363) | (E)-3-(2-(3-(2-((1,5-dimethyl-1H-pyrazol-3-yl)amino)-5-methylpyrimidin-4-yl)-1H-indol-7-yl)-1-oxoisoindolin-4-yl)-N-methylacrylamide |
| 364) | (E)-3-(2-(3-(2-((1,5-dimethyl-1HI-pyrazol-3-yl)amino)-5-methylpyrimidin-4-yl)-1H-indol-7-yl)-1-oxoisoindolin-4-yl)-N-ethylacrylamide |
| 365) | (E)-N-cyclopropyl-3-(2-(3-(2-((1,5-dimethyl-1H-pyrazol-3-yl)amino)-5-methylpyrimidin-4-yl)-1H-indol-7-yl)-1-oxoisoindolin-4-yl)acrylamide |
| 366) | (E)-3-(2-(3-(2-((1,5-dimethyl-1H-pyrazol-3-yl)amino)-5-methylpyrimidin-4-yl)-1H-indol-7-yl)-1-oxoisoindolin-4-yl)acrylohydrazide |
| 367) | (E)-3-(2-(3-(2-((1,5-dimethyl-1H-pyrazol-3-yl)amino)-5-methylpyrimidin-4-yl)-1H-indol-7-yl)-1-oxoisoindolin-4-yl)acrylic acid |
| 368) | (E)-3-(2-(3-(2-((1,5-dimethyl-1H-pyrazol-3-yl)amino)-5-methylpyrimidin-4-yl)-1H-indol-7-yl)-1-oxoisoindolin-4-yl)-N,N-diethylacrylamide |
| 369) | (E)-N,N-dibutyl-3-(2-(3-(2-((1,5-dimethyl-1H-pyrazol-3-yl)amino)-5-methylpyrimidin-4-yl)-1H-indol-7-yl)-1-oxoisoindolin-4-yl)acrylamide |
| 370) | (E)-3-(2-(3-(2-((1,5-dimethyl-1H-pyrazol-3-yl)amino)-5-methylpyrimidin-4-yl)-1H-indol-7-yl)-1-oxoisoindolin-4-yl)-N-isopropylacrylamide |
| 371) | (E)-N-(tert-butyl)-3-(2-(3-(2-((1,5-dimethyl-1H-pyrazol-3-yl)amino)-5-methylpyrimidin-4-yl)-1H-indol-7-yl)-1-oxoisoindolin-4-yl)acrylamide |
| 372) | (E)-3-(2-(3-(2-((1,5-dimethyl-1H-pyrazol-3-yl)amino)-5-methylpyrimidin-4-yl)-1H-indol-7-yl)-1-oxoisoindolin-4-yl)-N-(2-hydroxyethyl)acrylamide |
| 373) | (E)-3-(2-(3-(2-((1,5-dimethyl-1H-pyrazol-3-yl)amino)-5-methylpyrimidin-4-yl)-1H-indol-7-yl)-1-oxoisoindolin-4-yl)-N-propylacrylamide |
| 374) | (E)-3-(2-(3-(2-((1,5-dimethyl-1H-pyrazol-3-yl)amino)-5-methylpyrimidin-4-yl)-1H-indol-7-yl)-1-oxoisoindolin-4-yl)-N-(2-methoxyethyl)acrylamide |
| 375) | (E)-2-(3-(2-((1,5-dimethyl-1H-pyrazol-3-yl)amino)-5-methylpyrimidin-4-yl)-1H-indol-7-yl)-4-(3-hydroxyprop-1-en-1-yl)isoindolin-1-one |
| 376) | (E)-3-(2-(3-(2-((1,5-dimethyl-1H-pyrazol-3-yl)amino)-5-methylpyrimidin-4-yl)-1H-indol-7-yl)-1-oxoisoindolin-4-yl)-N-ethyl-2-methylacrylamide |
| 377) | 2-(3-(2-((1,5-dimethyl-1H-pyrazol-3-yl)amino)-5-methylpyrimidin-4-yl)-1H-indol-7-yl)-4-phenylisoindolin-1-one |
| 378) | 2-(3-(2-((1,5-dimethyl-1H-pyrazol-3-yl)amino)-5-methylpyrimidin-4-yl)-1H-indol-7-yl)-5-phenylisoindolin-1-one |
| 379) | 2-(3-(2-((1,5-dimethyl-1H-pyrazol-3-yl)amino)-5-methylpyrimidin-4-yl)-1H-indol-7-yl)-6-phenylisoindolin-1-one |
| 380) | 2-(3-(2-((1,5-dimethyl-1H-pyrazol-3-yl)amino)-5-methylpyrimidin-4-yl)-1H-indol-7-yl)-6-(pyridin-4-yl)isoindolin-1-one |
| 381) | 2-(3-(2-((1,5-dimethyl-1H-pyrazol-3-yl)amino)-5-methylpyrimidin-4-yl)-1H-indol-7-yl)-6-(1,2,3,6-tetrahydropyridin-4-yl)isoindolin-1-one |
| 382) | 2-(3-(2-((1,5-dimethyl-1H-pyrazol-3-yl)amino)-5-methylpyrimidin-4-yl)-1H-indol-7-yl)-7-phenylisoindolin-1-one |
| 383) | 2-(3-(2-((1,5-dimethyl-1H-pyrazol-3-yl)amino)-5-methylpyrimidin-4-yl)-1H-indol-7-yl)-7-(pyridin-4-yl)isoindolin-1-one |
| 384) | 7-(cyclohex-1-en-1-yl)-2-(3-(2-((1,5-dimethyl-1H-pyrazol-3-yl)amino)-5-methylpyrimidin-4-yl)-1H-indol-7-yl)isoindolin-1-one |
| 385) | 7-(3,6-dihydro-2H-pyran-4-yl)-2-(3-(2-((1,5-dimethyl-1H-pyrazol-3-yl)amino)-5-methylpyrimidin-4-yl)-1H-indol-7-yl)isoindolin-1-one |
| 386) | 2-(3-(2-((1,5-dimethyl-1H-pyrazol-3-yl)amino)-5-methylpyrimidin-4-yl)-1H-indol-7-yl)-7-(1H-pyrazol-4-yl)isoindolin-1-one |
| 387) | 2-(3-(2-((1,5-dimethyl-1H-pyrazol-3-yl)amino)-5-methylpyrimidin-4-yl)-1H-indol-7-yl)-4-(pyridin-4-yl)isoindolin-1-one |
| 388) | 2-(3-(2-((1,5-dimethyl-1H-pyrazol-3-yl)amino)-5-methylpyrimidin-4-yl)-1H-indol-7-yl)-4-(pyridin-3-yl)isoindolin-1-one |
| 389) | 2-(3-(2-((1,5-dimethyl-1H-pyrazol-3-yl)amino)-5-methylpyrimidin-4-yl)-1H-indol-7-yl)-4-(1-methyl-1H-pyrazol-4-yl)isoindolin-1-one |
| 390) | 2-(3-(2-((1,5-dimethyl-1H-pyrazol-3-yl)amino)-5-methylpyrimidin-4-yl)-1H-indol-7-yl)-4-(1H-pyrazol-4-yl)isoindolin-1-one |
| 391) | 4-(cyclohex-1-en-1-yl)-2-(3-(2-((1,5-dimethyl-1H-pyrazol-3-yl)amino)-5-methylpyrimidin-4-yl)-1H-indol-7-yl)isoindolin-1-one |
| 392) | 4-(3,6-dihydro-2H-pyran-4-yl)-2-(3-(2-((1,5-dimethyl-1H-pyrazol-3-yl)amino)-5-methylpyrimidin-4-yl)-1H-indol-7-yl)isoindolin-1-one |
| 393) | 2-(3-(2-((1,5-dimethyl-1H-pyrazol-3-yl)amino)-5-methylpyrimidin-4-yl)-1H-indol-7-yl)-4-(furan-3-yl)isoindolin-1-one |
| 394) | 2-(3-(2-((1,5-dimethyl-1H-pyrazol-3-yl)amino)-5-methylpyrimidin-4-yl)-1H-indol-7-yl)-4-(1,2,3,6-tetrahydropyridin-4-yl)isoindolin-1-one |
| 395) | 2-(3-(2-((1,5-dimethyl-1H-pyrazol-3-yl)amino)-5-methylpyrimidin-4-yl)-1H-indol-7-yl)-4-(4-(trifluoromethoxy)phenyl)isoindolin-1-one |
| 396) | 4-(4-aminophenyl)-2-(3-(2-((1,5-dimethyl-1H-pyrazol-3-yl)amino)-5-methylpyrimidin-4-yl)-1H-indol-7-yl)isoindolin-1-one |
| 397) | tert-butyl 4-(2-(3-(2-((1,5-dimethyl-1H-pyrazol-3-yl)amino)-5-methylpyrimidin-4-yl)-1H-indol-7-yl)-1-oxoisoindolin-4-yl)-3,6-dihydropyridine-1(2H)-carboxylate |
| 398) | tert-butyl (4-(2-(3-(2-((1,5-dimethyl-1H-pyrazol-3-yl)amino)-5-methylpyrimidin-4-yl)-1H-indol-7-yl)-1-oxoisoindolin-4-yl)phenyl)carbamate |

| | |
|---|---|
| 399) | 4-(2-aminopyridin-4-yl)-2-(3-(2-((1,5-dimethyl-1H-pyrazol-3-yl)amino)-5-methylpyrimidin-4-yl)-1H-indol-7-yl)isoindolin-1-one |
| 400) | 2-(3-(2-((1,5-dimethyl-1H-pyrazol-3-yl)amino)-5-methylpyrimidin-4-yl)-1H-indol-7-yl)-4-(3-fluoropyridin-4-yl)isoindolin-1-one |
| 401) | 2-(3-(2-((1,5-dimethyl-1H-pyrazol-3-yl)amino)-5-methylpyrimidin-4-yl)-1H-indol-7-yl)-4-(6-hydroxypyridin-3-yl)isoindolin-1-one |
| 402) | 4-(2-chloropyridin-4-yl)-2-(3-(2-((1,5-dimethyl-1H-pyrazol-3-yl)amino)-5-methylpyrimidin-4-yl)-1H-indol-7-yl)isoindolin-1-one |
| 403) | 2-(3-(2-((1,5-dimethyl-1H-pyrazol-3-yl)amino)-5-methylpyrimidin-4-yl)-1H-indol-7-yl)-4-(5-fluoro-2-methoxypyridin-4-yl)isoindolin-1-one |
| 404) | 2-(3-(2-((1,5-dimethyl-1H-pyrazol-3-yl)amino)-5-methylpyrimidin-4-yl)-1H-indol-7-yl)-4-(2-fluoropyridin-4-yl)isoindolin-1-one |
| 405) | 4-(6-chloropyridin-3-yl)-2-(3-(2-((1,5-dimethyl-1H-pyrazol-3-yl)amino)-5-methylpyrimidin-4-yl)-1H-indol-7-yl)isoindolin-1-one |
| 406) | 2-(3-(2-((1,5-dimethyl-1H-pyrazol-3-yl)amino)-5-methylpyrimidin-4-yl)-1H-indol-7-yl)-4-(6-methoxypyridin-3-yl)isoindolin-1-one |
| 407) | 2-(3-(2-((1,5-dimethyl-1H-pyrazol-3-yl)amino)-5-methylpyrimidin-4-yl)-1H-indol-7-yl)-4-(6-fluoro-5-methylpyridin-3-yl)isoindolin-1-one |
| 408) | 2-(3-(2-((1,5-dimethyl-1H-pyrazol-3-yl)amino)-5-methylpyrimidin-4-yl)-1H-indol-7-yl)-4-(2-(piperazin-1-yl)pyridin-4-yl)isoindolin-1-one |
| 409) | 2-(3-(2-((1,5-dimethyl-1H-pyrazol-3-yl)amino)-5-methylpyrimidin-4-yl)-1H-indol-7-yl)-4-(4-(pyrrolidin-1-ylsulfonyl)phenyl)isoindolin-1-one |
| 410) | (E)-2-(3-(2-((1,5-dimethyl-1H-pyrazol-3-yl)amino)-5-methylpyrimidin-4-yl)-1H-indol-7-yl)-4-(3-fluorostyryl)isoindolin-1-one |
| 411) | 2-(3-(2-((1,5-dimethyl-1H-pyrazol-3-yl)amino)-5-methylpyrimidin-4-yl)-1H-indol-7-yl)-4-(1H-pyrrolo[2,3-b]pyridin-4-yl)isoindolin-1-one |
| 412) | 2-(3-(2-((1,5-dimethyl-1H-pyrazol-3-yl)amino)-5-methylpyrimidin-4-yl)-1H-indol-7-yl)-4-(4-(4-oxopiperidine-1-carbonyl)phenyl)isoindolin-1-one |
| 413) | 4-(3,6-dihydro-2H-thiopyran-4-yl)-2-(3-(2-((1,5-dimethyl-1H-pyrazol-3-yl)amino)-5-methylpyrimidin-4-yl)-1H-indol-7-yl)isoindolin-1-one |
| 414) | 2-(3-(2-((1,5-dimethyl-1H-pyrazol-3-yl)amino)-5-methylpyrimidin-4-yl)-1H-indol-7-yl)-4-(2-(dimethylamino)pyrimidin-5-yl)isoindolin-1-one |
| 415) | 4-(1-(cyclopropylmethyl)-1H-pyrazol-4-yl)-2-(3-(2-((1,5-dimethyl-1H-pyrazol-3-yl)amino)-5-methylpyrimidin-4-yl)-1H-indol-7-yl)isoindolin-1-one |
| 416) | 2-(3-(2-((1,5-dimethyl-1H-pyrazol-3-yl)amino)-5-methylpyrimidin-4-yl)-1H-indol-7-yl)-4-(1-(2-morpholinoethyl)-1H-pyrazol-4-yl)isoindolin-1-one |
| 417) | 2-(3-(2-((1,5-dimethyl-1H-pyrazol-3-yl)amino)-5-methylpyrimidin-4-yl)-1H-indol-7-yl)-4-(pyrimidin-5-yl)isoindolin-1-one |
| 418) | 4-(2-aminopyrimidin-5-yl)-2-(3-(2-((1,5-dimethyl-1H-pyrazol-3-yl)amino)-5-methylpyrimidin-4-yl)-1H-indol-7-yl)isoindolin-1-one |
| 419) | 4-(5-aminopyridin-3-yl)-2-(3-(2-((1,5-dimethyl-1H-pyrazol-3-yl)amino)-5-methylpyrimidin-4-yl)-1H-indol-7-yl)isoindolin-1-one |
| 420) | 4-(6-aminopyridin-3-yl)-2-(3-(2-((1,5-dimethyl-1H-pyrazol-3-yl)amino)-5-methylpyrimidin-4-yl)-1H-indol-7-yl)isoindolin-1-one |
| 421) | 2-(3-(2-((1,5-dimethyl-1H-pyrazol-3-yl)amino)-5-methylpyrimidin-4-yl)-1H-indol-7-yl)-4-(pyrimidin-4-yl)isoindolin-1-one |
| 422) | 4-(2-aminopyrimidin-4-yl)-2-(3-(2-((1,5-dimethyl-1H-pyrazol-3-yl)amino)-5-methylpyrimidin-4-yl)-1H-indol-7-yl)isoindolin-1-one |
| 423) | 2-(3-(2-((1,5-dimethyl-1HI-pyrazol-3-yl)amino)-5-methylpyrimidin-4-yl)-1H-indol-7-yl)-4-(4-(4-methylpiperazin-1-yl)pyridin-2-yl)isoindolin-1-one |
| 424) | 2-(3-(2-((1,5-dimethyl-1H-pyrazol-3-yl)amino)-5-methylpyrimidin-4-yl)-1H-indol-7-yl)-4-(2-(piperazin-1-yl)pyrimidin-5-yl)isoindolin-1-one |
| 425) | 2-(3-(2-((1,5-dimethyl-1H-pyrazol-3-yl)amino)-5-methylpyrimidin-4-yl)-1H-indol-7-yl)-4-(6-morpholinopyridin-3-yl)isoindolin-1-one |
| 426) | 2-(3-(2-((1,5-dimethyl-1H-pyrazol-3-yl)amino)-5-methylpyrimidin-4-yl)-1H-indol-7-yl)-4-(4-(4-methylpiperazin-1-yl)phenyl)isoindolin-1-one |
| 427) | 4-(2,6-difluoropyridin-4-yl)-2-(3-(2-((1,5-dimethyl-1H-pyrazol-3-yl)amino)-5-methylpyrimidin-4-yl)-1H-indol-7-yl)isoindolin-1-one |
| 428) | 4-(3,5-difluoropyridin-4-yl)-2-(3-(2-((1,5-dimethyl-1H-pyrazol-3-yl)amino)-5-methylpyrimidin-4-yl)-1H-indol-7-yl)isoindolin-1-one |
| 429) | 2-(3-(2-((1,5-dimethyl-1H-pyrazol-3-yl)amino)-5-methylpyrimidin-4-yl)-1H-indol-7-yl)-4-(2-methylpyridin-4-yl)isoindolin-1-one |
| 430) | 2-(3-(2-((1,5-dimethyl-1H-pyrazol-3-yl)amino)-5-methylpyrimidin-4-yl)-1H-indol-7-yl)-[4,5'-biisoindolin]-1-one |
| 431) | 2-(3-(2-((1,5-dimethyl-1H-pyrazol-3-yl)amino)-5-methylpyrimidin-4-yl)-1H-indol-7-yl)-4-(2-fluoropyridin-3-yl)isoindolin-1-one |
| 432) | 4-(2-(3-(2-((1,5-dimethyl-1H-pyrazol-3-yl)amino)-5-methylpyrimidin-4-yl)-1H-indol-7-yl)-1-oxoisoindolin-4-yl)benzonitrile |
| 433) | 4-(2-(3-(2-((1,5-dimethyl-1H-pyrazol-3-yl)amino)-5-methylpyrimidin-4-yl)-1H-indol-7-yl)-1-oxoisoindolin-4-yl)-3-fluorobenzonitrile |
| 434) | 2-(3-(2-((1,5-dimethyl-1H-pyrazol-3-yl)amino)-5-methylpyrimidin-4-yl)-1H-indol-7-yl)-4-(2-(trifluoromethyl)phenyl)isoindolin-1-one |
| 435) | 2-(3-(2-((1,5-dimethyl-1H-pyrazol-3-yl)amino)-5-methylpyrimidin-4-yl)-1H-indol-7-yl)-4-(2-methoxypyridin-3-yl)isoindolin-1-one |
| 436) | 2-(3-(2-((1,5-dimethyl-1H-pyrazol-3-yl)amino)-5-methylpyrimidin-4-yl)-1H-indol-7-yl)-4-(4-(dimethylamino)phenyl)isoindolin-1-one |
| 437) | 2-(3-(2-((1,5-dimethyl-1H-pyrazol-3-yl)amino)-5-methylpyrimidin-4-yl)-1H-indol-7-yl)-4-(2-(hydroxymethyl)phenyl)isoindolin-1-one |

| | |
|---|---|
| 438) | 2-(3-(2-((1,5-dimethyl-1H-pyrazol-3-yl)amino)-5-methylpyrimidin-4-yl)-1H-indol-7-yl)-4-(2-methoxyphenyl)isoindolin-1-one |
| 439) | 4-([1,1'-biphenyl]-2-yl)-2-(3-(2-((1,5-dimethyl-1H-pyrazol-3-yl)amino)-5-methylpyrimidin-4-yl)-1H-indol-7-yl)isoindolin-1-one |
| 440) | 2-(3-(2-((1,5-dimethyl-1H-pyrazol-3-yl)amino)-5-methylpyrimidin-4-yl)-1H-indol-7-yl)-4-(o-tolyl)isoindolin-1-one |
| 441) | 2-(3-(2-((1,5-dimethyl-1H-pyrazol-3-yl)amino)-5-methylpyrimidin-4-yl)-1H-indol-7-yl)-4-(2-hydroxyphenyl)isoindolin-1-one |
| 442) | 2-(3-(2-((1,5-dimethyl-1H-pyrazol-3-yl)amino)-5-methylpyrimidin-4-yl)-1H-indol-7-yl)-4-(1H-pyrrol-2-yl)isoindolin-1-one |
| 443) | tert-butyl 2-(2-(3-(2-((1,5-dimethyl-1H-pyrazol-3-yl)amino)-5-methylpyrimidin-4-yl)-1H-indol-7-yl)-1-oxoisoindolin-4-yl)-1H-pyrrole-1-carboxylate |
| 444) | 2-(3-(2-((1,5-dimethyl-1H-pyrazol-3-yl)amino)-5-methylpyrimidin-4-yl)-1H-indol-7-yl)-4-(3,5-dimethylisoxazol-4-yl)isoindolin-1-one |
| 445) | 2-(3-(2-((1,5-dimethyl-1H-pyrazol-3-yl)amino)-5-methylpyrimidin-4-yl)-1H-indol-7-yl)-4-(2-methoxypyridin-4-yl)isoindolin-1-one |
| 446) | 2-(3-(2-((1,5-dimethyl-1H-pyrazol-3-yl)amino)-5-methylpyrimidin-4-yl)-1H-indol-7-yl)-4-(2-hydroxypyridin-4-yl)isoindolin-1-one |
| 447) | 4-(3-aminopyridin-4-yl)-2-(3-(2-((1,5-dimethyl-1H-pyrazol-3-yl)amino)-5-methylpyrimidin-4-yl)-1H-indol-7-yl)isoindolin-1-one |
| 448) | 2-(3-(2-((1,5-dimethyl-1H-pyrazol-3-yl)amino)-5-methylpyrimidin-4-yl)-1H-indol-7-yl)-4-(isoquinolin-7-yl)isoindolin-1-one |
| 449) | 2-(3-(2-((1,5-dimethyl-1H-pyrazol-3-yl)amino)-5-methylpyrimidin-4-yl)-1H-indol-7-yl)-4-(1-methyl-1H-indazol-5-yl)isoindolin-1-one |
| 450) | 2-(3-(2-((1,5-dimethyl-1H-pyrazol-3-yl)amino)-5-methylpyrimidin-4-yl)-1H-indol-7-yl)-4-(1-methyl-1H-indazol-6-yl)isoindolin-1-one |
| 451) | 2-(3-(2-((1,5-dimethyl-1H-pyrazol-3-yl)amino)-5-methylpyrimidin-4-yl)-1H-indol-7-yl)-4-(5-methylthiophen-2-yl)isoindolin-1-one |
| 452) | 4-(2,3-dihydro-1H-inden-5-yl)-2-(3-(2-((1,5-dimethyl-1H-pyrazol-3-yl)amino)-5-methylpyrimidin-4-yl)-1H-indol-7-yl)isoindolin-1-one |
| 453) | 2-(3-(2-((1,5-dimethyl-1H-pyrazol-3-yl)amino)-5-methylpyrimidin-4-yl)-1H-indol-7-yl)-4-(4-methylthiophen-3-yl)isoindolin-1-one |
| 454) | 2-(3-(2-((1,5-dimethyl-1H-pyrazol-3-yl)amino)-5-methylpyrimidin-4-yl)-1H-indol-7-yl)-7-fluoro-4-(2-methylpyridin-4-yl)isoindolin-1-one |
| 455) | 2-(3-(2-((1,5-dimethyl-1H-pyrazol-3-yl)amino)-5-methylpyrimidin-4-yl)-1H-indol-7-yl)-4-(3-methylpyridin-4-yl)isoindolin-1-one |
| 456) | 4-(6-aminopyrimidin-4-yl)-2-(3-(2-((1,5-dimethyl-1H-pyrazol-3-yl)amino)-5-methylpyrimidin-4-yl)-1H-indol-7-yl)isoindolin-1-one |
| 457) | 2-(3-(2-((1,5-dimethyl-1H-pyrazol-3-yl)amino)-5-methylpyrimidin-4-yl)-1H-indol-7-yl)-4-(1H-indazol-4-yl)isoindolin-1-one |
| 458) | 2-(2-(3-(2-((1,5-dimethyl-1H-pyrazol-3-yl)amino)-5-methylpyrimidin-4-yl)-1H-indol-7-yl)-1-oxoisoindolin-4-yl)benzoic acid |
| 459) | 2-(3-(2-((1,5-dimethyl-1H-pyrazol-3-yl)amino)-5-methylpyrimidin-4-yl)-1H-indol-7-yl)-4-(2-(hydroxymethyl)phenyl)isoindolin-1-one |
| 460) | 2-(3-(2-((1,5-dimethyl-1H-pyrazol-3-yl)amino)-5-methylpyrimidin-4-yl)-1H-indol-7-yl)-4-(4-(hydroxymethyl)phenyl)isoindolin-1-one |
| 461) | 2-(3-(2-((1,5-dimethyl-1H-pyrazol-3-yl)amino)-5-methylpyrimidin-4-yl)-1H-indol-7-yl)-4-(thiophen-3-yl)isoindolin-1-one |
| 462) | 4-(2-aminophenyl)-2-(3-(2-((1,5-dimethyl-1H-pyrazol-3-yl)amino)-5-methylpyrimidin-4-yl)-1H-indol-7-yl)isoindolin-1-one |
| 463) | methyl 2-(2-(3-(2-((1,5-dimethyl-1H-pyrazol-3-yl)amino)-5-methylpyrimidin-4-yl)-1H-indol-7-yl)-1-oxoisoindolin-4-yl)benzoate |
| 464) | 2-(3-(2-((1,5-dimethyl-1H-pyrazol-3-yl)amino)-5-methylpyrimidin-4-yl)-1H-indol-7-yl)-4-(1-methyl-1,2,3,6-tetrahydropyridin-4-yl)isoindolin-1-one |
| 465) | 2-(3-(2-((1,5-dimethyl-1H-pyrazol-3-yl)amino)-5-methylpyrimidin-4-yl)-1H-indol-7-yl)-4-(1-(methylsulfonyl)-1,2,3,6-tetrahydropyridin-4-yl)isoindolin-1-one |
| 466) | 4-(1-acetyl-1,2,3,6-tetrahydropyridin-4-yl)-2-(3-(2-((1,5-dimethyl-1H-pyrazol-3-yl)amino)-5-methylpyrimidin-4-yl)-1H-indol-7-yl)isoindolin-1-one |
| 467) | 4-(2-(3-(2-((1,5-dimethyl-1H-pyrazol-3-yl)amino)-5-methylpyrimidin-4-yl)-1H-indol-7-yl)-1-oxoisoindolin-4-yl)-3,6-dihydropyridine-1(2H)-carboxamide |
| 468) | 2-(3-(2-((1,5-dimethyl-1H-pyrazol-3-yl)amino)-5-methylpyrimidin-4-yl)-1H-indol-7-yl)-4-(1,1-dioxido-3,6-dihydro-2H-thiopyran-4-yl)isoindolin-1-one |
| 469) | 4-(2-(3-(2-((1,5-dimethyl-1H-pyrazol-3-yl)amino)-5-methylpyrimidin-4-yl)-1H-indol-7-yl)-1-oxoisoindolin-4-yl)picolinonitrile |
| 470) | 5-(2-(3-(2-((1,5-dimethyl-1H-pyrazol-3-yl)amino)-5-methylpyrimidin-4-yl)-1H-indol-7-yl)-1-oxoisoindolin-4-yl)picolinonitrile |
| 471) | 2-(3-(2-((1,5-dimethyl-1H-pyrazol-3-yl)amino)-5-methylpyrimidin-4-yl)-1H-indol-7-yl)-4-(3-(hydroxymethyl)pyridin-4-yl)isoindolin-1-one |
| 472) | 2-(3-(2-((1,5-dimethyl-1H-pyrazol-3-yl)amino)-5-methylpyrimidin-4-yl)-1H-indol-7-yl)-4-(2-(hydroxymethyl)pyridin-4-yl)isoindolin-1-one |
| 473) | 4-(2-(3-(2-((1,5-dimethyl-1H-pyrazol-3-yl)amino)-5-methylpyrimidin-4-yl)-1H-indol-7-yl)-1-oxoisoindolin-4-yl)picolinamide |
| 474) | 5-(2-(3-(2-((1,5-dimethyl-1H-pyrazol-3-yl)amino)-5-methylpyrimidin-4-yl)-1H-indol-7-yl)-1-oxoisoindolin-4-yl)picolinamide |
| 475) | 2-(3-(2-((1,5-dimethyl-1H-pyrazol-3-yl)amino)-5-methylpyrimidin-4-yl)-1H-indol-7-yl)-4-(2-(dimethylamino)pyridin-4-yl)isoindolin-1-one |

-continued

| | |
|---|---|
| 476) | 2-(3-(2-((1,5-dimethyl-1H-pyrazol-3-yl)amino)-5-methylpyrimidin-4-yl)-1H-indol-7-yl)-4-(2-(methylamino)pyridin-4-yl)isoindolin-1-one |
| 477) | 2-(3-(2-((1,5-dimethyl-1H-pyrazol-3-yl)amino)-5-methylpyrimidin-4-yl)-1H-indol-7-yl)-4-(5-methylpyridin-3-yl)isoindolin-1-one |
| 478) | 2-(3-(2-((1,5-dimethyl-1H-pyrazol-3-yl)amino)-5-methylpyrimidin-4-yl)-1H-indol-7-yl)-4-(5-fluoropyridin-3-yl)isoindolin-1-one |
| 479) | 2-(3-(2-((1,5-dimethyl-1H-pyrazol-3-yl)amino)-5-methylpyrimidin-4-yl)-1H-indol-7-yl)-4-(2,6-dimethylpyridin-4-yl)isoindolin-1-one |
| 480) | 2-(3-(2-((1,5-dimethyl-1H-pyrazol-3-yl)amino)-5-methylpyrimidin-4-yl)-1H-indol-7-yl)-7-fluoro-4-(pyridin-4-yl)isoindolin-1-one |
| 481) | 2-(3-(2-((1,5-dimethyl-1H-pyrazol-3-yl)amino)-5-methylpyrimidin-4-yl)-1H-indol-7-yl)-7-fluoro-4-(2-methoxypyridin-4-yl)isoindolin-1-one |
| 482) | 2-(3-(2-((1,5-dimethyl-1H-pyrazol-3-yl)amino)-5-methylpyrimidin-4-yl)-1H-indol-7-yl)-7-fluoro-4-(2-(methylamino)pyridin-4-yl)isoindolin-1-one |
| 483) | 2-(3-(2-((1,5-dimethyl-1H-pyrazol-3-yl)amino)-5-methylpyrimidin-4-yl)-1H-indol-7-yl)-4-(2-(dimethylamino)pyridin-4-yl)-7-fluoroisoindolin-1-one |
| 484) | 2-(3-(2-((1,5-dimethyl-1H-pyrazol-3-yl)amino)-5-methylpyrimidin-4-yl)-1H-indol-7-yl)-7-fluoro-4-(5-fluoropyridin-3-yl)isoindolin-1-one |
| 485) | 2-(3-(2-((1,5-dimethyl-1H-pyrazol-3-yl)amino)-5-methylpyrimidin-4-yl)-1H-indol-7-yl)-7-fluoro-4-(2-fluoropyridin-4-yl)isoindolin-1-one |
| 486) | 2-(3-(2-((1,5-dimethyl-1H-pyrazol-3-yl)amino)-5-methylpyrimidin-4-yl)-1H-indol-7-yl)-7-fluoro-4-(5-methylpyridin-3-yl)isoindolin-1-one |
| 487) | 2-(3-(2-((1,5-dimethyl-1H-pyrazol-3-yl)amino)-5-methylpyrimidin-4-yl)-1H-indol-7-yl)-7-fluoro-4-(3-methylpyridin-4-yl)isoindolin-1-one |
| 488) | 2-(3-(2-((1,5-dimethyl-1H-pyrazol-3-yl)amino)-5-methylpyrimidin-4-yl)-1H-indol-7-yl)-4-(2,6-dimethylpyridin-4-yl)-7-fluoroisoindolin-1-one |
| 489) | 2-(3-(2-((1,5-dimethyl-1H-pyrazol-3-yl)amino)-5-methylpyrimidin-4-yl)-1H-indol-7-yl)-7-nitro-4-(pyridin-4-yl)isoindolin-1-one |
| 490) | 2-(3-(2-((1,5-dimethyl-1H-pyrazol-3-yl)amino)-5-methylpyrimidin-4-yl)-1H-indol-7-yl)-7-(dimethylamino)-4-(pyridin-4-yl)isoindolin-1-one |
| 491) | 2-(3-(2-((1,5-dimethyl-1H-pyrazol-3-yl)amino)-5-methylpyrimidin-4-yl)-1H-indol-7-yl)-7-(methylamino)-4-(pyridin-4-yl)isoindolin-1-one |
| 492) | 2-(3-(2-((1,5-dimethyl-1H-pyrazol-3-yl)amino)-5-methylpyrimidin-4-yl)-1H-indol-7-yl)-7-iodo-4-phenylisoindolin-1-one |
| 493) | 6-(3-(2-((1,5-dimethyl-1H-pyrazol-3-yl)amino)-5-methylpyrimidin-4-yl)-1H-indol-7-yl)-4-phenyl-5,6-dihydro-7H-pyrrolo[3,4-b]pyridin-7-one |
| 494) | 6-(3-(2-((1,5-dimethyl-1H-pyrazol-3-yl)amino)-5-methylpyrimidin-4-yl)-1H-indol-7-yl)-4-(pyridin-4-yl)-5,6-dihydro-7H-pyrrolo[3,4-b]pyridin-7-one |
| 495) | 6-(3-(2-((1,5-dimethyl-1H-pyrazol-3-yl)amino)-5-methylpyrimidin-4-yl)-1H-indol-7-yl)-4-(pyridin-3-yl)-5,6-dihydro-7H-pyrrolo[3,4-b]pyridin-7-one |
| 496) | 6-(3-(2-((1,5-dimethyl-1H-pyrazol-3-yl)amino)-5-methylpyrimidin-4-yl)-1H-indol-7-yl)-4-(1,2,3,6-tetrahydropyridin-4-yl)-5,6-dihydro-7H-pyrrolo[3,4-b]pyridin-7-one |
| 497) | 6-(3-(2-((1,5-dimethyl-1H-pyrazol-3-yl)amino)-5-methylpyrimidin-4-yl)-1H-indol-7-yl)-3-(pyridin-4-yl)-5,6-dihydro-7H-pyrrolo[3,4-b]pyridin-7-one |
| 498) | 6-(3-(2-((1,5-dimethyl-1H-pyrazol-3-yl)amino)-5-methylpyrimidin-4-yl)-1H-indol-7-yl)-3-(1,2,3,6-tetrahydropyridin-4-yl)-5,6-dihydro-7H-pyrrolo[3,4-b]pyridin-7-one |
| 499) | 2-(3-(2-((1,5-dimethyl-1H-pyrazol-3-yl)amino)-5-methylpyrimidin-4-yl)-1H-indol-7-yl)-7-(1,2,3,6-tetrahydropyridin-4-yl)-1,2-dihydro-3H-pyrrolo[3,4-c]pyridin-3-one |
| 500) | 2-(3-(2-((1,5-dimethyl-1H-pyrazol-3-yl)amino)-5-methylpyrimidin-4-yl)-1H-indol-7-yl)-7-(pyridin-4-yl)-1,2-dihydro-3H-pyrrolo[3,4-c]pyridin-3-one |
| 501) | 2-(3-(2-((1,5-dimethyl-1H-pyrazol-3-yl)amino)-5-methylpyrimidin-4-yl)-1H-indol-7-yl)-4-(pyridin-4-yl)-2,3-dihydro-1H-pyrrolo[3,4-c]pyridin-1-one |
| 502) | 2-(3-(2-((1,5-dimethyl-1H-pyrazol-3-yl)amino)-5-methylpyrimidin-4-yl)-1H-indol-7-yl)-4-(2-methylpyridin-4-yl)-2,3-dihydro-1H-pyrrolo[3,4-c]pyridin-1-one |
| 503) | 2-(3-(2-((1,5-dimethyl-1H-pyrazol-3-yl)amino)-5-methylpyrimidin-4-yl)-1H-indol-7-yl)-4-(5-fluoropyridin-3-yl)-2,3-dihydro-1H-pyrrolo[3,4-c]pyridin-1-one |
| 504) | 2-(3-(2-((1,5-dimethyl-1H-pyrazol-3-yl)amino)-5-methylpyrimidin-4-yl)-1H-indol-7-yl)-4-(2-fluoropyridin-4-yl)-2,3-dihydro-1H-pyrrolo[3,4-c]pyridin-1-one |
| 505) | 2-(3-(2-((1,5-dimethyl-1H-pyrazol-3-yl)amino)-5-methylpyrimidin-4-yl)-1H-indol-7-yl)-4-(5-methylpyridin-3-yl)-2,3-dihydro-1H-pyrrolo[3,4-c]pyridin-1-one |
| 506) | 2-(3-(2-((1,5-dimethyl-1H-pyrazol-3-yl)amino)-5-methylpyrimidin-4-yl)-1H-indol-7-yl)-4-(3-methylpyridin-4-yl)-2,3-dihydro-1H-pyrrolo[3,4-c]pyridin-1-one |

(6) The present invention provides a pharmaceutical composition for preventing or treating GCN2 activation-related diseases, comprising the compound, the stereoisomer thereof, the pharmaceutically acceptable salt thereof, or the solvate thereof according to (1), (2), (3), (4) or (5) as an active ingredient.

(7) The pharmaceutical composition according to (6), the composition further comprises one or more therapeutic agent selected from the group consisting of chemotherapy agent, radiotherapy agent, immunotherapy agent and tumor microenvironment modulating agent.

(8) The present invention provides a method for preventing or treating GCN2 activation-related diseases, comprising administering a therapeutically effective amount of the compound, the stereoisomer thereof, the pharmaceutically acceptable salt thereof, or the solvate thereof according (1), (2), (3), (4) or (5); or the pharmaceutical composition according to (6) or (7) into a subject.

(9) The method according to (8), wherein the GCN2 activation-related diseases comprise a cancer, a neurodegenerative disease, a chronic infection and a metabolic disease.

(10) The method according to (9), wherein the cancer is one more selected from the group consisting of thyroid cancer, melanoma, prostate cancer, endometrial cancer, lung cancer, head and neck cancer, pancreatic cancer, glioma, stomach cancer, urothelial cancer, skin cancer, breast cancer, colorectal cancer, renal cancer, fibrosarcoma, bone sarcoma, connective tissue sarcoma, giant cell carcinoma, squamous cell carcinoma, leukemia, skin cancer, soft tissue cancer, liver cancer, adenocarcinoma, hepatocellular carcinoma, multiple myeloma, myelodysplastic syndrome, myeloproliferative neoplasm, malignant glioma, non-Hodgkin's lymphoma, Hodgkin's lymphoma, Burkitt's lymphoma, chronic lymphocytic leukemia, chronic myeloid leukemia, hairy cell leukemia, plasmacytoma, lymphoplasmacytic lymphoma, acute lymphoblastic leukemia, acute myeloid leukemia, chronic myelomonocytic leukemia, juvenile myelomonocytic leukemia, large granular lymphocytic leukemia, B-cell prolymphocytic leukemia, T-cell prolymphocytic leukemia, small cell lung cancer and pediatric neuroblastoma.

(11) The present invention provides a method for inhibiting GCN2 activity, comprising administering a therapeutically effective amount of the compound, the tautomer thereof, the stereoisomer thereof, the pharmaceutically acceptable salt thereof, or the solvate thereof according (1), (2), (3), (4) or (5); or the pharmaceutical composition according to (6) or (7) into a subject.

Matters mentioned in the use, composition and therapeutic method of the present invention are equally applied, if not contradictory to each other.

MODE FOR INVENTION

Hereinafter, preferred Examples will be suggested for better understanding of the present invention. However, the following Examples are provided only for the purpose of illustrating the present invention, and thus the present invention is not limited thereto.

All chemical reagents were commercially available. Flash column chromatography means silica gel chromatography unless specified otherwise, which was performed on Teledyne Combiflash-RF200 System. $^1$H NMR spectra ($\delta$, ppm) are recorded on 400 MHz or 600 MHz instrument. Mass spectroscopy data (ESI, m/z) for a positive ionization method were measured from Agilent technologies single quadrupole G6120B equipped with Agilent technologies 1260 Infinity system. Preparative HPLC (Prep HPLC) was performed on Agilent technologies G1361A.

Hereinafter, the following Examples may be appropriately changed and modified by those skilled in the art within the scope of the present invention.

Preparing Example: Synthesis of 3-(2-((1,5-dimethyl-1H-pyrazol-3-yl)amino)-5-methylpyrimidin-4-yl)-1H-indol-7-amine and 2-chloro-N-(3-(2-((1,5-dimethyl-1H-pyrazol-3-yl)amino)-5-methylpyrimidin-4-yl)-1H-indol-7-yl)acetamide

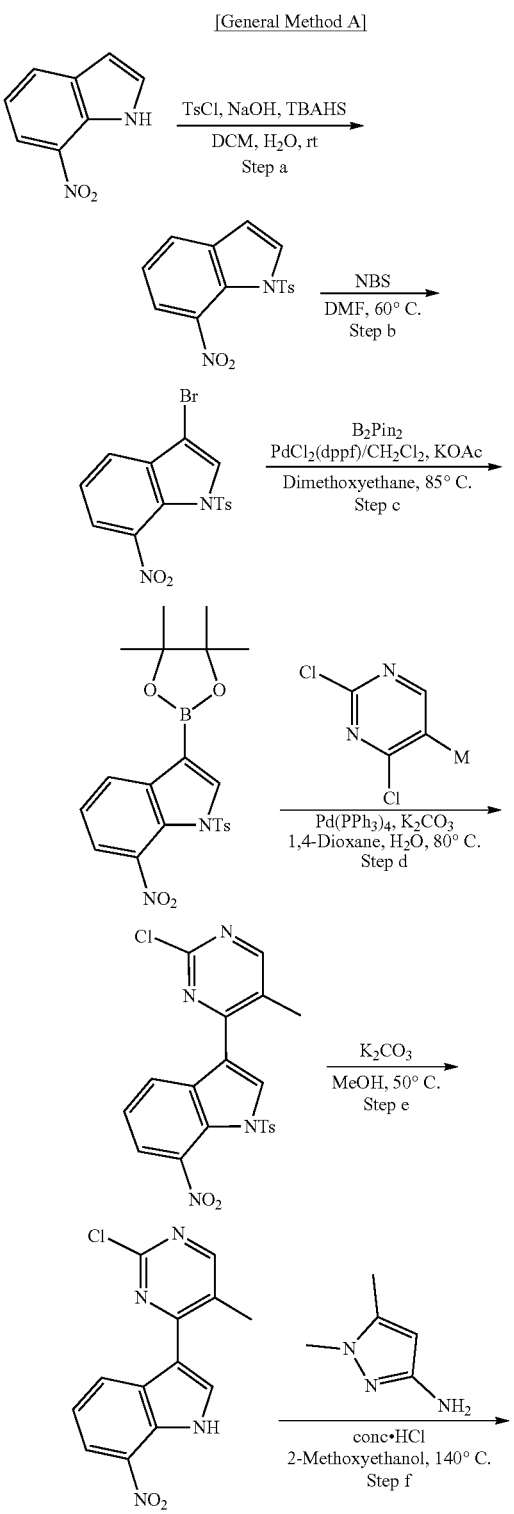

[General Method A]

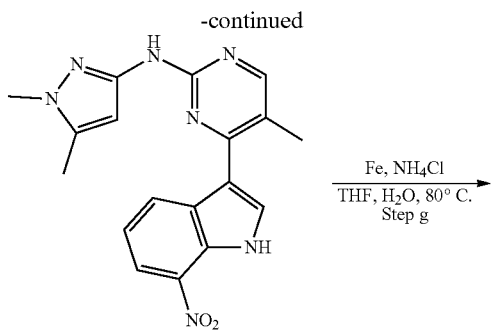

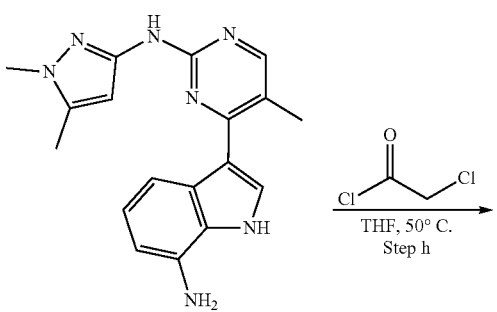

Intermediate 001

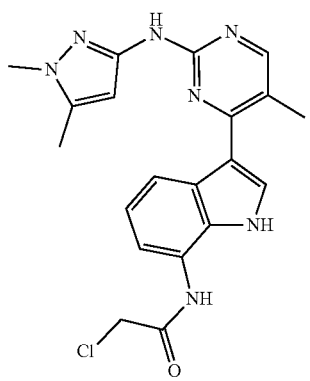

Intermediate 002

[Step a] Preparation of 7-nitro-1-tosyl-1H-indole. In an oven-dried 3 L round bottom flask containing a magnetic stirring bar, a mixture of 7-nitro-1H-indole (CAS Number: 6960-42-5, 81, 500 mmol) and tosyl chloride (TsCl, 114 g, 600 mmol) in DCM (660 mL) was cooled to 0° C. with stirring. To the mixture was added a solution of NaOH (200 g, 5,000 mmol) in water (330 mL) slowly. The reaction was allowed to warm up to room temperature and stirred for 2 h. The reaction mixture was poured into 1 L of water, extracted with DCM (3×2 L), washed with 10% $K_2CO_3$ aqueous solution (400 mL) and 1 N HCl aqueous solution (400 mL), dried over anhydrous $Na_2SO_4$, and concentrated under reduced pressure. Then, the crude product was triturated with MeOH (300 mL), filtered, and dried in vacuo to give the desired product as a white solid (yield, 95%).

MS (ESI, m/z): 317.0 [M+H]$^+$ $^1$H NMR (400 MHz, DMSO) δ 8.05 (d, J=3.7 Hz, 1H), 7.97 (dd, J=7.8, 0.9 Hz, 1H), 7.83 (dt, J=7.9, 1.9 Hz, 1H), 7.80-7.76 (m, 2H), 7.48 (d, J=7.8 Hz, 1H), 7.44 (d, J=8.3 Hz, 2H), 7.08 (d, J=3.7 Hz, 1H), 2.37 (s, 3H).

[Step b] Preparation of 3-bromo-7-nitro-1-tosyl-1H-indole. In an oven-dried 5 L round bottom flask containing a magnetic stirring bar, to a mixture of 7-nitro-1-tosyl-1H-indole (145.5 g, 460 mmol) in DMF (500 mL) was added a solution of N-bromosuccinmide (NBS, 98.0 g) in DMF (300 mL) slowly. The reaction mixture was heated to 60° C. for 3 h. After cooling to room temperature, the reaction mixture was poured into 3 L of water with stirring to give the yellow precipitate. The precipitate was filtered and dissolved again in DCM (10 L) to wash with 1 N NaOH aqueous solution (4 L) and water (2 L). Then, the product was dried over anhydrous $Na_2SO_4$, concentrated under reduced pressure, triturated with MeOH (250 mL), filtered, and dried in vacuo to give the desired product as a white solid (yield, 91%).

MS (ESI, m/z): 394.9 [M+H]$^+$ $^1$H NMR (400 MHz, dmso) δ 8.47 (s, 1H), 7.97 (dd, J=7.9, 0.9 Hz, 1H), 7.89-7.84 (m, 3H), 7.59 (t, J=7.9 Hz, 1H), 7.48 (dd, J=8.6, 0.6 Hz, 2H), 2.40 (s, 3H).

[Step c] Preparation of 7-nitro-3-(4,4,5,5-tetramethyl-1,3,2-dioxaborolan-2-yl)-1-tosyl-1H-indole. In an oven-dried 5 L round bottom flask containing a magnetic stirring bar under $N_2$ atmosphere, a mixture of 3-bromo-7-nitro-1-tosyl-1H-indole (130 g, 330 mmol), bis(pinacolato)diboron ($B_2pin_2$, 117 g, 462 mmol), Pd(dppf)$Cl_2$/$CH_2Cl_2$ (27 g, 33 mmol), and KOAc (65 g, 660 mmol) in dimethoxyethane (DME, 2 L) was heated to 85° C. for 12 h. After cooling to room temperature, the reaction mixture was filtered with the Celite® and concentrated under reduced pressure. The residue was then triturated with MeOH (3×400 mL), filtered, and dried in vacuo to give the desired product as a light gray solid (yield, 68%).

MS (ESI, m/z): 443.1 [M+H]$^+$ $^1$H NMR (400 MHz, dmso) δ 8.32 (s, 1H), 8.18 (dd, J=7.9, 1.1 Hz, 1H), 8.01-7.96 (m, 2H), 7.86 (dd, J=7.9, 1.0 Hz, 1H), 7.54 (d, J=7.9 Hz, 1H), 7.52-7.47 (m, 2H), 2.42 (s, 3H), 1.34 (s, 12H).

[Step d] Preparation of 3-(2-chloro-5-methylpyrimidin-4-yl)-7-nitro-1-tosyl-1H-indole. In an oven-dried 2 L round bottom flask containing a magnetic stirring, a mixture of 7-nitro-3-(4,4,5,5-tetramethyl-1,3,2-dioxaborolan-2-yl)-1-tosyl-1H-indole (63 g, 142 mmol), Pd(PPh$_3$)$_4$ (16 g, 14 mmol), 2,4-dichloro-5-methylpyrimidine (30 g, 185 mmol), and $K_2CO_3$ (39 g, 284 mmol) in 1,4-dioxane (700 mL) and water (260 mL) was heated to 80° C. for 12 h. After cooling to room temperature, the reaction mixture was poured into water (500 mL), extracted with DCM (3×1.5 L), washed with brine, dried over anhydrous $Na_2SO_4$, and concentrated under reduce pressure. Then, the residue was triturated with MeOH (250 mL), filtered, and dried in vacuo to give the desired product as a white solid (yield, 91%).

MS (ESI, m/z): 443.0 [M+H]$^+$ $^1$H NMR (400 MHz, dmso) δ 8.78 (t, J=6.7 Hz, 1H), 8.63 (s, 1H), 8.39 (dt, J=19.8, 9.9 Hz, 1H), 7.97 (dd, J=7.9, 0.9 Hz, 1H), 7.92 (dd, J=8.7, 2.0 Hz, 2H), 7.61 (t, J=8.0 Hz, 1H), 7.52-7.46 (m, 2H), 2.44 (s, 3H), 2.40 (s, 3H).

[Step e] Preparation of 3-(2-chloro-5-methylpyrimidin-4-yl)-7-nitro-1H-indole. To a solution of 3-(2-chloro-5-methylpyrimidin-4-yl)-7-nitro-1-tosyl-1H-indole (47 g, 107 mmol) in MeOH (1 L) was added $K_2CO_3$ (30 g, 214 mmol).

The reaction was heated to 50° C. for 6 h and cooled to room temperature. Then, the reaction mixture was poured into water (400 mL) with stirring to give the precipitate. The precipitate was filtered, washed with MeOH, and dried in vacuo to give the desired product as a brown solid (yield, 98%).

MS (ESI, m/z): 289.0 [M+H]$^+$ $^1$H NMR (400 MHz, dmso) δ 12.65 (s, 1H), 8.89 (dd, J=8.0, 1.0 Hz, 1H), 8.62 (d, J=0.7 Hz, 1H), 8.24 (dd, J=8.1, 1.0 Hz, 1H), 8.19 (d, J=3.9 Hz, 1H), 7.46 (t, J=8.0 Hz, 1H), 2.51 (t, J=0.9 Hz, 3H).

[Step f] Preparation of N-(1,5-dimethyl-1H-pyrazol-3-yl)-5-methyl-4-(7-nitro-1H-indol-3-yl)pyrimidin-2-amine. A mixture of 3-(2-chloro-5-methylpyrimidin-4-yl)-7-nitro-1H-indole (5.80 g, 20 mmol), 1,5-dimethyl-1H-pyrazol-3-amine (2.80 g, 25 mmol), and conc. HCl (1.67 mL, 20 mmol) in 2-methoxyethanol (40 mL) was heated to 130° C. for 72 h. After cooling to room temperature, the reaction mixture was mixed with 10 mL of isopropyl alcohol (IPA) to give the precipitate. The precipitate was filtered, washed with IPA (100 mL), and dried in vacuo to give the desired product as a yellowish solid (yield, 83%).

MS (ESI, m/z): 364.1 [M+H]$^+$ $^1$H NMR (400 MHz, dmso) δ 12.83 (s, 1H), 11.21 (s, 1H), 9.27 (d, J=7.8 Hz, 1H), 8.37 (s, 1H), 8.34 (d, J=3.1 Hz, 1H), 8.28-8.24 (m, 1H), 7.46 (t, J=8.0 Hz, 1H), 6.12 (s, 1H), 3.77 (s, 3H), 2.50 (s, 3H), 2.29 (s, 3H).

[Step g] Synthesis of 3-(2-((1,5-dimethyl-1H-pyrazol-3-yl)amino)-5-methylpyrimidin-4-yl)-1H-indol-7-amine (Intermediate 001). A mixture of N-(1,5-dimethyl-1H-pyrazol-3-yl)-5-methyl-4-(7-nitro-1H-indol-3-yl)pyrimidin-2-amine (15 g, 40 mmol), Fe (powder form, 11 g, 200 mmol), and NH$_4$Cl (21 g, 400 mmol) in THF (560 mL) and water (260 mL) was heated to reflux for 8 h. After cooling to room temperature, the reaction mixture was filtered to remove the black slurry. Then, the filtrate concentrated under reduced pressure and solidified from the mixed solvent of MeOH (250 mL) and DCM (750 mL). The precipitate was filtered, washed with MeOH (100 mL), and dried in vacuo to give the desired product as a white solid (yield, 93%).

MS (ESI, m/z): 334.1 [M+H]$^+$ $^1$H NMR (400 MHz, dmso) δ 11.25 (s, 1H), 9.10 (s, 1H), 8.17 (s, 1H), 7.88 (d, J=2.6 Hz, 1H), 7.79 (d, J=8.2 Hz, 1H), 6.81 (t, J=7.7 Hz, 1H), 6.46 (s, 1H), 6.41 (d, J=7.3 Hz, 1H), 5.11 (s, 2H), 3.62 (s, 3H), 2.33 (s, 3H), 2.19 (s, 3H).

[Step h] Preparation of 2-chloro-N-(3-(2-((1,5-dimethyl-1H-pyrazol-3-yl)amino)-5-methylpyrimidin-4-yl)-1H-indol-7-yl)acetamide (Intermediate 002). A mixture of 3-(2-((1,5-dimethyl-1H-pyrazol-3-yl)amino)-5-methylpyrimidin-4-yl)-1H-indol-7-amine (10 g, 30 mmol) in THF (300 mL) was heated to 60° C. for 2 h to be dissolved clearly. The mixture was cooled to room temperature and 2-chloroacetyl chloride (7.6 mL, 100 mmol) was added dropwise. The reaction was heated to reflux for 12 h. After cooling to room temperature, the reaction mixture was concentrated under reduced pressure to remove solvent and triturated with MeOH (100 mL) to give the precipitate. The precipitate was filtered, washed with MeOH (100 mL), and dried in vacuo to give the desired product as a light green solid (yield, 70%).

MS (ESI, m/z): 410.1 [M+H]$^+$ $^1$H NMR (600 MHz, cd$_3$od) δ 8.70 (s, 1H), 8.30 (s, 1H), 8.18 (s, 1H), 7.35-7.16 (m, 2H), 5.99 (s, 1H), 4.35 (s, 2H), 3.80 (s, 3H), 2.53 (s, 3H), 2.32 (s, 3H).

Example 1: Synthesis of (S)-2-(3-((2-(cyclopropylamino)pyrimidin-4-yl)oxy)pyrrolidin-1-yl)-N-(3-(2-((1,5-dimethyl-1H-pyrazol-3-yl)amino)-5-methylpyrimidin-4-yl)-6-fluoro-1H-indol-7-yl)acetamide

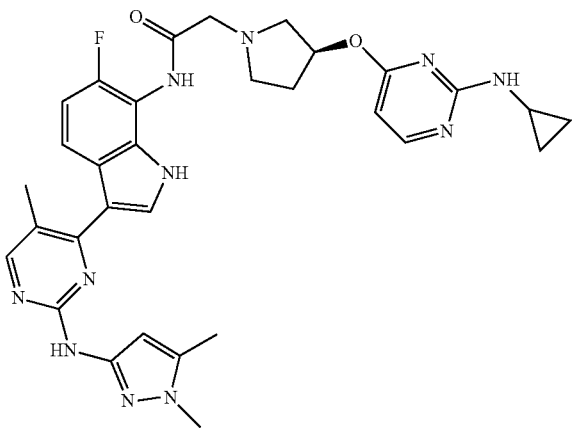 [SMILES: Cc1cnc(Nc2cc(C)n(C)n2)nc1-c1c[nH]c2c(NC(=O)CN3CC[C@H](Oc4ccnc(NC5CC5)n4)C3)c(F)ccc12]

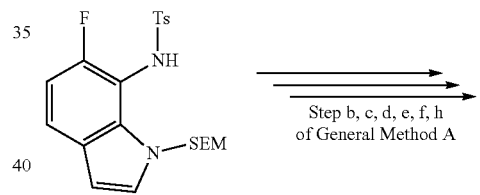

[General Method B]

Step b, c, d, e, f, h of General Method A

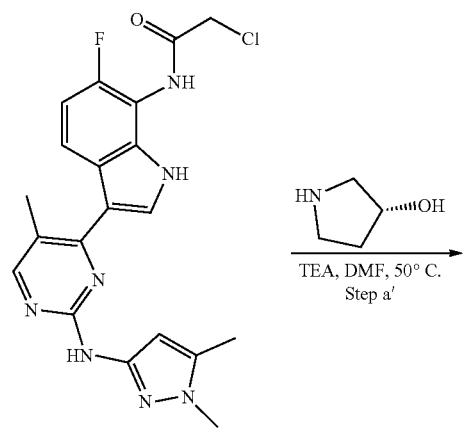

Intermediate 002'

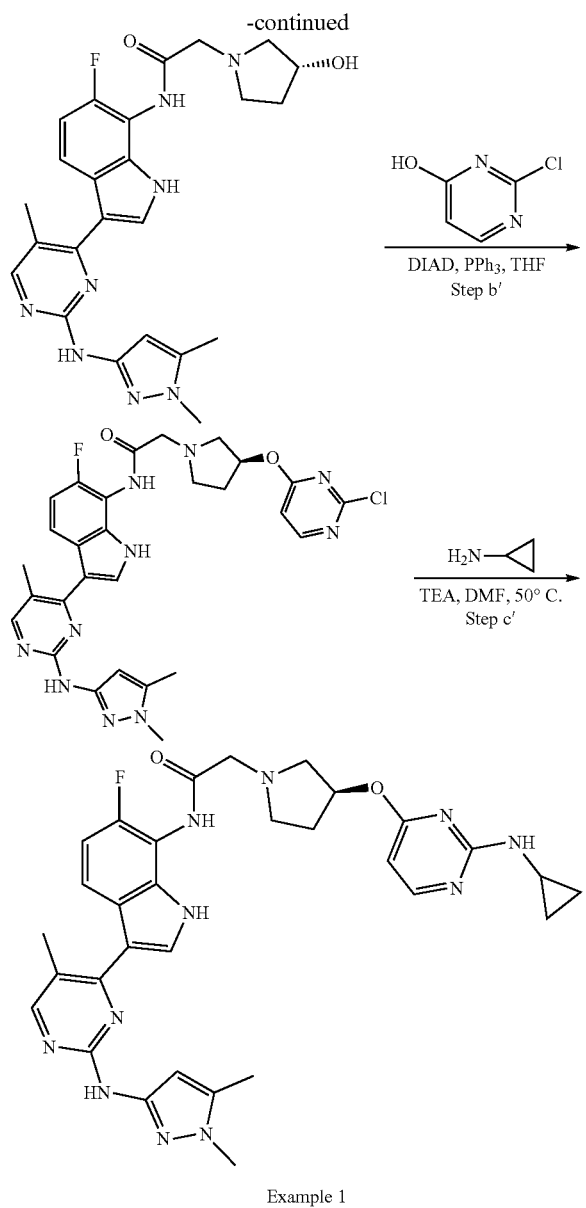

Example 1

[Step a'] A solution of 2-chloro-N-(3-(2-((1,5-dimethyl-1H-pyrazol-3-yl)amino)-5-methylpyrimidin-4-yl)-6-fluoro-1H-indol-7-yl)acetamide (Intermediate 002'; 345 mg, 0.8 mmol) and (R)-pyrrolidin-3-ol (104 mg, 1.2 mmol) in DMF (3 mL) was treated with triethylamine (0.22 mL, 1.6 mmol) and stirred for 2 h at 50° C. The mixture was concentrated in vacuo and purified by column chromatography (0-30% MeOH in DCM) to give (R)—N-(3-(2-((1,5-dimethyl-1H-pyrazol-3-yl)amino)-5-methylpyrimidin-4-yl)-6-fluoro-1H-indol-7-yl)-2-(3-hydroxypyrrolidin-1-yl)acetamide (280 mg, 72%). MS (ESI, m/z): 479.2 [M+H]$^+$

[Step b'] A solution of (R)—N-(3-(2-((1,5-dimethyl-1H-pyrazol-3-yl)amino)-5-methylpyrimidin-4-yl)-6-fluoro-1H-indol-7-yl)-2-(3-hydroxypyrrolidin-1-yl)acetamide (191 mg, 0.4 mmol), 2-chloropyrimidin-4-ol (65 mg, 0.5 mmol) and triphenylphosphine (157 mg, 0.6 mmol) in THF (3 mL) was treated with diisopropyl azodicarboxylate (0.157 mL, 0.8 mmol) and stirred for 2 h. The mixture was concentrated in vacuo and purified by column chromatography (0-30% MeOH in DCM) to give (S)-2-(3-((2-chloropyrimidin-4-yl) oxy)pyrrolidin-1-yl)-N-(3-(2-((1,5-dimethyl-1H-pyrazol-3-yl)amino)-5-methylpyrimidin-4-yl)-6-fluoro-1H-indol-7-yl)acetamide (170 mg, 71%). MS (ESI, m/z): 591.2 [M+H]$^+$

[Step c'] A solution of (S)-2-(3-((2-chloropyrimidin-4-yl)oxy) pyrrolidin-1-yl)-N-(3-(2-((1,5-dimethyl-1H-pyrazol-3-yl)amino)-5-methylpyrimidin-4-yl)-6-fluoro-1H-indol-7-yl)acetamide (118 mg, 0.2 mmol) and cyclopropylamine (20 μL, 0.3 mmol) in DMF (1 mL) was treated with triethylamine (70 μL, 0.5 mmol) and stirred for 2 h at 5° C. Then, the mixture was separated from the UCT SPE CUBCX cartridge and purified by the Prep HPLC to afford a corresponding product as a white solid (60 mg, 49%). MS (ESI, m/z): 612.3 [M+H]$^+$ 2-chloro-N-(3-(2-((1,5-dimethyl-1H-pyrazol-3-yl)amino)-5-methylpyrimidin-4-yl)-6-fluoro-1H-indol-7-yl)acetamide was afforded using 2-chloro-N-(3-(2-((1,5-dimethyl-1H-pyrazol-3-yl)amino)-5-methylpyrimidin-4-yl)-6-fluoro-1H-indol-7-yl)acetamide which was prepared by Step b, c, d, f, g and h of General method A using N-(6-fluoro-1-((2-(trimethylsilyl)ethoxy)methyl)-1H-indol-7-yl)-4-methylbenzenesulfonamide instead of 7-nitro-1-tosyl-1H-indole.

Example 2: Synthesis of (S)—N-(5-amino-3-(2-((1,5-dimethyl-1H-pyrazol-3-yl)amino)-5-methylpyrimidin-4-yl)-1H-indol-7-yl)-2-(3-((2-(cyclopropylamino)pyrimidin-4-yl)oxy)pyrrolidin-1-yl)acetamide

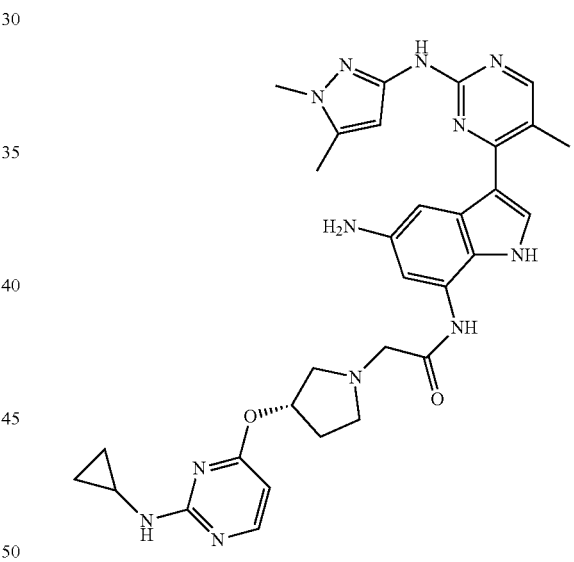

The title product was afforded using (S)-2-(3-((2-(cyclopropylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide which prepared by General method B using Intermediate 002'.

Step a''. At 0° C., a solution of (S)-2-(3-((2-(cyclopropylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide (297 mg, 0.5 mmol) in c-H$_2$SO$_4$ (3 mL) was treated with HNO$_3$ (0.1 mL) and stirred for 8 h. The mixture was diluted with water (10 mL), basified with sodium bicarbonate (9 g) and filtered to give (S)-2-(3-((2-(cyclopropylamino)pyrimidin-4-yl)oxy)pyrrolidin-1-yl)-N-(3-(2-((1,5-dimethyl-1H-pyrazol-3-yl)amino)-5-methylpyrimidin-4-yl)-5-nitro-1H-indol-7-yl)acetamide (35 mg, 10%).

Step b". A solution of (S)-2-(3-((2-(cyclopropylamino)pyrimidin-4-yl)oxy)pyrrolidin-1-yl)-N-(3-(2-((1,5-dimethyl-1H-pyrazol-3-yl)amino)-5-methylpyrimidin-4-yl)-5-nitro-1H-indol-7-yl)acetamide (33 mg, 0.05 mmol) and 10% Pd/C (10 mg) in MeOH (1 mL) was stirred under $H_2$ gas for 1 h. Then, the mixture was separated from the UCT SPE CUBCX cartridge and purified by the Prep HPLC to afford a corresponding product as a white solid (16 mg, 52%). MS (ESI, m/z): 609.3 [M+H]$^+$ Example 3: Synthesis of(S)-2-(3-((2-(cyclopropylamino)pyrimidin-4-yl)oxy)pyrrolidin-1-yl)-N-(3-(2-((1,5-dimethyl-1H-pyrazol-3-yl)amino)-5-methylpyrimidin-4-yl)-6-(dimethylamino)-1H-indol-7-yl)acetamide

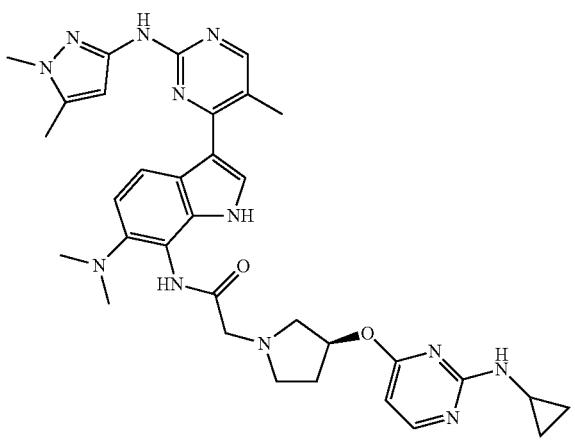 [SMILES: Cc1cnc(Nc2cc(C)n(C)n2)nc1-c1c[nH]c2c(NC(=O)CN3CC[C@H](Oc4ccnc(NC5CC5)n4)C3)c(N(C)C)ccc12]

The title product was afforded by General Method B using 2-chloro-N-(3-(2-((1,5-dimethyl-1H-pyrazol-3-yl)amino)-5-methylpyrimidin-4-yl)-6-(dimethylamino)-1H-indol-7-yl)acetamide instead of 2-chloro-N-(3-(2-((1,5-dimethyl-1H-pyrazol-3-yl)amino)-5-methylpyrimidin-4-yl)-6-fluoro-1H-indol-7-yl)acetamide, which was prepared by General Method A using N,N-dimethyl-7-nitro-1H-indol-6-amine instead of 7-nitro-1H-indole. MS (ESI, m/z): 637.3 [M+H]$^+$ Example 4: Synthesis of (S)-2-(3-((2-(cyclopropylamino)pyrimidin-4-yl)oxy)pyrrolidin-1-yl)-N-(3-(2-((1,5-dimethyl-1H-pyrazol-3-yl)amino)-5-methylpyrimidin-4-yl)-6-methoxy-1H-indol-7-yl)acetamide

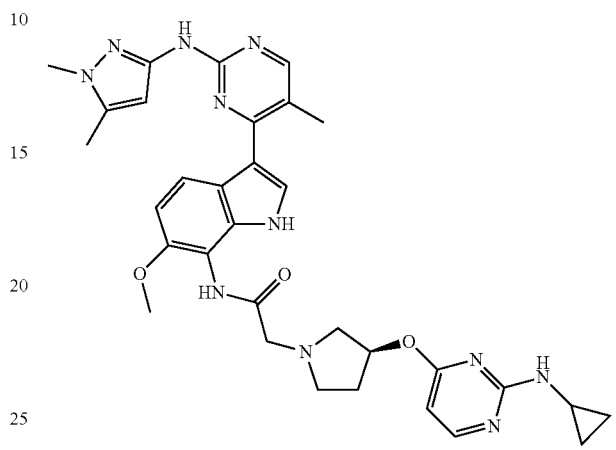

The title product was afforded by a procedure similar to that described for the synthesis of Example 3 using 6-methoxy-7-nitro-1H-indole instead of 7-nitro-1H-indole. MS (ESI, m/z): 624.3 [M+H]$^+$ Example 5: Synthesis of (S)—N-(3-(2-((1,5-dimethyl-1H-pyrazol-3-yl)amino)-5-methylpyrimidin-4-yl)-6-(dimethylamino)-1H-inden-7-yl)-2-(3-((2-((2,2,2-trifluoroethyl)amino)pyrimidin-4-yl)oxy)pyrrolidin-1-yl)acetamide

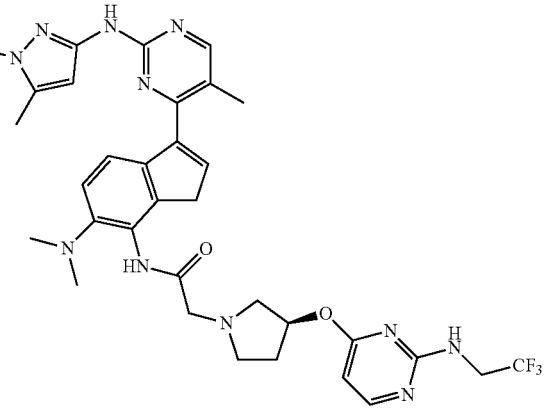

The title product was afforded by a procedure similar to that described for the synthesis of Example 3 using 2,2,2-trifluoroethan-1-amine instead of cyclopropylamine. MS (ESI, m/z): 678.3 [M+H]$^+$ Example 6: Synthesis of (S)—N-(3-(2-((1,5-dimethyl-1H-pyrazol-3-yl)amino)-5-methylpyrimidin-4-yl)-6-methoxy-1H-indol-7-yl)-2-(3-((2-((2,2,2-trifluoroethyl)amino)pyrimidin-4-yl)oxy)pyrrolidin-1-yl)acetamide

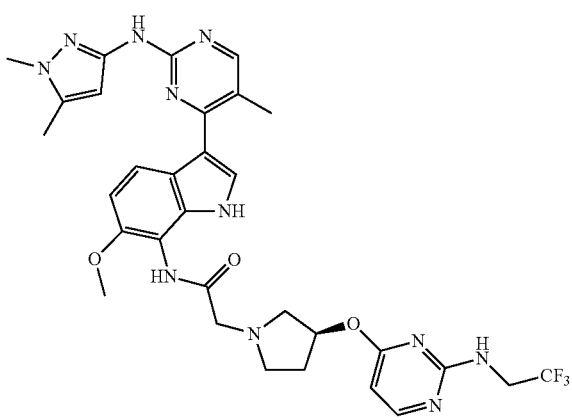 [SMILES: COc1ccc2c(-c3nc(Nc4cc(C)n(C)n4)ncc3C)c[nH]c2c1NC(=O)CN1CC[C@H](Oc2ccnc(NCC(F)(F)F)n2)C1]

The title product was afforded by a procedure similar to that described for the synthesis of Example 4 using 2,2,2-trifluoroethan-1-amine instead of cyclopropylamine. MS (ESI, m/z): 666.3 [M+H]+

Example 7: Synthesis of (S)-2-(3-((6-(cyclopropylamino)pyrimidin-4-yl)oxy)pyrrolidin-1-yl)-N-(3-(2-((1,5-dimethyl-1H-pyrazol-3-yl)amino)pyrimidin-4-yl)-1H-indol-7-yl)acetamide

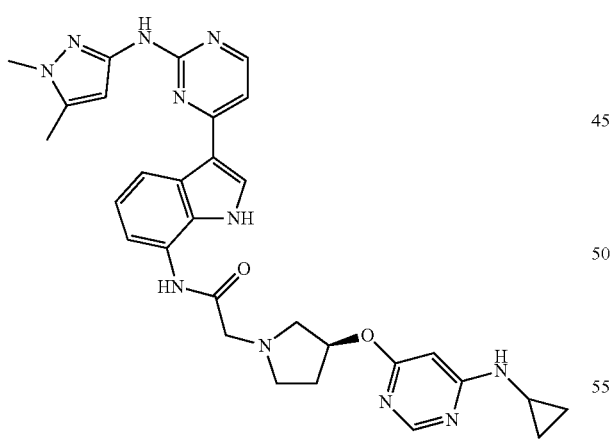

The title product was afforded by a procedure similar to that described for the synthesis of Example 3 using 7-nitro-1H-indole instead of N,N-dimethyl-7-nitro-1H-indol-6-amine, 2,4-dichloropyrimidine instead of 2,4-dichloro-5-methylpyrimidine and 6-chloropyrimidin-4-ol instead of 2-chloropyrimidin-4-ol. MS (ESI, m/z): 580.3 [M+H]+

Example 8: Synthesis of (S)—N-(3-(2-((1,5-dimethyl-1H-pyrazol-3-yl)amino)-5-fluoropyrimidin-4-yl)-1H-indol-7-yl)-2-(3-(pyridin-4-yloxy)pyrrolidin-1-yl)acetamide

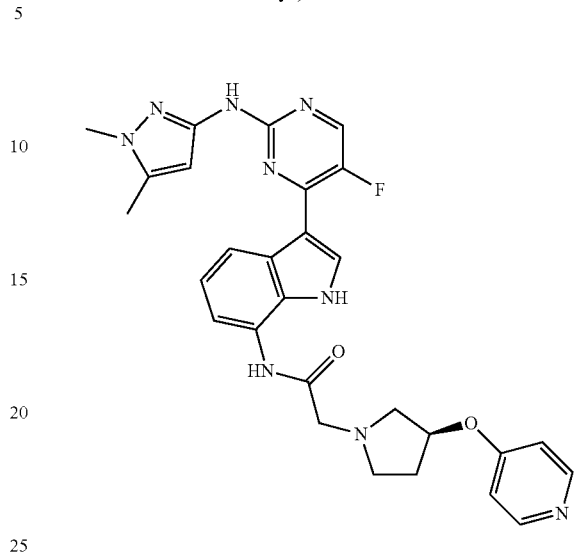

The title product was afforded by a procedure similar to that described for the synthesis of Example 7 using 2,4-dichloro-5-fluoropyrimidine instead of 2,4-dichloropyrimidine and pyridin-4-ol instead of 6-chloropyrimidin-4-ol. MS (ESI, m/z): 542.2 [M+H]+

Example 9: Synthesis of (S)—N-(3-(5-chloro-2-((1,5-dimethyl-1H-pyrazol-3-yl)amino)pyrimidin-4-yl)-1H-indol-7-yl)-2-(3-(pyridin-4-yloxy)pyrrolidin-1-yl)acetamide

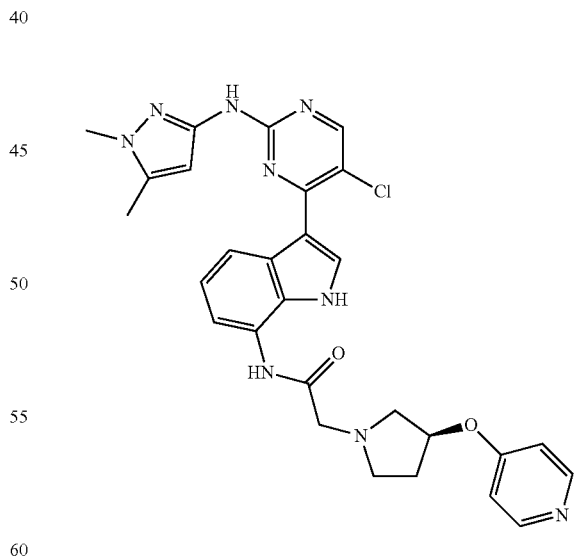

The title product was afforded by a procedure similar to that described for the synthesis of Example 8 using 2,4-dichloro-5-chloropyrimidine instead of 2,4-dichloro-5-fluoropyrimidine. MS (ESI, m/z): 558.2 [M+H]+

Example 10: Synthesis of (S)—N-(3-(5-chloro-2-((1,5-dimethyl-1H-pyrazol-3-yl)amino)pyrimidin-4-yl)-1H-indol-7-yl)-2-(3-((2-(cyclopropylamino)pyrimidin-4-yl)oxy)pyrrolidin-1-yl)acetamide

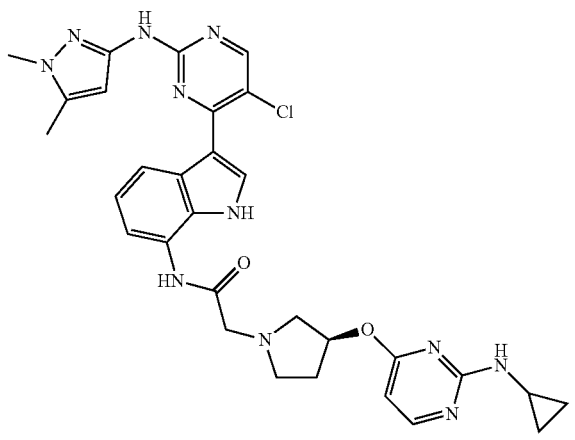 [SMILES: Cc1cc(Nc2ncc(Cl)c(-c3c[nH]c4c(NC(=O)CN5CC[C@H](Oc6ccnc(NC7CC7)n6)C5)cccc34)n2)nn1C]

The title product was afforded by a procedure similar to that described for the synthesis of Example 7 using 2,4,5-trichloropyrimidine instead of 2,4-dichloropyrimidine and 2-chloropyrimidine instead of 6-chloropyrimidin-4-ol. MS (ESI, m/z): 614.2 [M+H]+

Example 11: Synthesis of (S)-2-(3-((2-(cyclopropylamino)pyrimidin-4-yl)oxy)pyrrolidin-1-yl)-N-(3-(2-((1,5-dimethyl-1H-pyrazol-3-yl)amino)-5-ethylpyrimidin-4-yl)-1H-indol-7-yl)acetamide

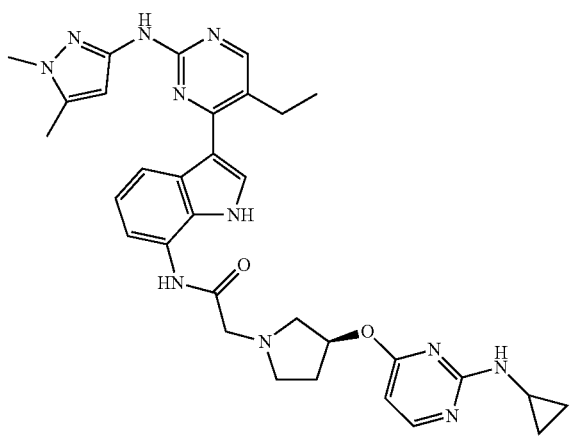 [SMILES: CCc1cnc(Nc2cc(C)n(C)n2)nc1-c1c[nH]c2c(NC(=O)CN3CC[C@H](Oc4ccnc(NC5CC5)n4)C3)cccc12]

The title product was afforded by a procedure similar to that described for the synthesis of Example 10 using 2,4-dichloro-5-ethylpyrimidine instead of 2,4,5-trichloropyrimidine. MS (ESI, m/z): 608.3 [M+H]+

Example 12: Synthesis of (S)—N-(3-(5-cyclopropyl-2-((1,5-dimethyl-1H-pyrazol-3-yl)amino)pyrimidin-4-yl)-1H-indol-7-yl)-2-(3-((2-(cyclopropylamino)pyrimidin-4-yl)oxy)pyrrolidin-1-yl)acetamide

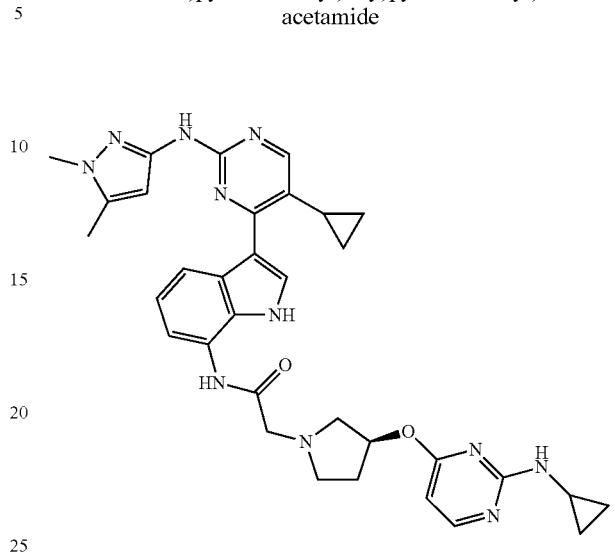

The title product was afforded by a procedure similar to that described for the synthesis of Example 10 using 2,4-dichloro-5-cyclopropylpyrimidine instead of 2,4,5-trichloropyrimidine. MS (ESI, m/z): 620.3 [M+H]+

Example 13: Synthesis of (S)-2-(3-((2-(cyclopropylamino)pyrimidin-4-yl)oxy)pyrrolidin-1-yl)-N-(3-(2-((1,5-dimethyl-1H-pyrazol-3-yl)amino)-5-methoxypyrimidin-4-yl)-1H-indol-7-yl)acetamide

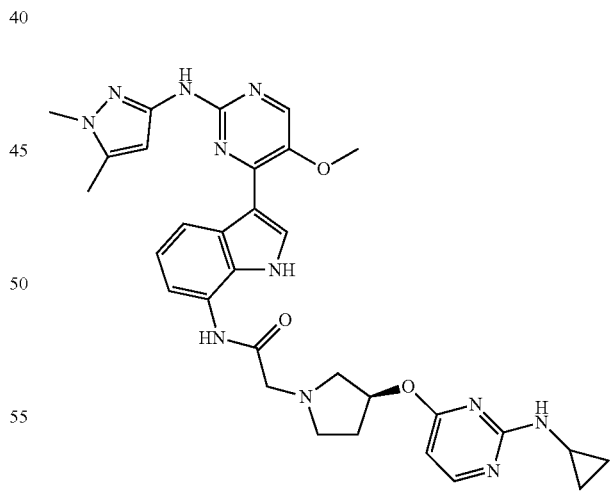

The title product was afforded by a procedure similar to that described for the synthesis of Example 10 using 2,4-dichloro-5-methoxypyrimidine instead of 2,4,5-trichloropyrimidine. MS (ESI, m/z): 610.3 [M+H]+

Example 14: Synthesis of (S)-2-(3-((3-(cyclopropylamino)-1,2,4-triazin-5-yl)oxy)pyrrolidin-1-yl)-N-(3-(2-(((1,5-dimethyl-1H-pyrazol-3-yl)amino)-5-methoxypyrimidin-4-yl)-1H-indol-7-yl)acetamide

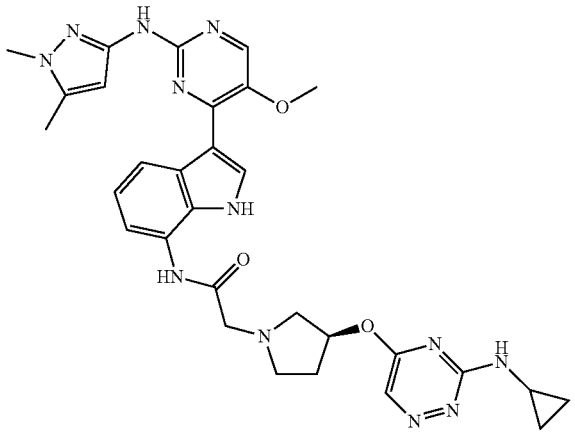 [SMILES: COc1cnc(Nc2cc(C)n(C)n2)nc1-c1c[nH]c2c(NC(=O)CN3CC[C@H](Oc4cnnc(NC5CC5)n4)C3)cccc12]

The title product was afforded by a procedure similar to that described for the synthesis of Example 13 using 3-chloro-1,2,4-triazin-5-ol instead of 2-chloropyrimidin-4-ol. MS (ESI, m/z): 611.3 [M+H]$^+$

Example 15: Synthesis of (S)—N-(3-(2-((5,6-dihydro-4H-pyrrolo[1,2-b]pyrazol-2-yl)amino)-5-methylpyrimidin-4-yl)-1H-indol-7-yl)-2-(3-(pyrimidin-4-yloxy)pyrrolidin-1-yl)acetamide

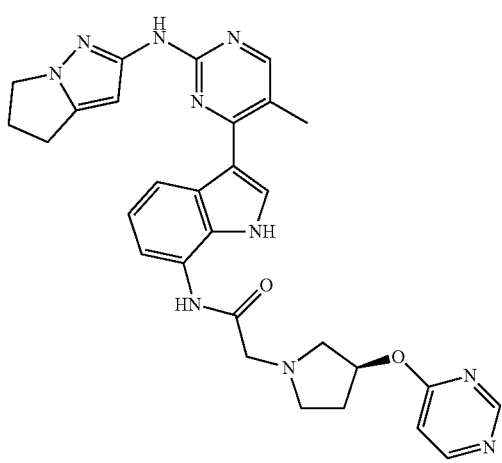 [SMILES: Cc1cnc(Nc2cc3n(n2)CCC3)nc1-c1c[nH]c2c(NC(=O)CN3CC[C@H](Oc4ccncn4)C3)cccc12]

The title product was afforded by General Method A using 5,6-dihydro-4H-pyrrolo[1,2-b]pyrazol-2-amine instead of 1,5-dimethyl-1H-pyrazol-3-amine and General Method B using pyrimidin-4-ol instead of 2-chloropyrimidin-4-ol. MS (ESI, m/z): 551.3 [M+H]$^+$

Example 16: Synthesis of (S)-2-(3-((2-(cyclopropylamino)pyrimidin-4-yl)oxy)pyrrolidin-1-yl)-N-(3-(2-((5,6-dihydro-4H-pyrrolo[1,2-b]pyrazol-2-yl)amino)-5-methylpyrimidin-4-yl)-1H-indol-7-yl)acetamide

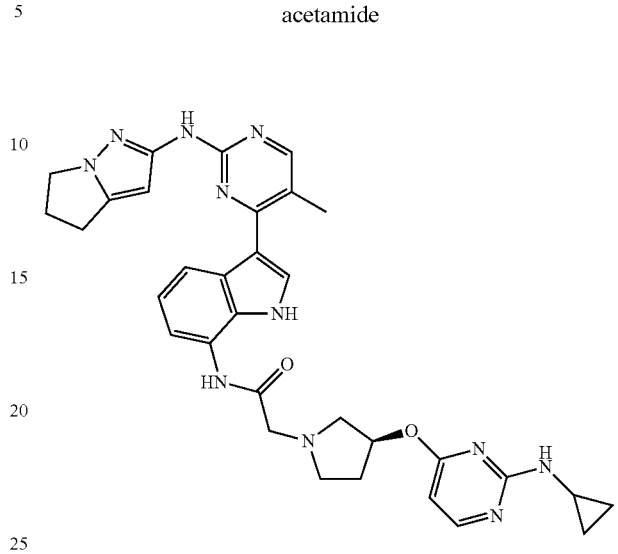

The title product was afforded by General Method A using 5,6-dihydro-4H-pyrrolo[1,2-b]pyrazol-2-amine instead of 1,5-dimethyl-1H-pyrazol-3-amine and General Method B. MS (ESI, m/z): 606.3 [M+H]$^+$

Example 17: Synthesis of (S)-2-(3-((2-(cyclopropylamino)pyrimidin-4-yl)oxy)pyrrolidin-1-yl)-N-(3-(5-methyl-2-((5-methyl-1-(2-morpholinoethyl)-1H-pyrazol-3-yl)amino)pyrimidin-4-yl)-1H-indol-7-yl)acetamide

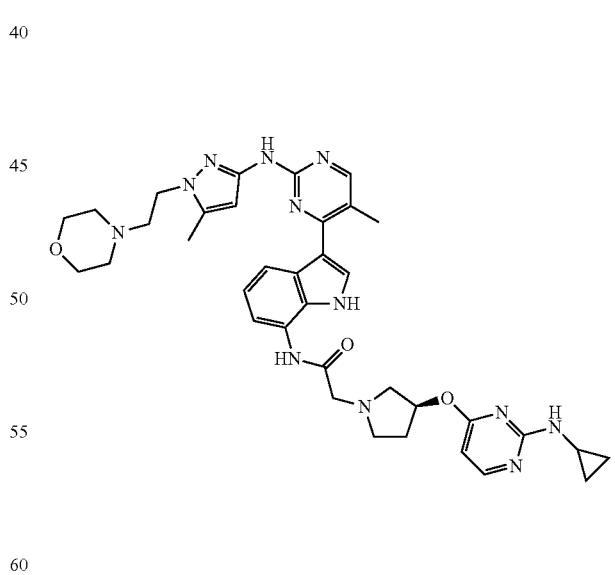

The title product was afforded by a procedure similar to that described for the synthesis of Example 16 using 5-methyl-1-(2-morpholinoethyl)-1H-pyrazol-3-amine instead of 5,6-dihydro-4H-pyrrolo[1,2-b]pyrazol-2-amine. MS (ESI, m/z): 693.4 [M+H]$^+$

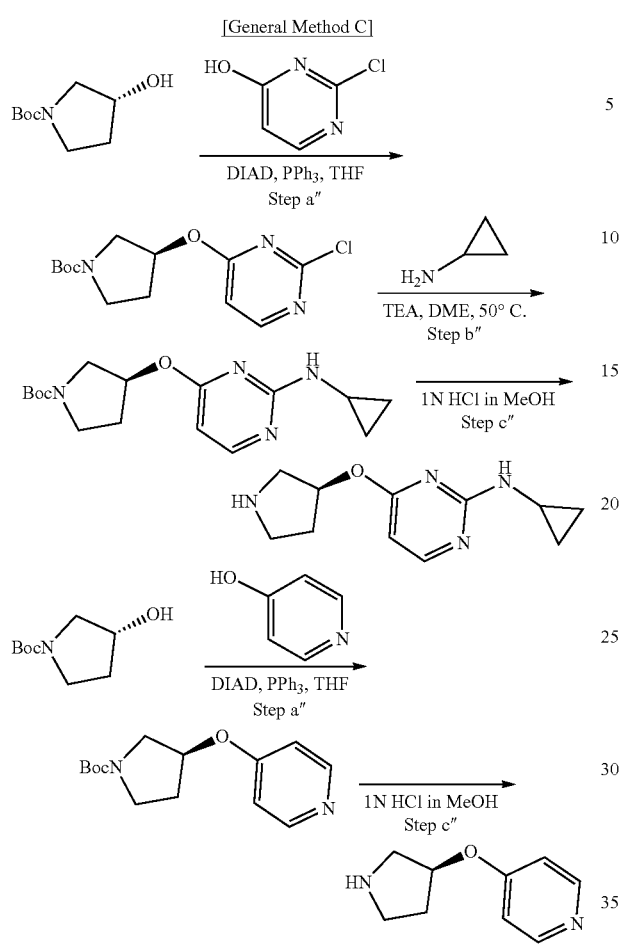

[Step a″] A solution of tert-butyl (R)-3-hydroxypyrrolidine-1-carboxylate (187 mg, 1 mmol), 2-chloropyrimidin-4-ol (156 mg, 1.2 mmol) (or pyridin-4-ol (114 mg, 1.2 mmol)) and triphenylphosphine (367 mg, 1.4 mmol) in THF (5 mL) was treated with diisopropyl azodicarboxylate (0.354 mL, 1.8 mmol) and stirred for 2 h. The mixture was concentrated in vacuo and purified by column chromatography (0-40% EA in Hx) to give tert-butyl (S)-3-((2-chloropyrimidin-4-yl)oxy)pyrrolidine-1-carboxylate (220 mg, 73%). MS (ESI, m/z): 300.1 [M+H]+ (or tert-butyl (S)-3-(pyridin-4-yloxy)pyrrolidine-1-carboxylate (200 mg, 75%). MS (ESI, m/z): 265.2 [M+H]+)

[Step b″] A solution of (S)-3-((2-chloropyrimidin-4-yl)oxy)pyrrolidine-1-carboxylate (450 mg, 1.5 mmol) and cyclopropylamine (200 μL, 3 mmol) in DMF (2 mL) was treated with triethylamine (420 μL, 3 mmol) and stirred for 2 h at 50° C. Then, the mixture was concentrated in vacuo and purified by column chromatography (0-50% EA in Hx) to give tert-butyl (S)-3-((2-(cyclopropylamino)pyrimidin-4-yl)oxy)pyrrolidine-1-carboxylate (300 mg, 62%). MS (ESI, m/z): 321.2 [M+H]+

[Step c″] tert-butyl (S)-3-((2-(cyclopropylamino)pyrimidin-4-yl)oxy)pyrrolidine-1-carboxylate (160 mg, 0.5 mmol) (or tert-butyl (S)-3-(pyridin-4-yloxy)pyrrolidine-1-carboxylate (132 mg, 0.5 mmol)) was dissolved in 1N HCl in MeOH (2 mL). The mixture was stirred for 2 h and separated from the UCT SPE CUBCX cartridge and purified by the Prep HPLC to afford a corresponding product quantitatively. MS (ESI, m/z): 221.1 [M+H]+ (or MS (ESI, m/z): 165.1 [M+H]+)

Example 18: Synthesis of (S)—N-(3-(2-((1,5-dimethyl-1H-pyrazol-3-yl)amino)-5-methylpyrimidin-4-yl)-1H-indol-7-yl)-2-oxo-2-(3-(pyridin-4-yloxy)pyrrolidin-1-yl)acetamide

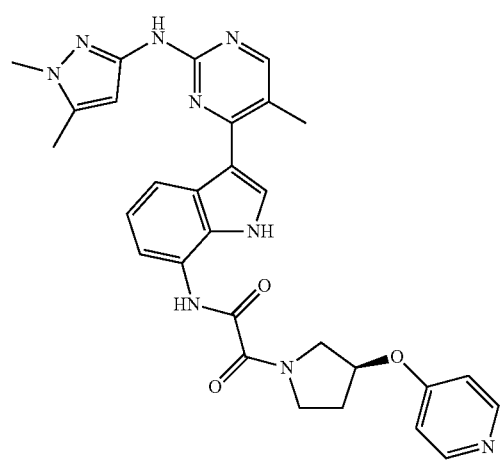 [SMILES: Cc1cnc(Nc2cc(C)n(C)n2)nc1-c1c[nH]c2c(NC(=O)C(=O)N3CC[C@H](Oc4ccncc4)C3)cccc12]

To a stirred mixture of 2-((3-(2-((1,5-dimethyl-1H-pyrazol-4-yl)amino)-5-methylpyrimidin-4-yl)-1H-indol-7-yl)amino)-2-oxoacetic acid (20 mg, 0.05 mmol), HATU (23 mg, 0.06 mmol), and Et₃N (14 uL, 0.10 mmol) in 0.5 mL of DMF was added (S)-4-(pyrrolidin-3-yloxy)pyridine (10 mg, 0.06 mmol). The reaction mixture was heated to 50° C. for 3 h. Then, the mixture was separated from the UCT SPE CUBCX cartridge and purified by the Prep HPLC to afford a corresponding product as a white solid (yield, 40%).
MS (ESI, m/z): 552.2 [M+H]+

Example 19: Synthesis of N-(3-(2-((1,5-dimethyl-1H-pyrazol-3-yl)amino)-5-methylpyrimidin-4-yl)-1H-indol-7-yl)-2-oxo-2-(3-(pyridin-2-yloxy)pyrrolidin-1-yl)acetamide

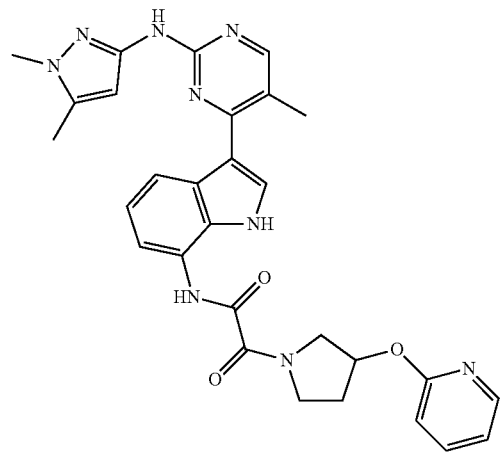 [SMILES: Cc1cnc(Nc2cc(C)n(C)n2)nc1-c1c[nH]c2c(NC(=O)C(=O)N3CCC(Oc4ccccn4)C3)cccc12]

The title product was afforded by a procedure similar to that described for the synthesis of Example 18 using 2-(pyrrolidin-3-yloxy)pyridine instead of (S)-4-(pyrrolidin-3-yloxy)pyridine. MS (ESI, m/z): 552.2 [M+H]⁺

Example 20: Synthesis of (S)-2-(3-((2-(cyclopropylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)-2-oxoacetamide

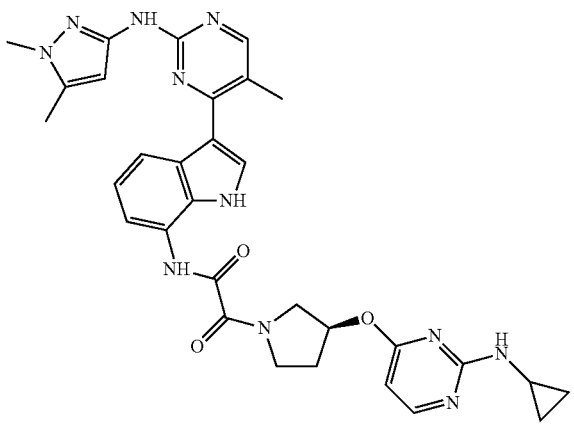 [SMILES: Cc1cnc(Nc2cc(C)n(C)n2)nc1-c1c[nH]c2c(NC(=O)C(=O)N3CC[C@H](Oc4ccnc(NC5CC5)n4)C3)cccc12]

The title product was afforded by a procedure similar to that described for the synthesis of Example 18 using (S)—N-cyclopropyl-4-(pyrrolidin-3-yloxy)pyrimidin-2-amine instead of (S)-4-(pyrrolidin-3-yloxy)pyridine. MS (ESI, m/z): 608.3 [M+H]⁺

Example 21: Synthesis of (S)—N-(3-(2-((1,5-dimethyl-1H-pyrazol-3-yl)amino)-5-methylpyrimidin-4-yl)-1H-indol-7-yl)-N-methyl-2-(3-(pyrimidin-4-yloxy)pyrrolidin-1-yl)acetamide

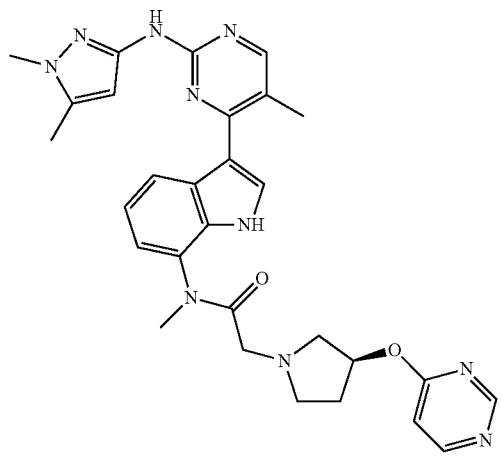 [SMILES: Cc1cnc(Nc2cc(C)n(C)n2)nc1-c1c[nH]c2c(N(C)C(=O)CN3CC[C@H](Oc4ccncn4)C3)cccc12]

The title compound was afforded by General Method A using N-(1H-indol-7-yl)-N,4-dimethylbenzenesulfonamide instead of 7-nitro-1H-indole and General Method B using pyrimidin-4-ol instead of 2-chloropyrimidin-4-ol. MS (ESI, m/z): 553.3 [M+H]⁺

Example 22: Synthesis of N-(3-(2-((1,5-dimethyl-1H-pyrazol-3-yl)amino)-5-methylpyrimidin-4-yl)-1H-indol-7-yl)-2-(pyrrolidin-1-yl)propanamide

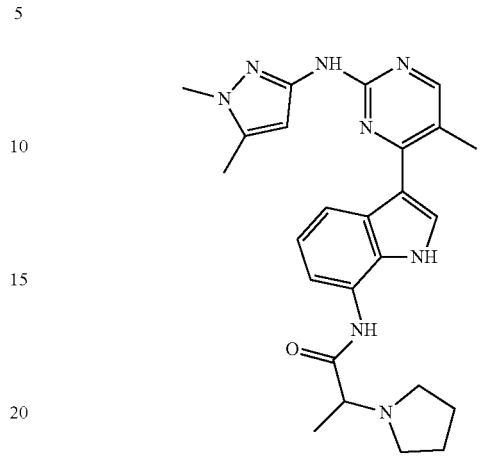

The title compound was afforded by General Method A using 2-chloropropanoyl chloride instead of 2-chloroacetyl chloride and General Method B using pyrrolidine instead of (R)-pyrrolidin-3-ol. MS (ESI, m/z): 459.3 [M+H]⁺

Example 23: Synthesis of N-(3-(2-((1,5-dimethyl-1H-pyrazol-3-yl)amino)-5-methylpyrimidin-4-yl)-1H-indol-7-yl)-2-((S)-3-(pyridin-4-yloxy)pyrrolidin-1-yl)propanamide

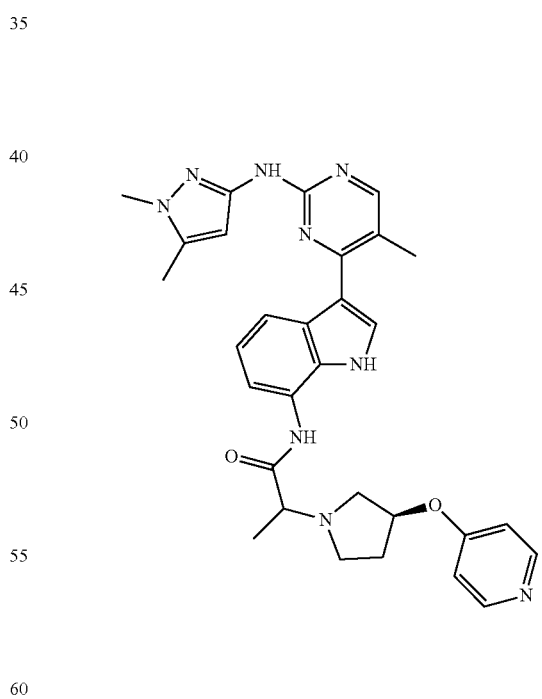

The title product was afforded by a procedure similar to that described for the synthesis of Example 22 using (S)-4-(pyrrolidin-3-yloxy)pyridine instead of pyrrolidine. MS (ESI, m/z): 551.3 [M+H]⁺

Example 24: Synthesis of N-(3-(2-((1,5-dimethyl-1H-pyrazol-3-yl)amino)-5-methylpyrimidin-4-yl)-1H-indol-7-yl)-2-methyl-2-(pyrrolidin-1-yl)propanamide

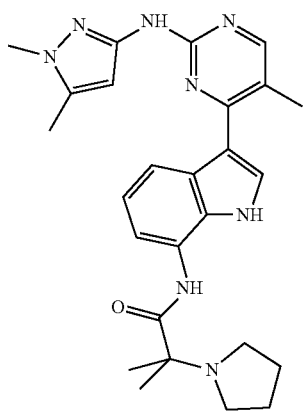

The title product was afforded by a procedure similar to that described for the synthesis of Example 22 using 2-chloro-2-methylpropanoyl chloride instead of 2-chloropropanoyl chloride. MS (ESI, m/z): 473.3 [M+H]$^+$ Example 25: Synthesis of (S)—N-(3-(2-((1,5-dimethyl-1H-pyrazol-3-yl)amino)-5-methylpyrimidin-4-yl)-1H-indol-7-yl)-2-methyl-2-(3-(pyridin-4-yloxy)pyrrolidin-1-yl)propanamide

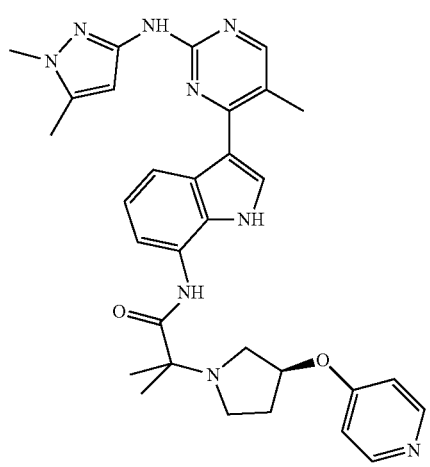 [SMILES: Cc1cnc(Nc2cc(C)n(C)n2)nc1-c1c[nH]c2c(NC(=O)C(C)(C)N3CC[C@H](Oc4ccncc4)C3)cccc12]

The title product was afforded by a procedure similar to that described for the synthesis of Example 23 using 2-chloro-2-methylpropanoyl chloride instead of 2-chloropropanoyl chloride. MS (ESI, m/z): 566.3 [M+H]$^+$ Example 26: Synthesis of N-(3-(2-((1,5-dimethyl-1H-pyrazol-3-yl)amino)-5-methylpyrimidin-4-yl)-1H-indol-7-yl)-2-(3-hydroxyazetidin-1-yl)acetamide

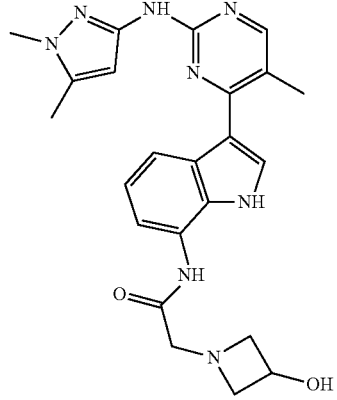 [SMILES: Cc1cnc(Nc2cc(C)n(C)n2)nc1-c1c[nH]c2c(NC(=O)CN3CC(O)C3)cccc12]

The title product was afforded by a procedure similar to Step a' of General Method B using azetidin-3-ol instead of (R)-pyrrolidin-3-ol from Intermediate 002 prepared by Method A. MS (ESI, m/z): 447.2 [M+H]$^+$ Example 27: Synthesis of N-(3-(2-((1,5-dimethyl-1H-pyrazol-3-yl)amino)-5-methylpyrimidin-4-yl)-1H-indol-7-yl)-2-(3-(pyridin-4-ylmethoxy)azetidin-1-yl)acetamide

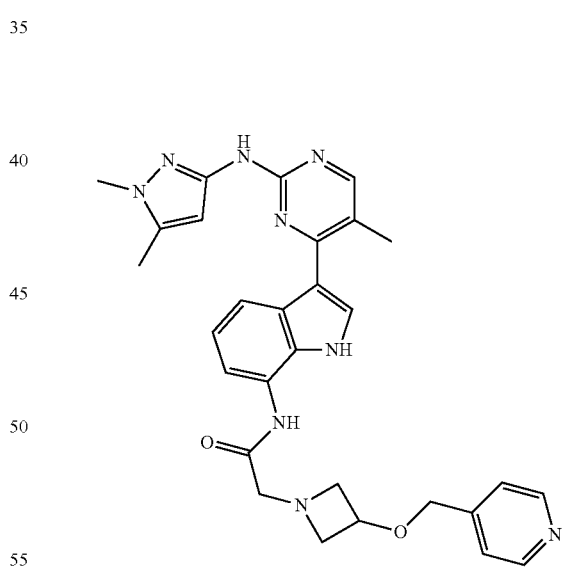

A solution of Example 26 (223 mg, 0.5 mmol) and cesium carbonate (325 mg, 1 mmol) in DMF (2 mL) was treated with 4-(bromomethyl)pyridine (120 mg, 0.7 mmol). Then, the mixture was separated from the UCT SPE CUBCX cartridge and purified by the Prep HPLC to afford a corresponding product (100 mg, 37%). MS (ESI, m/z): 538.3 [M+H]$^+$ Example 28: Synthesis of N-(3-(2-((1,5-dimethyl-1H-pyrazol-3-yl)amino)-5-methylpyrimidin-4-yl)-1H-indol-7-yl)-2-(3-(pyridin-4-yloxy)azetidin-1-yl)acetamide

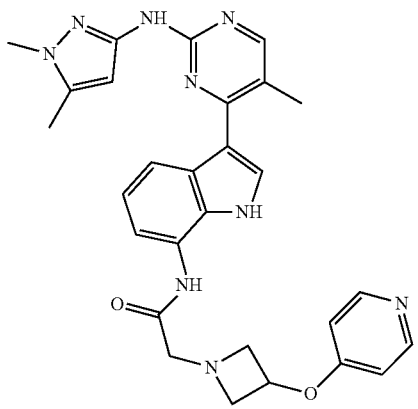 [SMILES: Cc1cnc(Nc2cc(C)n(C)n2)nc1-c1c[nH]c2c(NC(=O)CN3CC(Oc4ccncc4)C3)cccc12]

The title product was afforded by a procedure similar to that described for the synthesis of Example 26 using 4-(azetidin-3-yloxy)pyridine instead of azetidin-3-ol. 4-(azetidin-3-yloxy)pyridine was prepared by a procedure similar to General Method C using tert-butyl 3-hydroxyazetidine-1-carboxylate instead of tert-butyl (R)-3-hydroxypyrrolidine-1-carboxylate. MS (ESI, m/z): 524.2 [M+H]$^+$ Example 29: Synthesis of N-(3-(2-((1,5-dimethyl-1H-pyrazol-3-yl)amino)-5-methylpyrimidin-4-yl)-1H-indol-7-yl)-2-(3-(pyrimidin-4-yloxy)azetidin-1-yl)acetamide

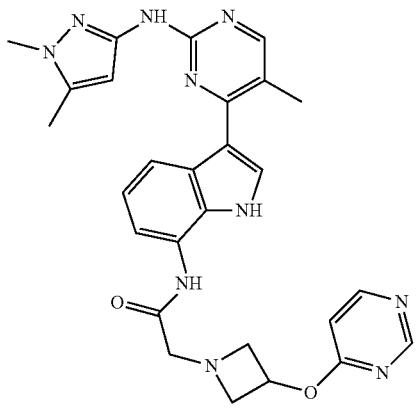 [SMILES: Cc1cnc(Nc2cc(C)n(C)n2)nc1-c1c[nH]c2c(NC(=O)CN3CC(Oc4ccncn4)C3)cccc12]

The title product was afforded by a procedure similar to that described for the synthesis of Example 28 using 4-(azetidin-3-yloxy)pyrimidine instead of 4-(azetidin-3-yloxy)pyridine. MS (ESI, m/z): 525.2 [M+H]$^+$ Example 30: Synthesis of N-(3-(2-((1,5-dimethyl-1H-pyrazol-3-yl)amino)-5-methylpyrimidin-4-yl)-1H-indol-7-yl)-2-(3-(pyridin-3-yloxy)azetidin-1-yl)acetamide

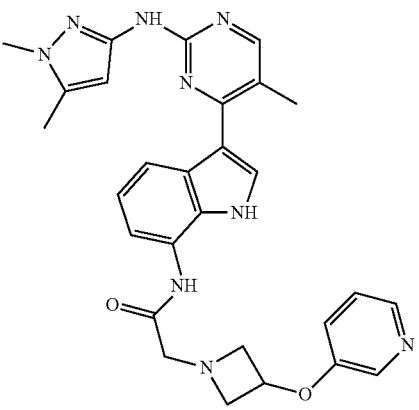 [SMILES: Cc1cnc(Nc2cc(C)n(C)n2)nc1-c1c[nH]c2c(NC(=O)CN3CC(Oc4cccnc4)C3)cccc12]

The title product was afforded by a procedure similar to that described for the synthesis of Example 28 using 3-(azetidin-3-yloxy)pyridine instead of 4-(azetidin-3-yloxy)pyridine. MS (ESI, m/z): 524.2 [M+H]$^+$ Example 31: Synthesis of methyl 1-(2-((3-(2-((1,5-dimethyl-1H-pyrazol-3-yl)amino)-5-methylpyrimidin-4-yl)-1H-indol-7-yl)amino)-2-oxoethyl)azetidine-3-carboxylate

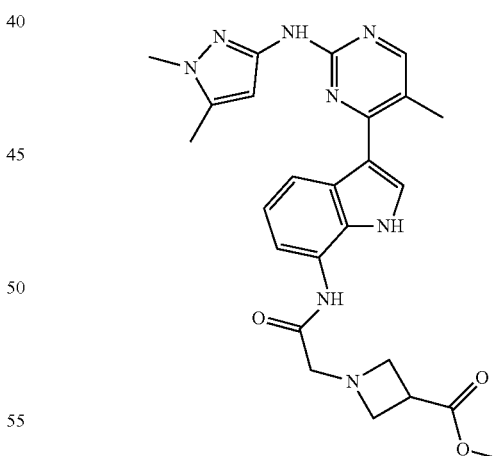

The title product was afforded by a procedure similar to that described for the synthesis of Example 26 using methyl azetidine-3-carboxylate instead of azetidin-3-ol.

MS (ESI, m/z): 489.2 [M+H]$^+$

Example 32: Synthesis of 1-(2-((3-(2-((1,5-dimethyl-1H-pyrazol-3-yl)amino)-5-methylpyrimidin-4-yl)-1H-indol-7-yl)amino)-2-oxoethyl)azetidine-3-carboxylic acid

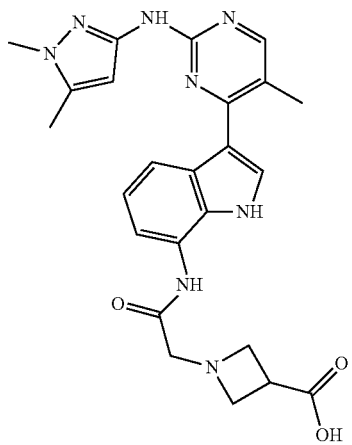 [SMILES: Cc1cnc(Nc2cc(C)n(C)n2)nc1-c1c[nH]c2c(NC(=O)CN3CC(C(=O)O)C3)cccc12]

The title product was afforded by a procedure similar to that described for the synthesis of Example 26 using azetidine-3-carboxylic acid instead of azetidin-3-ol. MS (ESI, m/z): 475.2 [M+H]$^+$ Example 33: Synthesis of N-cyclopropyl-3-((1-(2-((3-(2-((1,5-dimethyl-1H-pyrazol-3-yl)amino)-5-methylpyrimidin-4-yl)-1H-indol-7-yl)amino)-2-oxoethyl)azetidin-3-yl)oxy)isoxazole-5-carboxamide

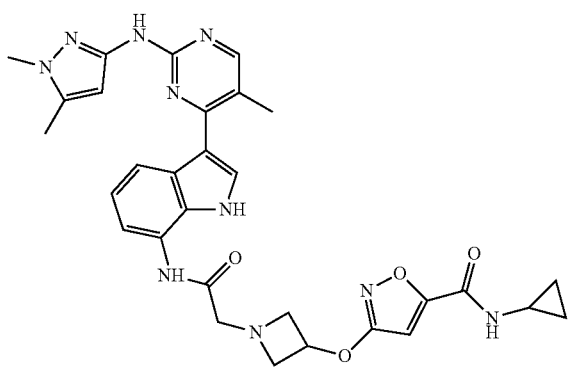 [SMILES: Cc1cnc(Nc2cc(C)n(C)n2)nc1-c1c[nH]c2c(NC(=O)CN3CC(Oc4cc(C(=O)NC5CC5)on4)C3)cccc12]

A solution of Example 26 (446 mg, 1 mmol), methyl 3-hydroxyisoxazole-5-carboxylate (143 mg, 1 mmol) and triphenylphosphine (314 mg, 1.2 mmol) in THF (3 mL) was treated with diisopropyl azodicarboxylate (0.314 mL, 1.6 mmol) and stirred for 2 h. The mixture was concentrated in vacuo and purified by column chromatography (0-30% MeOH in DCM) to give methyl 3-((1-(2-((3-(2-((1,5-dimethyl-1H-pyrazol-3-yl)amino)-5-methylpyrimidin-4-yl)-1H-indol-7-yl)amino)-2-oxoethyl)azetidin-3-yl)oxy)isoxazole-5-carboxylate (480 mg, 84%).

A solution of methyl 3-((1-(2-((3-(2-((1,5-dimethyl-1H-pyrazol-3-yl)amino)-5-methylpyrimidin-4-yl)-1H-indol-7-yl)amino)-2-oxoethyl)azetidin-3-yl)oxy)isoxazole-5-carboxylate (400 mg, 0.7 mmol) in MeOH (1 mL) was treated with 1N NaOH in MeOH (0.5 mL) and stirred for 1 h. The mixture was concentrated in vacuo and neutralized with 1N HCl to give 3-((1-(2-((3-(2-((1,5-dimethyl-1H-pyrazol-3-yl)amino)-5-methylpyrimidin-4-yl)-1H-indol-7-yl)amino)-2-oxoethyl)azetidin-3-yl)oxy)isoxazole-5-carboxylic acid quantitatively.

A solution of 3-((1-(2-((3-(2-((1,5-dimethyl-1H-pyrazol-3-yl)amino)-5-methylpyrimidin-4-yl)-1H-indol-7-yl)amino)-2-oxoethyl)azetidin-3-yl)oxy)isoxazole-5-carboxylic acid (278 mg, 0.5 mmol), cyclopropylamine (60 μL, 0.9 mmol), HATU (460 mg, 1.2 mmol) in DMF (2 mL) was treated with triethylamine (210 μL, 1.5 mmol) and stirred for 2 h. Then, the mixture was separated from the UCT SPE CUBCX cartridge and purified by the Prep HPLC to afford a corresponding product (200 mg, 67%). MS (ESI, m/z): 597.3 [M+H]$^+$ Example 34: Synthesis of 2-(5,6-dihydro-[4,4'-bipyridin]-1(2H)-yl)-N-(3-(2-((1,5-dimethyl-1H-pyrazol-3-yl)amino)-5-methylpyrimidin-4-yl)-1H-indol-7-yl)acetamide

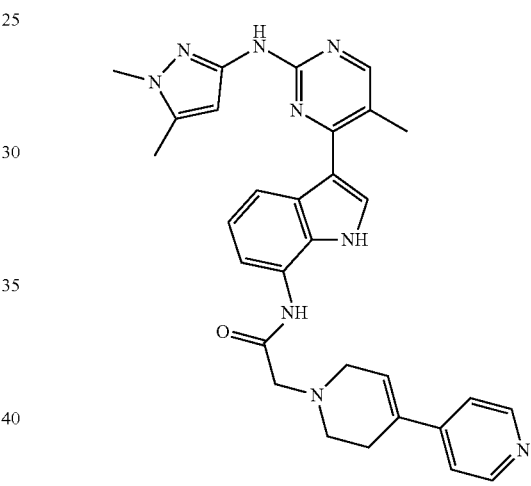

A solution of Intermediate 002 (818 mg, 2 mmol) prepared by Method A and 4-(4,4,5,5-tetramethyl-1,3,2-dioxaborolan-2-yl)-1,2,3,6-tetrahydropyridine (501 mg, 2.4 mmol) in DMF (3 mL) was treated with triethylamine (0.55 mL, 4 mmol) and stirred for 2 h at 50° C. The mixture was concentrated in vacuo and purified by column chromatography (0-30% MeOH in DCM) to give N-(3-(2-((1,5-dimethyl-1H-pyrazol-3-yl)amino)-5-methylpyrimidin-4-yl)-1H-indol-7-yl)-2-(4-(4,4,5,5-tetramethyl-1,3,2-dioxaborolan-2-yl)-3,6-dihydropyridin-1(2H)-yl)acetamide (720 mg, 62%). MS (ESI, m/z): 583.3 [M+H]$^+$ A solution of N-(3-(2-((1,5-dimethyl-1H-pyrazol-3-yl)amino)-5-methylpyrimidin-4-yl)-1H-indol-7-yl)-2-(4-(4,4,5,5-tetramethyl-1,3,2-dioxaborolan-2-yl)-3,6-dihydropyridin-1(2H)-yl)acetamide (291 mg, 0.5 mmol), Pd(PPh$_3$)$_4$ (58 mg, 0.05 mmol), 4-bromopyridine (126 mg, 0.8 mmol), and K$_2$CO$_3$ (207 mg, 1.5 mmol) in 1,4-dioxane (0.9 mL) and water (0.3 mL) was heated to 80° C. for 12 h. Then, the mixture was separated from the UCT SPE CUBCX cartridge and purified by the Prep HPLC to afford a corresponding product (170 mg, 64%). MS (ESI, m/z): 534.3 [M+H]$^+$ Example 35: Synthesis of N-(3-(2-((1,5-dimethyl-1H-pyrazol-3-yl)amino)-5-methylpyrimidin-4-yl)-1H-indol-7-yl)-2-(4-(1-methyl-1H-pyrazol-4-yl)-5,6-dihydropyridin-1(2H)-yl)acetamide

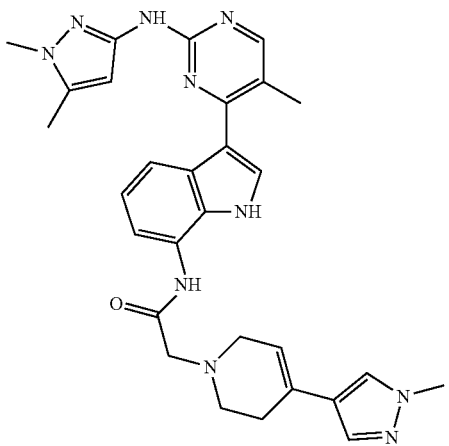

The title product was afforded by a procedure similar to that described for the synthesis of Example 34 using 4-bromo-1-methyl-1H-pyrazole instead of 4-bromopyridine. MS (ESI, m/z): 537.3 [M+H]$^+$ Example 36: Synthesis of N-(3-(2-((1,5-dimethyl-1H-pyrazol-3-yl)amino)-5-methylpyrimidin-4-yl)-1H-indol-7-yl)-2-(4-(4-methylpiperazin-1-yl)piperidin-1-yl)acetamide

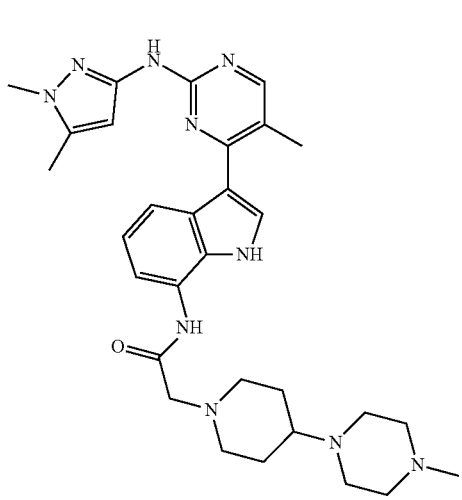

A solution of Intermediate 002 (818 mg, 2 mmol) prepared by Method A and piperidin-4-ol (303 mg, 3 mmol) in DMF (3 mL) was treated with triethylamine (0.55 mL, 4 mmol) and stirred for 2 h at 50° C. The mixture was concentrated in vacuo and purified by column chromatography (0-20% MeOH in DCM) to give N-(3-(2-((1,5-dimethyl-1H-pyrazol-3-yl)amino)-5-methylpyrimidin-4-yl)-1H-indol-7-yl)-2-(4-hydroxypiperidin-1-yl)acetamide (820 mg, 86%). MS (ESI, m/z): 475.2 [M+H]$^+$ A solution of N-(3-(2-((1,5-dimethyl-1H-pyrazol-3-yl)amino)-5-methylpyrimidin-4-yl)-1H-indol-7-yl)-2-(4-hydroxypiperidin-1-yl)acetamide (711 mg, 1.5 mmol) and mesyl chloride (193 µL, 2.5 mmol) was treated with triethylamine (0.7 mL, 5 mmol) and stirred for 3 h at 0° C. The mixture was concentrated in vacuo and purified by column chromatography (0-20% MeOH in DCM) to give 1-(2-((3-(2-((1,5-dimethyl-1H-pyrazol-3-yl)amino)-5-methylpyrimidin-4-yl)-1H-indol-7-yl)amino)-2-oxoethyl)piperidin-4-yl methanesulfonate (620 mg, 75%). MS (ESI, m/z): 553.2 [M+H]$^+$ A solution of 1-(2-((3-(2-((1,5-dimethyl-1H-pyrazol-3-yl)amino)-5-methylpyrimidin-4-yl)-1H-indol-7-yl)amino)-2-oxoethyl)piperidin-4-yl methanesulfonate (552 mg, 1 mmol) and 1-methylpiperazine (200 mg, 2 mmol) in DMF (3 mL) was treated with triethylamine (0.42 mL, 3 mmol) and stirred for 2 h at 50° C. Then, the mixture was separated from the UCT SPE CUBCX cartridge and purified by the Prep HPLC to afford a corresponding product (310 mg, 55%). MS (ESI, m/z): 557.3 [M+H]$^+$ Example 37: Synthesis of N-(3-(2-((1,5-dimethyl-1H-pyrazol-3-yl)amino)-5-methylpyrimidin-4-yl)-1H-indol-7-yl)-2-(4-morpholinopiperidin-1-yl)acetamide

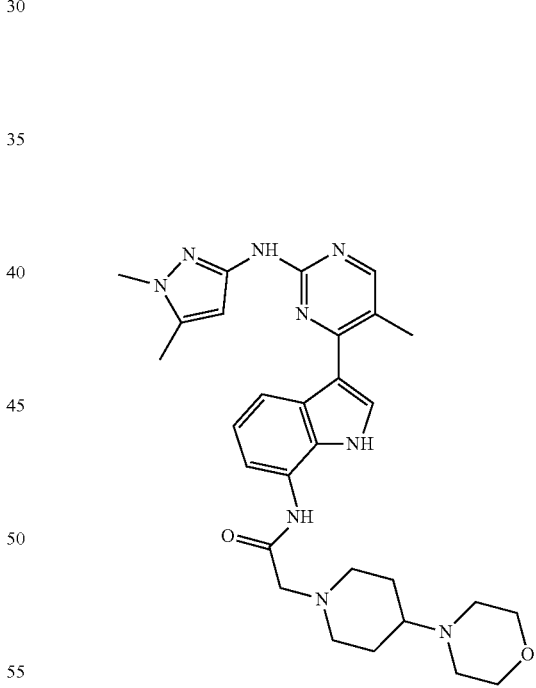

The title product was afforded by a procedure similar to that described for the synthesis of Example 36 using morpholine instead of 1-methylpiperazine. MS (ESI, m/z): 544.3 [M+H]$^+$ Example 38: Synthesis of N-(3-(2-((1,5-dimethyl-1H-pyrazol-3-yl)amino)-5-methylpyrimidin-4-yl)-1H-indol-7-yl)-2-(4-(pyridin-3-yloxy)piperidin-1-yl)acetamide

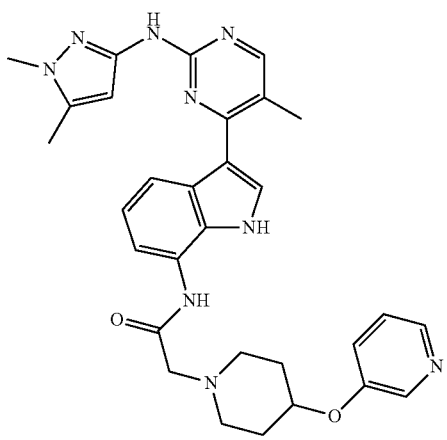 [SMILES: Cc1cnc(Nc2cc(C)n(C)n2)nc1-c1c[nH]c2c(NC(=O)CN3CCC(Oc4cccnc4)CC3)cccc12]

The title product was afforded by a procedure similar to that described for the synthesis of Example 36 using pyridin-3-ol instead of 1-methylpiperazine. MS (ESI, m/z): 552.3 [M+H]$^+$ Example 39: Synthesis of N-(3-(2-((1,5-dimethyl-1H-pyrazol-3-yl)amino)-5-methylpyrimidin-4-yl)-1H-indol-7-yl)-2-(4-(pyridin-2-yloxy)piperidin-1-yl)acetamide

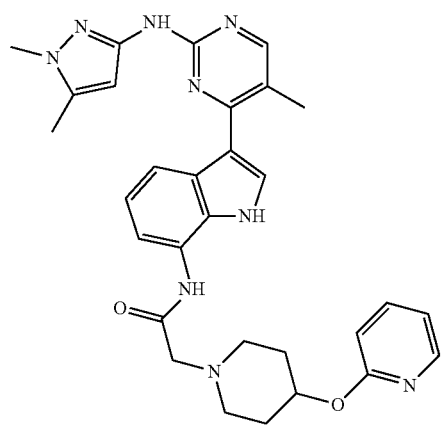 [SMILES: Cc1cnc(Nc2cc(C)n(C)n2)nc1-c1c[nH]c2c(NC(=O)CN3CCC(Oc4ccccn4)CC3)cccc12]

The title product was afforded by a procedure similar to that described for the synthesis of Example 36 using pyridin-2-ol instead of 1-methylpiperazine. MS (ESI, m/z): 552.3 [M+H]$^+$ Example 40: Synthesis of N-(3-(2-((1,5-dimethyl-1H-pyrazol-3-yl)amino)-5-methylpyrimidin-4-yl)-1H-indol-7-yl)-2-(4-(pyridin-4-yloxy)piperidin-1-yl)acetamide

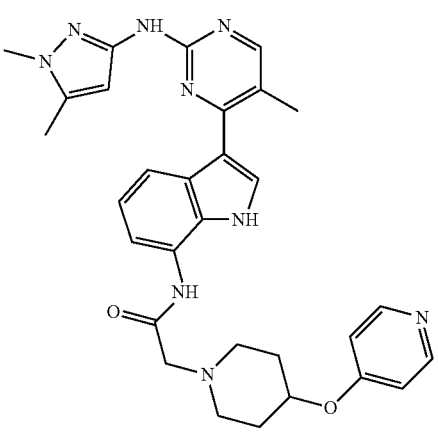 [SMILES: Cc1cnc(Nc2cc(C)n(C)n2)nc1-c1c[nH]c2c(NC(=O)CN3CCC(Oc4ccncc4)CC3)cccc12]

The title product was afforded by a procedure similar to that described for the synthesis of Example 36 using pyridin-4-ol instead of 1-methylpiperazine. MS (ESI, m/z): 552.3 [M+H]$^+$ Example 41: Synthesis of N-(3-(2-((1,5-dimethyl-1H-pyrazol-3-yl)amino)-5-methylpyrimidin-4-yl)-1H-indol-7-yl)-2-(4-(pyrimidin-2-yloxy)piperidin-1-yl)acetamide

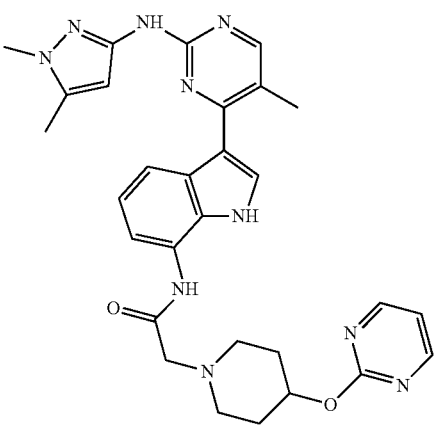 [SMILES: Cc1cnc(Nc2cc(C)n(C)n2)nc1-c1c[nH]c2c(NC(=O)CN3CCC(Oc4ncccn4)CC3)cccc12]

The title product was afforded by a procedure similar to that described for the synthesis of Example 36 using pyrimidin-2-ol instead of 1-methylpiperazine. MS (ESI, m/z): 553.3 [M+H]$^+$ Example 42: Synthesis of N-(3-(2-((1,5-dimethyl-1H-pyrazol-3-yl)amino)-5-methylpyrimidin-4-yl)-1H-indol-7-yl)-2-(4-((4,6-dimethylpyrimidin-2-yl)oxy)piperidin-1-yl)acetamide

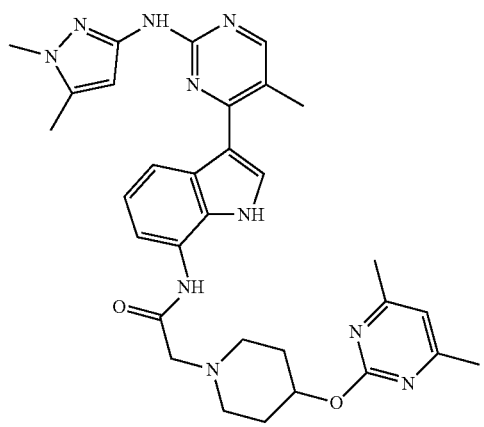

The title product was afforded by a procedure similar to that described for the synthesis of Example 36 using 4,6-dimethylpyrimidin-2-ol instead of 1-methylpiperazine. MS (ESI, m/z): 581.3 [M+H]$^+$ Example 43: Synthesis of N-cyclopropyl-3-((1-(2-((3-(2-((1,5-dimethyl-1H-pyrazol-3-yl)amino)-5-methylpyrimidin-4-yl)-1H-indol-7-yl)amino)-2-oxo-ethyl)piperidin-4-yl)oxy)isoxazole-5-carboxamide

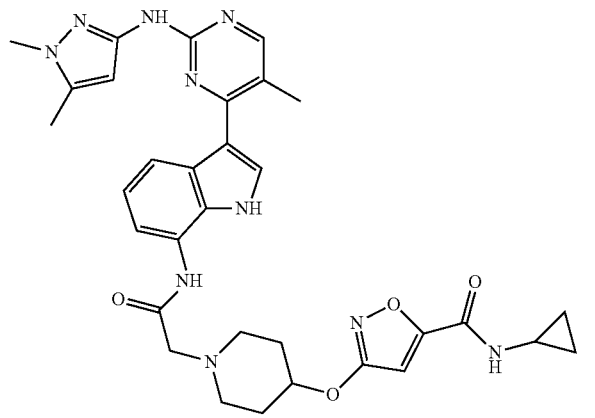 [SMILES: Cc1cnc(Nc2cc(C)n(C)n2)nc1-c1c[nH]c2c(NC(=O)CN3CCC(Oc4cc(C(=O)NC5CC5)on4)CC3)cccc12]

The title product was afforded by a procedure similar to that described for the synthesis of Example 33 using piperidin-4-ol instead of azetidin-3-ol. MS (ESI, m/z): 625.3 [M+H]$^+$ Example 44: Synthesis of N-cyclopropyl-3-((1-(2-((3-(2-((1,5-dimethyl-1H-pyrazol-3-yl)amino)-5-methylpyrimidin-4-yl)-1H-indol-7-yl)amino)-2-oxo-ethyl)piperidin-3-yl)oxy)isoxazole-5-carboxamide

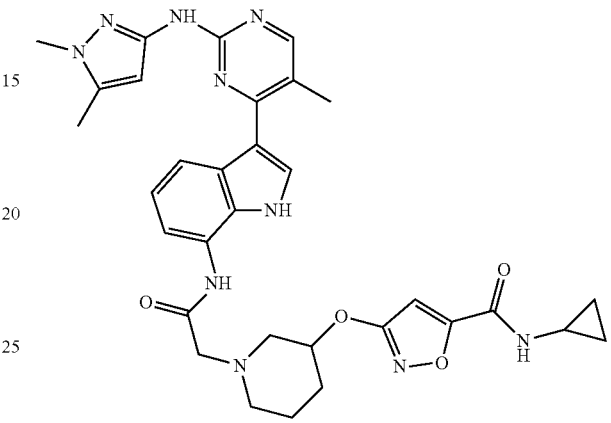

The title product was afforded by a procedure similar to that described for the synthesis of Example 33 using piperidin-3-ol instead of azetidin-3-ol. MS (ESI, m/z): 625.3 [M+H]$^+$ Example 45: Synthesis of 2-(3-(cyanomethyl)pyrrolidin-1-yl)-N-(3-(2-((1,5-dimethyl-1H-pyrazol-3-yl)amino)-5-methylpyrimidin-4-yl)-1H-indol-7-yl)acetamide

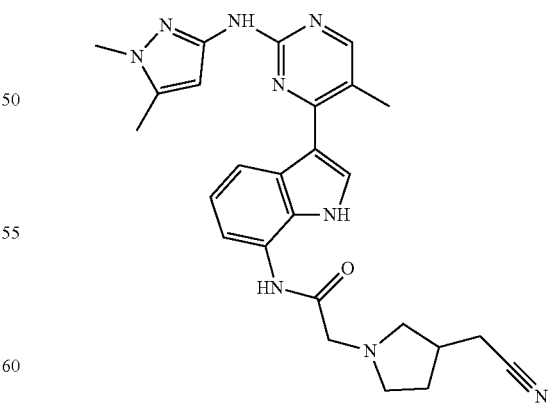

The title product was afforded by a procedure similar to that described for the synthesis of Example 26 using 2-(pyrrolidin-3-yl)acetonitrile instead of azetidin-3-ol.

MS (ESI, m/z): 484.3 [M+H]$^+$

Example 46: Synthesis of (R)-2-(3-(cyanomethyl)pyrrolidin-1-yl)-N-(3-(2-((1,5-dimethyl-1H-pyrazol-3-yl)amino)-5-methylpyrimidin-4-yl)-1H-indol-7-yl)acetamide

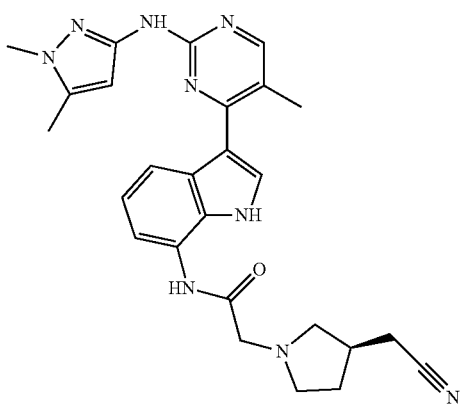 [SMILES: Cc1cnc(Nc2cc(C)n(C)n2)nc1-c1c[nH]c2c(NC(=O)CN3CC[C@H](CC#N)C3)cccc12]

The title product was afforded by a procedure similar to that described for the synthesis of Example 26 using (R)-2-(pyrrolidin-3-yl)acetonitrile instead of azetidin-3-ol. MS (ESI, m/z): 484.3 [M+H]$^+$ Example 47: Synthesis of (S)—N-(3-(2-((1,5-dimethyl-1H-pyrazol-3-yl)amino)-5-methylpyrimidin-4-yl)-1H-indol-7-yl)-2-(3-(pyrimidin-4-ylamino)pyrrolidin-1-yl)acetamide

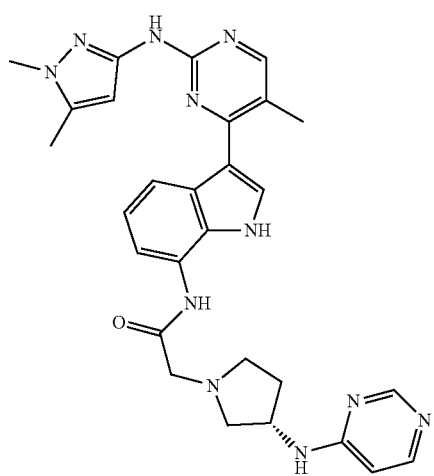 [SMILES: Cc1cnc(Nc2cc(C)n(C)n2)nc1-c1c[nH]c2c(NC(=O)CN3CC[C@H](Nc4ccncn4)C3)cccc12]

A solution of Intermediate 002 (410 mg, 1 mmol) prepared by Method A and tert-butyl (S)-pyrrolidin-3-ylcarbamate (223 mg, 1.2 mmol) in DMF (3 mL) was treated with triethylamine (0.29 mL, 2 mmol) and stirred for 2 h at 50° C. The mixture was concentrated in vacuo and purified by column chromatography (0-20% MeOH in DCM) to give tert-butyl (S)-(1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)carbamate. (520 mg, 93%). MS (ESI, m/z): 560.3 [M+H]$^+$ tert-butyl (S)-(1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)carbamate (280 mg, 0.5 mmol) was dissolved in 1N HCl in MeOH (2 mL). The mixture was concentrated in vacuo and purified by column chromatography (0-40% MeOH in DCM) to give (S)-2-(3-aminopyrrolidin-1-yl)-N-(3-(2-((1,5-dimethyl-1H-pyrazol-3-yl)amino)-5-methylpyrimidin-4-yl)-1H-indol-7-yl)acetamide quantitatively. MS (ESI, m/z): 460.2 [M+H]$^+$.

A solution of (S)-2-(3-aminopyrrolidin-1-yl)-N-(3-(2-((1,5-dimethyl-1H-pyrazol-3-yl)amino)-5-methylpyrimidin-4-yl)-1H-indol-7-yl)acetamide (230 mg, 0.5 mmol) and 4-chloropyrimidine (80 mg, 0.7 mmol) in DMF (2 mL) was treated with triethylamine (0.29 mL, 2 mmol) and stirred for 2 h at 50° C. The mixture was stirred for 2 h and separated from the UCT SPE CUBCX cartridge and purified by the Prep HPLC to afford (S)—N-(3-(2-((1,5-dimethyl-1H-pyrazol-3-yl)amino)-5-methylpyrimidin-4-yl)-1H-indol-7-yl)-2-(3-(pyrimidin-4-ylamino)pyrrolidin-1-yl)acetamide (200 mg, 74%). MS (ESI, m/z): 538.3 [M+H]$^+$.

Example 48: Synthesis of (R)—N-(3-(2-((1,5-dimethyl-1H-pyrazol-3-yl)amino)-5-methylpyrimidin-4-yl)-1H-indol-7-yl)-2-(3-(pyrimidin-4-ylamino)pyrrolidin-1-yl)acetamide

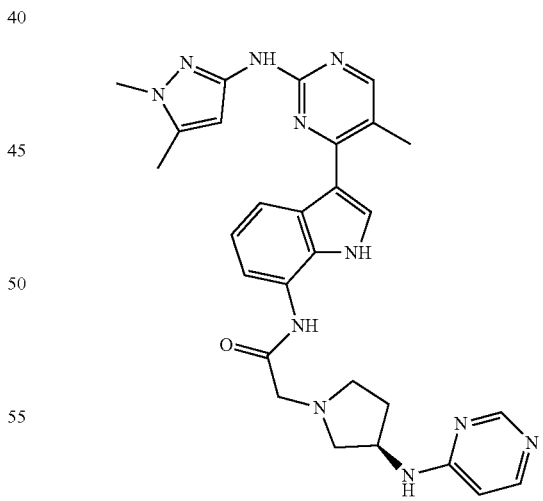

The title product was afforded by a procedure similar to that described for the synthesis of Example 47 using tert-butyl (R)-pyrrolidin-3-ylcarbamate instead of tert-butyl (S)-pyrrolidin-3-ylcarbamate. MS (ESI, m/z): 538.3 [M+H]$^+$ Example 49: Synthesis of (R)—N-(3-(2-((1,5-dimethyl-1H-pyrazol-3-yl)amino)-5-methylpyrimidin-4-yl)-1H-indol-7-yl)-2-(3-(pyridin-4-ylamino)pyrrolidin-1-yl)acetamide

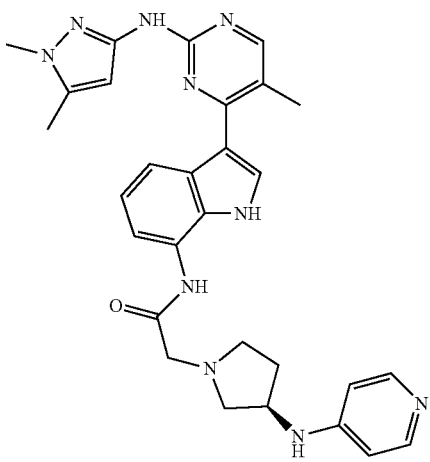 [SMILES: Cc1cnc(Nc2cc(C)n(C)n2)nc1-c1c[nH]c2c(NC(=O)CN3CC[C@@H](Nc4ccncc4)C3)cccc12]

The title product was afforded by a procedure similar to that described for the synthesis of Example 48 using 4-chloropyridine instead of 4-chloropyrimidine. MS (ESI, m/z): 537.3 [M+H]+

Example 50: Synthesis of N-(3-(2-((1,5-dimethyl-1H-pyrazol-3-yl)amino)-5-methylpyrimidin-4-yl)-1H-indol-7-yl)-2-((3R,4S)-3-fluoro-4-hydroxypyrrolidin-1-yl)acetamide

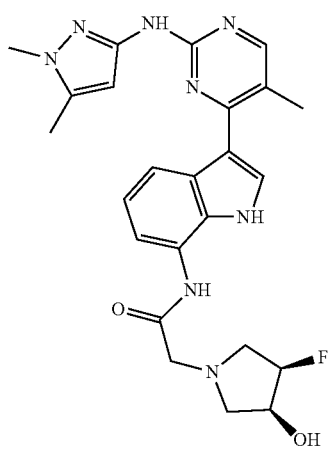 [SMILES: Cc1cnc(Nc2cc(C)n(C)n2)nc1-c1c[nH]c2c(NC(=O)CN3C[C@@H](F)[C@@H](O)C3)cccc12]

The title product was afforded by a procedure similar to Step a' of General Method B using (3S,4R)-4-fluoropyrrolidin-3-ol instead of (R)-pyrrolidin-3-ol. MS (ESI, m/z): 479.2 [M+H]+

Example 51: Synthesis of N-(3-(2-((1,5-dimethyl-1H-pyrazol-3-yl)amino)-5-methylpyrimidin-4-yl)-1H-indol-7-yl)-2-((3R,4R)-3-fluoro-4-(pyridin-4-yloxy)pyrrolidin-1-yl)acetamide

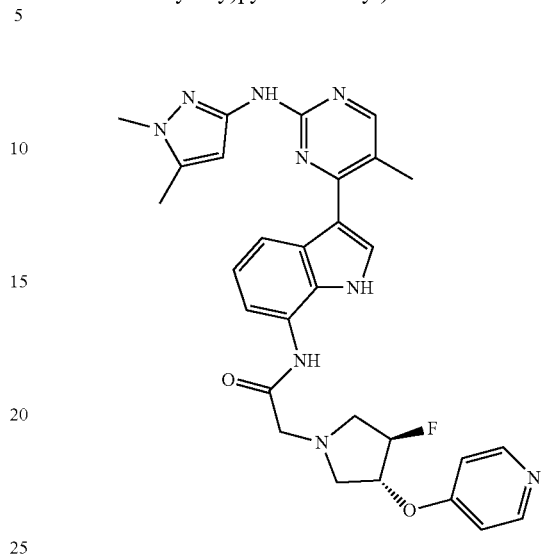

The title product was afforded by a procedure similar to Step a' and b' of General Method B using (3S,4R)-4-fluoropyrrolidin-3-ol and pyridin-4-ol instead of (R)-pyrrolidin-3-ol and 2-chloropyrimidin-4-ol. MS (ESI, m/z): 556.3 [M+H]+

Example 52: Synthesis of 2-((3R,4S)-3-((2-(cyclopropylamino)pyrimidin-4-yl)oxy)-4-fluoropyrrolidin-1-yl)-N-(3-(2-((1,5-dimethyl-1H-pyrazol-3-yl)amino)-5-methylpyrimidin-4-yl)-1H-indol-7-yl)acetamide

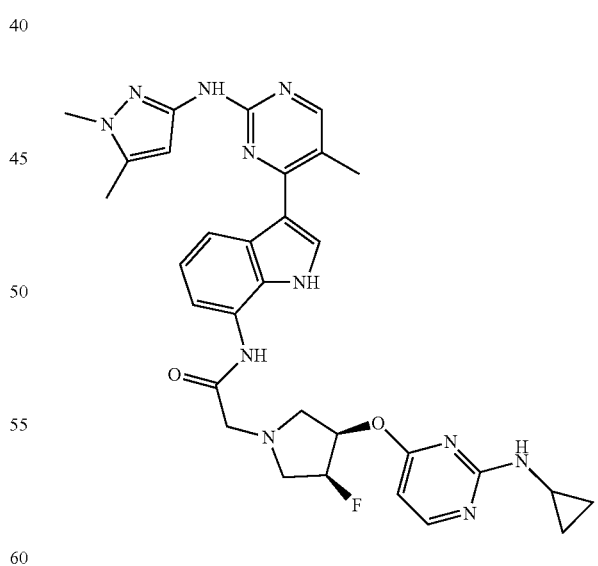

The title product was afforded by a procedure similar to General Method B using (3S,4S)-4-fluoropyrrolidin-3-ol instead of (R)-pyrrolidin-3-ol. MS (ESI, m/z): 612.3 [M+H]+

Example 53: Synthesis of 2-((3R,4R)-3-((2-(cyclopropylamino)pyrimidin-4-yl)oxy)-4-fluoropyrrolidin-1-yl)-N-(3-(2-((1,5-dimethyl-1H-pyrazol-3-yl)amino)-5-methylpyrimidin-4-yl)-1H-indol-7-yl)acetamide

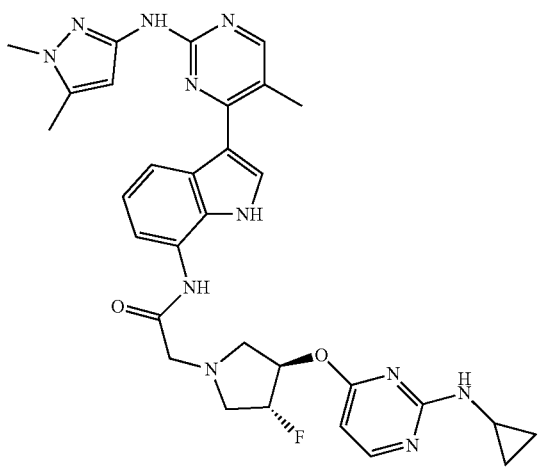 [SMILES: Cc1cnc(Nc2cc(C)n(C)n2)nc1-c1c[nH]c2c(NC(=O)CN3C[C@@H](F)[C@H](Oc4ccnc(NC5CC5)n4)C3)cccc12]

The title product was afforded by a procedure similar to General Method B using (3S,4R)-4-fluoropyrrolidin-3-ol instead of (R)-pyrrolidin-3-ol. MS (ESI, m/z): 612.3 [M+H]$^+$ Example 54: Synthesis of 2-((3S,4R)-3-((2-(cyclopropylamino)pyrimidin-4-yl)oxy)-4-fluoropyrrolidin-1-yl)-N-(3-(2-((1,5-dimethyl-1H-pyrazol-3-yl)amino)-5-methylpyrimidin-4-yl)-1H-indol-7-yl)acetamide

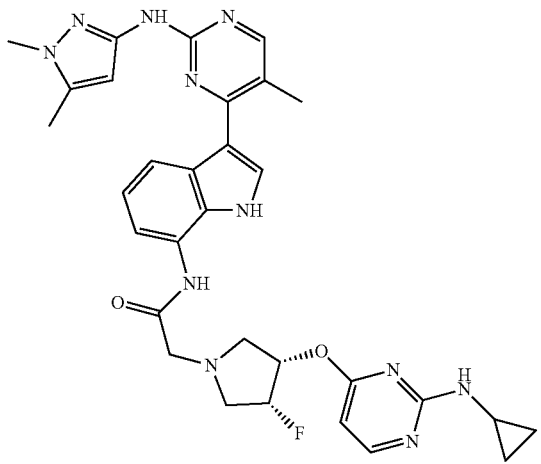 [SMILES: Cc1cnc(Nc2cc(C)n(C)n2)nc1-c1c[nH]c2c(NC(=O)CN3C[C@@H](F)[C@@H](Oc4ccnc(NC5CC5)n4)C3)cccc12]

The title product was afforded by a procedure similar to General Method B using (3R,4R)-4-fluoropyrrolidin-3-ol instead of (R)-pyrrolidin-3-ol. MS (ESI, m/z): 612.3 [M+H]$^+$ Example 55: Synthesis of methyl (2S,4S)-4-((2-(cyclopropylamino)pyrimidin-4-yl)oxy)-1-(2-((3-(2-((1,5-dimethyl-1H-pyrazol-3-yl)amino)-5-methylpyrimidin-4-yl)-1H-indol-7-yl)amino)-2-oxoethyl)pyrrolidine-2-carboxylate

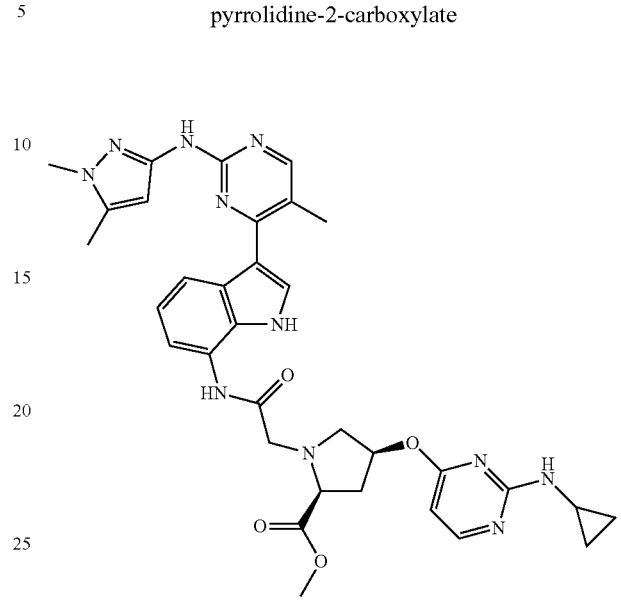

The title product was afforded by a procedure similar to General Method B using methyl (2S,4S)-4-hydroxypyrrolidine-2-carboxylate instead of (R)-pyrrolidin-3-ol. MS (ESI, m/z): 652.3 [M+H]$^+$ Example 56: Synthesis of (2S,4S)-4-((2-(cyclopropylamino)pyrimidin-4-yl)oxy)-1-(2-((3-(2-((1,5-dimethyl-1H-pyrazol-3-yl)amino)-5-methylpyrimidin-4-yl)-1H-indol-7-yl)amino)-2-oxoethyl)pyrrolidine-2-carboxylic acid

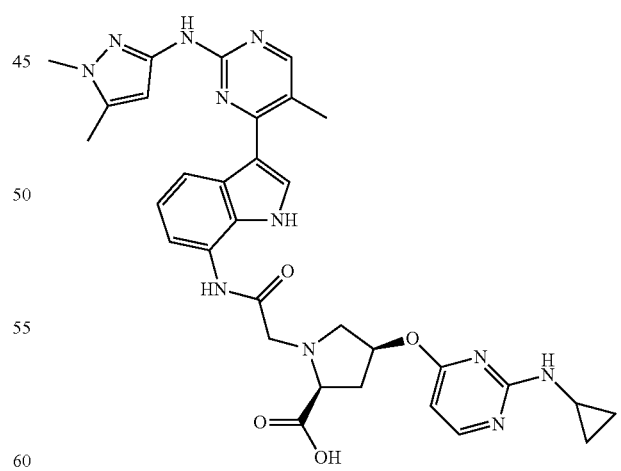

Example 55 (195 mg, 0.3 mmol) was dissolved in 1N LiOH in MeOH (2 mL). The mixture was stirred for 2 h and separated from the UCT SPE CUBCX cartridge and purified by the Prep HPLC to afford a corresponding product quantitatively. MS (ESI, m/z): 638.3 [M+H]$^+$ Example 57: Synthesis of 2-((2S,4S)-4-((2-(cyclopropylamino)pyrimidin-4-yl)oxy)-2-(hydroxymethyl)pyrrolidin-1-yl)-N-(3-(2-((1,5-dimethyl-1H-pyrazol-3-yl)amino)-5-methylpyrimidin-4-yl)-1H-indol-7-yl)acetamide

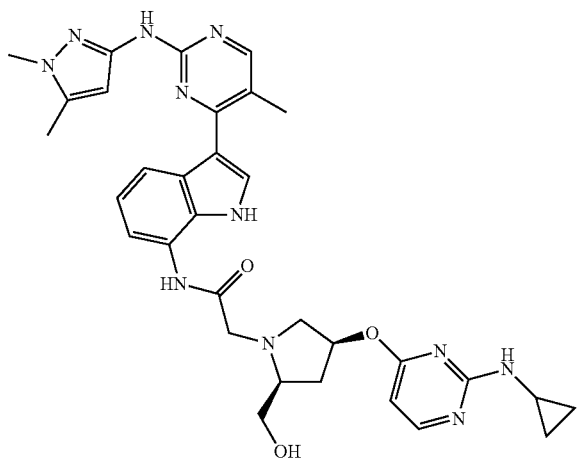 [SMILES: Cc1cnc(Nc2cc(C)n(C)n2)nc1-c1c[nH]c2c(NC(=O)CN3C[C@@H](Oc4ccnc(NC5CC5)n4)C[C@H]3CO)cccc12]

A solution of Example 55 (326 mg, 0.5 mmol) in THF (1 mL) was treated with LAH (1N in THF, 1 mL) at 0° C. and stirred for 4 h. The mixture was diluted with EA (5 mL), washed with water (5 mL×2), concentrated in vacuo. The crude was separated from the UCT SPE CUBCX cartridge and purified by the Prep HPLC to afford a corresponding product (120 mg, 38%). MS (ESI, m/z): 624.3 [M+H]$^+$ Example 58: Synthesis of (2S,4S)-4-((2-(cyclopropylamino)pyrimidin-4-yl)oxy)-1-(2-((3-(2-((1,5-dimethyl-1H-pyrazol-3-yl)amino)-5-methylpyrimidin-4-yl)-1H-indol-7-yl)amino)-2-oxoethyl)pyrrolidine-2-carboxamide

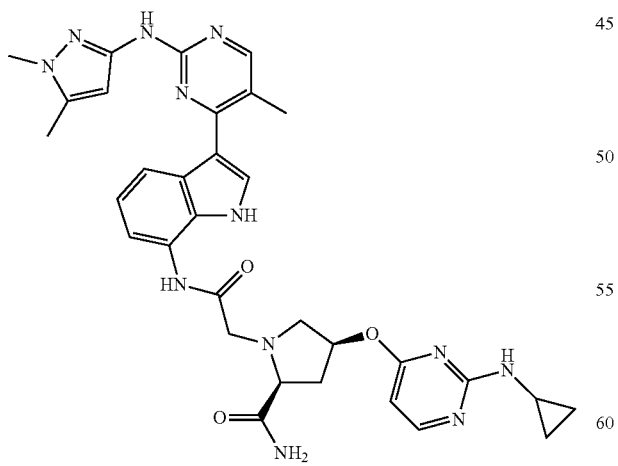

A solution of Example 56 (320 mg, 0.5 mmol), HATU (304 mg, 0.8 mmol) and NH$_4$OH (30% solution, 30 µL) in DMF (2 mL) was treated with triethylamine (280 µL, 2 mmol) and stirred for 1 h. The mixture was separated from the UCT SPE CUBCX cartridge and purified by the Prep HPLC to afford a corresponding product (95 mg, 29%). MS (ESI, m/z): 637.3 [M+H]$^+$ Example 59: Synthesis of 2-((2S,4S)-2-(aminomethyl)-4-((2-(cyclopropylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

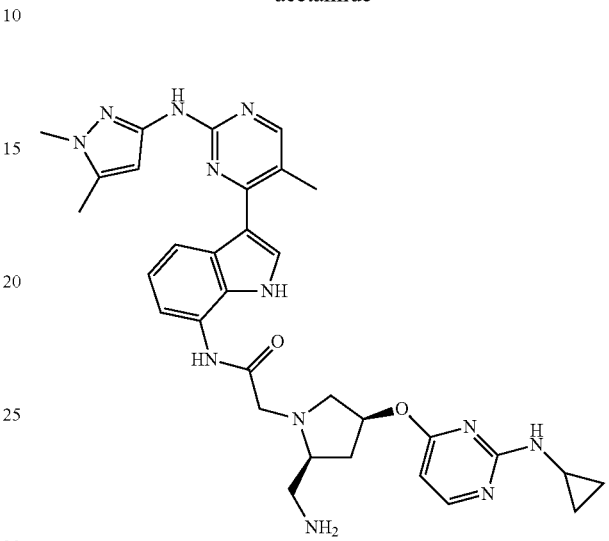

A solution of Example 58 (63 mg, 0.1 mmol) in THF (1 mL) was treated with LAH (1N in THF, 1 mL) at 0° C. and stirred for 4 h. The mixture was diluted with EA (3 mL), washed with water (3 mL×2), concentrated in vacuo. The crude was separated from the UCT SPE CUBCX cartridge and purified by the Prep HPLC to afford a corresponding product (23 mg, 37%). MS (ESI, m/z): 623.3 [M+H]$^+$ Example 60: Synthesis of (S)-2-(3-((2-(cyclopropylamino)pyrimidin-4-yl)oxy)-2-oxopyrrolidin-1-yl)-N-(3-(2-((1,5-dimethyl-1H-pyrazol-3-yl)amino)-5-methylpyrimidin-4-yl)-1H-indol-7-yl)acetamide

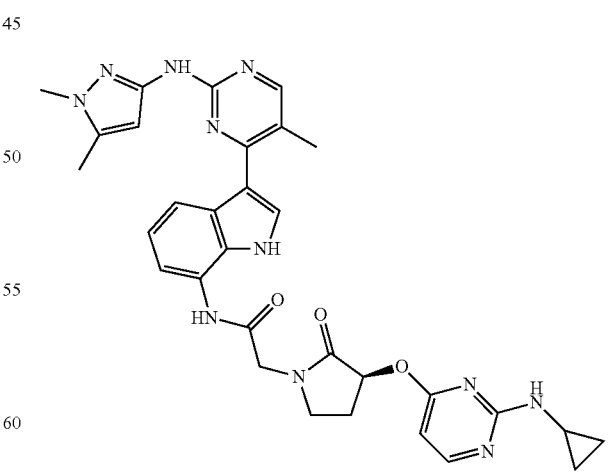

The title product was afforded by a procedure similar to General Method B using (S)-3-hydroxypyrrolidin-2-one instead of (R)-pyrrolidin-3-ol. MS (ESI, m/z): 608.3 [M+H]$^+$ Example 61: Synthesis of (S)-2-(4-((2-(cyclopropylamino)pyrimidin-4-yl)oxy)-2-oxopyrrolidin-1-yl)-N-(3-(2-((1,5-dimethyl-1H-pyrazol-3-yl)amino)-5-methylpyrimidin-4-yl)-1H-indol-7-yl)acetamide

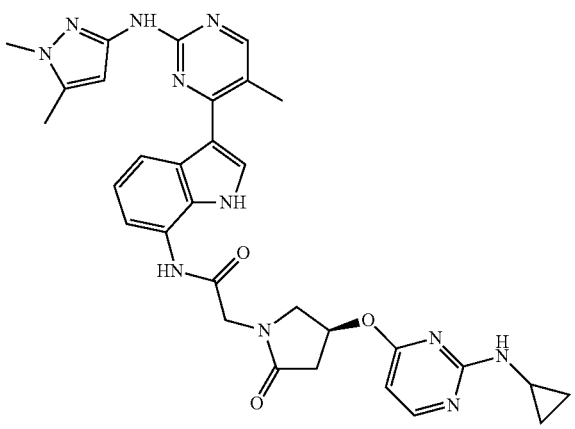 [SMILES: Cc1cnc(Nc2cc(C)n(C)n2)nc1-c1c[nH]c2c(NC(=O)CN3C[C@@H](Oc4ccnc(NC5CC5)n4)CC3=O)cccc12]

The title product was afforded by a procedure similar to General Method B using (S)-4-hydroxypyrrolidin-2-one instead of (R)-pyrrolidin-3-ol. MS (ESI, m/z): 608.3 [M+H]$^+$ Example 62: Synthesis of (S)—N-(3-(2-((1,5-dimethyl-1H-pyrazol-3-yl)amino)-5-methylpyrimidin-4-yl)-1H-indol-7-yl)-2-(3-(3-oxopiperazine-1-carbonyl)pyrrolidin-1-yl)acetamide A solution of Intermediate 002 (4090 mg, 10 mmol) prepared by Method A and methyl (S)-pyrrolidine-3-carboxylate (1548 mg, 12 mmol) in DMF (20 mL) was treated with triethylamine (2.8 mL, 20 mmol) and stirred for 4 h at 50° C. The mixture was concentrated in vacuo and purified by column chromatography (0-20% MeOH in DCM) to give methyl (S)-1-(2-((3-(2-((1,5-dimethyl-1H-pyrazol-3-yl)amino)-5-methylpyrimidin-4-yl)-1H-indol-7-yl)amino)-2-oxoethyl)pyrrolidine-3-carboxylate (4600 mg, 91%). MS (ESI, m/z): 503.2 [M+H]$^+$ (S)-1-(2-((3-(2-((1,5-dimethyl-1H-pyrazol-3-yl)amino)-5-methylpyrimidin-4-yl)-1H-indol-7-yl)amino)-2-oxoethyl)pyrrolidine-3-carboxylate (4518 mg, 9 mmol) was dissolved in 1N LiOH in MeOH (20 mL). The mixture was concentrated in vacuo and purified by column chromatography (0-50% MeOH in DCM) to give (S)-1-(2-((3-(2-((1,5-dimethyl-1H-pyrazol-3-yl)amino)-5-methylpyrimidin-4-yl)-1H-indol-7-yl)amino)-2-oxoethyl)pyrrolidine-3-carboxylic acid quantitatively. MS (ESI, m/z): 489.2 [M+H]$^+$ A solution of (S)-1-(2-((3-(2-((1,5-dimethyl-1H-pyrazol-3-yl)amino)-5-methylpyrimidin-4-yl)-1H-indol-7-yl)amino)-2-oxoethyl)pyrrolidine-3-carboxylic acid (244 mg, 0.5 mmol), HATU (304 mg, 0.8 mmol) and piperazin-2-one (70 mg, 0.7 mmol) in DMF (2 mL) was treated with triethylamine (280 μL, 2 mmol) and stirred for 3 h. The mixture was separated from the UCT SPE CUBCX cartridge and purified by the Prep HPLC to afford a corresponding product (160 mg, 56%). MS (ESI, m/z): 571.3 [M+H]$^+$ Example 63: Synthesis of (S)—N-(3-(2-((1,5-dimethyl-1H-pyrazol-3-yl)amino)-5-methylpyrimidin-4-yl)-1H-indol-7-yl)-2-(3-(morpholine-4-carbonyl)pyrrolidin-1-yl)acetamide

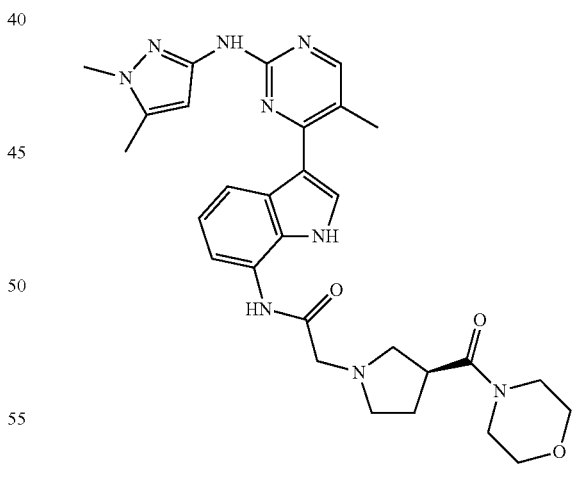

The title product was afforded by a procedure similar to that described for the synthesis of Example 62 using morpholine instead of piperazin-2-one. MS (ESI, m/z): 558.3 [M+H]$^+$ Example 64: Synthesis of (S)—N-(3-(2-((1,5-dimethyl-1H-pyrazol-3-yl)amino)-5-methylpyrimidin-4-yl)-1H-indol-7-yl)-2-(3-(thiomorpholine-4-carbonyl)pyrrolidin-1-yl)acetamide

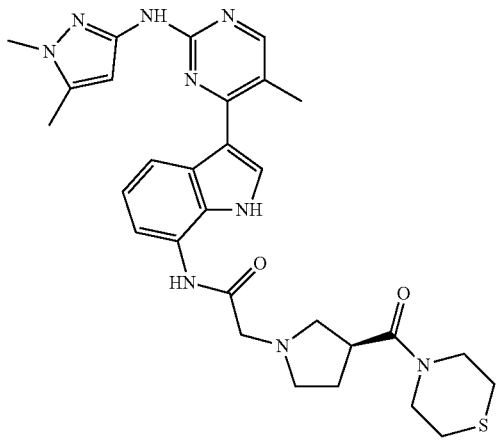 [SMILES: Cc1cnc(Nc2cc(C)n(C)n2)nc1-c1c[nH]c2c(NC(=O)CN3CC[C@H](C(=O)N4CCSCC4)C3)cccc12]

The title product was afforded by a procedure similar to that described for the synthesis of Example 62 using thiomorpholine instead of piperazin-2-one. MS (ESI, m/z): 574.3 [M+H]$^+$ Example 65: Synthesis of (R)—N-(3-(2-((1,5-dimethyl-1H-pyrazol-3-yl)amino)-5-methylpyrimidin-4-yl)-1H-indol-7-yl)-2-(3-(4-methylpiperazine-1-carbonyl)pyrrolidin-1-yl)acetamide

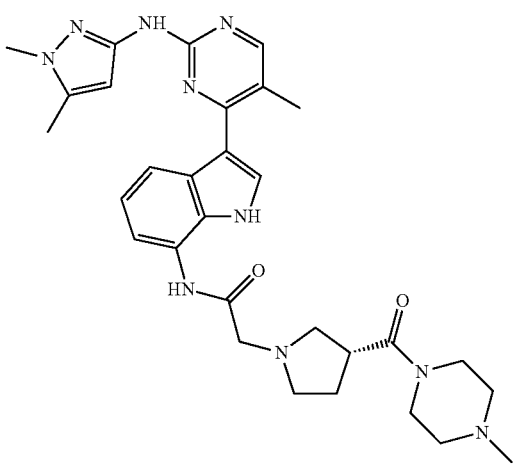

The title product was afforded by a procedure similar to that described for the synthesis of Example 62 using methyl (R)-pyrrolidine-3-carboxylate and 1-methylpiperazine instead of methyl (S)-pyrrolidine-3-carboxylate and piperazin-2-one. MS (ESI, m/z): 571.3 [M+H]$^+$ Example 66: Synthesis of (R)—N-(3-(2-((1,5-dimethyl-1H-pyrazol-3-yl)amino)-5-methylpyrimidin-4-yl)-1H-indol-7-yl)-2-(3-(3-oxopiperazine-1-carbonyl)pyrrolidin-1-yl)acetamide The title product was afforded by a procedure similar to that described for the synthesis of Example 65 using piperazin-2-one instead of 1-methylpiperazine. MS (ESI, m/z): 571.3 [M+H]$^+$ Example 67: Synthesis of (R)—N-(3-(2-((1,5-dimethyl-1H-pyrazol-3-yl)amino)-5-methylpyrimidin-4-yl)-1H-indol-7-yl)-2-(3-(morpholine-4-carbonyl)pyrrolidin-1-yl)acetamide

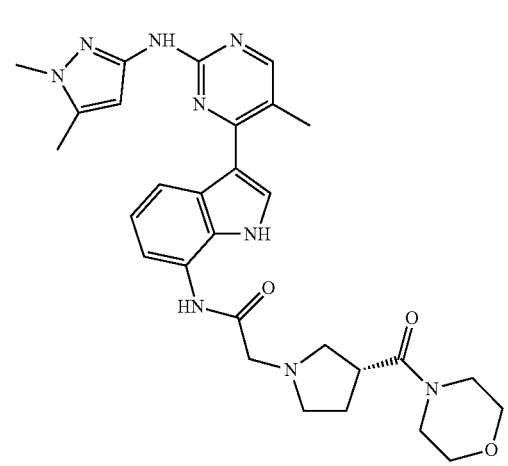

The title product was afforded by a procedure similar to that described for the synthesis of Example 65 using morpholine instead of 1-methylpiperazine. MS (ESI, m/z): 558.3 [M+H]$^+$ Example 68: Synthesis of (R)—N-(3-(2-((1,5-dimethyl-1H-pyrazol-3-yl)amino)-5-methylpyrimidin-4-yl)-1H-indol-7-yl)-2-(3-(thiomorpholine-4-carbonyl)pyrrolidin-1-yl)acetamide

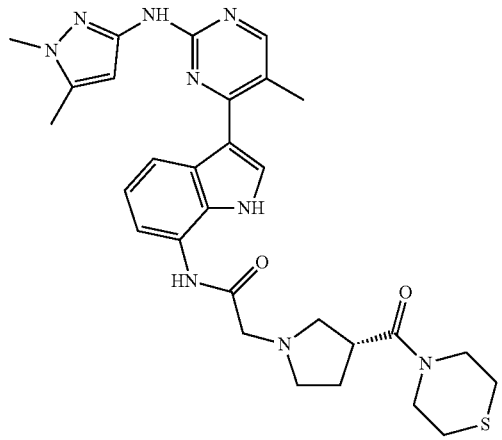 [SMILES: Cc1cnc(Nc2cc(C)n(C)n2)nc1-c1c[nH]c2c(NC(=O)CN3CC[C@@H](C(=O)N4CCOCC4)C3)cccc12]

The title product was afforded by a procedure similar to that described for the synthesis of Example 65 using thiomorpholine instead of 1-methylpiperazine. MS (ESI, m/z): 574.3 [M+H]$^+$ Example 69: Synthesis of (S)—N-(3-(2-((1,5-dimethyl-1H-pyrazol-3-yl)amino)-5-methylpyrimidin-4-yl)-1H-indol-7-yl)-2-(3-(1,2,3,6-tetrahydropyridine-1-carbonyl)pyrrolidin-1-yl)acetamide

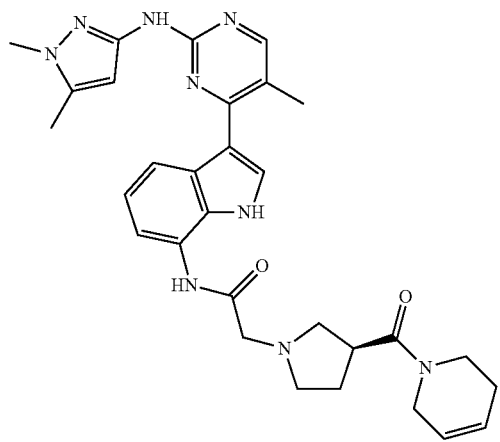 [SMILES: Cc1cnc(Nc2cc(C)n(C)n2)nc1-c1c[nH]c2c(NC(=O)CN3CC[C@H](C(=O)N4CC=CCC4)C3)cccc12]

The title product was afforded by a procedure similar to that described for the synthesis of Example 62 using 1,2,3,6-tetrahydropyridine instead of piperazin-2-one.

MS (ESI, m/z): 554.3 [M+H]$^+$

Example 70: Synthesis of N-(3-(2-((1,5-dimethyl-1H-pyrazol-3-yl)amino)-5-methylpyrimidin-4-yl)-1H-indol-7-yl)-2-(3-hydroxypyrrolidin-1-yl)acetamide

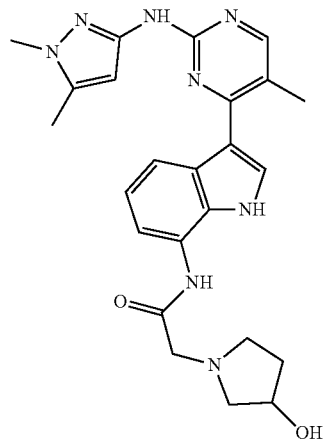

The title product was afforded by a procedure similar to Step a' of General Method B using pyrrolidin-3-ol instead of (R)-pyrrolidin-3-ol from Intermediate 002 prepared by Method A. MS (ESI, m/z): 461.2 [M+H]$^+$ Example 71: Synthesis of (R)—N-(3-(2-((1,5-dimethyl-1H-pyrazol-3-yl)amino)-5-methylpyrimidin-4-yl)-1H-indol-7-yl)-2-(3-hydroxypyrrolidin-1-yl)acetamide

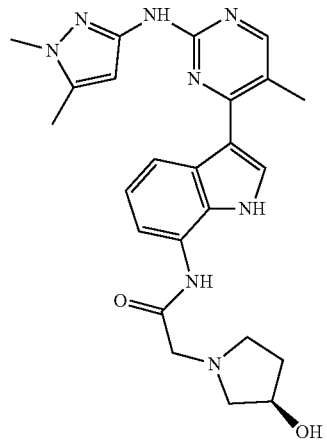

The title product was afforded by a procedure similar to Step a' of General Method B from Intermediate 002 prepared by Method A. MS (ESI, m/z): 461.2 [M+H]$^+$ Example 72: Synthesis of (S)—N-(3-(2-((1,5-dimethyl-1H-pyrazol-3-yl)amino)-5-methylpyrimidin-4-yl)-1H-indol-7-yl)-2-(3-hydroxypyrrolidin-1-yl)acetamide

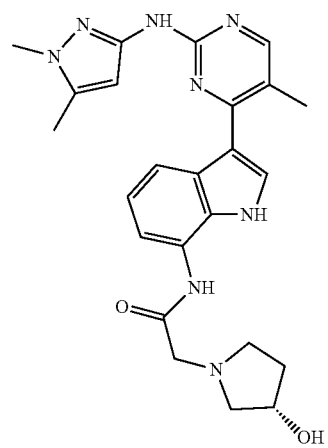

The title product was afforded by a procedure similar to Step a' of General Method B using (S)-pyrrolidin-3-ol instead of (R)-pyrrolidin-3-ol from Intermediate 002. MS (ESI, m/z): 461.2 [M+H]$^+$ Example 73: Synthesis of (S)—N-(3-(2-((1,5-dimethyl-1H-pyrazol-3-yl)amino)-5-methylpyrimidin-4-yl)-1H-indol-7-yl)-2-(3-(pyridin-2-yloxy)pyrrolidin-1-yl)acetamide

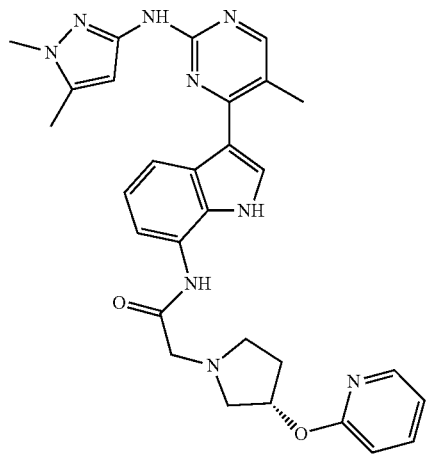 [SMILES: Cc1cnc(Nc2cc(C)n(C)n2)nc1-c1c[nH]c2c(NC(=O)CN3CC[C@H](Oc4ccccn4)C3)cccc12]

The title product was afforded by a procedure similar to that described for the synthesis of Example 39 using (R)-pyrrolidin-3-ol instead of piperidin-4-ol. MS (ESI, m/z): 538.3 [M+H]$^+$ Example 74: Synthesis of (S)—N-(3-(2-((1,5-dimethyl-1H-pyrazol-3-yl)amino)-5-methylpyrimidin-4-yl)-1H-indol-7-yl)-2-(3-(pyridin-4-yloxy)pyrrolidin-1-yl)acetamide

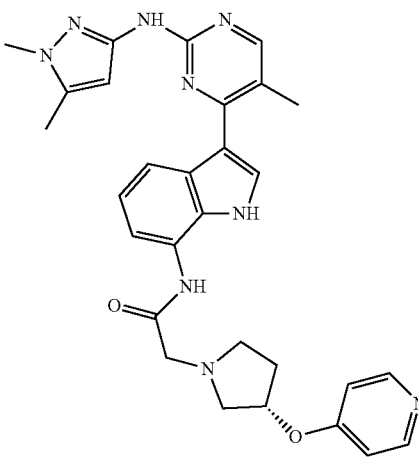

The title product was afforded by a procedure similar to that described for the synthesis of Example 73 using pyridin-4-ol instead of pyridin-2-ol. MS (ESI, m/z): 538.3 [M+H]$^+$ Example 75: Synthesis of (S)—N-(3-(2-((1,5-dimethyl-1H-pyrazol-3-yl)amino)-5-methylpyrimidin-4-yl)-1H-indol-7-yl)-2-(3-(pyridin-3-yloxy)pyrrolidin-1-yl)acetamide

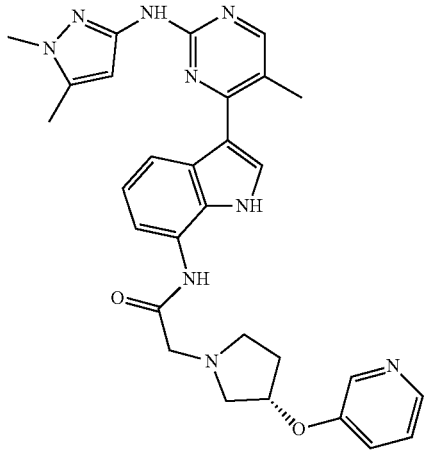 [SMILES: Cc1cnc(Nc2cc(C)n(C)n2)nc1-c1c[nH]c2c(NC(=O)CN3CC[C@H](Oc4cccnc4)C3)cccc12]

The title product was afforded by a procedure similar to that described for the synthesis of Example 73 using pyridin-3-ol instead of pyridin-2-ol. MS (ESI, m/z): 538.3 [M+H]$^+$ Example 76: Synthesis of N-(3-(2-((1,5-dimethyl-1H-pyrazol-3-yl)amino)-5-methylpyrimidin-4-yl)-1H-indol-7-yl)-2-(3-(pyridin-4-yloxy)pyrrolidin-1-yl)acetamide

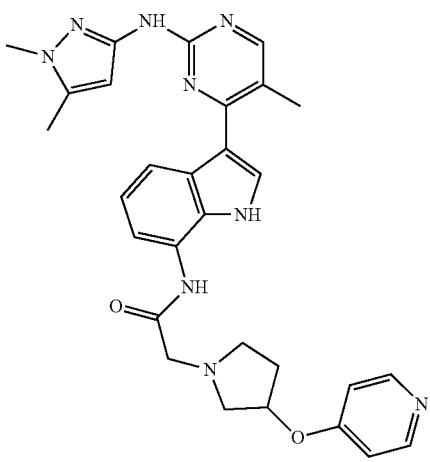 [SMILES: Cc1cnc(Nc2cc(C)n(C)n2)nc1-c1c[nH]c2c(NC(=O)CN3CCC(Oc4ccncc4)C3)cccc12]

The title product was afforded by a procedure similar to that described for the synthesis of Example 74 using pyrrolidin-3-ol instead of (R)-pyrrolidin-3-ol. MS (ESI, m/z): 538.3 [M+H]$^+$ Example 77: Synthesis of (R)—N-(3-(2-((1,5-dimethyl-1H-pyrazol-3-yl)amino)-5-methylpyrimidin-4-yl)-1H-indol-7-yl)-2-(3-(pyridin-4-yloxy)pyrrolidin-1-yl)acetamide

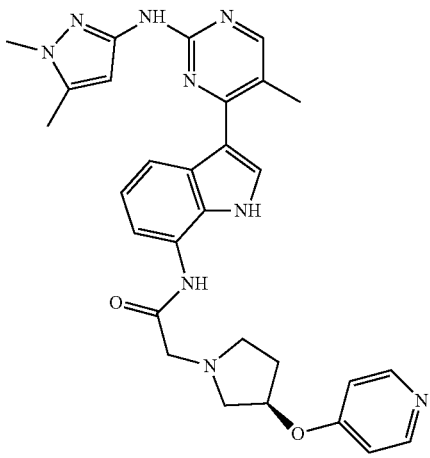 [SMILES: Cc1cnc(Nc2cc(C)n(C)n2)nc1-c1c[nH]c2c(NC(=O)CN3CC[C@@H](Oc4ccncc4)C3)cccc12]

The title product was afforded by a procedure similar to that described for the synthesis of Example 74 using (S)-pyrrolidin-3-ol instead of (R)-pyrrolidin-3-ol. MS (ESI, m/z): 538.3 [M+H]$^+$ Example 78: Synthesis of (S)—N-(3-(2-((1,5-dimethyl-1H-pyrazol-3-yl)amino)-5-methylpyrimidin-4-yl)-1H-indol-7-yl)-2-(3-(pyrimidin-4-yloxy)pyrrolidin-1-yl)acetamide

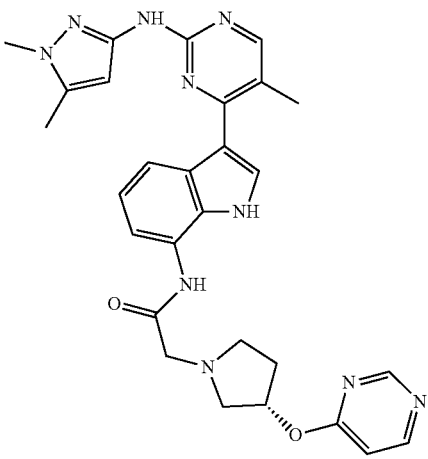 [SMILES: Cc1cnc(Nc2cc(C)n(C)n2)nc1-c1c[nH]c2c(NC(=O)CN3CC[C@H](Oc4ccncn4)C3)cccc12]

The title product was afforded by a procedure similar to that described for the synthesis of Example 73 using pyrimidin-4-ol instead of pyridin-2-ol. MS (ESI, m/z): 539.3 [M+H]$^+$ Example 79: Synthesis of (S)—N-(3-(2-((1,5-dimethyl-1H-pyrazol-3-yl)amino)-5-methylpyrimidin-4-yl)-1H-indol-7-yl)-2-(3-(pyrazin-2-yloxy)pyrrolidin-1-yl)acetamide

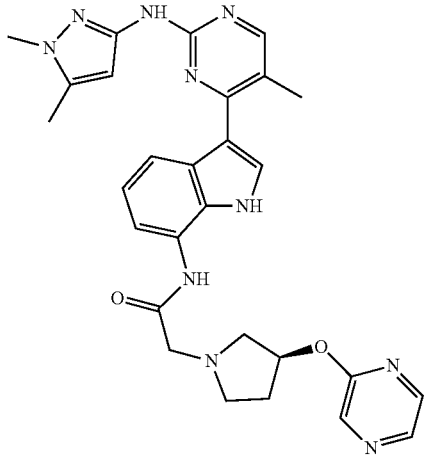 [SMILES: Cc1cnc(Nc2cc(C)n(C)n2)nc1-c1c[nH]c2c(NC(=O)CN3CC[C@H](Oc4cnccn4)C3)cccc12]

The title product was afforded by a procedure similar to that described for the synthesis of Example 73 using pyrazin-2-ol instead of pyridin-2-ol. MS (ESI, m/z): 539.3 [M+H]$^+$ Example 80: Synthesis of (S)—N-(3-(2-((1,5-dimethyl-1H-pyrazol-3-yl)amino)-5-methylpyrimidin-4-yl)-1H-indol-7-yl)-2-(3-(4-fluorophenoxy)pyrrolidin-1-yl)acetamide

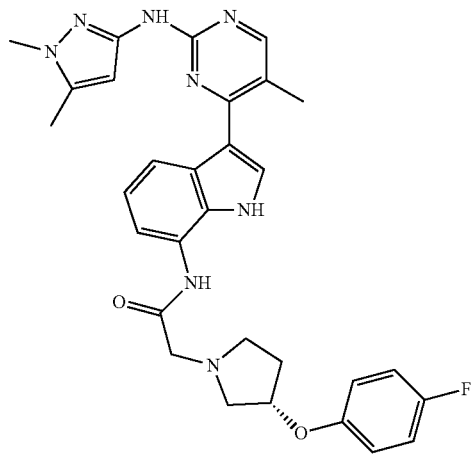 [SMILES: Cc1cnc(Nc2cc(C)n(C)n2)nc1-c1c[nH]c2c(NC(=O)CN3CC[C@H](Oc4ccc(F)cc4)C3)cccc12]

The title product was afforded by a procedure similar to that described for the synthesis of Example 73 using 4-fluorophenol instead of pyridin-2-ol. MS (ESI, m/z): 555.3 [M+H]$^+$ Example 81: Synthesis of (S)—N-(3-(2-((1,5-dimethyl-1H-pyrazol-3-yl)amino)-5-methylpyrimidin-4-yl)-1H-indol-7-yl)-2-(3-(3-fluorophenoxy)pyrrolidin-1-yl)acetamide

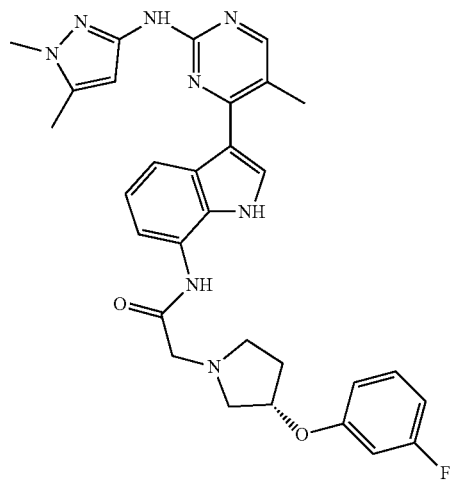 [SMILES: Cc1cnc(Nc2cc(C)n(C)n2)nc1-c1c[nH]c2c(NC(=O)CN3CC[C@H](Oc4cccc(F)c4)C3)cccc12]

The title product was afforded by a procedure similar to that described for the synthesis of Example 73 using 3-fluorophenol instead of pyridin-2-ol. MS (ESI, m/z): 555.3 [M+H]$^+$ Example 82: Synthesis of (S)-2-(3-(4-chlorophenoxy)pyrrolidin-1-yl)-N-(3-(2-((1,5-dimethyl-1H-pyrazol-3-yl)amino)-5-methylpyrimidin-4-yl)-1H-indol-7-yl)acetamide

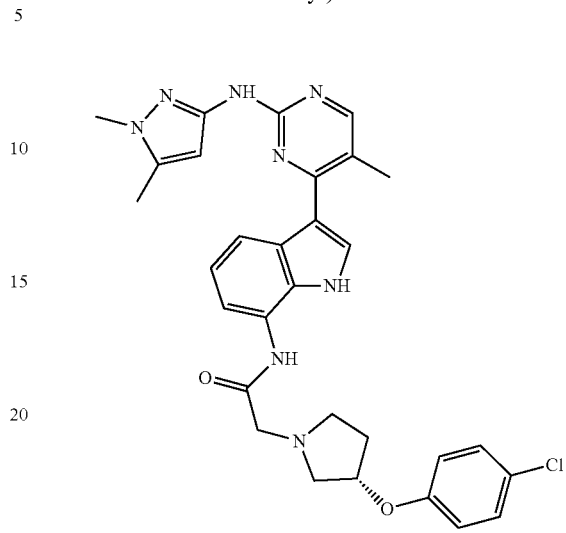

The title product was afforded by a procedure similar to that described for the synthesis of Example 73 using 4-chlorophenol instead of pyridin-2-ol. MS (ESI, m/z): 571.2 [M+H]$^+$ Example 83: Synthesis of (S)-2-(3-(2,4-difluorophenoxy)pyrrolidin-1-yl)-N-(3-(2-((1,5-dimethyl-1H-pyrazol-3-yl)amino)-5-methylpyrimidin-4-yl)-1H-indol-7-yl)acetamide

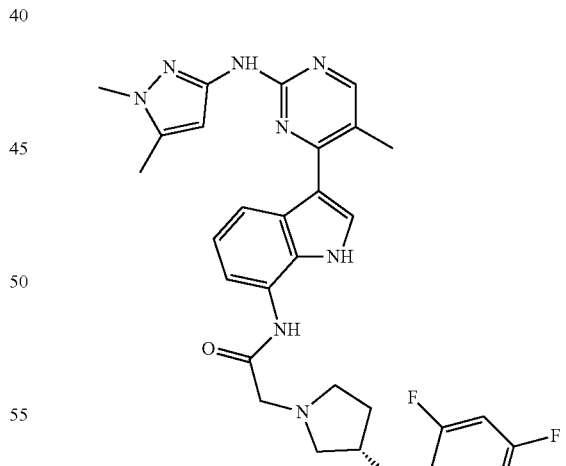

The title product was afforded by a procedure similar to that described for the synthesis of Example 73 using 2,4-difluorophenol instead of pyridin-2-ol. MS (ESI, m/z): 573.3 [M+H]$^+$ Example 84: Synthesis of (S)-2-(3-(3,4-difluorophenoxy)pyrrolidin-1-yl)-N-(3-(2-((1,5-dimethyl-1H-pyrazol-3-yl)amino)-5-methylpyrimidin-4-yl)-1H-indol-7-yl)acetamide

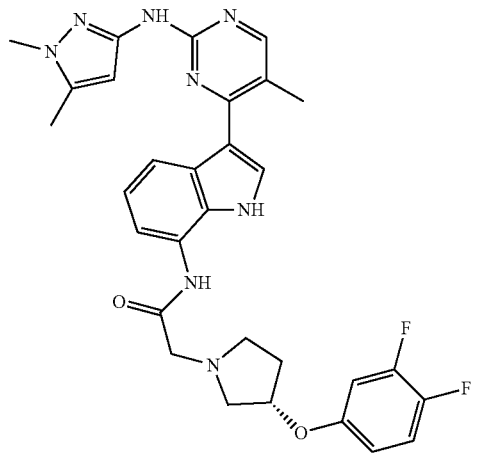 [SMILES: Cc1cnc(Nc2cc(C)n(C)n2)nc1-c1c[nH]c2c(NC(=O)CN3CC[C@H](Oc4ccc(F)c(F)c4)C3)cccc12]

The title product was afforded by a procedure similar to that described for the synthesis of Example 73 using 3,4-difluorophenol instead of pyridin-2-ol. MS (ESI, m/z): 573.3 [M+H]$^+$ Example 85: Synthesis of (S)-2-(3-(2-chloro-4-fluorophenoxy)pyrrolidin-1-yl)-N-(3-(2-((1,5-dimethyl-1H-pyrazol-3-yl)amino)-5-methylpyrimidin-4-yl)-1H-indol-7-yl)acetamide

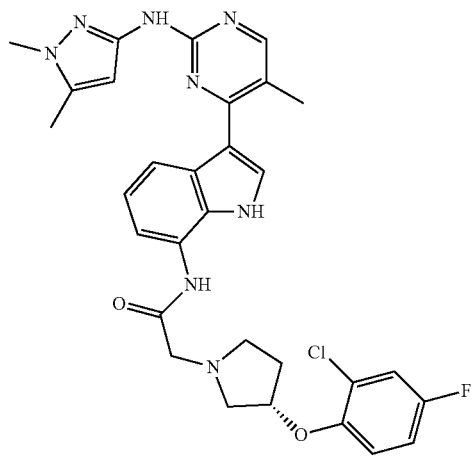 [SMILES: Cc1cnc(Nc2cc(C)n(C)n2)nc1-c1c[nH]c2c(NC(=O)CN3CC[C@H](Oc4ccc(F)cc4Cl)C3)cccc12]

The title product was afforded by a procedure similar to that described for the synthesis of Example 73 using 2-chloro-4-fluorophenol instead of pyridin-2-ol. MS (ESI, m/z): 589.2 [M+H]$^+$ Example 86: Synthesis of (S)-2-(3-(3,5-difluorophenoxy)pyrrolidin-1-yl)-N-(3-(2-((1,5-dimethyl-1H-pyrazol-3-yl)amino)-5-methylpyrimidin-4-yl)-1H-indol-7-yl)acetamide

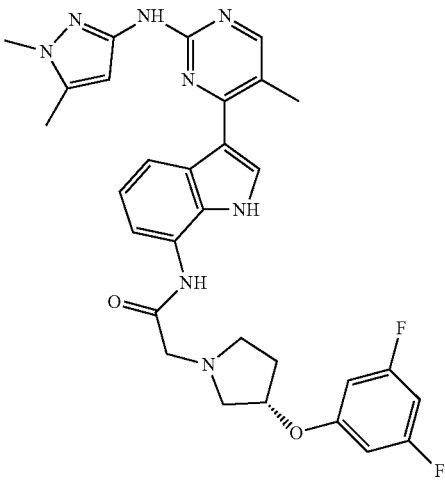 [SMILES: Cc1cnc(Nc2cc(C)n(C)n2)nc1-c1c[nH]c2c(NC(=O)CN3CC[C@H](Oc4cc(F)cc(F)c4)C3)cccc12]

The title product was afforded by a procedure similar to that described for the synthesis of Example 73 using 3,5-difluorophenol instead of pyridin-2-ol. MS (ESI, m/z): 573.3 [M+H]$^+$ Example 87: Synthesis of (S)-2-(3-(3-amino-4-fluorophenoxy)pyrrolidin-1-yl)-N-(3-(2-((1,5-dimethyl-1H-pyrazol-3-yl)amino)-5-methylpyrimidin-4-yl)-1H-indol-7-yl)acetamide

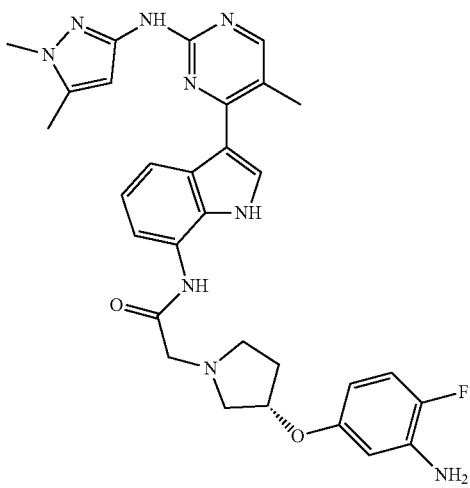 [SMILES: Cc1cnc(Nc2cc(C)n(C)n2)nc1-c1c[nH]c2c(NC(=O)CN3CC[C@H](Oc4ccc(F)c(N)c4)C3)cccc12]

The title product was afforded by a procedure similar to that described for the synthesis of Example 73 using 3-amino-4-fluorophenol instead of pyridin-2-ol. MS (ESI, m/z): 570.3 [M+H]$^+$ Example 88: Synthesis of (S)-2-(3-(3-(diethyl-amino)phenoxy)pyrrolidin-1-yl)-N-(3-(2-((1,5-dimethyl-1H-pyrazol-3-yl)amino)-5-methylpyrimidin-4-yl)-1H-indol-7-yl)acetamide

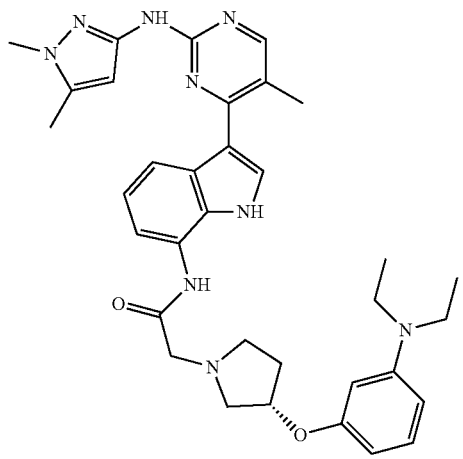 [SMILES: CCN(CC)c1cccc(O[C@H]2CCN(CC(=O)Nc3cccc4c(-c5nc(Nc6cc(C)n(C)n6)ncc5C)c[nH]c34)C2)c1]

The title product was afforded by a procedure similar to that described for the synthesis of Example 73 using 3-(diethylamino)phenol instead of pyridin-2-ol. MS (ESI, m/z): 608.3 [M+H]$^+$ Example 89: Synthesis of (S)-2-(3-(3-aminophenoxy)pyrrolidin-1-yl)-N-(3-(2-((1,5-dimethyl-1H-pyrazol-3-yl)amino)-5-methylpyrimidin-4-yl)-1H-indol-7-yl)acetamide

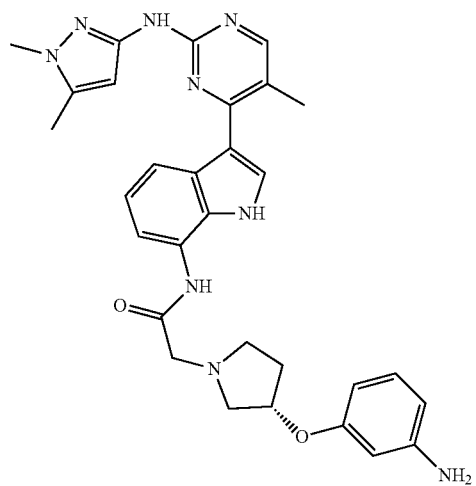 [SMILES: Cc1cnc(Nc2cc(C)n(C)n2)nc1-c1c[nH]c2c(NC(=O)CN3CC[C@H](Oc4cccc(N)c4)C3)cccc12]

The title product was afforded by a procedure similar to that described for the synthesis of Example 73 using 3-aminophenol instead of pyridin-2-ol. MS (ESI, m/z): 552.3 [M+H]$^+$ Example 90: Synthesis of (S)-2-(3-((2-aminopyridin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

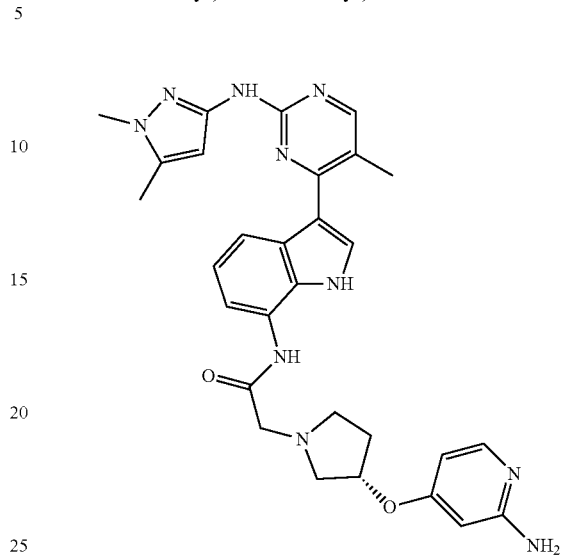

The title product was afforded by a procedure similar to that described for the synthesis of Example 73 using 2-aminopyridin-4-ol instead of pyridin-2-ol. MS (ESI, m/z): 553.3 [M+H]$^+$ Example 91: Synthesis of (S)-2-(3-((2-chloropyridin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

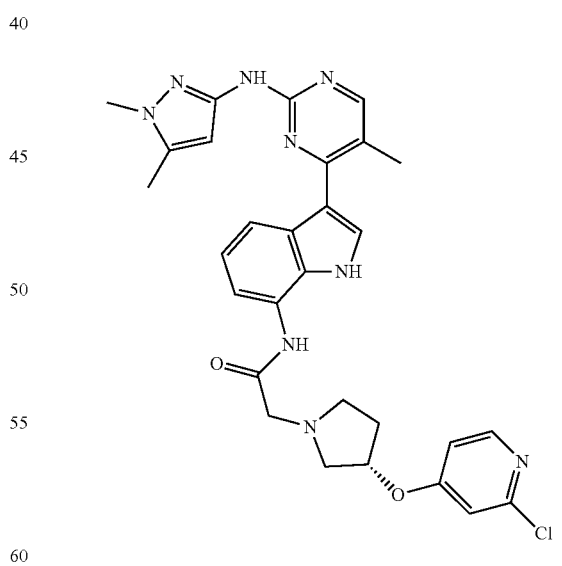

The title product was afforded by a procedure similar to that described for the synthesis of Example 73 using 2-chloropyridin-4-ol instead of pyridin-2-ol. MS (ESI, m/z): 572.2 [M+H]$^+$ Example 92: Synthesis of (S)-2-(3-((6-aminopyrazin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

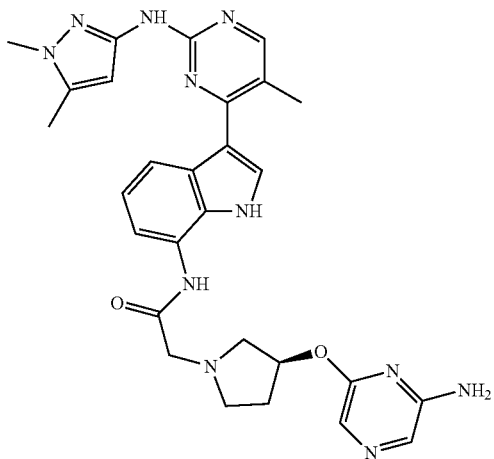 [SMILES: Cc1cnc(Nc2cc(C)n(C)n2)nc1-c1c[nH]c2c(NC(=O)CN3CC[C@H](Oc4cncc(N)n4)C3)cccc12]

The title product was afforded by a procedure similar to that described for the synthesis of Example 73 using 6-aminopyrazin-2-ol instead of pyridin-2-ol. MS (ESI, m/z): 554.3 [M+H]$^+$ Example 93: Synthesis of (S)—N-(3-(2-((1,5-dimethyl-1H-pyrazol-3-yl)amino)-5-methylpyrimidin-4-yl)-1H-indol-7-yl)-2-(3-((5-fluoropyrimidin-2-yl)oxy)pyrrolidin-1-yl)acetamide

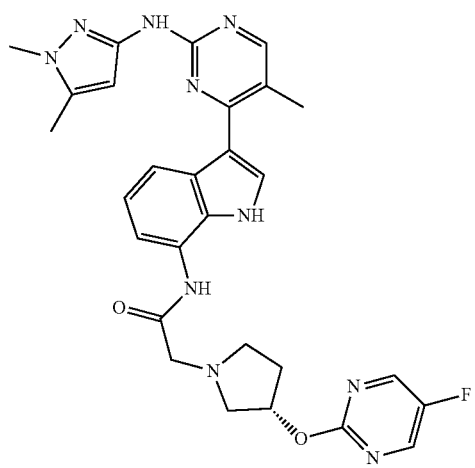 [SMILES: Cc1cnc(Nc2cc(C)n(C)n2)nc1-c1c[nH]c2c(NC(=O)CN3CC[C@H](Oc4ncc(F)cn4)C3)cccc12]

The title product was afforded by a procedure similar to that described for the synthesis of Example 73 using 5-fluoropyrimidin-2-ol instead of pyridin-2-ol. MS (ESI, m/z): 557.3 [M+H]$^+$ Example 94: Synthesis of (S)-2-(3-((6-chloro-5-methylpyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

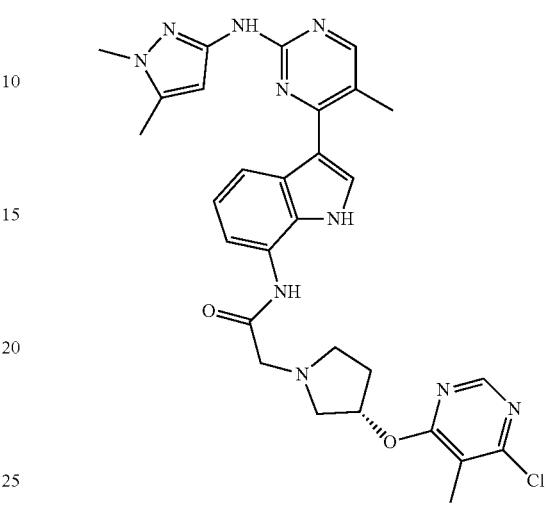

The title product was afforded by a procedure similar to that described for the synthesis of Example 73 using 6-chloro-5-methylpyrimidin-4-ol instead of pyridin-2-ol. MS (ESI, m/z): 587.2 [M+H]$^+$ Example 95: Synthesis of (S)-2-(3-((2-amino-6-methylpyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

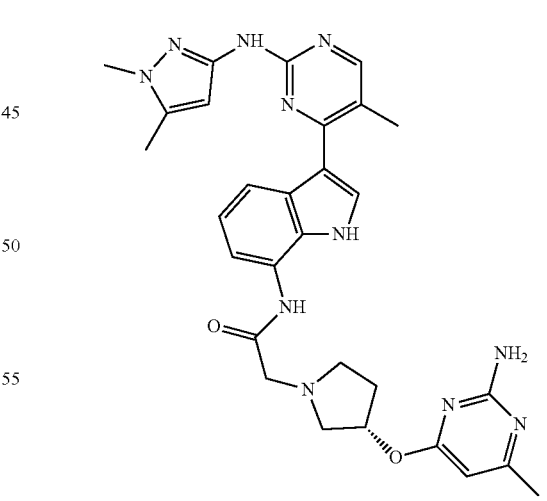

The title product was afforded by a procedure similar to that described for the synthesis of Example 73 using 2-amino-6-methylpyrimidin-4-ol instead of pyridin-2-ol. MS (ESI, m/z): 568.3 [M+H]$^+$ Example 96: Synthesis of (S)-2-(3-((5-amino-2-chloropyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

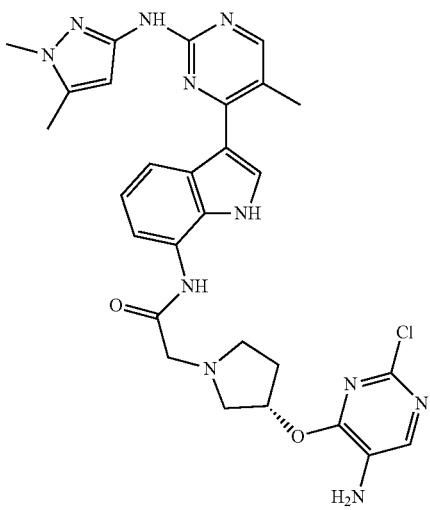 [SMILES: Cc1cnc(Nc2cc(C)n(C)n2)nc1-c1c[nH]c2c(NC(=O)CN3CC[C@H](Oc4nc(Cl)ncc4N)C3)cccc12]

The title product was afforded by a procedure similar to that described for the synthesis of Example 73 using 5-amino-2-chloropyrimidin-4-ol instead of pyridin-2-ol. MS (ESI, m/z): 588.2 [M+H]$^+$ Example 97: Synthesis of (S)-2-(3-((5-bromo-2-methylpyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

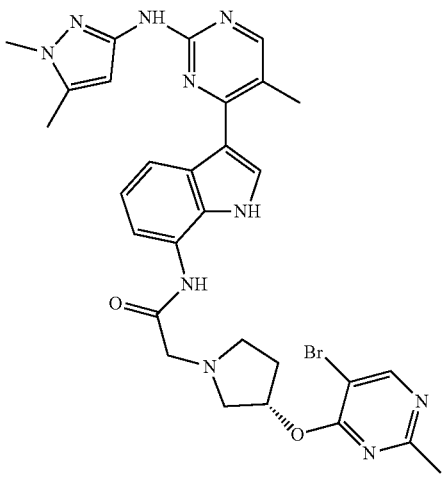

The title product was afforded by a procedure similar to that described for the synthesis of Example 73 using 5-bromo-2-methylpyrimidin-4-ol instead of pyridin-2-ol. MS (ESI, m/z): 631.2 [M+H]$^+$ Example 98: Synthesis of (S)-2-(3-((2-amino-6-(5-chloro-2-fluorophenyl)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

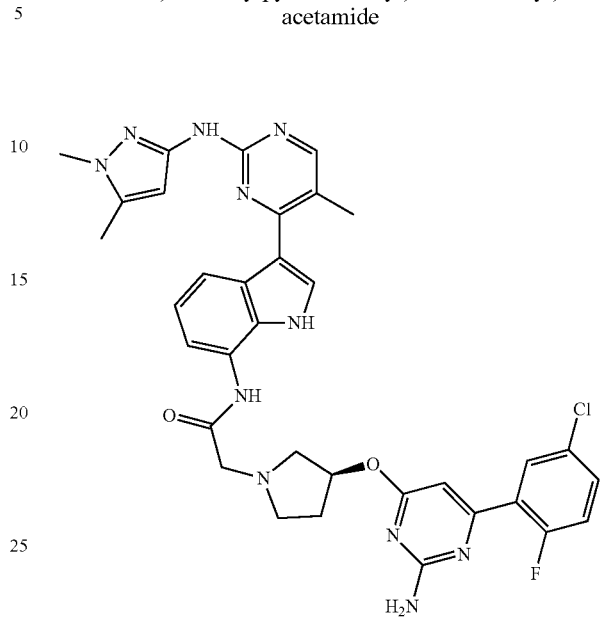

The title product was afforded by a procedure similar to that described for the synthesis of Example 73 using 2-amino-6-(5-chloro-2-fluorophenyl)-2-methylpyrimidin-4-ol instead of pyridin-2-ol. MS (ESI, m/z): 682.3 [M+H]$^+$ Example 99: Synthesis of (S)-2-(3-((2-amino-6-(trifluoromethyl)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

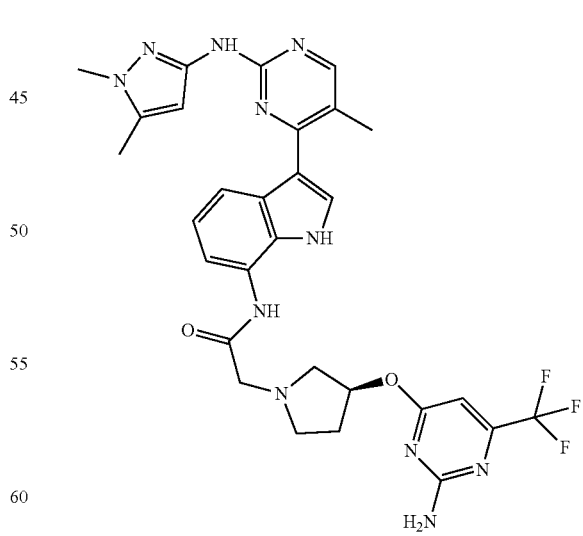

The title product was afforded by a procedure similar to that described for the synthesis of Example 73 using 2-amino-6-(trifluoromethyl)pyrimidin-4-ol instead of pyridin-2-ol. MS (ESI, m/z): 622.3 [M+H]$^+$ Example 100: Synthesis of (S)-2-(3-([1,1'-biphenyl]-4-yloxy)pyrrolidin-1-yl)-N-(3-(2-((1,5-dimethyl-1H-pyrazol-3-yl)amino)-5-methylpyrimidin-4-yl)-1H-indol-7-yl)acetamide

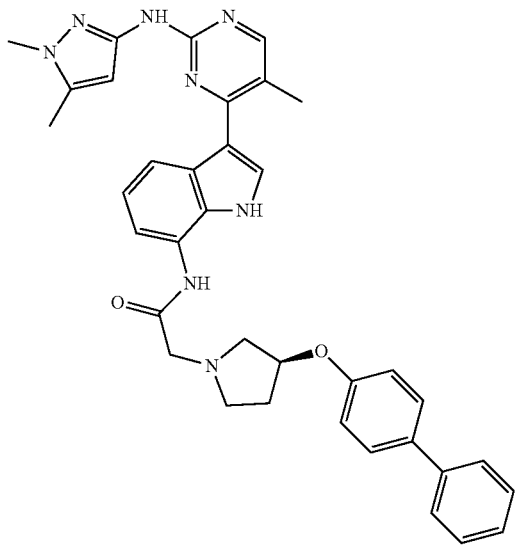 [SMILES: Cc1cnc(Nc2cc(C)n(C)n2)nc1-c1c[nH]c2c(NC(=O)CN3CC[C@H](Oc4ccc(-c5ccccc5)cc4)C3)cccc12]

The title product was afforded by a procedure similar to that described for the synthesis of Example 73 using [1,1'-biphenyl]-4-ol instead of pyridin-2-ol. MS (ESI, m/z): 613.3 [M+H]$^+$ Example 101: Synthesis of (S)—N-(3-(2-((1,5-dimethyl-1H-pyrazol-3-yl)amino)-5-methylpyrimidin-4-yl)-1H-indol-7-yl)-2-(3-(4-(2-phenylpropan-2-yl)phenoxy)pyrrolidin-1-yl)acetamide

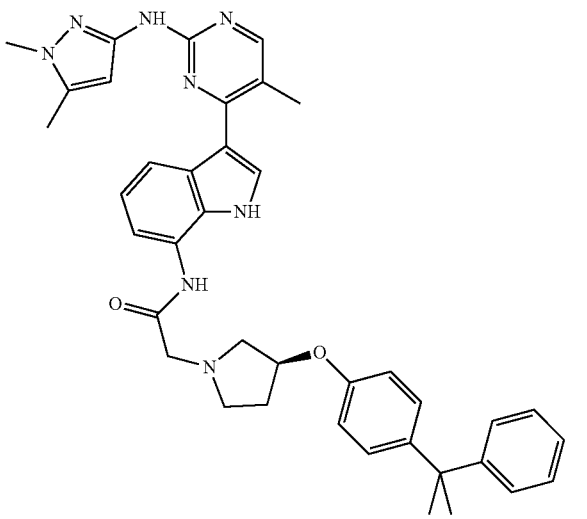 [SMILES: Cc1cnc(Nc2cc(C)n(C)n2)nc1-c1c[nH]c2c(NC(=O)CN3CC[C@H](Oc4ccc(C(C)(C)c5ccccc5)cc4)C3)cccc12]

The title product was afforded by a procedure similar to that described for the synthesis of Example 73 using 4-(2-phenylpropan-2-yl)phenol instead of pyridin-2-ol.
MS (ESI, m/z): 655.3 [M+H]$^+$ Example 102: Synthesis of (S)—N-(3-(2-((1,5-dimethyl-1H-pyrazol-3-yl)amino)-5-methylpyrimidin-4-yl)-1H-indol-7-yl)-2-(3-((5-pentylpyrimidin-2-yl)oxy)pyrrolidin-1-yl)acetamide

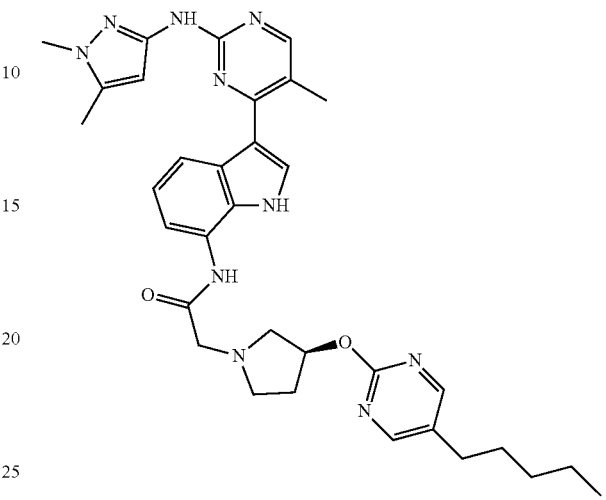

The title product was afforded by a procedure similar to that described for the synthesis of Example 73 using 5-pentylpyrimidin-2-ol instead of pyridin-2-ol. MS (ESI, m/z): 609.3 [M+H]$^+$ Example 103: Synthesis of (S)—N-(3-(2-((1,5-dimethyl-1H-pyrazol-3-yl)amino)-5-methylpyrimidin-4-yl)-1H-indol-7-yl)-2-(3-(4-((4-methylpiperazin-1-yl)methyl)phenoxy)pyrrolidin-1-yl)acetamide

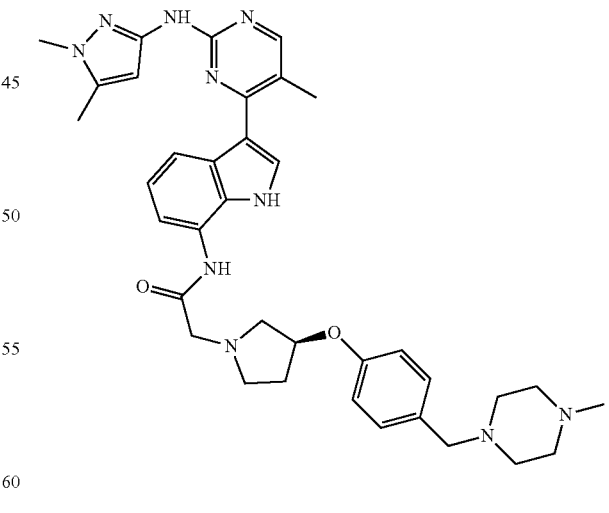

The title product was afforded by a procedure similar to that described for the synthesis of Example 73 using 4-((4-methylpiperazin-1-yl)methyl)phenol instead of pyridin-2-ol.
MS (ESI, m/z): 649.4 [M+H]$^+$ Example 104: Synthesis of (S)—N-(3-(2-((1,5-dimethyl-1H-pyrazol-3-yl)amino)-5-methylpyrimidin-4-yl)-1H-indol-7-yl)-2-(3-((1-methyl-1H-pyrazol-5-yl)oxy)pyrrolidin-1-yl)acetamide

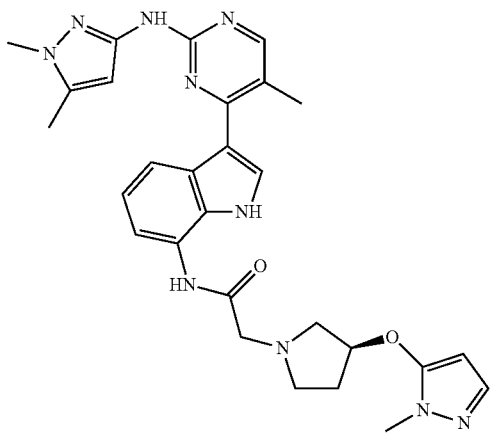 [SMILES: Cc1cnc(Nc2cc(C)n(C)n2)nc1-c1c[nH]c2c(NC(=O)CN3CC[C@H](Oc4ccnn4C)C3)cccc12]

The title product was afforded by a procedure similar to that described for the synthesis of Example 73 using 1-methyl-1H-pyrazol-5-ol instead of pyridin-2-ol. MS (ESI, m/z): 541.3 [M+H]$^+$ Example 105: Synthesis of (S)—N-(3-(2-((1,5-dimethyl-1H-pyrazol-3-yl)amino)-5-methylpyrimidin-4-yl)-1H-indol-7-yl)-2-(3-((1-methyl-1H-pyrazol-3-yl)oxy)pyrrolidin-1-yl)acetamide

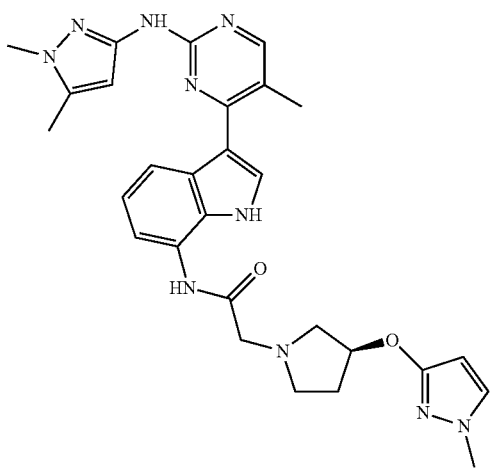 [SMILES: Cc1cnc(Nc2cc(C)n(C)n2)nc1-c1c[nH]c2c(NC(=O)CN3CC[C@H](Oc4ccn(C)n4)C3)cccc12]

The title product was afforded by a procedure similar to that described for the synthesis of Example 73 using 1-methyl-1H-pyrazol-3-ol instead of pyridin-2-ol. MS (ESI, m/z): 541.3 [M+H]$^+$ Example 106: Synthesis of methyl (S)-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)benzo[b]thiophene-2-carboxylate

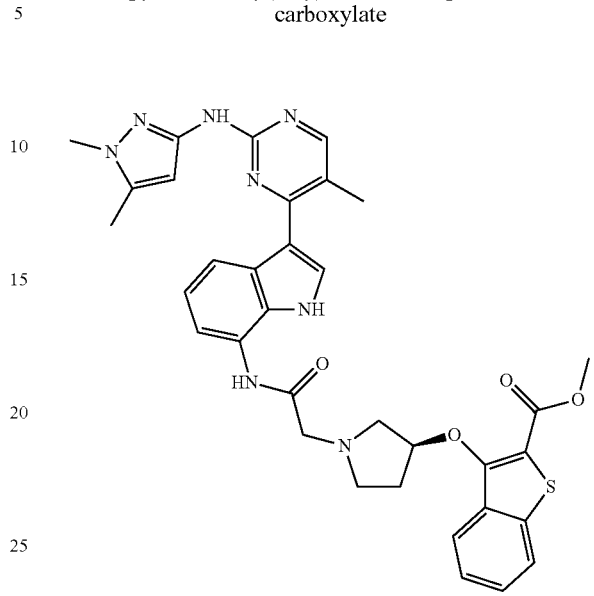

The title product was afforded by a procedure similar to that described for the synthesis of Example 73 using methyl 3-hydroxybenzo[b]thiophene-2-carboxylate instead of pyridin-2-ol. MS (ESI, m/z): 651.2 [M+H]$^+$ Example 107: Synthesis of methyl (S)-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)thiophene-2-carboxylate

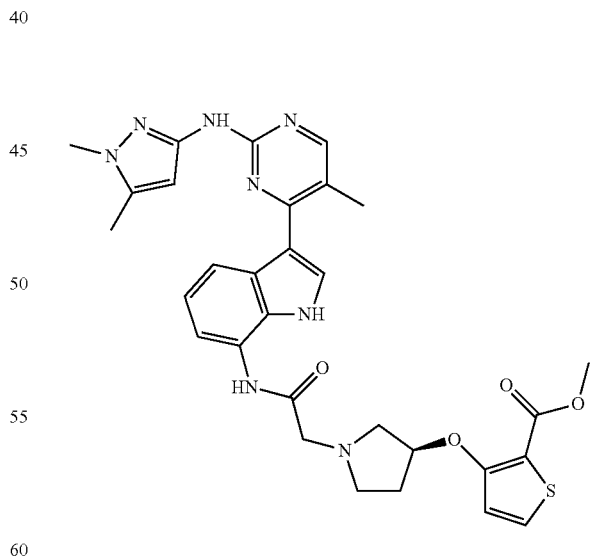

The title product was afforded by a procedure similar to that described for the synthesis of Example 73 using methyl 3-hydroxythiophene-2-carboxylate instead of pyridin-2-ol. MS (ESI, m/z): 601.2 [M+H]$^+$ Example 108: Synthesis of (S)-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)thiophene-2-carboxylic acid

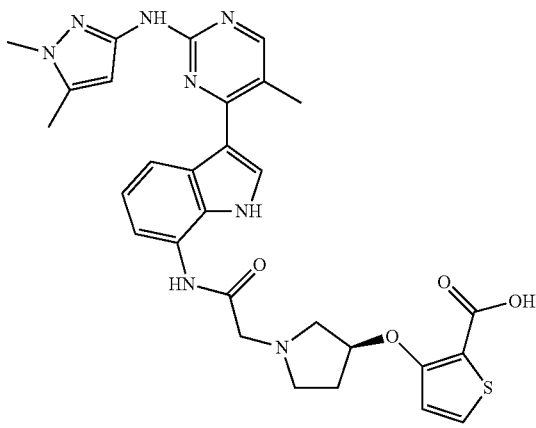 [SMILES: Cc1cnc(Nc2cc(C)n(C)n2)nc1-c1c[nH]c2c(NC(=O)CN3CC[C@H](Oc4ccsc4C(=O)O)C3)cccc12]

The title product was afforded using Example 107 by a procedure similar to that described for the synthesis of Example 56 from Example 55. MS (ESI, m/z): 587.2 [M+H]$^+$ Example 109: Synthesis of (S)-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)thiophene-2-carboxamide

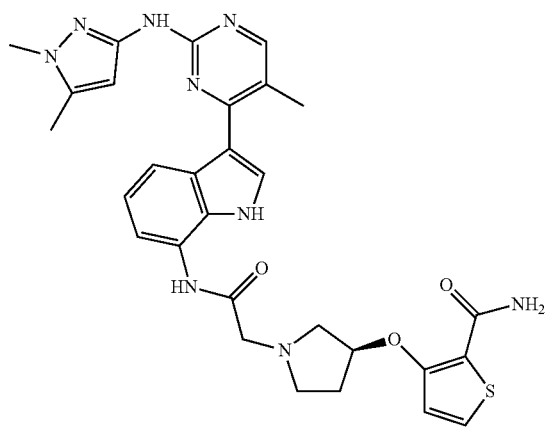 [SMILES: Cc1cnc(Nc2cc(C)n(C)n2)nc1-c1c[nH]c2c(NC(=O)CN3CC[C@H](Oc4ccsc4C(N)=O)C3)cccc12]

The title product was afforded using Example 107 by a procedure similar to that described for the synthesis of Example 58 from Example 55. MS (ESI, m/z): 586.2 [M+H]$^+$ Example 110: Synthesis of (S)-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)-N-methylthiophene-2-carboxamide

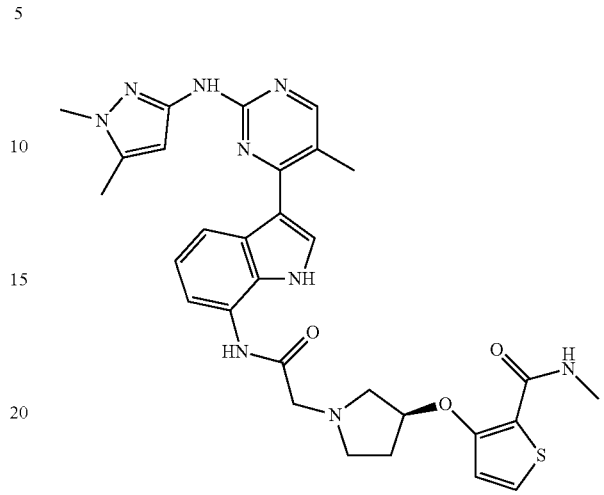

The title product was afforded by a procedure similar to that described for the synthesis of Example 109 using methylamine instead of ammonium hydroxide. MS (ESI, m/z): 600.2 [M+H]$^+$ Example 111: Synthesis of (S)—N-cyclopropyl-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)thiophene-2-carboxamide

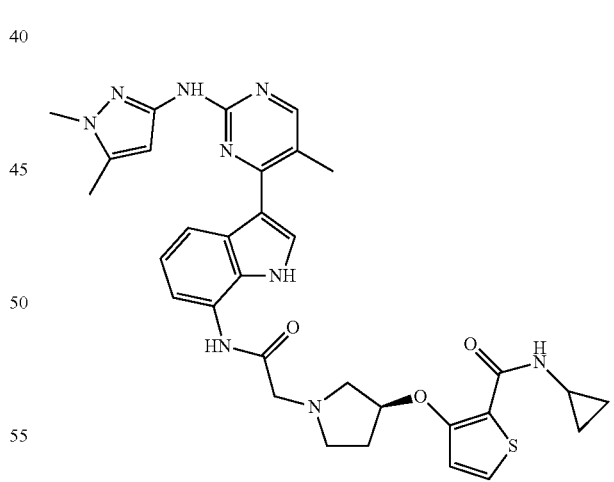

The title product was afforded by a procedure similar to that described for the synthesis of Example 109 using cyclopropylamine instead of ammonium hydroxide.
MS (ESI, m/z): 626.3 [M+H]$^+$ Example 112: Synthesis of (S)—N-(3-(2-((1,5-dimethyl-1H-pyrazol-3-yl)amino)-5-methylpyrimidin-4-yl)-1H-indol-7-yl)-2-(3-((5-methylisoxazol-3-yl)oxy)pyrrolidin-1-yl)acetamide

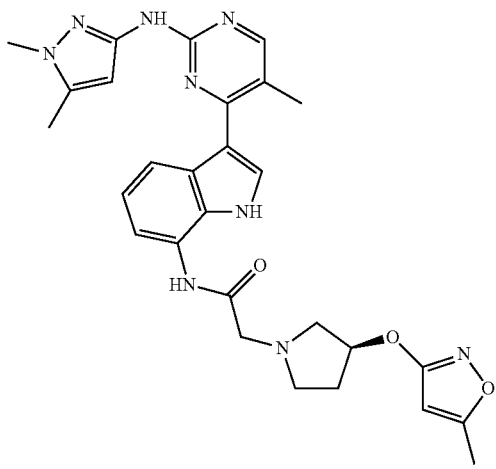 [SMILES: Cc1cc(O[C@H]2CCN(CC(=O)Nc3cccc4c(-c5nc(Nc6cc(C)n(C)n6)ncc5C)c[nH]c34)C2)no1]

The title product was afforded by a procedure similar to that described for the synthesis of Example 73 using 5-methylisoxazol-3-ol instead of pyridin-2-ol. MS (ESI, m/z): 542.3 [M+H]$^+$ Example 113: Synthesis of (S)-2-(3-(benzo[d]isoxazol-3-yloxy)pyrrolidin-1-yl)-N-(3-(2-((1,5-dimethyl-1H-pyrazol-3-yl)amino)-5-methylpyrimidin-4-yl)-1H-indol-7-yl)acetamide

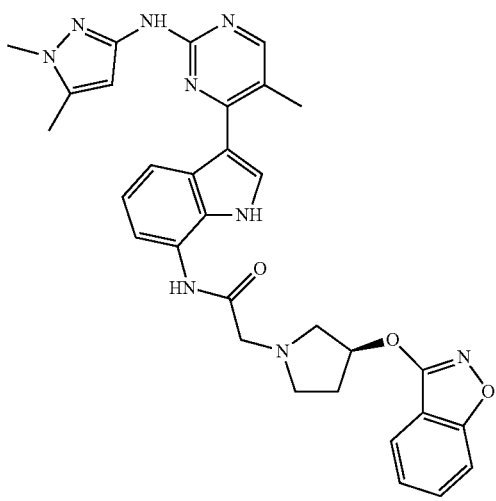 [SMILES: Cc1cnc(Nc2cc(C)n(C)n2)nc1-c1c[nH]c2c(NC(=O)CN3CC[C@H](Oc4noc5ccccc45)C3)cccc12]

The title product was afforded by a procedure similar to that described for the synthesis of Example 73 using benzo[d]isoxazol-3-ol instead of pyridin-2-ol. MS (ESI, m/z): 578.3 [M+H]$^+$ Example 114: Synthesis of (S)—N-(3-(2-((1,5-dimethyl-1H-pyrazol-3-yl)amino)-5-methylpyrimidin-4-yl)-1H-indol-7-yl)-2-(3-(isothiazol-3-yloxy)pyrrolidin-1-yl)acetamide

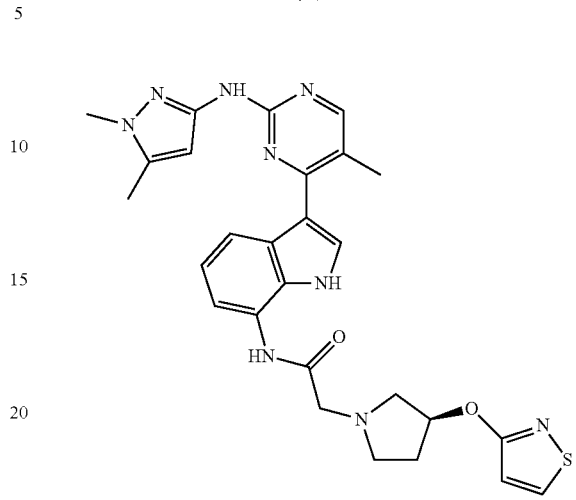

The title product was afforded by a procedure similar to that described for the synthesis of Example 73 using isothiazol-3-ol instead of pyridin-2-ol. MS (ESI, m/z): 544.2 [M+H]$^+$ Example 115: Synthesis of (S)—N-(3-(2-((1,5-dimethyl-1H-pyrazol-3-yl)amino)-5-methylpyrimidin-4-yl)-1H-indol-7-yl)-2-(3-((2-methylthiophen-3-yl)oxy)pyrrolidin-1-yl)acetamide

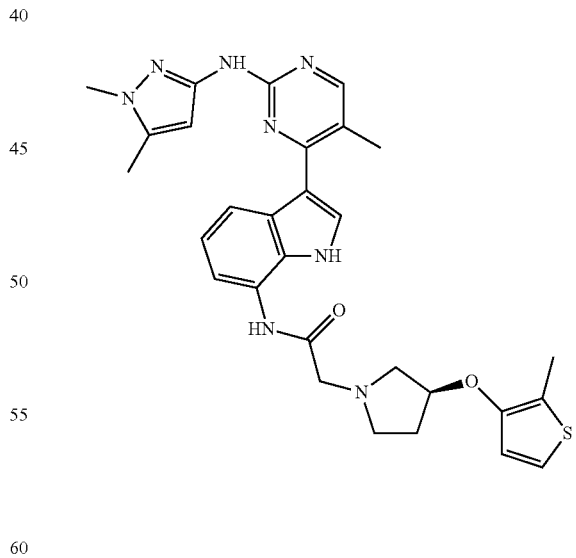

The title product was afforded by a procedure similar to that described for the synthesis of Example 73 using 2-methylthiophen-3-ol instead of pyridin-2-ol. MS (ESI, m/z): 557.2 [M+H]$^+$ Example 116: Synthesis of (S)-2-(3-((1H-pyrazol-3-yl)oxy)pyrrolidin-1-yl)-N-(3-(2-(((1,5-dimethyl-1H-pyrazol-3-yl)amino)-5-methylpyrimidin-4-yl)-1H-indol-7-yl)acetamide

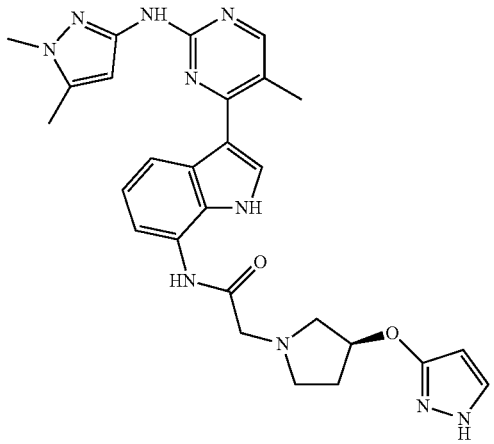 [SMILES: Cc1cnc(Nc2cc(C)n(C)n2)nc1-c1c[nH]c2c(NC(=O)CN3CC[C@H](Oc4cc[nH]n4)C3)cccc12]

The title product was afforded by a procedure similar to that described for the synthesis of Example 73 using 1H-pyrazol-3-ol instead of pyridin-2-ol. MS (ESI, m/z): 527.3 [M+H]$^+$ Example 117: Synthesis of (S)—N-(3-(2-((1,5-dimethyl-1H-pyrazol-3-yl)amino)-5-methylpyrimidin-4-yl)-1H-indol-7-yl)-2-(3-((1-methyl-5-(trifluoromethyl)-1H-pyrazol-3-yl)oxy)pyrrolidin-1-yl)acetamide

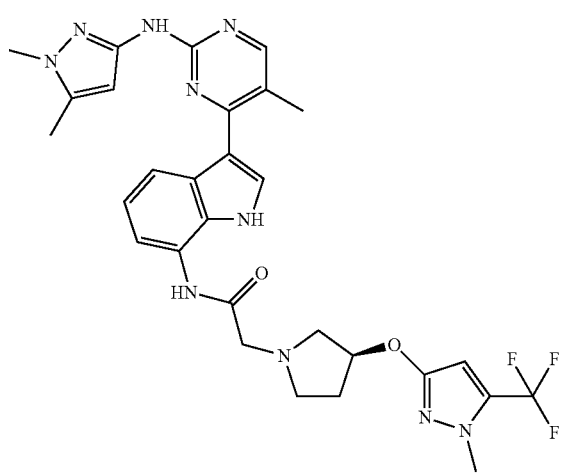 [SMILES: Cc1cnc(Nc2cc(C)n(C)n2)nc1-c1c[nH]c2c(NC(=O)CN3CC[C@H](Oc4cc(C(F)(F)F)n(C)n4)C3)cccc12]

The title product was afforded by a procedure similar to that described for the synthesis of Example 73 using 1-methyl-5-(trifluoromethyl)-1H-pyrazol-3-ol instead of pyridin-2-ol. MS (ESI, m/z): 609.3 [M+H]$^+$ Example 118: Synthesis of (S)—N-(3-(2-(((1,5-dimethyl-1H-pyrazol-3-yl)amino)-5-methylpyrimidin-4-yl)-1H-indol-7-yl)-2-(3-(isoxazol-3-yloxy)pyrrolidin-1-yl)acetamide

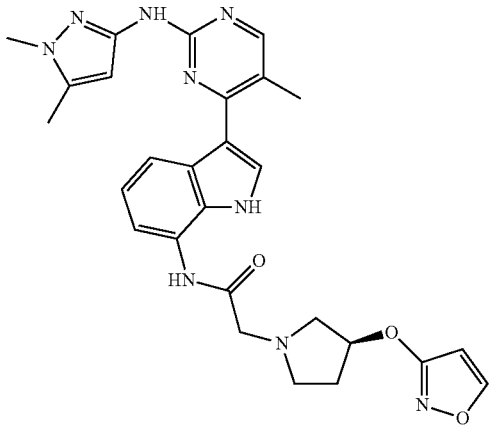 [SMILES: Cc1cnc(Nc2cc(C)n(C)n2)nc1-c1c[nH]c2c(NC(=O)CN3CC[C@H](Oc4ccon4)C3)cccc12]

The title product was afforded by a procedure similar to that described for the synthesis of Example 73 using isoxazol-3-ol instead of pyridin-2-ol. MS (ESI, m/z): 528.2 [M+H]$^+$ Example 119: Synthesis of (S)-2-(3-((5-amino-1H-pyrazol-3-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

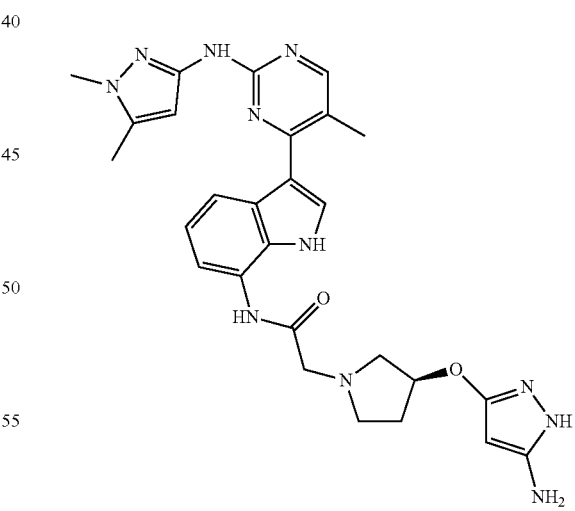

The title product was afforded by a procedure similar to that described for the synthesis of Example 73 using 5-amino-1H-pyrazol-3-ol instead of pyridin-2-ol. MS (ESI, m/z): 542.3 [M+H]$^+$ Example 120: Synthesis of methyl (S)-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)-1H-pyrrole-2-carboxylate

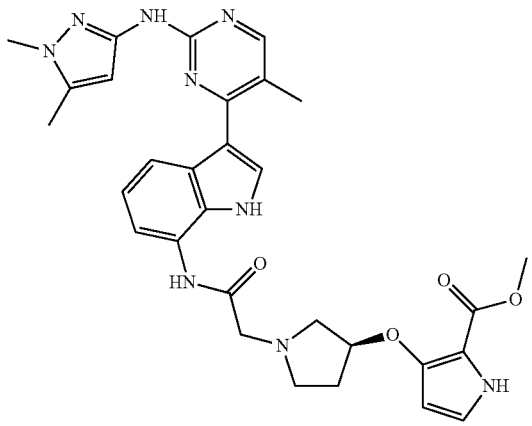

The title product was afforded by a procedure similar to that described for the synthesis of Example 73 using methyl 3-hydroxy-1H-pyrrole-2-carboxylate instead of pyridin-2-ol. MS (ESI, m/z): 584.3 [M+H]$^+$ Example 121: Synthesis of ethyl (S)-5-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)isoxazole-4-carboxylate

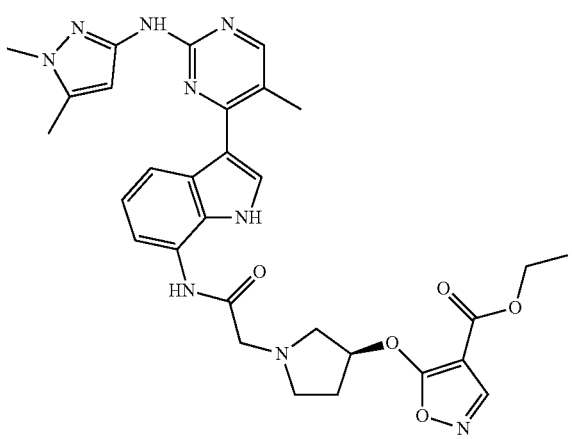 [SMILES: CCOC(=O)c1cnoc1O[C@H]1CCN(CC(=O)Nc2cccc3c(-c4nc(Nc5cc(C)n(C)n5)ncc4C)c[nH]c23)C1]

The title product was afforded by a procedure similar to that described for the synthesis of Example 73 using ethyl 5-hydroxyisoxazole-4-carboxylate instead of pyridin-2-ol. MS (ESI, m/z): 600.3 [M+H]$^+$ Example 122: Synthesis of (S)-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)isoxazole-5-carboxamide

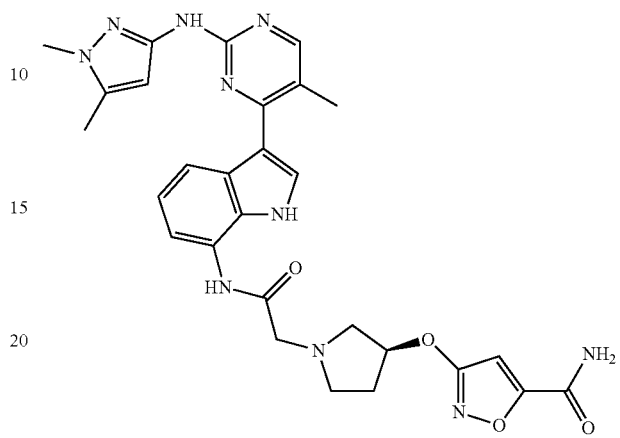

The title product was afforded by a procedure similar to that described for the synthesis of Example 73 using 3-hydroxyisoxazole-5-carboxamide instead of pyridin-2-ol. MS (ESI, m/z): 571.3 [M+H]$^+$ Example 123: Synthesis of (S)-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)-N-methylisoxazole-5-carboxamide

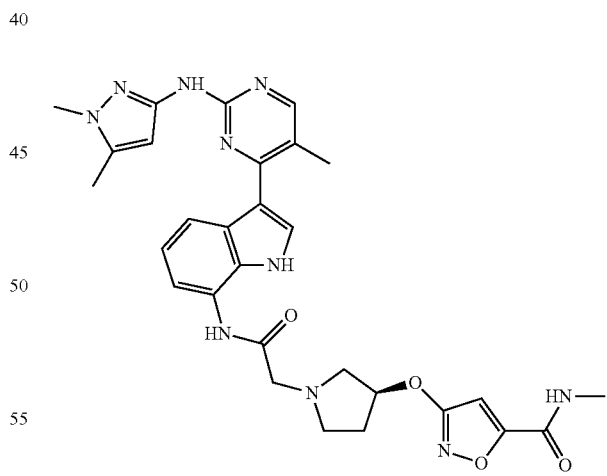

The title product was afforded by a procedure similar to that described for the synthesis of Example 73 using 3-hydroxy-N-methylisoxazole-5-carboxamide instead of pyridin-2-ol. MS (ESI, m/z): 585.3 [M+H]$^+$ Example 124: Synthesis of (S)—N-cyclopropyl-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)isoxazole-5-carboxamide

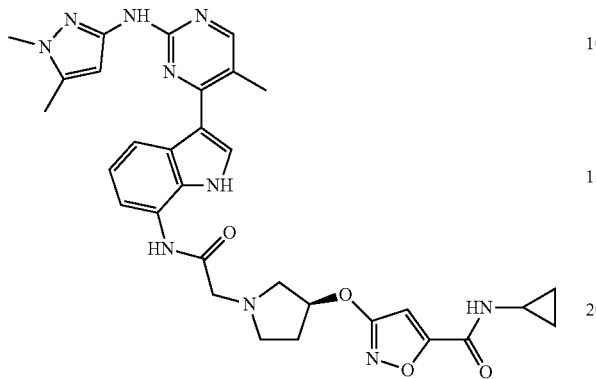

The title product was afforded by a procedure similar to that described for the synthesis of Example 73 using N-cyclopropyl-3-hydroxyisoxazole-5-carboxamide instead of pyridin-2-ol. MS (ESI, m/z): 611.3 [M+H]$^+$ Example 125: Synthesis of (S)-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)-N,N-dimethylisoxazole-5-carboxamide

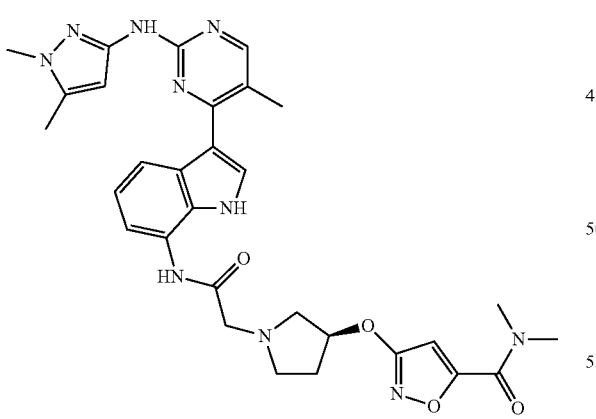 [SMILES: Cc1cnc(Nc2cc(C)n(C)n2)nc1-c1c[nH]c2c(NC(=O)CN3CC[C@H](Oc4cc(C(=O)NC5CC5)on4)C3)cccc12]

The title product was afforded by a procedure similar to that described for the synthesis of Example 73 using 3-hydroxy-N,N-dimethylisoxazole-5-carboxamide instead of pyridin-2-ol. MS (ESI, m/z): 599.3 [M+H]$^+$ Example 126: Synthesis of (S)—N-cyclopropyl-2-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)oxazole-5-carboxamide

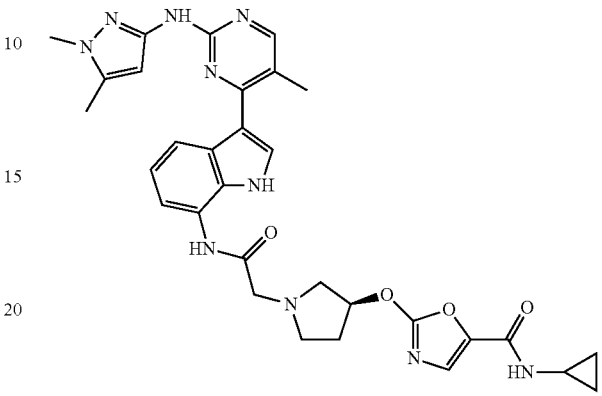

The title product was afforded by a procedure similar to that described for the synthesis of Example 73 using N-cyclopropyl-2-hydroxyoxazole-5-carboxamide instead of pyridin-2-ol. MS (ESI, m/z): 611.3 [M+H]$^+$ Example 127: Synthesis of (S)—N-cyclopropyl-2-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)oxazole-4-carboxamide

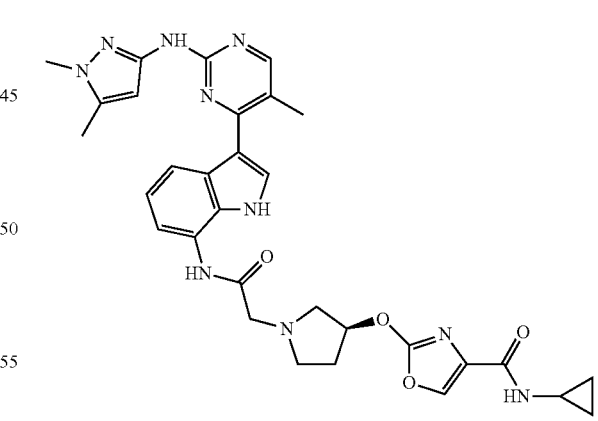

The title product was afforded by a procedure similar to that described for the synthesis of Example 73 using N-cyclopropyl-2-hydroxyoxazole-4-carboxamide instead of pyridin-2-ol. MS (ESI, m/z): 611.3 [M+H]$^+$ Example 128: Synthesis of (S)-2-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)pyrimidine-4-carboxylic acid

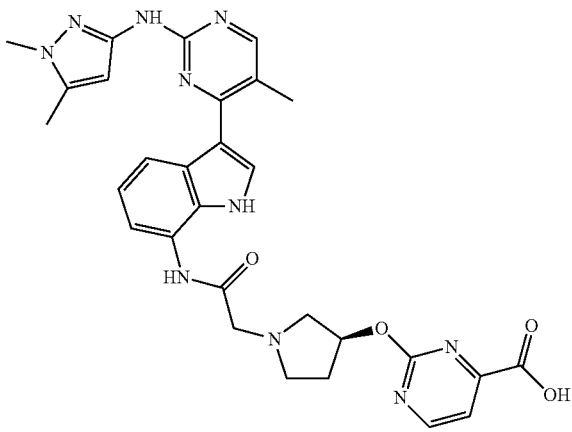 [SMILES: Cc1cnc(Nc2cc(C)n(C)n2)nc1-c1c[nH]c2c(NC(=O)CN3CC[C@H](Oc4nccc(C(=O)O)n4)C3)cccc12]

The title product was afforded by a procedure similar to that described for the synthesis of Example 73 using 2-hydroxypyrimidine-4-carboxylic acid instead of pyridin-2-ol. MS (ESI, m/z): 583.3 [M+H]+

Example 129: Synthesis of (S)-2-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)pyrimidine-4-carboxamide

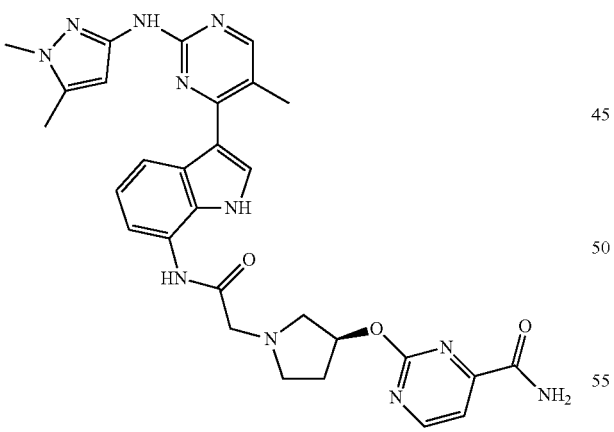

The title product was afforded by a procedure similar to that described for the synthesis of Example 73 using 2-hydroxypyrimidine-4-carboxamide instead of pyridin-2-ol. MS (ESI, m/z): 582.3 [M+H]+

Example 130: Synthesis of (S)-2-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)-N-methylpyrimidine-4-carboxamide

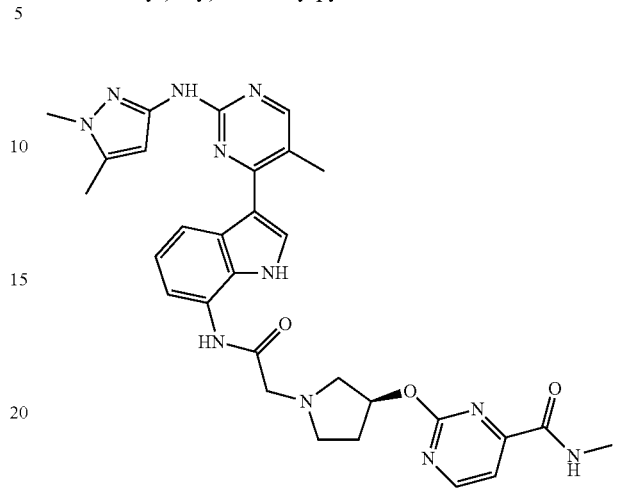

The title product was afforded by a procedure similar to that described for the synthesis of Example 73 using 2-hydroxy-N-methylpyrimidine-4-carboxamide instead of pyridin-2-ol. MS (ESI, m/z): 596.3 [M+H]+

Example 131: Synthesis of (S)-2-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)-N,N-dimethylpyrimidine-4-carboxamide

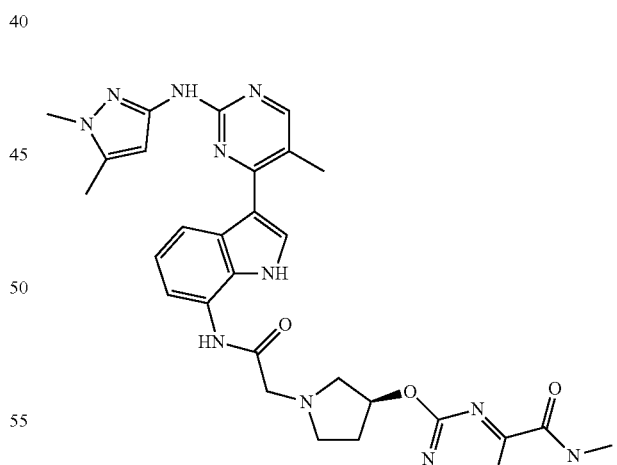

The title product was afforded by a procedure similar to that described for the synthesis of Example 73 using 2-hydroxy-N,N-dimethylpyrimidine-4-carboxamide instead of pyridin-2-ol. MS (ESI, m/z): 610.3 [M+H]+

Example 132: Synthesis of (S)-6-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)pyrazine-2-carboxamide

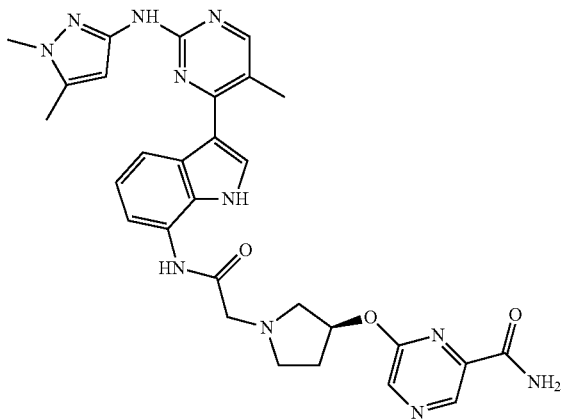 [SMILES: Cc1cnc(Nc2cc(C)n(C)n2)nc1-c1c[nH]c2c(NC(=O)CN3CC[C@H](Oc4cncc(C(N)=O)n4)C3)cccc12]

The title product was afforded by a procedure similar to that described for the synthesis of Example 73 using 6-hydroxypyrazine-2-carboxamide instead of pyridin-2-ol. MS (ESI, m/z): 582.3 [M+H]$^+$ Example 133: Synthesis of (S)-6-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)-N-methylpyrazine-2-carboxamide

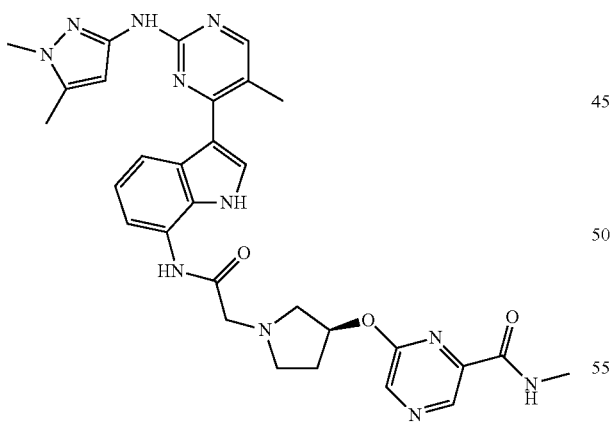

The title product was afforded by a procedure similar to that described for the synthesis of Example 73 using 6-hydroxy-N-methylpyrazine-2-carboxamide instead of pyridin-2-ol. MS (ESI, m/z): 596.3 [M+H]$^+$ Example 134: Synthesis of (S)-2-(3-((4-amino-1,3,5-triazin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

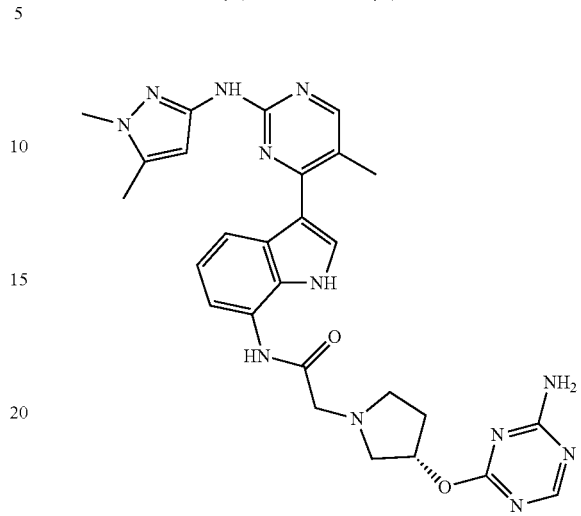

The title product was afforded by a procedure similar to General Method B using 4-chloro-1,3,5-triazin-2-ol and ammonium hydroxide instead of 2-chloropyrimidin-4-ol and cyclopropylamine. MS (ESI, m/z): 555-3 [M+H]$^+$ Example 135: Synthesis of (S)—N-(3-(2-((1,5-dimethyl-1H-pyrazol-3-yl)amino)-5-methylpyrimidin-4-yl)-1H-indol-7-yl)-2-(3-((4-(methylamino)-1,3,5-triazin-2-yl)oxy)pyrrolidin-1-yl)acetamide

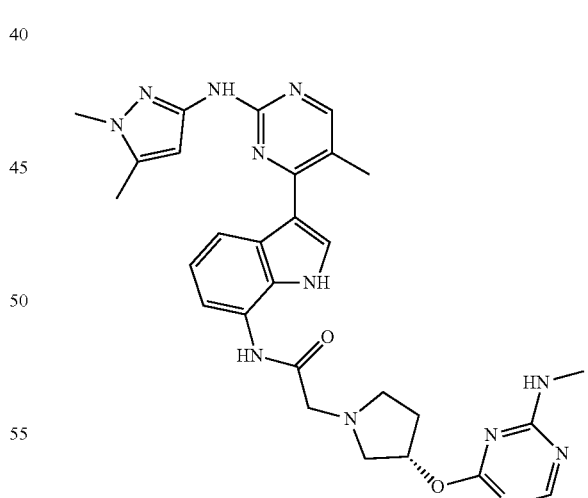

The title product was afforded by a procedure similar to that described for the synthesis of Example 134 using methylamine instead of ammonium hydroxide. MS (ESI, m/z): 569.3 [M+H]$^+$ Example 136: Synthesis of (S)—N-(3-(2-((1,5-dimethyl-1H-pyrazol-3-yl)amino)-5-methylpyrimidin-4-yl)-1H-indol-7-yl)-2-(3-((4-(dimethylamino)-1,3,5-triazin-2-yl)oxy)pyrrolidin-1-yl)acetamide

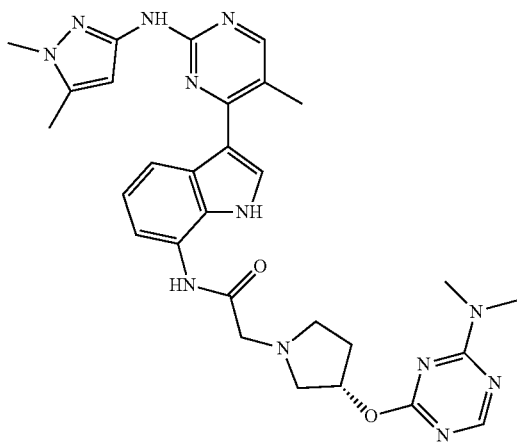

The title product was afforded by a procedure similar to that described for the synthesis of Example 134 using dimethylamine instead of ammonium hydroxide. MS (ESI, m/z): 583.3 [M+H]$^+$ Example 137: Synthesis of (S)-2-(3-((4-(cyclopropylamino)-1,3,5-triazin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

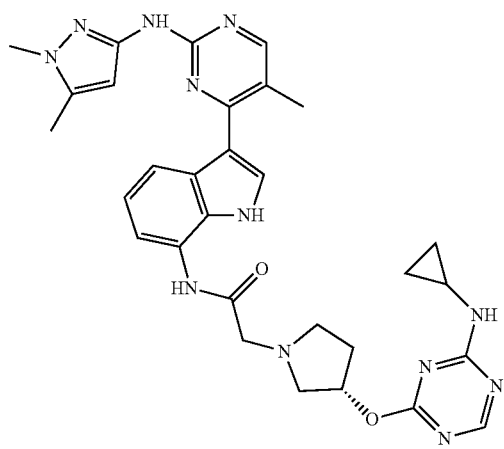 [SMILES: Cc1cnc(Nc2cc(C)n(C)n2)nc1-c1c[nH]c2c(NC(=O)CN3CC[C@H](Oc4ncnc(NC5CC5)n4)C3)cccc12]

The title product was afforded by a procedure similar to that described for the synthesis of Example 134 using cyclopropylamine instead of ammonium hydroxide.
MS (ESI, m/z): 595.3 [M+H]$^+$ Example 138: Synthesis of (S)-2-(3-((4,6-diamino-1,3,5-triazin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

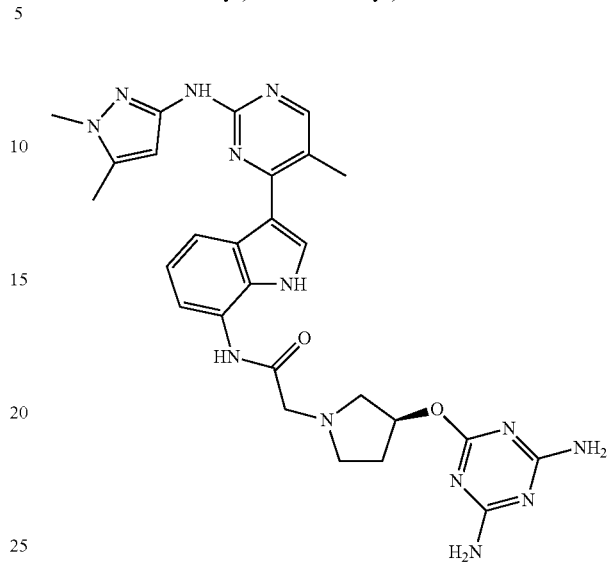

The title product was afforded by a procedure similar to that described for the synthesis of Example 134 using 4-amino-6-chloro-1,3,5-triazin-2-ol instead of 4-chloro-1,3,5-triazin-2-ol. MS (ESI, m/z): 570.3 [M+H]$^+$ Example 139: Synthesis of (S)-2-(3-((4-amino-6-(pyrrolidin-1-yl)-1,3,5-triazin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

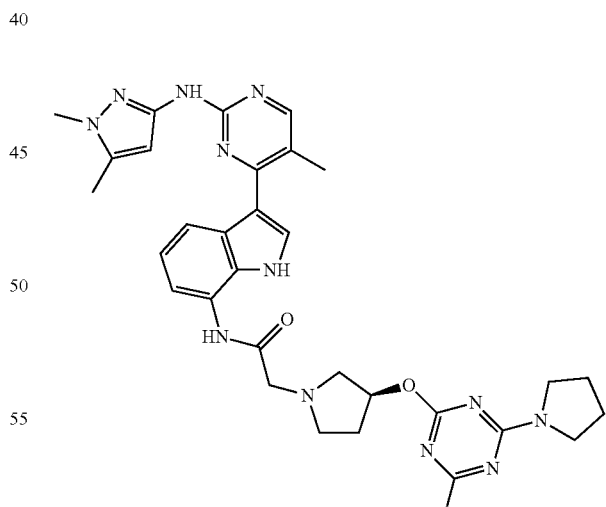

The title product was afforded by a procedure similar to that described for the synthesis of Example 138 using pyrrolidine instead of ammonium hydroxide. MS (ESI, m/z): 624.3 [M+H]$^+$ Example 140: Synthesis of (S)-2-(3-((6-aminopyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

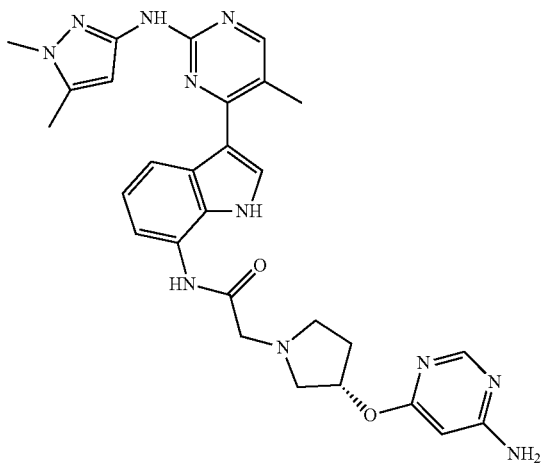 [SMILES: Cc1cnc(Nc2cc(C)n(C)n2)nc1-c1c[nH]c2c(NC(=O)CN3CC[C@H](Oc4cc(N)ncn4)C3)cccc12]

The title product was afforded by a procedure similar to that described for the synthesis of Example 134 using 6-chloropyrimidin-4-ol instead of 4-chloro-1,3,5-triazin-2-ol. MS (ESI, m/z): 554.3 [M+H]$^+$ Example 141: Synthesis of (S)—N-(3-(2-((1,5-dimethyl-1H-pyrazol-3-yl)amino)-5-methylpyrimidin-4-yl)-1H-indol-7-yl)-2-(3-((6-(methylamino)pyrimidin-4-yl)oxy)pyrrolidin-1-yl)acetamide

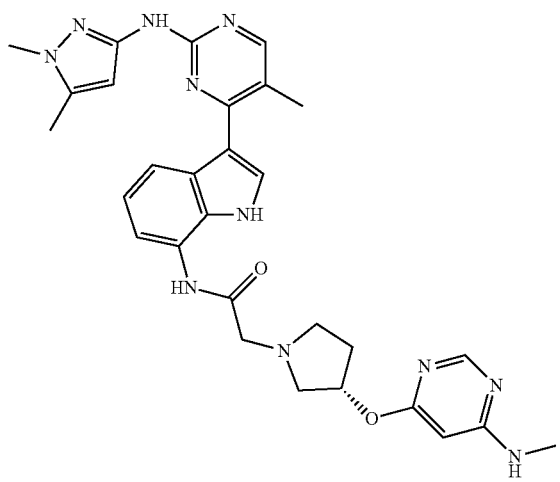

The title product was afforded by a procedure similar to that described for the synthesis of Example 140 using methylamine instead of ammonium hydroxide. MS (ESI, m/z): 568.3 [M+H]$^+$ Example 142: Synthesis of (S)—N-(3-(2-((1,5-dimethyl-1H-pyrazol-3-yl)amino)-5-methylpyrimidin-4-yl)-1H-indol-7-yl)-2-(3-((6-(ethylamino)pyrimidin-4-yl)oxy)pyrrolidin-1-yl)acetamide

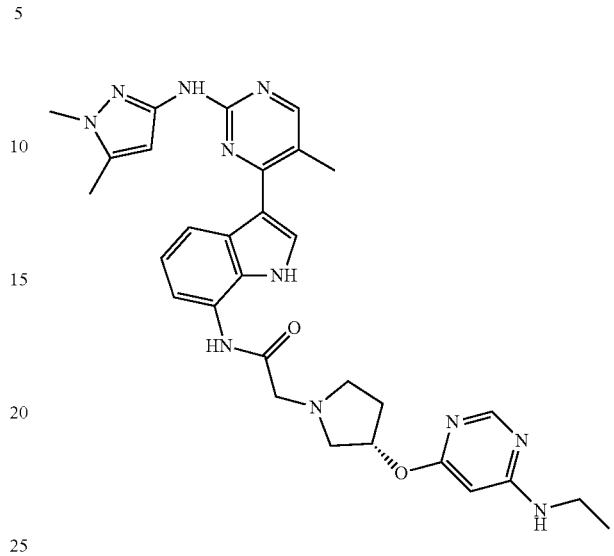

The title product was afforded by a procedure similar to that described for the synthesis of Example 140 using ethylamine instead of ammonium hydroxide. MS (ESI, m/z): 582.3 [M+H]$^+$ Example 143: Synthesis of (S)—N-(3-(2-((1,5-dimethyl-1H-pyrazol-3-yl)amino)-5-methylpyrimidin-4-yl)-1H-indol-7-yl)-2-(3-((6-(propylamino)pyrimidin-4-yl)oxy)pyrrolidin-1-yl)acetamide

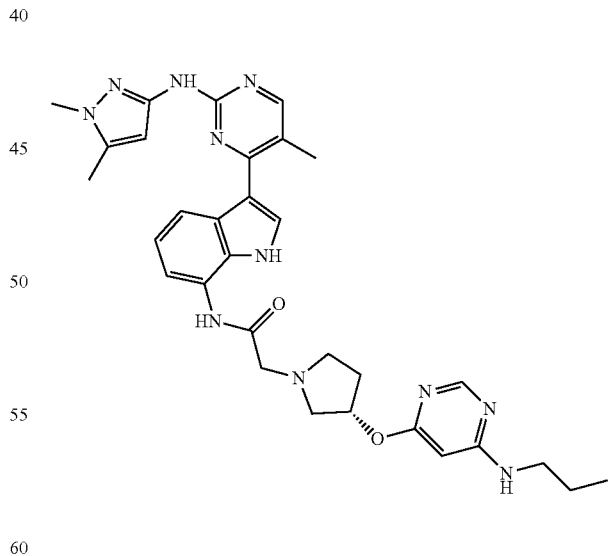

The title product was afforded by a procedure similar to that described for the synthesis of Example 140 using n-propylamine instead of ammonium hydroxide. MS (ESI, m/z): 596.3 [M+H]$^+$ Example 144: Synthesis of (S)-2-(3-((6-(butylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

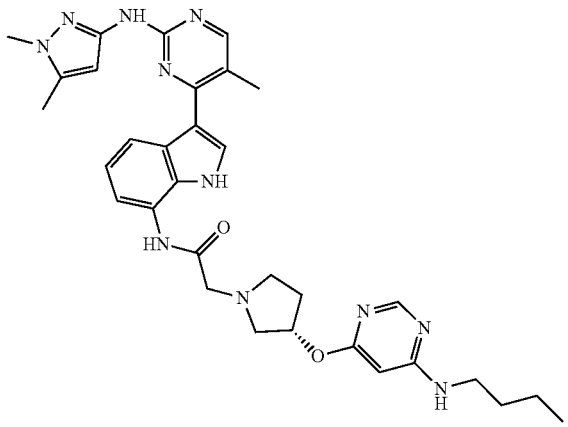 [SMILES: CCCCNc1cc(O[C@H]2CCN(CC(=O)Nc3cccc4c(-c5nc(Nc6cc(C)n(C)n6)ncc5C)c[nH]c34)C2)ncn1]

The title product was afforded by a procedure similar to that described for the synthesis of Example 140 using n-butylamine instead of ammonium hydroxide. MS (ESI, m/z): 610.3 [M+H]$^+$ Example 145: Synthesis of (S)—N-(3-(2-((1,5-dimethyl-1H-pyrazol-3-yl)amino)-5-methylpyrimidin-4-yl)-1H-indol-7-yl)-2-(3-((6-((2-hydroxyethyl)amino)pyrimidin-4-yl)oxy)pyrrolidin-1-yl)acetamide

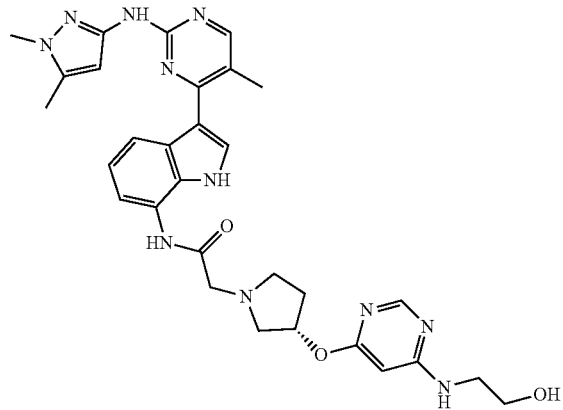 [SMILES: Cc1cnc(Nc2cc(C)n(C)n2)nc1-c1c[nH]c2c(NC(=O)CN3CC[C@H](Oc4cc(NCCO)ncn4)C3)cccc12]

The title product was afforded by a procedure similar to that described for the synthesis of Example 140 using 2-aminoethan-1-ol instead of ammonium hydroxide.
MS (ESI, m/z): 598.3 [M+H]$^+$ Example 146: Synthesis of (S)—N-(3-(2-((1,5-dimethyl-1H-pyrazol-3-yl)amino)-5-methylpyrimidin-4-yl)-1H-indol-7-yl)-2-(3-((6-((3-hydroxypropyl)amino)pyrimidin-4-yl)oxy)pyrrolidin-1-yl)acetamide The title product was afforded by a procedure similar to that described for the synthesis of Example 140 using 3-aminopropan-1-ol instead of ammonium hydroxide.

MS (ESI, m/z): 612.3 [M+H]$^+$

Example 147: Synthesis of (S)—N-(3-(2-((1,5-dimethyl-1H-pyrazol-3-yl)amino)-5-methylpyrimidin-4-yl)-1H-indol-7-yl)-2-(3-((6-((2-methoxyethyl)amino)pyrimidin-4-yl)oxy)pyrrolidin-1-yl)acetamide The title product was afforded by a procedure similar to that described for the synthesis of Example 140 using 2-methoxyethan-1-amine instead of ammonium hydroxide.
MS (ESI, m/z): 612.3 [M+H]$^+$ Example 148: Synthesis of (S)—N-(3-(2-((1,5-dimethyl-1H-pyrazol-3-yl)amino)-5-methylpyrimidin-4-yl)-1H-indol-7-yl)-2-(3-((6-((3-(dimethylamino)propyl)amino)pyrimidin-4-yl)oxy)pyrrolidin-1-yl)acetamide

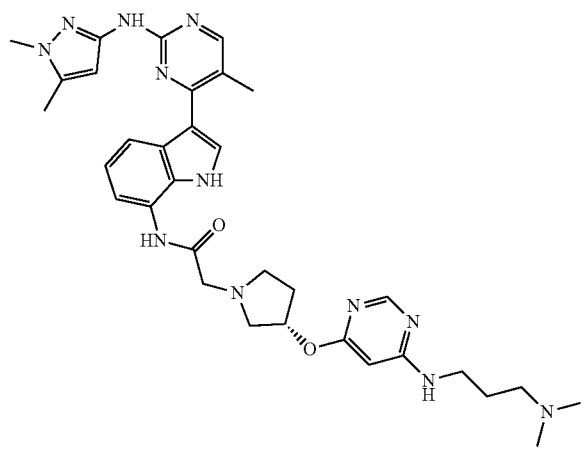

The title product was afforded by a procedure similar to that described for the synthesis of Example 140 using N1,N1-dimethylpropane-1,3-diamine instead of ammonium hydroxide. MS (ESI, m/z): 639.4 [M+H]+

Example 149: Synthesis of (S)-2-(3-((6-(benzylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

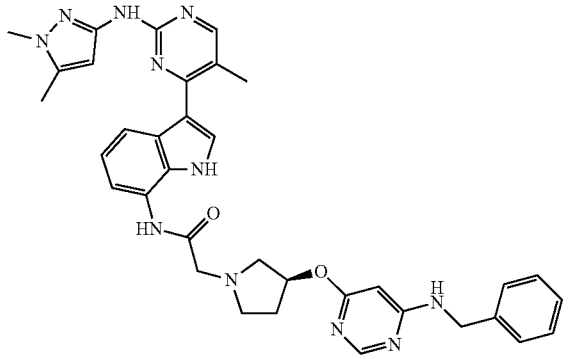 [SMILES: Cc1cnc(Nc2cc(C)n(C)n2)nc1-c1c[nH]c2c(NC(=O)CN3CC[C@H](Oc4cc(NCc5ccccc5)ncn4)C3)cccc12]

The title product was afforded by a procedure similar to that described for the synthesis of Example 140 using benzylamine instead of ammonium hydroxide. MS (ESI, m/z): 644.3 [M+H]+

Example 150: Synthesis of (S)—N-(3-(2-((1,5-dimethyl-1H-pyrazol-3-yl)amino)-5-methylpyrimidin-4-yl)-1H-indol-7-yl)-2-(3-((6-(phenethylamino)pyrimidin-4-yl)oxy)pyrrolidin-1-yl)acetamide

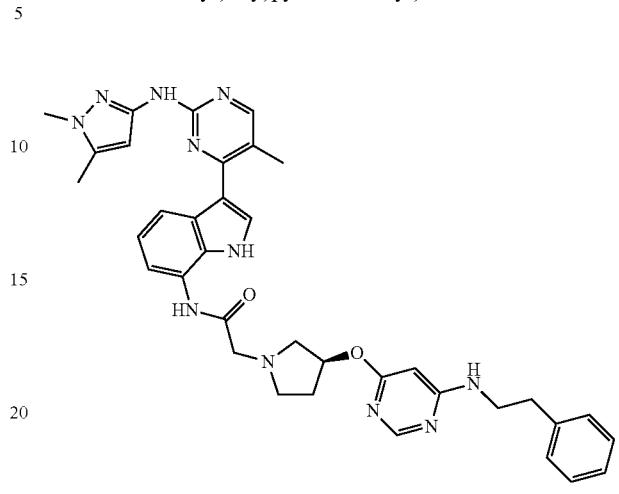

The title product was afforded by a procedure similar to that described for the synthesis of Example 140 using 2-phenylethan-1-amine instead of ammonium hydroxide. MS (ESI, m/z): 658.3 [M+H]+

Example 151: Synthesis of (S)-2-(3-((6-(cyclopropylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

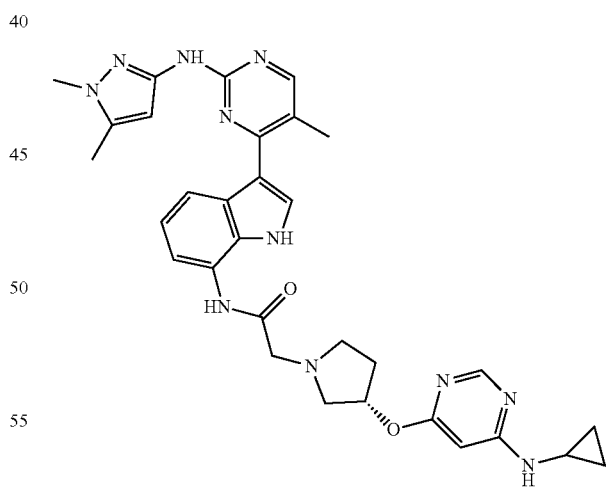

The title product was afforded by a procedure similar to that described for the synthesis of Example 140 using cyclopropylamine instead of ammonium hydroxide.

MS (ESI, m/z): 594.3 [M+H]+

Example 152: Synthesis of (S)-2-(3-((6-(cyclohexylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

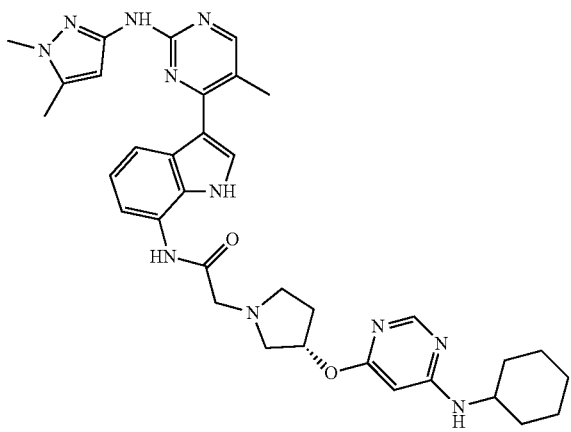 [SMILES: Cc1cnc(Nc2cc(C)n(C)n2)nc1-c1c[nH]c2c(NC(=O)CN3CC[C@H](Oc4cc(NC5CCCCC5)ncn4)C3)cccc12]

The title product was afforded by a procedure similar to that described for the synthesis of Example 140 using cyclohexanamine instead of ammonium hydroxide.

MS (ESI, m/z): 636.3 [M+H]$^+$

Example 153: Synthesis of (S)—N-(3-(2-((1,5-dimethyl-1H-pyrazol-3-yl)amino)-5-methylpyrimidin-4-yl)-1H-indol-7-yl)-2-(3-((6-(dimethylamino)pyrimidin-4-yl)oxy)pyrrolidin-1-yl)acetamide

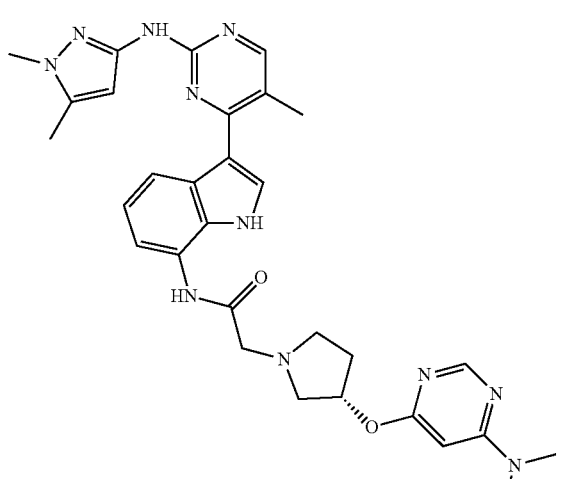

The title product was afforded by a procedure similar to that described for the synthesis of Example 140 using dimethylamine instead of ammonium hydroxide. MS (ESI, m/z): 582.3 [M+H]$^+$ Example 154: Synthesis of (S)—N-(3-(2-((1,5-dimethyl-1H-pyrazol-3-yl)amino)-5-methylpyrimidin-4-yl)-1H-indol-7-yl)-2-(3-((6-(ethyl(methyl)amino)pyrimidin-4-yl)oxy)pyrrolidin-1-yl)acetamide

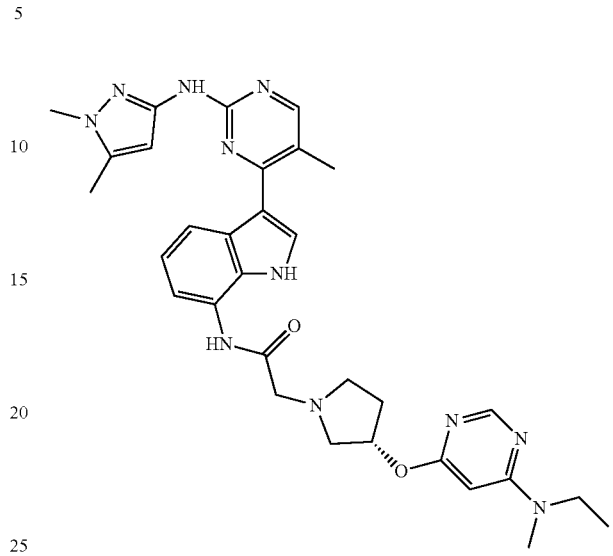

The title product was afforded by a procedure similar to that described for the synthesis of Example 140 using N-methylethanamine instead of ammonium hydroxide. MS (ESI, m/z): 596.3 [M+H]$^+$ Example 155: Synthesis of (S)-2-(3-((6-(diethylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

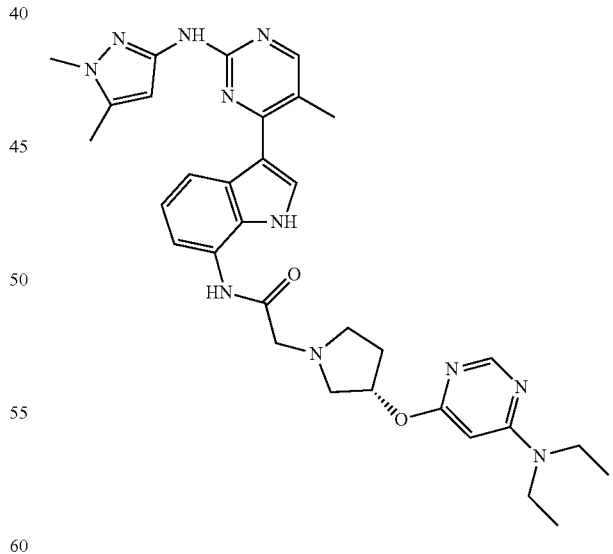

The title product was afforded by a procedure similar to that described for the synthesis of Example 140 using diethylamine instead of ammonium hydroxide. MS (ESI, m/z): 610.3 [M+H]$^+$ Example 156: Synthesis of (S)—N-(3-(2-((1,5-dimethyl-1H-pyrazol-3-yl)amino)-5-methylpyrimidin-4-yl)-1H-indol-7-yl)-2-(3-((6-(ethyl(propyl)amino)pyrimidin-4-yl)oxy)pyrrolidin-1-yl)acetamide

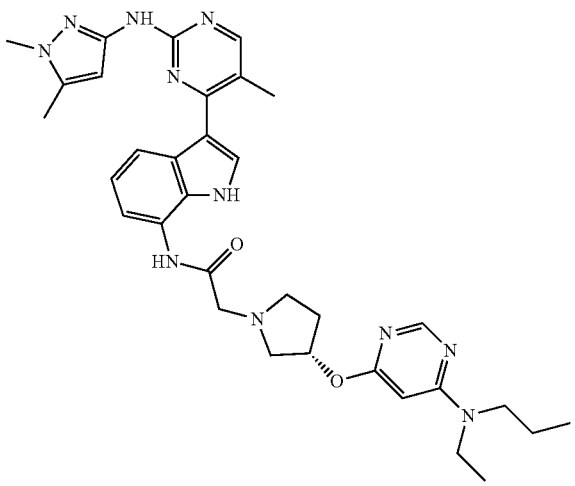 [SMILES: CCCN(CC)c1cc(O[C@H]2CCN(CC(=O)Nc3cccc4c(-c5nc(Nc6cc(C)n(C)n6)ncc5C)c[nH]c34)C2)ncn1]

The title product was afforded by a procedure similar to that described for the synthesis of Example 140 using N-ethylpropan-1-amine instead of ammonium hydroxide. MS (ESI, m/z): 624.3 [M+H]+

Example 157: Synthesis of (S)-2-(3-((6-(butyl(ethyl)amino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

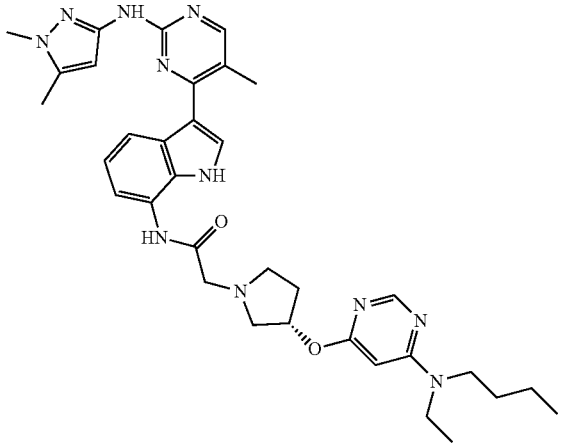 [SMILES: CCCCN(CC)c1cc(O[C@H]2CCN(CC(=O)Nc3cccc4c(-c5nc(Nc6cc(C)n(C)n6)ncc5C)c[nH]c34)C2)ncn1]

The title product was afforded by a procedure similar to that described for the synthesis of Example 140 using N-ethylbutan-1-amine instead of ammonium hydroxide. MS (ESI, m/z): 638.4 [M+H]+

Example 158: Synthesis of (S)—N-(3-(2-((1,5-dimethyl-1H-pyrazol-3-yl)amino)-5-methylpyrimidin-4-yl)-1H-indol-7-yl)-2-(3-((6-(pyrrolidin-1-yl)pyrimidin-4-yl)oxy)pyrrolidin-1-yl)acetamide

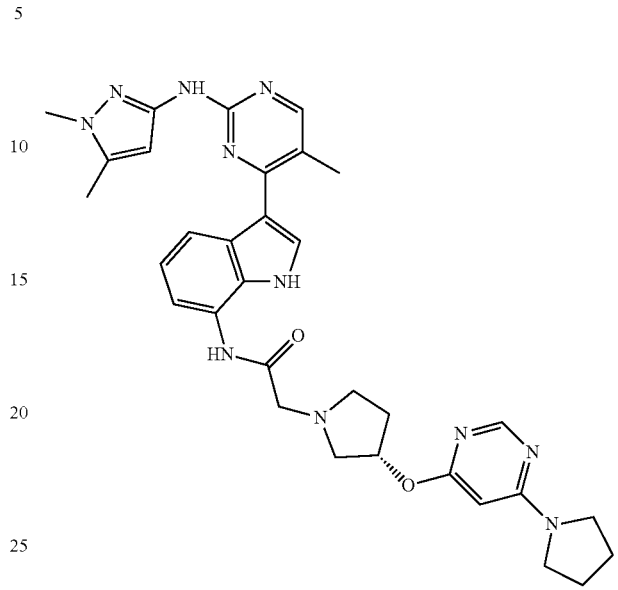

The title product was afforded by a procedure similar to that described for the synthesis of Example 140 using pyrrolidine instead of ammonium hydroxide. MS (ESI, m/z): 608.3 [M+H]+

Example 159: Synthesis of N-(3-(2-((1,5-dimethyl-1H-pyrazol-3-yl)amino)-5-methylpyrimidin-4-yl)-1H-indol-7-yl)-2-((3S)-3-((6-(3-hydroxypyrrolidin-1-yl)pyrimidin-4-yl)oxy)pyrrolidin-1-yl)acetamide

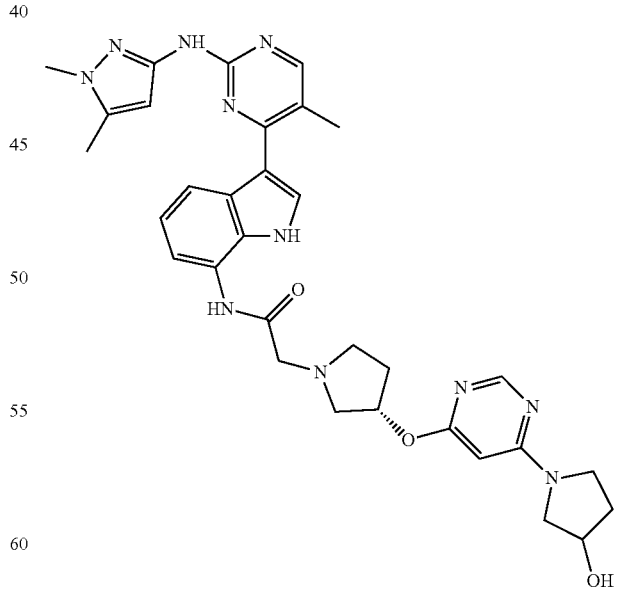

The title product was afforded by a procedure similar to that described for the synthesis of Example 140 using pyrrolidin-3-ol instead of ammonium hydroxide. MS (ESI, m/z): 624.3 [M+H]+

Example 160: Synthesis of N-(3-(2-((1,5-dimethyl-1H-pyrazol-3-yl)amino)-5-methylpyrimidin-4-yl)-1H-indol-7-yl)-2-((S)-3-((6-((R)-3-hydroxypyrrolidin-1-yl)pyrimidin-4-yl)oxy)pyrrolidin-1-yl)acetamide

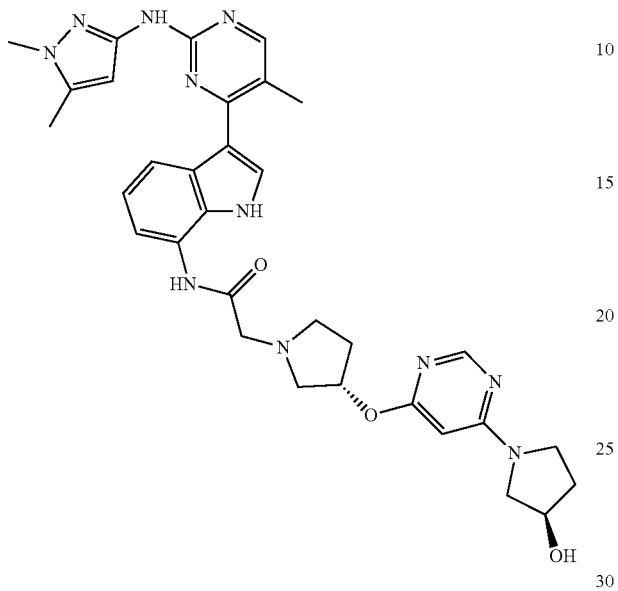

The title product was afforded by a procedure similar to that described for the synthesis of Example 140 using (R)-pyrrolidin-3-ol instead of ammonium hydroxide.
MS (ESI, m/z): 624.3 [M+H]$^+$ Example 161: Synthesis of N-(3-(2-((1,5-dimethyl-1H-pyrazol-3-yl)amino)-5-methylpyrimidin-4-yl)-1H-indol-7-yl)-2-((S)-3-((6-((S)-3-hydroxypyrrolidin-1-yl)pyrimidin-4-yl)oxy)pyrrolidin-1-yl)acetamide

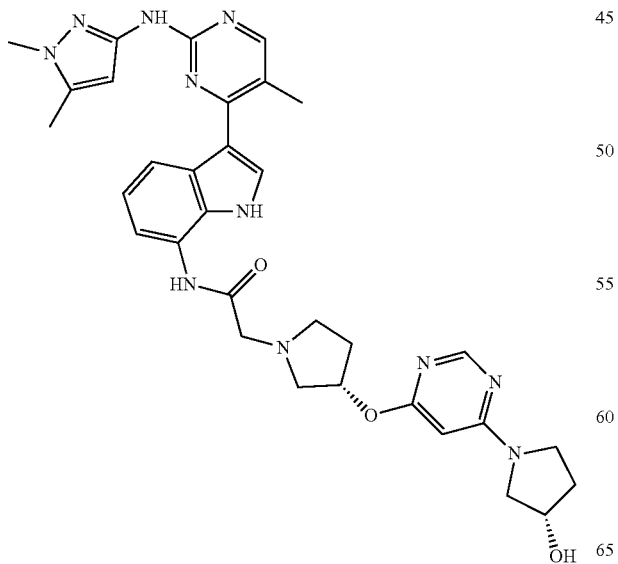

The title product was afforded by a procedure similar to that described for the synthesis of Example 140 using (S)-pyrrolidin-3-ol instead of ammonium hydroxide.
MS (ESI, m/z): 624.3 [M+H]$^+$ Example 162: Synthesis of (S)—N-(3-(2-((1,5-dimethyl-1H-pyrazol-3-yl)amino)-5-methylpyrimidin-4-yl)-1H-indol-7-yl)-2-(3-((6-(piperidin-1-yl)pyrimidin-4-yl)oxy)pyrrolidin-1-yl)acetamide

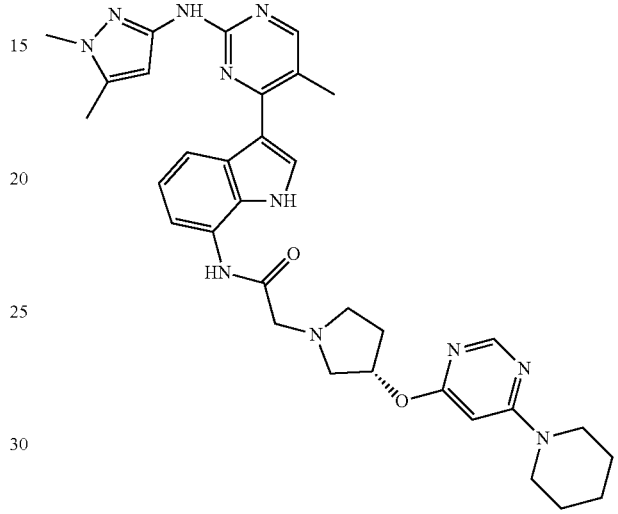

The title product was afforded by a procedure similar to that described for the synthesis of Example 140 using piperidine instead of ammonium hydroxide. MS (ESI, m/z): 622.3 [M+H]$^+$ Example 163: Synthesis of (S)—N-(3-(2-((1,5-dimethyl-1H-pyrazol-3-yl)amino)-5-methylpyrimidin-4-yl)-1H-indol-7-yl)-2-(3-((6-(4-hydroxypiperidin-1-yl)pyrimidin-4-yl)oxy)pyrrolidin-1-yl)acetamide

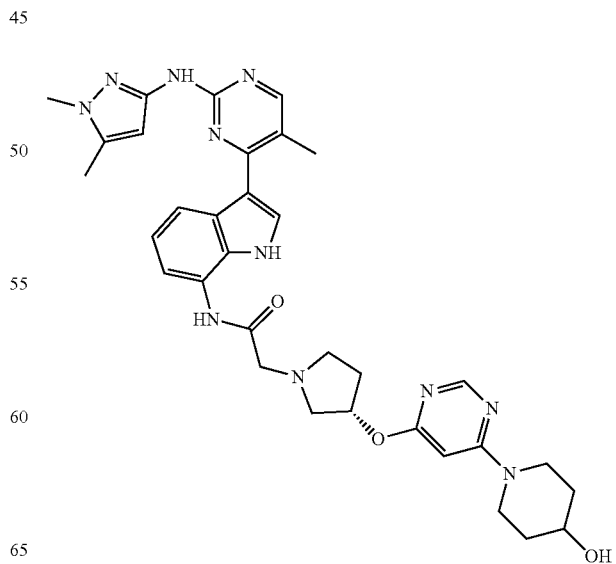

The title product was afforded by a procedure similar to that described for the synthesis of Example 140 using piperidin-4-ol instead of ammonium hydroxide. MS (ESI, m/z): 638.3 [M+H]+

Example 164: Synthesis of (S)—N-(3-(2-((1,5-dimethyl-1H-pyrazol-3-yl)amino)-5-methylpyrimidin-4-yl)-1H-indol-7-yl)-2-(3-((6-morpholinopyrimidin-4-yl)oxy)pyrrolidin-1-yl)acetamide

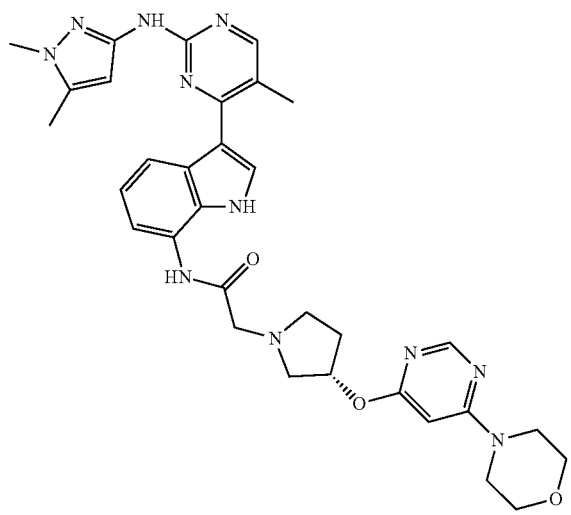 [SMILES: Cc1cnc(Nc2cc(C)n(C)n2)nc1-c1c[nH]c2c(NC(=O)CN3CC[C@H](Oc4cc(N5CCCCC5)ncn4)C3)cccc12]

The title product was afforded by a procedure similar to that described for the synthesis of Example 140 using morpholine instead of ammonium hydroxide. MS (ESI, m/z): 624.3 [M+H]+

Example 165: Synthesis of (S)—N-(3-(2-((1,5-dimethyl-1H-pyrazol-3-yl)amino)-5-methylpyrimidin-4-yl)-1H-indol-7-yl)-2-(3-((6-(4-methylpiperazin-1-yl)pyrimidin-4-yl)oxy)pyrrolidin-1-yl)acetamide

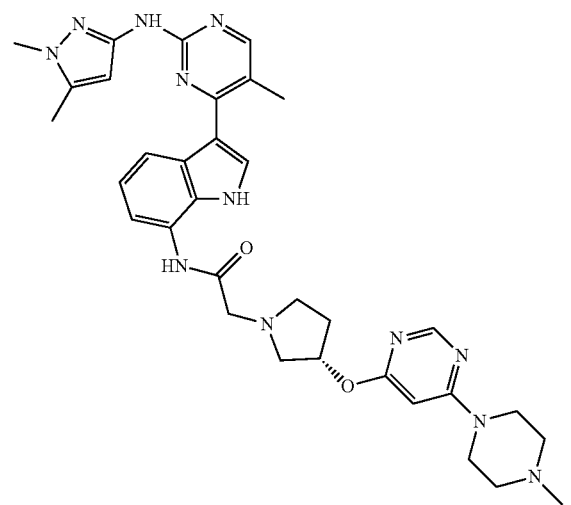

The title product was afforded by a procedure similar to that described for the synthesis of Example 140 using 1-methylpiperazine instead of ammonium hydroxide. MS (ESI, m/z): 637.3 [M+H]+

Example 166: Synthesis of (S)-2-(3-((2-amino-6-(methylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

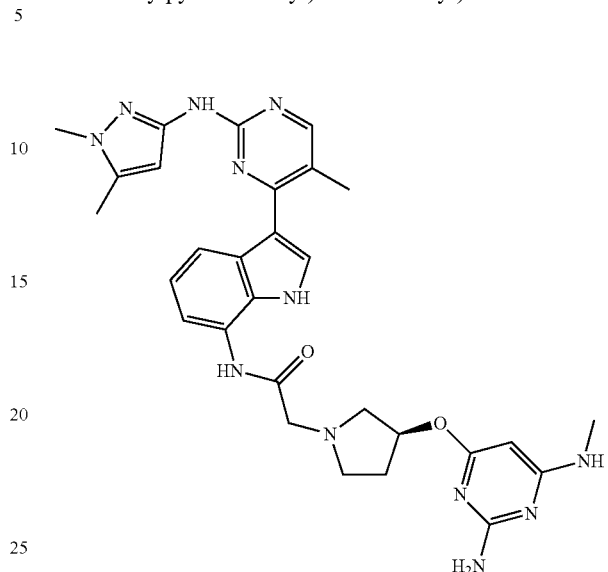

The title product was afforded by a procedure similar to that described for the synthesis of Example 141 using 2-amino-6-chloropyrimidin-4-ol instead of 6-chloropyrimidin-4-ol. MS (ESI, m/z): 583.3 [M+H]+

Example 167: Synthesis of (S)-2-(3-((2-amino-6-(pyrrolidin-1-yl)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

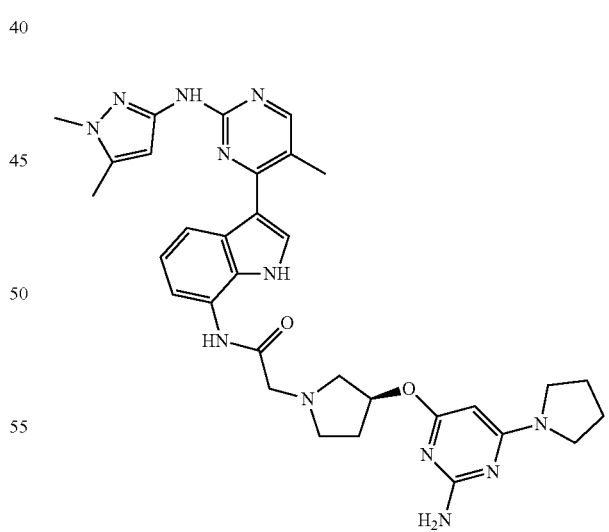

The title product was afforded by a procedure similar to that described for the synthesis of Example 166 using pyrrolidine instead of methylamine. MS (ESI, m/z): 623.3 [M+H]+

Example 168: Synthesis of (S)-2-(3-((4-aminopyrimidin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

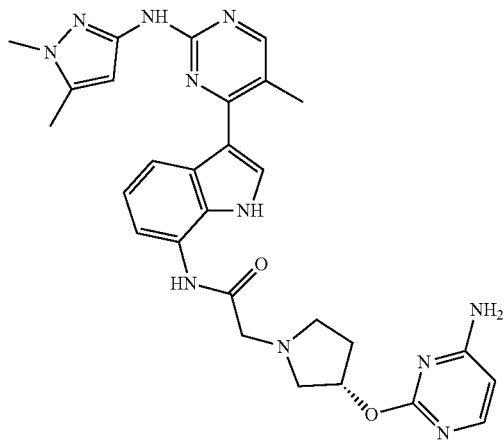 [SMILES: Cc1cnc(Nc2cc(C)n(C)n2)nc1-c1c[nH]c2c(NC(=O)CN3CC[C@H](Oc4nccc(N)n4)C3)cccc12]

The title product was afforded by a procedure similar to that described for the synthesis of Example 140 using 4-chloropyrimidin-2-ol instead of 6-chloropyrimidin-4-ol. MS (ESI, m/z): 554.3 [M+H]$^+$ Example 169: Synthesis of (S)—N-(3-(2-((1,5-dimethyl-1H-pyrazol-3-yl)amino)-5-methylpyrimidin-4-yl)-1H-indol-7-yl)-2-(3-((4-(methylamino)pyrimidin-2-yl)oxy)pyrrolidin-1-yl)acetamide

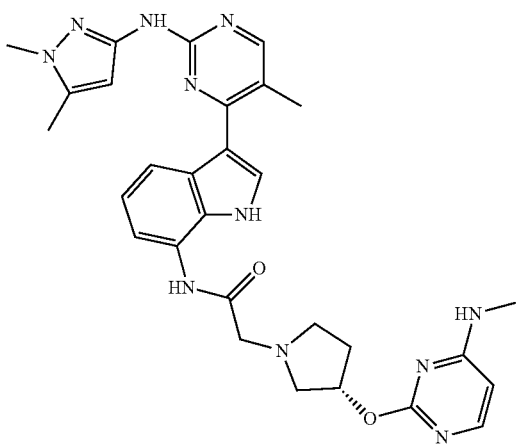

The title product was afforded by a procedure similar to that described for the synthesis of Example 168 using methylamine instead of ammonium hydroxide. MS (ESI, m/z): 568.3 [M+H]$^+$ Example 170: Synthesis of (S)—N-(3-(2-((1,5-dimethyl-1H-pyrazol-3-yl)amino)-5-methylpyrimidin-4-yl)-1H-indol-7-yl)-2-(3-((4-(dimethylamino)pyrimidin-2-yl)oxy)pyrrolidin-1-yl)acetamide

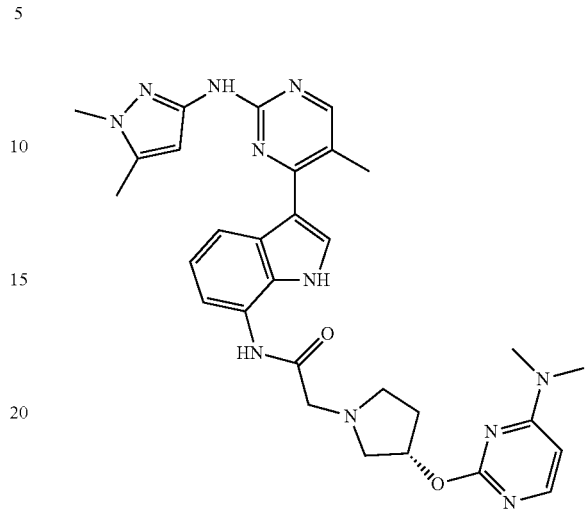

The title product was afforded by a procedure similar to that described for the synthesis of Example 168 using dimethylamine instead of ammonium hydroxide. MS (ESI, m/z): 582.3 [M+H]$^+$ Example 171: Synthesis of (S)—N-(3-(2-((1,5-dimethyl-1H-pyrazol-3-yl)amino)-5-methylpyrimidin-4-yl)-1H-indol-7-yl)-2-(3-((4-(ethyl(methyl)amino)pyrimidin-2-yl)oxy)pyrrolidin-1-yl)acetamide

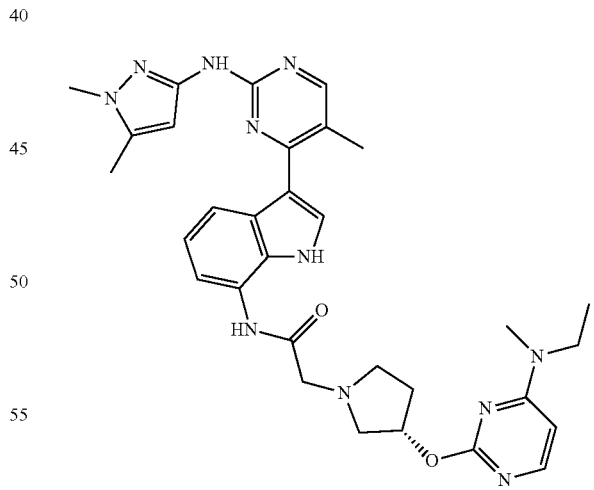

The title product was afforded by a procedure similar to that described for the synthesis of Example 168 using N-methylethanamine instead of ammonium hydroxide. MS (ESI, m/z): 596.3 [M+H]$^+$ Example 172: Synthesis of (S)-2-(3-((4-(diethyl-amino)pyrimidin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

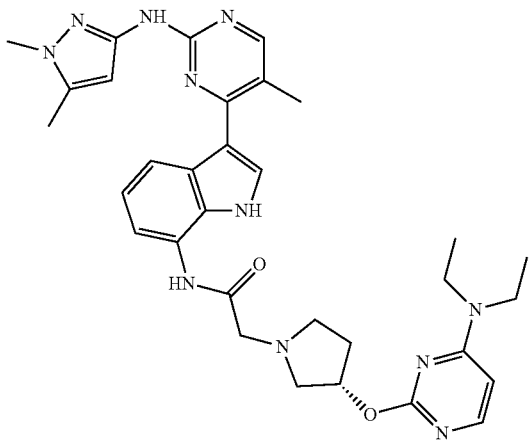 [SMILES: CCN(CC)c1ccnc(O[C@H]2CCN(CC(=O)Nc3cccc4c(-c5nc(Nc6cc(C)n(C)n6)ncc5C)c[nH]c34)C2)n1]

The title product was afforded by a procedure similar to that described for the synthesis of Example 168 using diethylamine instead of ammonium hydroxide. MS (ESI, m/z): 610.3 [M+H]$^+$ Example 173: Synthesis of (S)—N-(3-(2-((1,5-dimethyl-1H-pyrazol-3-yl)amino)-5-methylpyrimidin-4-yl)-1H-indol-7-yl)-2-(3-((4-(pyrrolidin-1-yl)pyrimidin-2-yl)oxy)pyrrolidin-1-yl)acetamide

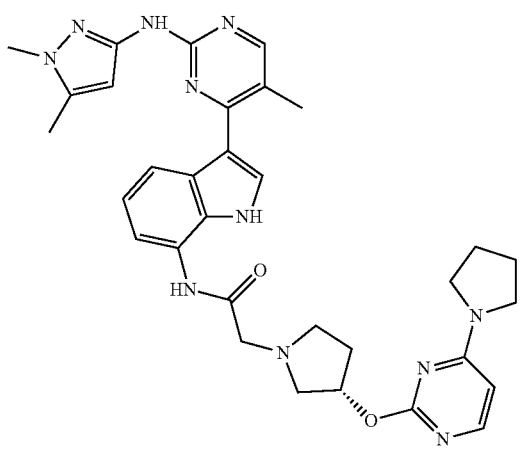 [SMILES: Cc1cnc(Nc2cc(C)n(C)n2)nc1-c1c[nH]c2c(NC(=O)CN3CC[C@H](Oc4nccc(N5CCCC5)n4)C3)cccc12]

The title product was afforded by a procedure similar to that described for the synthesis of Example 168 using pyrrolidine instead of ammonium hydroxide. MS (ESI, m/z): 608.3 [M+H]$^+$ Example 174: Synthesis of (S)—N-(3-(2-((1,5-dimethyl-1H-pyrazol-3-yl)amino)-5-methylpyrimidin-4-yl)-1H-indol-7-yl)-2-(3-((4-(piperidin-1-yl)pyrimidin-2-yl)oxy)pyrrolidin-1-yl)acetamide

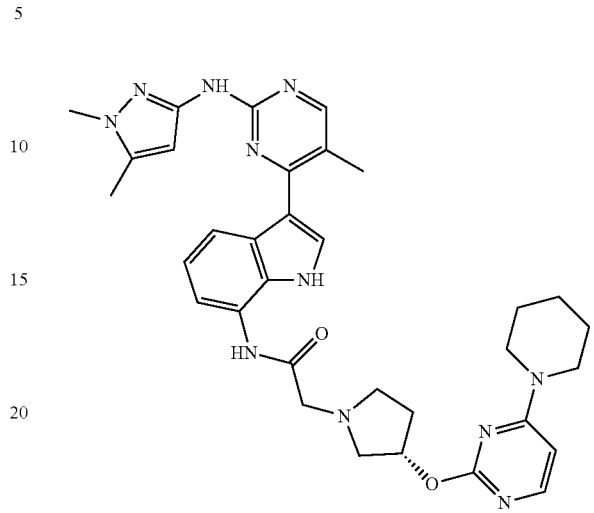

The title product was afforded by a procedure similar to that described for the synthesis of Example 168 using piperidine instead of ammonium hydroxide. MS (ESI, m/z): 622.3 [M+H]$^+$ Example 175: Synthesis of (S)-2-(3-((4-(cyclopropylamino)pyrimidin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

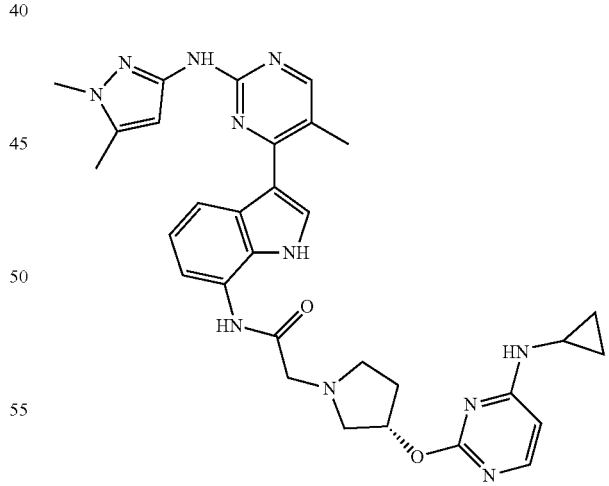

The title product was afforded by a procedure similar to that described for the synthesis of Example 168 using cyclopropylamine instead of ammonium hydroxide.

MS (ESI, m/z): 594.3 [M+H]$^+$

Example 176: Synthesis of (S)-2-(3-((4-amino-5-fluoropyrimidin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

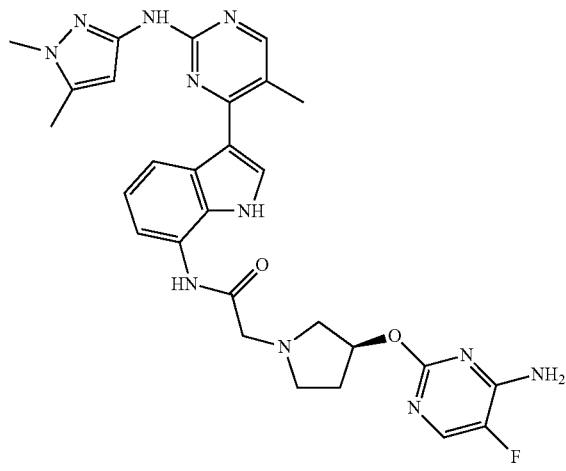 [SMILES: Cc1cnc(Nc2cc(C)n(C)n2)nc1-c1c[nH]c2c(NC(=O)CN3CC[C@H](Oc4ncc(F)c(N)n4)C3)cccc12]

The title product was afforded by a procedure similar to that described for the synthesis of Example 140 using 4-chloro-5-fluoropyrimidin-2-ol instead of 6-chloropyrimidin-4-ol. MS (ESI, m/z): 572.3 [M+H]$^+$ Example 177: Synthesis of (S)—N-(3-(2-((1,5-dimethyl-1H-pyrazol-3-yl)amino)-5-methylpyrimidin-4-yl)-1H-indol-7-yl)-2-(3-((5-fluoro-4-(methylamino)pyrimidin-2-yl)oxy)pyrrolidin-1-yl)acetamide

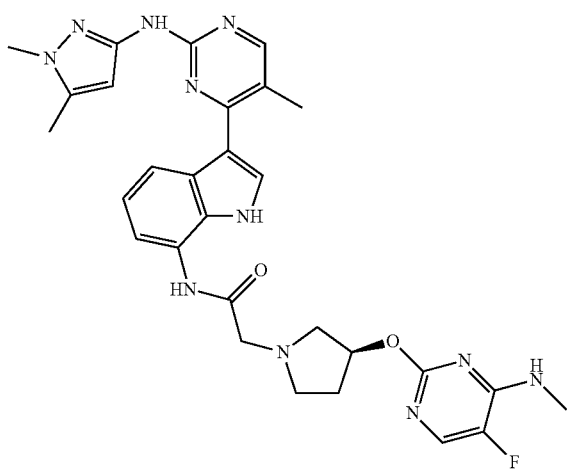

The title product was afforded by a procedure similar to that described for the synthesis of Example 176 using methylamine instead of ammonium hydroxide. MS (ESI, m/z): 586.3 [M+H]$^+$ Example 178: Synthesis of (S)—N-(3-(2-((1,5-dimethyl-1H-pyrazol-3-yl)amino)-5-methylpyrimidin-4-yl)-1H-indol-7-yl)-2-(3-((4-(ethylamino)-5-fluoropyrimidin-2-yl)oxy)pyrrolidin-1-yl)acetamide

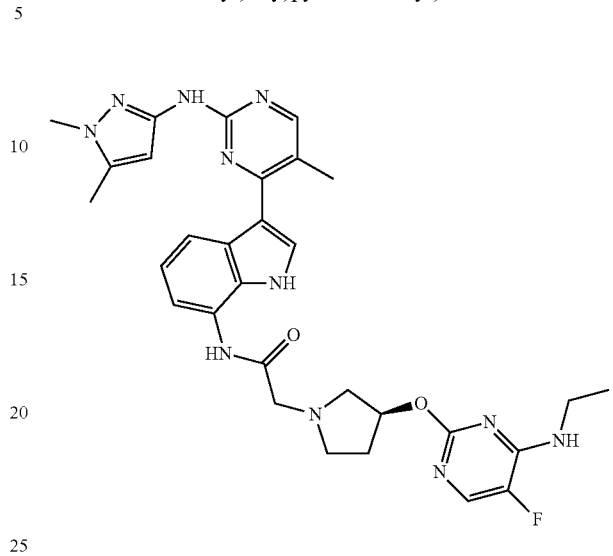

The title product was afforded by a procedure similar to that described for the synthesis of Example 176 using ethylamine instead of ammonium hydroxide. MS (ESI, m/z): 600.3 [M+H]$^+$ Example 179: Synthesis of (S)-2-(3-((4-(cyclopropylamino)-5-fluoropyrimidin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

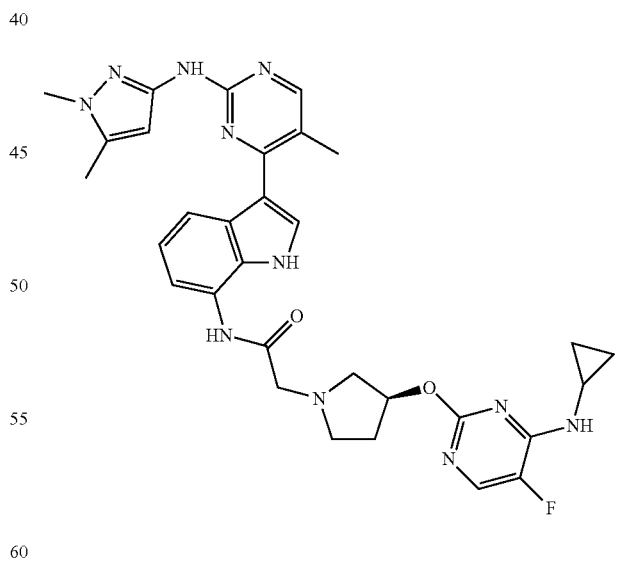

The title product was afforded by a procedure similar to that described for the synthesis of Example 176 using cyclopropylamine instead of ammonium hydroxide.

MS (ESI, m/z): 612.3 [M+H]$^+$

Example 180: Synthesis of (S)-2-(3-((4-(cyclohexylamino)-5-fluoropyrimidin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

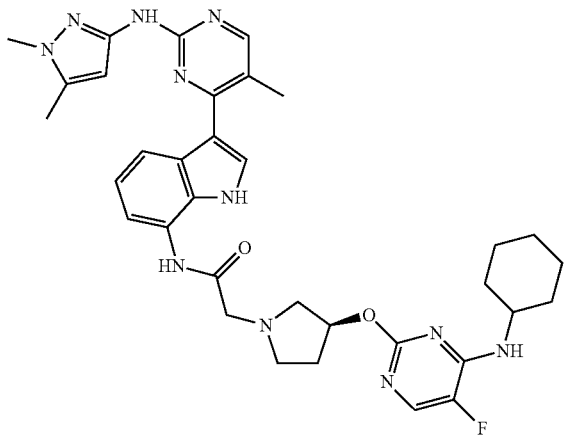 [SMILES: Cc1cnc(Nc2cc(C)n(C)n2)nc1-c1c[nH]c2c(NC(=O)CN3CC[C@H](Oc4ncc(F)c(NC5CCCCC5)n4)C3)cccc12]

The title product was afforded by a procedure similar to that described for the synthesis of Example 176 using cyclohexylamine instead of ammonium hydroxide. MS (ESI, m/z): 654.3 [M+H]$^+$ Example 181: Synthesis of (S)—N-(3-(2-((1,5-dimethyl-1H-pyrazol-3-yl)amino)-5-methylpyrimidin-4-yl)-1H-indol-7-yl)-2-(3-((4-(dimethylamino)-5-fluoropyrimidin-2-yl)oxy)pyrrolidin-1-yl)acetamide

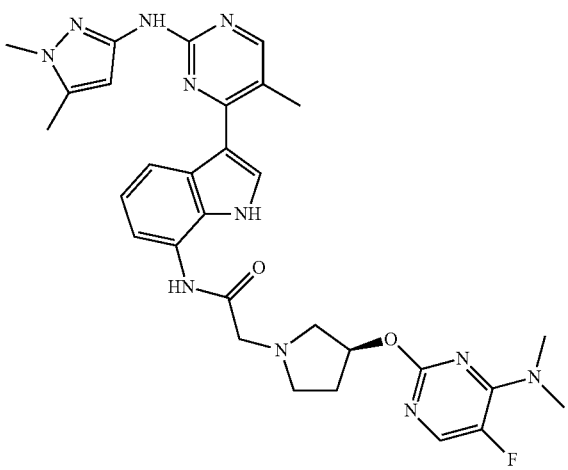

The title product was afforded by a procedure similar to that described for the synthesis of Example 176 using dimethylamine instead of ammonium hydroxide. MS (ESI, m/z): 600.3 [M+H]$^+$ Example 182: Synthesis of (S)—N-(3-(2-((1,5-dimethyl-1H-pyrazol-3-yl)amino)-5-methylpyrimidin-4-yl)-1H-indol-7-yl)-2-(3-((4-(ethyl(methyl)amino)-5-fluoropyrimidin-2-yl)oxy)pyrrolidin-1-yl)acetamide

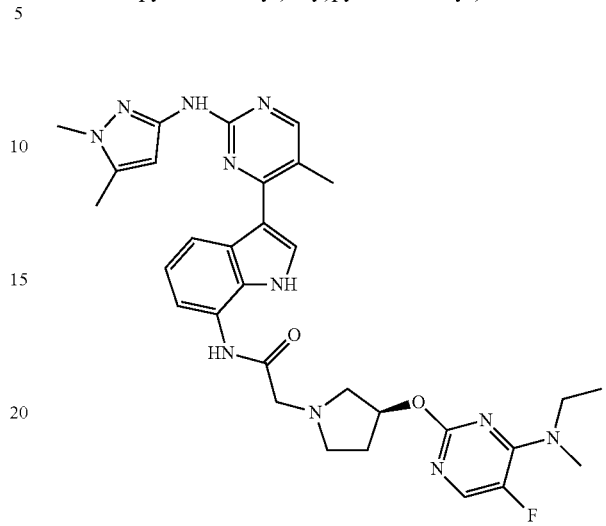

The title product was afforded by a procedure similar to that described for the synthesis of Example 176 using N-methylethanamine instead of ammonium hydroxide.
MS (ESI, m/z): 614.3 [M+H]$^+$ Example 183: Synthesis of (S)-2-(3-((4-(diethylamino)-5-fluoropyrimidin-2-yl)oxy)pyrrolidin-1-yl)-N-(3-(2-((1,5-dimethyl-H-pyrazol-3-yl)amino)-5-methylpyrimidin-4-yl)-1H-indol-7-yl)acetamide

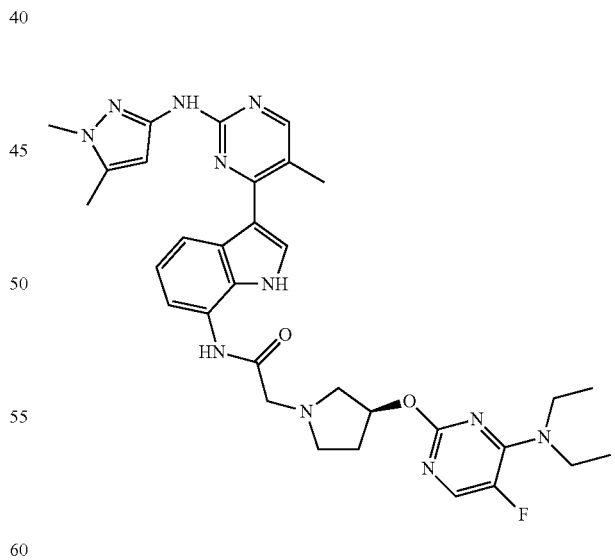

The title product was afforded by a procedure similar to that described for the synthesis of Example 176 using diethylamine instead of ammonium hydroxide. MS (ESI, m/z): 628.3 [M+H]$^+$ Example 184: Synthesis of (S)—N-(3-(2-((1,5-dimethyl-1H-pyrazol-3-yl)amino)-5-methylpyrimidin-4-yl)-1H-indol-7-yl)-2-(3-((5-fluoro-4-(methyl(phenyl)amino)pyrimidin-2-yl)oxy)pyrrolidin-1-yl)acetamide

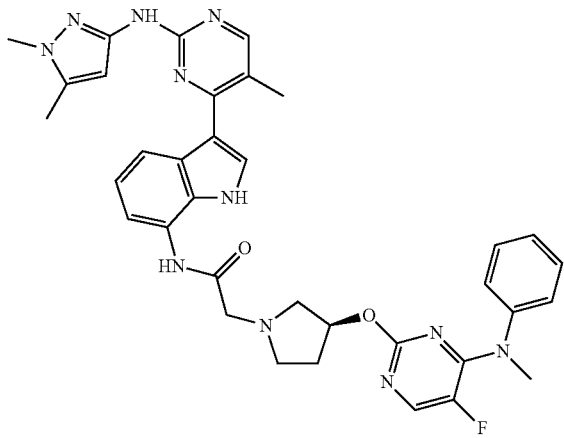 [SMILES: Cc1cnc(Nc2cc(C)n(C)n2)nc1-c1c[nH]c2c(NC(=O)CN3CC[C@H](Oc4ncc(F)c(N(C)c5ccccc5)n4)C3)cccc12]

The title product was afforded by a procedure similar to that described for the synthesis of Example 176 using N-methylaniline instead of ammonium hydroxide. MS (ESI, m/z): 662.3 [M+H]$^+$ Example 185: Synthesis of (S)-2-(3-((4-(benzyl(methyl)amino)-5-fluoropyrimidin-2-yl)oxy)pyrrolidin-1-yl)-N-(3-(2-((1,5-dimethyl-H-pyrazol-3-yl)amino)-5-methylpyrimidin-4-yl)-1H-indol-7-yl)acetamide

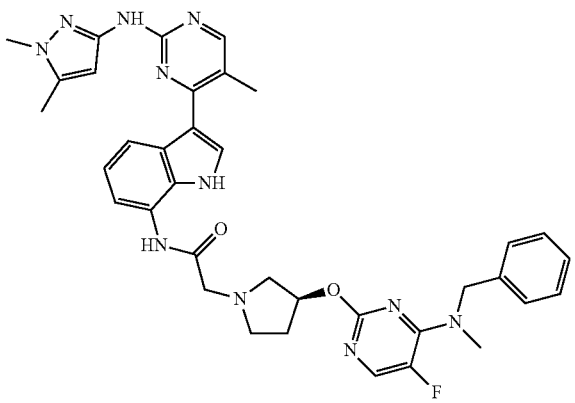 [SMILES: Cc1cnc(Nc2cc(C)n(C)n2)nc1-c1c[nH]c2c(NC(=O)CN3CC[C@H](Oc4ncc(F)c(N(C)Cc5ccccc5)n4)C3)cccc12]

The title product was afforded by a procedure similar to that described for the synthesis of Example 176 using N-methylbenzylamine instead of ammonium hydroxide. MS (ESI, m/z): 676.3 [M+H]$^+$ Example 186: Synthesis of (S)—N-(3-(2-((1,5-dimethyl-1H-pyrazol-3-yl)amino)-5-methylpyrimidin-4-yl)-1H-indol-7-yl)-2-(3-((5-fluoro-4-(pyrrolidin-1-yl)pyrimidin-2-yl)oxy)pyrrolidin-1-yl)acetamide

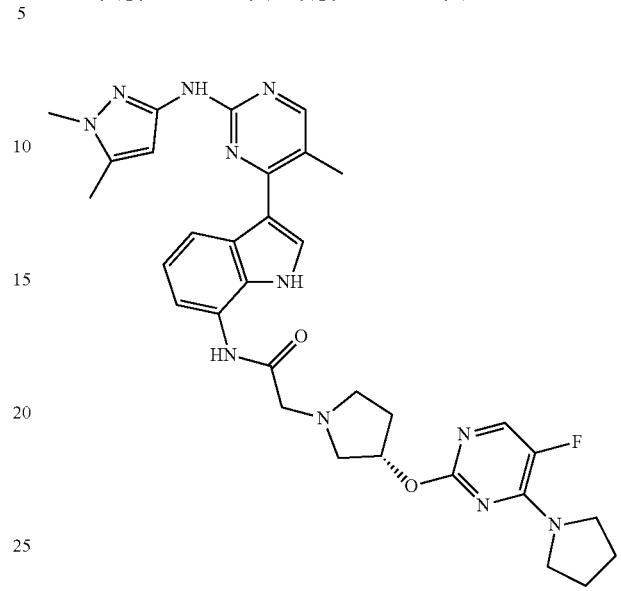

The title product was afforded by a procedure similar to that described for the synthesis of Example 176 using pyrrolidine instead of ammonium hydroxide. MS (ESI, m/z): 626.3 [M+H]$^+$ Example 187: Synthesis of (S)—N-(3-(2-((1,5-dimethyl-1H-pyrazol-3-yl)amino)-5-methylpyrimidin-4-yl)-1H-indol-7-yl)-2-(3-((5-fluoro-4-(piperidin-1-yl)pyrimidin-2-yl)oxy)pyrrolidin-1-yl)acetamide

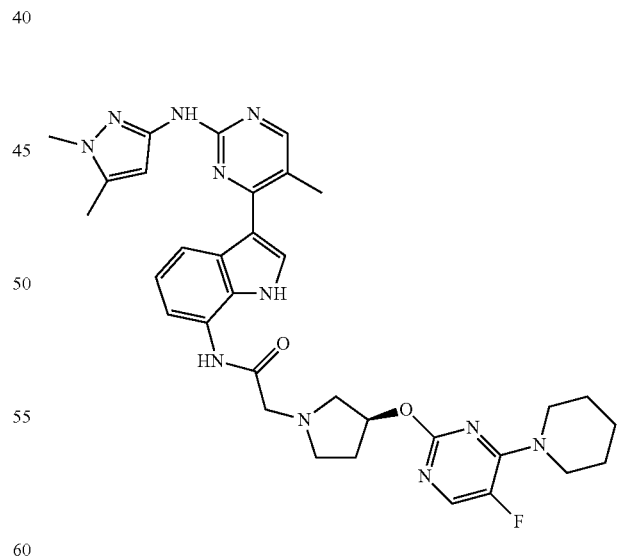

The title product was afforded by a procedure similar to that described for the synthesis of Example 176 using piperidine instead of ammonium hydroxide. MS (ESI, m/z): 640.3 [M+H]$^+$ Example 188: Synthesis of (S)—N-(3-(2-((1,5-dimethyl-1H-pyrazol-3-yl)amino)-5-methylpyrimidin-4-yl)-1H-indol-7-yl)-2-(3-((5-fluoro-4-morpholinopyrimidin-2-yl)oxy)pyrrolidin-1-yl)acetamide

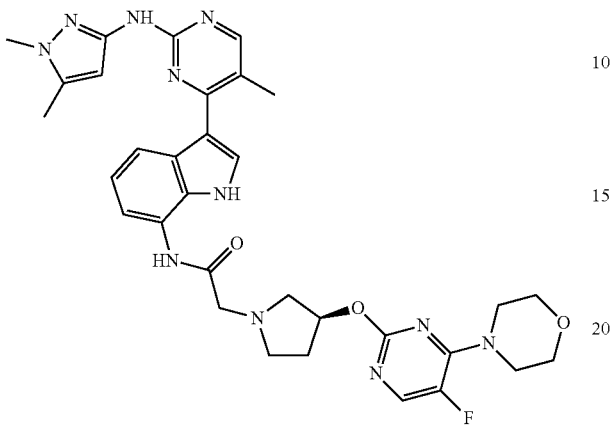

The title product was afforded by a procedure similar to that described for the synthesis of Example 176 using morpholine instead of ammonium hydroxide. MS (ESI, m/z): 642.3 [M+H]$^+$ Example 189: Synthesis of (S)—N-(3-(2-((1,5-dimethyl-1H-pyrazol-3-yl)amino)-5-methylpyrimidin-4-yl)-1H-indol-7-yl)-2-(3-((5-fluoro-4-thiomorpholinopyrimidin-2-yl)oxy)pyrrolidin-1-yl)acetamide

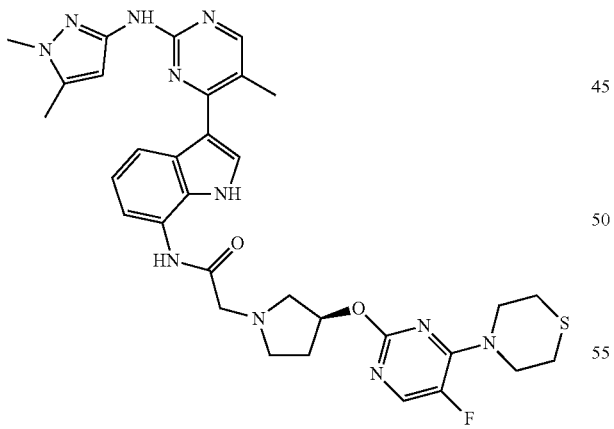

The title product was afforded by a procedure similar to that described for the synthesis of Example 176 using thiomorpholine instead of ammonium hydroxide. MS (ESI, m/z): 658.3 [M+H]$^+$ Example 190: Synthesis of (S)—N-(3-(2-((1,5-dimethyl-1H-pyrazol-3-yl)amino)-5-methylpyrimidin-4-yl)-1H-indol-7-yl)-2-(3-((5-fluoro-4-(4-methylpiperazin-1-yl)pyrimidin-2-yl)oxy)pyrrolidin-1-yl)acetamide

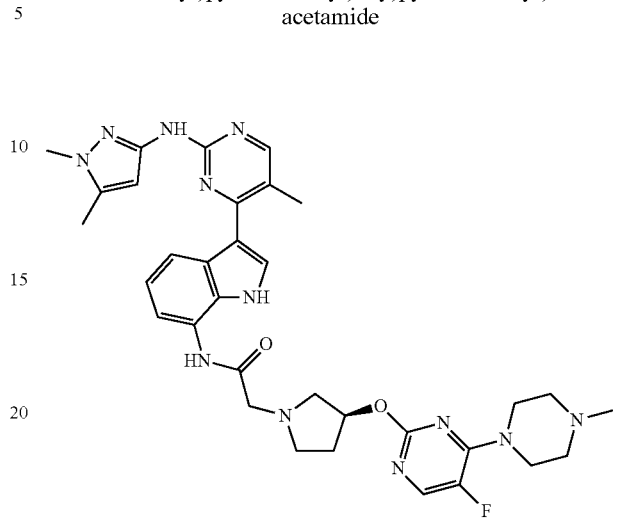

The title product was afforded by a procedure similar to that described for the synthesis of Example 176 using 1-methylpiperazine instead of ammonium hydroxide. MS (ESI, m/z): 655.3 [M+H]$^+$ Example 191: Synthesis of (S)-2-(3-((4-(cyclopropylamino)-5-methylpyrimidin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

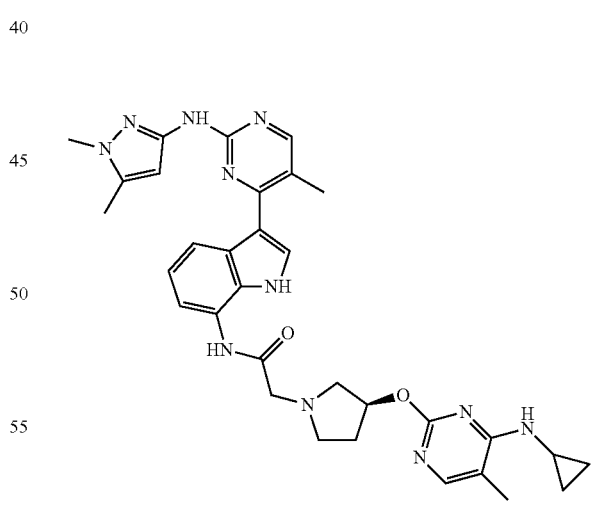

The title product was afforded by a procedure similar to that described for the synthesis of Example 179 using 4-chloro-5-methylpyrimidin-2-ol instead of 4-chloro-5-fluoropyrimidin-2-ol. MS (ESI, m/z): 608.3 [M+H]$^+$ Example 192: Synthesis of (S)-2-(3-((2-aminopyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

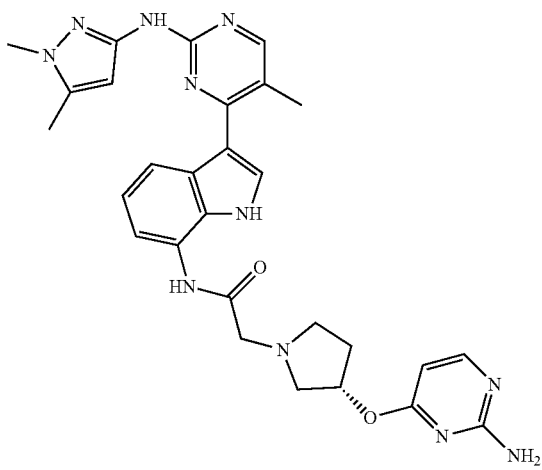 [SMILES: Cc1cnc(Nc2cc(C)n(C)n2)nc1-c1c[nH]c2c(NC(=O)CN3CC[C@H](Oc4ccnc(N)n4)C3)cccc12]

The title product was afforded by a procedure similar to that described for the synthesis of Example 140 using 2-chloropyrimidin-4-ol instead of 6-chloropyrimidin-4-ol. MS (ESI, m/z): 554.3 [M+H]$^+$ Example 193: Synthesis of (S)—N-(3-(2-((1,5-dimethyl-1H-pyrazol-3-yl)amino)-5-methylpyrimidin-4-yl)-1H-indol-7-yl)-2-(3-((2-(methylthio)pyrimidin-4-yl)oxy)pyrrolidin-1-yl)acetamide

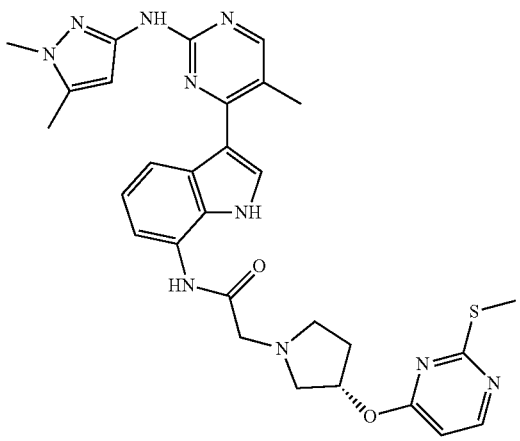

The title product was afforded by a procedure similar to that described for the synthesis of Example 192 using sodium thiomethoxide instead of ammonium hydroxide. MS (ESI, m/z): 585.2 [M+H]$^+$ Example 194: Synthesis of (S)—N-(3-(2-((1,5-dimethyl-1H-pyrazol-3-yl)amino)-5-methylpyrimidin-4-yl)-1H-indol-7-yl)-2-(3-((2-methoxypyrimidin-4-yl)oxy)pyrrolidin-1-yl)acetamide

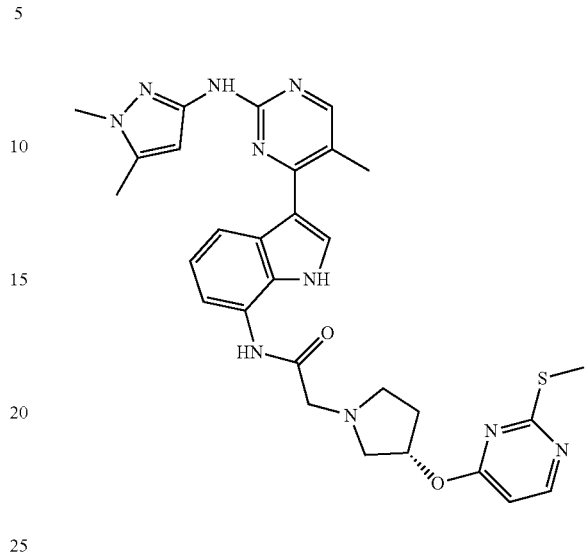

The title product was afforded by a procedure similar to that described for the synthesis of Example 192 using sodium methoxide instead of ammonium hydroxide.

MS (ESI, m/z): 569.3 [M+H]$^+$

Example 195: Synthesis of (S)-2-(3-((2-(benzyloxy)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

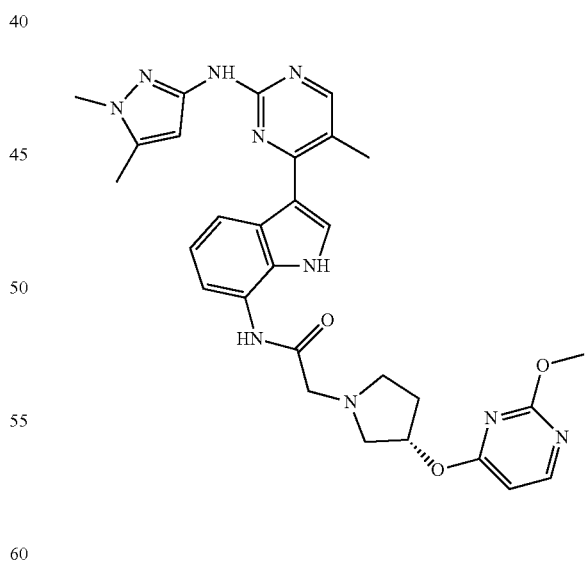

The title product was afforded by a procedure similar to that described for the synthesis of Example 192 using sodium benzyloxide instead of ammonium hydroxide.

MS (ESI, m/z): 645.3 [M+H]$^+$

Example 196: Synthesis of (S)-2-(3-((2-acetamidopyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

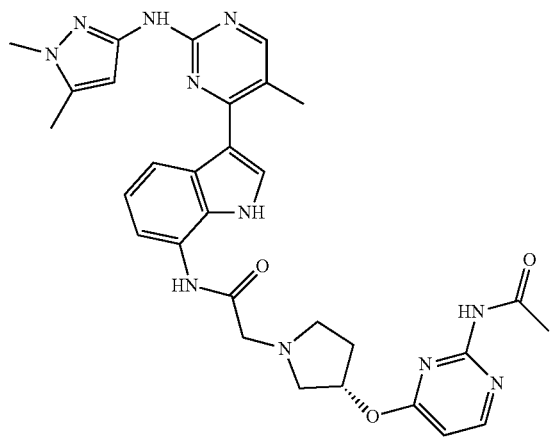 [SMILES: CC(=O)Nc1nccc(O[C@H]2CCN(CC(=O)Nc3cccc4c(-c5nc(Nc6cc(C)n(C)n6)ncc5C)c[nH]c34)C2)n1]

A solution of Example 192 (110 mg, 0.2 mmol) in MeOH (1 mL) was treated with acetyl chloride (10 μL) and stirred for 1 h. The crude was separated from the UCT SPE CUBCX cartridge and purified by the Prep HPLC to afford a corresponding product (74 mg, 62%). MS (ESI, m/z): 596.3 [M+H]$^+$

Example 197: Synthesis of (S)—N-(3-(2-((1,5-dimethyl-1H-pyrazol-3-yl)amino)-5-methylpyrimidin-4-yl)-1H-indol-7-yl)-2-(3-((2-(methylamino)pyrimidin-4-yl)oxy)pyrrolidin-1-yl)acetamide

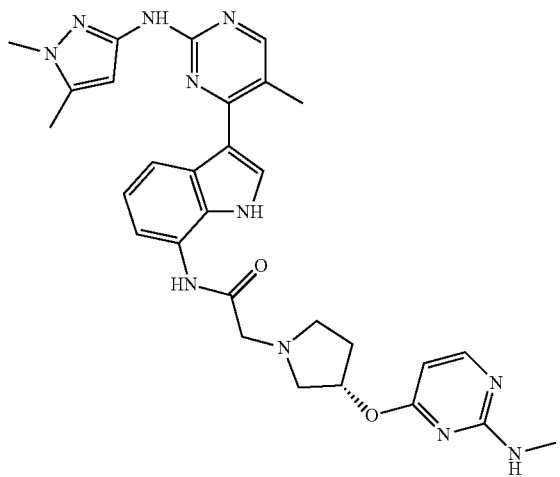

The title product was afforded by a procedure similar to that described for the synthesis of Example 192 using methylamine instead of ammonium hydroxide. MS (ESI, m/z): 568.3 [M+H]$^+$

Example 198: Synthesis of (S)—N-(3-(2-((1,5-dimethyl-1H-pyrazol-3-yl)amino)-5-methylpyrimidin-4-yl)-1H-indol-7-yl)-2-(3-((2-((2,2,2-trifluoroethyl)amino)pyrimidin-4-yl)oxy)pyrrolidin-1-yl)acetamide

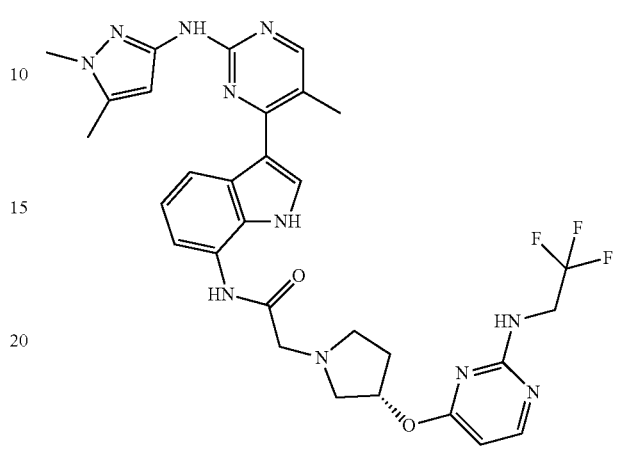

The title product was afforded by a procedure similar to that described for the synthesis of Example 192 using 2,2,2-trifluoroethan-1-amine instead of ammonium hydroxide. MS (ESI, m/z): 636.3 [M+H]$^+$

Example 199: Synthesis of (S)-2-(3-((2-((2,2-difluoropropyl)amino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

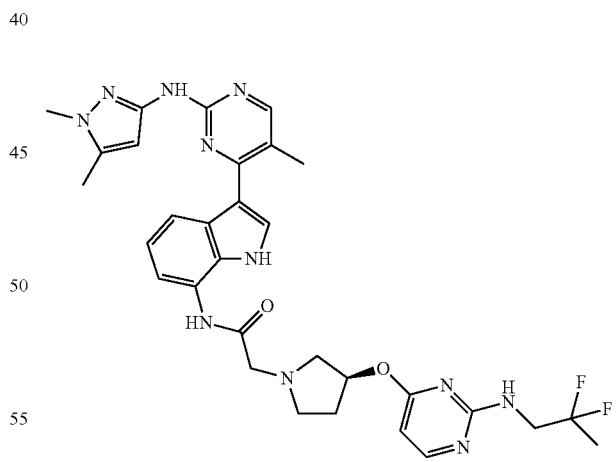

The title product was afforded by a procedure similar to that described for the synthesis of Example 192 using 2,2-difluoropropan-1-amine instead of ammonium hydroxide. MS (ESI, m/z): 632.3 [M+H]$^+$ Example 200: Synthesis of (S)-2-(3-((2-((2,2-difluoroethyl)amino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

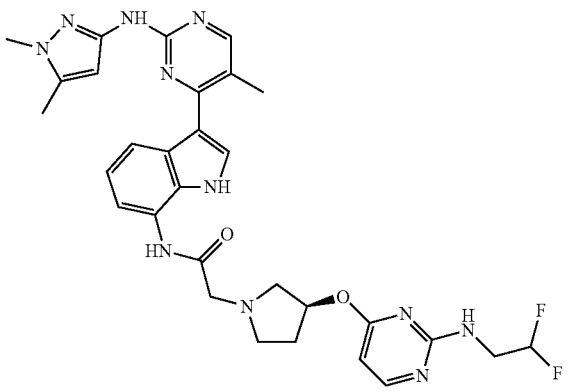 [SMILES: Cc1cnc(Nc2cc(C)n(C)n2)nc1-c1c[nH]c2c(NC(=O)CN3CC[C@H](Oc4ccnc(NCC(F)F)n4)C3)cccc12]

The title product was afforded by a procedure similar to that described for the synthesis of Example 192 using 2,2-difluoroethan-1-amine instead of ammonium hydroxide. MS (ESI, m/z): 618.3 [M+H]+

Example 201: Synthesis of N-(3-(2-((1,5-dimethyl-1H-pyrazol-3-yl)amino)-5-methylpyrimidin-4-yl)-1H-indol-7-yl)-2-((3S)-3-((2-((1,1,1-trifluoropropan-2-yl)amino)pyrimidin-4-yl)oxy)pyrrolidin-1-yl)acetamide

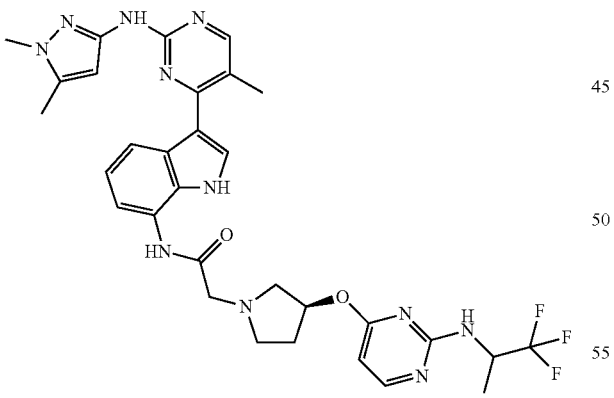

The title product was afforded by a procedure similar to that described for the synthesis of Example 192 using 1,1,1-trifluoropropan-2-amine instead of ammonium hydroxide. MS (ESI, m/z): 650.3 [M+H]+

Example 202: Synthesis of (S)—N-(3-(2-((1,5-dimethyl-1H-pyrazol-3-yl)amino)-5-methylpyrimidin-4-yl)-1H-indol-7-yl)-2-(3-((2-((2-fluoroethyl)amino)pyrimidin-4-yl)oxy)pyrrolidin-1-yl)acetamide

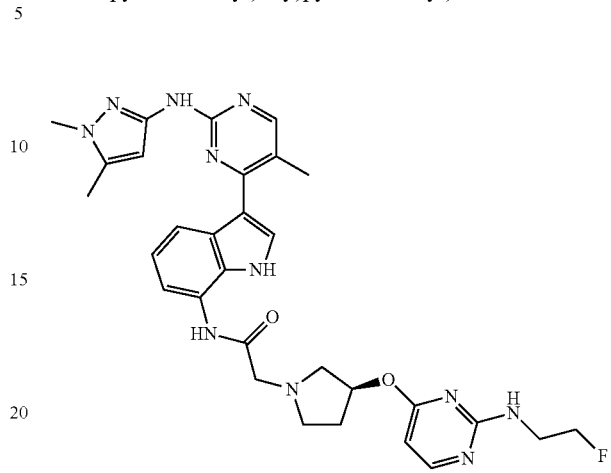

The title product was afforded by a procedure similar to that described for the synthesis of Example 192 using 2-fluoroethan-1-amine instead of ammonium hydroxide. MS (ESI, m/z): 600.3 [M+H]+

Example 203: Synthesis of (S)—N-(3-(2-((1,5-dimethyl-1H-pyrazol-3-yl)amino)-5-methylpyrimidin-4-yl)-1H-indol-7-yl)-2-(3-((2-(ethylamino)pyrimidin-4-yl)oxy)pyrrolidin-1-yl)acetamide

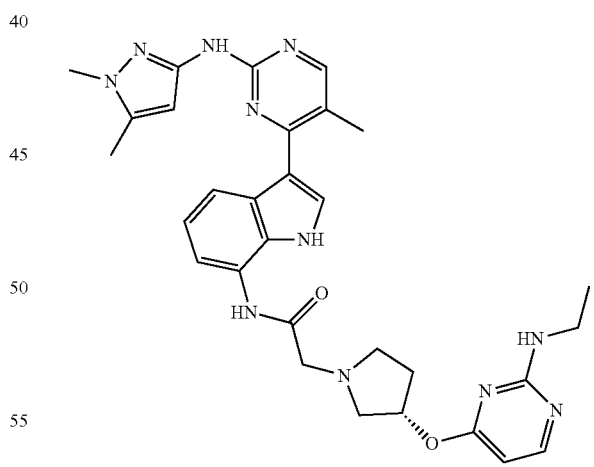

The title product was afforded by a procedure similar to that described for the synthesis of Example 192 using ethylamine instead of ammonium hydroxide. MS (ESI, m/z): 582.3 [M+H]+

Example 204: Synthesis of (S)—N-(3-(2-((1,5-dimethyl-1H-pyrazol-3-yl)amino)-5-methylpyrimidin-4-yl)-1H-indol-7-yl)-2-(3-((2-(propylamino)pyrimidin-4-yl)oxy)pyrrolidin-1-yl)acetamide

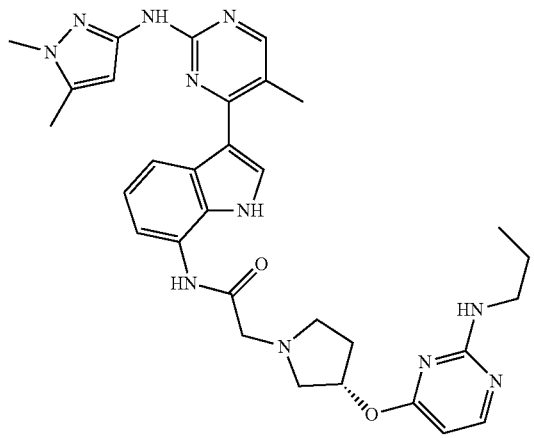 [SMILES: CCCNc1nccc(O[C@H]2CCN(CC(=O)Nc3cccc4c(-c5nc(Nc6cc(C)n(C)n6)ncc5C)c[nH]c34)C2)n1]

The title product was afforded by a procedure similar to that described for the synthesis of Example 192 using n-propylamine instead of ammonium hydroxide. MS (ESI, m/z): 596.3 [M+H]$^+$ Example 205: Synthesis of (S)-2-(3-((2-(butylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

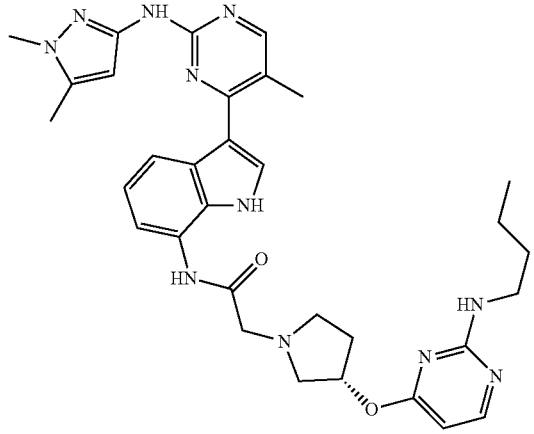 [SMILES: CCCCNc1nccc(O[C@H]2CCN(CC(=O)Nc3cccc4c(-c5nc(Nc6cc(C)n(C)n6)ncc5C)c[nH]c34)C2)n1]

The title product was afforded by a procedure similar to that described for the synthesis of Example 192 using n-butylamine instead of ammonium hydroxide. MS (ESI, m/z): 610.3 [M+H]$^+$ Example 206: Synthesis of (S)—N-(3-(2-((1,5-dimethyl-1H-pyrazol-3-yl)amino)-5-methylpyrimidin-4-yl)-1H-indol-7-yl)-2-(3-((2-((3-hydroxypropyl)amino)pyrimidin-4-yl)oxy)pyrrolidin-1-yl)acetamide

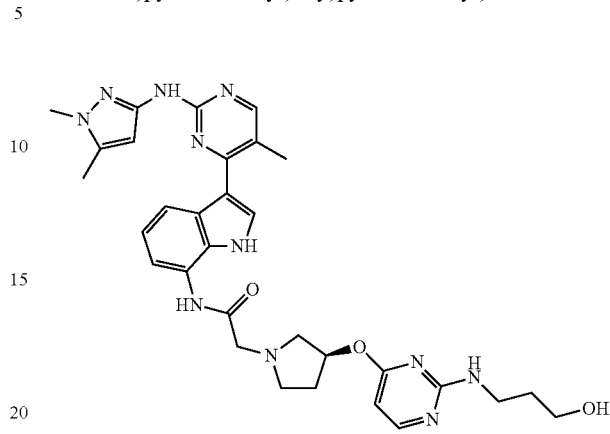

The title product was afforded by a procedure similar to that described for the synthesis of Example 192 using 3-aminopropan-1-ol instead of ammonium hydroxide.

MS (ESI, m/z): 612.3 [M+H]$^+$

Example 207: Synthesis of (S)-2-(3-((2-(cyclopropylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

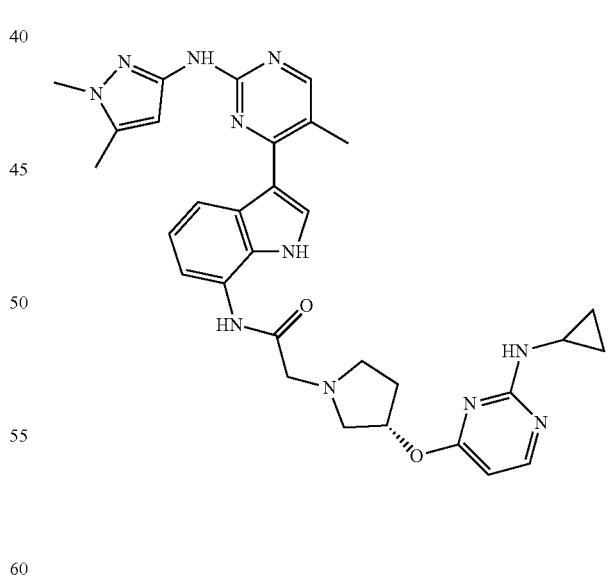

The title product was afforded by a procedure similar to that described for the synthesis of Example 192 using cyclopropylamine instead of ammonium hydroxide.

MS (ESI, m/z): 594.3 [M+H]$^+$

Example 208: Synthesis of (S)-2-(3-((2-(cyclobutylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

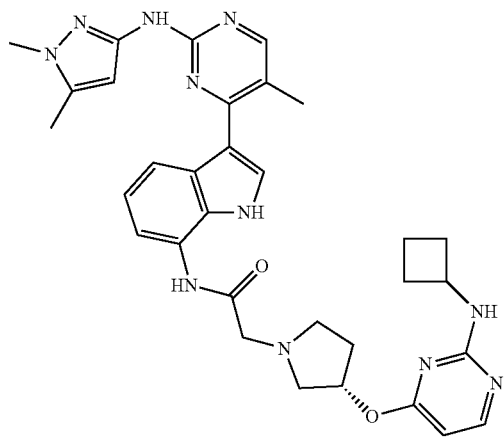 [SMILES: Cc1cnc(Nc2cc(C)n(C)n2)nc1-c1c[nH]c2c(NC(=O)CN3CC[C@H](Oc4ccnc(NC5CCC5)n4)C3)cccc12]

The title product was afforded by a procedure similar to that described for the synthesis of Example 192 using cyclobutylamine instead of ammonium hydroxide. MS (ESI, m/z): 608.3 [M+H]$^+$ Example 209: Synthesis of (S)-2-(3-((2-(cyclopentylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

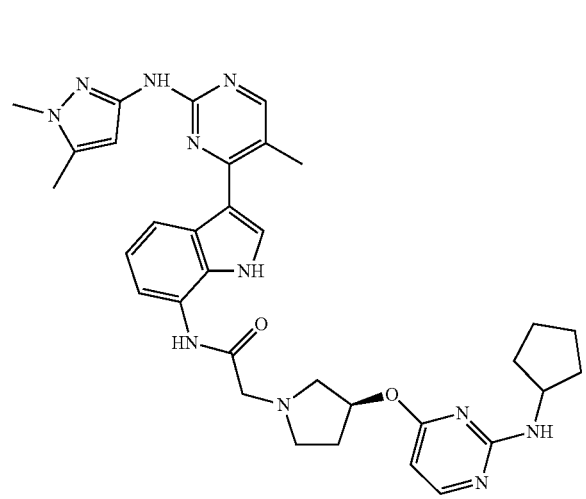 [SMILES: Cc1cnc(Nc2cc(C)n(C)n2)nc1-c1c[nH]c2c(NC(=O)CN3CC[C@H](Oc4ccnc(NC5CCCC5)n4)C3)cccc12]

The title product was afforded by a procedure similar to that described for the synthesis of Example 192 using cyclopentylamine instead of ammonium hydroxide.
MS (ESI, m/z): 622.3 [M+H]$^+$ Example 210: Synthesis of (S)-2-(3-((2-(cyclohexylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

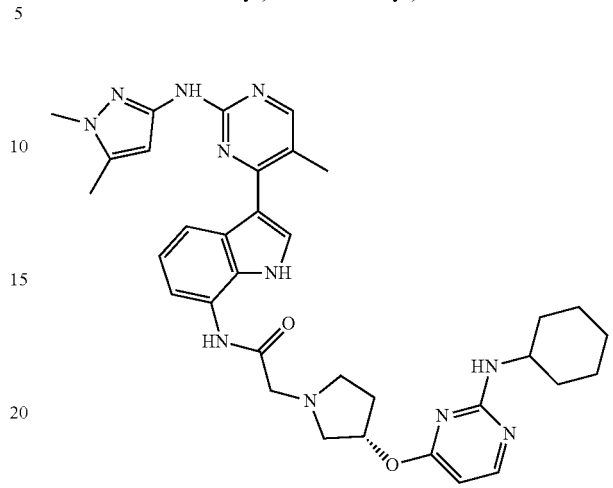

The title product was afforded by a procedure similar to that described for the synthesis of Example 192 using cyclohexylamine instead of ammonium hydroxide. MS (ESI, m/z): 606.3 [M+H]$^+$ Example 211: Synthesis of (S)—N-(3-(2-((1,5-dimethyl-1H-pyrazol-3-yl)amino)-5-methylpyrimidin-4-yl)-1H-indol-7-yl)-2-(3-((2-(isopropylamino)pyrimidin-4-yl)oxy)pyrrolidin-1-yl)acetamide

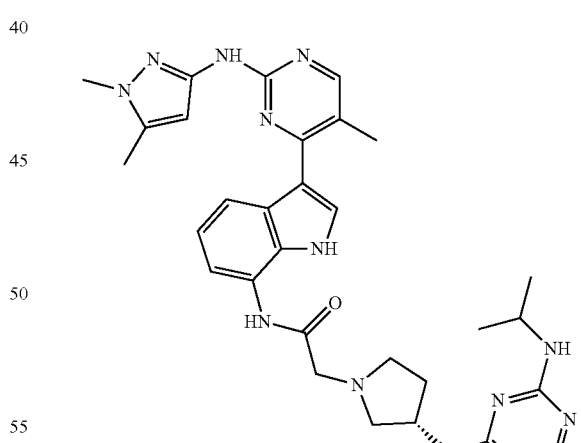

The title product was afforded by a procedure similar to that described for the synthesis of Example 192 using isopropylamine instead of ammonium hydroxide. MS (ESI, m/z): 596.3 [M+H]$^+$ Example 212: Synthesis of 2-((3S)-3-((2-(sec-butylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

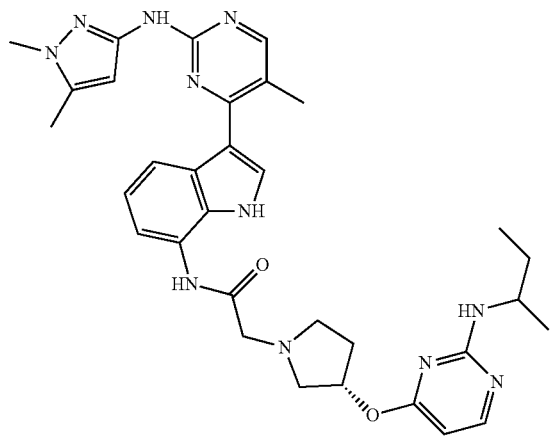 [SMILES: CCC(C)Nc1nccc(O[C@H]2CCN(CC(=O)Nc3cccc4c(-c5nc(Nc6cc(C)n(C)n6)ncc5C)c[nH]c34)C2)n1]

The title product was afforded by a procedure similar to that described for the synthesis of Example 192 using sec-butylamine instead of ammonium hydroxide. MS (ESI, m/z): 610.3 [M+H]$^+$ Example 213: Synthesis of (S)-2-(3-((2-((cyclopropylmethyl)amino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

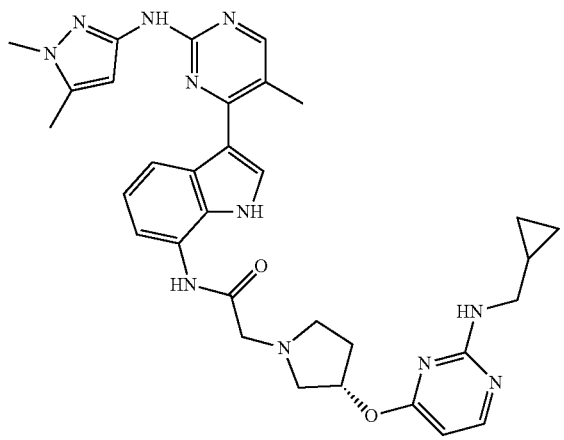 [SMILES: Cc1cnc(Nc2cc(C)n(C)n2)nc1-c1c[nH]c2c(NC(=O)CN3CC[C@H](Oc4ccnc(NCC5CC5)n4)C3)cccc12]

The title product was afforded by a procedure similar to that described for the synthesis of Example 192 using cyclopropylmethylamine instead of ammonium hydroxide. MS (ESI, m/z): 608.3 [M+H]$^+$ Example 214: Synthesis of (S)-2-(3-((2-(benzylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

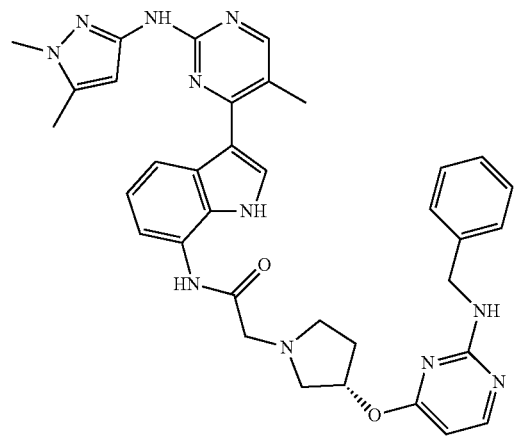 [SMILES: Cc1cnc(Nc2cc(C)n(C)n2)nc1-c1c[nH]c2c(NC(=O)CN3CC[C@H](Oc4ccnc(NCc5ccccc5)n4)C3)cccc12]

The title product was afforded by a procedure similar to that described for the synthesis of Example 192 using benzylamine instead of ammonium hydroxide. MS (ESI, m/z): 644.3 [M+H]$^+$ Example 215: Synthesis of (S)—N-(3-(2-((1,5-dimethyl-1H-pyrazol-3-yl)amino)-5-methylpyrimidin-4-yl)-1H-indol-7-yl)-2-(3-((2-((2-hydroxyethyl)amino)pyrimidin-4-yl)oxy)pyrrolidin-1-yl)acetamide

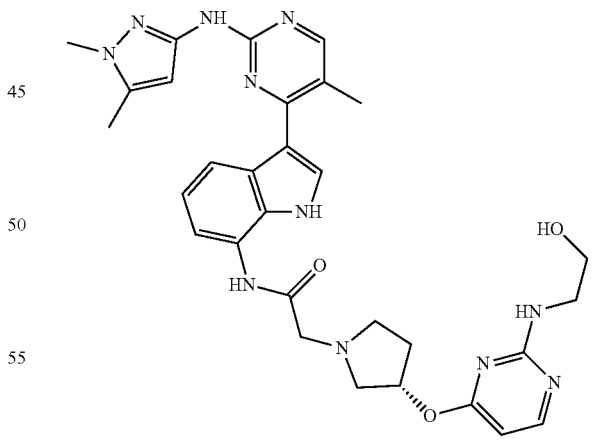

The title product was afforded by a procedure similar to that described for the synthesis of Example 192 using ethanolamine instead of ammonium hydroxide. MS (ESI, m/z): 598.3 [M+H]$^+$ Example 216: Synthesis of (S)—N-(3-(2-((1,5-dim-
ethyl-1H-pyrazol-3-yl)amino)-5-methylpyrimidin-4-
yl)-1H-indol-7-yl)-2-(3-((2-((2-methoxyethyl)amino)
pyrimidin-4-yl)oxy)pyrrolidin-1-yl)acetamide

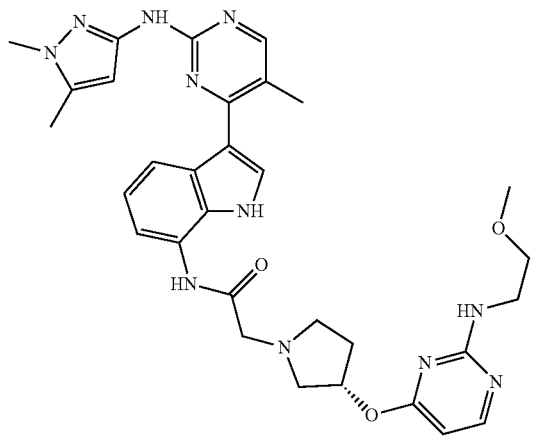 [SMILES: COCCNc1nccc(O[C@H]2CCN(CC(=O)Nc3cccc4c(-c5nc(Nc6cc(C)n(C)n6)ncc5C)c[nH]c34)C2)n1]

The title product was afforded by a procedure similar to that described for the synthesis of Example 192 using 2-methoxyethan-1-amine instead of ammonium hydroxide. MS (ESI, m/z): 612.3 [M+H]$^+$ Example 217: Synthesis of (S)—N-(3-(2-((1,5-dim-
ethyl-1H-pyrazol-3-yl)amino)-5-methylpyrimidin-4-
yl)-1H-indol-7-yl)-2-(3-((2-((2-(dimethylamino)
ethyl)amino)pyrimidin-4-yl)oxy)pyrrolidin-1-yl)
acetamide

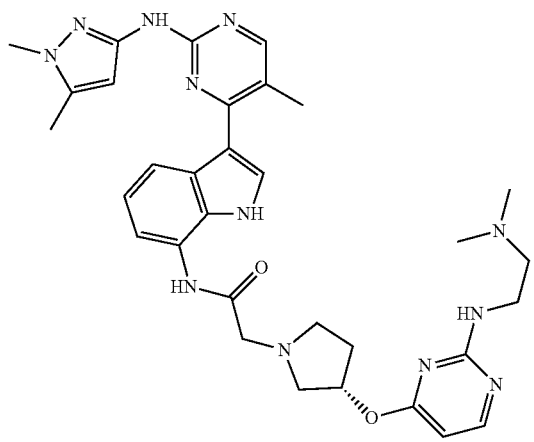 [SMILES: Cc1cnc(Nc2cc(C)n(C)n2)nc1-c1c[nH]c2c(NC(=O)CN3CC[C@H](Oc4ccnc(NCCN(C)C)n4)C3)cccc12]

The title product was afforded by a procedure similar to that described for the synthesis of Example 192 using N1,N1-dimethylethane-1,2-diamine instead of ammonium hydroxide. MS (ESI, m/z): 625.3 [M+H]$^+$ Example 218: Synthesis of (S)—N-(3-(2-((1,5-dim-
ethyl-1H-pyrazol-3-yl)amino)-5-methylpyrimidin-4-
yl)-1H-indol-7-yl)-2-(3-((2-((3-(dimethylamino)
propyl)amino)pyrimidin-4-yl)oxy)pyrrolidin-1-yl)
acetamide

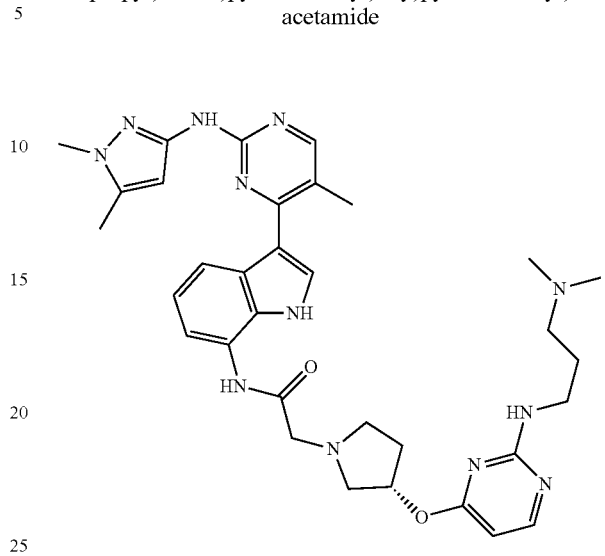

The title product was afforded by a procedure similar to that described for the synthesis of Example 192 using N1,N1-dimethylpropane-1,3-diamine instead of ammonium hydroxide. MS (ESI, m/z): 639.4 [M+H]$^+$ Example 219: Synthesis of (S)—N-(3-(2-((1,5-dim-
ethyl-1H-pyrazol-3-yl)amino)-5-methylpyrimidin-4-
yl)-1H-indol-7-yl)-2-(3-((2-(methoxyamino)pyrimi-
din-4-yl)oxy)pyrrolidin-1-yl)acetamide

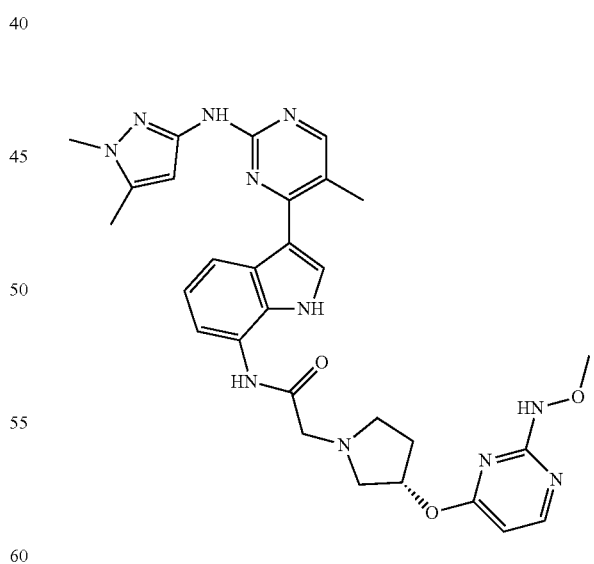

The title product was afforded by a procedure similar to that described for the synthesis of Example 192 using O-methylhydroxylamine instead of ammonium hydroxide. MS (ESI, m/z): 584.3 [M+H]$^+$ Example 220: Synthesis of (S)—N-(3-(2-((1,5-dimethyl-1H-pyrazol-3-yl)amino)-5-methylpyrimidin-4-yl)-1H-indol-7-yl)-2-(3-((2-(dimethylamino)pyrimidin-4-yl)oxy)pyrrolidin-1-yl)acetamide

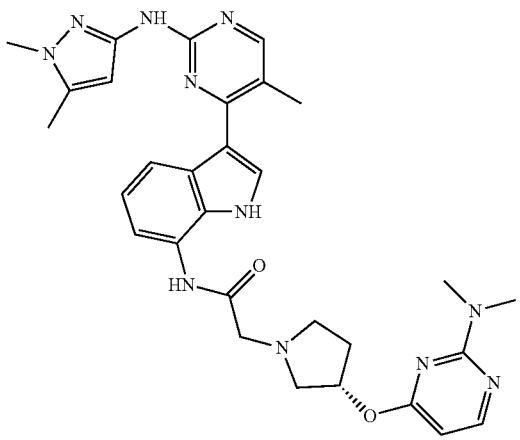

The title product was afforded by a procedure similar to that described for the synthesis of Example 192 using dimethylamine instead of ammonium hydroxide. MS (ESI, m/z): 582.3 [M+H]$^+$ Example 221: Synthesis of (S)-2-(3-((2-(benzyl(methyl)amino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

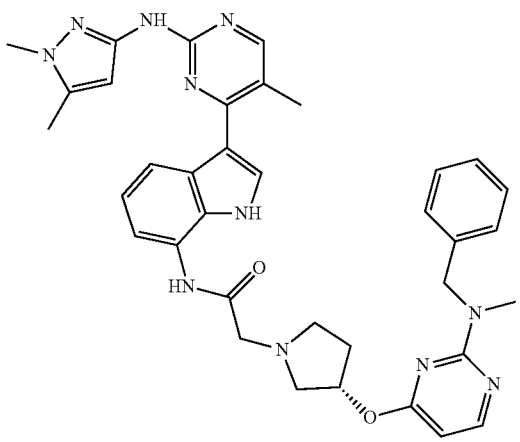

The title product was afforded by a procedure similar to that described for the synthesis of Example 192 using methylbenzylamine instead of ammonium hydroxide.
MS (ESI, m/z): 658.3 [M+H]$^+$ Example 222: Synthesis of (S)—N-(3-(2-((1,5-dimethyl-1H-pyrazol-3-yl)amino)-5-methylpyrimidin-4-yl)-1H-indol-7-yl)-2-(3-((2-(pyrrolidin-1-yl)pyrimidin-4-yl)oxy)pyrrolidin-1-yl)acetamide

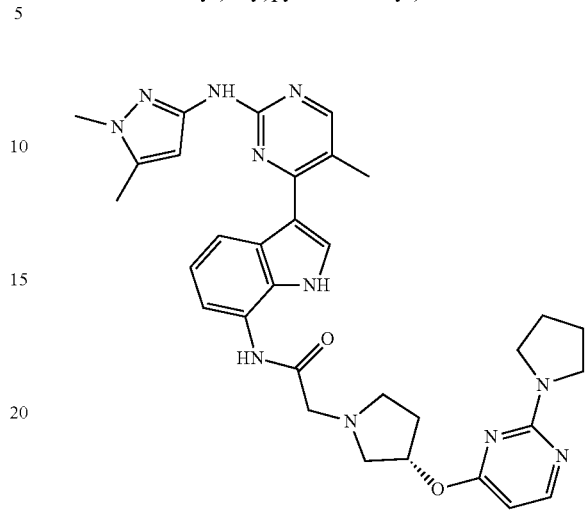

The title product was afforded by a procedure similar to that described for the synthesis of Example 192 using pyrrolidine instead of ammonium hydroxide. MS (ESI, m/z): 608.3 [M+H]$^+$ Example 223: Synthesis of (S)—N-(3-(2-((1,5-dimethyl-1H-pyrazol-3-yl)amino)-5-methylpyrimidin-4-yl)-1H-indol-7-yl)-2-(3-((2-(piperidin-1-yl)pyrimidin-4-yl)oxy)pyrrolidin-1-yl)acetamide

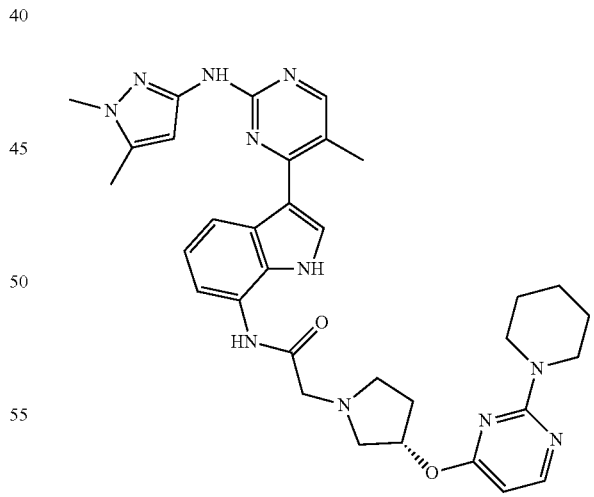

The title product was afforded by a procedure similar to that described for the synthesis of Example 192 using piperidine instead of ammonium hydroxide. MS (ESI, m/z): 622.3 [M+H]$^+$ Example 224: Synthesis of (S)—N-(3-(2-((1,5-dimethyl-1H-pyrazol-3-yl)amino)-5-methylpyrimidin-4-yl)-1H-indol-7-yl)-2-(3-((2-morpholinopyrimidin-4-yl)oxy)pyrrolidin-1-yl)acetamide

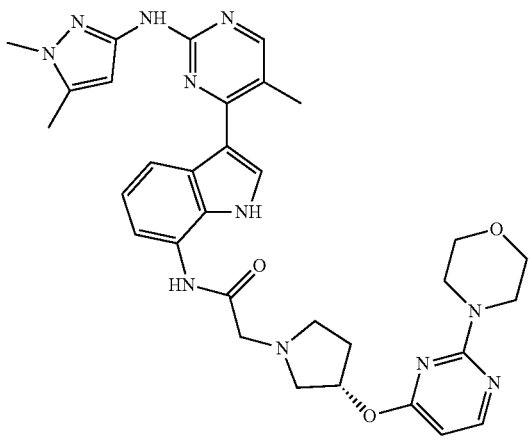 [SMILES: Cc1cnc(Nc2cc(C)n(C)n2)nc1-c1c[nH]c2c(NC(=O)CN3CC[C@H](Oc4ccnc(N5CCOCC5)n4)C3)cccc12]

The title product was afforded by a procedure similar to that described for the synthesis of Example 192 using morpholine instead of ammonium hydroxide. MS (ESI, m/z): 624.3 [M+H]$^+$ Example 225: Synthesis of (S)—N-(3-(2-((1,5-dimethyl-1H-pyrazol-3-yl)amino)-5-methylpyrimidin-4-yl)-1H-indol-7-yl)-2-(3-((2-(4-methylpiperazin-1-yl)pyrimidin-4-yl)oxy)pyrrolidin-1-yl)acetamide

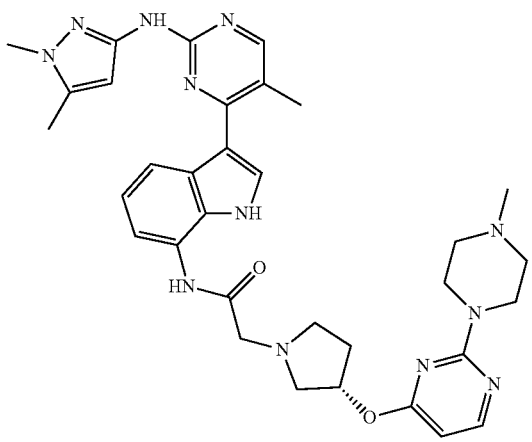 [SMILES: Cc1cnc(Nc2cc(C)n(C)n2)nc1-c1c[nH]c2c(NC(=O)CN3CC[C@H](Oc4ccnc(N5CCN(C)CC5)n4)C3)cccc12]

The title product was afforded by a procedure similar to that described for the synthesis of Example 192 using 1-methylpiperazine instead of ammonium hydroxide.
MS (ESI, m/z): 637.3 [M+H]$^+$ Example 226: Synthesis of (S)-2-(3-((2-amino-5-fluoropyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

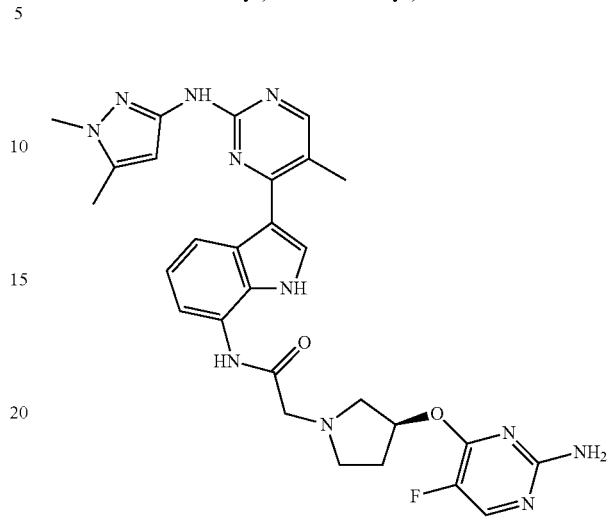

The title product was afforded by a procedure similar to that described for the synthesis of Example 140 using 2-chloro-5-fluoropyrimidin-4-ol instead of 6-chloropyrimidin-4-ol. MS (ESI, m/z): 572.3 [M+H]$^+$ Example 227: Synthesis of (S)-2-(3-((2-(cyclopropylamino)-5-fluoropyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

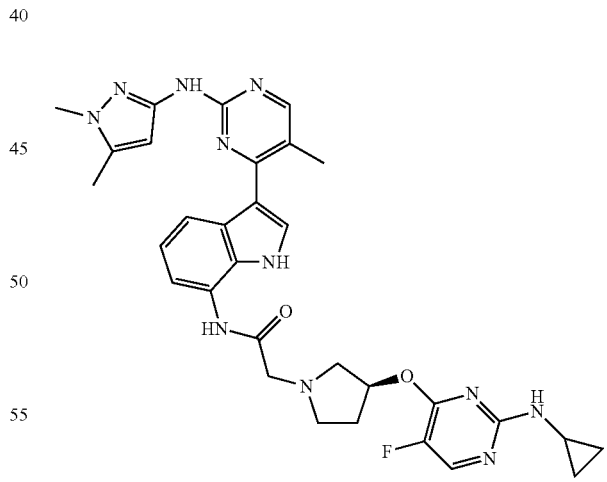

The title product was afforded by a procedure similar to that described for the synthesis of Example 226 using cyclopropylamine instead of ammonium hydroxide.
MS (ESI, m/z): 612.3 [M+H]$^+$ Example 228: Synthesis of (S)-2-(3-((2-(cyclohexylamino)-5-fluoropyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

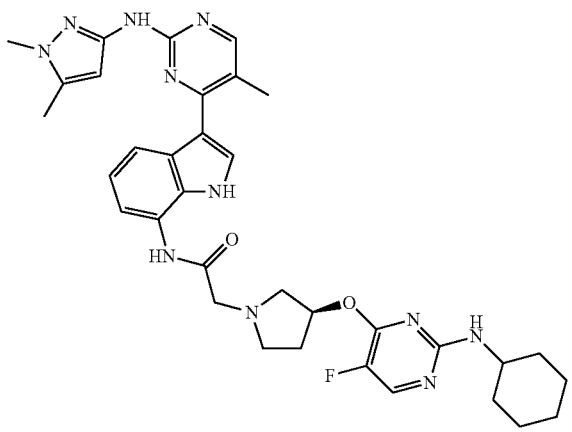 [SMILES: Cc1cnc(Nc2cc(C)n(C)n2)nc1-c1c[nH]c2c(NC(=O)CN3CC[C@H](Oc4nc(NC5CCCCC5)ncc4F)C3)cccc12]

The title product was afforded by a procedure similar to that described for the synthesis of Example 226 using cyclohexylamine instead of ammonium hydroxide. MS (ESI, m/z): 654.3 [M+H]+

Example 229: Synthesis of (S)-2-(3-((2-((cyclopropylmethyl)amino)-5-fluoropyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

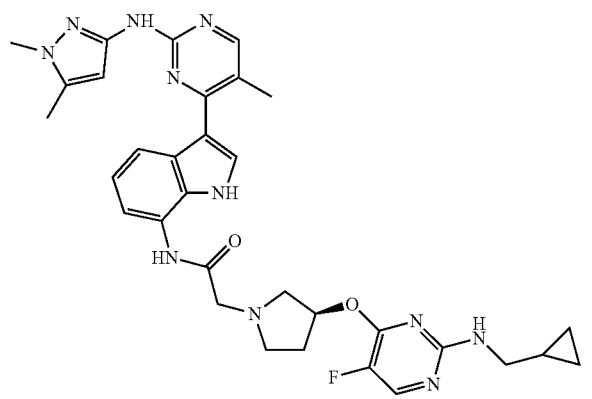 [SMILES: Cc1cnc(Nc2cc(C)n(C)n2)nc1-c1c[nH]c2c(NC(=O)CN3CC[C@H](Oc4nc(NCC5CC5)ncc4F)C3)cccc12]

The title product was afforded by a procedure similar to that described for the synthesis of Example 226 using cyclopropylmethylamine instead of ammonium hydroxide. MS (ESI, m/z): 626.3 [M+H]+

Example 230: Synthesis of (S)-2-(3-((2-(benzylamino)-5-fluoropyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

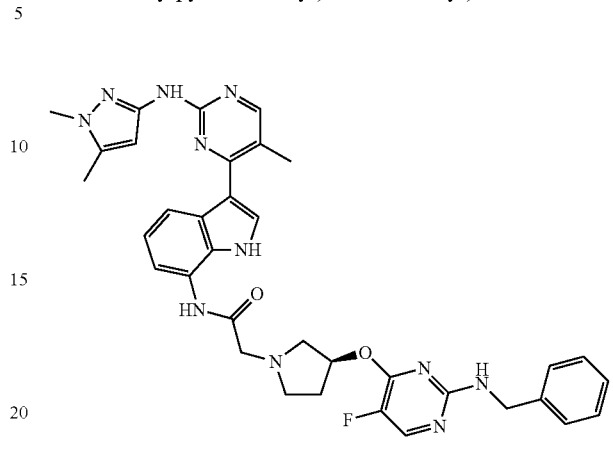

The title product was afforded by a procedure similar to that described for the synthesis of Example 226 using benzylamine instead of ammonium hydroxide. MS (ESI, m/z): 662.3 [M+H]+

Example 231: Synthesis of (S)—N-(3-(2-((1,5-dimethyl-1H-pyrazol-3-yl)amino)-5-methylpyrimidin-4-yl)-1H-indol-7-yl)-2-(3-((2-(dimethylamino)-5-fluoropyrimidin-4-yl)oxy)pyrrolidin-1-yl)acetamide

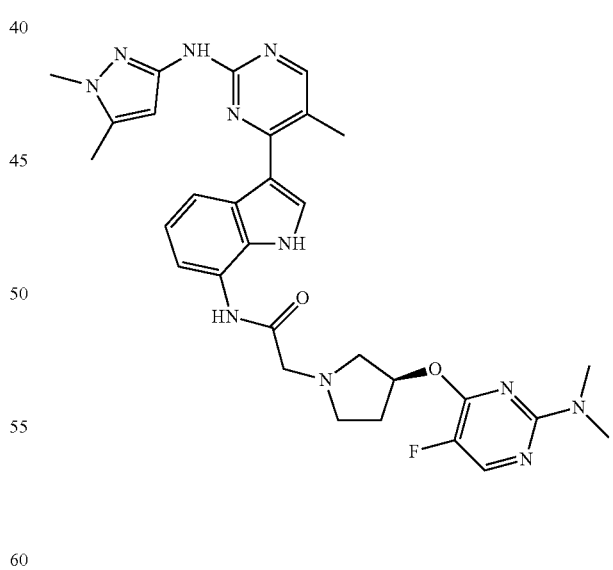

The title product was afforded by a procedure similar to that described for the synthesis of Example 226 using dimethylamine instead of ammonium hydroxide. MS (ESI, m/z): 600.3 [M+H]+

Example 232: Synthesis of (S)—N-(3-(2-((1,5-dimethyl-1H-pyrazol-3-yl)amino)-5-methylpyrimidin-4-yl)-1H-indol-7-yl)-2-(3-((5-fluoro-2-morpholinopyrimidin-4-yl)oxy)pyrrolidin-1-yl)acetamide

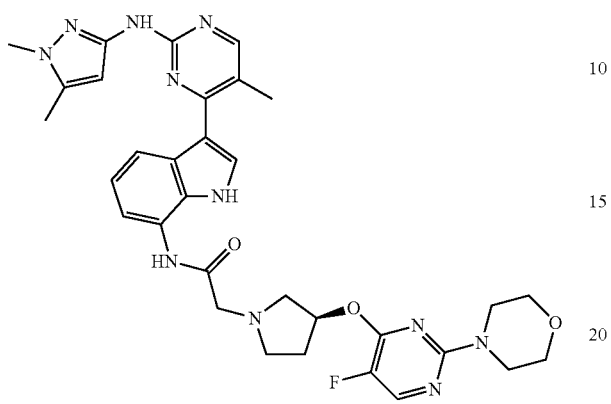

The title product was afforded by a procedure similar to that described for the synthesis of Example 226 using morpholine instead of ammonium hydroxide. MS (ESI, m/z): 642.3 [M+H]$^+$ Example 233: Synthesis of (S)—N-(3-(2-((1,5-dimethyl-1H-pyrazol-3-yl)amino)-5-methylpyrimidin-4-yl)-1H-indol-7-yl)-2-(3-((5-fluoro-2-(4-methylpiperazin-1-yl)pyrimidin-4-yl)oxy)pyrrolidin-1-yl)acetamide

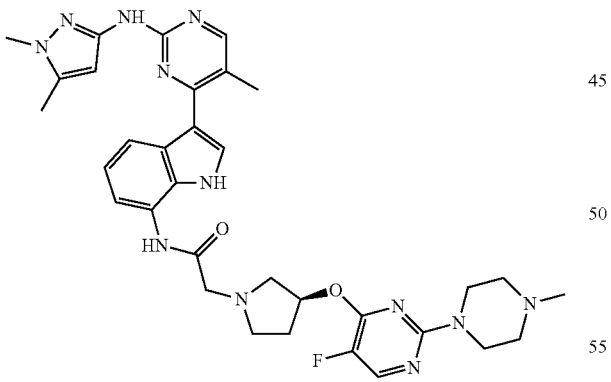

The title product was afforded by a procedure similar to that described for the synthesis of Example 226 using 1-methylpiperazine instead of ammonium hydroxide.
MS (ESI, m/z): 655.3 [M+H]$^+$ Example 234: Synthesis of (S)-2-(3-((2-(cyclopropylamino)-6-fluoropyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

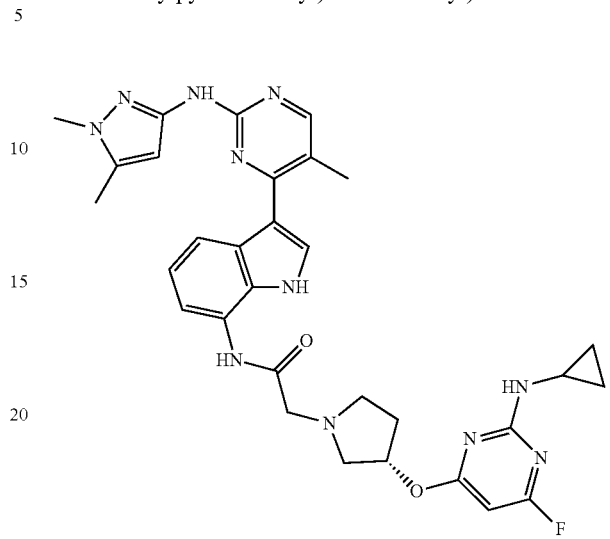

The title product was afforded by a procedure similar to that described for the synthesis of Example 227 using 2-chloro-6-fluoropyrimidin-4-ol instead of 2-chloro-5-fluoropyrimidin-4-ol. MS (ESI, m/z): 612.3 [M+H]$^+$ Example 235: Synthesis of (S)-2-(3-((2-(cyclopropylamino)-5-methylpyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

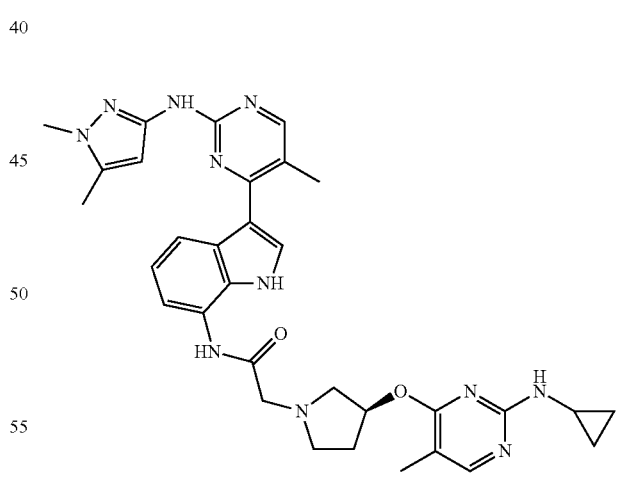

The title product was afforded by a procedure similar to that described for the synthesis of Example 227 using 2-chloro-5-methylpyrimidin-4-ol instead of 2-chloro-5-fluoropyrimidin-4-ol. MS (ESI, m/z): 608.3 [M+H]$^+$ Example 236: Synthesis of (S)-2-(3-((2-(cyclopropylamino)-6-methylpyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

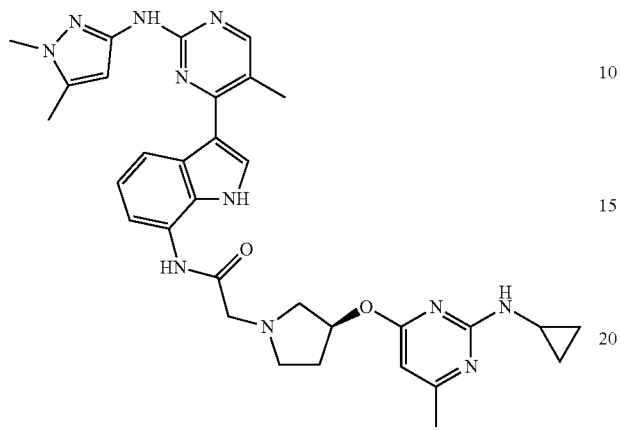

The title product was afforded by a procedure similar to that described for the synthesis of Example 227 using 2-chloro-6-methylpyrimidin-4-ol instead of 2-chloro-5-fluoropyrimidin-4-ol. MS (ESI, m/z): 608.3 [M+H]+

Example 237: Synthesis of (S)-2-(3-((2-(cyclopropylamino)-6-(trifluoromethyl)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

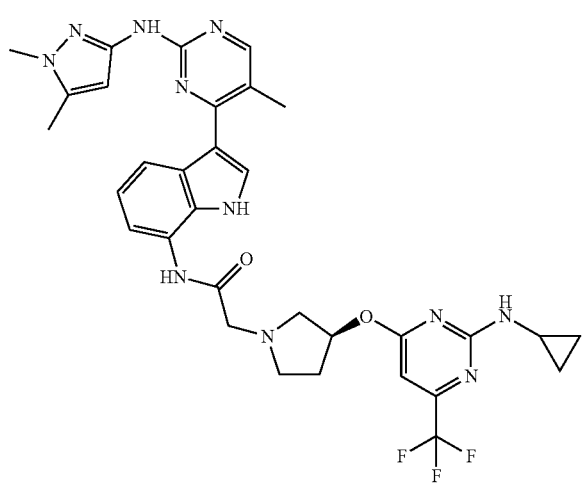 [SMILES: Cc1cnc(Nc2cc(C)n(C)n2)nc1-c1c[nH]c2c(NC(=O)CN3CC[C@H](Oc4cc(C(F)(F)F)nc(NC5CC5)n4)C3)cccc12]

The title product was afforded by a procedure similar to that described for the synthesis of Example 227 using 2-chloro-6-(trifluoromethyl)pyrimidin-4-ol instead of 2-chloro-5-fluoropyrimidin-4-ol. MS (ESI, m/z): 662.3 [M+H]+

Example 238: Synthesis of (S)-2-(3-((2-(cyclopropylamino)-6-methoxypyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

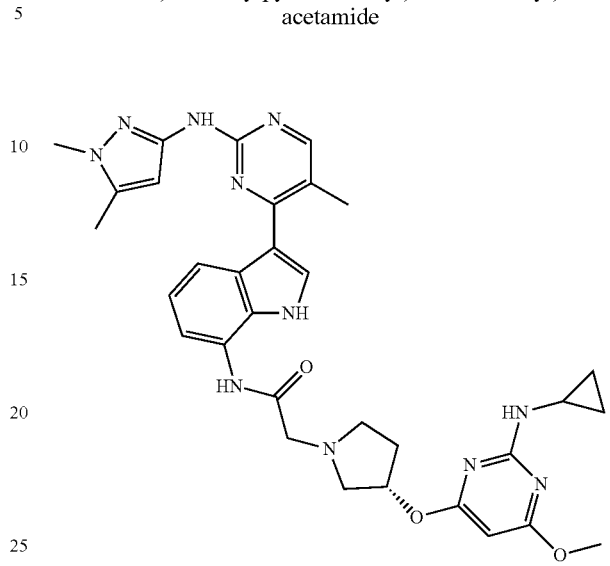

The title product was afforded by a procedure similar to that described for the synthesis of Example 227 using 2-chloro-6-methoxypyrimidin-4-ol instead of 2-chloro-5-fluoropyrimidin-4-ol. MS (ESI, m/z): 624.3 [M+H]+

Example 239: Synthesis of (S)—N-(3-(2-((1,5-dimethyl-1H-pyrazol-3-yl)amino)-5-methylpyrimidin-4-yl)-1H-indol-7-yl)-2-(3-((2-((2-(dimethylamino)ethyl)amino)pyrimidin-5-yl)oxy)pyrrolidin-1-yl)acetamide

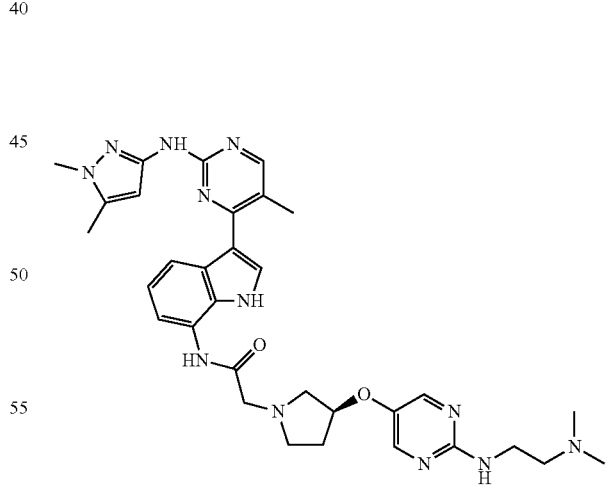

The title product was afforded by a procedure similar to that described for the synthesis of Example 217 using 2-chloropyrimidin-5-ol instead of 2-chloropyrimidin-4-ol. MS (ESI, m/z): 625.3 [M+H]+

Example 240: Synthesis of (S)—N-(3-(2-((1,5-dimethyl-1H-pyrazol-3-yl)amino)-5-methylpyrimidin-4-yl)-1H-indol-7-yl)-2-(3-((2-(dimethylamino)pyrimidin-5-yl)oxy)pyrrolidin-1-yl)acetamide

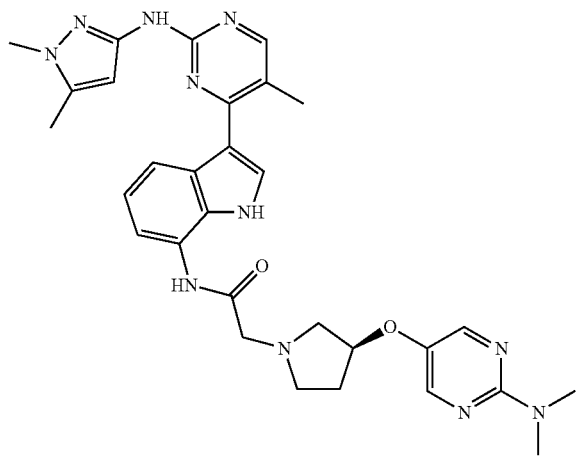

The title product was afforded by a procedure similar to that described for the synthesis of Example 239 using dimethylamine instead of N1,N1-dimethylethane-1,2-diamine. MS (ESI, m/z): 582.3 $[M+H]^+$ Example 241: Synthesis of (S)—N-(3-(2-((1,5-dimethyl-1H-pyrazol-3-yl)amino)-5-methylpyrimidin-4-yl)-1H-indol-7-yl)-2-(3-((2-morpholinopyrimidin-5-yl)oxy)pyrrolidin-1-yl)acetamide

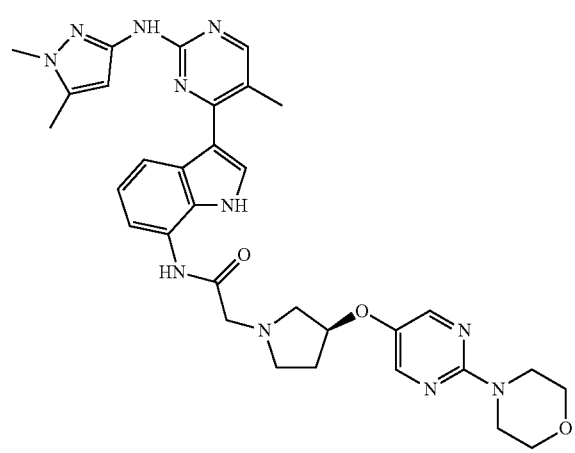 [SMILES: Cc1cnc(Nc2cc(C)n(C)n2)nc1-c1c[nH]c2c(NC(=O)CN3CC[C@H](Oc4cnc(N5CCOCC5)nc4)C3)cccc12]

The title product was afforded by a procedure similar to that described for the synthesis of Example 239 using morpholine instead of N1,N1-dimethylethane-1,2-diamine. MS (ESI, m/z): 624.3 $[M+H]^+$ Example 242: Synthesis of (S)—N-(3-(2-((1,5-dimethyl-1H-pyrazol-3-yl)amino)-5-methylpyrimidin-4-yl)-1H-indol-7-yl)-2-(3-((2-(4-methylpiperazin-1-yl)pyrimidin-5-yl)oxy)pyrrolidin-1-yl)acetamide

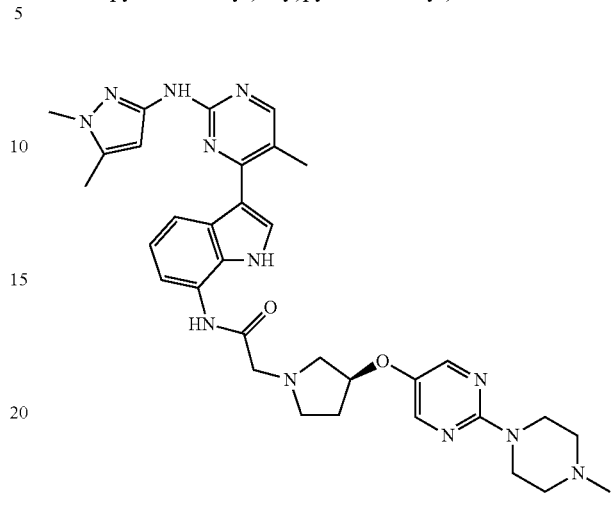

The title product was afforded by a procedure similar to that described for the synthesis of Example 239 using 1-methylpiperazine instead of N1,N1-dimethylethane-1,2-diamine. MS (ESI, m/z): 637.3 $[M+H]^+$ Example 243: Synthesis of (S)-2-(3-((6-(cyclopropylamino)pyrazin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

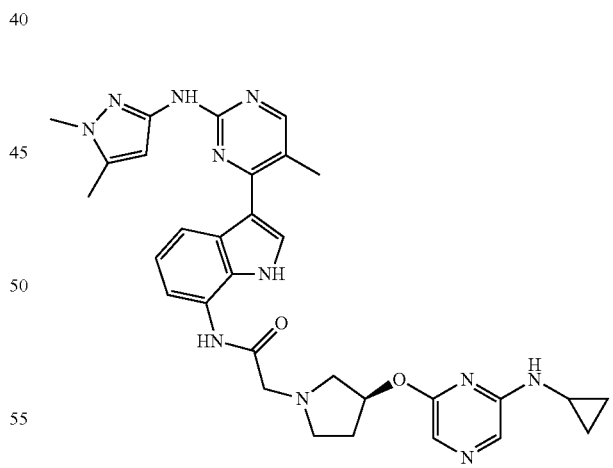

The title product was afforded by a procedure similar to that described for the synthesis of Example 227 using 6-chloropyrazin-2-ol instead of 2-chloro-5-fluoropyrimidin-4-ol. MS (ESI, m/z): 594.3 $[M+H]^+$ Example 244: Synthesis of (S)—N-(3-(2-((1,5-dimethyl-1H-pyrazol-3-yl)amino)-5-methylpyrimidin-4-yl)-1H-indol-7-yl)-2-(3-((6-(ethylamino)pyrazin-2-yl)oxy)pyrrolidin-1-yl)acetamide

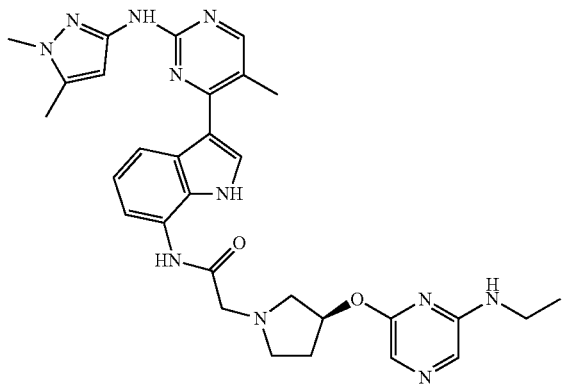 [SMILES: CCNc1cncc(O[C@H]2CCN(CC(=O)Nc3cccc4c(-c5nc(Nc6cc(C)n(C)n6)ncc5C)c[nH]c34)C2)n1]

The title product was afforded by a procedure similar to that described for the synthesis of Example 243 using ethylamine instead of cyclopropylamine. MS (ESI, m/z): 582.3 [M+H]⁺

Example 245: Synthesis of (S)—N-(3-(2-((1,5-dimethyl-1H-pyrazol-3-yl)amino)-5-methylpyrimidin-4-yl)-1H-indol-7-yl)-2-(3-((6-(propylamino)pyrazin-2-yl)oxy)pyrrolidin-1-yl)acetamide The title product was afforded by a procedure similar to that described for the synthesis of Example 243 using n-propylamine instead of cyclopropylamine. MS (ESI, m/z): 596.3 [M+H]⁺

Example 246: Synthesis of (S)—N-(3-(2-((1,5-dimethyl-1H-pyrazol-3-yl)amino)-5-methylpyrimidin-4-yl)-1H-indol-7-yl)-2-(3-((6-((2-hydroxyethyl)amino)pyrazin-2-yl)oxy)pyrrolidin-1-yl)acetamide

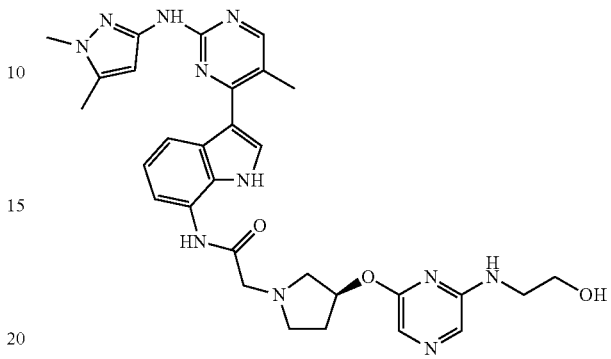

The title product was afforded by a procedure similar to that described for the synthesis of Example 243 using ethanolamine instead of cyclopropylamine. MS (ESI, m/z): 598.3 [M+H]⁺

Example 247: Synthesis of (S)—N-(3-(2-((1,5-dimethyl-1H-pyrazol-3-yl)amino)-5-methylpyrimidin-4-yl)-1H-indol-7-yl)-2-(3-((6-((2-(dimethylamino)ethyl)amino)pyrazin-2-yl)oxy)pyrrolidin-1-yl)acetamide

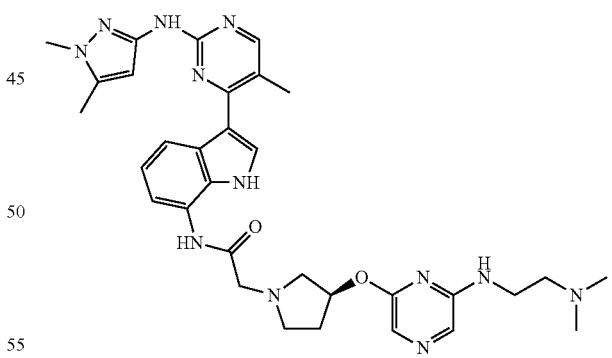

The title product was afforded by a procedure similar to that described for the synthesis of Example 243 using N1,N1-dimethylethane-1,2-diamine instead of cyclopropylamine. MS (ESI, m/z): 625.3 [M+H]⁺

Example 248: Synthesis of (S)—N-(3-(2-((1,5-dimethyl-1H-pyrazol-3-yl)amino)-5-methylpyrimidin-4-yl)-1H-indol-7-yl)-2-(3-((6-phenylpyrimidin-4-yl)oxy)pyrrolidin-1-yl)acetamide

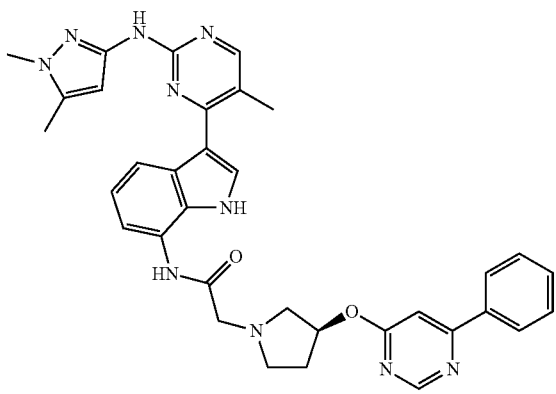 [SMILES: Cc1cnc(Nc2cc(C)n(C)n2)nc1-c1c[nH]c2c(NC(=O)CN3CC[C@H](Oc4cc(-c5ccccc5)ncn4)C3)cccc12]

(S)-2-(3-((6-chloropyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide was intermediate in the synthesis of Example 140.

A solution of (S)-2-(3-((6-chloropyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide (286 mg, 0.5 mmol) Pd(PPh$_3$)$_4$ (58 mg, 0.05 mmol), phenylboronic acid (97 mg, 0.8 mmol), and K$_2$CO$_3$ (207 mg, 1.5 mmol) in 1,4-dioxane (0.9 mL) and water (0.3 mL) was heated to 80° C. for 4 h. Then, the mixture was separated from the UCT SPE CUBCX cartridge and purified by the Prep HPLC to afford a corresponding product (180 mg, 58%). MS (ESI, m/z): 615.3 [M+H]$^+$ Example 249: Synthesis of (S)—N-(3-(2-((1,5-dimethyl-1H-pyrazol-3-yl)amino)-5-methylpyrimidin-4-yl)-1H-indol-7-yl)-2-(3-((6-(1-methyl-1H-pyrazol-4-yl)pyrimidin-4-yl)oxy)pyrrolidin-1-yl)acetamide

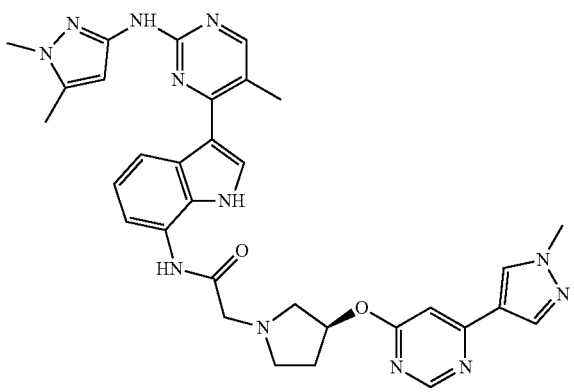

The title product was afforded by a procedure similar to that described for the synthesis of Example 248 using (1-methyl-1H-pyrazol-4-yl)boronic acid instead of phenylboronic acid. MS (ESI, m/z): 619.3 [M+H]$^+$ Example 250: Synthesis of (S)—N-(3-(2-((1,5-dimethyl-1H-pyrazol-3-yl)amino)-5-methylpyrimidin-4-yl)-1H-indol-7-yl)-2-(3-((6-(4,4-dimethylcyclohex-1-en-1-yl)pyrimidin-4-yl)oxy)pyrrolidin-1-yl)acetamide

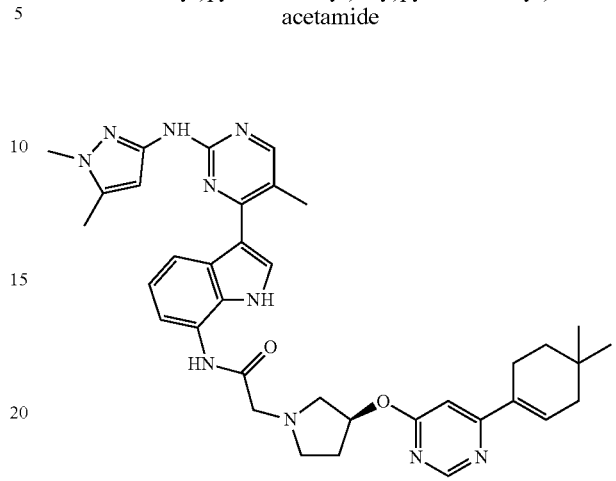

The title product was afforded by a procedure similar to that described for the synthesis of Example 248 using (4,4-dimethylcyclohex-1-en-1-yl)boronic acid instead of phenylboronic acid. MS (ESI, m/z): 647.3 [M+H]$^+$ Example 251: Synthesis of (S)-2-(3-((6-(3,6-dihydro-2H-pyran-4-yl)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

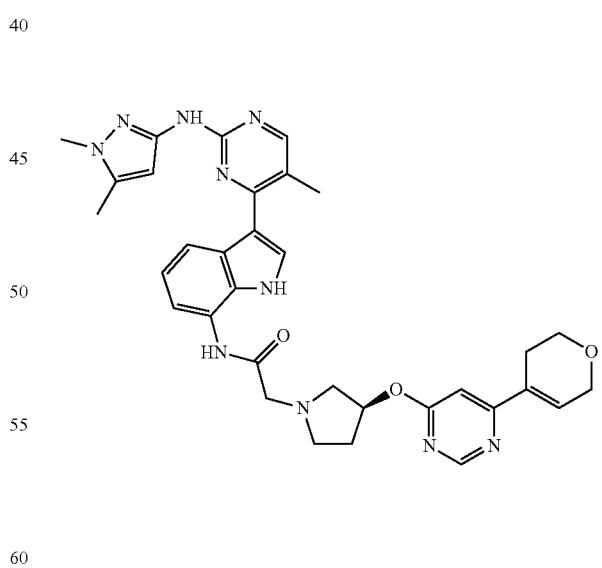

The title product was afforded by a procedure similar to that described for the synthesis of Example 248 using (3,6-dihydro-2H-pyran-4-yl)boronic acid instead of phenylboronic acid. MS (ESI, m/z): 621.3 [M+H]$^+$ Example 252: Synthesis of (S)—N-(3-(2-((1,5-dimethyl-1H-pyrazol-3-yl)amino)-5-methylpyrimidin-4-yl)-1H-indol-7-yl)-2-(3-((4-(4,4-dimethylcyclohex-1-en-1-yl)pyrimidin-2-yl)oxy)pyrrolidin-1-yl)acetamide

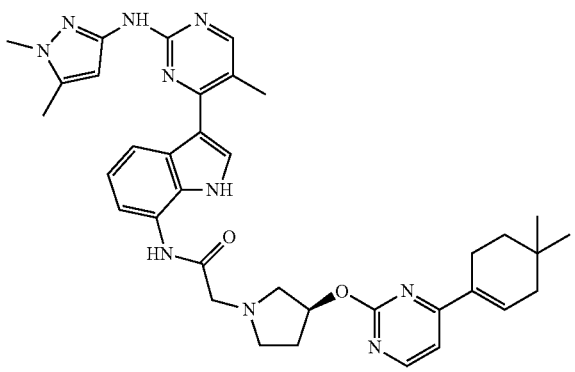

The title product was afforded by a procedure similar to that described for the synthesis of Example 250 using 4-chloropyrimidin-2-ol instead of 6-chloropyrimidin-4-ol. MS (ESI, m/z): 647.4 [M+H]$^+$ Example 253: Synthesis of (S)-2-(3-((4-(3,6-dihydro-2H-pyran-4-yl)pyrimidin-2-yl)oxy)pyrrolidin-1-yl)-N-(3-(2-(((1,5-dimethyl-1H-pyrazol-3-yl)amino)-5-methylpyrimidin-4-yl)-1H-indol-7-yl)acetamide

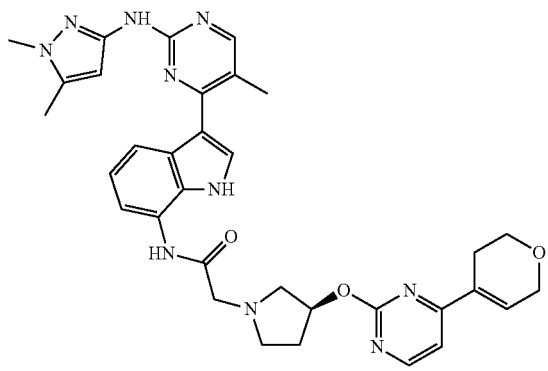 [SMILES: Cc1cnc(Nc2cc(C)n(C)n2)nc1-c1c[nH]c2c(NC(=O)CN3CC[C@H](Oc4nccc(C5=CCOCC5)n4)C3)cccc12]

The title product was afforded by a procedure similar to that described for the synthesis of Example 251 using 4-chloropyrimidin-2-ol instead of 6-chloropyrimidin-4-ol. MS (ESI, m/z): 621.3 [M+H]$^+$ Example 254: Synthesis of (S)—N-(3-(2-((1,5-dimethyl-1H-pyrazol-3-yl)amino)-5-methylpyrimidin-4-yl)-1H-indol-7-yl)-2-(3-((4-phenylpyrimidin-2-yl)oxy)pyrrolidin-1-yl)acetamide

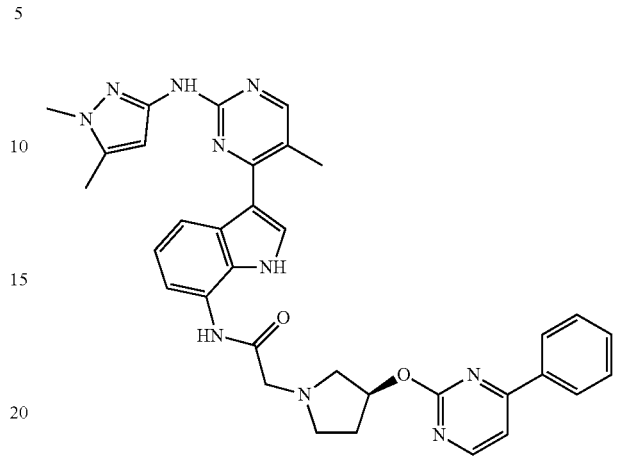

The title product was afforded by a procedure similar to that described for the synthesis of Example 248 using 4-chloropyrimidin-2-ol instead of 6-chloropyrimidin-4-ol. MS (ESI, m/z): 614.3 [M+H]$^+$ Example 255: Synthesis of (S)—N-(3-(2-((1,5-dimethyl-1H-pyrazol-3-yl)amino)-5-methylpyrimidin-4-yl)-1H-indol-7-yl)-2-(3-((5-(pyridin-3-yl)pyrimidin-2-yl)oxy)pyrrolidin-1-yl)acetamide

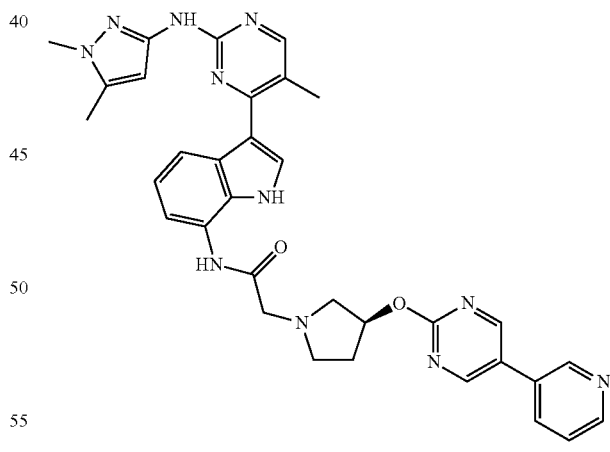

The title product was afforded by a procedure similar to that described for the synthesis of Example 248 using 5-chloropyrimidin-2-ol and pyridin-3-ylboronic acid instead of 6-chloropyrimidin-4-ol and phenylboronic acid. MS (ESI, m/z): 616.3 [M+H]$^+$ Example 256: Synthesis of (S)—N-(3-(2-((1,5-dimethyl-1H-pyrazol-3-yl)amino)-5-methylpyrimidin-4-yl)-1H-indol-7-yl)-2-(3-((5-(pyridin-4-yl)pyrimidin-2-yl)oxy)pyrrolidin-1-yl)acetamide

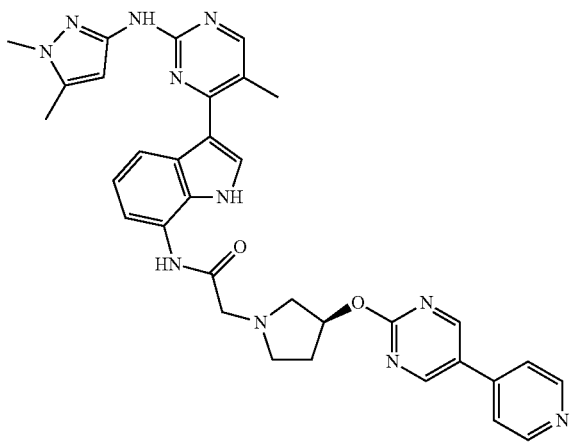 [SMILES: Cc1cnc(Nc2cc(C)n(C)n2)nc1-c1c[nH]c2c(NC(=O)CN3CC[C@H](Oc4ncc(-c5ccncc5)cn4)C3)cccc12]

The title product was afforded by a procedure similar to that described for the synthesis of Example 255 using pyridin-4-ylboronic acid instead of pyridin-3-ylboronic acid. MS (ESI, m/z): 616.3 [M+H]$^+$ Example 257: Synthesis of (S)—N-(3-(2-((1,5-dimethyl-1H-pyrazol-3-yl)amino)-5-methylpyrimidin-4-yl)-1H-indol-7-yl)-2-(3-((2-phenylpyrimidin-5-yl)oxy)pyrrolidin-1-yl)acetamide

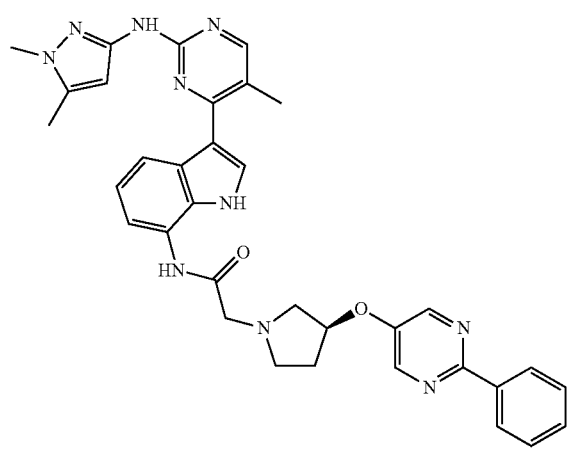 [SMILES: Cc1cnc(Nc2cc(C)n(C)n2)nc1-c1c[nH]c2c(NC(=O)CN3CC[C@H](Oc4cnc(-c5ccccc5)nc4)C3)cccc12]

The title product was afforded by a procedure similar to that described for the synthesis of Example 248 using 2-chloropyrimidin-5-ol instead of 6-chloropyrimidin-4-ol. MS (ESI, m/z): 615.3 [M+H]$^+$ Example 258: Synthesis of (S)—N-(3-(2-((1,5-dimethyl-1H-pyrazol-3-yl)amino)-5-methylpyrimidin-4-yl)-1H-indol-7-yl)-2-(3-((2-(pyridin-3-yl)pyrimidin-5-yl)oxy)pyrrolidin-1-yl)acetamide

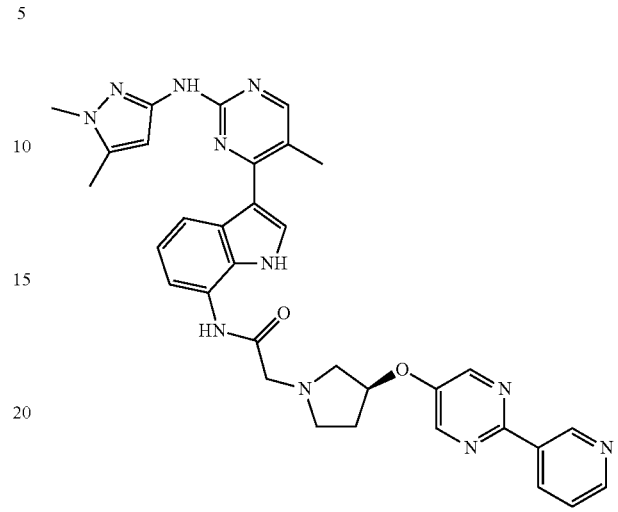

The title product was afforded by a procedure similar to that described for the synthesis of Example 257 using pyridin-3-ylboronic acid instead of phenylboronic acid. MS (ESI, m/z): 616.3 [M+H]$^+$ Example 259: Synthesis of (S)—N-(3-(2-((1,5-dimethyl-1H-pyrazol-3-yl)amino)-5-methylpyrimidin-4-yl)-1H-indol-7-yl)-2-(3-((2-(pyridin-4-yl)pyrimidin-5-yl)oxy)pyrrolidin-1-yl)acetamide

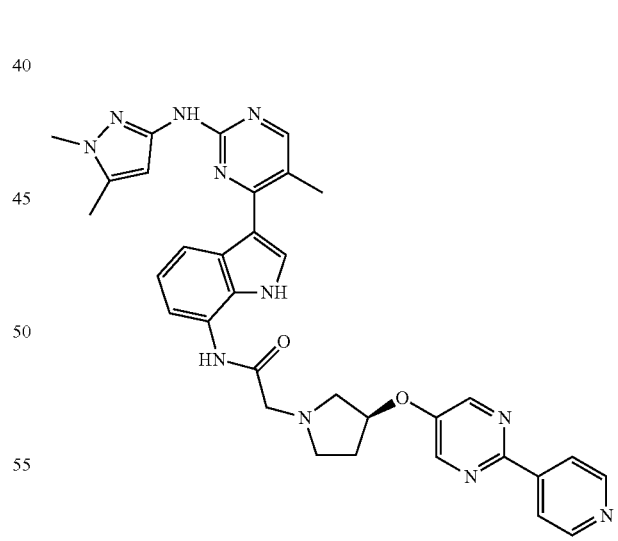

The title product was afforded by a procedure similar to that described for the synthesis of Example 257 using pyridin-4-ylboronic acid instead of phenylboronic acid. MS (ESI, m/z): 616.3 [M+H]$^+$

Example 260: Synthesis of 2-(3-(2-((1,5-dimethyl-1H-pyrazol-3-yl)amino)-5-methylpyrimidin-4-yl)-1H-indol-7-yl)isoindoline-1,3-dione

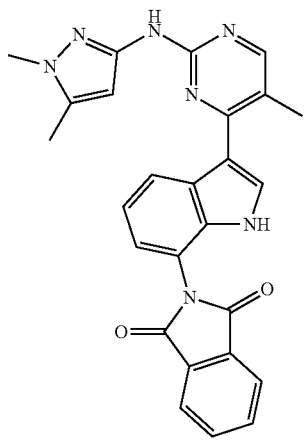

[General Method D]

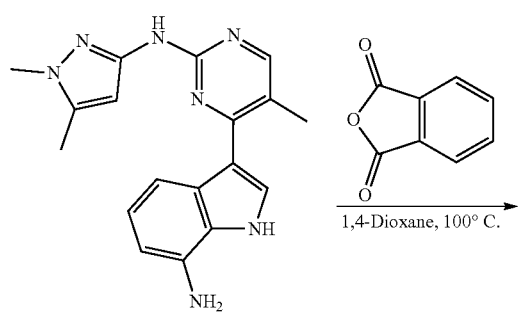

Intermediate 001

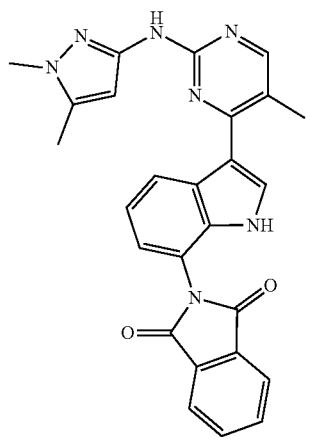

Example 260

A mixture of 3-[2-[(1,5-dimethylpyrazol-3-yl)amino]-5-methyl-pyrimidin-4-yl]-1H-indol-7-amine (1.00 eq, 15 mg, 0.0450 mmol) and isobenzofuran-1,3-dione (2.00 eq, 13 mg, 0.0900 mmol) in 1,4-Dioxane (0.5000 mL) was stirred at 100° C. for overnight. After cooling to room temperature, the reaction mixture was separated with the Prep HPLC, and dried in vacuo to give the desired product as a white solid (yield, 50%).

$^1$H NMR (600 MHz, cd$_3$od) δ 8.94 (s, 1H), 8.35 (s, 1H), 8.16 (s, 1H), 8.09-8.00 (m, 2H), 7.99-7.86 (m, 2H), 7.42 (t, J=7.8 Hz, 1H), 7.33 (d, J=7.4 Hz, 1H), 5.97 (s, 1H), 3.82 (s, 3H), 2.53 (s, 3H), 2.34 (s, 3H). MS (ESI, m/z): 464.1 [M+H]$^+$

Example 261: Synthesis of 2-(3-(2-((1,5-dimethyl-1H-pyrazol-3-yl)amino)-5-methylpyrimidin-4-yl)-1H-indol-7-yl)-4-fluoroisoindoline-1,3-dione

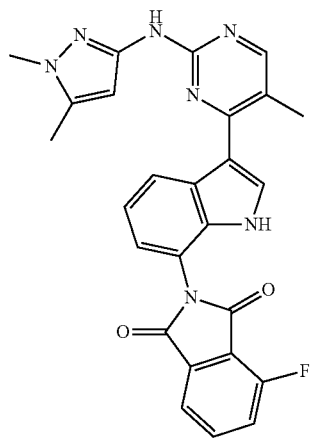 [SMILES: Cc1cnc(Nc2cc(C)n(C)n2)nc1-c1c[nH]c2c(N3C(=O)c4cccc(F)c4C3=O)cccc12]

Using 4-fluoroisobenzofuran-1,3-dione, the title product was afforded as described for Example 260 in General Method D. MS (ESI, m/z): 482.1 [M+H]$^+$

Example 262: Synthesis of 4-bromo-2-(3-(2-((1,5-dimethyl-1H-pyrazol-3-yl)amino)-5-methylpyrimidin-4-yl)-1H-indol-7-yl)isoindoline-1,3-dione

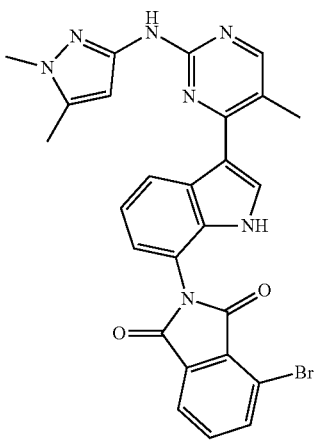 [SMILES: Cc1cnc(Nc2cc(C)n(C)n2)nc1-c1c[nH]c2c(N3C(=O)c4cccc(Br)c4C3=O)cccc12]

Using 4-bromoisobenzofuran-1,3-dione, the title product was afforded as described for Example 260 in General Method D. MS (ESI, m/z): 542.1 [M+H]$^+$ Example 263: Synthesis of 2-(3-(2-((1,5-dimethyl-1H-pyrazol-3-yl)amino)-5-methylpyrimidin-4-yl)-1H-indol-7-yl)-4-hydroxyisoindoline-1,3-dione

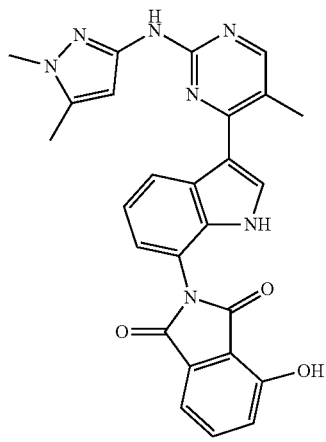 [SMILES: Cc1cnc(Nc2cc(C)n(C)n2)nc1-c1c[nH]c2c(N3C(=O)c4cccc(O)c4C3=O)cccc12]

Using 4-hydroxyisobenzofuran-1,3-dione, the title product was afforded as described for Example 260 in General Method D. MS (ESI, m/z): 480.1 [M+H]$^+$ Example 264: Synthesis of 2-(3-(2-((1,5-dimethyl-1H-pyrazol-3-yl)amino)-5-methylpyrimidin-4-yl)-1H-indol-7-yl)-5-nitroisoindoline-1,3-dione

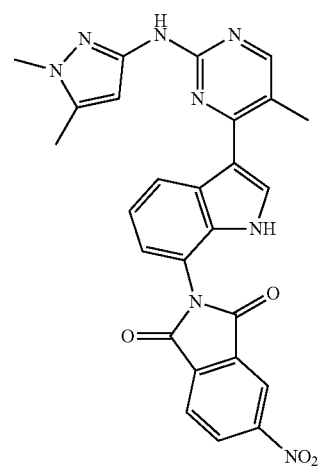

Using 5-nitroisobenzofuran-1,3-dione, the title product was afforded as described for Example 260 in General Method D. MS (ESI, m/z): 509.1 [M+H]$^+$ Example 265: Synthesis of 6-(3-(2-((1,5-dimethyl-1H-pyrazol-3-yl)amino)-5-methylpyrimidin-4-yl)-1H-indol-7-yl)-5H-pyrrolo[3,4-b]pyridine-5,7(6H)-dione

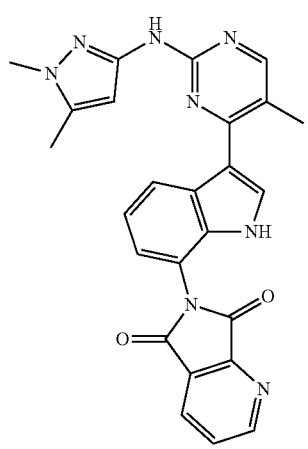

Using furo[3,4-b]pyridine-5,7-dione, the title product was afforded as described for Example 260 in General Method D. MS (ESI, m/z): 465.1 [M+H]$^+$ Example 266: Synthesis of 4-bromo-2-(3-(2-((1,5-dimethyl-1H-pyrazol-3-yl)amino)-5-methylpyrimidin-4-yl)-1H-indol-7-yl)isoindolin-1-one

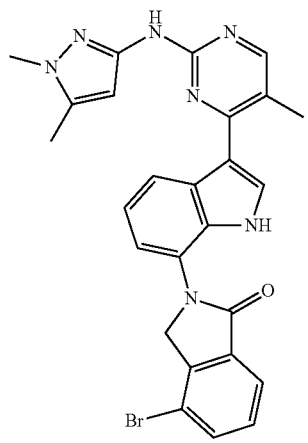

[General Method E]

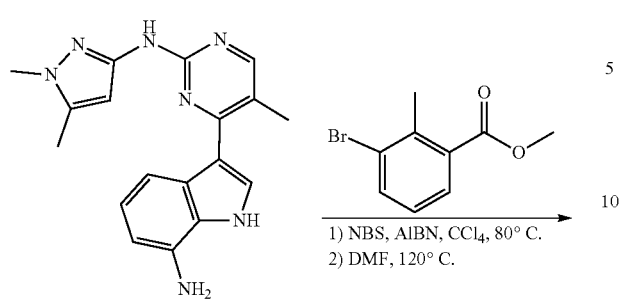

Intermediate 001

1) NBS, AIBN, CCl₄, 80° C.
2) DMF, 120° C.

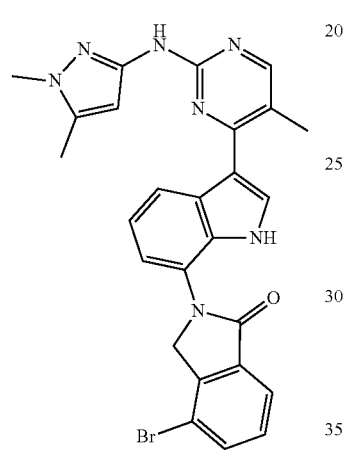

Example 266

A suspension of methyl 3-bromo-2-methylbenzoate (1.15 g, 5.000 mmol) in CCl₄ (17 mL) was treated NBS (1.07 g, 6.000 mmol) and ABIN (410.5 mg, 2.500 mmol) under N₂. The resulting mixture was heated at 80° C. for overnight. The reaction mixture was cooled to room temperature, and was then extracted into DCM (2×20 mL) from water (20 mL). The combined organic extracts were dried over Na₂SO₄, filtered and concentrated in vacuo. The crude was then purified by flash column chromatography eluting %30 EtOAc in n-Hex. The desired fractions were concentrated to dryness in vacuo to give the brominated intermediate, methyl 3-bromo-2-(bromomethyl)benzoate, as a colorless liquid. To a suspension of methyl 3-bromo-2-(bromomethyl) benzoate (44.7 mg, 0.10 mmol) in DMF (1 mL) was treated 3-(2-((1,5-dimethyl-1H-pyrazol-3-yl)amino)-5-methylpyrimidin-4-yl)-1H-indol-7-amine (33.3 mg, 0.10 mmol). The resulting mixture was heated at 120° C. for overnight.

The reaction mixture was cooled to room temperature, purified from the Prep HPLC, and dried in vacuo to give the desired product as a white solid (2 steps yield, 45%). 1H NMR (600 MHz, cd₃od) δ 8.86 (brs, 1H), 8.34 (s, 1H), 8.17 (brs, 1H), 7.93 (d, J=7.8 Hz, 2H), 7.89 (d, J=7.8 Hz, 1H), 7.57 (t, J=7.8 Hz, 1H), 7.39-7.44 (m, 2H), 5.96 (s, 1H), 4.99 (s, 2H), 3.80 (s, 3H), 2.53 (s, 3H), 2.33 (s, 3H). MS (ESI, m/z): 528.1 [M+H]⁺

Example 267: Synthesis of 2-(3-(2-((1,5-dimethyl-1H-pyrazol-3-yl)amino)-5-methylpyrimidin-4-yl)-1H-indol-7-yl)isoindolin-1-one

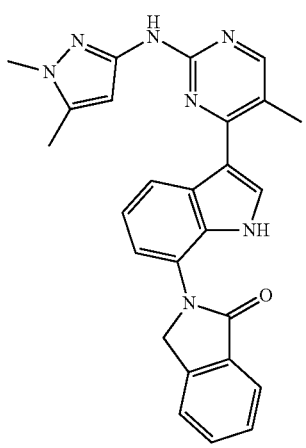

Using methyl 2-methylbenzoate, the title product was afforded as described for Example 266 in General Method E. MS (ESI, m/z): 450.2 [M+H]⁺

Example 268: Synthesis of 2-(3-(2-((1,5-dimethyl-1H-pyrazol-3-yl)amino)-5-methylpyrimidin-4-yl)-1H-indol-7-yl)-6-nitroisoindolin-1-one

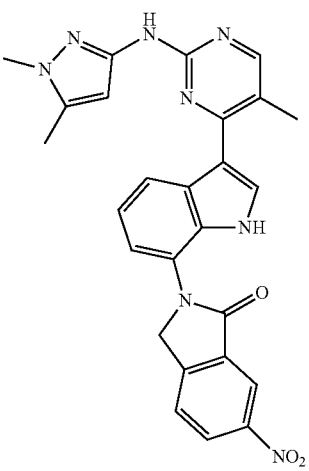

Using methyl 2-methyl-5-nitrobenzoate, the title product was afforded as described for Example 266 in General Method E. MS (ESI, m/z): 495.1 [M+H]⁺

Example 269: Synthesis of 6-amino-2-(3-(2-((1,5-dimethyl-1H-pyrazol-3-yl)amino)-5-methylpyrimidin-4-yl)-1H-indol-7-yl)isoindolin-1-one

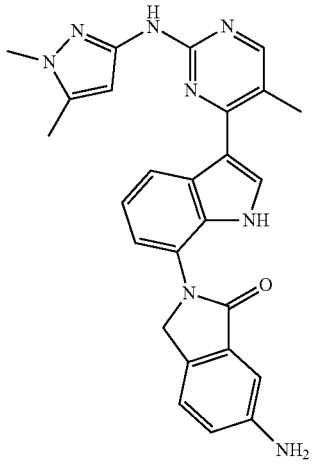

Using methyl 5-amino-2-methylbenzoate, the title product was afforded as described for Example 266 in General Method E. MS (ESI, m/z): 465.2 [M+H]$^+$ Example 270: Synthesis of 5-bromo-2-(3-(2-((1,5-dimethyl-1H-pyrazol-3-yl)amino)-5-methylpyrimidin-4-yl)-1H-indol-7-yl)isoindolin-1-one

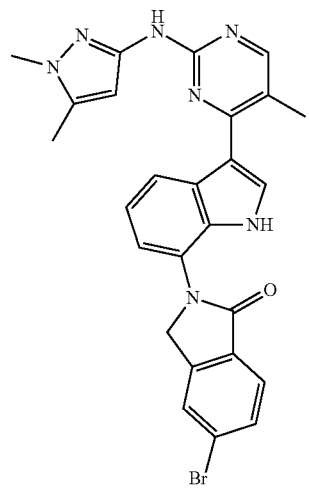

Using methyl 4-bromo-2-methylbenzoate, the title product was afforded as described for Example 266 in General Method E. MS (ESI, m/z): 528.1 [M+H]$^+$ Example 271: Synthesis of 2-(3-(2-((1,5-dimethyl-1H-pyrazol-3-yl)amino)-5-methylpyrimidin-4-yl)-1H-indol-7-yl)-4-nitroisoindolin-1-one

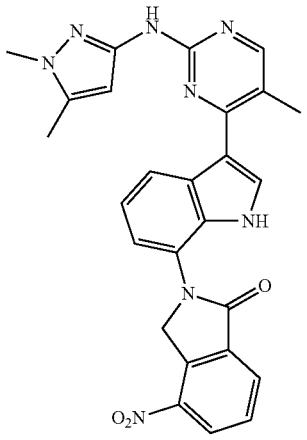

Using methyl 2-methyl-3-nitrobenzoate, the title product was afforded as described for Example 266 in General Method E. MS (ESI, m/z): 495.2 [M+H]$^+$ Example 272: Synthesis of 4-amino-2-(3-(2-((1,5-dimethyl-1H-pyrazol-3-yl)amino)-5-methylpyrimidin-4-yl)-1H-indol-7-yl)isoindolin-1-one

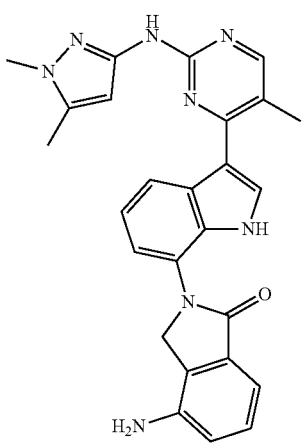

Using methyl 3-amino-2-methylbenzoate, the title product was afforded as described for Example 266 in General Method E. MS (ESI, m/z): 465.2 [M+H]$^+$ Example 273: Synthesis of 7-chloro-2-(3-(2-((1,5-dimethyl-1H-pyrazol-3-yl)amino)-5-methylpyrimidin-4-yl)-1H-indol-7-yl)isoindolin-1-one

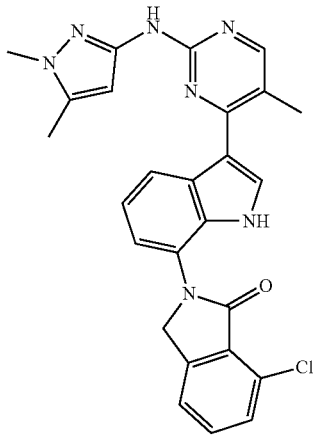 [SMILES: Cc1cnc(Nc2cc(C)n(C)n2)nc1-c1c[nH]c2c(N3Cc4cccc(Cl)c4C3=O)cccc12]

Using methyl 2-chloro-6-methylbenzoate, the title product was afforded as described for Example 266 in General Method E. MS (ESI, m/z): 484.1 [M+H]$^+$ Example 274: Synthesis of 2-(3-(2-((1,5-dimethyl-1H-pyrazol-3-yl)amino)-5-methylpyrimidin-4-yl)-1H-indol-7-yl)-7-nitroisoindolin-1-one

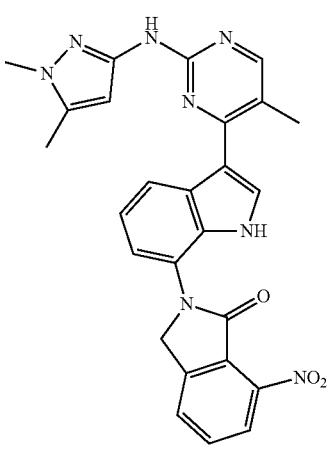 [SMILES: Cc1cnc(Nc2cc(C)n(C)n2)nc1-c1c[nH]c2c(N3Cc4cccc([N+](=O)[O-])c4C3=O)cccc12]

Using methyl 2-methyl-6-nitrobenzoate, the title product was afforded as described for Example 266 in General Method E. MS (ESI, m/z): 495.1 [M+H]$^+$ Example 275: Synthesis of 2-(3-(2-((1,5-dimethyl-1H-pyrazol-3-yl)amino)-5-methylpyrimidin-4-yl)-1H-indol-7-yl)-7-iodoisoindolin-1-one

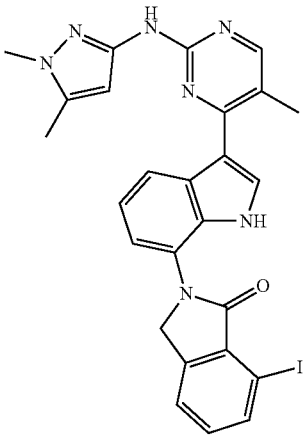 [SMILES: Cc1cnc(Nc2cc(C)n(C)n2)nc1-c1c[nH]c2c(N3Cc4cccc(I)c4C3=O)cccc12]

Using methyl 2-iodo-6-methylbenzoate, the title product was afforded as described for Example 266 in General Method E. MS (ESI, m/z): 576.1 [M+H]$^+$ Example 276: Synthesis of 7-amino-2-(3-(2-((1,5-dimethyl-1H-pyrazol-3-yl)amino)-5-methylpyrimidin-4-yl)-1H-indol-7-yl)isoindolin-1-one

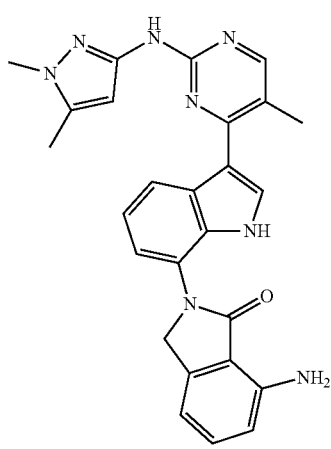

Using methyl 2-amino-6-methylbenzoate, the title product was afforded as described for Example 266 in General Method E. MS (ESI, m/z): 465.2 [M+H]$^+$ Example 277: Synthesis of 7-bromo-2-(3-(2-((1,5-dimethyl-1H-pyrazol-3-yl)amino)-5-methylpyrimidin-4-yl)-1H-indol-7-yl)isoindolin-1-one

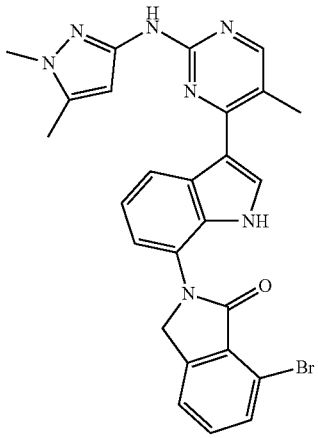 [SMILES: Cc1cnc(Nc2cc(C)n(C)n2)nc1-c1c[nH]c2c(N3Cc4cccc(Br)c4C3=O)cccc12]

Using methyl 2-bromo-6-methylbenzoate, the title product was afforded as described for Example 266 in General Method E. MS (ESI, m/z): 528.1 [M+H]$^+$ Example 278: Synthesis of 2-(3-(2-((1,5-dimethyl-1H-pyrazol-3-yl)amino)-5-methylpyrimidin-4-yl)-1H-indol-7-yl)-4-iodoisoindolin-1-one

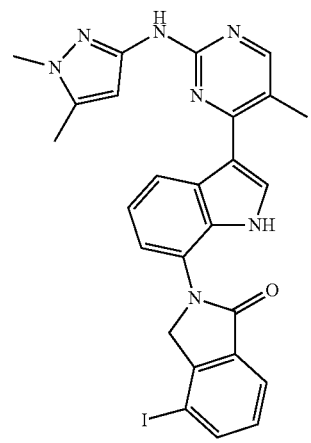

Using methyl 3-iodo-2-methylbenzoate, the title product was afforded as described for Example 266 in General Method E. MS (ESI, m/z): 576.1 [M+H]$^+$ Example 279: Synthesis of 2-(3-(2-((1,5-dimethyl-1H-pyrazol-3-yl)amino)-5-methylpyrimidin-4-yl)-1H-indol-7-yl)-6-methoxyisoindolin-1-one

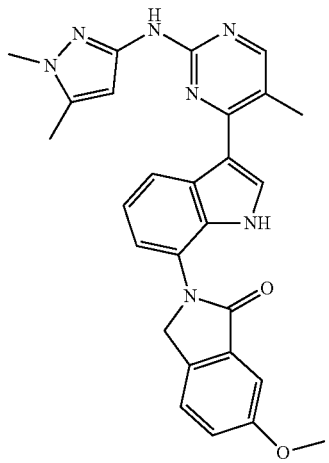

Using methyl 5-methoxy-2-methylbenzoate, the title product was afforded as described for Example 266 in General Method E. MS (ESI, m/z): 480.2 [M+H]$^+$ Example 280: Synthesis of 2-(3-(2-((1,5-dimethyl-1H-pyrazol-3-yl)amino)-5-methylpyrimidin-4-yl)-1H-indol-7-yl)-4,6-dimethoxyisoindolin-1-one

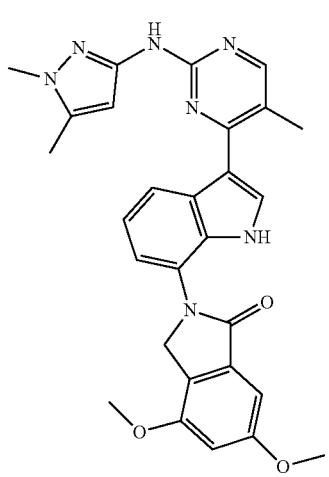

Using methyl 3,5-dimethoxy-2-methylbenzoate, the title product was afforded as described for Example 266 in General Method E. MS (ESI, m/z): 510.2 [M+H]$^+$ Example 281: Synthesis of 2-(3-(2-((1,5-dimethyl-1H-pyrazol-3-yl)amino)-5-methylpyrimidin-4-yl)-1H-indol-7-yl)-4-hydroxyisoindolin-1-one

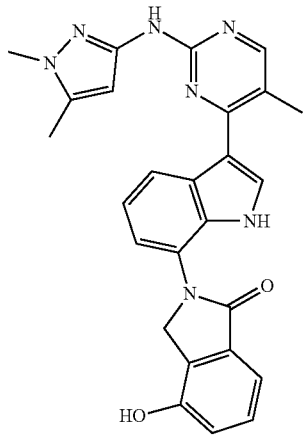

Using methyl 3-hydroxy-2-methylbenzoate, the title product was afforded as described for Example 266 in General Method E. MS (ESI, m/z): 466.2 [M+H]+

Example 282: Synthesis of 2-(3-(2-((1,5-dimethyl-1H-pyrazol-3-yl)amino)-5-methylpyrimidin-4-yl)-1H-indol-7-yl)-7-fluoroisoindolin-1-one

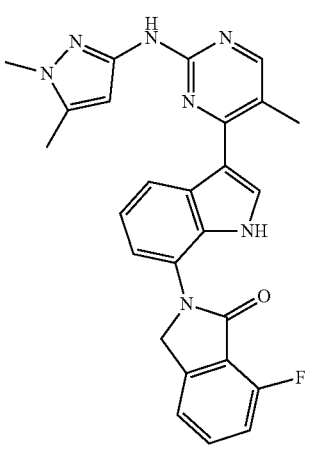 [SMILES: Cc1cnc(Nc2cc(C)n(C)n2)nc1-c1c[nH]c2c(N3Cc4cccc(F)c4C3=O)cccc12]

Using methyl 2-fluoro-6-methylbenzoate, the title product was afforded as described for Example 266 in General Method E. MS (ESI, m/z): 468.2 [M+H]+

Example 283: Synthesis of 4-bromo-2-(3-(2-((1,5-dimethyl-1H-pyrazol-3-yl)amino)-5-methylpyrimidin-4-yl)-1H-indol-7-yl)-7-fluoroisoindolin-1-one

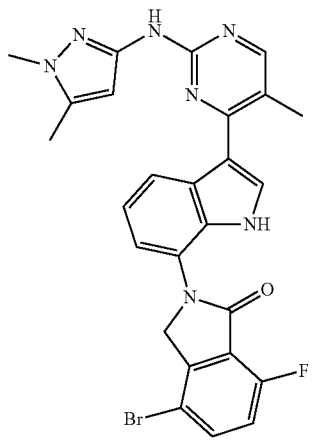 [SMILES: Cc1cnc(Nc2cc(C)n(C)n2)nc1-c1c[nH]c2c(N3Cc4c(Br)ccc(F)c4C3=O)cccc12]

Using methyl 3-bromo-6-fluoro-2-methylbenzoate, the title product was afforded as described for Example 266 in General Method E. MS (ESI, m/z): 546.1 [M+H]+

Example 284: Synthesis of 6-bromo-2-(3-(2-((1,5-dimethyl-1H-pyrazol-3-yl)amino)-5-methylpyrimidin-4-yl)-1H-indol-7-yl)isoindolin-1-one

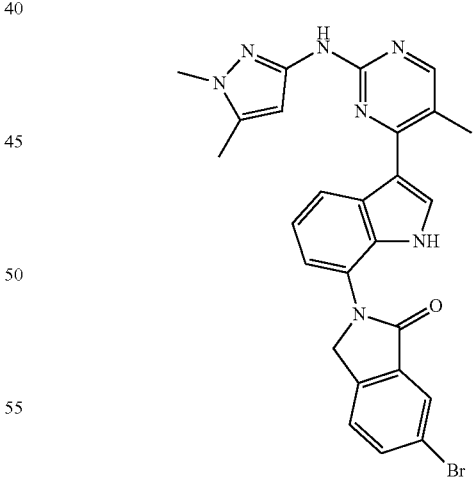

Using methyl 5-bromo-2-methylbenzoate, the title product was afforded as described for Example 266 in General Method E. MS (ESI, m/z): 528.1 [M+H]+

Example 285: Synthesis of 3-bromo-6-(3-(2-((1,5-dimethyl-1H-pyrazol-3-yl)amino)-5-methylpyrimidin-4-yl)-1H-indol-7-yl)-5,6-dihydro-7H-pyrrolo[3,4-b]pyridin-7-one

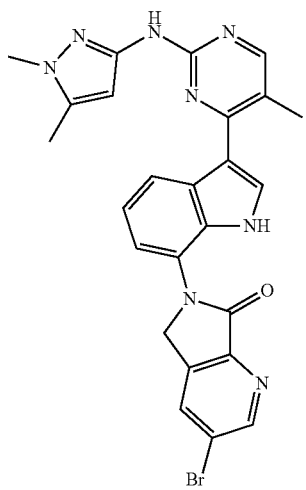

Using methyl 5-bromo-3-methylpicolinate, the title product was afforded as described for Example 266 in General Method E. MS (ESI, m/z): 529.1 [M+H]+

Example 286: Synthesis of 4-bromo-6-(3-(2-((1,5-dimethyl-1H-pyrazol-3-yl)amino)-5-methylpyrimidin-4-yl)-1H-indol-7-yl)-5,6-dihydro-7H-pyrrolo[3,4-b]pyridin-7-one

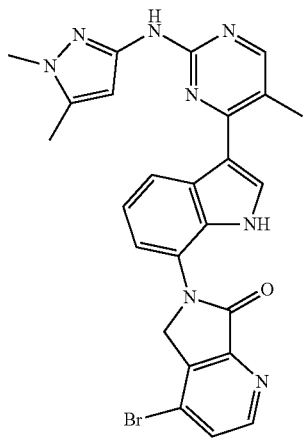

Using methyl 4-bromo-3-methylpicolinate, the title product was afforded as described for Example 266 in General Method E. MS (ESI, m/z): 529.1 [M+H]+

Example 287: Synthesis of 6-(3-(2-((1,5-dimethyl-1H-pyrazol-3-yl)amino)-5-methylpyrimidin-4-yl)-1H-indol-7-yl)-3-methyl-5,6-dihydro-7H-pyrrolo[3,4-b]pyridin-7-one

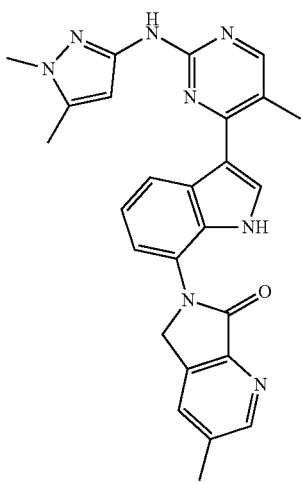

Using methyl 3,5-dimethylpicolinate, the title product was afforded as described for Example 266 in General Method E. MS (ESI, m/z): 465.2 [M+H]+

Example 288: Synthesis of 6-(3-(2-((1,5-dimethyl-1H-pyrazol-3-yl)amino)-5-methylpyrimidin-4-yl)-1H-indol-7-yl)-5,6-dihydro-7H-pyrrolo[3,4-b]pyridin-7-one

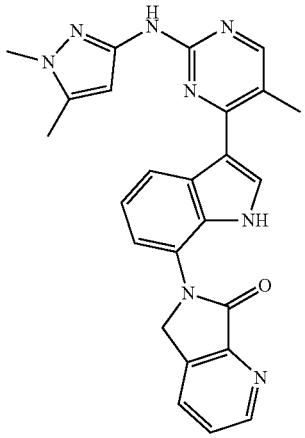

Using methyl 3-methylpicolinate, the title product was afforded as described for Example 266 in General Method E. MS (ESI, m/z): 451.2 [M+H]+

Example 289: Synthesis of 7-bromo-2-(3-(2-((1,5-dimethyl-1H-pyrazol-3-yl)amino)-5-methylpyrimidin-4-yl)-1H-indol-7-yl)-1,2-dihydro-3H-pyrrolo[3,4-c]pyridin-3-one

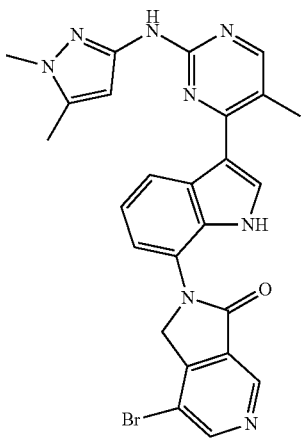

Using methyl 5-bromo-4-methylnicotinate, the title product was afforded as described for Example 266 in General Method E. MS (ESI, m/z): 529.1 [M+H]$^+$ Example 290: Synthesis of 4-bromo-2-(3-(2-((1,5-dimethyl-1H-pyrazol-3-yl)amino)-5-methylpyrimidin-4-yl)-1H-indol-7-yl)-2,3-dihydro-1H-pyrrolo[3,4-c]pyridin-1-one

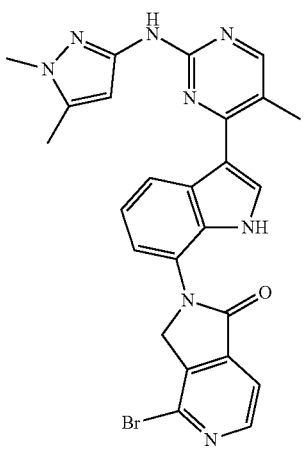

Using methyl 2-bromo-3-methylisonicotinate, the title product was afforded as described for Example 266 in General Method E. MS (ESI, m/z): 529.1 [M+H]$^+$ Example 291: Synthesis of N-(2-(3-(2-((1,5-dimethyl-1H-pyrazol-3-yl)amino)-5-methylpyrimidin-4-yl)-1H-indol-7-yl)-3-oxoisoindolin-5-yl)cyclopropanecarboxamide

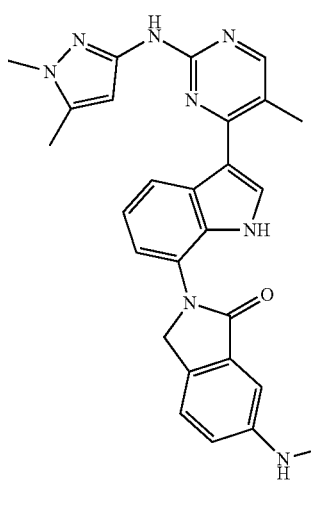

[General Method F]

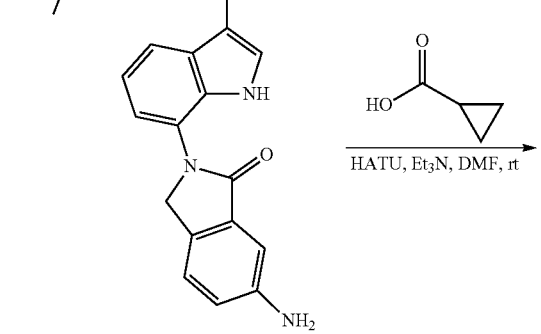

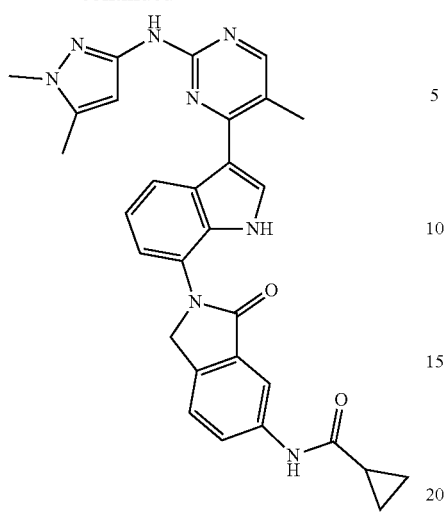

Example 291

To a stirred solution of 6-amino-2-(3-(2-((1,5-dimethyl-1H-pyrazol-3-yl)amino)-5-methylpyrimidin-4-yl)-1H-indol-7-yl)isoindolin-1-one (46 mg, 0.10 mmol), HATU (39 mg, 0.10 mmol), and Et₃N (28 uL, 0.20 mmol) in DMF (0.5 mL) was added cyclopropanecarboxylic acid (9 mg, 0.11 mmol). The reaction was stirred at room temperature for overnight. Then, the reaction mixture was separated from the UCT SPE CUBCX cartridge and purified by the Prep HPLC to afford a corresponding product as a white solid (yield, 60%). MS (ESI, m/z): 533.2 [M+H]⁺

Example 292: Synthesis of N-(2-(3-(2-((1,5-dimethyl-1H-pyrazol-3-yl)amino)-5-methylpyrimidin-4-yl)-1H-indol-7-yl)-3-oxoisoindolin-4-yl)cyclohexanecarboxamide

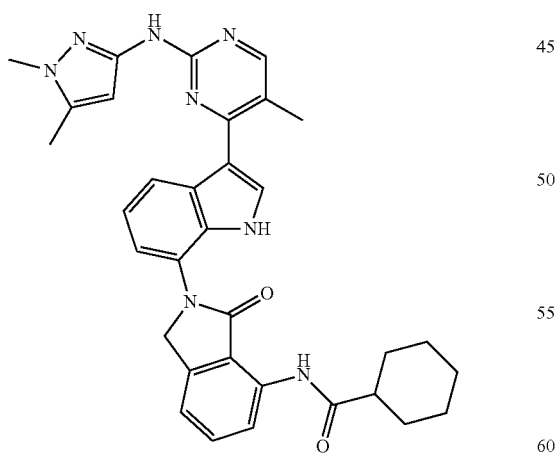

Using 7-amino-2-(3-(2-((1,5-dimethyl-1H-pyrazol-3-yl)amino)-5-methylpyrimidin-4-yl)-1H-indol-7-yl)isoindolin-1-one and cyclohexanecarboxylic acid, the title product was afforded as described for Example 291 in General Method F. MS (ESI, m/z): 575.2 [M+H]⁺

Example 293: Synthesis of N-(2-(3-(2-((1,5-dimethyl-1H-pyrazol-3-yl)amino)-5-methylpyrimidin-4-yl)-1H-indol-7-yl)-3-oxoisoindolin-4-yl)benzamide

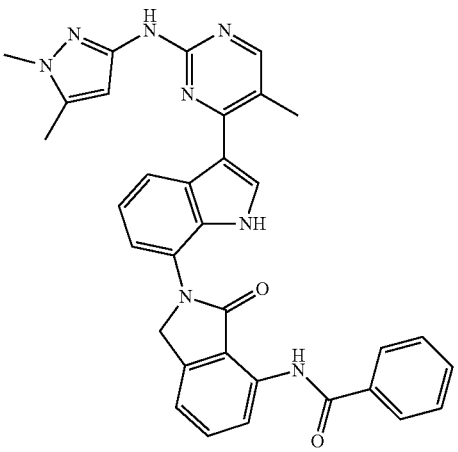 [SMILES: Cc1cnc(Nc2cc(C)n(C)n2)nc1-c1c[nH]c2c(N3Cc4cccc(NC(=O)c5ccccc5)c4C3=O)cccc12]

Using 7-amino-2-(3-(2-((1,5-dimethyl-1H-pyrazol-3-yl)amino)-5-methylpyrimidin-4-yl)-1H-indol-7-yl)isoindolin-1-one and benzoic acid, the title product was afforded as described for Example 291 in General Method F. MS (ESI, m/z): 569.2 [M+H]⁺

Example 294: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)benzamide

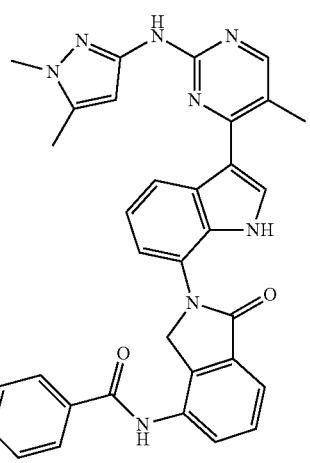

Using 4-amino-2-(3-(2-((1,5-dimethyl-1H-pyrazol-3-yl)amino)-5-methylpyrimidin-4-yl)-1H-indol-7-yl)isoindolin-1-one and benzoic acid, the title product was afforded as described for Example 291 in General Method F. MS (ESI, m/z): 569.2 [M+H]⁺

Example 295: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)cyclohexanecarboxamide

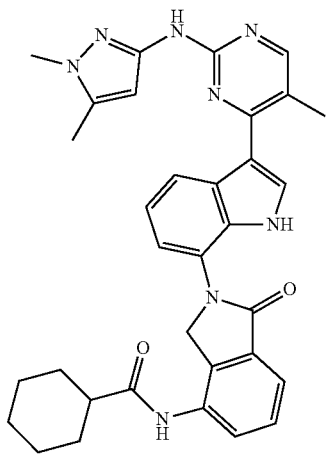 [SMILES: Cc1cnc(Nc2cc(C)n(C)n2)nc1-c1c[nH]c2c(N3Cc4c(NC(=O)C5CCCCC5)cccc4C3=O)cccc12]

Using 4-amino-2-(3-(2-((1,5-dimethyl-1H-pyrazol-3-yl)amino)-5-methylpyrimidin-4-yl)-1H-indol-7-yl)isoindolin-1-one and cyclohexanecarboxylic acid, the title product was afforded as described for Example 291 in General Method F. MS (ESI, m/z): 575.2 [M+H]$^+$ Example 296: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)morpholine-4-carboxamide

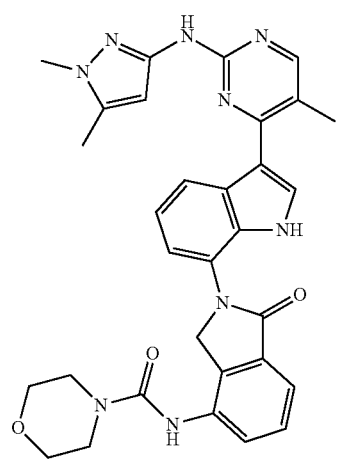 [SMILES: Cc1cnc(Nc2cc(C)n(C)n2)nc1-c1c[nH]c2c(N3Cc4c(NC(=O)N5CCOCC5)cccc4C3=O)cccc12]

Using 4-amino-2-(3-(2-((1,5-dimethyl-1H-pyrazol-3-yl)amino)-5-methylpyrimidin-4-yl)-1H-indol-7-yl)isoindolin-1-one and morpholine-4-carboxylic acid, the title product was afforded as described for Example 291 in General Method F. MS (ESI, m/z): 578.2 [M+H]$^+$ Example 297: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)picolinamide

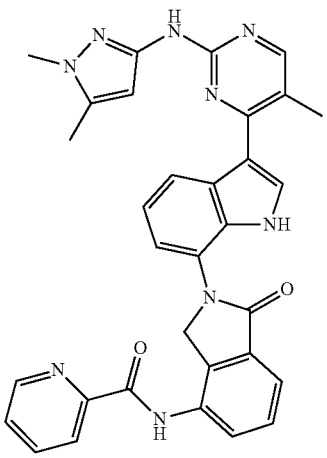 [SMILES: Cc1cnc(Nc2cc(C)n(C)n2)nc1-c1c[nH]c2c(N3Cc4c(NC(=O)c5ccccn5)cccc4C3=O)cccc12]

Using 4-amino-2-(3-(2-((1,5-dimethyl-1H-pyrazol-3-yl)amino)-5-methylpyrimidin-4-yl)-1H-indol-7-yl)isoindolin-1-one and picolinic acid, the title product was afforded as described for Example 291 in General Method F. MS (ESI, m/z): 570.2 [M+H]$^+$ Example 298: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)nicotinamide

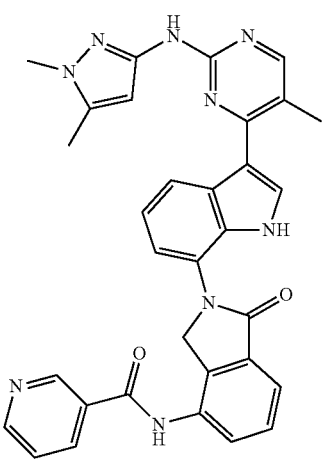 [SMILES: Cc1cnc(Nc2cc(C)n(C)n2)nc1-c1c[nH]c2c(N3Cc4c(NC(=O)c5cccnc5)cccc4C3=O)cccc12]

Using 4-amino-2-(3-(2-((1,5-dimethyl-1H-pyrazol-3-yl)amino)-5-methylpyrimidin-4-yl)-1H-indol-7-yl)isoindolin-1-one and nicotinic acid, the title product was afforded as described for Example 291 in General Method F. MS (ESI, m/z): 570.2 [M+H]$^+$ Example 299: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)oxazole-4-carboxamide

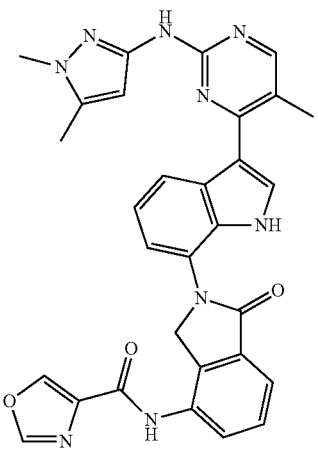 [SMILES: Cc1cnc(Nc2cc(C)n(C)n2)nc1-c1c[nH]c2c(N3Cc4c(NC(=O)c5cocn5)cccc4C3=O)cccc12]

Using 4-amino-2-(3-(2-((1,5-dimethyl-1H-pyrazol-3-yl)amino)-5-methylpyrimidin-4-yl)-1H-indol-7-yl)isoindolin-1-one and oxazole-4-carboxylic acid, the title product was afforded as described for Example 291 in General Method F. MS (ESI, m/z): 560.2 [M+H]+

Example 300: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)cyclopropanecarboxamide

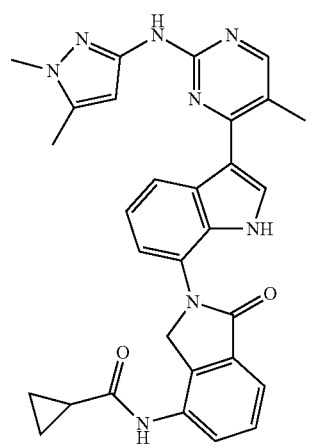

Using 4-amino-2-(3-(2-((1,5-dimethyl-1H-pyrazol-3-yl)amino)-5-methylpyrimidin-4-yl)-1H-indol-7-yl)isoindolin-1-one and cyclopropanecarboxylic acid, the title product was afforded as described for Example 291 in General Method F. MS (ESI, m/z): 533.2 [M+H]+

Example 301: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)isonicotinamide

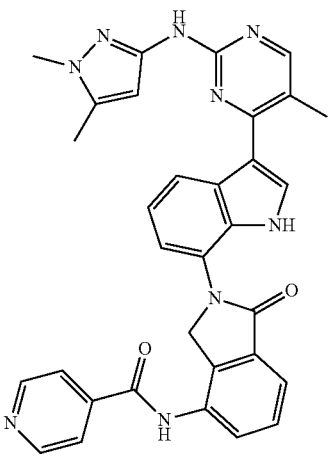 [SMILES: Cc1cnc(Nc2cc(C)n(C)n2)nc1-c1c[nH]c2c(N3Cc4c(NC(=O)c5ccncc5)cccc4C3=O)cccc12]

Using 4-amino-2-(3-(2-((1,5-dimethyl-1H-pyrazol-3-yl)amino)-5-methylpyrimidin-4-yl)-1H-indol-7-yl)isoindolin-1-one and isonicotinic acid, the title product was afforded as described for Example 291 in General Method F. MS (ESI, m/z): 570.2 [M+H]+

Example 302: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)pyridazine-4-carboxamide

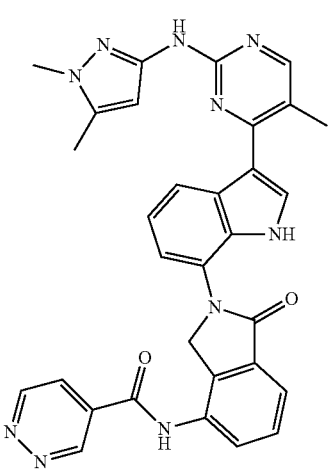 [SMILES: Cc1cnc(Nc2cc(C)n(C)n2)nc1-c1c[nH]c2c(N3Cc4c(NC(=O)c5ccnnc5)cccc4C3=O)cccc12]

Using 4-amino-2-(3-(2-((1,5-dimethyl-1H-pyrazol-3-yl)amino)-5-methylpyrimidin-4-yl)-1H-indol-7-yl)isoindolin-1-one and pyridazine-4-carboxylic acid, the title product was afforded as described for Example 291 in General Method F. MS (ESI, m/z): 571.2 [M+H]+

Example 303: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)-4-methylcyclohexane-1-carboxamide

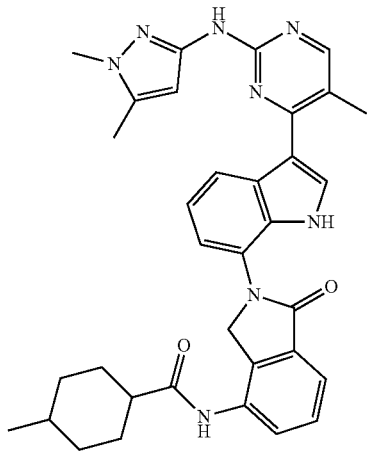

Using 4-amino-2-(3-(2-((1,5-dimethyl-1H-pyrazol-3-yl)amino)-5-methylpyrimidin-4-yl)-1H-indol-7-yl)isoindolin-1-one and 4-methylcyclohexane-1-carboxylic acid, the title product was afforded as described for Example 291 in General Method F. MS (ESI, m/z): 589.3 [M+H]$^+$

Example 304: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)-2-(3-hydroxyphenyl)acetamide

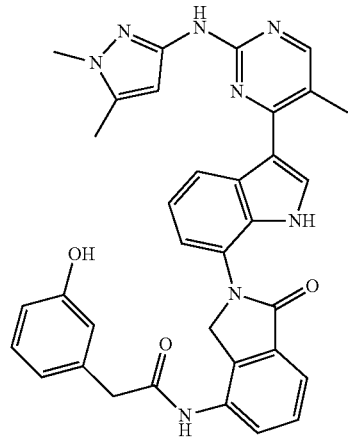 [SMILES: Cc1cnc(Nc2cc(C)n(C)n2)nc1-c1c[nH]c2c(N3Cc4c(NC(=O)Cc5cccc(O)c5)cccc4C3=O)cccc12]

Using 4-amino-2-(3-(2-((1,5-dimethyl-1H-pyrazol-3-yl)amino)-5-methylpyrimidin-4-yl)-1H-indol-7-yl)isoindolin-1-one and 2-(3-hydroxyphenyl)acetic acid, the title product was afforded as described for Example 291 in General Method F. MS (ESI, m/z): 599.2 [M+H]$^+$

Example 305: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)-2-phenylacetamide

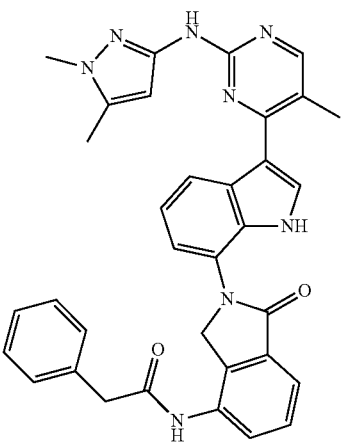 [SMILES: Cc1cnc(Nc2cc(C)n(C)n2)nc1-c1c[nH]c2c(N3Cc4c(NC(=O)Cc5ccccc5)cccc4C3=O)cccc12]

Using 4-amino-2-(3-(2-((1,5-dimethyl-1H-pyrazol-3-yl)amino)-5-methylpyrimidin-4-yl)-1H-indol-7-yl)isoindolin-1-one and 2-phenylacetic acid, the title product was afforded as described for Example 291 in General Method F. MS (ESI, m/z): 583.2 [M+H]$^+$

Example 306: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)-1-methylpiperidine-4-carboxamide

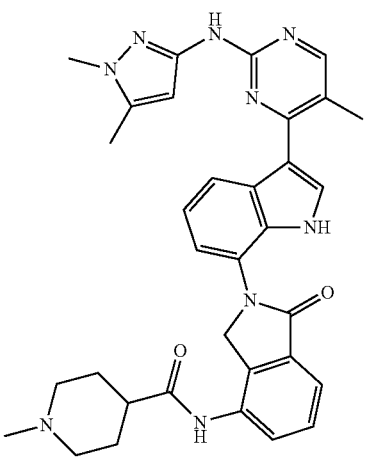

Using 4-amino-2-(3-(2-((1,5-dimethyl-1H-pyrazol-3-yl)amino)-5-methylpyrimidin-4-yl)-1H-indol-7-yl)isoindolin-1-one and 1-methylpiperidine-4-carboxylic acid, the title product was afforded as described for Example 291 in General Method F. MS (ESI, m/z): 590.3 [M+H]$^+$ Example 307: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)-1-methylpiperidine-3-carboxamide

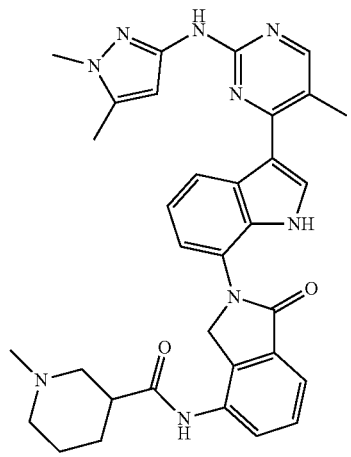

Using 4-amino-2-(3-(2-((1,5-dimethyl-1H-pyrazol-3-yl)amino)-5-methylpyrimidin-4-yl)-1H-indol-7-yl)isoindolin-1-one and 1-methylpiperidine-3-carboxylic acid, the title product was afforded as described for Example 291 in General Method F. MS (ESI, m/z): 590.3 [M+H]$^+$ Example 308: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)-5-oxopyrrolidine-2-carboxamide

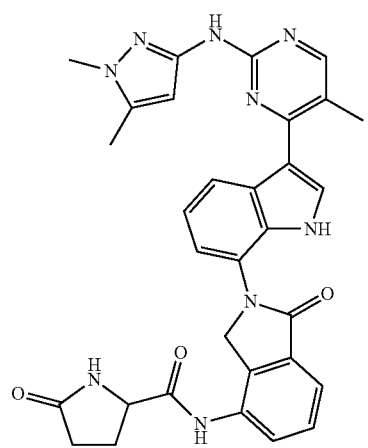 [SMILES: Cc1cnc(Nc2cc(C)n(C)n2)nc1-c1c[nH]c2c(N3Cc4c(NC(=O)C5CCC(=O)N5)cccc4C3=O)cccc12]

Using 4-amino-2-(3-(2-((1,5-dimethyl-1H-pyrazol-3-yl)amino)-5-methylpyrimidin-4-yl)-1H-indol-7-yl)isoindolin-1-one and 5-oxopyrrolidine-2-carboxylic acid, the title product was afforded as described for Example 291 in General Method F. MS (ESI, m/z): 576.2 [M+H]$^+$ Example 309: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)cyclohex-3-ene-1-carboxamide

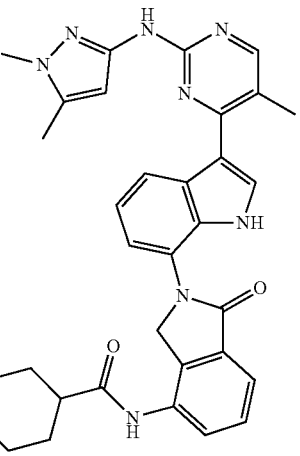

Using 4-amino-2-(3-(2-((1,5-dimethyl-1H-pyrazol-3-yl)amino)-5-methylpyrimidin-4-yl)-1H-indol-7-yl)isoindolin-1-one and cyclohex-3-ene-1-carboxylic acid, the title product was afforded as described for Example 291 in General Method F. MS (ESI, m/z): 573.2 [M+H]$^+$ Example 310: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)cyclopent-3-ene-1-carboxamide

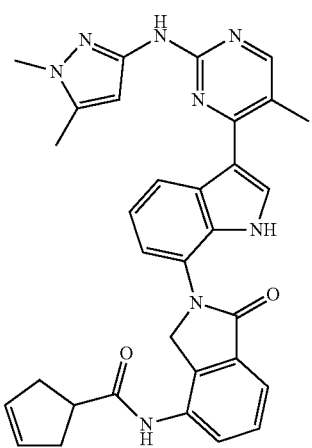 [SMILES: Cc1cnc(Nc2cc(C)n(C)n2)nc1-c1c[nH]c2c(N3Cc4c(NC(=O)C5CC=CC5)cccc4C3=O)cccc12]

Using 4-amino-2-(3-(2-((1,5-dimethyl-1H-pyrazol-3-yl)amino)-5-methylpyrimidin-4-yl)-1H-indol-7-yl)isoindolin-1-one and cyclopent-3-ene-1-carboxylic acid, the title product was afforded as described for Example 291 in General Method F. MS (ESI, m/z): 559.2 [M+H]$^+$ Example 311: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)-1-methylcyclopent-3-ene-1-carboxamide

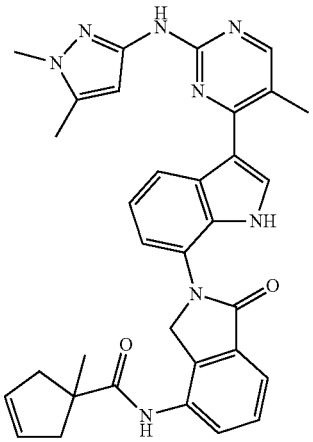 [SMILES: Cc1cnc(Nc2cc(C)n(C)n2)nc1-c1c[nH]c2c(N3Cc4c(NC(=O)C5(C)CC=CC5)cccc4C3=O)cccc12]

Using 4-amino-2-(3-(2-((1,5-dimethyl-1H-pyrazol-3-yl)amino)-5-methylpyrimidin-4-yl)-1H-indol-7-yl)isoindolin-1-one and 1-methylcyclopent-3-ene-1-carboxylic acid, the title product was afforded as described for Example 291 in General Method F. MS (ESI, m/z): 573.2 [M+H]$^+$ Example 312: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)cycloheptanecarboxamide

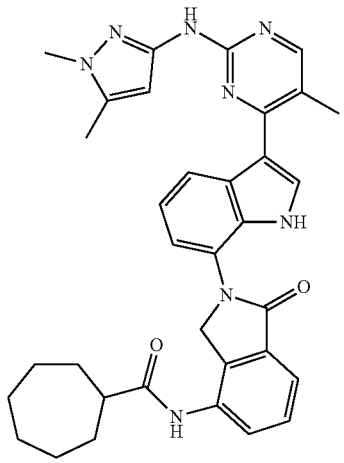 [SMILES: Cc1cnc(Nc2cc(C)n(C)n2)nc1-c1c[nH]c2c(N3Cc4c(NC(=O)C5CCCCCC5)cccc4C3=O)cccc12]

Using 4-amino-2-(3-(2-((1,5-dimethyl-1H-pyrazol-3-yl)amino)-5-methylpyrimidin-4-yl)-1H-indol-7-yl)isoindolin-1-one and cycloheptanecarboxylic acid, the title product was afforded as described for Example 291 in General Method F. MS (ESI, m/z): 589.3 [M+H]$^+$ Example 313: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)-2-oxoimidazolidine-1-carboxamide

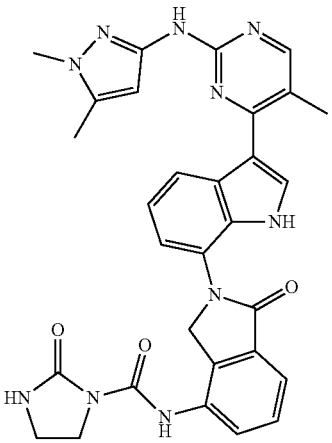 [SMILES: Cc1cnc(Nc2cc(C)n(C)n2)nc1-c1c[nH]c2c(N3Cc4c(NC(=O)N5CCNC5=O)cccc4C3=O)cccc12]

Using 4-amino-2-(3-(2-((1,5-dimethyl-1H-pyrazol-3-yl)amino)-5-methylpyrimidin-4-yl)-1H-indol-7-yl)isoindolin-1-one and 2-oxoimidazolidine-1-carboxylic acid, the title product was afforded as described for Example 291 in General Method F. MS (ESI, m/z): 577.2 [M+H]$^+$ Example 314: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)-2,3-dihydro-1H-indene-2-carboxamide

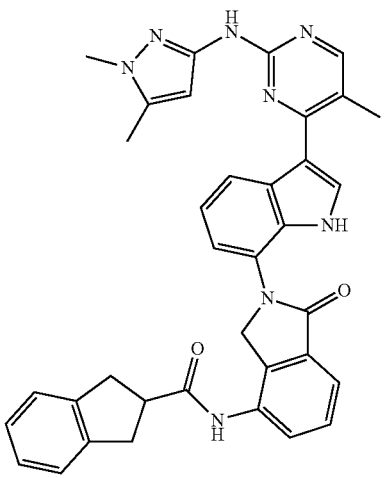 [SMILES: Cc1cnc(Nc2cc(C)n(C)n2)nc1-c1c[nH]c2c(N3Cc4c(NC(=O)C5Cc6ccccc6C5)cccc4C3=O)cccc12]

Using 4-amino-2-(3-(2-((1,5-dimethyl-1H-pyrazol-3-yl)amino)-5-methylpyrimidin-4-yl)-1H-indol-7-yl)isoindolin-1-one and 2,3-dihydro-1H-indene-2-carboxylic acid, the title product was afforded as described for Example 291 in General Method F. MS (ESI, m/z): 609.2 [M+H]$^+$

Example 315: Synthesis of (R)—N-(2-(3-(2-((1,5-dimethyl-1H-pyrazol-3-yl)amino)-5-methylpyrimidin-4-yl)-1H-indol-7-yl)-1-oxoisoindolin-4-yl)pyrrolidine-3-carboxamide

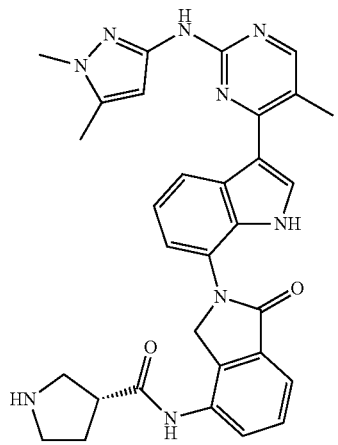 [SMILES: Cc1cnc(Nc2cc(C)n(C)n2)nc1-c1c[nH]c2c(N3Cc4c(NC(=O)[C@@H]5CCNC5)cccc4C3=O)cccc12]

Using 4-amino-2-(3-(2-((1,5-dimethyl-1H-pyrazol-3-yl)amino)-5-methylpyrimidin-4-yl)-1H-indol-7-yl)isoindolin-1-one and (R)-pyrrolidine-3-carboxylic acid, the title product was afforded as described for Example 291 in General Method F. MS (ESI, m/z): 562.2 [M+H]$^+$

Example 316: Synthesis of (S)—N-(2-(3-(2-((1,5-dimethyl-1H-pyrazol-3-yl)amino)-5-methylpyrimidin-4-yl)-1H-indol-7-yl)-1-oxoisoindolin-4-yl)pyrrolidine-3-carboxamide

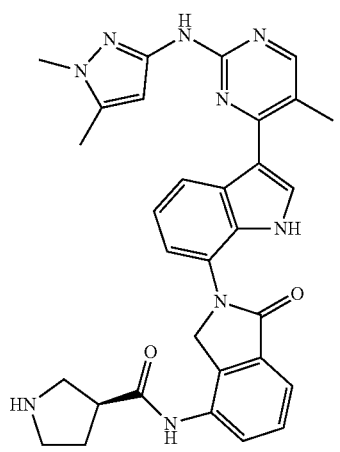 [SMILES: Cc1cnc(Nc2cc(C)n(C)n2)nc1-c1c[nH]c2c(N3Cc4c(NC(=O)[C@H]5CCNC5)cccc4C3=O)cccc12]

Using 4-amino-2-(3-(2-((1,5-dimethyl-1H-pyrazol-3-yl)amino)-5-methylpyrimidin-4-yl)-1H-indol-7-yl)isoindolin-1-one and (S)-pyrrolidine-3-carboxylic acid, the title product was afforded as described for Example 291 in General Method F. MS (ESI, m/z): 562.2 [M+H]$^+$

Example 317: Synthesis of (S)—N-(2-(3-(2-((1,5-dimethyl-1H-pyrazol-3-yl)amino)-5-methylpyrimidin-4-yl)-1H-indol-7-yl)-1-oxoisoindolin-4-yl)-5-oxopyrrolidine-2-carboxamide

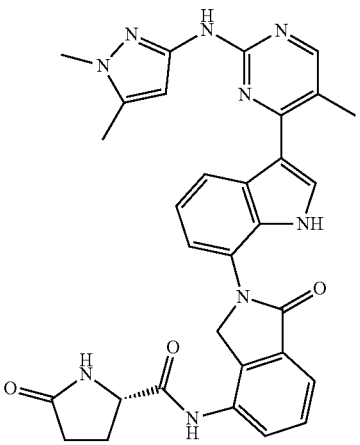 [SMILES: Cc1cnc(Nc2cc(C)n(C)n2)nc1-c1c[nH]c2c(N3Cc4c(NC(=O)[C@@H]5CCC(=O)N5)cccc4C3=O)cccc12]

Using 4-amino-2-(3-(2-((1,5-dimethyl-1H-pyrazol-3-yl)amino)-5-methylpyrimidin-4-yl)-1H-indol-7-yl)isoindolin-1-one and (S)-5-oxopyrrolidine-2-carboxylic acid, the title product was afforded as described for Example 291 in General Method F. MS (ESI, m/z): 576.2 [M+H]$^+$

Example 318: Synthesis of (R)—N-(2-(3-(2-((1,5-dimethyl-1H-pyrazol-3-yl)amino)-5-methylpyrimidin-4-yl)-1H-indol-7-yl)-1-oxoisoindolin-4-yl)-5-oxopyrrolidine-2-carboxamide

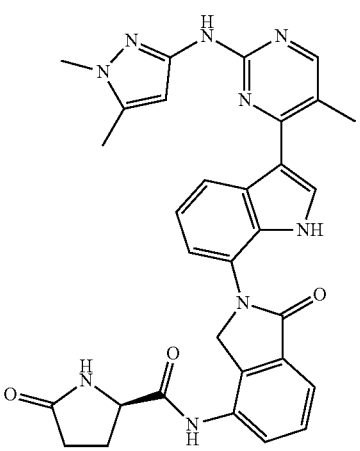 [SMILES: Cc1cnc(Nc2cc(C)n(C)n2)nc1-c1c[nH]c2c(N3Cc4c(NC(=O)[C@H]5CCC(=O)N5)cccc4C3=O)cccc12]

Using 4-amino-2-(3-(2-((1,5-dimethyl-1H-pyrazol-3-yl)amino)-5-methylpyrimidin-4-yl)-1H-indol-7-yl)isoindolin-1-one and (R)-5-oxopyrrolidine-2-carboxylic acid, the title product was afforded as described for Example 291 in General Method F. MS (ESI, m/z): 576.2 [M+H]$^+$ Example 319: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)piperidine-3-carboxamide

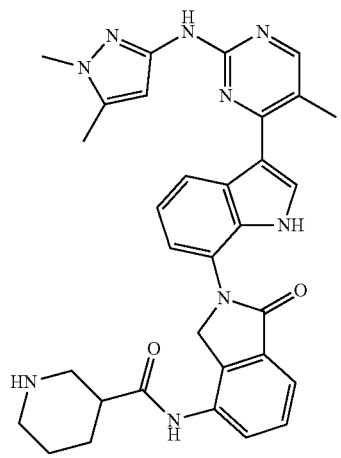 [SMILES: Cc1cnc(Nc2cc(C)n(C)n2)nc1-c1c[nH]c2c(N3Cc4c(NC(=O)C5CCCNC5)cccc4C3=O)cccc12]

Using 4-amino-2-(3-(2-((1,5-dimethyl-1H-pyrazol-3-yl)amino)-5-methylpyrimidin-4-yl)-1H-indol-7-yl)isoindolin-1-one and piperidine-3-carboxylic acid, the title product was afforded as described for Example 291 in General Method F. MS (ESI, m/z): 576.2 [M+H]+

Example 320: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)-4-oxocyclohexane-1-carboxamide

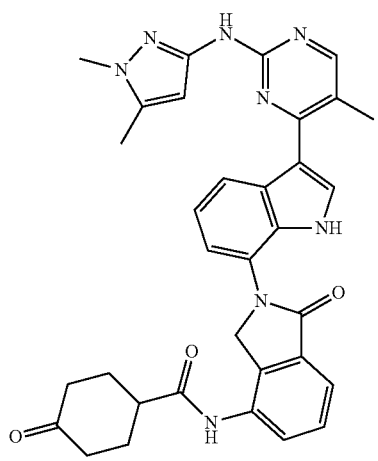 [SMILES: Cc1cnc(Nc2cc(C)n(C)n2)nc1-c1c[nH]c2c(N3Cc4c(NC(=O)C5CCC(=O)CC5)cccc4C3=O)cccc12]

Using 4-amino-2-(3-(2-((1,5-dimethyl-1H-pyrazol-3-yl)amino)-5-methylpyrimidin-4-yl)-1H-indol-7-yl)isoindolin-1-one and 4-oxocyclohexane-1-carboxylic acid, the title product was afforded as described for Example 291 in General Method F. MS (ESI, m/z): 589.2 [M+H]+

Example 321: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)-5-methylisoxazole-4-carboxamide

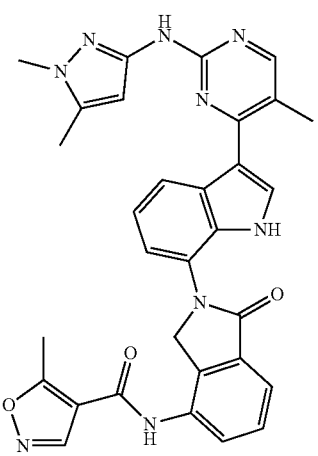 [SMILES: Cc1cnc(Nc2cc(C)n(C)n2)nc1-c1c[nH]c2c(N3Cc4c(NC(=O)c5cnoc5C)cccc4C3=O)cccc12]

Using 4-amino-2-(3-(2-((1,5-dimethyl-1H-pyrazol-3-yl)amino)-5-methylpyrimidin-4-yl)-1H-indol-7-yl)isoindolin-1-one and 5-methylisoxazole-4-carboxylic acid, the title product was afforded as described for Example 291 in General Method F. MS (ESI, m/z): 574.2 [M+H]+

Example 322: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)-2-methyloxazole-4-carboxamide

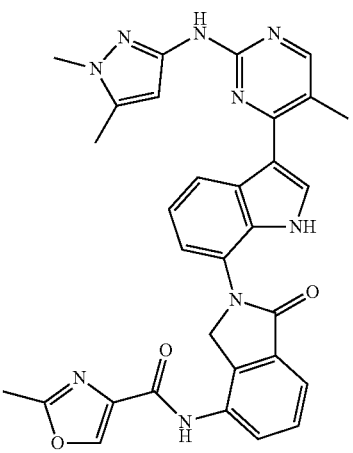

Using 4-amino-2-(3-(2-((1,5-dimethyl-1H-pyrazol-3-yl)amino)-5-methylpyrimidin-4-yl)-1H-indol-7-yl)isoindolin-1-one and 2-methyloxazole-4-carboxylic acid, the title product was afforded as described for Example 291 in General Method F. MS (ESI, m/z): 574.2 [M+H]+

Example 323: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)oxazole-5-carboxamide

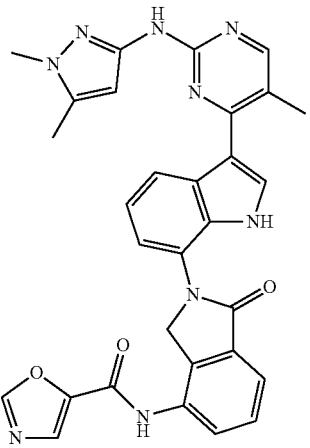 [SMILES: Cc1cnc(Nc2cc(C)n(C)n2)nc1-c1c[nH]c2c(N3Cc4c(NC(=O)c5cnco5)cccc4C3=O)cccc12]

Using 4-amino-2-(3-(2-((1,5-dimethyl-1H-pyrazol-3-yl)amino)-5-methylpyrimidin-4-yl)-1H-indol-7-yl)isoindolin-1-one and oxazole-5-carboxylic acid, the title product was afforded as described for Example 291 in General Method F. MS (ESI, m/z): 560.2 [M+H]$^+$ Example 324: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)isoxazole-3-carboxamide

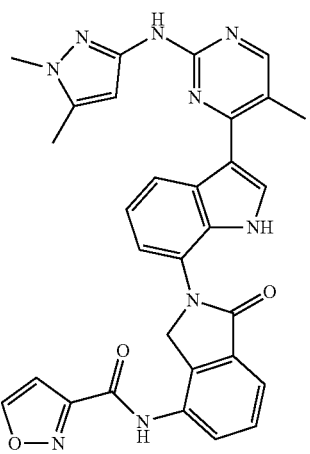 [SMILES: Cc1cnc(Nc2cc(C)n(C)n2)nc1-c1c[nH]c2c(N3Cc4c(NC(=O)c5ccon5)cccc4C3=O)cccc12]

Using 4-amino-2-(3-(2-((1,5-dimethyl-1H-pyrazol-3-yl)amino)-5-methylpyrimidin-4-yl)-1H-indol-7-yl)isoindolin-1-one and isoxazole-3-carboxylic acid, the title product was afforded as described for Example 291 in General Method F. MS (ESI, m/z): 560.2 [M+H]$^+$ Example 325: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)-5-methylisoxazole-3-carboxamide

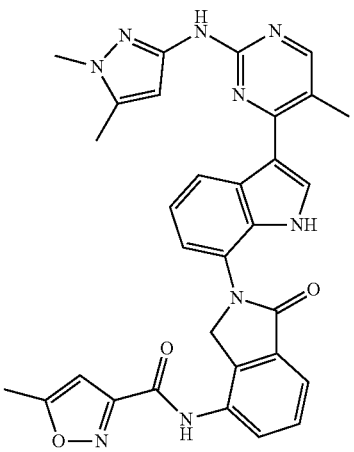

Using 4-amino-2-(3-(2-((1,5-dimethyl-1H-pyrazol-3-yl)amino)-5-methylpyrimidin-4-yl)-1H-indol-7-yl)isoindolin-1-one and 5-methylisoxazole-3-carboxylic acid, the title product was afforded as described for Example 291 in General Method F. MS (ESI, m/z): 574.2 [M+H]$^+$ Example 326: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)tetrahydrofuran-3-carboxamide

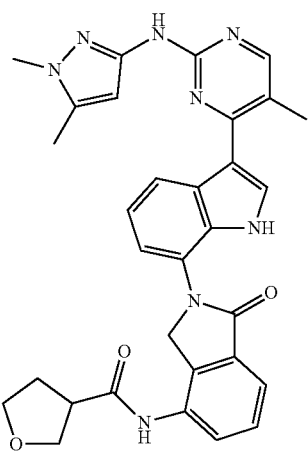 [SMILES: Cc1cnc(Nc2cc(C)n(C)n2)nc1-c1c[nH]c2c(N3Cc4c(NC(=O)C5CCOC5)cccc4C3=O)cccc12]

Using 4-amino-2-(3-(2-((1,5-dimethyl-1H-pyrazol-3-yl)amino)-5-methylpyrimidin-4-yl)-1H-indol-7-yl)isoindolin-1-one and tetrahydrofuran-3-carboxylic acid, the title product was afforded as described for Example 291 in General Method F. MS (ESI, m/z): 563.2 [M+H]$^+$

Example 327: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)tetrahydro-2H-pyran-3-carboxamide

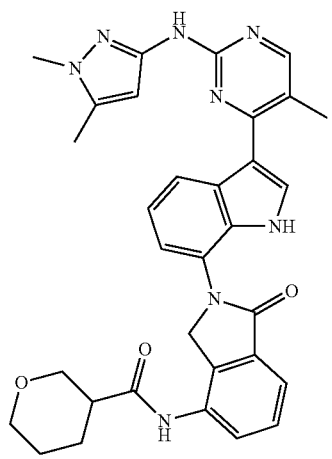 [SMILES: Cc1cnc(Nc2cc(C)n(C)n2)nc1-c1c[nH]c2c(N3Cc4c(NC(=O)C5CCCOC5)cccc4C3=O)cccc12]

Using 4-amino-2-(3-(2-((1,5-dimethyl-1H-pyrazol-3-yl)amino)-5-methylpyrimidin-4-yl)-1H-indol-7-yl)isoindolin-1-one and tetrahydro-2H-pyran-3-carboxylic acid, the title product was afforded as described for Example 291 in General Method F. MS (ESI, m/z): 577.2 [M+H]$^+$

Example 328: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)-4-methyltetrahydro-2H-pyran-4-carboxamide

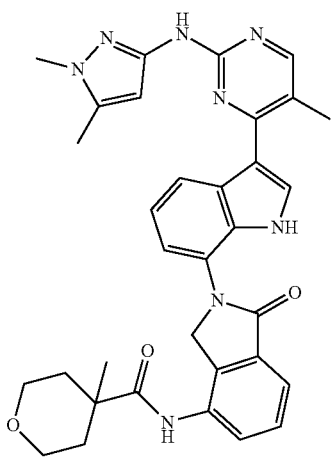 [SMILES: Cc1cnc(Nc2cc(C)n(C)n2)nc1-c1c[nH]c2c(N3Cc4c(NC(=O)C5(C)CCOCC5)cccc4C3=O)cccc12]

Using 4-amino-2-(3-(2-((1,5-dimethyl-1H-pyrazol-3-yl)amino)-5-methylpyrimidin-4-yl)-1H-indol-7-yl)isoindolin-1-one and 4-methyltetrahydro-2H-pyran-4-carboxylic acid, the title product was afforded as described for Example 291 in General Method F. MS (ESI, m/z): 591.2 [M+H]$^+$

Example 329: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)-3-methylcyclohexane-1-carboxamide

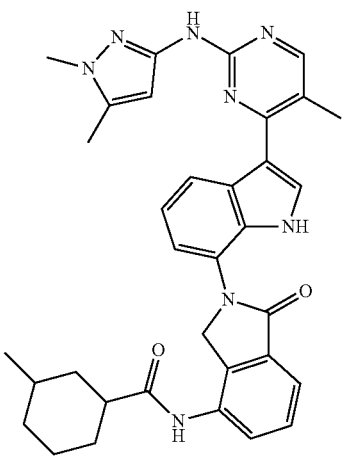

Using 4-amino-2-(3-(2-((1,5-dimethyl-1H-pyrazol-3-yl)amino)-5-methylpyrimidin-4-yl)-1H-indol-7-yl)isoindolin-1-one and 3-methylcyclohexane-1-carboxylic acid, the title product was afforded as described for Example 291 in General Method F. MS (ESI, m/z): 589.3 [M+H]$^+$

Example 330: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)-4-methylcyclohex-3-ene-1-carboxamide

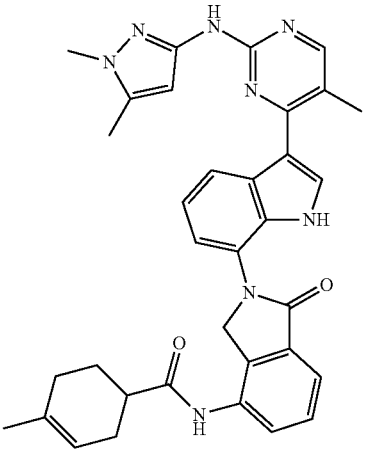

Using 4-amino-2-(3-(2-((1,5-dimethyl-1H-pyrazol-3-yl)amino)-5-methylpyrimidin-4-yl)-1H-indol-7-yl)isoindolin-1-one and 4-methylcyclohex-3-ene-1-carboxylic acid, the title product was afforded as described for Example 291 in General Method F. MS (ESI, m/z): 587.2 [M+H]$^+$ Example 331: Synthesis of (2R,4S)-4-amino-N-(2-(3-(2-((1,5-dimethyl-1H-pyrazol-3-yl)amino)-5-methylpyrimidin-4-yl)-1H-indol-7-yl)-1-oxoisoindolin-4-yl)pyrrolidine-2-carboxamide

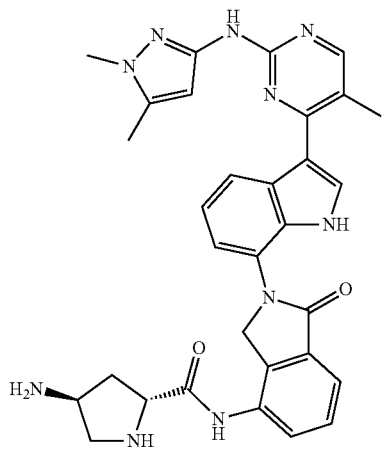 [SMILES: Cc1cnc(Nc2cc(C)n(C)n2)nc1-c1c[nH]c2c(N3Cc4c(NC(=O)[C@H]5C[C@H](N)CN5)cccc4C3=O)cccc12]

Using 4-amino-2-(3-(2-((1,5-dimethyl-1H-pyrazol-3-yl)amino)-5-methylpyrimidin-4-yl)-1H-indol-7-yl)isoindolin-1-one and (2R,4S)-4-aminopyrrolidine-2-carboxylic acid, the title product was afforded as described for Example 291 in General Method F. MS (ESI, m/z): 577.2 [M+H]$^+$ Example 332: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)-3-methylpiperidine-3-carboxamide

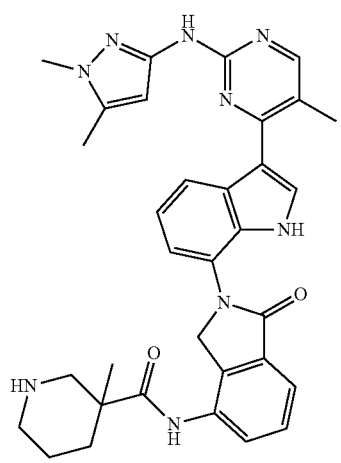

Using 4-amino-2-(3-(2-((1,5-dimethyl-1H-pyrazol-3-yl)amino)-5-methylpyrimidin-4-yl)-1H-indol-7-yl)isoindolin-1-one and 3-methylpiperidine-3-carboxylic acid, the title product was afforded as described for Example 291 in General Method F. MS (ESI, m/z): 590.3 [M+H]$^+$ Example 333: Synthesis of (R)—N-(2-(3-(2-((1,5-dimethyl-1H-pyrazol-3-yl)amino)-5-methylpyrimidin-4-yl)-1H-indol-7-yl)-1-oxoisoindolin-4-yl)-1-methylpyrrolidine-3-carboxamide

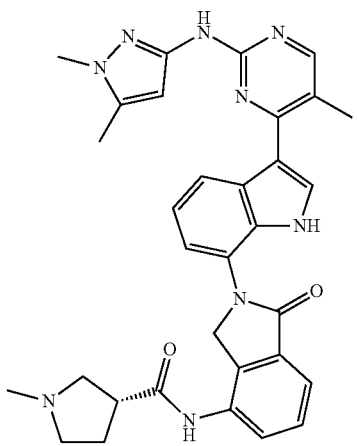

Using 4-amino-2-(3-(2-((1,5-dimethyl-1H-pyrazol-3-yl)amino)-5-methylpyrimidin-4-yl)-1H-indol-7-yl)isoindolin-1-one and (R)-1-methylpyrrolidine-3-carboxylic acid, the title product was afforded as described for Example 291 in General Method F. MS (ESI, m/z): 576.2 [M+H]$^+$ Example 334: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)-5-methylnicotinamide

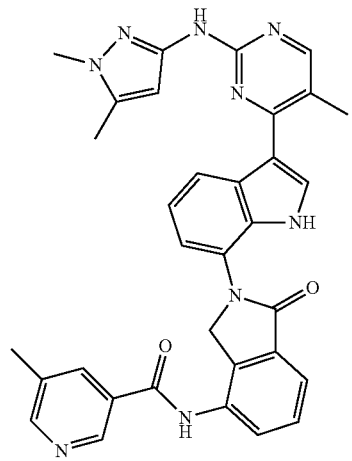

Using 4-amino-2-(3-(2-((1,5-dimethyl-1H-pyrazol-3-yl)amino)-5-methylpyrimidin-4-yl)-1H-indol-7-yl)isoindolin-1-one and 5-methylnicotinic acid, the title product was afforded as described for Example 291 in General Method F. MS (ESI, m/z): 584.2 [M+H]$^+$ Example 335: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)-2-(dimethylamino)acetamide

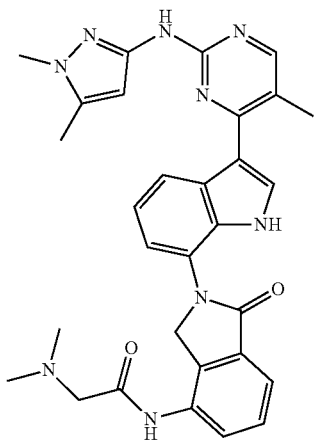

Using 4-amino-2-(3-(2-((1,5-dimethyl-1H-pyrazol-3-yl)amino)-5-methylpyrimidin-4-yl)-1H-indol-7-yl)isoindolin-1-one and dimethylglycine, the title product was afforded as described for Example 291 in General Method F. MS (ESI, m/z): 550.2 [M+H]$^+$ Example 336: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)cyclopentanecarboxamide

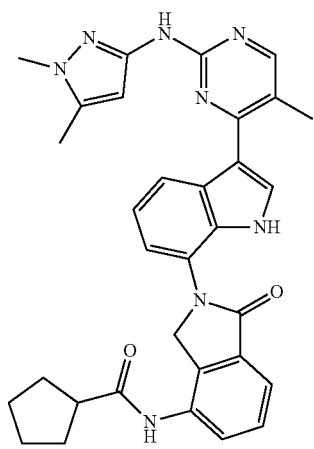 [SMILES: Cc1cnc(Nc2cc(C)n(C)n2)nc1-c1c[nH]c2c(N3Cc4c(NC(=O)C5CCCC5)cccc4C3=O)cccc12]

Using 4-amino-2-(3-(2-((1,5-dimethyl-1H-pyrazol-3-yl)amino)-5-methylpyrimidin-4-yl)-1H-indol-7-yl)isoindolin-1-one and cyclopentanecarboxylic acid, the title product was afforded as described for Example 291 in General Method F. MS (ESI, m/z): 561.2 [M+H]$^+$ Example 337: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)tetrahydro-2H-pyran-4-carboxamide

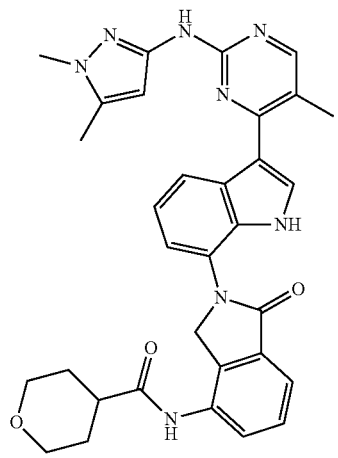 [SMILES: Cc1cnc(Nc2cc(C)n(C)n2)nc1-c1c[nH]c2c(N3Cc4c(NC(=O)C5CCOCC5)cccc4C3=O)cccc12]

Using 4-amino-2-(3-(2-((1,5-dimethyl-1H-pyrazol-3-yl)amino)-5-methylpyrimidin-4-yl)-1H-indol-7-yl)isoindolin-1-one and tetrahydro-2H-pyran-4-carboxylic acid, the title product was afforded as described for Example 291 in General Method F. MS (ESI, m/z): 577.2 [M+H]$^+$ Example 338: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)furan-3-carboxamide

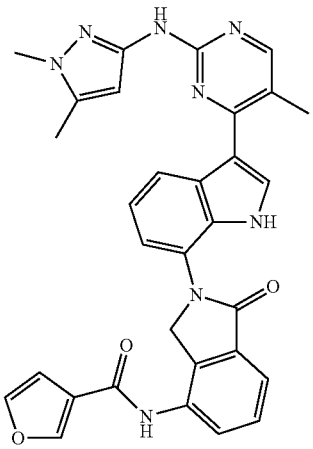

Using 4-amino-2-(3-(2-((1,5-dimethyl-1H-pyrazol-3-yl)amino)-5-methylpyrimidin-4-yl)-1H-indol-7-yl)isoindolin-1-one and furan-3-carboxylic acid, the title product was afforded as described for Example 291 in General Method F. MS (ESI, m/z): 559.2 [M+H]$^+$

Example 339: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)-6-hydroxypyrimidine-4-carboxamide

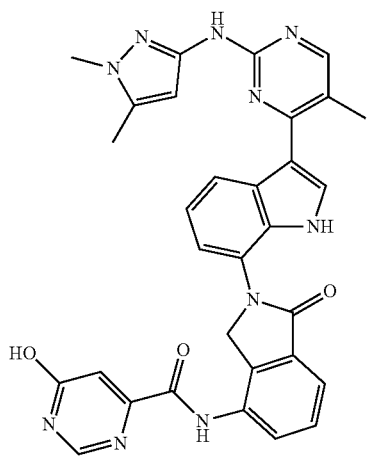 [SMILES: Cc1cnc(Nc2cc(C)n(C)n2)nc1-c1c[nH]c2c(N3Cc4c(NC(=O)c5cc(O)ncn5)cccc4C3=O)cccc12]

Using 4-amino-2-(3-(2-((1,5-dimethyl-1H-pyrazol-3-yl)amino)-5-methylpyrimidin-4-yl)-1H-indol-7-yl)isoindolin-1-one and 6-hydroxypyrimidine-4-carboxylic acid, the title product was afforded as described for Example 291 in General Method F. MS (ESI, m/z): 587.2 [M+H]$^+$

Example 340: Synthesis of N-(2-(3-(2-((1,5-dimethyl-1H-pyrazol-3-yl)amino)-5-methylpyrimidin-4-yl)-1H-indol-7-yl)-3-oxoisoindolin-4-yl)benzenesulfonamide

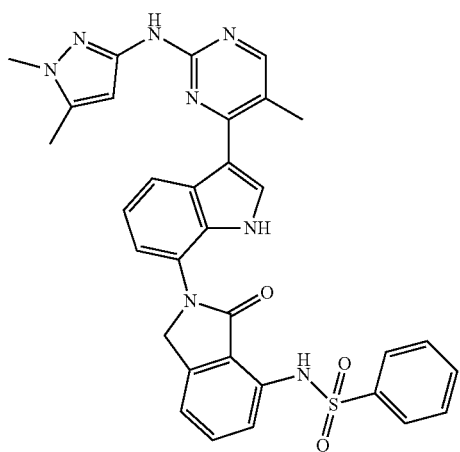 [SMILES: Cc1cnc(Nc2cc(C)n(C)n2)nc1-c1c[nH]c2c(N3Cc4cccc(NS(=O)(=O)c5ccccc5)c4C3=O)cccc12]

A mixture of 7-amino-2-(3-(2-((1,5-dimethyl-1H-pyrazol-3-yl)amino)-5-methylpyrimidin-4-yl)-1H-indol-7-yl)isoindolin-1-one (46 mg, 0.10 mmol) and benzenesulfonyl chloride (19 mg, 0.11 mmol) in pyridine (0.5 mL) was heated to reflux for 12 h. After cooling to room temperature, the reaction mixture was separated from the UCT SPE CUBCX cartridge and purified by the Prep HPLC to afford a corresponding product as a white solid (yield, 55%).

$^1$H NMR (600 MHz, cd$_3$od) δ 8.99 (s, 1H), 8.38 (s, 1H), 8.18 (s, 1H), 8.19-8.00 (m, 5H), 7.99-7.86 (m, 3H), 7.42-7.33 (m, 2H), 5.99 (s, 1H), 4.77 (s, 2H), 3.85 (s, 3H), 2.59 (s, 3H), 2.35 (s, 3H). MS (ESI, m/z): 605.2 [M+H]$^+$

Example 341: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)benzenesulfonamide

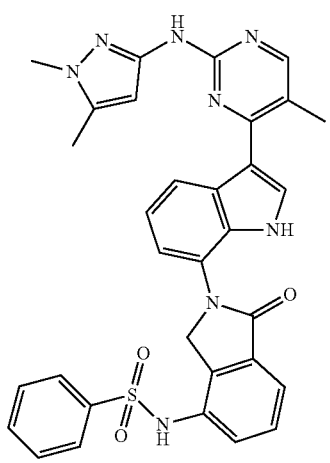 [SMILES: Cc1cnc(Nc2cc(C)n(C)n2)nc1-c1c[nH]c2c(N3Cc4c(NS(=O)(=O)c5ccccc5)cccc4C3=O)cccc12]

Using 4-amino-2-(3-(2-((1,5-dimethyl-1H-pyrazol-3-yl)amino)-5-methylpyrimidin-4-yl)-1H-indol-7-yl)isoindolin-1-one and benzenesulfonyl chloride, the title product was afforded as described for Example 340 in General Method G. MS (ESI, m/z): 605.2 [M+H]$^+$

Example 342: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)methanesulfonamide

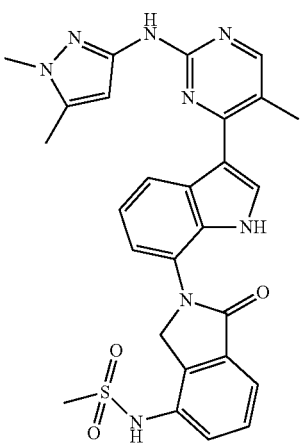

Using 4-amino-2-(3-(2-((1,5-dimethyl-1H-pyrazol-3-yl)amino)-5-methylpyrimidin-4-yl)-1H-indol-7-yl)isoindolin-1-one and methanesulfonyl chloride, the title product was afforded as described for Example 340 in General Method G. MS (ESI, m/z): 543.1 [M+H]$^+$ Example 343: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)-4-methylbenzenesulfonamide

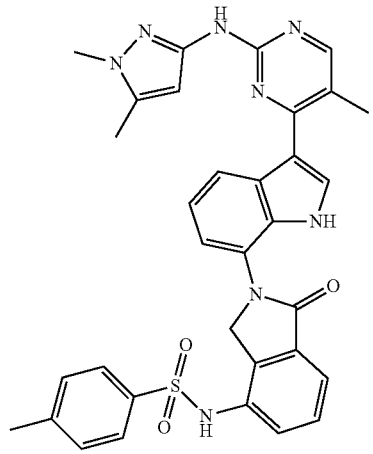

Using 4-amino-2-(3-(2-((1,5-dimethyl-1H-pyrazol-3-yl)amino)-5-methylpyrimidin-4-yl)-1H-indol-7-yl)isoindolin-1-one and 4-methylbenzenesulfonyl chloride, the title product was afforded as described for Example 340 in General Method G. MS (ESI, m/z): 619.2 [M+H]⁺

Example 344: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)propane-2-sulfonamide

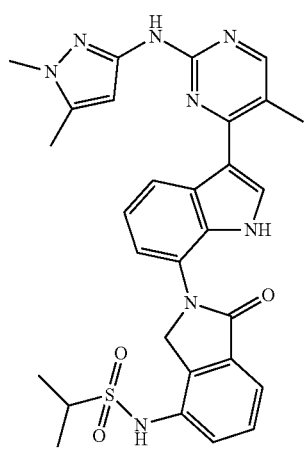

Using 4-amino-2-(3-(2-((1,5-dimethyl-1H-pyrazol-3-yl)amino)-5-methylpyrimidin-4-yl)-1H-indol-7-yl)isoindolin-1-one and propane-2-sulfonyl chloride, the title product was afforded as described for Example 340 in General Method G. MS (ESI, m/z): 571.2 [M+H]⁺

Example 345: Synthesis of N-(2-(3-(2-((1,5-dimethyl-1H-pyrazol-3-yl)amino)-5-methylpyrimidin-4-yl)-1H-indol-7-yl)-1-oxoisoindolin-4-yl)-4-fluoro-3-methylbenzenesulfonamide

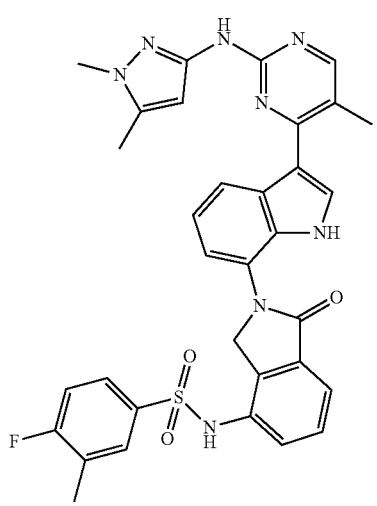 [SMILES: Cc1cc(S(=O)(=O)Nc2cccc3c2CN(c2cccc4c(-c5nc(Nc6cc(C)n(C)n6)ncc5C)c[nH]c24)C3=O)ccc1F]

Using 4-amino-2-(3-(2-((1,5-dimethyl-1H-pyrazol-3-yl)amino)-5-methylpyrimidin-4-yl)-1H-indol-7-yl)isoindolin-1-one and 4-fluoro-3-methylbenzenesulfonyl chloride, the title product was afforded as described for Example 340 in General Method G. MS (ESI, m/z): 637.2 [M+H]⁺

Example 346: Synthesis of 2-(3-(2-((1,5-dimethyl-1H-pyrazol-3-yl)amino)-5-methylpyrimidin-4-yl)-1H-indol-7-yl)-7-(phenylamino)isoindolin-1-one

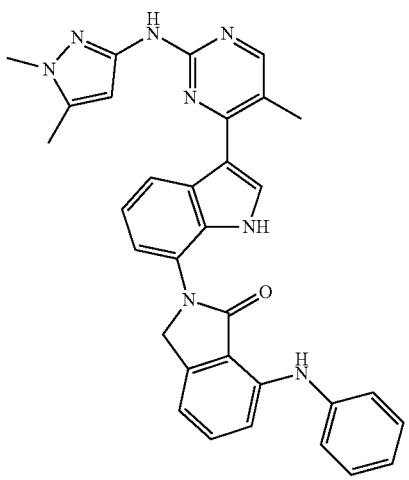 [SMILES: Cc1cnc(Nc2cc(C)n(C)n2)nc1-c1c[nH]c2c(N3Cc4cccc(Nc5ccccc5)c4C3=O)cccc12]

[General Method G]

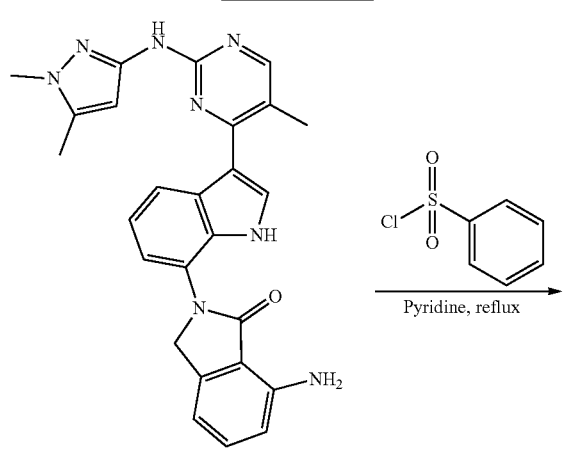

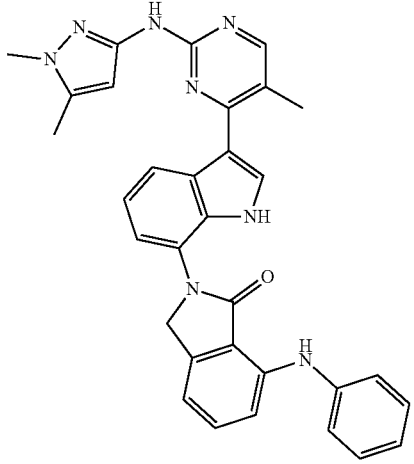

Example 346

A mixture of 7-chloro-2-(3-(2-((1,5-dimethyl-1H-pyrazol-3-yl)amino)-5-methylpyrimidin-4-yl)-1H-indol-7-yl)isoindolin-1-one (prepared as an Example 273, 48 mg, 0.10 mmol), aniline (10 mg, 0.11 mmol), Pd(dba)₂ (5.8 mg, 0.01 mmol), BINAP (12 mg, 0.02 mmol), and NaOtBu (29 mg, 0.300 mmol) was heated to 100° C. for 12 h.

After cooling to room temperature, the reaction mixture was separated from the UCT SPE CUBCX cartridge and purified by the Prep HPLC to afford a corresponding product as a white solid (yield, 35%).

¹H NMR (600 MHz, cd₃od) δ 8.82 (s, 1H), 8.36 (s, 1H), 8.19 (s, 1H), 7.48-7.28 (m, 8H), 7.08 (m, 1H), 6.98 (m, 1H), 5.96 (s, 1H), 5.01 (s, 2H), 3.80 (s, 3H), 2.56 (s, 3H), 2.33 (s, 3H). MS (ESI, m/z): 541.2 [M+H]⁺

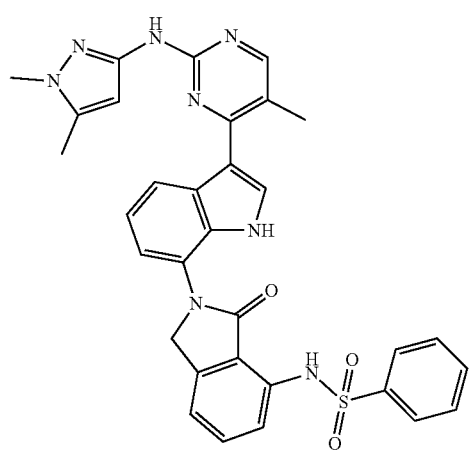

Example 340

Example 347: Synthesis of 2-(3-(2-((1,5-dimethyl-1H-pyrazol-3-yl)amino)-5-methylpyrimidin-4-yl)-1H-indol-7-yl)-7-morpholinoisoindolin-1-one

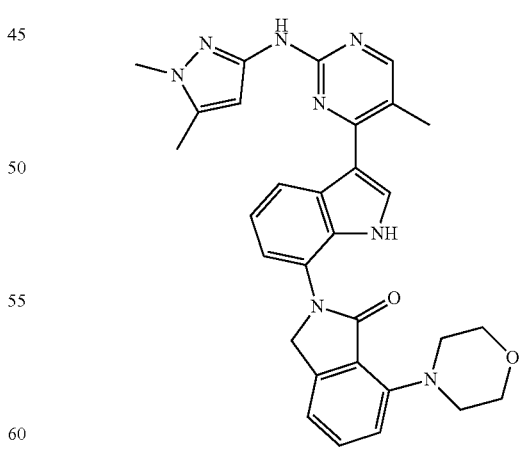

[General Method H]

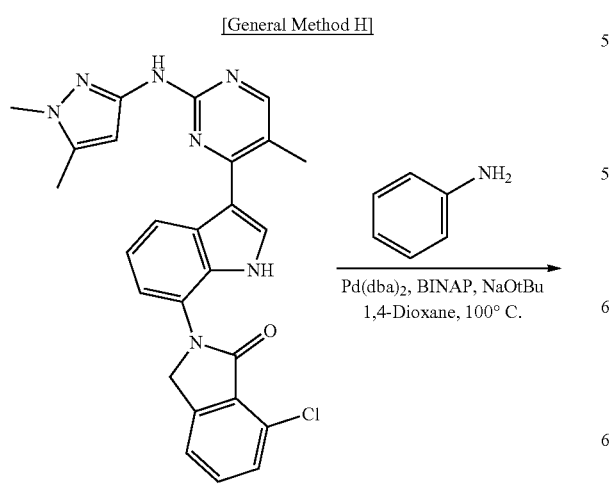

Using 7-chloro-2-(3-(2-((1,5-dimethyl-1H-pyrazol-3-yl)amino)-5-methylpyrimidin-4-yl)-1H-indol-7-yl)isoindolin-1-one and morpholine, the title product was afforded as described for Example 346 in General Method H. MS (ESI, m/z): 535.2 [M+H]⁺

Example 348: Synthesis of 2-(3-(2-((1,5-dimethyl-1H-pyrazol-3-yl)amino)-5-methylpyrimidin-4-yl)-1H-indol-7-yl)-7-(4-methylpiperazin-1-yl)isoindolin-1-one

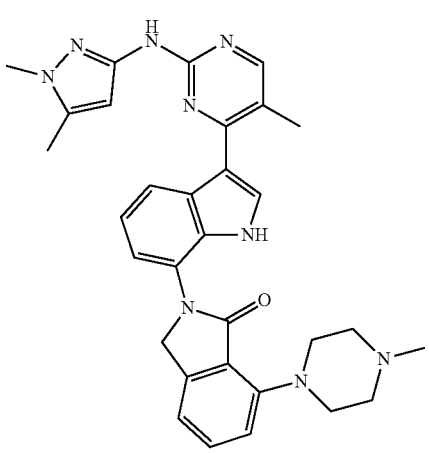

Using 7-chloro-2-(3-(2-((1,5-dimethyl-1H-pyrazol-3-yl)amino)-5-methylpyrimidin-4-yl)-1H-indol-7-yl)isoindolin-1-one and 1-methylpiperazine, the title product was afforded as described for Example 346 in General Method H. MS (ESI, m/z): 548.2 [M+H]+

Example 349: Synthesis of 2-(3-(2-((1,5-dimethyl-1H-pyrazol-3-yl)amino)-5-methylpyrimidin-4-yl)-1H-indol-7-yl)-7-(dimethylamino)isoindolin-1-one

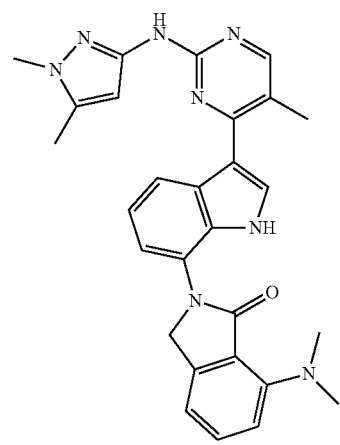

Using 7-chloro-2-(3-(2-((1,5-dimethyl-1H-pyrazol-3-yl)amino)-5-methylpyrimidin-4-yl)-1H-indol-7-yl)isoindolin-1-one and dimethylamine hydrochloride, the title product was afforded as described for Example 346 in General Method H. MS (ESI, m/z): 493.2 [M+H]+

Example 350: Synthesis of 7-(benzylamino)-2-(3-(2-((1,5-dimethyl-1H-pyrazol-3-yl)amino)-5-methylpyrimidin-4-yl)-1H-indol-7-yl)isoindolin-1-one

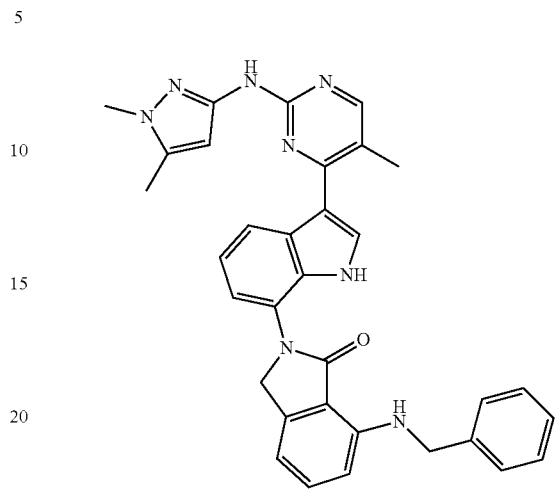

Using 7-chloro-2-(3-(2-((1,5-dimethyl-1H-pyrazol-3-yl)amino)-5-methylpyrimidin-4-yl)-1H-indol-7-yl)isoindolin-1-one and phenylmethanamine, the title product was afforded as described for Example 346 in General Method H. MS (ESI, m/z): 555.2 [M+H]+

Example 351: Synthesis of 7-((cyclopropylmethyl)amino)-2-(3-(2-((1,5-dimethyl-1H-pyrazol-3-yl)amino)-5-methylpyrimidin-4-yl)-1H-indol-7-yl)isoindolin-1-one

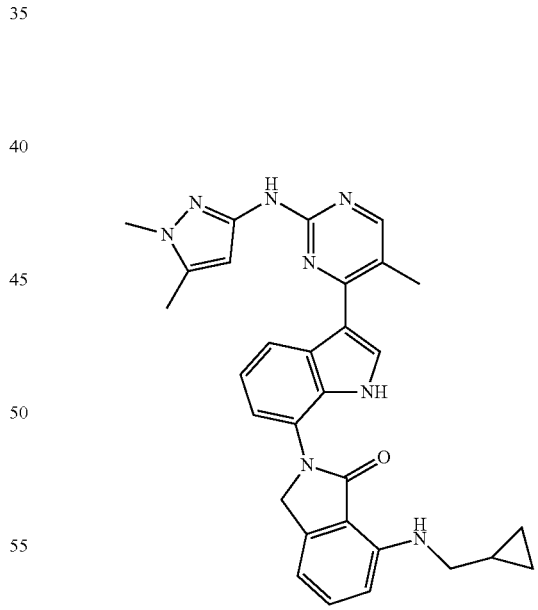

Using 7-chloro-2-(3-(2-((1,5-dimethyl-1H-pyrazol-3-yl)amino)-5-methylpyrimidin-4-yl)-1H-indol-7-yl)isoindolin-1-one and cyclopropylmethanamine, the title product was afforded as described for Example 346 in General Method H. MS (ESI, m/z): 519.2 [M+H]+

Example 352: Synthesis of 2-(3-(2-((1,5-dimethyl-1H-pyrazol-3-yl)amino)-5-methylpyrimidin-4-yl)-1H-indol-7-yl)-4-morpholinoisoindolin-1-one

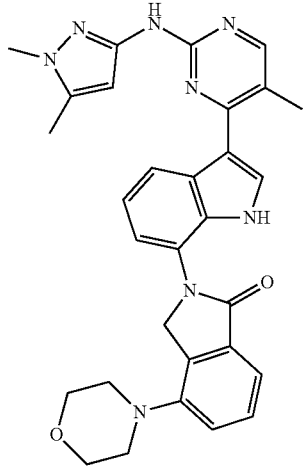

Using 4-bromo-2-(3-(2-((1,5-dimethyl-1H-pyrazol-3-yl)amino)-5-methylpyrimidin-4-yl)-1H-indol-7-yl)isoindolin-1-one and morpholine, the title product was afforded as described for Example 346 in General Method H. MS (ESI, m/z): 535.2 [M+H]$^+$ Example 353: Synthesis of 4-((cyclopropylmethyl)amino)-2-(3-(2-((1,5-dimethyl-1H-pyrazol-3-yl)amino)-5-methylpyrimidin-4-yl)-1H-indol-7-yl)isoindolin-1-one

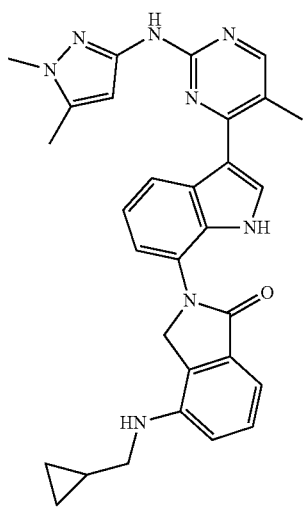

Using 4-bromo-2-(3-(2-((1,5-dimethyl-1H-pyrazol-3-yl)amino)-5-methylpyrimidin-4-yl)-1H-indol-7-yl)isoindolin-1-one and cyclopropylmethanamine, the title product was afforded as described for Example 346 in General Method H. MS (ESI, m/z): 519.2 [M+H]$^+$ Example 354: Synthesis of 4-(benzylamino)-2-(3-(2-((1,5-dimethyl-1H-pyrazol-3-yl)amino)-5-methylpyrimidin-4-yl)-1H-indol-7-yl)isoindolin-1-one

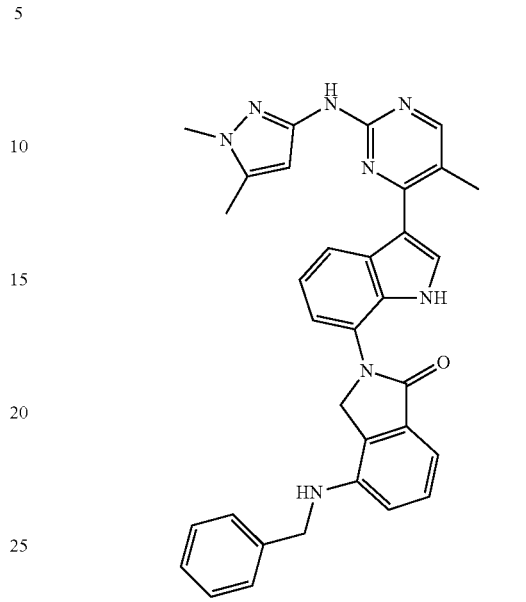

Using 4-bromo-2-(3-(2-((1,5-dimethyl-1H-pyrazol-3-yl)amino)-5-methylpyrimidin-4-yl)-1H-indol-7-yl)isoindolin-1-one and phenylmethanamine, the title product was afforded as described for Example 346 in General Method H. MS (ESI, m/z): 555.2 [M+H]$^+$ Example 355: Synthesis of 2-(3-(2-((1,5-dimethyl-1H-pyrazol-3-yl)amino)-5-methylpyrimidin-4-yl)-1H-indol-7-yl)-6-(phenylethynyl)isoindolin-1-one

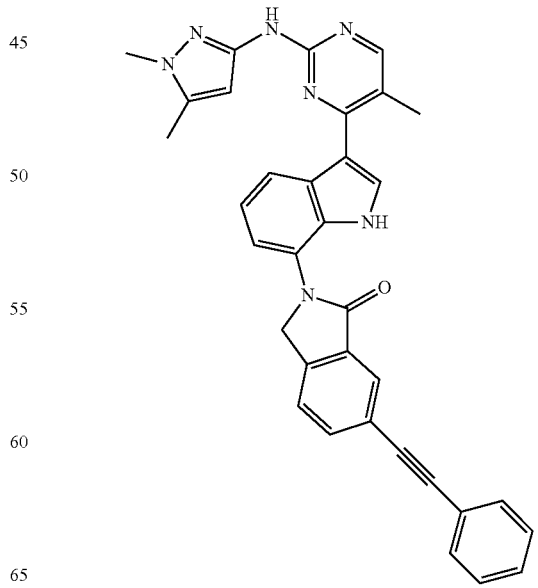

[General Method I]

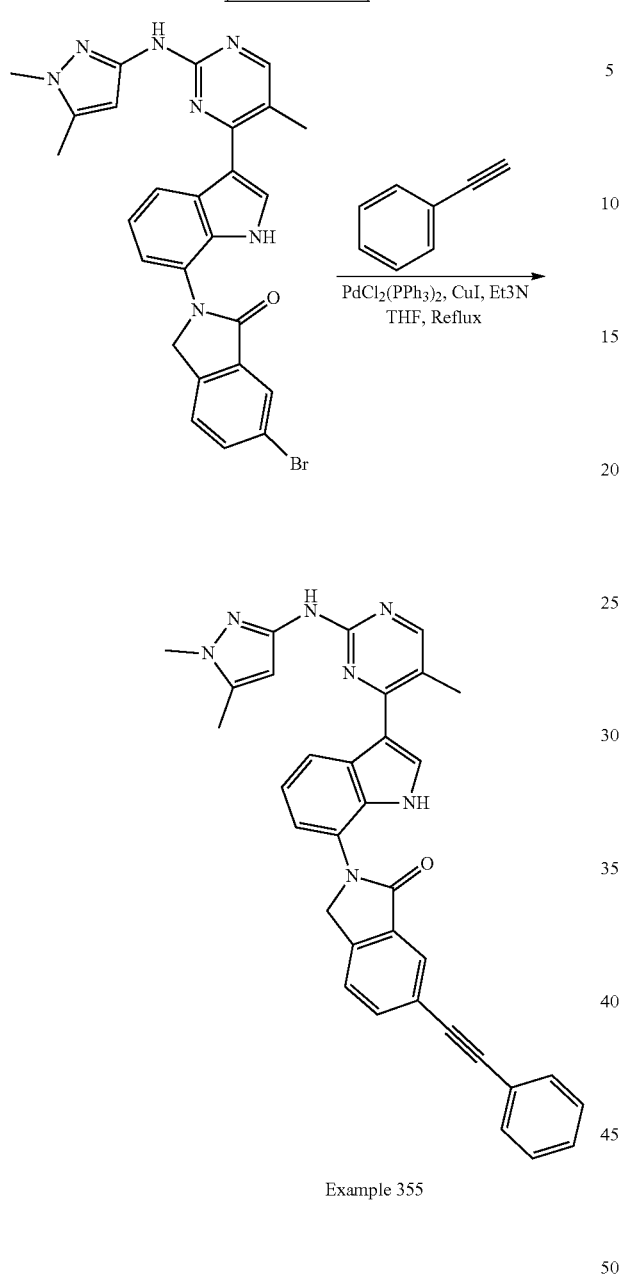

Example 355

A stirred mixture of 6-bromo-2-(3-(2-((1,5-dimethyl-1H-pyrazol-3-yl)amino)-5-methylpyrimidin-4-yl)-1H-indol-7-yl)isoindolin-1-one (prepared as Example 284, 53 mg, 0.10 mmol), PdCl$_2$(PPh$_3$)$_2$ (70 mg, 0.10 mmol) and CuI (19 mg, 0.10 mmol), Et$_3$N (42 uL, 0.03 mmol), and ethynylbenzene (11 mg, 0.11 mmol) in THF (1 mL) was heated to reflux for 12 h. After cooling to room temperature, the reaction mixture was separated from the UCT SPE CUBCX cartridge and purified by the Prep HPLC to afford a corresponding product as a white solid (yield, 70%).

$^1$H NMR (600 MHz, cd$_3$od) δ 8.84 (s, 1H), 8.31 (s, 1H), 8.14 (s, 1H), 7.91 (d, J=7.8 Hz, 1H), 7.84 (d, J=7.8 Hz, 1H), 7.65 (t, J=7.4 Hz, 1H), 7.58-7.54 (m, 2H), 7.43-7.37 (m, 5H), 5.94 (s, 1H), 5.15 (s, 2H), 3.79 (s, 3H), 2.52 (s, 3H), 2.32 (s, 3H).

MS (ESI, m/z): 550.2 [M+H]$^+$

Example 356: Synthesis of 2-(3-(2-((1,5-dimethyl-1H-pyrazol-3-yl)amino)-5-methylpyrimidin-4-yl)-1H-indol-7-yl)-4-(phenylethynyl)isoindolin-1-one

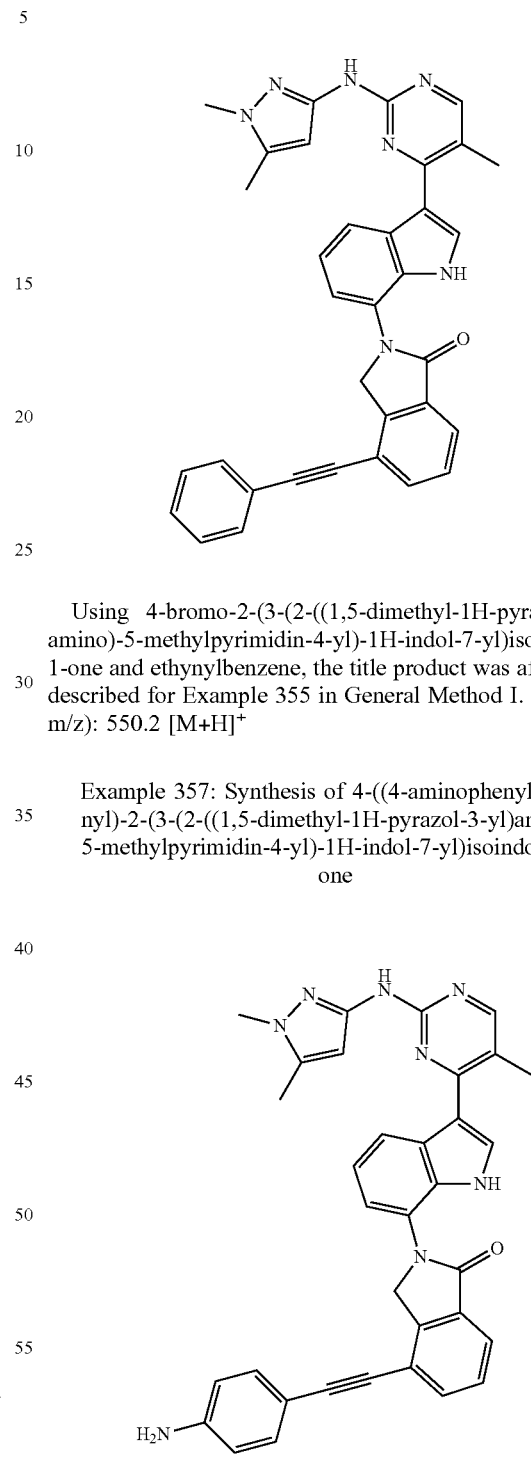

Using 4-bromo-2-(3-(2-((1,5-dimethyl-1H-pyrazol-3-yl)amino)-5-methylpyrimidin-4-yl)-1H-indol-7-yl)isoindolin-1-one and ethynylbenzene, the title product was afforded as described for Example 355 in General Method I. MS (ESI, m/z): 550.2 [M+H]$^+$ Example 357: Synthesis of 4-((4-aminophenyl)ethynyl)-2-(3-(2-((1,5-dimethyl-1H-pyrazol-3-yl)amino)-5-methylpyrimidin-4-yl)-1H-indol-7-yl)isoindolin-1-one

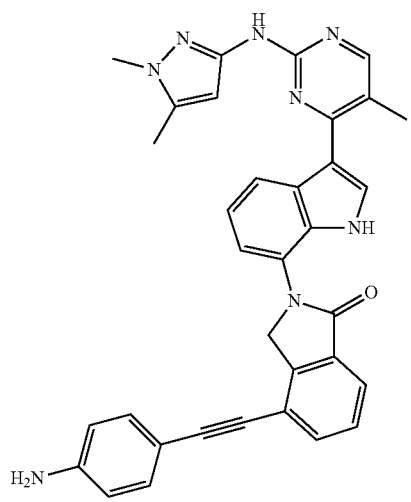 [SMILES: Cc1cnc(Nc2cc(C)n(C)n2)nc1-c1c[nH]c2c(N3Cc4c(C#Cc5ccc(N)cc5)cccc4C3=O)cccc12]

Using 4-bromo-2-(3-(2-((1,5-dimethyl-1H-pyrazol-3-yl)amino)-5-methylpyrimidin-4-yl)-1H-indol-7-yl)isoindolin-1-one and 4-ethynylaniline, the title product was afforded as described for Example 355 in General Method I. MS (ESI, m/z): 565.2 [M+H]$^+$ Example 358: Synthesis of (E)-3-(2-(3-(2-((1,5-dimethyl-1H-pyrazol-3-yl)amino)-5-methylpyrimidin-4-yl)-1H-indol-7-yl)-1-oxoisoindolin-4-yl)acrylamide

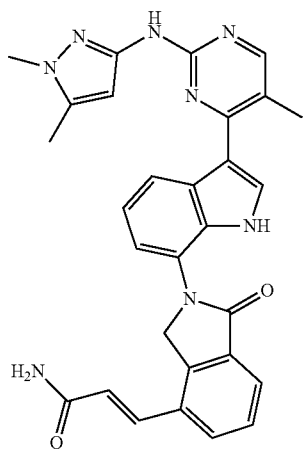

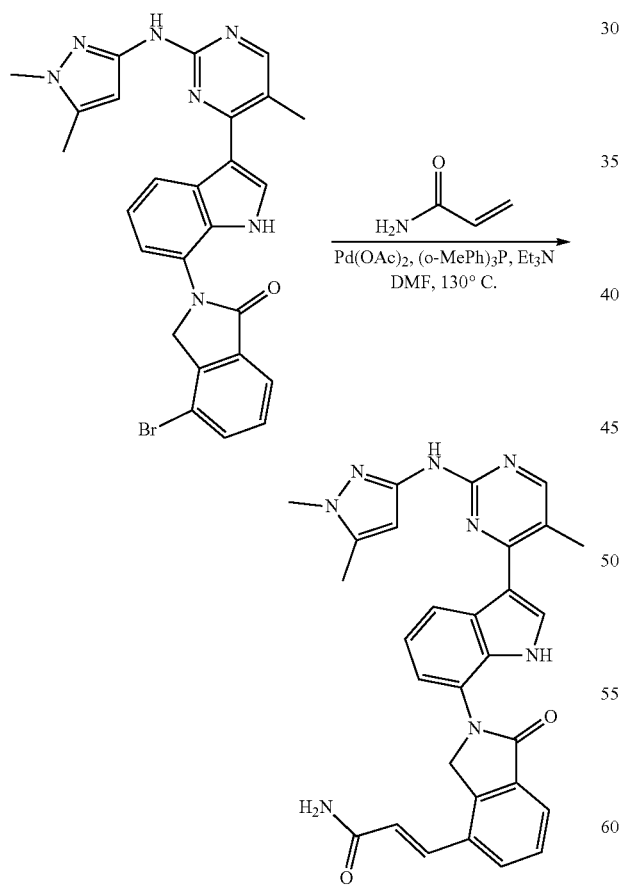

Example 358

A mixture of 4-bromo-2-(3-(2-((1,5-dimethyl-1H-pyrazol-3-yl)amino)-5-methylpyrimidin-4-yl)-1H-indol-7-yl) isoindolin-1-one (prepared as Example 266, 53 mg, 0.10 mmol), Pd(OAc)₂ (2 mg, 0.010 mmol), (o-MePh)₃P (6 mg, 0.020 mmol), Et₃N (42 uL, 0.030 mmol), and acrylamide (8 mg, 0.11 mmol) in DMF (1 mL) was heated to 130° C. for 12 h. After cooling to room temperature, the reaction mixture was separated from the UCT SPE CUBCX cartridge and purified by the Prep HPLC to afford a corresponding product as a white solid (yield, 75%).

$^1$H NMR (400 MHz, cd₃od) δ 8.88 (m, 2H), 8.39 (s, 1H), 8.23 (s, 1H), 8.03-7.90 (m, 1H), 7.71 (m, 2H), 7.47 (m, 2H), 6.78 (d, J=15.9 Hz, 1H), 5.98 (d, J=0.6 Hz, 1H), 5.26 (s, 2H), 3.83 (s, 3H), 2.58 (s, 3H), 2.35 (s, 3H). MS (ESI, m/z): 519.2 [M+H]⁺

Example 359: Synthesis of (E)-3-(2-(3-(2-((1,5-dimethyl-1H-pyrazol-3-yl)amino)-5-methylpyrimidin-4-yl)-1H-indol-7-yl)-7-fluoro-1-oxoisoindolin-4-yl)-N,N-dimethylacrylamide

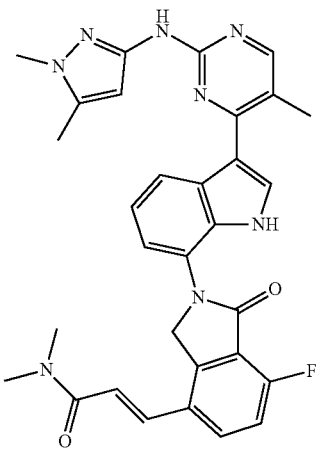 [SMILES: Cc1cnc(Nc2cc(C)n(C)n2)nc1-c1c[nH]c2c(N3Cc4c(/C=C/C(=O)N(C)C)ccc(F)c4C3=O)cccc12]

Using 4-bromo-2-(3-(2-((1,5-dimethyl-1H-pyrazol-3-yl)amino)-5-methylpyrimidin-4-yl)-1H-indol-7-yl)-7-fluoroisoindolin-1-one and N,N-dimethylacrylamide, the title product was afforded as described for Example 358 in General Method J. MS (ESI, m/z): 565.2 [M+H]⁺

Example 360: Synthesis of (E)-3-(2-(3-(2-((1,5-dimethyl-1H-pyrazol-3-yl)amino)-5-methylpyrimidin-4-yl)-1H-indol-7-yl)-1-oxoisoindolin-4-yl)-N,N-dimethylacrylamide

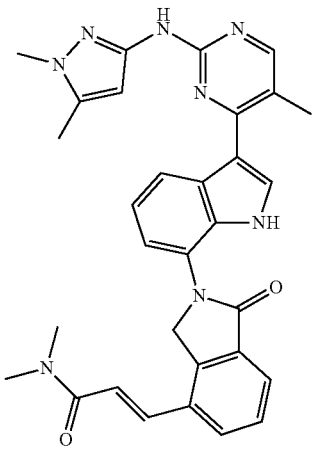

Using 4-bromo-2-(3-(2-((1,5-dimethyl-1H-pyrazol-3-yl)amino)-5-methylpyrimidin-4-yl)-1H-indol-7-yl)isoindolin-1-one and N,N-dimethylacrylamide, the title product was afforded as described for Example 358 in General Method J. MS (ESI, m/z): 547.2 [M+H]+

Example 361: Synthesis of (E)-3-(2-(3-(2-((1,5-dimethyl-1H-pyrazol-3-yl)amino)-5-methylpyrimidin-4-yl)-1H-indol-7-yl)-1-oxoisoindolin-4-yl)-2-methylacrylamide

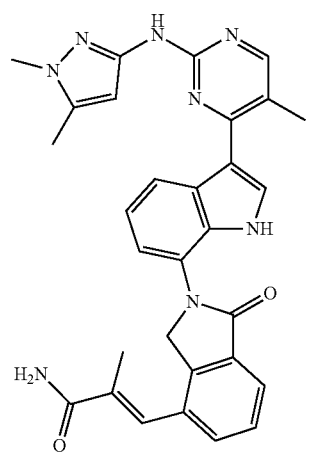

Using 4-bromo-2-(3-(2-((1,5-dimethyl-1H-pyrazol-3-yl)amino)-5-methylpyrimidin-4-yl)-1H-indol-7-yl)isoindolin-1-one and methacrylamide, the title product was afforded as described for Example 358 in General Method J. MS (ESI, m/z): 533.2 [M+H]+

Example 362: Synthesis of (E)-2-(3-(2-((1,5-dimethyl-1H-pyrazol-3-yl)amino)-5-methylpyrimidin-4-yl)-1H-indol-7-yl)-4-(3-oxobut-1-en-1-yl)isoindolin-1-one

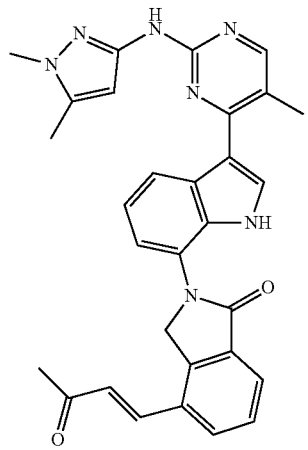

Using 4-bromo-2-(3-(2-((1,5-dimethyl-1H-pyrazol-3-yl)amino)-5-methylpyrimidin-4-yl)-1H-indol-7-yl)isoindolin-1-one and but-3-en-2-one, the title product was afforded as described for Example 358 in General Method J. MS (ESI, m/z): 518.2 [M+H]+

Example 363: Synthesis of (E)-3-(2-(3-(2-((1,5-dimethyl-1H-pyrazol-3-yl)amino)-5-methylpyrimidin-4-yl)-1H-indol-7-yl)-1-oxoisoindolin-4-yl)-N-methylacrylamide

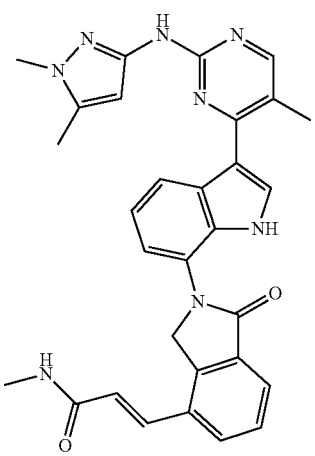

Using 4-bromo-2-(3-(2-((1,5-dimethyl-1H-pyrazol-3-yl)amino)-5-methylpyrimidin-4-yl)-1H-indol-7-yl)isoindolin-1-one and N-methylacrylamide, the title product was afforded as described for Example 358 in General Method J. MS (ESI, m/z): 533.2 [M+H]+

Example 364: Synthesis of (E)-3-(2-(3-(2-((1,5-dimethyl-1H-pyrazol-3-yl)amino)-5-methylpyrimidin-4-yl)-1H-indol-7-yl)-1-oxoisoindolin-4-yl)-N-ethylacrylamide

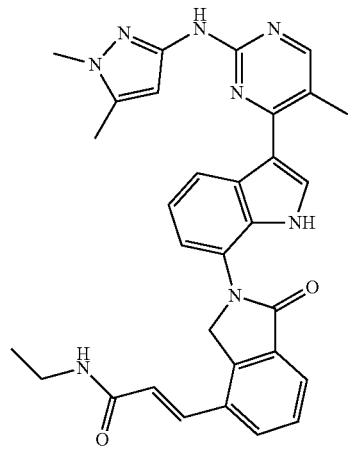 [SMILES: CCNC(=O)/C=C/c1cccc2c1CN(c1cccc3c(-c4nc(Nc5cc(C)n(C)n5)ncc4C)c[nH]c13)C2=O]

Using 4-bromo-2-(3-(2-((1,5-dimethyl-1H-pyrazol-3-yl)amino)-5-methylpyrimidin-4-yl)-1H-indol-7-yl)isoindolin-1-one and N-ethylacrylamide, the title product was afforded as described for Example 358 in General Method J. MS (ESI, m/z): 547.2 [M+H]$^+$ Example 365: Synthesis of (E)-N-cyclopropyl-3-(2-(3-(2-((1,5-dimethyl-1H-pyrazol-3-yl)amino)-5-methylpyrimidin-4-yl)-1H-indol-7-yl)-1-oxoisoindolin-4-yl)acrylamide

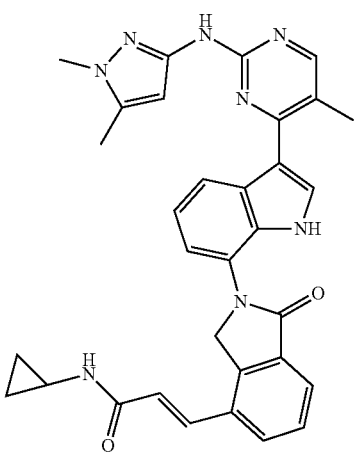 [SMILES: Cc1cnc(Nc2cc(C)n(C)n2)nc1-c1c[nH]c2c(N3Cc4c(/C=C/C(=O)NC5CC5)cccc4C3=O)cccc12]

Using 4-bromo-2-(3-(2-((1,5-dimethyl-1H-pyrazol-3-yl)amino)-5-methylpyrimidin-4-yl)-1H-indol-7-yl)isoindolin-1-one and N-cyclopropylacrylamide, the title product was afforded as described for Example 358 in General Method J. MS (ESI, m/z): 559.2 [M+H]$^+$ Example 366: Synthesis of (E)-3-(2-(3-(2-((1,5-dimethyl-1H-pyrazol-3-yl)amino)-5-methylpyrimidin-4-yl)-1H-indol-7-yl)-1-oxoisoindolin-4-yl)acrylohydrazide

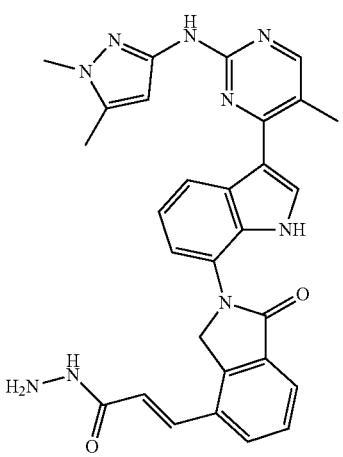 [SMILES: Cc1cnc(Nc2cc(C)n(C)n2)nc1-c1c[nH]c2c(N3Cc4c(/C=C/C(=O)NN)cccc4C3=O)cccc12]

Using 4-bromo-2-(3-(2-((1,5-dimethyl-1H-pyrazol-3-yl)amino)-5-methylpyrimidin-4-yl)-1H-indol-7-yl)isoindolin-1-one and acrylohydrazide, the title product was afforded as described for Example 358 in General Method J. MS (ESI, m/z): 534.2 [M+H]$^+$ Example 367: Synthesis of (E)-3-(2-(3-(2-((1,5-dimethyl-1H-pyrazol-3-yl)amino)-5-methylpyrimidin-4-yl)-1H-indol-7-yl)-1-oxoisoindolin-4-yl) acrylic acid

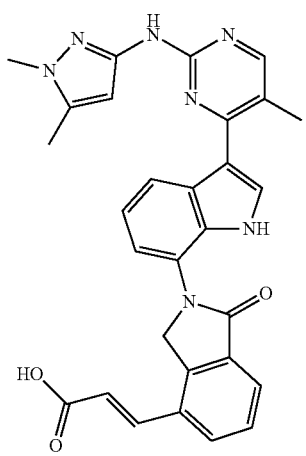

Using 4-bromo-2-(3-(2-((1,5-dimethyl-1H-pyrazol-3-yl)amino)-5-methylpyrimidin-4-yl)-1H-indol-7-yl)isoindolin-1-one and acrylic acid, the title product was afforded as described for Example 358 in General Method J. MS (ESI, m/z): 520.2 [M+H]$^+$ Example 368: Synthesis of (E)-3-(2-(3-(2-((1,5-dimethyl-1H-pyrazol-3-yl)amino)-5-methylpyrimidin-4-yl)-1H-indol-7-yl)-1-oxoisoindolin-4-yl)-N,N-diethylacrylamide

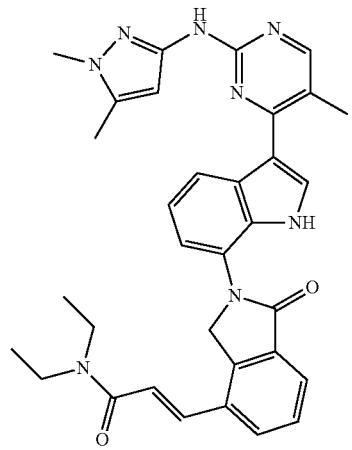 [SMILES: CCN(CC)C(=O)/C=C/c1cccc2c1CN(c1cccc3c(-c4nc(Nc5cc(C)n(C)n5)ncc4C)c[nH]c13)C2=O]

Using 4-bromo-2-(3-(2-((1,5-dimethyl-1H-pyrazol-3-yl)amino)-5-methylpyrimidin-4-yl)-1H-indol-7-yl)isoindolin-1-one and N,N-diethylacrylamide, the title product was afforded as described for Example 358 in General Method J. MS (ESI, m/z): 575.2 [M+H]$^+$ Example 369: Synthesis of (E)-N,N-dibutyl-3-(2-(3-(2-((1,5-dimethyl-1H-pyrazol-3-yl)amino)-5-methylpyrimidin-4-yl)-1H-indol-7-yl)-1-oxoisoindolin-4-yl)acrylamide

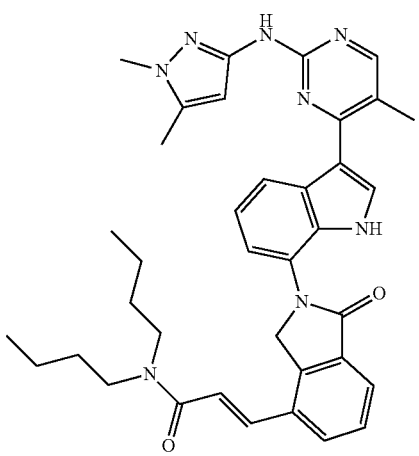 [SMILES: CCCCN(CCCC)C(=O)/C=C/c1cccc2c1CN(c1cccc3c(-c4nc(Nc5cc(C)n(C)n5)ncc4C)c[nH]c13)C2=O]

Using 4-bromo-2-(3-(2-((1,5-dimethyl-1H-pyrazol-3-yl)amino)-5-methylpyrimidin-4-yl)-1H-indol-7-yl)isoindolin-1-one and N,N-dibutylacrylamide, the title product was afforded as described for Example 358 in General Method J. MS (ESI, m/z): 631.3 [M+H]$^+$ Example 370: Synthesis of (E)-3-(2-(3-(2-((1,5-dimethyl-1H-pyrazol-3-yl)amino)-5-methylpyrimidin-4-yl)-1H-indol-7-yl)-1-oxoisoindolin-4-yl)-N-isopropylacrylamide

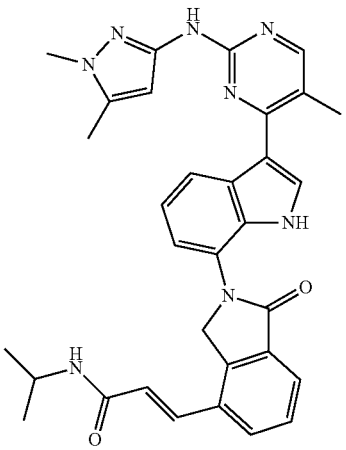 [SMILES: Cc1cnc(Nc2cc(C)n(C)n2)nc1-c1c[nH]c2c(N3Cc4c(/C=C/C(=O)NC(C)C)cccc4C3=O)cccc12]

Using 4-bromo-2-(3-(2-((1,5-dimethyl-1H-pyrazol-3-yl)amino)-5-methylpyrimidin-4-yl)-1H-indol-7-yl)isoindolin-1-one and N-isopropylacrylamide, the title product was afforded as described for Example 358 in General Method J. MS (ESI, m/z): 577.3 [M+H]$^+$ Example 371: Synthesis of (E)-N-(tert-butyl)-3-(2-(3-(2-((1,5-dimethyl-1H-pyrazol-3-yl)amino)-5-methylpyrimidin-4-yl)-1H-indol-7-yl)-1-oxoisoindolin-4-yl)acrylamide

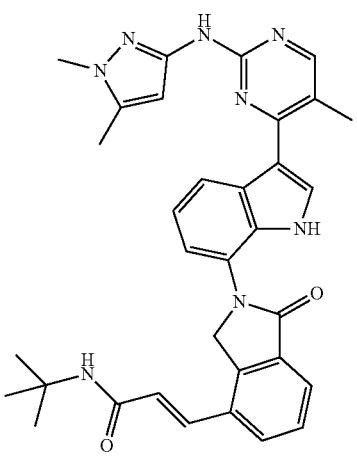 [SMILES: Cc1cnc(Nc2cc(C)n(C)n2)nc1-c1c[nH]c2c(N3Cc4c(/C=C/C(=O)NC(C)(C)C)cccc4C3=O)cccc12]

Using 4-bromo-2-(3-(2-((1,5-dimethyl-1H-pyrazol-3-yl)amino)-5-methylpyrimidin-4-yl)-1H-indol-7-yl)isoindolin-1-one and N-(tert-butyl)acrylamide, the title product was afforded as described for Example 358 in General Method J. MS (ESI, m/z): 575.2 [M+H]$^+$ Example 372: Synthesis of (E)-3-(2-(3-(2-((1,5-dimethyl-1H-pyrazol-3-yl)amino)-5-methylpyrimidin-4-yl)-1H-indol-7-yl)-1-oxoisoindolin-4-yl)-N-(2-hydroxyethyl)acrylamide

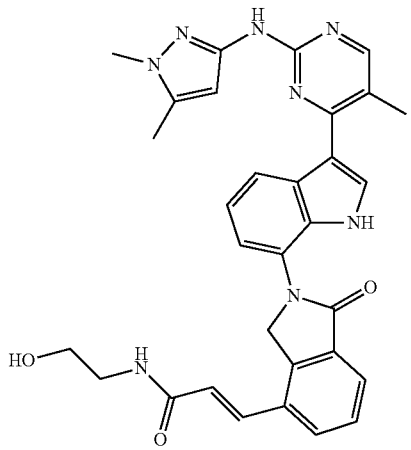 [SMILES: Cc1cnc(Nc2cc(C)n(C)n2)nc1-c1c[nH]c2c(N3Cc4c(/C=C/C(=O)NCCO)cccc4C3=O)cccc12]

Using 4-bromo-2-(3-(2-((1,5-dimethyl-1H-pyrazol-3-yl)amino)-5-methylpyrimidin-4-yl)-1H-indol-7-yl)isoindolin-1-one and N-(2-hydroxyethyl)acrylamide, the title product was afforded as described for Example 358 in General Method J. MS (ESI, m/z): 563.2 [M+H]$^+$ Example 373: Synthesis of (E)-3-(2-(3-(2-((1,5-dimethyl-1H-pyrazol-3-yl)amino)-5-methylpyrimidin-4-yl)-1H-indol-7-yl)-1-oxoisoindolin-4-yl)-N-propylacrylamide

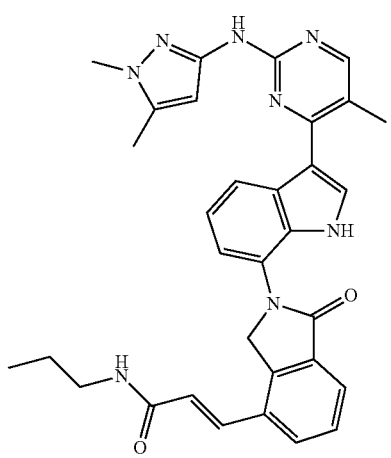 [SMILES: CCCNC(=O)/C=C/c1cccc2c1CN(c1cccc3c(-c4nc(Nc5cc(C)n(C)n5)ncc4C)c[nH]c13)C2=O]

Using 4-bromo-2-(3-(2-((1,5-dimethyl-1H-pyrazol-3-yl)amino)-5-methylpyrimidin-4-yl)-1H-indol-7-yl)isoindolin-1-one and N-propylacrylamide, the title product was afforded as described for Example 358 in General Method J. MS (ESI, m/z): 561.2 [M+H]$^+$ Example 374: Synthesis of (E)-3-(2-(3-(2-((1,5-dimethyl-1H-pyrazol-3-yl)amino)-5-methylpyrimidin-4-yl)-1H-indol-7-yl)-1-oxoisoindolin-4-yl)-N-(2-methoxyethyl)acrylamide

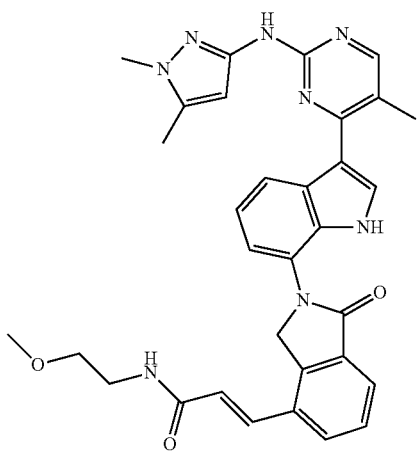

Using 4-bromo-2-(3-(2-((1,5-dimethyl-1H-pyrazol-3-yl)amino)-5-methylpyrimidin-4-yl)-1H-indol-7-yl)isoindolin-1-one and N-(2-methoxyethyl)acrylamide, the title product was afforded as described for Example 358 in General Method J. MS (ESI, m/z): 577.2 [M+H]$^+$ Example 375: Synthesis of (E)-2-(3-(2-((1,5-dimethyl-1H-pyrazol-3-yl)amino)-5-methylpyrimidin-4-yl)-1H-indol-7-yl)-4-(3-hydroxyprop-1-en-1-yl)isoindolin-1-one

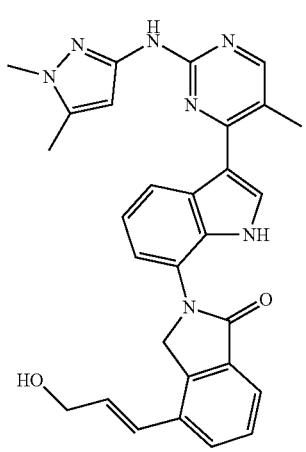

Using 4-bromo-2-(3-(2-((1,5-dimethyl-1H-pyrazol-3-yl)amino)-5-methylpyrimidin-4-yl)-1H-indol-7-yl)isoindolin-1-one and prop-2-en-1-ol, the title product was afforded as described for Example 358 in General Method J. MS (ESI, m/z): 506.2 [M+H]$^+$ Example 376: Synthesis of (E)-3-(2-(3-(2-((1,5-dimethyl-1H-pyrazol-3-yl)amino)-5-methylpyrimidin-4-yl)-1H-indol-7-yl)-1-oxoisoindolin-4-yl)-N-ethyl-2-methylacrylamide

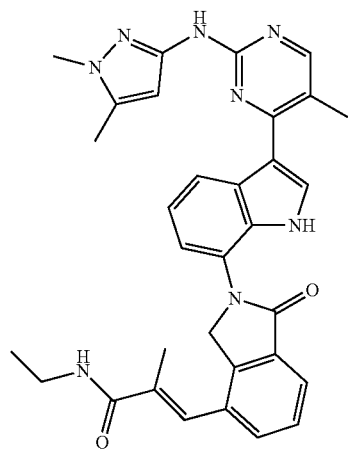 [SMILES: CCNC(=O)/C(C)=C/c1cccc2c1CN(c1cccc3c(-c4nc(Nc5cc(C)n(C)n5)ncc4C)c[nH]c13)C2=O]

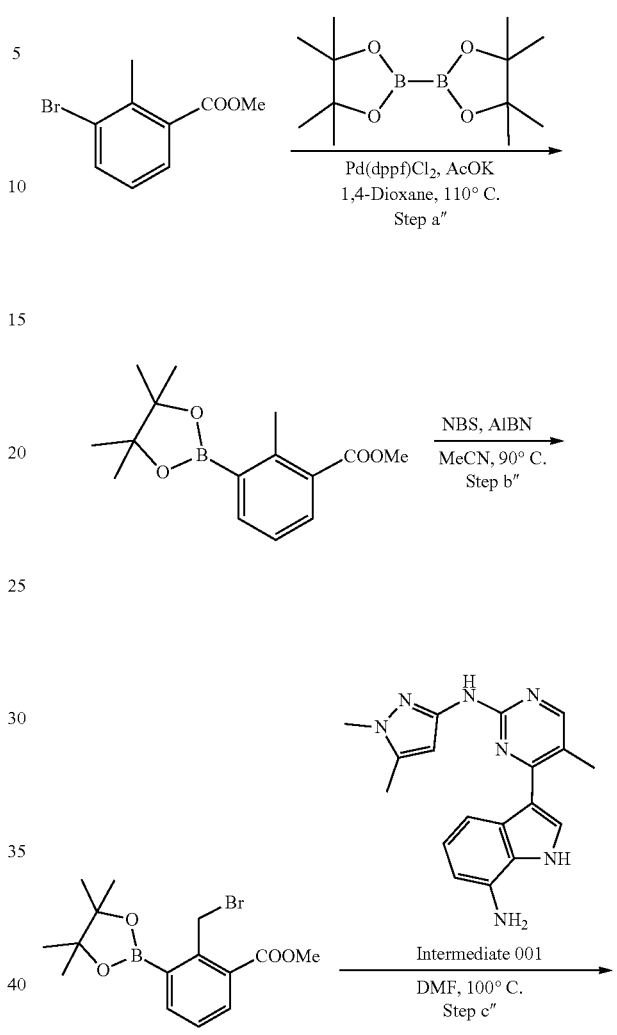

[General Method K]

Using 4-bromo-2-(3-(2-((1,5-dimethyl-1H-pyrazol-3-yl)amino)-5-methylpyrimidin-4-yl)-1H-indol-7-yl)isoindolin-1-one and N-ethylmethacrylamide, the title product was afforded as described for Example 358 in General Method J. MS (ESI, m/z): 561.2 [M+H]+

Example 377: Synthesis of 2-(3-(2-((1,5-dimethyl-1H-pyrazol-3-yl)amino)-5-methylpyrimidin-4-yl)-1H-indol-7-yl)-4-phenylisoindolin-1-one

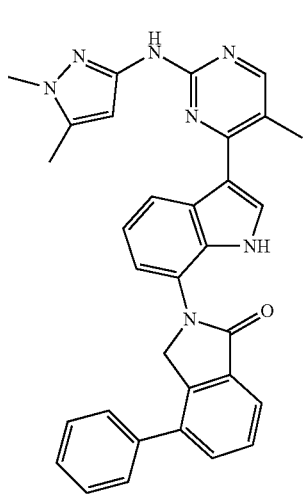

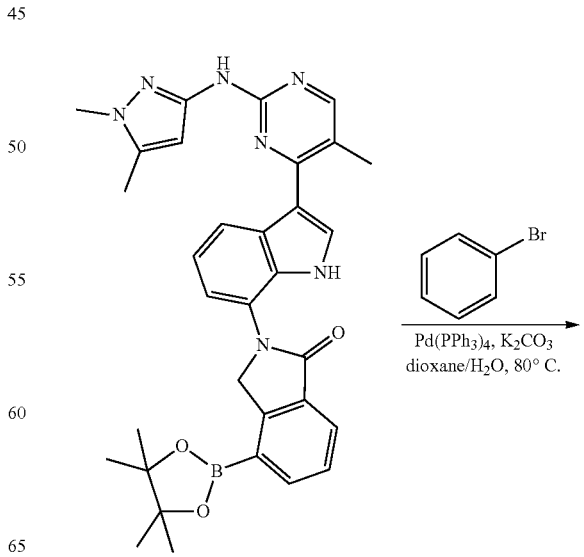

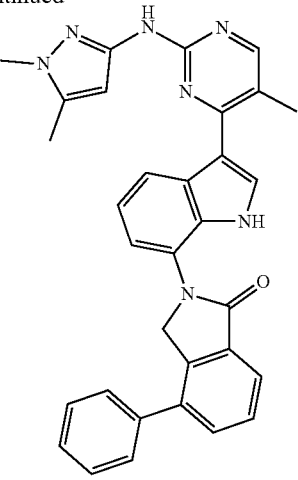

Example 377

[Step a'''] Preparation of Methyl 2-methyl-3-(4,4,5,5-tetramethyl-1,3,2-dioxaborolan-2-yl)benzoate. A suspension of methyl 3-bromo-2-methylbenzoate (1.150 g, 5.0 mmol) in 1,4-Dioxane (18 mL) were treated with 4,4,4',4',5,5,5',5'-octamethyl-2,2'-bi(1,3,2-dioxaborolane) (1.90 g, 7.50 mmol), Pd(dppf)Cl$_2$ (182.9 mg, 0.250 mmol) and potassium acetate (1.47 g, 15.0 mmol). The resulting mixture was heated at 110° C. for overnight. After cooling to room temperature, the reaction mixture was filtrated with the Celite®. Then, the filtrate was concentrated to dryness in vacuo, and purified from the flash column chromatography eluting %30 EtOAc in n-Hex. The desired fractions were concentrated to dryness in vacuo to the corresponding product as a colorless oil (yield, 85%). $^1$H NMR (600 MHz, CDCl$_3$) δ 7.55-7.81 (m, 2H), 7.19 (t, 1H), 3.86 (s, 3H), 2.72 (s, 3H), 1.34 (s, 12H). MS (ESI, m/z): 277.1 [M+H]$^+$

[Step b'''] Preparation of methyl 2-(bromomethyl)-3-(4,4,5,5-tetramethyl-1,3,2-dioxaborolan-2-yl)benzoate. A suspension of methyl 2-methyl-3-(4,4,5,5-tetramethyl-1,3,2-dioxaborolan-2-yl)benzoate (1.18 g, 4.27 mmol) in MeCN (15 mL) were treated with NBS (912.9 mg, 5.12 mmol) and ABIN (350.9 mg, 2.13 mmol) under N$_2$. The resulting mixture was heated at 90° C. for 3 h. The reaction mixture was cooled to room temperature and extracted into DCM (3×50 mL) from water (50 mL). The combined organic extracts were dried over Na$_2$SO$_4$, filtered and concentrated in vacuo.

The crude was then purified by flash column chromatography eluting %30 EtOAc in n-Hex. The desired fractions were concentrated to dryness in vacuo to afford the corresponding product as a colorless oil (yield, 84%). $^1$H NMR (600 MHz, CDCl$_3$) δ 7.84-7.86 (m, 2H) 7.24 (t, 1H), 5.33 (s, 2H), 3.84 (s, 3H), 1.28 (s, 12H). MS (ESI, m/z): 355.0 [M+H]$^+$

[Step c'''] A suspension of 3-(2-((1,5-dimethyl-1H-pyrazol-3-yl)amino)-5-methylpyrimidin-4-yl)-1H-indol-7-amine (prepared as an Intermediate 001, 166.5 mg, 0.50 mmol) in DMF (2 mL) was treated methyl 2-(bromomethyl)-3-(4,4,5,5-tetramethyl-1,3,2-dioxaborolan-2-yl)benzoate (212.4 mg, 0.60 mmol). The resulting mixture was heated at 100° C. for 1 h. The reaction mixture was cooled to room temperature and extracted into DCM (3×50 mL) from water (50 mL). The combined organic extracts were dried over Na$_2$SO$_4$, filtered and concentrated in vacuo. The resulting mixture was dried in vacuo and used without further purifications. MS (ESI, m/z): 576.2 [M+H]$^+$ To a mixture of 2-(3-(2-(((1,5-dimethyl-1H-pyrazol-3-yl)amino)-5-methylpyrimidin-4-yl)-1H-indol-7-yl)-4-(4,4,5,5-tetramethyl-1,3,2-dioxaborolan-2-yl)isoindolin-1-one (48 mg, 0.084 mmol), Pd(PPh$_3$)$_4$ (8 mg, 0.007 mmol), and potassium carbonate (19 mg, 0.140 mmol) in 1,4-Dioxane (0.7 mL) and H$_2$O (0.3 mL) was added bromobenzene (11 mg, 0.070 mmol). The reaction mixture was heated to 100° C. for 12 h. After cooling to room temperature, the reaction mixture was separated from the UCT SPE CUBCX cartridge and purified by the Prep HPLC to afford a corresponding product as a white solid (yield, 50%).

$^1$H NMR (600 MHz, cd$_3$od) δ 8.88 (brs, 1H), 8.81 (s, 1H), 8.39 (s, 1H), 8.22 (brs, 1H), 8.12 (d, J=7.8 Hz, 1H), 8.07 (d, J=7.8 Hz, 1H), 8.00 (d, J=7.8 Hz, 1H), 7.85-7.75 (m, 3H), 7.41-7.47 (m, 3H), 5.97 (s, 1H), 5.33 (s, 2H), 3.82 (s, 3H), 2.57 (s, 3H), 2.34 (s, 3H). MS (ESI, m/z): 526.2 [M+H]$^+$ Example 378: Synthesis of 2-(3-(2-((1,5-dimethyl-1H-pyrazol-3-yl)amino)-5-methylpyrimidin-4-yl)-1H-indol-7-yl)-5-phenylisoindolin-1-one

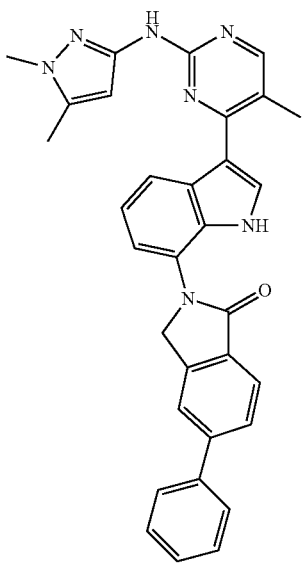

Using methyl 4-bromo-2-methylbenzoate and bromobenzene, the title product was afforded as described for Example 377 in General Method K. MS (ESI, m/z): 526.2 [M+H]$^+$ Example 379: Synthesis of 2-(3-(2-((1,5-dimethyl-1H-pyrazol-3-yl)amino)-5-methylpyrimidin-4-yl)-1H-indol-7-yl)-6-phenylisoindolin-1-one

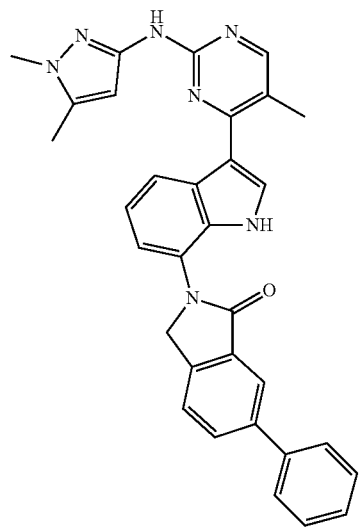 [SMILES: Cc1cnc(Nc2cc(C)n(C)n2)nc1-c1c[nH]c2c(N3Cc4ccc(-c5ccccc5)cc4C3=O)cccc12]

Using methyl 5-bromo-2-methylbenzoate and bromobenzene, the title product was afforded as described for Example 377 in General Method K. MS (ESI, m/z): 526.2 [M+H]+

Example 380: Synthesis of 2-(3-(2-((1,5-dimethyl-1H-pyrazol-3-yl)amino)-5-methylpyrimidin-4-yl)-1H-indol-7-yl)-6-(pyridin-4-yl)isoindolin-1-one

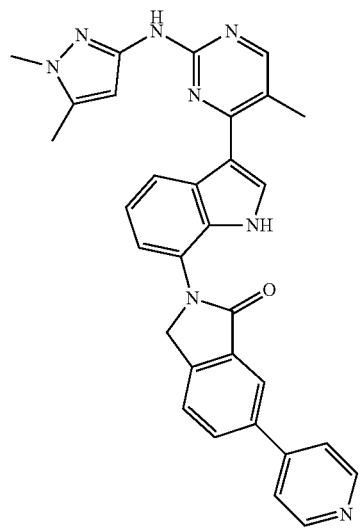 [SMILES: Cc1cnc(Nc2cc(C)n(C)n2)nc1-c1c[nH]c2c(N3Cc4ccc(-c5ccncc5)cc4C3=O)cccc12]

Using methyl 5-bromo-2-methylbenzoate and 4-bromopyridine, the title product was afforded as described for Example 377 in General Method K. MS (ESI, m/z): 527.2 [M+H]+

Example 381: Synthesis of 2-(3-(2-((1,5-dimethyl-1H-pyrazol-3-yl)amino)-5-methylpyrimidin-4-yl)-1H-indol-7-yl)-6-(1,2,3,6-tetrahydropyridin-4-yl)isoindolin-1-one

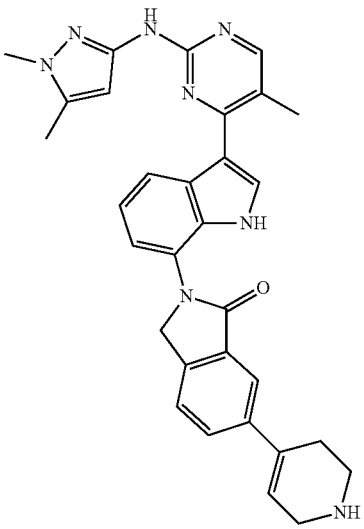 [SMILES: Cc1cnc(Nc2cc(C)n(C)n2)nc1-c1c[nH]c2c(N3Cc4ccc(C5=CCNCC5)cc4C3=O)cccc12]

Using methyl 5-bromo-2-methylbenzoate and tert-butyl 4-bromo-3,6-dihydropyridine-1(2H)-carboxylate, the title product was afforded as described for Example 377 in General Method K (Boc group of the product was deprotected during the reaction). MS (ESI, m/z): 531.2 [M+H]+

Example 382: Synthesis of 2-(3-(2-((1,5-dimethyl-1H-pyrazol-3-yl)amino)-5-methylpyrimidin-4-yl)-1H-indol-7-yl)-7-phenylisoindolin-1-one

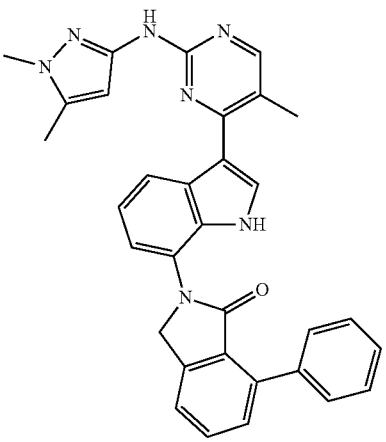 [SMILES: Cc1cnc(Nc2cc(C)n(C)n2)nc1-c1c[nH]c2c(N3Cc4cccc(-c5ccccc5)c4C3=O)cccc12]

Using methyl 2-bromo-6-methylbenzoate and bromobenzene, the title product was afforded as described for Example 377 in General Method K. MS (ESI, m/z): 526.2 [M+H]+

Example 383: Synthesis of 2-(3-(2-((1,5-dimethyl-1H-pyrazol-3-yl)amino)-5-methylpyrimidin-4-yl)-1H-indol-7-yl)-7-(pyridin-4-yl)isoindolin-1-one

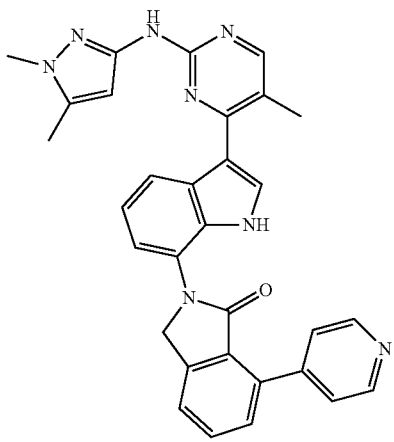 [SMILES: Cc1cnc(Nc2cc(C)n(C)n2)nc1-c1c[nH]c2c(N3Cc4cccc(-c5ccncc5)c4C3=O)cccc12]

Using methyl 2-bromo-6-methylbenzoate and 4-bromopyridine, the title product was afforded as described for Example 377 in General Method K. MS (ESI, m/z): 527.2 [M+H]⁺

Example 384: Synthesis of 7-(cyclohex-1-en-1-yl)-2-(3-(2-((1,5-dimethyl-1H-pyrazol-3-yl)amino)-5-methylpyrimidin-4-yl)-1H-indol-7-yl)isoindolin-1-one

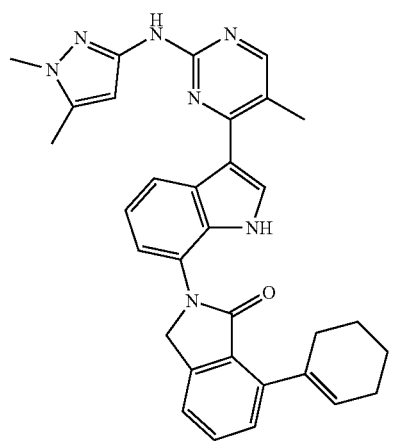 [SMILES: Cc1cnc(Nc2cc(C)n(C)n2)nc1-c1c[nH]c2c(N3Cc4cccc(C5=CCCCC5)c4C3=O)cccc12]

Using methyl 2-bromo-6-methylbenzoate and 1-bromocyclohex-1-ene, the title product was afforded as described for Example 377 in General Method K. MS (ESI, m/z): 530.2 [M+H]⁺

Example 385: Synthesis of 7-(3,6-dihydro-2H-pyran-4-yl)-2-(3-(2-((1,5-dimethyl-1H-pyrazol-3-yl)amino)-5-methylpyrimidin-4-yl)-1H-indol-7-yl)isoindolin-1-one

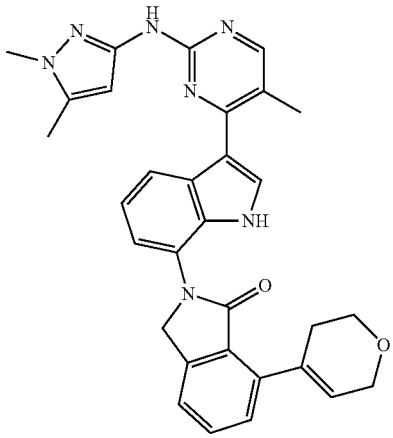 [SMILES: Cc1cnc(Nc2cc(C)n(C)n2)nc1-c1c[nH]c2c(N3Cc4cccc(C5=CCOCC5)c4C3=O)cccc12]

Using methyl 2-bromo-6-methylbenzoate and 4-bromo-3,6-dihydro-2H-pyran, the title product was afforded as described for Example 377 in General Method K. MS (ESI, m/z): 532.2 [M+H]⁺

Example 386: Synthesis of 2-(3-(2-((1,5-dimethyl-1H-pyrazol-3-yl)amino)-5-methylpyrimidin-4-yl)-1H-indol-7-yl)-7-(1H-pyrazol-4-yl)isoindolin-1-one

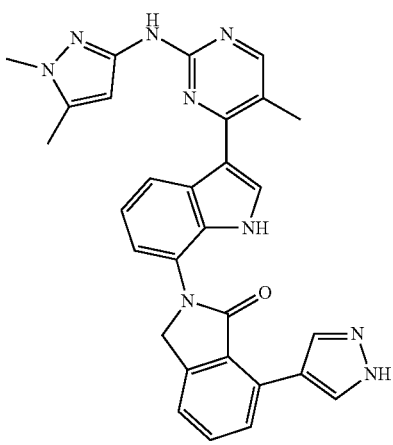 [SMILES: Cc1cnc(Nc2cc(C)n(C)n2)nc1-c1c[nH]c2c(N3Cc4cccc(-c5cn[nH]c5)c4C3=O)cccc12]

Using methyl 2-bromo-6-methylbenzoate and 4-bromo-1H-pyrazole, the title product was afforded as described for Example 377 in General Method K. MS (ESI, m/z): 516.2 [M+H]⁺

Example 387: Synthesis of 2-(3-(2-((1,5-dimethyl-1H-pyrazol-3-yl)amino)-5-methylpyrimidin-4-yl)-1H-indol-7-yl)-4-(pyridin-4-yl)isoindolin-1-one

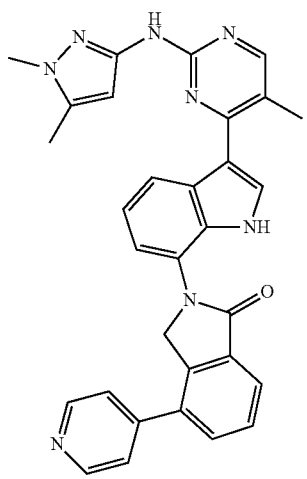

Using methyl 3-bromo-2-methylbenzoate and 4-bromopyridine, the title product was afforded as described for Example 377 in General Method K. MS (ESI, m/z): 527.2 [M+H]+

Example 388: Synthesis of 2-(3-(2-((1,5-dimethyl-1H-pyrazol-3-yl)amino)-5-methylpyrimidin-4-yl)-1H-indol-7-yl)-4-(pyridin-3-yl)isoindolin-1-one

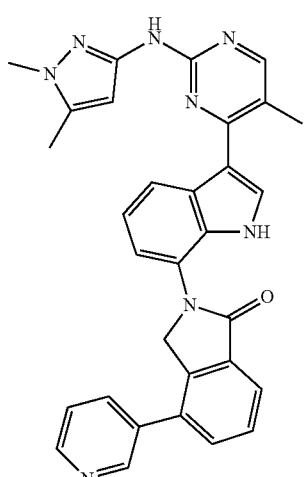

Using methyl 3-bromo-2-methylbenzoate and 3-chloropyridine, the title product was afforded as described for Example 377 in General Method K. MS (ESI, m/z): 527.2 [M+H]+

Example 389: Synthesis of 2-(3-(2-((1,5-dimethyl-1H-pyrazol-3-yl)amino)-5-methylpyrimidin-4-yl)-1H-indol-7-yl)-4-(1-methyl-1H-pyrazol-4-yl)isoindolin-1-one

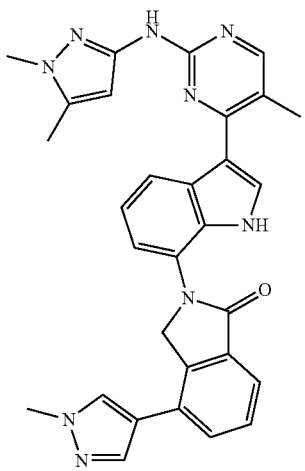

Using methyl 3-bromo-2-methylbenzoate and 4-bromo-1-methyl-1H-pyrazole, the title product was afforded as described for Example 377 in General Method K. MS (ESI, m/z): 530.2 [M+H]+

Example 390: Synthesis of 2-(3-(2-((1,5-dimethyl-1H-pyrazol-3-yl)amino)-5-methylpyrimidin-4-yl)-1H-indol-7-yl)-4-(1H-pyrazol-4-yl)isoindolin-1-one

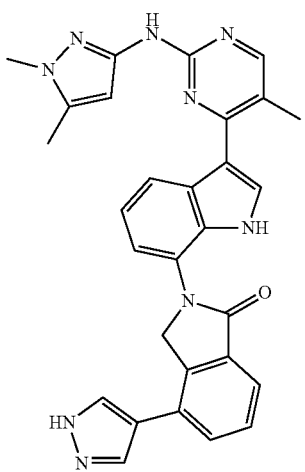

Using methyl 3-bromo-2-methylbenzoate and 4-bromo-1H-pyrazole, the title product was afforded as described for Example 377 in General Method K. MS (ESI, m/z): 516.2 [M+H]+

Example 391: Synthesis of 4-(cyclohex-1-en-1-yl)-2-(3-(2-((1,5-dimethyl-1H-pyrazol-3-yl)amino)-5-methylpyrimidin-4-yl)-1H-indol-7-yl)isoindolin-1-one

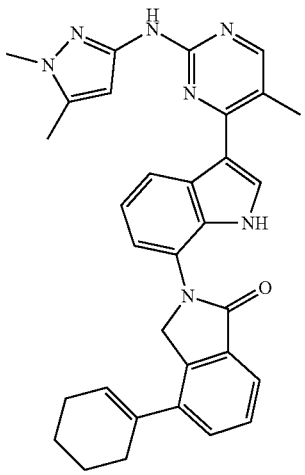

Using methyl 3-bromo-2-methylbenzoate and 1-bromocyclohex-1-ene, the title product was afforded as described for Example 377 in General Method K. MS (ESI, m/z): 530.2 [M+H]$^+$ Example 392: Synthesis of 4-(3,6-dihydro-2H-pyran-4-yl)-2-(3-(2-((1,5-dimethyl-1H-pyrazol-3-yl)amino)-5-methylpyrimidin-4-yl)-1H-indol-7-yl)isoindolin-1-one

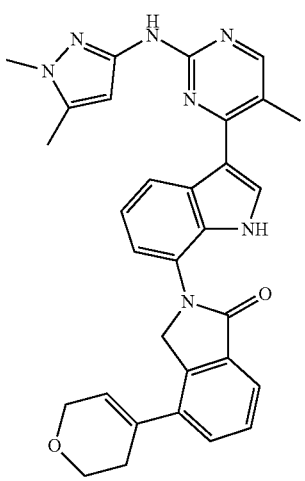

Using methyl 3-bromo-2-methylbenzoate and 4-bromo-3,6-dihydro-2H-pyran, the title product was afforded as described for Example 377 in General Method K. MS (ESI, m/z): 532.2 [M+H]$^+$ Example 393: Synthesis of 2-(3-(2-((1,5-dimethyl-1H-pyrazol-3-yl)amino)-5-methylpyrimidin-4-yl)-1H-indol-7-yl)-4-(furan-3-yl)isoindolin-1-one

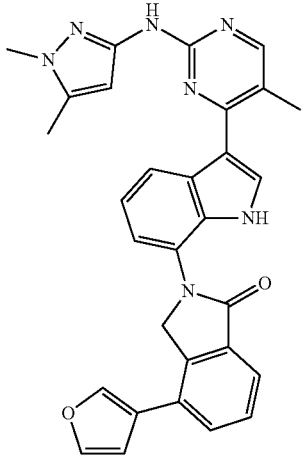

Using methyl 3-bromo-2-methylbenzoate and 3-bromofuran, the title product was afforded as described for Example 377 in General Method K. MS (ESI, m/z): 516.2 [M+H]$^+$ Example 394: Synthesis of 2-(3-(2-((1,5-dimethyl-1H-pyrazol-3-yl)amino)-5-methylpyrimidin-4-yl)-1H-indol-7-yl)-4-(1,2,3,6-tetrahydropyridin-4-yl)isoindolin-1-one

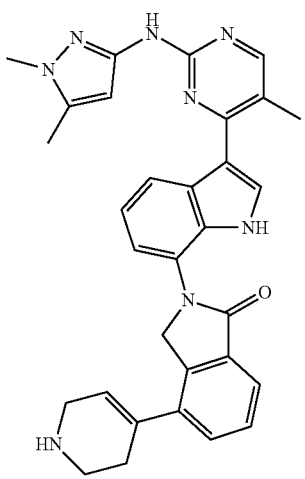

Using methyl 3-bromo-2-methylbenzoate and tert-butyl 4-bromo-3,6-dihydropyridine-1(2H)-carboxylate, the title product was afforded as described for Example 377 in General Method K (Boc group of the product was deprotected during the reaction). MS (ESI, m/z): 531.2 [M+H]$^+$ Example 395: Synthesis of 2-(3-(2-((1,5-dimethyl-1H-pyrazol-3-yl)amino)-5-methylpyrimidin-4-yl)-1H-indol-7-yl)-4-(4-(trifluoromethoxy)phenyl)isoindolin-1-one

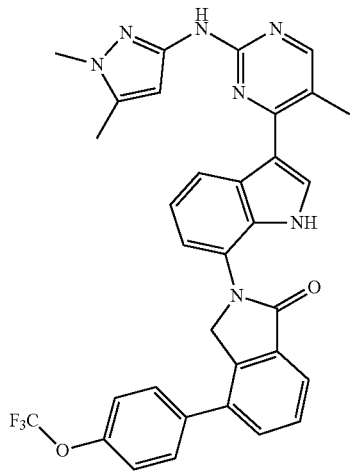 [SMILES: Cc1cnc(Nc2cc(C)n(C)n2)nc1-c1c[nH]c2c(N3Cc4c(cccc4-c4ccc(OC(F)(F)F)cc4)C3=O)cccc12]

Using methyl 3-bromo-2-methylbenzoate and 1-bromo-4-(trifluoromethoxy)benzene, the title product was afforded as described for Example 377 in General Method K. MS (ESI, m/z): 610.2 [M+H]$^+$ Example 396: Synthesis of 4-(4-aminophenyl)-2-(3-(2-((1,5-dimethyl-1H-pyrazol-3-yl)amino)-5-methylpyrimidin-4-yl)-1H-indol-7-yl)isoindolin-1-one

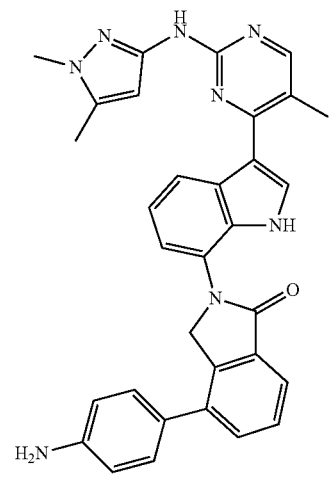

Using methyl 3-bromo-2-methylbenzoate and 4-bromoaniline, the title product was afforded as described for Example 377 in General Method K. MS (ESI, m/z): 541.2 [M+H]$^+$ Example 397: Synthesis of tert-butyl 4-(2-(3-(2-((1,5-dimethyl-1H-pyrazol-3-yl)amino)-5-methylpyrimidin-4-yl)-1H-indol-7-yl)-1-oxoisoindolin-4-yl)-5,6-dihydropyridine-1(2H)-carboxylate

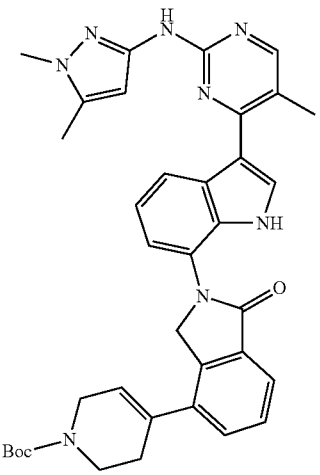

Using methyl 3-bromo-2-methylbenzoate and tert-butyl 4-bromo-3,6-dihydropyridine-1(2H)-carboxylate, the title product was afforded as described for Example 377 in General Method K. MS (ESI, m/z): 631.3 [M+H]$^+$ Example 398: Synthesis of tert-butyl (4-(2-(3-(2-((1,5-dimethyl-1H-pyrazol-3-yl)amino)-5-methylpyrimidin-4-yl)-1H-indol-7-yl)-1-oxoisoindolin-4-yl)phenyl)carbamate

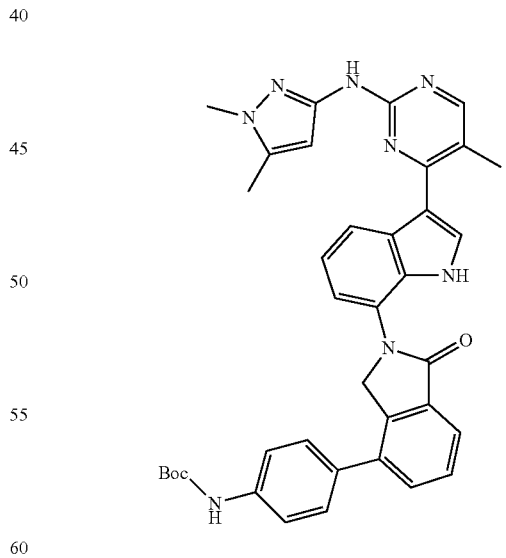

Using methyl 3-bromo-2-methylbenzoate and tert-butyl (4-bromophenyl)carbamate, the title product was afforded as described for Example 377 in General Method K. MS (ESI, m/z): 641.3 [M+H]$^+$ Example 399: Synthesis of 4-(2-aminopyridin-4-yl)-2-(3-(2-((1,5-dimethyl-1H-pyrazol-3-yl)amino)-5-methylpyrimidin-4-yl)-1H-indol-7-yl)isoindolin-1-one

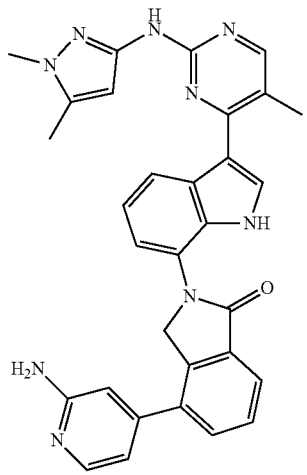

Using methyl 3-bromo-2-methylbenzoate and 4-bromopyridin-2-amine, the title product was afforded as described for Example 377 in General Method K. MS (ESI, m/z): 542.2 [M+H]$^+$ Example 400: Synthesis of 2-(3-(2-((1,5-dimethyl-1H-pyrazol-3-yl)amino)-5-methylpyrimidin-4-yl)-1H-indol-7-yl)-4-(3-fluoropyridin-4-yl)isoindolin-1-one

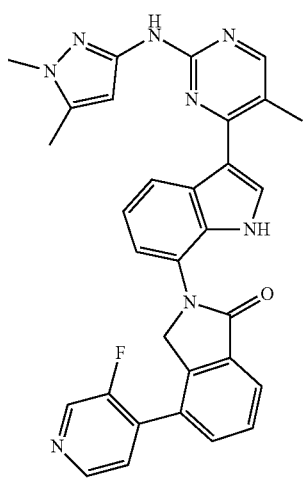

Using methyl 3-bromo-2-methylbenzoate and 4-bromo-3-fluoropyridine, the title product was afforded as described for Example 377 in General Method K. MS (ESI, m/z): 545.2 [M+H]$^+$ Example 401: Synthesis of 2-(3-(2-((1,5-dimethyl-1H-pyrazol-3-yl)amino)-5-methylpyrimidin-4-yl)-1H-indol-7-yl)-4-(6-hydroxypyridin-3-yl)isoindolin-1-one

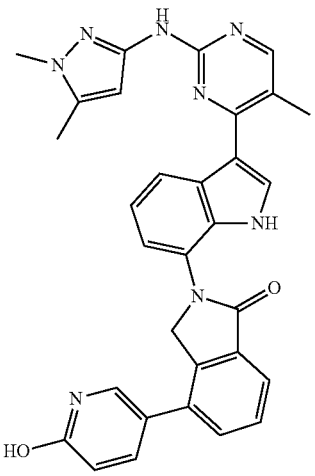

Using methyl 3-bromo-2-methylbenzoate and 5-bromopyridin-2-ol, the title product was afforded as described for Example 377 in General Method K. MS (ESI, m/z): 543.2 [M+H]$^+$ Example 402: Synthesis of 4-(2-chloropyridin-4-yl)-2-(3-(2-((1,5-dimethyl-1H-pyrazol-3-yl)amino)-5-methylpyrimidin-4-yl)-1H-indol-7-yl)isoindolin-1-one

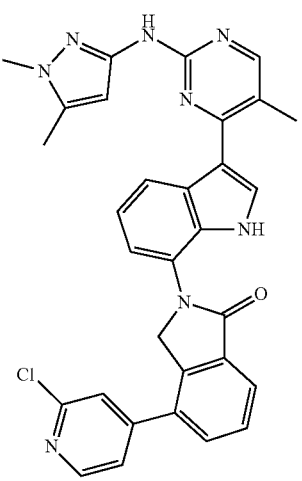

Using methyl 3-bromo-2-methylbenzoate and 4-bromo-2-chloropyridine, the title product was afforded as described for Example 377 in General Method K. MS (ESI, m/z): 561.2 [M+H]$^+$ Example 403: Synthesis of 2-(3-(2-((1,5-dimethyl-1H-pyrazol-3-yl)amino)-5-methylpyrimidin-4-yl)-1H-indol-7-yl)-4-(5-fluoro-2-methoxypyridin-4-yl)isoindolin-1-one

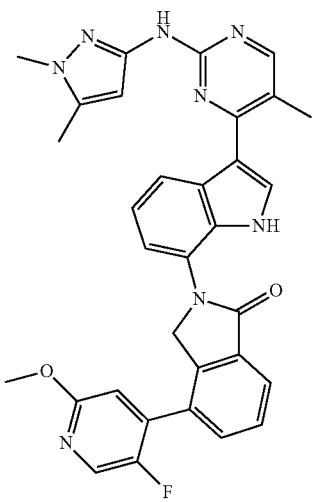

Using methyl 3-bromo-2-methylbenzoate and 4-bromo-5-fluoro-2-methoxypyridine, the title product was afforded as described for Example 377 in General Method K. MS (ESI, m/z): 575.2 [M+H]$^+$ Example 404: Synthesis of 2-(3-(2-((1,5-dimethyl-1H-pyrazol-3-yl)amino)-5-methylpyrimidin-4-yl)-1H-indol-7-yl)-4-(2-fluoropyridin-4-yl)isoindolin-1-one

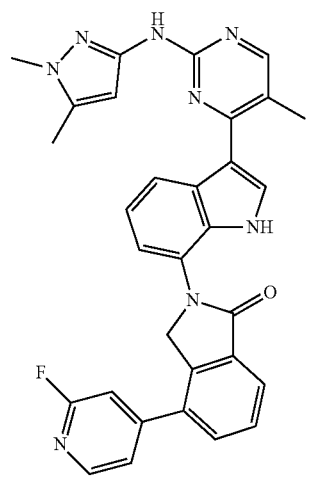

Using methyl 3-bromo-2-methylbenzoate and 4-bromo-2-fluoropyridine, the title product was afforded as described for Example 377 in General Method K. MS (ESI, m/z): 545.2 [M+H]$^+$ Example 405: Synthesis of 4-(6-chloropyridin-3-yl)-2-(3-(2-((1,5-dimethyl-1H-pyrazol-3-yl)amino)-5-methylpyrimidin-4-yl)-1H-indol-7-yl)isoindolin-1-one

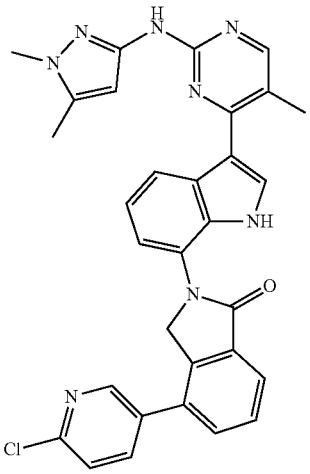

Using methyl 3-bromo-2-methylbenzoate and 5-bromo-2-chloropyridine, the title product was afforded as described for Example 377 in General Method K. MS (ESI, m/z): 561.2 [M+H]$^+$ Example 406: Synthesis of 2-(3-(2-((1,5-dimethyl-1H-pyrazol-3-yl)amino)-5-methylpyrimidin-4-yl)-1H-indol-7-yl)-4-(6-methoxypyridin-3-yl)isoindolin-1-one

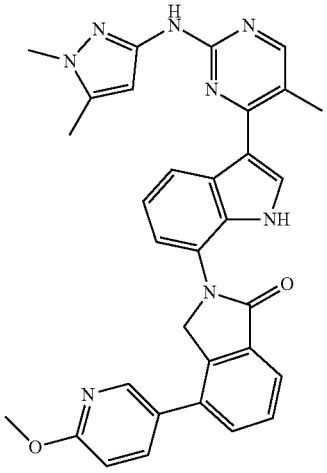

Using methyl 3-bromo-2-methylbenzoate and 5-bromo-2-methoxypyridine, the title product was afforded as described for Example 377 in General Method K. MS (ESI, m/z): 557.2 [M+H]$^+$ Example 407: Synthesis of 2-(3-(2-((1,5-dimethyl-1H-pyrazol-3-yl)amino)-5-methylpyrimidin-4-yl)-1H-indol-7-yl)-4-(6-fluoro-5-methylpyridin-3-yl)isoindolin-1-one

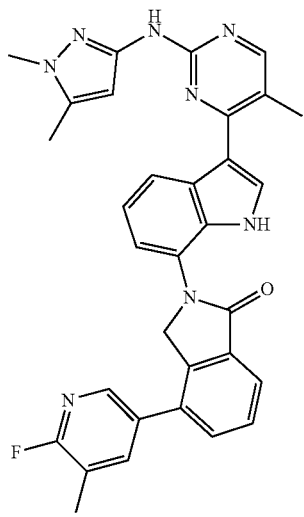

Using methyl 3-bromo-2-methylbenzoate and 5-bromo-2-fluoro-3-methylpyridine, the title product was afforded as described for Example 377 in General Method K. MS (ESI, m/z): 559.2 [M+H]+

Example 408: Synthesis of 2-(3-(2-((1,5-dimethyl-1H-pyrazol-3-yl)amino)-5-methylpyrimidin-4-yl)-1H-indol-7-yl)-4-(2-(piperazin-1-yl)pyridin-4-yl)isoindolin-1-one

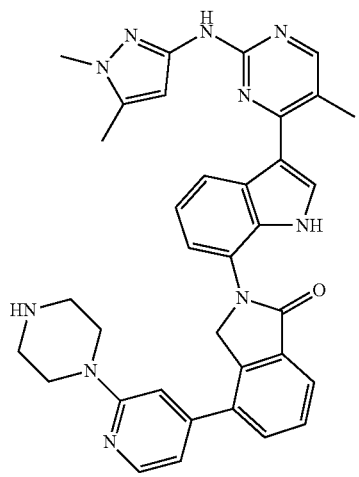 [SMILES: Cc1cnc(Nc2cc(C)n(C)n2)nc1-c1c[nH]c2c(N3Cc4c(cccc4-c4ccnc(N5CCNCC5)c4)C3=O)cccc12]

Using methyl 3-bromo-2-methylbenzoate and 1-(4-bromopyridin-2-yl)piperazine, the title product was afforded as described for Example 377 in General Method K. MS (ESI, m/z): 611.3 [M+H]+

Example 409: Synthesis of 2-(3-(2-((1,5-dimethyl-1H-pyrazol-3-yl)amino)-5-methylpyrimidin-4-yl)-1H-indol-7-yl)-4-(4-(pyrrolidin-1-ylsulfonyl)phenyl)isoindolin-1-one

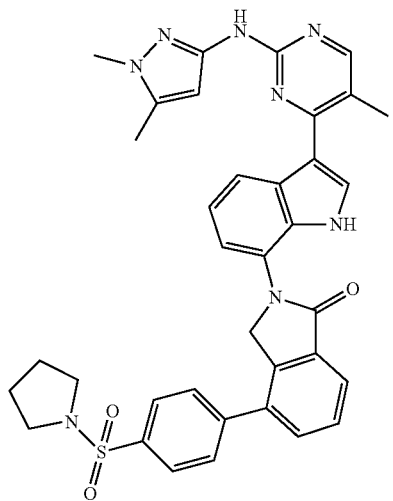 [SMILES: Cc1cnc(Nc2cc(C)n(C)n2)nc1-c1c[nH]c2c(N3Cc4c(cccc4-c4ccc(S(=O)(=O)N5CCCC5)cc4)C3=O)cccc12]

Using methyl 3-bromo-2-methylbenzoate and 1-((4-bromophenyl)sulfonyl)pyrrolidine, the title product was afforded as described for Example 377 in General Method K. MS (ESI, m/z): 659.2 [M+H]+

Example 410: Synthesis of (E)-2-(3-(2-((1,5-dimethyl-1H-pyrazol-3-yl)amino)-5-methylpyrimidin-4-yl)-1H-indol-7-yl)-4-(3-fluorostyryl)isoindolin-1-one

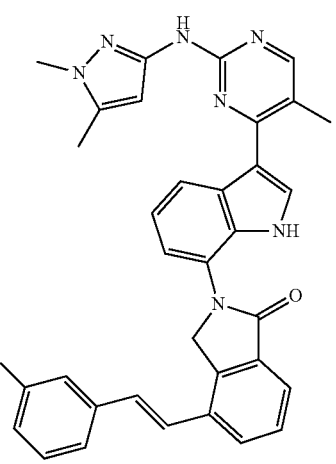

Using methyl 3-bromo-2-methylbenzoate and (E)-1-(2-bromovinyl)-3-fluorobenzene, the title product was afforded as described for Example 377 in General Method K. MS (ESI, m/z): 570.2 [M+H]+

Example 411: Synthesis of 2-(3-(2-((1,5-dimethyl-1H-pyrazol-3-yl)amino)-5-methylpyrimidin-4-yl)-1H-indol-7-yl)-4-(1H-pyrrolo[2,3-b]pyridin-4-yl)isoindolin-1-one

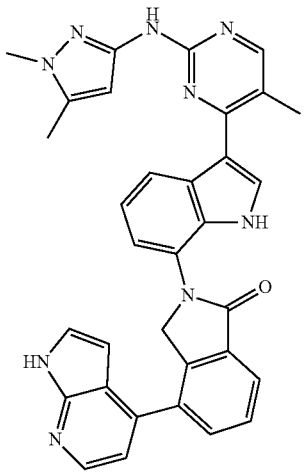

Using methyl 3-bromo-2-methylbenzoate and 4-bromo-1H-pyrrolo[2,3-b]pyridine, the title product was afforded as described for Example 377 in General Method K. MS (ESI, m/z): 566.2 [M+H]$^+$ Example 412: Synthesis of 2-(3-(2-((1,5-dimethyl-1H-pyrazol-3-yl)amino)-5-methylpyrimidin-4-yl)-1H-indol-7-yl)-4-(4-(4-oxopiperidine-1-carbonyl)phenyl)isoindolin-1-one

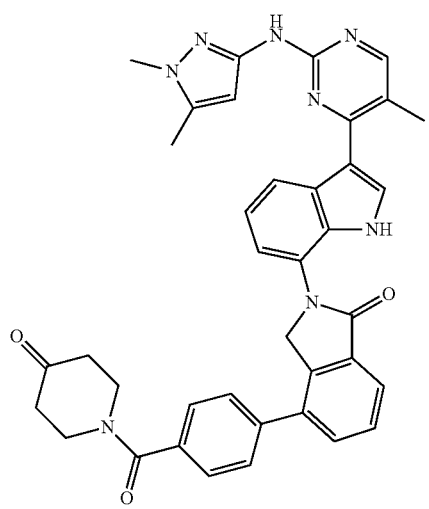 [SMILES: Cc1cnc(Nc2cc(C)n(C)n2)nc1-c1c[nH]c2c(N3Cc4c(cccc4-c4ccc(C(=O)N5CCC(=O)CC5)cc4)C3=O)cccc12]

Using methyl 3-bromo-2-methylbenzoate and 1-(4-bromobenzoyl)piperidin-4-one, the title product was afforded as described for Example 377 in General Method K. MS (ESI, m/z): 651.2 [M+H]$^+$ Example 413: Synthesis of 4-(3,6-dihydro-2H-thiopyran-4-yl)-2-(3-(2-((1,5-dimethyl-1H-pyrazol-3-yl)amino)-5-methylpyrimidin-4-yl)-1H-indol-7-yl)isoindolin-1-one

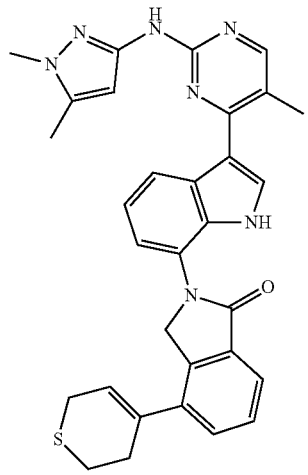

Using methyl 3-bromo-2-methylbenzoate and 4-bromo-3,6-dihydro-2H-thiopyran, the title product was afforded as described for Example 377 in General Method K. MS (ESI, m/z): 548.2 [M+H]$^+$ Example 414: Synthesis of 2-(3-(2-((1,5-dimethyl-1H-pyrazol-3-yl)amino)-5-methylpyrimidin-4-yl)-1H-indol-7-yl)-4-(2-(dimethylamino)pyrimidin-5-yl)isoindolin-1-one

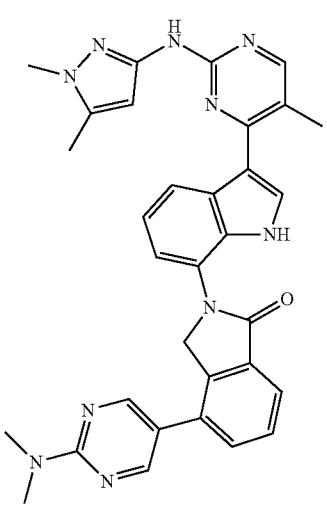

Using methyl 3-bromo-2-methylbenzoate and 5-bromo-N,N-dimethylpyrimidin-2-amine, the title product was afforded as described for Example 377 in General Method K. MS (ESI, m/z): 571.2 [M+H]$^+$ Example 415: Synthesis of 4-(1-(cyclopropylmethyl)-1H-pyrazol-4-yl)-2-(3-(2-((1,5-dimethyl-1H-pyrazol-3-yl)amino)-5-methylpyrimidin-4-yl)-1H-indol-7-yl)isoindolin-1-one

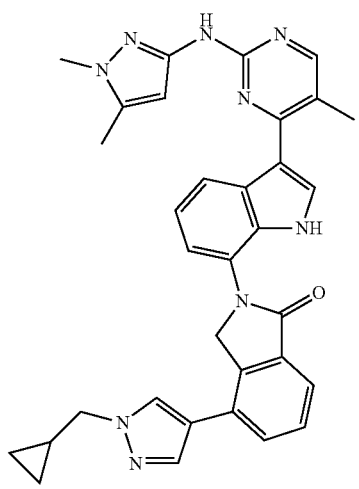 [SMILES: Cc1cnc(Nc2cc(C)n(C)n2)nc1-c1c[nH]c2c(N3Cc4c(cccc4-c4cnn(CC5CC5)c4)C3=O)cccc12]

Using methyl 3-bromo-2-methylbenzoate and 4-bromo-1-(cyclopropylmethyl)-1H-pyrazole, the title product was afforded as described for Example 377 in General Method K. MS (ESI, m/z): 570.2 [M+H]$^+$ Example 416: Synthesis of 2-(3-(2-((1,5-dimethyl-1H-pyrazol-3-yl)amino)-5-methylpyrimidin-4-yl)-1H-indol-7-yl)-4-(1-(2-morpholinoethyl)-1H-pyrazol-4-yl)isoindolin-1-one

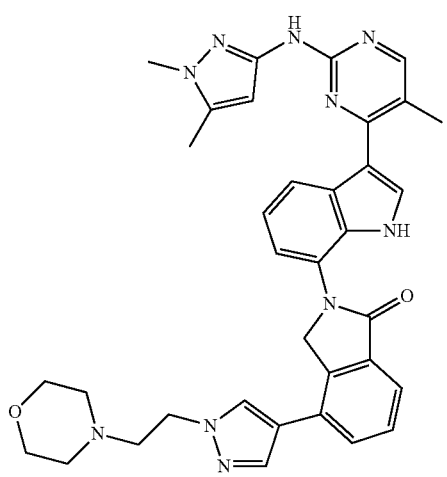 [SMILES: Cc1cnc(Nc2cc(C)n(C)n2)nc1-c1c[nH]c2c(N3Cc4c(cccc4-c4cnn(CCN5CCOCC5)c4)C3=O)cccc12]

Using methyl 3-bromo-2-methylbenzoate and 4-(2-(4-bromo-1H-pyrazol-1-yl)ethyl)morpholine, the title product was afforded as described for Example 377 in General Method K. MS (ESI, m/z): 629.3 [M+H]$^+$ Example 417: Synthesis of 2-(3-(2-((1,5-dimethyl-1H-pyrazol-3-yl)amino)-5-methylpyrimidin-4-yl)-1H-indol-7-yl)-4-(pyrimidin-5-yl)isoindolin-1-one

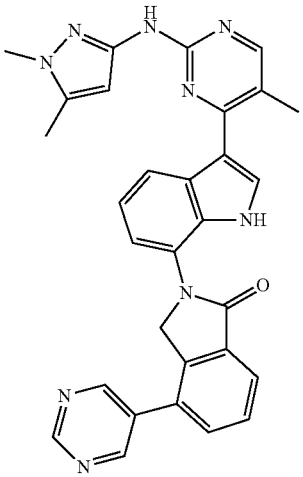

Using methyl 3-bromo-2-methylbenzoate and 5-bromopyrimidine, the title product was afforded as described for Example 377 in General Method K. MS (ESI, m/z): 528.2 [M+H]$^+$ Example 418: Synthesis of 4-(2-aminopyrimidin-5-yl)-2-(3-(2-((1,5-dimethyl-1H-pyrazol-3-yl)amino)-5-methylpyrimidin-4-yl)-1H-indol-7-yl)isoindolin-1-one

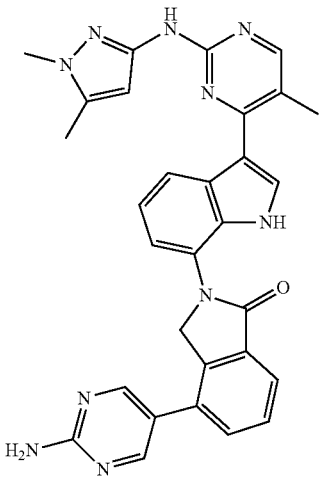

Using methyl 3-bromo-2-methylbenzoate and 5-bromopyrimidin-2-amine, the title product was afforded as described for Example 377 in General Method K. MS (ESI, m/z): 543.2 [M+H]$^+$ Example 419: Synthesis of 4-(5-aminopyridin-3-yl)-2-(3-(2-((1,5-dimethyl-1H-pyrazol-3-yl)amino)-5-methylpyrimidin-4-yl)-1H-indol-7-yl)isoindolin-1-one

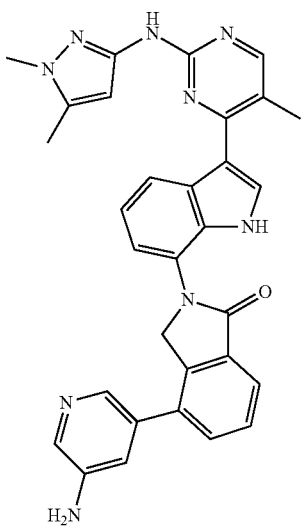

Using methyl 3-bromo-2-methylbenzoate and 5-bromopyridin-3-amine, the title product was afforded as described for Example 377 in General Method K. MS (ESI, m/z): 542.2 [M+H]$^+$ Example 420: Synthesis of 4-(6-aminopyridin-3-yl)-2-(3-(2-((1,5-dimethyl-1H-pyrazol-3-yl)amino)-5-methylpyrimidin-4-yl)-1H-indol-7-yl)isoindolin-1-one

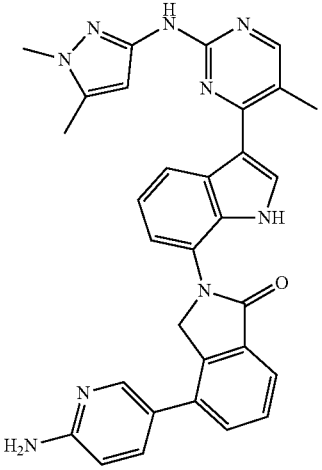

Using methyl 3-bromo-2-methylbenzoate and 5-bromopyridin-2-amine, the title product was afforded as described for Example 377 in General Method K. MS (ESI, m/z): 542.2 [M+H]$^+$ Example 421: Synthesis of 2-(3-(2-((1,5-dimethyl-1H-pyrazol-3-yl)amino)-5-methylpyrimidin-4-yl)-1H-indol-7-yl)-4-(pyrimidin-4-yl)isoindolin-1-one

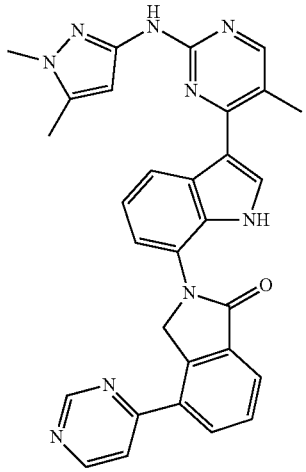

Using methyl 3-bromo-2-methylbenzoate and 4-bromopyrimidine, the title product was afforded as described for Example 377 in General Method K. MS (ESI, m/z): 528.2 [M+H]$^+$ Example 422: Synthesis of 4-(2-aminopyrimidin-4-yl)-2-(3-(2-((1,5-dimethyl-1H-pyrazol-3-yl)amino)-5-methylpyrimidin-4-yl)-1H-indol-7-yl)isoindolin-1-one

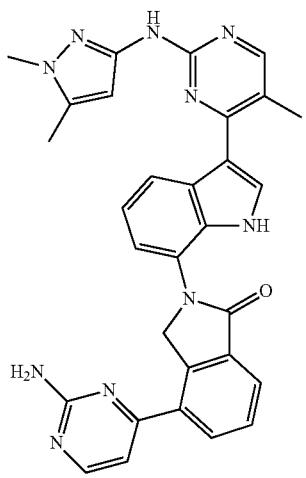

Using methyl 3-bromo-2-methylbenzoate and 4-bromopyrimidin-2-amine, the title product was afforded as described for Example 377 in General Method K. MS (ESI, m/z): 543.2 [M+H]$^+$ Example 423: Synthesis of 2-(3-(2-((1,5-dimethyl-1H-pyrazol-3-yl)amino)-5-methylpyrimidin-4-yl)-1H-indol-7-yl)-4-(4-(4-methylpiperazin-1-yl)pyridin-2-yl)isoindolin-1-one

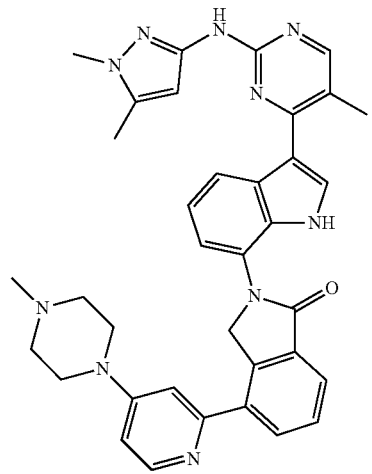

Using methyl 3-bromo-2-methylbenzoate and 1-(2-bromopyridin-4-yl)-4-methylpiperazine, the title product was afforded as described for Example 377 in General Method K. MS (ESI, m/z): 625.3 [M+H]$^+$ Example 424: Synthesis of 2-(3-(2-((1,5-dimethyl-1H-pyrazol-3-yl)amino)-5-methylpyrimidin-4-yl)-1H-indol-7-yl)-4-(2-(piperazin-1-yl)pyrimidin-5-yl)isoindolin-1-one

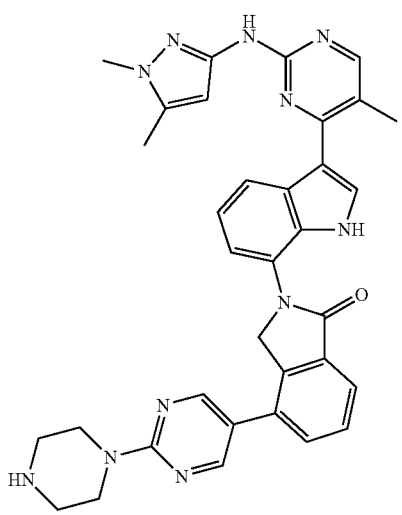 [SMILES: Cc1cnc(Nc2cc(C)n(C)n2)nc1-c1c[nH]c2c(N3Cc4c(cccc4-c4cnc(N5CCNCC5)nc4)C3=O)cccc12]

Using methyl 3-bromo-2-methylbenzoate and 5-bromo-2-(piperazin-1-yl)pyrimidine, the title product was afforded as described for Example 377 in General Method K. MS (ESI, m/z): 612.3 [M+H]$^+$ Example 425: Synthesis of 2-(3-(2-((1,5-dimethyl-1H-pyrazol-3-yl)amino)-5-methylpyrimidin-4-yl)-1H-indol-7-yl)-4-(6-morpholinopyridin-3-yl)isoindolin-1-one

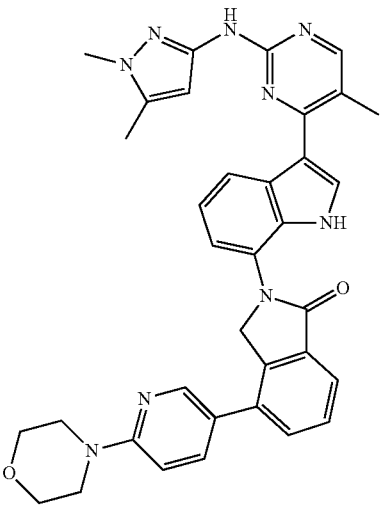 [SMILES: Cc1cnc(Nc2cc(C)n(C)n2)nc1-c1c[nH]c2c(N3Cc4c(cccc4-c4ccc(N5CCOCC5)nc4)C3=O)cccc12]

Using methyl 3-bromo-2-methylbenzoate and 4-(5-bromopyridin-2-yl)morpholine, the title product was afforded as described for Example 377 in General Method K. MS (ESI, m/z): 612.2 [M+H]$^+$ Example 426: Synthesis of 2-(3-(2-((1,5-dimethyl-1H-pyrazol-3-yl)amino)-5-methylpyrimidin-4-yl)-1H-indol-7-yl)-4-(4-(4-methylpiperazin-1-yl)phenyl)isoindolin-1-one

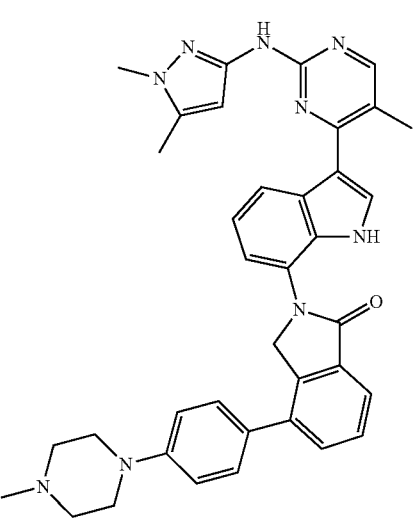

Using methyl 3-bromo-2-methylbenzoate and 1-(4-bromophenyl)-4-methylpiperazine, the title product was afforded as described for Example 377 in General Method K. MS (ESI, m/z): 624.3 [M+H]$^+$ Example 427: Synthesis of 4-(2,6-difluoropyridin-4-yl)-2-(3-(2-((1,5-dimethyl-1H-pyrazol-3-yl)amino)-5-methylpyrimidin-4-yl)-1H-indol-7-yl)isoindolin-1-one

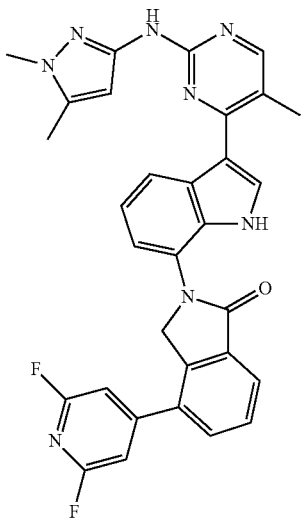

Using methyl 3-bromo-2-methylbenzoate and 4-bromo-2,6-difluoropyridine, the title product was afforded as described for Example 377 in General Method K. MS (ESI, m/z): 563.2 [M+H]+

Example 428: Synthesis of 4-(3,5-difluoropyridin-4-yl)-2-(3-(2-((1,5-dimethyl-1H-pyrazol-3-yl)amino)-5-methylpyrimidin-4-yl)-1H-indol-7-yl)isoindolin-1-one

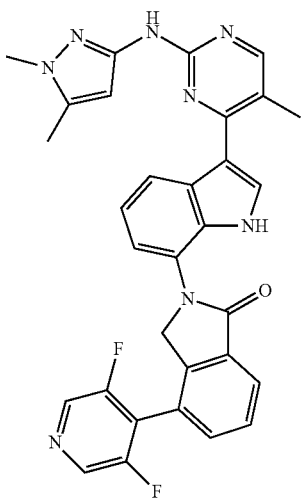

Using methyl 3-bromo-2-methylbenzoate and 4-bromo-3,5-difluoropyridine, the title product was afforded as described for Example 377 in General Method K. MS (ESI, m/z): 563.2 [M+H]+

Example 429: Synthesis of 2-(3-(2-((1,5-dimethyl-1H-pyrazol-3-yl)amino)-5-methylpyrimidin-4-yl)-1H-indol-7-yl)-4-(2-methylpyridin-4-yl)isoindolin-1-one

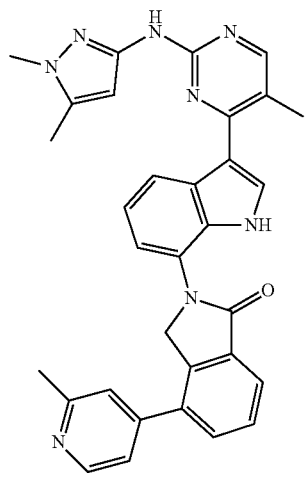

Using methyl 3-bromo-2-methylbenzoate and 4-bromo-2-methylpyridine, the title product was afforded as described for Example 377 in General Method K. MS (ESI, m/z): 541.2 [M+H]+

Example 430: Synthesis of 2-(3-(2-((1,5-dimethyl-1H-pyrazol-3-yl)amino)-5-methylpyrimidin-4-yl)-1H-indol-7-yl)-[4,5'-biisoindolin]-1-one

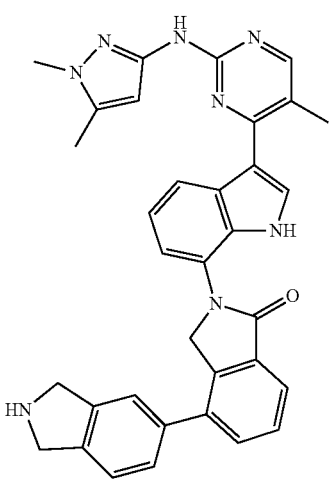 [SMILES: Cc1cnc(Nc2cc(C)n(C)n2)nc1-c1c[nH]c2c(N3Cc4c(cccc4-c4ccc5c(c4)CNC5)C3=O)cccc12]

Using methyl 3-bromo-2-methylbenzoate and 5-bromoisoindoline, the title product was afforded as described for Example 377 in General Method K. MS (ESI, m/z): 567.2 [M+H]+

Example 431: Synthesis of 2-(3-(2-((1,5-dimethyl-1H-pyrazol-3-yl)amino)-5-methylpyrimidin-4-yl)-1H-indol-7-yl)-4-(2-fluoropyridin-3-yl)isoindolin-1-one

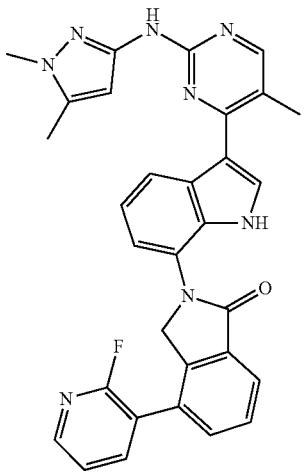

Using methyl 3-bromo-2-methylbenzoate and 3-bromo-2-fluoropyridine, the title product was afforded as described for Example 377 in General Method K. MS (ESI, m/z): 545.2 [M+H]+

Example 432: Synthesis of 4-(2-(3-(2-((1,5-dimethyl-1H-pyrazol-3-yl)amino)-5-methylpyrimidin-4-yl)-1H-indol-7-yl)-1-oxoisoindolin-4-yl)benzonitrile

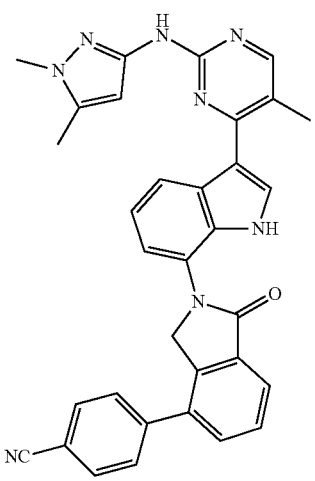

Using methyl 3-bromo-2-methylbenzoate and 4-bromobenzonitrile, the title product was afforded as described for Example 377 in General Method K. MS (ESI, m/z): 551.2 [M+H]+

Example 433: Synthesis of 4-(2-(3-(2-((1,5-dimethyl-1H-pyrazol-3-yl)amino)-5-methylpyrimidin-4-yl)-1H-indol-7-yl)-1-oxoisoindolin-4-yl)-3-fluorobenzonitrile

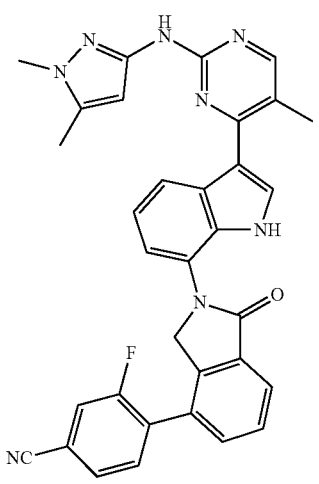

Using methyl 3-bromo-2-methylbenzoate and 4-bromo-3-fluorobenzonitrile, the title product was afforded as described for Example 377 in General Method K. MS (ESI, m/z): 569.2 [M+H]+

Example 434: Synthesis of 2-(3-(2-((1,5-dimethyl-1H-pyrazol-3-yl)amino)-5-methylpyrimidin-4-yl)-1H-indol-7-yl)-4-(2-(trifluoromethyl)phenyl)isoindolin-1-one

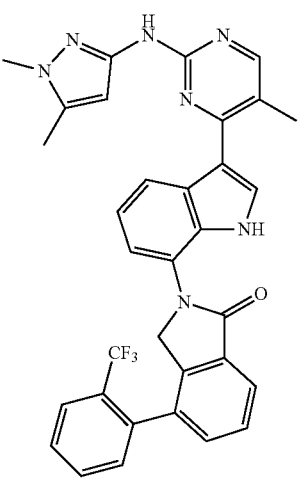

Using methyl 3-bromo-2-methylbenzoate and 1-bromo-2-(trifluoromethyl)benzene, the title product was afforded as described for Example 377 in General Method K. MS (ESI, m/z): 594.2 [M+H]+

Example 435: Synthesis of 2-(3-(2-((1,5-dimethyl-1H-pyrazol-3-yl)amino)-5-methylpyrimidin-4-yl)-1H-indol-7-yl)-4-(2-methoxypyridin-3-yl)isoindolin-1-one

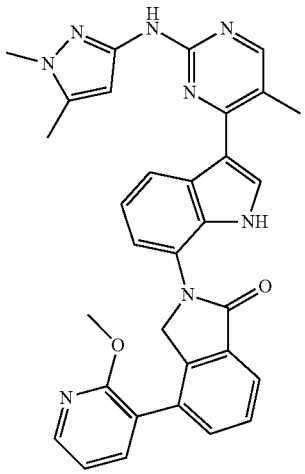

Using methyl 3-bromo-2-methylbenzoate and 3-bromo-2-methoxypyridine, the title product was afforded as described for Example 377 in General Method K. MS (ESI, m/z): 557.2 [M+H]$^+$ Example 436: Synthesis of 2-(3-(2-((1,5-dimethyl-1H-pyrazol-3-yl)amino)-5-methylpyrimidin-4-yl)-1H-indol-7-yl)-4-(4-(dimethylamino)phenyl)isoindolin-1-one

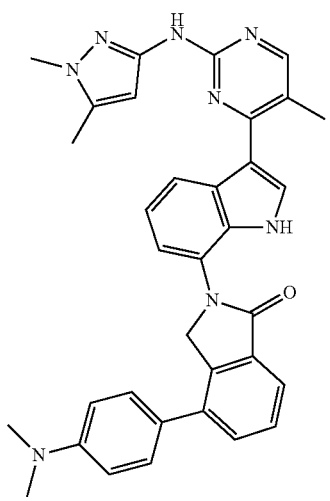

Using methyl 3-bromo-2-methylbenzoate and 4-bromo-N,N-dimethylaniline, the title product was afforded as described for Example 377 in General Method K. MS (ESI, m/z): 569.2 [M+H]$^+$ Example 437: Synthesis of 2-(3-(2-((1,5-dimethyl-1H-pyrazol-3-yl)amino)-5-methylpyrimidin-4-yl)-1H-indol-7-yl)-4-(2-(hydroxymethyl)phenyl)isoindolin-1-one

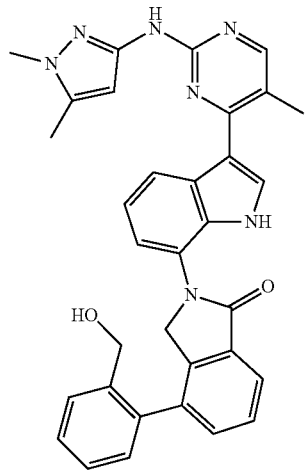

Using methyl 3-bromo-2-methylbenzoate and (2-bromophenyl)methanol, the title product was afforded as described for Example 377 in General Method K. MS (ESI, m/z): 556.2 [M+H]$^+$ Example 438: Synthesis of 2-(3-(2-((1,5-dimethyl-1H-pyrazol-3-yl)amino)-5-methylpyrimidin-4-yl)-1H-indol-7-yl)-4-(2-methoxyphenyl)isoindolin-1-one

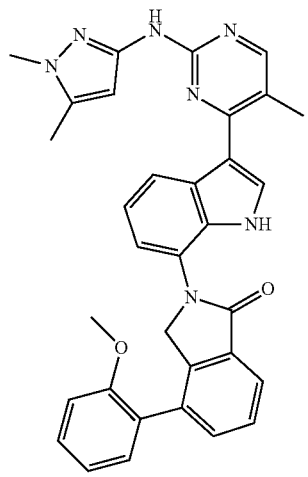

Using methyl 3-bromo-2-methylbenzoate and 1-bromo-2-methoxybenzene, the title product was afforded as described for Example 377 in General Method K. MS (ESI, m/z): 556.2 [M+H]$^+$ Example 439: Synthesis of 4-([1,1'-biphenyl]-2-yl)-2-(3-(2-((1,5-dimethyl-1H-pyrazol-3-yl)amino)-5-methylpyrimidin-4-yl)-1H-indol-7-yl)isoindolin-1-one

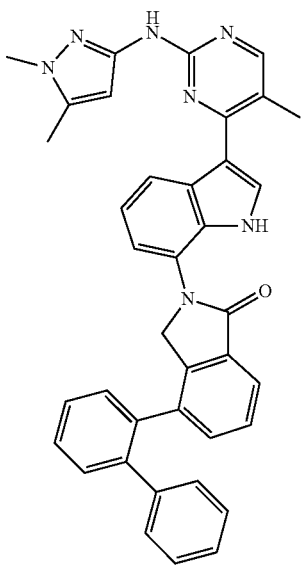

Using methyl 3-bromo-2-methylbenzoate and 2-bromo-1,1'-biphenyl, the title product was afforded as described for Example 377 in General Method K. MS (ESI, m/z): 602.2 [M+H]$^+$ Example 440: Synthesis of 2-(3-(2-((1,5-dimethyl-1H-pyrazol-3-yl)amino)-5-methylpyrimidin-4-yl)-1H-indol-7-yl)-4-(o-tolyl)isoindolin-1-one

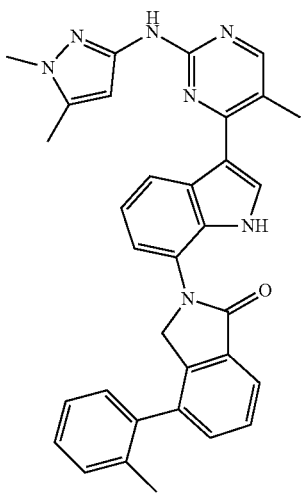

Using methyl 3-bromo-2-methylbenzoate and 1-bromo-2-methylbenzene, the title product was afforded as described for Example 377 in General Method K. MS (ESI, m/z): 540.2 [M+H]$^+$ Example 441: Synthesis of 2-(3-(2-((1,5-dimethyl-1H-pyrazol-3-yl)amino)-5-methylpyrimidin-4-yl)-1H-indol-7-yl)-4-(2-hydroxyphenyl)isoindolin-1-one

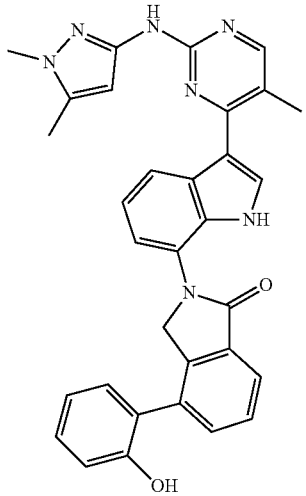

Using methyl 3-bromo-2-methylbenzoate and 2-bromophenol, the title product was afforded as described for Example 377 in General Method K. MS (ESI, m/z): 542.2 [M+H]$^+$ Example 442: Synthesis of 2-(3-(2-((1,5-dimethyl-1H-pyrazol-3-yl)amino)-5-methylpyrimidin-4-yl)-1H-indol-7-yl)-4-(1H-pyrrol-2-yl)isoindolin-1-one

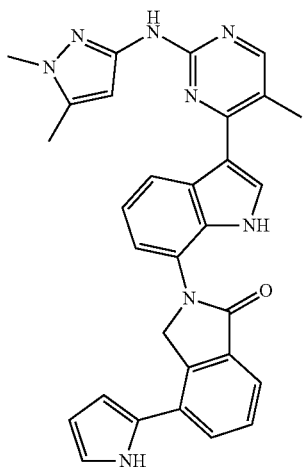

Using methyl 3-bromo-2-methylbenzoate and 2-bromo-1H-pyrrole, the title product was afforded as described for Example 377 in General Method K. MS (ESI, m/z): 515.2 [M+H]$^+$

Example 443: Synthesis of tert-butyl 2-(2-(3-(2-((1,5-dimethyl-1H-pyrazol-3-yl)amino)-5-methylpyrimidin-4-yl)-1H-indol-7-yl)-1-oxoisoindolin-4-yl)-1H-pyrrole-1-carboxylate

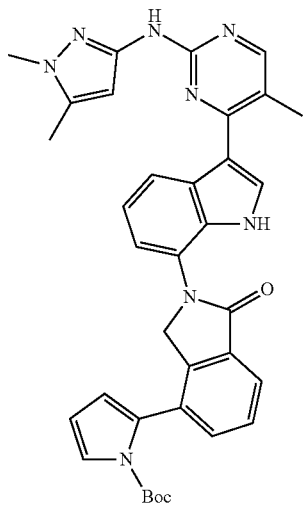

Using methyl 3-bromo-2-methylbenzoate and tert-butyl 2-bromo-1H-pyrrole-1-carboxylate, the title product was afforded as described for Example 377 in General Method K. MS (ESI, m/z): 615.2 [M+H]+

Example 444: Synthesis of 2-(3-(2-((1,5-dimethyl-1H-pyrazol-3-yl)amino)-5-methylpyrimidin-4-yl)-1H-indol-7-yl)-4-(3,5-dimethylisoxazol-4-yl)isoindolin-1-one

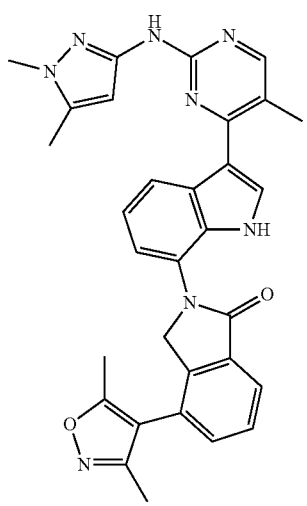

Using methyl 3-bromo-2-methylbenzoate and 4-bromo-3,5-dimethylisoxazole, the title product was afforded as described for Example 377 in General Method K. MS (ESI, m/z): 545.2 [M+H]+

Example 445: Synthesis of 2-(3-(2-((1,5-dimethyl-1H-pyrazol-3-yl)amino)-5-methylpyrimidin-4-yl)-1H-indol-7-yl)-4-(2-methoxypyridin-4-yl)isoindolin-1-one

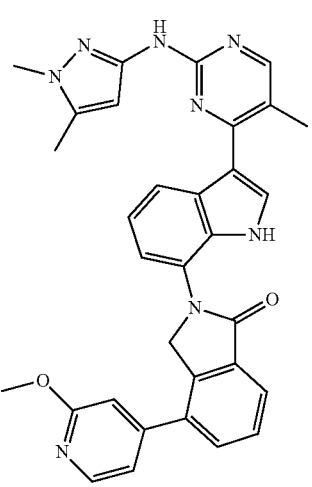

Using methyl 3-bromo-2-methylbenzoate and 4-bromo-2-methoxypyridine, the title product was afforded as described for Example 377 in General Method K. MS (ESI, m/z): 557.2 [M+H]+

Example 446: Synthesis of 2-(3-(2-((1,5-dimethyl-1H-pyrazol-3-yl)amino)-5-methylpyrimidin-4-yl)-1H-indol-7-yl)-4-(2-hydroxypyridin-4-yl)isoindolin-1-one

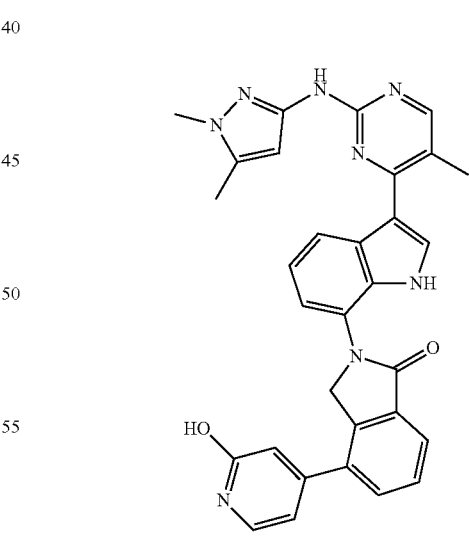

Using methyl 3-bromo-2-methylbenzoate and 4-bromopyridin-2-ol, the title product was afforded as described for Example 377 in General Method K. MS (ESI, m/z): 543.2 [M+H]+

Example 447: Synthesis of 4-(3-aminopyridin-4-yl)-2-(3-(2-((1,5-dimethyl-1H-pyrazol-3-yl)amino)-5-methylpyrimidin-4-yl)-1H-indol-7-yl)isoindolin-1-one

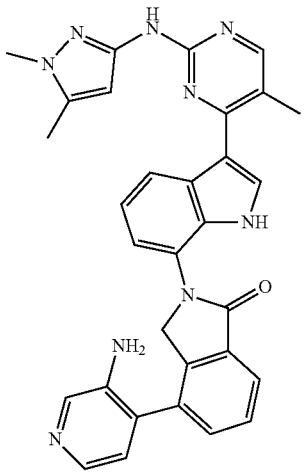

Using methyl 3-bromo-2-methylbenzoate and 4-bromopyridin-3-amine, the title product was afforded as described for Example 377 in General Method K. MS (ESI, m/z): 542.2 [M+H]$^+$

Example 448: Synthesis of 2-(3-(2-((1,5-dimethyl-1H-pyrazol-3-yl)amino)-5-methylpyrimidin-4-yl)-1H-indol-7-yl)-4-(isoquinolin-7-yl)isoindolin-1-one

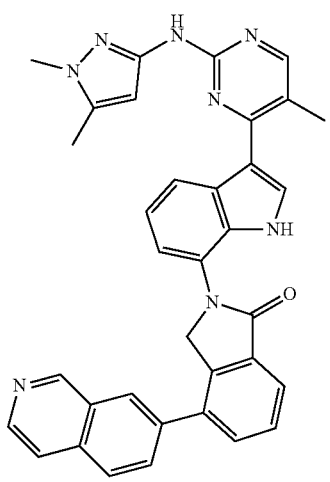 [SMILES: Cc1cnc(Nc2cc(C)n(C)n2)nc1-c1c[nH]c2c(N3Cc4c(cccc4-c4ccc5ccncc5c4)C3=O)cccc12]

Using methyl 3-bromo-2-methylbenzoate and 7-bromoisoquinoline, the title product was afforded as described for Example 377 in General Method K. MS (ESI, m/z): 577.2 [M+H]$^+$

Example 449: Synthesis of 2-(3-(2-((1,5-dimethyl-1H-pyrazol-3-yl)amino)-5-methylpyrimidin-4-yl)-1H-indol-7-yl)-4-(1-methyl-1H-indazol-5-yl)isoindolin-1-one

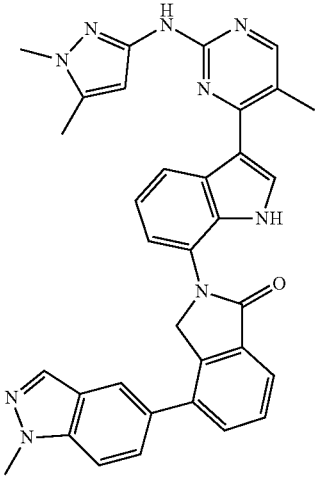

Using methyl 3-bromo-2-methylbenzoate and 5-bromo-1-methyl-1H-indazole, the title product was afforded as described for Example 377 in General Method K. MS (ESI, m/z): 580.2 [M+H]$^+$

Example 450: Synthesis of 2-(3-(2-((1,5-dimethyl-1H-pyrazol-3-yl)amino)-5-methylpyrimidin-4-yl)-1H-indol-7-yl)-4-(1-methyl-1H-indazol-6-yl)isoindolin-1-one

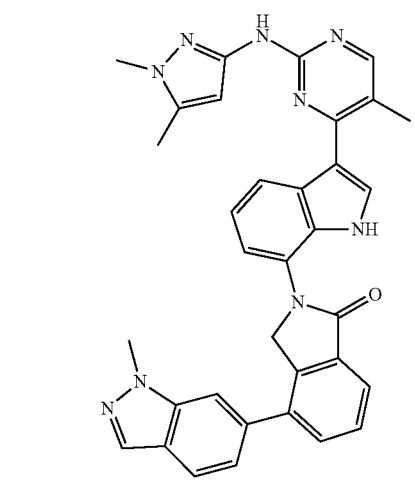 [SMILES: Cc1cnc(Nc2cc(C)n(C)n2)nc1-c1c[nH]c2c(N3Cc4c(cccc4-c4ccc5cnn(C)c5c4)C3=O)cccc12]

Using methyl 3-bromo-2-methylbenzoate and 6-bromo-1-methyl-1H-indazole, the title product was afforded as described for Example 377 in General Method K. MS (ESI, m/z): 580.2 [M+H]$^+$ Example 451: Synthesis of 2-(3-(2-((1,5-dimethyl-1H-pyrazol-3-yl)amino)-5-methylpyrimidin-4-yl)-1H-indol-7-yl)-4-(5-methylthiophen-2-yl)isoindolin-1-one

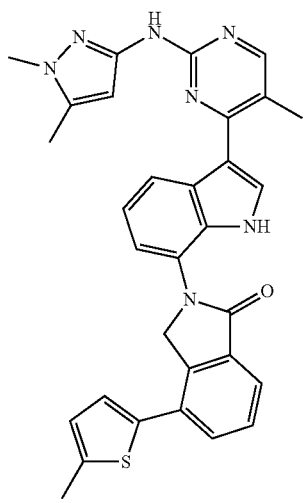

Using methyl 3-bromo-2-methylbenzoate and 2-bromo-5-methylthiophene, the title product was afforded as described for Example 377 in General Method K. MS (ESI, m/z): 546.2 [M+H]$^+$ Example 452: Synthesis of 4-(2,3-dihydro-1H-inden-5-yl)-2-(3-(2-((1,5-dimethyl-1H-pyrazol-3-yl)amino)-5-methylpyrimidin-4-yl)-1H-indol-7-yl)isoindolin-1-one

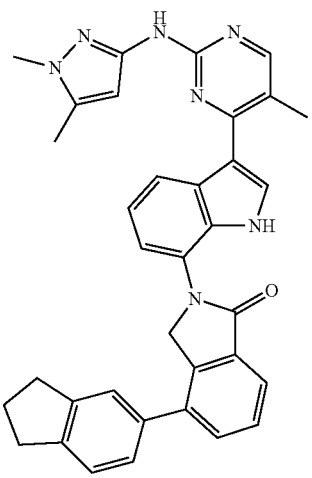 [SMILES: Cc1cnc(Nc2cc(C)n(C)n2)nc1-c1c[nH]c2c(N3Cc4c(cccc4-c4ccc5c(c4)CCC5)C3=O)cccc12]

Using methyl 3-bromo-2-methylbenzoate and 5-bromo-2,3-dihydro-1H-indene, the title product was afforded as described for Example 377 in General Method K. MS (ESI, m/z): 566.2 [M+H]$^+$ Example 453: Synthesis of 2-(3-(2-((1,5-dimethyl-1H-pyrazol-3-yl)amino)-5-methylpyrimidin-4-yl)-1H-indol-7-yl)-4-(4-methylthiophen-3-yl)isoindolin-1-one

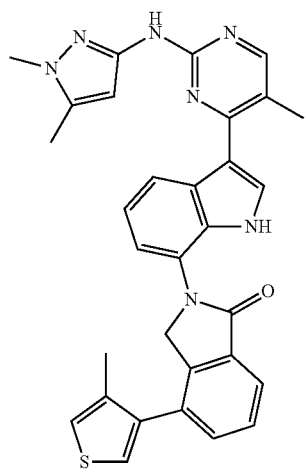

Using methyl 3-bromo-2-methylbenzoate and 3-bromo-4-methylthiophene, the title product was afforded as described for Example 377 in General Method K. MS (ESI, m/z): 546.2 [M+H]$^+$ Example 454: Synthesis of 2-(3-(2-((1,5-dimethyl-1H-pyrazol-3-yl)amino)-5-methylpyrimidin-4-yl)-1H-indol-7-yl)-7-fluoro-4-(2-methylpyridin-4-yl)isoindolin-1-one

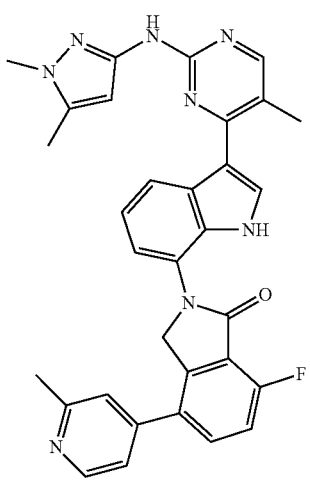 [SMILES: Cc1cc(-c2ccc(F)c3c2CN(c2cccc4c(-c5nc(Nc6cc(C)n(C)n6)ncc5C)c[nH]c24)C3=O)ccn1]

Using methyl 3-bromo-6-fluoro-2-methylbenzoate and 4-bromo-2-methylpyridine, the title product was afforded as described for Example 377 in General Method K. MS (ESI, m/z): 559.2 [M+H]$^+$ Example 455: Synthesis of 2-(3-(2-((1,5-dimethyl-1H-pyrazol-3-yl)amino)-5-methylpyrimidin-4-yl)-1H-indol-7-yl)-4-(3-methylpyridin-4-yl)isoindolin-1-one

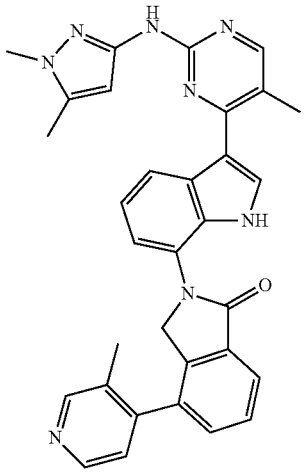

Using methyl 3-bromo-2-methylbenzoate and 4-bromo-3-methylpyridine, the title product was afforded as described for Example 377 in General Method K. MS (ESI, m/z): 541.2 [M+H]$^+$ Example 456: Synthesis of 4-(6-aminopyrimidin-4-yl)-2-(3-(2-((1,5-dimethyl-1H-pyrazol-3-yl)amino)-5-methylpyrimidin-4-yl)-1H-indol-7-yl)isoindolin-1-one

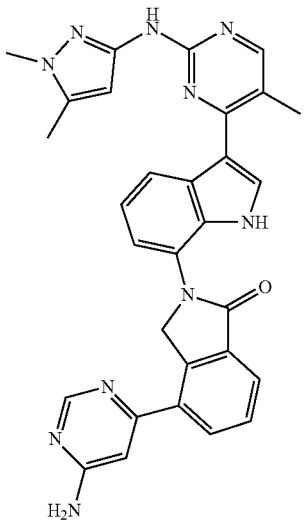

Using methyl 3-bromo-2-methylbenzoate and 6-bromopyrimidin-4-amine, the title product was afforded as described for Example 377 in General Method K. MS (ESI, m/z): 543.2 [M+H]$^+$ Example 457: Synthesis of 2-(3-(2-((1,5-dimethyl-1H-pyrazol-3-yl)amino)-5-methylpyrimidin-4-yl)-1H-indol-7-yl)-4-(1H-indazol-4-yl)isoindolin-1-one

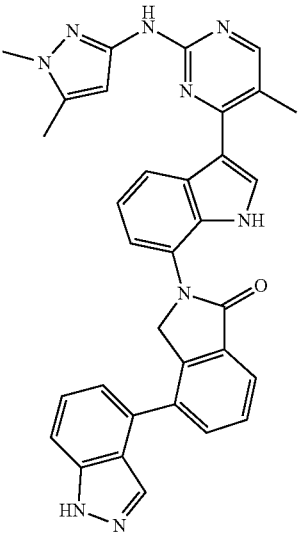

Using methyl 3-bromo-2-methylbenzoate and 4-bromo-1H-indazole, the title product was afforded as described for Example 377 in General Method K. MS (ESI, m/z): 566.2 [M+H]$^+$ Example 458: Synthesis of 2-(2-(3-(2-((1,5-dimethyl-1H-pyrazol-3-yl)amino)-5-methylpyrimidin-4-yl)-1H-indol-7-yl)-1-oxoisoindolin-4-yl)benzoic acid

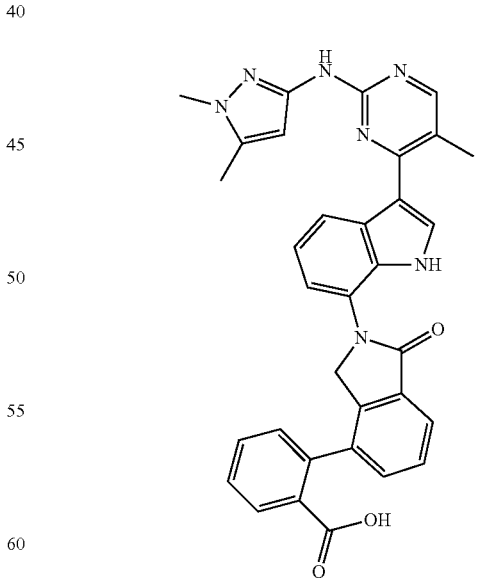

Using methyl 3-bromo-2-methylbenzoate and 2-bromobenzoic acid, the title product was afforded as described for Example 377 in General Method K. MS (ESI, m/z): 570.2 [M+H]$^+$ Example 460: Synthesis of 2-(3-(2-((1,5-dimethyl-1H-pyrazol-3-yl)amino)-5-methylpyrimidin-4-yl)-1H-indol-7-yl)-4-(4-(hydroxymethyl)phenyl)isoindolin-1-one

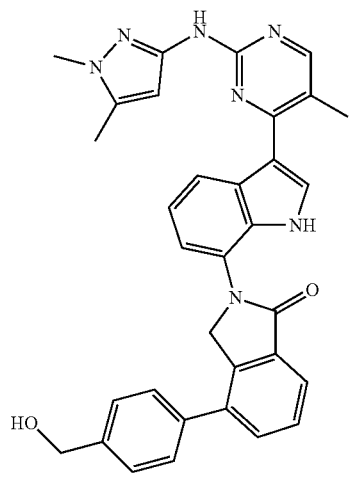 [SMILES: Cc1cnc(Nc2cc(C)n(C)n2)nc1-c1c[nH]c2c(N3Cc4c(cccc4-c4ccc(CO)cc4)C3=O)cccc12]

Using methyl 3-bromo-2-methylbenzoate and (4-bromophenyl)methanol, the title product was afforded as described for Example 377 in General Method K. MS (ESI, m/z): 556.2 [M+H]+

Example 461: Synthesis of 2-(3-(2-((1,5-dimethyl-1H-pyrazol-3-yl)amino)-5-methylpyrimidin-4-yl)-1H-indol-7-yl)-4-(thiophen-3-yl)isoindolin-1-one

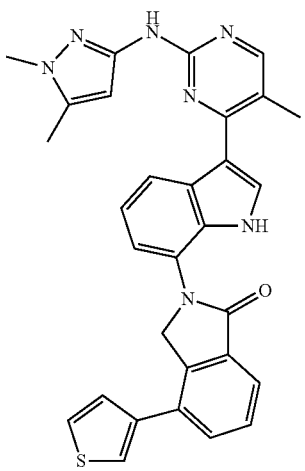

Using methyl 3-bromo-2-methylbenzoate and 3-bromothiophene, the title product was afforded as described for Example 377 in General Method K. MS (ESI, m/z): 532.1 [M+H]+

Example 462: Synthesis of 4-(2-aminophenyl)-2-(3-(2-((1,5-dimethyl-1H-pyrazol-3-yl)amino)-5-methylpyrimidin-4-yl)-1H-indol-7-yl)isoindolin-1-one

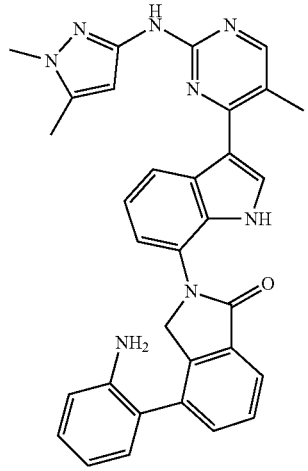

Using methyl 3-bromo-2-methylbenzoate and 2-bromoaniline, the title product was afforded as described for Example 377 in General Method K. MS (ESI, m/z): 541.2 [M+H]+

Example 463: Synthesis of methyl 2-(2-(3-(2-((1,5-dimethyl-1H-pyrazol-3-yl)amino)-5-methylpyrimidin-4-yl)-1H-indol-7-yl)-1-oxoisoindolin-4-yl)benzoate

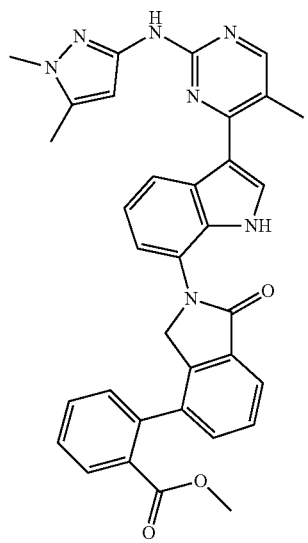

Using methyl 3-bromo-2-methylbenzoate and methyl 2-bromobenzoate, the title product was afforded as described for Example 377 in General Method K. MS (ESI, m/z): 584.2 [M+H]+

Example 464: Synthesis of 2-(3-(2-((1,5-dimethyl-1H-pyrazol-3-yl)amino)-5-methylpyrimidin-4-yl)-1H-indol-7-yl)-4-(1-methyl-1,2,3,6-tetrahydropyridin-4-yl)isoindolin-1-one

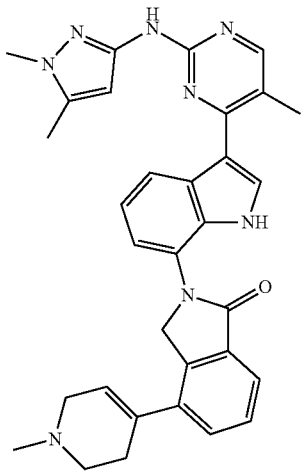

Using methyl 3-bromo-2-methylbenzoate and 4-bromo-1-methyl-1,2,3,6-tetrahydropyridine, the title product was afforded as described for Example 377 in General Method K. MS (ESI, m/z): 545.2 [M+H]$^+$ Example 465: Synthesis of 2-(3-(2-((1,5-dimethyl-1H-pyrazol-3-yl)amino)-5-methylpyrimidin-4-yl)-1H-indol-7-yl)-4-(1-(methylsulfonyl)-1,2,3,6-tetrahydropyridin-4-yl)isoindolin-1-one

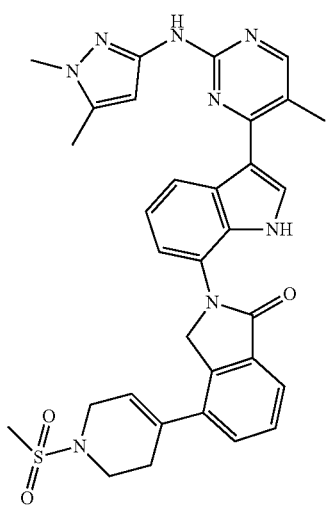

Using methyl 3-bromo-2-methylbenzoate and 4-bromo-1-(methylsulfonyl)-1,2,3,6-tetrahydropyridine, the title product was afforded as described for Example 377 in General Method K. MS (ESI, m/z): 609.2 [M+H]$^+$ Example 466: Synthesis of 4-(1-acetyl-1,2,3,6-tetrahydropyridin-4-yl)-2-(3-(2-((1,5-dimethyl-1H-pyrazol-3-yl)amino)-5-methylpyrimidin-4-yl)-1H-indol-7-yl)isoindolin-1-one

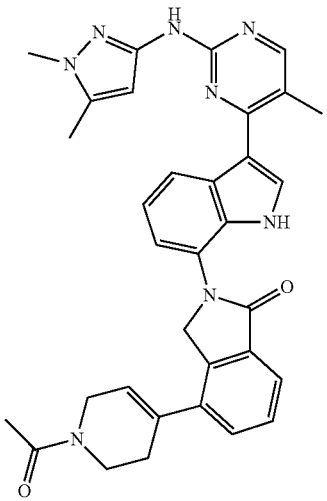 [SMILES: CC(=O)N1CC=C(c2cccc3c2CN(c2cccc4c(-c5nc(Nc6cc(C)n(C)n6)ncc5C)c[nH]c24)C3=O)CC1]

Using methyl 3-bromo-2-methylbenzoate and 1-(4-bromo-3,6-dihydropyridin-1(2H)-yl)ethan-1-one, the title product was afforded as described for Example 377 in General Method K. MS (ESI, m/z): 573.2 [M+H]$^+$ Example 467: Synthesis of 4-(2-(3-(2-((1,5-dimethyl-1H-pyrazol-3-yl)amino)-5-methylpyrimidin-4-yl)-1H-indol-7-yl)-1-oxoisoindolin-4-yl)-5,6-dihydropyridine-1(2H)-carboxamide

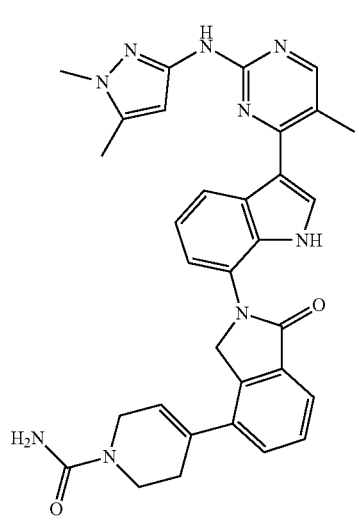 [SMILES: Cc1cnc(Nc2cc(C)n(C)n2)nc1-c1c[nH]c2c(N3Cc4c(cccc4C4=CCN(C(N)=O)CC4)C3=O)cccc12]

Using methyl 3-bromo-2-methylbenzoate and 4-bromo-3,6-dihydropyridine-1(2H)-carboxamide, the title product was afforded as described for Example 377 in General Method K. MS (ESI, m/z): 574.2 [M+H]$^+$ Example 468: Synthesis of 2-(3-(2-((1,5-dimethyl-1H-pyrazol-3-yl)amino)-5-methylpyrimidin-4-yl)-1H-indol-7-yl)-4-(1,1-dioxido-3,6-dihydro-2H-thiopyran-4-yl)isoindolin-1-one

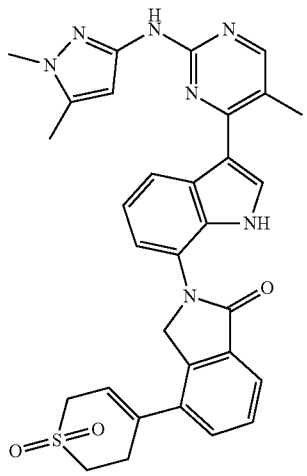

Using methyl 3-bromo-2-methylbenzoate and 4-bromo-3,6-dihydro-2H-thiopyran 1,1-dioxide, the title product was afforded as described for Example 377 in General Method K. MS (ESI, m/z): 580.2 [M+H]+

Example 469: Synthesis of 4-(2-(3-(2-((1,5-dimethyl-1H-pyrazol-3-yl)amino)-5-methylpyrimidin-4-yl)-1H-indol-7-yl)-1-oxoisoindolin-4-yl)picolinonitrile

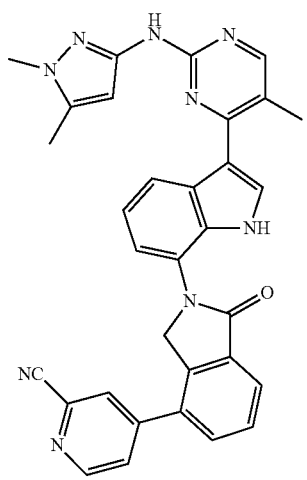

Using methyl 3-bromo-2-methylbenzoate and 4-bromopicolinonitrile, the title product was afforded as described for Example 377 in General Method K. MS (ESI, m/z): 552.2 [M+H]+

Example 470: Synthesis of 5-(2-(3-(2-((1,5-dimethyl-1H-pyrazol-3-yl)amino)-5-methylpyrimidin-4-yl)-1H-indol-7-yl)-1-oxoisoindolin-4-yl)picolinonitrile Using methyl 3-bromo-2-methylbenzoate and 5-bromopicolinonitrile, the title product was afforded as described for Example 377 in General Method K. MS (ESI, m/z): 552.2 [M+H]+

Example 471: Synthesis of 2-(3-(2-((1,5-dimethyl-1H-pyrazol-3-yl)amino)-5-methylpyrimidin-4-yl)-1H-indol-7-yl)-4-(3-(hydroxymethyl)pyridin-4-yl)isoindolin-1-one

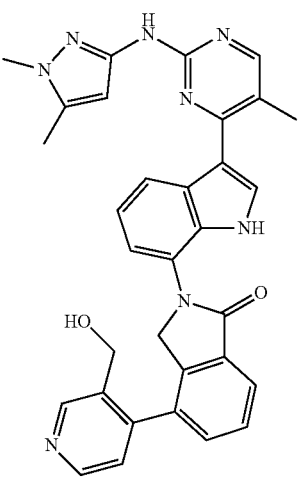

Using methyl 3-bromo-2-methylbenzoate and (4-bromopyridin-3-yl)methanol, the title product was afforded as described for Example 377 in General Method K. MS (ESI, m/z): 557.2 [M+H]+

Example 472: Synthesis of 2-(3-(2-((1,5-dimethyl-1H-pyrazol-3-yl)amino)-5-methylpyrimidin-4-yl)-1H-indol-7-yl)-4-(2-(hydroxymethyl)pyridin-4-yl)isoindolin-1-one

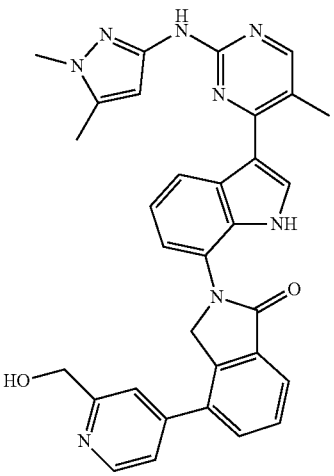 [SMILES: Cc1cnc(Nc2cc(C)n(C)n2)nc1-c1c[nH]c2c(N3Cc4c(cccc4-c4ccnc(CO)c4)C3=O)cccc12]

Using methyl 3-bromo-2-methylbenzoate and (4-bromopyridin-2-yl)methanol, the title product was afforded as described for Example 377 in General Method K. MS (ESI, m/z): 557.2 [M+H]+

Example 473: Synthesis of 4-(2-(3-(2-((1,5-dimethyl-1H-pyrazol-3-yl)amino)-5-methylpyrimidin-4-yl)-1H-indol-7-yl)-1-oxoisoindolin-4-yl)picolinamide

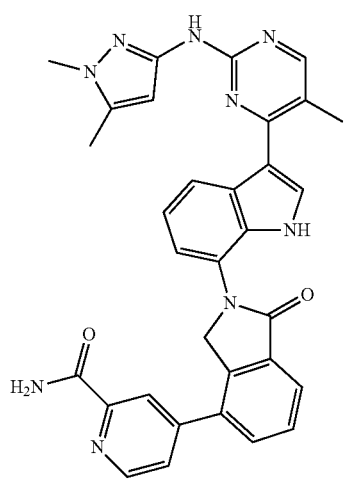 [SMILES: Cc1cnc(Nc2cc(C)n(C)n2)nc1-c1c[nH]c2c(N3Cc4c(cccc4-c4ccnc(C(N)=O)c4)C3=O)cccc12]

Using methyl 3-bromo-2-methylbenzoate and 4-bromopicolinamide, the title product was afforded as described for Example 377 in General Method K. MS (ESI, m/z): 570.2 [M+H]+

Example 474: Synthesis of 5-(2-(3-(2-((1,5-dimethyl-1H-pyrazol-3-yl)amino)-5-methylpyrimidin-4-yl)-1H-indol-7-yl)-1-oxoisoindolin-4-yl)picolinamide

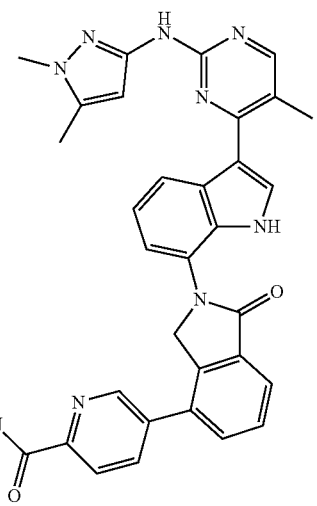

Using methyl 3-bromo-2-methylbenzoate and 5-bromopicolinamide, the title product was afforded as described for Example 377 in General Method K. MS (ESI, m/z): 570.2 [M+H]+

Example 475: Synthesis of 2-(3-(2-((1,5-dimethyl-1H-pyrazol-3-yl)amino)-5-methylpyrimidin-4-yl)-1H-indol-7-yl)-4-(2-(dimethylamino)pyridin-4-yl)isoindolin-1-one

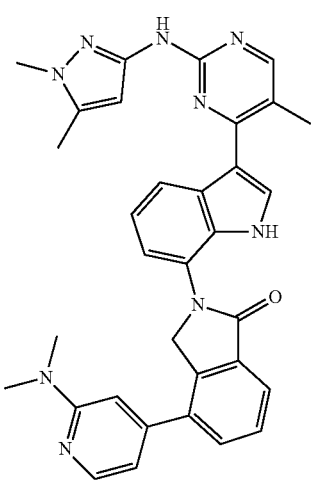

Using methyl 3-bromo-2-methylbenzoate and 4-bromo-N,N-dimethylpyridin-2-amine, the title product was afforded as described for Example 377 in General Method K. MS (ESI, m/z): 570.2 [M+H]+

Example 476: Synthesis of 2-(3-(2-((1,5-dimethyl-1H-pyrazol-3-yl)amino)-5-methylpyrimidin-4-yl)-1H-indol-7-yl)-4-(2-(methylamino)pyridin-4-yl)isoindolin-1-one

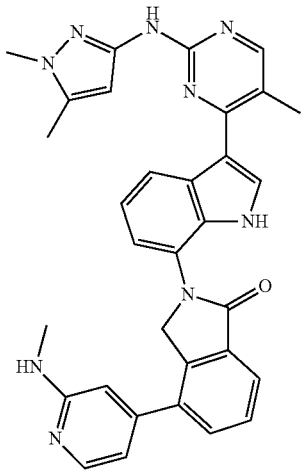

Using methyl 3-bromo-2-methylbenzoate and 4-bromo-N-methylpyridin-2-amine, the title product was afforded as described for Example 377 in General Method K. MS (ESI, m/z): 556.2 [M+H]$^+$ Example 477: Synthesis of 2-(3-(2-((1,5-dimethyl-1H-pyrazol-3-yl)amino)-5-methylpyrimidin-4-yl)-1H-indol-7-yl)-4-(5-methylpyridin-3-yl)isoindolin-1-one

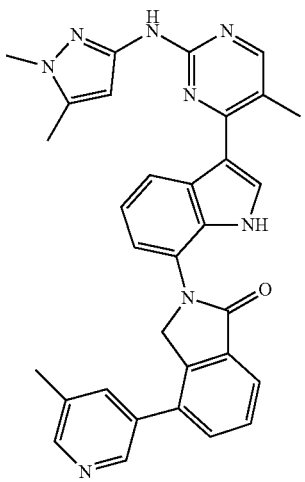

Using methyl 3-bromo-2-methylbenzoate and 3-bromo-5-methylpyridine, the title product was afforded as described for Example 377 in General Method K. MS (ESI, m/z): 541.2 [M+H]$^+$ Example 478: Synthesis of 2-(3-(2-((1,5-dimethyl-1H-pyrazol-3-yl)amino)-5-methylpyrimidin-4-yl)-1H-indol-7-yl)-4-(5-fluoropyridin-3-yl)isoindolin-1-one

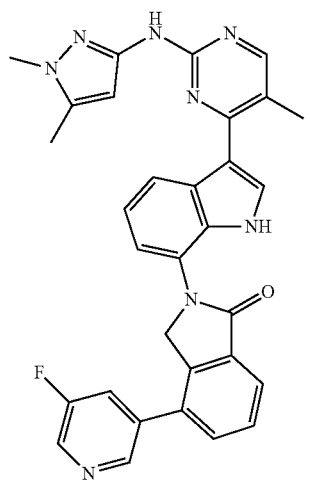

Using methyl 3-bromo-2-methylbenzoate and 3-bromo-5-fluoropyridine, the title product was afforded as described for Example 377 in General Method K. MS (ESI, m/z): 545.2 [M+H]$^+$ Example 479: Synthesis of 2-(3-(2-((1,5-dimethyl-1H-pyrazol-3-yl)amino)-5-methylpyrimidin-4-yl)-1H-indol-7-yl)-4-(2,6-dimethylpyridin-4-yl)isoindolin-1-one

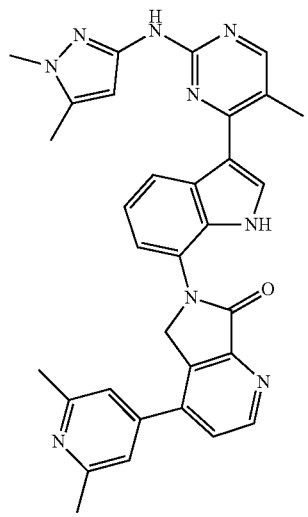

Using methyl 3-bromo-2-methylbenzoate and 4-bromo-2,6-dimethylpyridine, the title product was afforded as described for Example 377 in General Method K. MS (ESI, m/z): 555.2 [M+H]$^+$ Example 480: Synthesis of 2-(3-(2-((1,5-dimethyl-1H-pyrazol-3-yl)amino)-5-methylpyrimidin-4-yl)-1H-indol-7-yl)-7-fluoro-4-(pyridin-4-yl)isoindolin-1-one

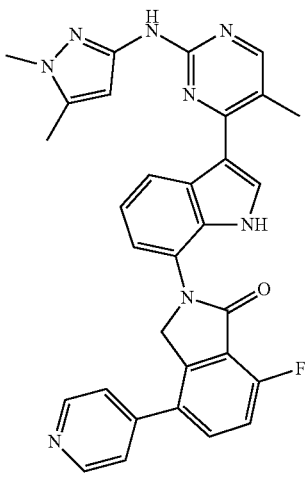 [SMILES: Cc1cnc(Nc2cc(C)n(C)n2)nc1-c1c[nH]c2c(N3Cc4c(-c5ccncc5)ccc(F)c4C3=O)cccc12]

Using methyl 3-bromo-6-fluoro-2-methylbenzoate and 4-bromopyridine, the title product was afforded as described for Example 377 in General Method K. MS (ESI, m/z): 545.2 [M+H]+

Example 481: Synthesis of 2-(3-(2-((1,5-dimethyl-1H-pyrazol-3-yl)amino)-5-methylpyrimidin-4-yl)-1H-indol-7-yl)-7-fluoro-4-(2-methoxypyridin-4-yl)isoindolin-1-one

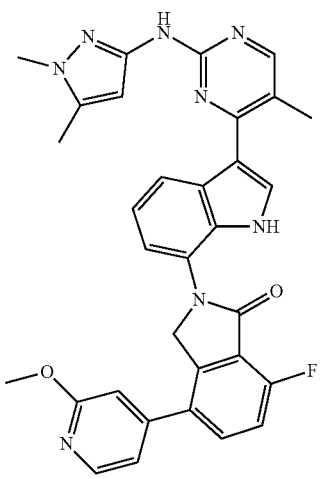 [SMILES: COc1cc(-c2ccc(F)c3c2CN(c2cccc4c(-c5nc(Nc6cc(C)n(C)n6)ncc5C)c[nH]c24)C3=O)ccn1]

Using methyl 3-bromo-6-fluoro-2-methylbenzoate and 4-bromo-2-methoxypyridine, the title product was afforded as described for Example 377 in General Method K. MS (ESI, m/z): 575.2 [M+H]+

Example 482: Synthesis of 2-(3-(2-((1,5-dimethyl-1H-pyrazol-3-yl)amino)-5-methylpyrimidin-4-yl)-1H-indol-7-yl)-7-fluoro-4-(2-(methylamino)pyridin-4-yl)isoindolin-1-one

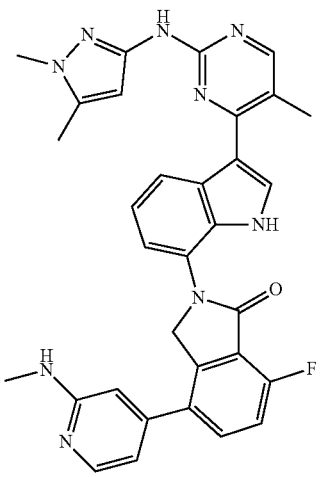 [SMILES: CNc1cc(-c2ccc(F)c3c2CN(c2cccc4c(-c5nc(Nc6cc(C)n(C)n6)ncc5C)c[nH]c24)C3=O)ccn1]

Using methyl 3-bromo-6-fluoro-2-methylbenzoate and 4-bromo-N-methylpyridin-2-amine, the title product was afforded as described for Example 377 in General Method K. MS (ESI, m/z): 574.2 [M+H]+

Example 483: Synthesis of 2-(3-(2-((1,5-dimethyl-1H-pyrazol-3-yl)amino)-5-methylpyrimidin-4-yl)-1H-indol-7-yl)-4-(2-(dimethylamino)pyridin-4-yl)-7-fluoroisoindolin-1-one

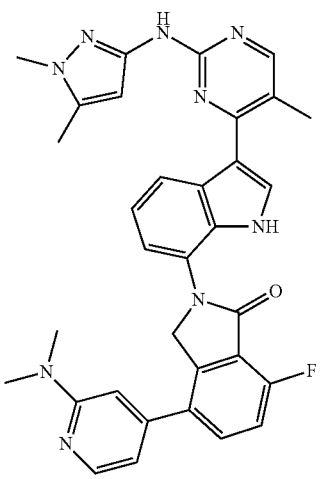 [SMILES: Cc1cnc(Nc2cc(C)n(C)n2)nc1-c1c[nH]c2c(N3Cc4c(-c5ccnc(N(C)C)c5)ccc(F)c4C3=O)cccc12]

Using methyl 3-bromo-6-fluoro-2-methylbenzoate and 4-bromo-N,N-dimethylpyridin-2-amine, the title product was afforded as described for Example 377 in General Method K. MS (ESI, m/z): 588.2 [M+H]+

Example 484: Synthesis of 2-(3-(2-((1,5-dimethyl-1H-pyrazol-3-yl)amino)-5-methylpyrimidin-4-yl)-1H-indol-7-yl)-7-fluoro-4-(5-fluoropyridin-3-yl)isoindolin-1-one

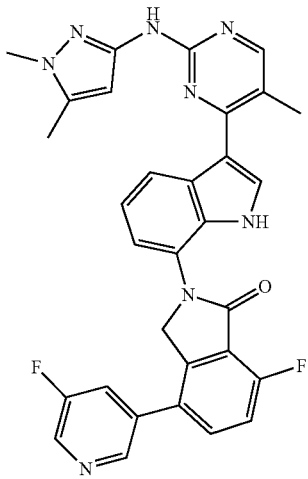 [SMILES: Cc1cnc(Nc2cc(C)n(C)n2)nc1-c1c[nH]c2c(N3Cc4c(-c5cncc(F)c5)ccc(F)c4C3=O)cccc12]

Using methyl 3-bromo-6-fluoro-2-methylbenzoate and 3-bromo-5-fluoropyridine, the title product was afforded as described for Example 377 in General Method K. MS (ESI, m/z): 563.2 [M+H]+

Example 485: Synthesis of 2-(3-(2-((1,5-dimethyl-1H-pyrazol-3-yl)amino)-5-methylpyrimidin-4-yl)-1H-indol-7-yl)-7-fluoro-4-(2-fluoropyridin-4-yl)isoindolin-1-one

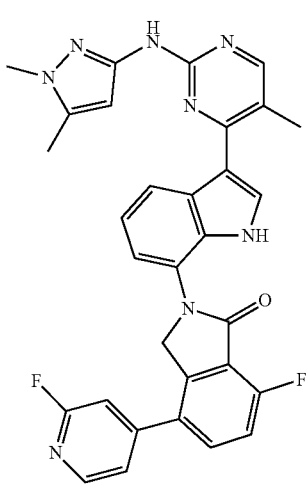 [SMILES: Cc1cnc(Nc2cc(C)n(C)n2)nc1-c1c[nH]c2c(N3Cc4c(-c5ccnc(F)c5)ccc(F)c4C3=O)cccc12]

Using methyl 3-bromo-6-fluoro-2-methylbenzoate and 4-bromo-2-fluoropyridine, the title product was afforded as described for Example 377 in General Method K. MS (ESI, m/z): 563.2 [M+H]+

Example 486: Synthesis of 2-(3-(2-((1,5-dimethyl-1H-pyrazol-3-yl)amino)-5-methylpyrimidin-4-yl)-1H-indol-7-yl)-7-fluoro-4-(5-methylpyridin-3-yl)isoindolin-1-one

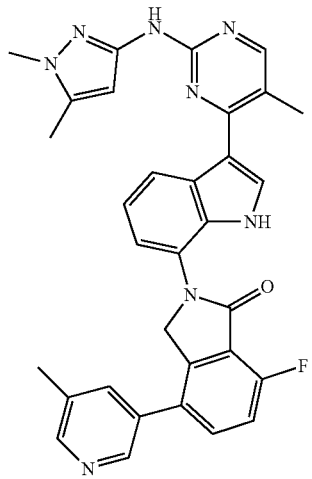 [SMILES: Cc1cncc(-c2ccc(F)c3c2CN(c2cccc4c(-c5nc(Nc6cc(C)n(C)n6)ncc5C)c[nH]c24)C3=O)c1]

Using methyl 3-bromo-6-fluoro-2-methylbenzoate and 3-bromo-5-methylpyridine, the title product was afforded as described for Example 377 in General Method K. MS (ESI, m/z): 559.2 [M+H]+

Example 487: Synthesis of 2-(3-(2-((1,5-dimethyl-1H-pyrazol-3-yl)amino)-5-methylpyrimidin-4-yl)-1H-indol-7-yl)-7-fluoro-4-(3-methylpyridin-4-yl)isoindolin-1-one

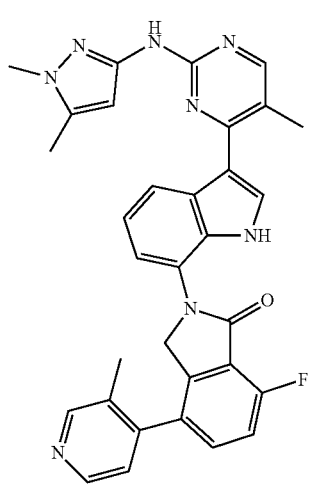 [SMILES: Cc1cnccc1-c1ccc(F)c2c1CN(c1cccc3c(-c4nc(Nc5cc(C)n(C)n5)ncc4C)c[nH]c13)C2=O]

Using methyl 3-bromo-6-fluoro-2-methylbenzoate and 4-bromo-3-methylpyridine, the title product was afforded as described for Example 377 in General Method K. MS (ESI, m/z): 559.2 [M+H]+

Example 488: Synthesis of 2-(3-(2-((1,5-dimethyl-1H-pyrazol-3-yl)amino)-5-methylpyrimidin-4-yl)-1H-indol-7-yl)-4-(2,6-dimethylpyridin-4-yl)-7-fluoroisoindolin-1-one

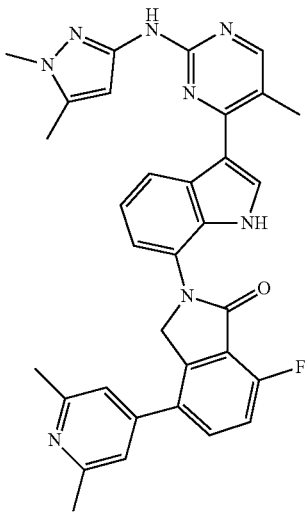 [SMILES: Cc1cc(-c2ccc(F)c3c2CN(c2cccc4c(-c5nc(Nc6cc(C)n(C)n6)ncc5C)c[nH]c24)C3=O)cc(C)n1]

Using methyl 3-bromo-6-fluoro-2-methylbenzoate and 4-bromo-2,6-dimethylpyridine, the title product was afforded as described for Example 377 in General Method K. MS (ESI, m/z): 573.2 [M+H]+

Example 489: Synthesis of 2-(3-(2-((1,5-dimethyl-1H-pyrazol-3-yl)amino)-5-methylpyrimidin-4-yl)-1H-indol-7-yl)-7-nitro-4-(pyridin-4-yl)isoindolin-1-one

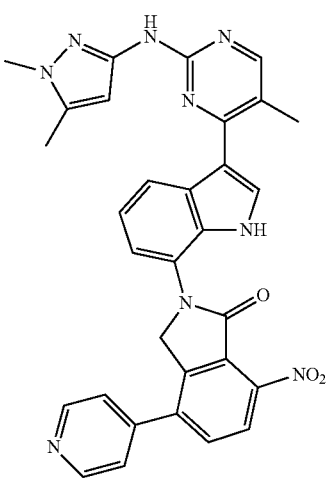 [SMILES: Cc1cnc(Nc2cc(C)n(C)n2)nc1-c1c[nH]c2c(N3Cc4c(-c5ccncc5)ccc([N+](=O)[O-])c4C3=O)cccc12]

Using methyl 3-bromo-2-methyl-6-nitrobenzoate and 4-bromopyridine, the title product was afforded as described for Example 377 in General Method K. MS (ESI, m/z): 572.2 [M+H]+

Example 490: Synthesis of 2-(3-(2-((1,5-dimethyl-1H-pyrazol-3-yl)amino)-5-methylpyrimidin-4-yl)-1H-indol-7-yl)-7-(dimethylamino)-4-(pyridin-4-yl)isoindolin-1-one

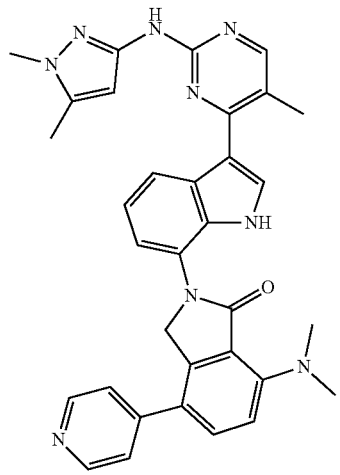

Using methyl 3-bromo-6-(dimethylamino)-2-methylbenzoate and 4-bromopyridine, the title product was afforded as described for Example 377 in General Method K. MS (ESI, m/z): 570.2 [M+H]+

Example 491: Synthesis of 2-(3-(2-((1,5-dimethyl-1H-pyrazol-3-yl)amino)-5-methylpyrimidin-4-yl)-1H-indol-7-yl)-7-(methylamino)-4-(pyridin-4-yl)isoindolin-1-one

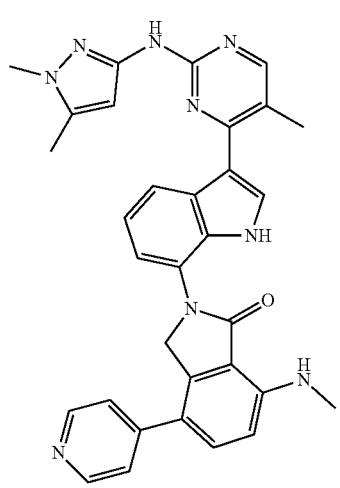

Using methyl 3-bromo-2-methyl-6-(methylamino)benzoate and 4-bromopyridine, the title product was afforded as described for Example 377 in General Method K. MS (ESI, m/z): 556.2 [M+H]+

Example 492: Synthesis of 2-(3-(2-((1,5-dimethyl-1H-pyrazol-3-yl)amino)-5-methylpyrimidin-4-yl)-1H-indol-7-yl)-7-iodo-4-phenylisoindolin-1-one

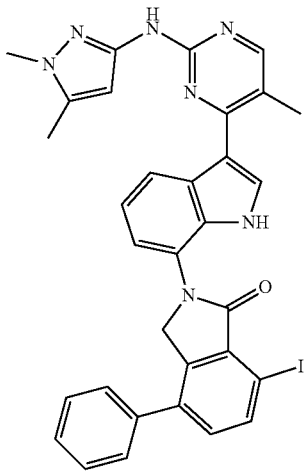

Using methyl 3-bromo-6-iodo-2-methylbenzoate and bromobenzene, the title product was afforded as described for Example 377 in General Method K. MS (ESI, m/z): 652.1 [M+H]+

Example 493: Synthesis of 6-(3-(2-((1,5-dimethyl-1H-pyrazol-3-yl)amino)-5-methylpyrimidin-4-yl)-1H-indol-7-yl)-4-phenyl-5,6-dihydro-7H-pyrrolo[3,4-b]pyridin-7-one

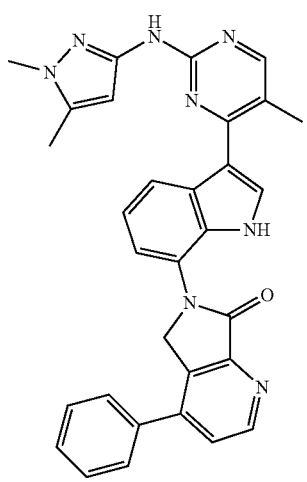

Using methyl 4-bromo-3-methylpicolinate and bromobenzene, the title product was afforded as described for Example 377 in General Method K. MS (ESI, m/z): 527.2 [M+H]+

Example 494: Synthesis of 6-(3-(2-((1,5-dimethyl-1H-pyrazol-3-yl)amino)-5-methylpyrimidin-4-yl)-1H-indol-7-yl)-4-(pyridin-4-yl)-5,6-dihydro-7H-pyrrolo[3,4-b]pyridin-7-one

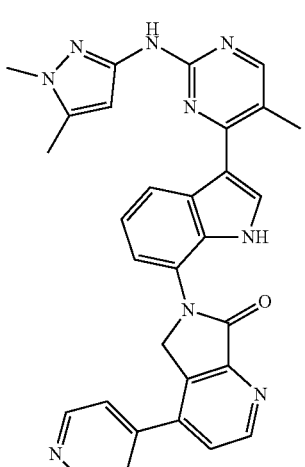

Using methyl 4-bromo-3-methylpicolinate and 4-bromopyridine, the title product was afforded as described for Example 377 in General Method K. MS (ESI, m/z): 528.2 [M+H]+

Example 495: Synthesis of 6-(3-(2-((1,5-dimethyl-1H-pyrazol-3-yl)amino)-5-methylpyrimidin-4-yl)-1H-indol-7-yl)-4-(pyridin-3-yl)-5,6-dihydro-7H-pyrrolo[3,4-b]pyridin-7-one

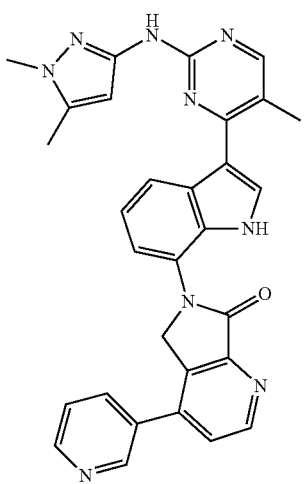

Using methyl 4-bromo-3-methylpicolinate and 3-bromopyridine, the title product was afforded as described for Example 377 in General Method K. MS (ESI, m/z): 528.2 [M+H]+

Example 496: Synthesis of 6-(3-(2-((1,5-dimethyl-1H-pyrazol-3-yl)amino)-5-methylpyrimidin-4-yl)-1H-indol-7-yl)-4-(1,2,3,6-tetrahydropyridin-4-yl)-5,6-dihydro-7H-pyrrolo[3,4-b]pyridin-7-one

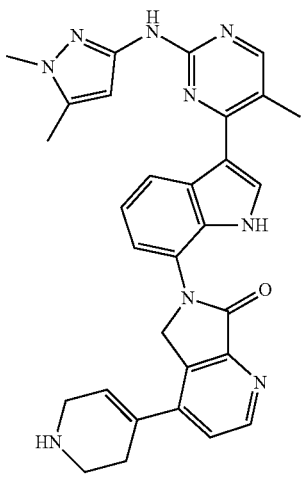

Using methyl 4-bromo-3-methylpicolinate and tert-butyl 4-bromo-3,6-dihydropyridine-1(2H)-carboxylate, the title product was afforded as described for Example 377 in General Method K (Boc group was deprotected during the reaction).
MS (ESI, m/z): 532.2 [M+H]$^+$ Example 497: Synthesis of 6-(3-(2-((1,5-dimethyl-1H-pyrazol-3-yl)amino)-5-methylpyrimidin-4-yl)-1H-indol-7-yl)-3-(pyridin-4-yl)-5,6-dihydro-7H-pyrrolo[3,4-b]pyridin-7-one

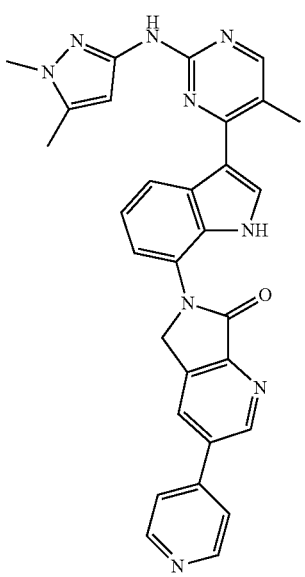

Using methyl 5-bromo-3-methylpicolinate and 4-bromopyridine, the title product was afforded as described for Example 377 in General Method K. MS (ESI, m/z): 528.2 [M+H]$^+$ Example 498: Synthesis of 6-(3-(2-((1,5-dimethyl-1H-pyrazol-3-yl)amino)-5-methylpyrimidin-4-yl)-1H-indol-7-yl)-3-(1,2,3,6-tetrahydropyridin-4-yl)-5,6-dihydro-7H-pyrrolo[3,4-b]pyridin-7-one

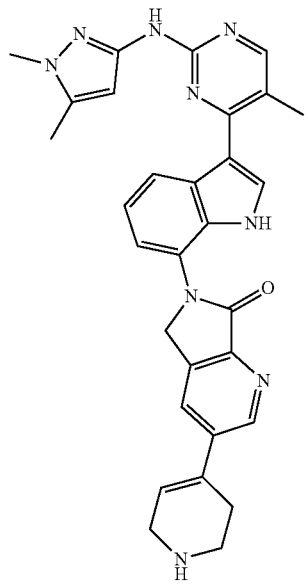

Using methyl 5-bromo-3-methylpicolinate and tert-butyl 4-bromo-3,6-dihydropyridine-1(2H)-carboxylate, the title product was afforded as described for Example 377 in General Method K (Boc group was deprotected during the reaction).
MS (ESI, m/z): 532.2 [M+H]$^+$ Example 499. 2-(3-(2-((1,5-dimethyl-1H-pyrazol-3-yl)amino)-5-methylpyrimidin-4-yl)-1H-indol-7-yl)-7-(1,2,3,6-tetrahydropyridin-4-yl)-1,2-dihydro-3H-pyrrolo[3,4-c]pyridin-3-one

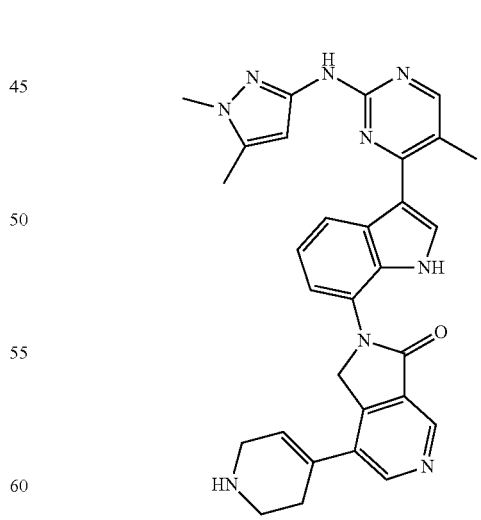

Using methyl 5-bromo-4-methylnicotinate and tert-butyl 4-bromo-3,6-dihydropyridine-1(2H)-carboxylate, the title product was afforded as described for Example 377 in General Method K (Boc group was deprotected during the reaction).

MS (ESI, m/z): 532.2 [M+H]⁺

Example 500: Synthesis of 2-(3-(2-((1,5-dimethyl-1H-pyrazol-3-yl)amino)-5-methylpyrimidin-4-yl)-1H-indol-7-yl)-7-(pyridin-4-yl)-1,2-dihydro-3H-pyrrolo[3,4-c]pyridin-3-one

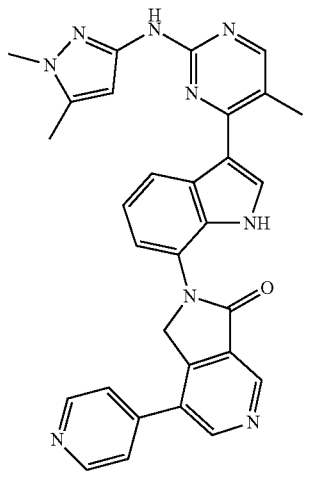

Using methyl 5-bromo-4-methylnicotinate and 4-bromopyridine, the title product was afforded as described for Example 377 in General Method K. MS (ESI, m/z): 528.2 [M+H]⁺

Example 501: Synthesis of 2-(3-(2-((1,5-dimethyl-1H-pyrazol-3-yl)amino)-5-methylpyrimidin-4-yl)-1H-indol-7-yl)-4-(pyridin-4-yl)-2,3-dihydro-1H-pyrrolo[3,4-c]pyridin-1-one

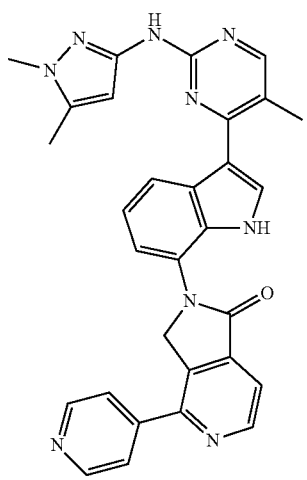

Using methyl 2-bromo-3-methylisonicotinate and 4-bromopyridine, the title product was afforded as described for Example 377 in General Method K. MS (ESI, m/z): 528.2 [M+H]⁺

Example 502: Synthesis of 2-(3-(2-((1,5-dimethyl-1H-pyrazol-3-yl)amino)-5-methylpyrimidin-4-yl)-1H-indol-7-yl)-4-(2-methylpyridin-4-yl)-2,3-dihydro-1H-pyrrolo[3,4-c]pyridin-1-one

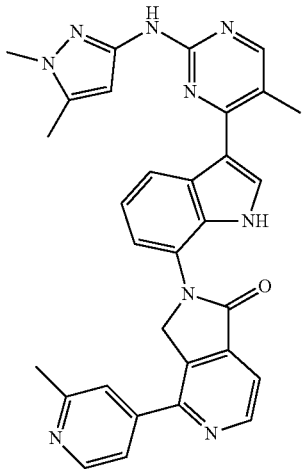

Using methyl 2-bromo-3-methylisonicotinate and 4-bromo-2-methylpyridine, the title product was afforded as described for Example 377 in General Method K. MS (ESI, m/z): 542.2 [M+H]⁺

Example 503: Synthesis of 2-(3-(2-((1,5-dimethyl-1H-pyrazol-3-yl)amino)-5-methylpyrimidin-4-yl)-1H-indol-7-yl)-4-(5-fluoropyridin-3-yl)-2,3-dihydro-1H-pyrrolo[3,4-c]pyridin-1-one

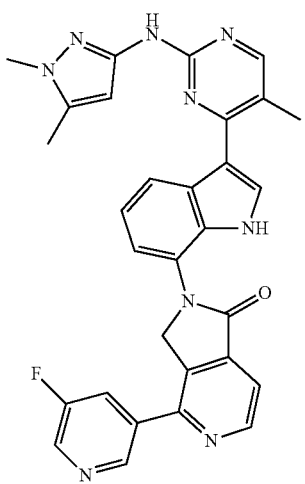

Using methyl 2-bromo-3-methylisonicotinate and 3-bromo-5-fluoropyridine, the title product was afforded as described for Example 377 in General Method K. MS (ESI, m/z): 546.2 [M+H]⁺

Example 504: Synthesis of 2-(3-(2-((1,5-dimethyl-1H-pyrazol-3-yl)amino)-5-methylpyrimidin-4-yl)-1H-indol-7-yl)-4-(2-fluoropyridin-4-yl)-2,3-dihydro-1H-pyrrolo[3,4-c]pyridin-1-one

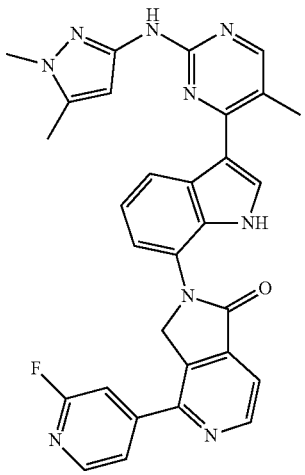

Using methyl 2-bromo-3-methylisonicotinate and 4-bromo-2-fluoropyridine, the title product was afforded as described for Example 377 in General Method K. MS (ESI, m/z): 546.2 [M+H]⁺

Example 505: Synthesis of 2-(3-(2-((1,5-dimethyl-1H-pyrazol-3-yl)amino)-5-methylpyrimidin-4-yl)-1H-indol-7-yl)-4-(5-methylpyridin-3-yl)-2,3-dihydro-1H-pyrrolo[3,4-c]pyridin-1-one

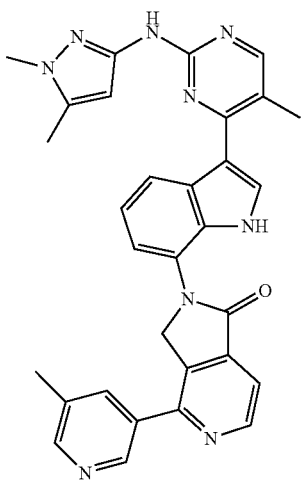

Using methyl 2-bromo-3-methylisonicotinate and 3-bromo-5-methylpyridine, the title product was afforded as described for Example 377 in General Method K. MS (ESI, m/z): 542.2 [M+H]⁺

Example 506: Synthesis of 2-(3-(2-((1,5-dimethyl-1H-pyrazol-3-yl)amino)-5-methylpyrimidin-4-yl)-1H-indol-7-yl)-4-(3-methylpyridin-4-yl)-2,3-dihydro-1H-pyrrolo[3,4-c]pyridin-1-one

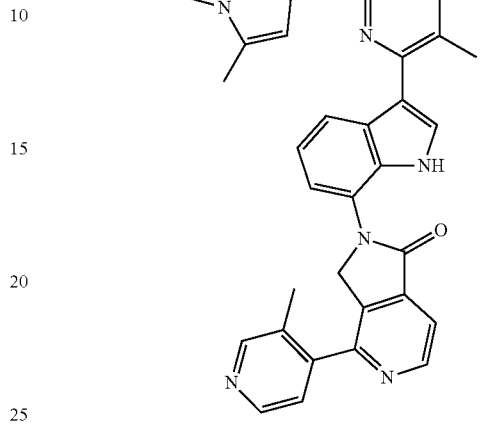

Using methyl 2-bromo-3-methylisonicotinate and 4-bromo-3-methylpyridine, the title product was afforded as described for Example 377 in General Method K. MS (ESI, m/z): 542.2 [M+H]⁺

Experimental Example 1: GCN2 Biochemical Assay

An inhibitory effect of the inventive compound on GCN2 was identified as follows.

384-well (Greiner #784075) (or 1536-well [Greiner #782075]) plates containing 60 nl (or 20 nl for 1536-well) of compound in 100% DMSO (10 concentrations serially diluted 3.16-fold) were prepared. Two copies of plates were used—one for the GCN2 assay and a second for an artifact plate. Working reagents were prepared as follows—reaction buffer: Tris pH 7.5 20 mM, MgCl2 5 mM, DTT 1 mM, Brij-35 0.005%, EGTA 0.5 mM in water; 2× enzyme solution: GCN2 (produced in-house) 1.6 nM in reaction buffer; 2× substrate solution: GFP-eIFS1 (Thermo Fisher Scientific, PV4809) 50 nM, ATP 0.2 mM, tRNA 0.4 mg/ml in reaction buffer; p-GFP-eIF2S1 (artifact) solution: p-GFP-eIFS1 (produced by incubation of 100 nM GFP-eIF2S1 in reaction buffer with 100 uM ATP and 1 nM PERK KD enzyme for 3 hr at room temperature) 2 nM in reaction buffer; 3× stop/antibody solution: p-GFP-EIF2S1 Tb-Ab (Thermo Fisher Scientific, PV4816) 6 nM, AZ13933939 3 uM, BSA 3% in reaction buffer. Reagents were loaded onto a liquid dispenser (Certus FLEX, Trajan Scientific and Medical), and 3 ul (1 ul for 1536-well) of 2× enzyme solution, followed by 3 ul (1 ul for 1536-well) of 2× substrate solution was added to the plates. When small numbers of plates were processed, the enzyme solution was added first to all plates, then the valve used for the substrate solution was primed immediately prior to use. Plates were tapped or spun 1 min/1K/RT to ensure proper mixing, followed by incubation at room temperature for 70 mins, covered/stacked in the dark. For the artifact plate, 6 ul of p-GFP-eIF2S1 solution was added prior to adding the stop/antibody solution. 3 ul (1 ul for 1536-well) of 3× stop/antibody solution was added to the plates, followed by a spin-down for 1 min/1K/RT, and incubation for 2-3 hr, sealed or covered with lids in the dark at room temperature. Plates were read on a plate reader (PHERAstar FSX, BMF Labtech) at Ex 340/Em 490/Em 520 nm.

The $IC_{50}$ of the compounds in examples above are disclosed in [Table 1] below:

TABLE 1

| Example | $IC_{50}$ (GCN2 Inhibitory Activity) |
|---|---|
| 1 | ++++ |
| 2 | +++ |
| 3 | ++++ |
| 4 | ++++ |
| 5 | ++++ |
| 6 | +++ |
| 7 | ++++ |
| 8 | ++++ |
| 9 | ++++ |
| 10 | ++++ |
| 11 | ++++ |
| 12 | +++ |
| 13 | ++++ |
| 14 | ++++ |
| 15 | ++++ |
| 16 | ++++ |
| 17 | ++++ |
| 18 | +++ |
| 19 | +++ |
| 20 | ++++ |
| 21 | +++ |
| 22 | ++ |
| 23 | ++ |
| 24 | ++ |
| 25 | + |
| 26 | +++ |
| 27 | +++ |
| 28 | +++ |
| 29 | +++ |
| 30 | ++ |
| 31 | +++ |
| 32 | +++ |
| 33 | +++ |
| 34 | ++ |
| 35 | ++ |
| 36 | ++ |
| 37 | ++ |
| 38 | ++ |
| 39 | ++ |
| 40 | ++ |
| 41 | +++ |
| 42 | +++ |
| 43 | +++ |
| 44 | ++ |
| 45 | ++ |
| 46 | ++ |
| 47 | +++ |
| 48 | +++ |
| 49 | +++ |
| 50 | +++ |
| 51 | +++ |
| 52 | ++++ |
| 53 | ++++ |
| 54 | +++ |
| 55 | ++++ |
| 56 | +++ |
| 57 | ++++ |
| 58 | ++++ |
| 59 | ++++ |
| 60 | +++ |
| 61 | ++++ |
| 62 | ++ |
| 63 | ++ |
| 64 | +++ |
| 65 | ++ |
| 66 | ++ |
| 67 | ++ |
| 68 | +++ |
| 69 | +++ |
| 70 | +++ |
| 71 | +++ |
| 72 | +++ |
| 73 | +++ |
| 74 | +++ |
| 75 | ++++ |
| 76 | ++++ |
| 77 | +++ |
| 78 | ++++ |
| 79 | ++++ |
| 80 | ++ |
| 81 | ++ |
| 82 | ++ |
| 83 | +++ |
| 84 | ++ |
| 85 | ++ |
| 86 | ++ |
| 87 | +++ |
| 88 | ++ |
| 89 | ++ |
| 90 | ++++ |
| 91 | +++ |
| 92 | ++++ |
| 93 | +++ |
| 94 | +++ |
| 95 | ++++ |
| 96 | +++ |
| 97 | +++ |
| 98 | ++ |
| 99 | +++ |
| 100 | ++ |
| 101 | + |
| 102 | +++ |
| 103 | +++ |
| 104 | ++++ |
| 105 | ++++ |
| 106 | ++ |
| 107 | ++++ |
| 108 | ++++ |
| 109 | ++++ |
| 110 | ++++ |
| 111 | ++++ |
| 112 | +++ |
| 113 | +++ |
| 114 | +++ |
| 115 | +++ |
| 116 | +++ |
| 117 | +++ |
| 118 | ++++ |
| 119 | +++ |
| 120 | ++++ |
| 121 | ++++ |
| 122 | +++ |
| 123 | +++ |
| 124 | ++++ |
| 125 | +++ |
| 126 | +++ |
| 127 | +++ |
| 128 | +++ |
| 129 | +++ |
| 130 | +++ |
| 131 | +++ |
| 132 | ++++ |
| 133 | ++++ |
| 134 | ++++ |
| 135 | ++++ |
| 136 | ++++ |
| 137 | ++++ |
| 138 | ++++ |
| 139 | ++++ |
| 140 | ++++ |
| 141 | ++++ |
| 142 | ++++ |
| 143 | ++++ |
| 144 | ++++ |
| 145 | ++++ |
| 146 | ++++ |
| 147 | ++++ |

TABLE 1-continued

| Example | IC$_{50}$ (GCN2 Inhibitory Activity) |
|---|---|
| 148 | ++++ |
| 149 | ++++ |
| 150 | +++ |
| 151 | ++++ |
| 152 | +++ |
| 153 | ++++ |
| 154 | ++++ |
| 155 | +++ |
| 156 | +++ |
| 157 | +++ |
| 158 | ++++ |
| 159 | ++++ |
| 160 | ++++ |
| 161 | ++++ |
| 162 | ++++ |
| 163 | ++++ |
| 164 | ++++ |
| 165 | ++++ |
| 166 | ++++ |
| 167 | +++ |
| 168 | ++++ |
| 169 | ++++ |
| 170 | ++++ |
| 171 | ++++ |
| 172 | ++++ |
| 173 | ++++ |
| 174 | ++++ |
| 175 | ++++ |
| 176 | +++ |
| 177 | ++++ |
| 178 | ++++ |
| 179 | ++++ |
| 180 | +++ |
| 181 | ++++ |
| 182 | ++++ |
| 183 | ++++ |
| 184 | +++ |
| 185 | ++++ |
| 186 | ++++ |
| 187 | ++++ |
| 188 | ++++ |
| 189 | ++++ |
| 190 | ++++ |
| 191 | ++++ |
| 192 | ++++ |
| 193 | ++++ |
| 194 | ++++ |
| 195 | +++ |
| 196 | ++++ |
| 197 | ++++ |
| 198 | ++++ |
| 199 | ++++ |
| 200 | ++++ |
| 201 | +++ |
| 202 | ++++ |
| 203 | ++++ |
| 204 | ++++ |
| 205 | ++++ |
| 206 | ++++ |
| 207 | ++++ |
| 208 | ++++ |
| 209 | +++ |
| 210 | +++ |
| 211 | ++++ |
| 212 | ++++ |
| 213 | ++++ |
| 214 | ++++ |
| 215 | ++++ |
| 216 | ++++ |
| 217 | ++++ |
| 218 | ++++ |
| 219 | ++++ |
| 220 | +++ |
| 221 | ++ |
| 222 | +++ |
| 223 | +++ |
| 224 | ++++ |
| 225 | ++++ |
| 226 | ++++ |
| 227 | ++++ |
| 228 | +++ |
| 229 | +++ |
| 230 | +++ |
| 231 | +++ |
| 232 | ++++ |
| 233 | ++++ |
| 234 | ++++ |
| 235 | +++ |
| 236 | ++++ |
| 237 | +++ |
| 238 | ++++ |
| 239 | +++ |
| 240 | +++ |
| 241 | +++ |
| 242 | +++ |
| 243 | +++ |
| 244 | +++ |
| 245 | +++ |
| 246 | +++ |
| 247 | ++++ |
| 248 | +++ |
| 249 | ++++ |
| 250 | ++ |
| 251 | +++ |
| 252 | +++ |
| 253 | +++ |
| 254 | +++ |
| 255 | +++ |
| 256 | +++ |
| 257 | ++ |
| 258 | +++ |
| 259 | +++ |
| 260 | ++++ |
| 261 | ++++ |
| 262 | ++++ |
| 263 | ++++ |
| 264 | ++++ |
| 265 | ++++ |
| 266 | ++++ |
| 267 | +++ |
| 268 | ++++ |
| 269 | ++++ |
| 270 | ++++ |
| 271 | ++++ |
| 272 | ++++ |
| 273 | ++++ |
| 274 | ++++ |
| 275 | +++ |
| 276 | +++ |
| 277 | +++ |
| 278 | ++++ |
| 279 | +++ |
| 280 | ++ |
| 281 | ++++ |
| 282 | ++++ |
| 283 | ++++ |
| 284 | +++ |
| 285 | ++++ |
| 286 | ++++ |
| 287 | ++++ |
| 288 | ++++ |
| 289 | ++++ |
| 290 | ++++ |
| 291 | ++++ |
| 292 | ++ |
| 293 | ++ |
| 294 | +++ |
| 295 | +++ |
| 296 | ++++ |
| 297 | ++++ |
| 298 | ++++ |
| 299 | ++++ |
| 300 | ++++ |
| 301 | ++++ |

TABLE 1-continued

| Example | IC$_{50}$ (GCN2 Inhibitory Activity) |
|---|---|
| 302 | ++++ |
| 303 | ++++ |
| 304 | ++++ |
| 305 | ++++ |
| 306 | ++++ |
| 307 | ++++ |
| 308 | ++++ |
| 309 | +++ |
| 310 | ++++ |
| 311 | +++ |
| 312 | +++ |
| 313 | ++++ |
| 314 | +++ |
| 315 | ++++ |
| 316 | +++ |
| 317 | ++++ |
| 318 | ++++ |
| 319 | ++++ |
| 320 | ++++ |
| 321 | ++++ |
| 322 | ++++ |
| 323 | ++++ |
| 324 | +++ |
| 325 | +++ |
| 326 | ++++ |
| 327 | ++++ |
| 328 | ++++ |
| 329 | ++ |
| 330 | +++ |
| 331 | ++++ |
| 332 | ++++ |
| 333 | ++++ |
| 334 | +++ |
| 335 | ++++ |
| 336 | +++ |
| 337 | ++++ |
| 338 | +++ |
| 339 | ++++ |
| 340 | ++ |
| 341 | ++++ |
| 342 | ++++ |
| 343 | +++ |
| 344 | ++++ |
| 345 | +++ |
| 346 | ++ |
| 347 | +++ |
| 348 | +++ |
| 349 | +++ |
| 350 | ++ |
| 351 | ++ |
| 352 | ++++ |
| 353 | +++ |
| 354 | +++ |
| 355 | + |
| 356 | ++ |
| 357 | +++ |
| 358 | ++++ |
| 359 | +++ |
| 360 | ++++ |
| 361 | ++++ |
| 362 | ++++ |
| 363 | ++++ |
| 364 | ++++ |
| 365 | ++++ |
| 366 | ++++ |
| 367 | ++++ |
| 368 | ++++ |
| 369 | +++ |
| 370 | ++++ |
| 371 | ++++ |
| 372 | ++++ |
| 373 | ++++ |
| 374 | ++++ |
| 375 | ++++ |
| 376 | ++++ |
| 377 | ++++ |
| 378 | + |
| 379 | ++ |
| 380 | ++++ |
| 381 | ++++ |
| 382 | +++ |
| 383 | ++++ |
| 384 | ++ |
| 385 | +++ |
| 386 | +++ |
| 387 | ++++ |
| 388 | ++++ |
| 389 | ++++ |
| 390 | ++++ |
| 391 | +++ |
| 392 | ++++ |
| 393 | ++++ |
| 394 | ++++ |
| 395 | +++ |
| 396 | ++++ |
| 397 | ++++ |
| 398 | +++ |
| 399 | ++++ |
| 400 | ++++ |
| 401 | ++++ |
| 402 | +++ |
| 403 | +++ |
| 404 | ++++ |
| 405 | +++ |
| 406 | +++ |
| 407 | +++ |
| 408 | ++++ |
| 409 | +++ |
| 410 | ++ |
| 411 | ++++ |
| 412 | ++++ |
| 413 | ++++ |
| 414 | ++++ |
| 415 | ++++ |
| 416 | ++++ |
| 417 | ++++ |
| 418 | ++++ |
| 419 | ++++ |
| 420 | ++++ |
| 421 | ++++ |
| 422 | ++++ |
| 423 | ++++ |
| 424 | ++++ |
| 425 | ++++ |
| 426 | ++++ |
| 427 | ++++ |
| 428 | ++++ |
| 429 | ++++ |
| 430 | ++++ |
| 431 | +++++ |
| 432 | ++++ |
| 433 | +++ |
| 434 | ++ |
| 435 | ++++ |
| 436 | +++ |
| 437 | ++++ |
| 438 | +++ |
| 439 | + |
| 440 | +++ |
| 441 | +++ |
| 442 | +++ |
| 443 | +++ |
| 444 | ++++ |
| 445 | ++++ |
| 446 | ++++ |
| 447 | ++++ |
| 448 | ++++ |
| 449 | +++ |
| 450 | +++ |
| 451 | +++ |
| 452 | ++ |
| 453 | +++ |
| 454 | ++++ |
| 455 | ++++ |

TABLE 1-continued

| Example | IC$_{50}$ (GCN2 Inhibitory Activity) |
|---|---|
| 456 | ++++ |
| 457 | ++++ |
| 458 | +++ |
| 459 | ++++ |
| 460 | ++++ |
| 461 | +++ |
| 462 | +++ |
| 463 | ++ |
| 464 | ++++ |
| 465 | ++++ |
| 466 | ++++ |
| 467 | ++++ |
| 468 | ++++ |
| 469 | ++++ |
| 470 | ++++ |
| 471 | ++++ |
| 472 | ++++ |
| 473 | ++++ |
| 474 | ++++ |
| 475 | ++++ |
| 476 | ++++ |
| 477 | ++++ |
| 478 | ++++ |
| 479 | ++++ |
| 480 | ++++ |
| 481 | ++++ |
| 482 | ++++ |
| 483 | ++++ |
| 484 | ++++ |
| 485 | ++++ |
| 486 | ++++ |
| 487 | ++++ |
| 488 | ++++ |
| 489 | ++++ |
| 490 | +++ |
| 491 | ++ |
| 492 | ++ |
| 493 | ++++ |
| 494 | ++++ |
| 495 | ++++ |
| 496 | ++++ |
| 497 | ++++ |
| 498 | ++++ |
| 499 | ++++ |
| 500 | ++++ |
| 501 | ++++ |
| 502 | ++++ |
| 503 | ++++ |
| 504 | ++++ |
| 505 | ++++ |
| 506 | ++++ |

+: 1000 nM < IC$_{50}$,
++: 100 nM < IC$_{50}$ < 1000 nM,
+++: 10 nM < IC$_{50}$ < 100 nM,
++++: IC$_{50}$ < 10 nM

The invention claimed is:

1. A compound represented by a following Formula (I), a stereoisomer thereof, a pharmaceutically acceptable salt thereof, or a solvate thereof:

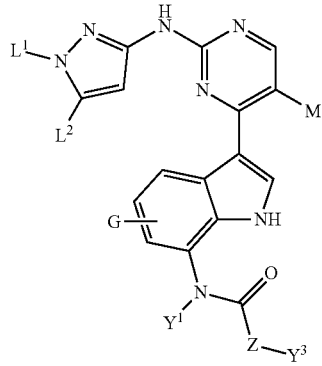

[Formula (I)]

wherein,
L$^1$ and L$^2$ each independently represent H; (C$_{1-5}$)alkyl; or L$^1$ and L$^2$ may be connected to form a 5 to 6-membered ring,
M represents H; halogen; (C$_{1-5}$)alkyl; (C$_{3-7}$)cycloalkyl; or (C$_{1-5}$)alkoxy,
G represents H; halogen; (C$_{1-5}$)alkyl; (C$_{1-5}$)alkoxy; or —NH$_2$, wherein at least one H of —NH$_2$ optionally substituted with (C$_{1-5}$)alkyl,
Y$^1$ represents H; or (C$_{1-5}$)alkyl,
Z represents —C(=O)—; or —CH$_2$— optionally substituted with one or more (C$_{1-5}$)alkyl; and/or Z may be connected to Y$^1$ to form a 5- to 6-membered ring,
Y$^3$ represents 4- to 6-membered heterocycloalkyl which is optionally substituted with W$^1$ and W$^2$; or Y$^3$ may be connected to Z to form an aryl or a heteroaryl in case that Z is connected to Y$^1$ to form the 5- to 6-membered ring,
W$^1$ and W$^2$ each independently represent H; halogen; —OH; (C$_{1-5}$)alkyl optionally substituted with —OH or —CN; 5- to 7-membered heterocycloalkyl optionally substituted with (C$_{1-5}$)alkyl; a heteroaryl optionally substituted with (C$_{1-5}$)alkyl; —COR$^1$; —OR$^2$ or —NH$_2$, wherein at least one H of —NH$_2$ optionally substituted with a heteroaryl,
R$^1$ represents (C$_{1-5}$)alkoxy; —OH; 5-7 membered heterocycloalkyl optionally substituted with (C$_{1-5}$)alkyl; or —NH$_2$, wherein at least one H of —NH$_2$ optionally substituted with (C$_{3-7}$)cycloalkyl,
R$^2$ represents (C$_{1-5}$)alkyl optionally substituted with a heteroaryl; an aryl; or a heteroaryl, wherein the aryl or the heteroaryl is optionally substituted with one or more R$^{2a}$,
R$^{2a}$ independently represents halogen, (C$_{1-5}$)alkyl optionally substituted with an aryl, or 5- to 7-membered heterocycloalkyl substituted with (C$_{1-5}$)alkyl; (C$_{5-6}$) cycloalkenyl optionally substituted with (C$_{1-5}$)alkyl; 5- to 7-membered heterocycloalkyl substituted with C$_{1-5}$) alkyl or —OH; —CF$_3$; (C$_{1-5}$)alkoxy optionally substituted with an aryl; an aryl; a heteroaryl optionally substituted with (C$_{1-5}$)alkyl; thio(C$_{1-5}$)alkyl; —COR$^1$; or NR$^3$R$^4$,
R$^3$ and R$^4$ each independently represent H; halogen; (C$_{1-5}$)alkyl optionally substituted with halogen, —CF$_3$, —OH, (C$_{1-5}$)alkoxy, (C$_{1-5}$)alkyl-N—(C$_{1-5}$)alkyl, an aryl or (C$_{3-7}$)cycloalkyl; (C$_{3-7}$)cycloalkyl; (C$_{1-5}$) alkoxy; an aryl; or —C(=O)(C$_{1-5}$)alkyl.

2. The compound, the stereoisomer thereof, the pharmaceutically acceptable salt thereof or the solvate thereof according to claim 1, wherein:

Y³ represents azetidinyl; pyrrolidinyl; piperidinyl; tetrahydropyridinyl; or oxopyrrolidinyl, which is optionally substituted with W¹ and W², W¹ and W² each independently represent H; halogen; —OH; (C$_{1-5}$)alkyl optionally substituted with —OH or —CN; methylpiperazinyl; morpholinyl; pyridinyl; methylpyrazolyl; —COR¹; —OR²; —NH₂; —NH(pyridinyl) or —NH(pyrimidinyl), R¹ represents (C$_{1-5}$)alkoxy; —OH; —NH₂; —NH—(C$_{3-7}$)cycloalkyl; oxopiperazinyl; morpholinyl; thiomorpholinyl; methylpiperazinyl; or tetrahydropyridinyl, R² represents (C$_{1-5}$)alkyl optionally substituted with pyridinyl; halophenyl; dihalophenyl; (amino)halophenyl; (methylpiperazinyl)(methyl)phenyl; (dimehtylamino)phenyl; aminophenyl; biphenyl; (phenylpropanyl)phenyl; (cyclopropylamino)pyrimidinyl; (trifluoroethylamino)pyrimidinyl; pyridinyl; pyrimidinyl; (cyclopropyl)(isoxazole)carboxamide; (dimethyl)pyrimidinyl; pyrazinyl; aminopyridinyl; halopyridinyl; aminopyrazinyl; halopyrimidinyl; (methyl)halopyrimidinyl; (amino)(methyl)pyrimidinyl; (amino)halopyrimidinyl; dihalopyrimidinyl; amino(dihalophenyl)pyrimidinyl; (amino)(trifluoromethyl)pyrimidinyl; pentylpyrimidinyl; methylpyrazolyl; methyl(benzothiophene)carboxylate; methyl(thiophene)carboxylate; (thiophene)carboxylic acid; (thiophene)carboxamide; methyl(thiophene)carboxamide; cyclopropyl(thiophene)carboxamide; methylisoxazolyl; benzoisoxazolyl; isothiazolyl; methylthiophenyl; pyrazolyl; (methyl)(trifluoromethyl)pyrazolyl; isoxazolyl; aminopyrazolyl; methyl(pyrrole)carboxylate; ethyl(isoxazole)carboxylate; (isoxazole)carboxamide; methyl(isoxazole)carboxamide; cyclopropyl(isoxazole)carboxamide; dimethyl(isoxazole)carboxamide; cyclopropyl(oxazole)carboxamide; (pyrimidine)carboxylic acid; (pyrimidine)carboxamide; methyl(pyrimidine)carboxamide; dimethyl(pyrimidine)carboxamide; (pyrazine)carboxamide; methyl(pyrazine)carboxamide; aminotriazinyl; (methylamino)triazinyl; (dimethylamino)triazinyl; (cyclopropylamino)triazinyl; diaminotriazinyl; (amino)(pyrrolidinyl)triazinyl; aminopyrimidinyl; (methylamino)pyrimidinyl; (ethylamino)pyrimidinyl; (propylamino)pyrimidinyl; (butylamino)pyrimidinyl; (hydroxyethylamino)pyrimidinyl; (hydroxypropylamino)pyrimidinyl; (methoxyethylamino)pyrimidinyl; (((dimethylamino)propyl)amino)pyrimidinyl; (benzylamino)pyrimidinyl; (phenethylamino)pyrimidinyl; (cyclohexylamino)pyrimidinyl; (dimethylamino)pyrimidinyl; (ethylmethylamino)pyrimidinyl; (diethylamino)pyrimidinyl; (ethylpropylamino)pyrimidinyl; (butylethylamino)pyrimidinyl; pyrrolidinylpyrimidinyl; (hydroxypyrrolidinyl)pyrimidinyl; piperidinylpyrimidinyl; (hydroxypiperidinyl)pyrimidinyl; morpholinopyrimidinyl; (methylpiperazinyl)pyrimidinyl; (amino)(methyl)pyrimidinyl; (amino)(pyrrolidinyl)pyrimidinyl; (methylamino)halopyrimidinyl; (ethylamino)halopyrimidinyl; (cyclopropylamino)halopyrimidinyl; (cyclohexylamino)halopyrimidinyl; (dimethylamino)halopyrimidinyl; (ethylmethylamino)halopyrimidinyl; (diethylamino)halopyrimidinyl; (methylphenylamino)halopyrimidinyl; (benzylmethylamino)halopyrimidinyl; (pyrrolidinyl)halopyrimidinyl; (piperidinyl)halopyrimidinyl; (morpholino)halopyrimidinyl; (thiomorpholino)halopyrimidinyl; (methylpiperazinyl)halopyrimidinyl; (cyclopropylamino)methylpyrimidinyl; (amino)pyrimidinyl; (methylthio)pyrimidinyl; (methoxy)pyrimidinyl; (benzyloxy)pyrimidinyl; acetamidopyrimidinyl; (difluoropropylamino)pyrimidinyl; (difluoroethylamino)pyrimidinyl; (trifluoropropylamino)pyrimidinyl; (fluoroethylamino)pyrimidinyl; (cyclobutylamino)pyrimidinyl; (cyclopentylamino)pyrimidinyl; (isopropylamino)pyrimidinyl; (sec-butylamino)pyrimidinyl; ((cyclopropylmethyl)amino)pyrimidinyl; (((dimethylamino)ethyl)amino)pyrimidinyl; (((dimethylamino)propyl)amino)pyrimidinyl; (methoxyamino)pyrimidinyl; (benzylmethylamino)pyrimidinyl; (cylclohexylamino)halopyrimidinyl; (cyclopropylmethylamino)halopyrimidinyl; (benzylamino)halopyrimidinyl; (cylclopropylamino)halopyrimidinyl; (cylclopropylamino)methylpyrimidinyl; (cyclopropylamino)(trifluoromethyl)pyrimidinyl; (cyclopropylamino)(methoxy)pyrimidinyl; (cyclopropylamino)pyrazinyl; (ethylamino)pyrazinyl; (propylamino)pyrazinyl; (hydroxyethylamino)pyrazinyl; (((dimethylamino)ethyl)amino)pyrazinyl; phenylpyrimidinyl; (methylpyrazolyl)pyrimidinyl; (dimethylcyclohexenyl)pyrimidinyl; dihydropyranylpyrimidinyl; or pyridinylpyrimidinyl.

3. The compound, the stereoisomer thereof, the pharmaceutically acceptable salt thereof, or the solvate thereof according to claim 1, wherein the compound represented by formula (I) above is a compound represented by a following Formula (Ib):

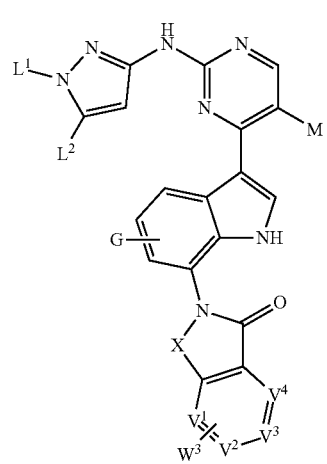

[Formula (Ib)]

X represents —CH₂—; or —C(=O)—,

V¹, V², V³ and V⁴ each independently represent CH or N, wherein V¹, V², V³ and V⁴ each independently be substituted with W³ in case that V¹, V², V³ and/or V⁴ are(is) CH, W³ independently represents H, halogen; (C$_{1-5}$)alkyl; (C$_{1-5}$)alkoxy; —OH; —NO₂; —NR⁵R⁶; —CH=CR⁷R⁸; —C≡C—R⁹; (C$_{5-6}$)cycloalkenyl; 5- to 7-membered heterocycloalkyl optionally substituted with (C$_{1-5}$)alkyl, —C(=O)O(C$_{1-5}$)alkyl, —S(=O)₂(C$_{1-5}$)alkyl, —C(=O)(C$_{1-5}$)alkyl or —C(=O)(NH₂); an aryl; or a heteroaryl, wherein the aryl or the heteroaryl may be optionally substituted with one or more R¹⁰, R⁵ and R⁶ each independently represent H; (C$_{1-5}$)alkyl optionally substituted with (C$_{3-7}$)cycloalkyl or an aryl; 5- to 7-membered heterocycloalkyl optionally substituted with (C$_{1-5}$)alkyl; an aryl; —C(=O)R¹¹; or —S(=O)₂R¹², R⁷ represents (C$_{1-5}$)alkyl optionally substituted with —OH; an aryl optionally substituted with halogen; or —C(=O)R¹³, R⁸ represents H; or (C$_{1-5}$)alkyl, R⁹ represents an aryl optionally substituted with —NH₂,
R¹⁰ independently represents H; halogen; —CN; —CF₃; —OH; —OCF₃; (C₁₋₅)alkyl optionally substituted with (C₃₋₇)cycloalkyl, 5- to 7-membered heterocycloalkyl, or —OH; (C₁₋₅)alkoxy; —NH₂ optionally substituted with one or more (C₁₋₅)alkyl; 5- to 7-membered heterocycloalkyl optionally substituted with (C₁₋₅)alkyl; —C(=O)R¹⁴; —S(=O)₂-(5- to 7-membered heterocycloalkyl); or an aryl, wherein R¹⁰ is optionally connected to each other to form 5 to 6-membered ring,
R¹¹ represents (C₁₋₅)alkyl optionally substituted with —N(CH₃)₂, an aryl, or a hydroxyaryl; (C₃₋₇)cycloalkyl optionally comprising C(=O); (C₃₋₇)cycloalkyl optionally substituted with (C₁₋₅)alkyl; (C₃₋₇)cycloalkyl fused with an aryl; (C₅₋₆)cycloalkenyl optionally substituted with (C₁₋₅)alkyl; 5- to 7-membered heterocycloalkyl optionally substituted with (C₁₋₅)alkyl or —NH₂; an aryl; or a heteroaryl optionally substituted with (C₁₋₅)alkyl or —OH,
R¹² represents (C₁₋₅)alkyl; or an aryl optionally substituted with (C₁₋₅)alkyl and/or halogen,
R¹³ represents (C₁₋₅)alkyl; (C₁₋₅)alkoxy; —OH; —NH₂, wherein at least one H of —NH₂ optionally substituted with (C₁₋₅)alkyl; (C₃₋₇)cycloalkyl; hydroxy(C₁₋₅)alkyl; (C₁₋₅)alkoxy(C₁₋₅)alkyl; —NH₂,
R¹⁴ represents 5- to 7-membered heterocycloalkyl; —NH₂; or —OH,
L¹, L², M, and G are as defined in claim 1.

4. The compound, the stereoisomer thereof, the pharmaceutically acceptable salt thereof, or the solvate thereof according to claim 3,
W³ independently represents H, halogen; (C₁₋₅)alkyl; (C₁₋₅)alkoxy; —OH; —NO₂; —NR⁵R⁶; —CH=CR⁷R⁸; —C≡C—R⁹; (C₅₋₆)cycloalkenyl; morpholinyl; tetrahydropyridinyl; dihydropyranyl; tert-butyl(tetrahydropyridine)carboxylate; dihydrothiopyranyl; methyltetrahydropyridinyl; (methylsulfonyl)tetrahydropyridinyl; acetyltetrahydropyridinyl; (tetrahydropyridine)carboxamide; 1,1-dioxide-dihydrothiopyranyl; phenyl; (trifluoromethoxy)phenyl; aminophenyl; tert-butyl(phenyl)carbamate; (pyrrolidinylsulfonyl)phenyl; oxopiperidine(carbonyl)phenyl; (methylpiperazinyl)phenyl; isoindolyl; cyanophenyl; cyanohalophenyl; (trifluoromethyl)phenyl; (dimethylamino)phenyl; hydroxybenzyl; methoxyphenyl; biphenyl; methylphenyl; hydroxyphenyl; dihydroindenyl; benzoic acid; methylbenzoate; pyridinyl; pyrazolyl; methylpyrazolyl; furanyl; aminopyridinyl; halopyridinyl; hydroxypyridinyl; (methoxy)halopyridinyl; methoxypyridinyl; (methyl)halopyridinyl; piperazinylpyridinyl; pyrrolopyridinyl; (dimethylamino)pyrimidinyl; (cyclopropylmethyl)pyrazolyl; (morpholinoethyl)pyrazolyl; pyrimidinyl; aminopyrimidinyl; (methylpiperazinyl)pyridinyl; piperazinylpyridinyl; morpholinopyridinyl; dihalopyridinyl; methylpyridinyl; pyrrolyl; tert-butyl(pyrrole)carboxylate; dimethylisoxazolyl; isoquinolinyl; methylindazolyl; methylthiophenyl; indazolyl; thiophenyl; cyanopyridinyl; (hydroxymethyl)pyridinyl; picolinamide; (dimethylamino)pyridinyl; (methylamino)pyridinyl; dimethylpyridinyl; or (methylamino)pyridinyl,
R⁵ and R⁶ each independently represent H; (C₁₋₅)alkyl optionally substituted with (C₃₋₇)cycloalkyl or phenyl; morpholinyl, or piperazinyl optionally substituted with (C₁₋₅)alkyl; phenyl; —C(=O)R¹¹; or —S(=O)₂R¹²,
R⁷ represents methyl optionally substituted with —OH; phenyl optionally substituted with halogen; or —C(=O)R¹³,
R⁹ represents phenyl optionally substituted with —NH₂,
R¹¹ represents (C₁₋₅)alkyl optionally substituted with —N(CH₃)₂, phenyl, or hydroxyphenyl; (C₃₋₇)cycloalkyl optionally comprising C(=O); (C₃₋₇)cycloalkyl substituted with (C₁₋₅)alkyl; (C₃₋₇)cycloalkyl fused with phenyl; (C₅₋₆)cycloalkenyl optionally substituted with (C₁₋₅)alkyl; morpholinyl; methylpiperidinyl; oxopyrrolidinyl; oxoimidazolidinyl; pyrrolidinyl; piperidinyl; tetrahydrofuranyl; tetrahydropyranyl; methyltetrahydropyranyl; aminopyrrolidinyl; methylpyrrolidinyl; phenyl; pyridinyl; oxazolyl; pyridazinyl; methylisoxazolyl; methyloxazolyl; isoxazolyl; methylpyridinyl; furanyl; or hydroxypyrimidinyl,
R¹² represents (C₁₋₅)alkyl; phenyl; methylphenyl; or (methyl)halophenyl,
R¹⁴ represents oxopiperidinyl; —NH₂; or —OH.

5. A pharmaceutical composition for treating GCN2 activation-related diseases, comprising the compound represented by formula (I) above, the stereoisomer thereof, the pharmaceutically acceptable salt thereof, or the solvate thereof according to claim 1 as an active ingredient.

6. A compound, a stereoisomer thereof, a pharmaceutically acceptable salt thereof, or a solvate thereof, wherein the compound is one selected from the group consisting of the following compounds:

1) 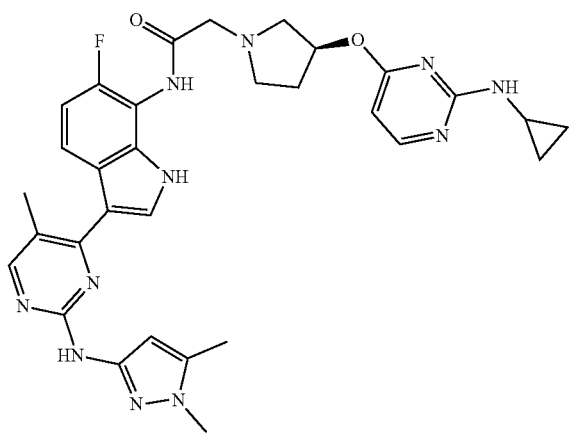 [SMILES: Cc1cnc(Nc2cc(C)n(C)n2)nc1-c1c[nH]c2c(NC(=O)CN3CC[C@H](Oc4ccnc(NC5CC5)n4)C3)c(F)ccc12]

(S)-2-(3-((2-(cyclopropylamino)pyrimidin-4-yl)oxy)pyrrolidin-1-yl)-N-(3-(2-((1,5-dimethyl-1H-pyrazol-3-yl)amino)-5-methylpyrimidin-4-yl)-6-fluoro-1H-indol-7-yl)acetamide -continued 2) 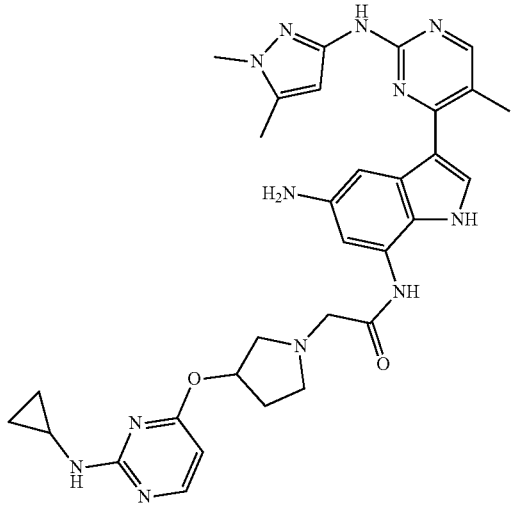 [SMILES: Cc1cnc(Nc2cc(C)n(C)n2)nc1-c1c[nH]c2c(NC(=O)CN3CCC(Oc4ccnc(NC5CC5)n4)C3)cc(N)cc12]

(S)-N-(5-amino-3-(2-((1,5-dimethyl-1H-pyrazol-3-yl)amino)-5-methylpyrimidin-4-yl)-1H-indol-7-yl)-2-(3-((2-(cyclopropylamino)pyrimidin-4-yl)oxy)pyrrolidin-1-yl)acetamide 3) 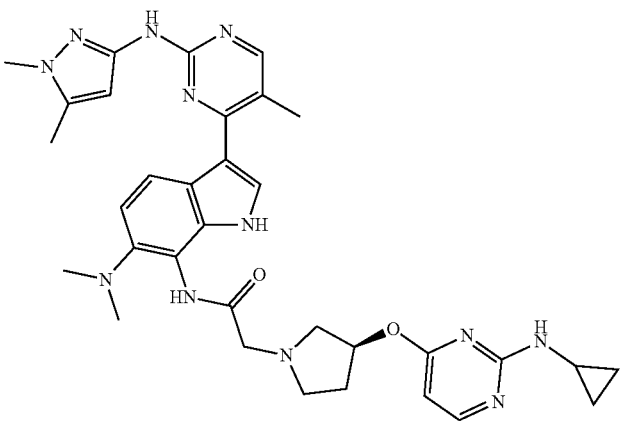 [SMILES: Cc1cnc(Nc2cc(C)n(C)n2)nc1-c1c[nH]c2c(NC(=O)CN3CC[C@H](Oc4ccnc(NC5CC5)n4)C3)c(N(C)C)ccc12]

(S)-2-(3-((2-(cyclopropylamino)pyrimidin-4-yl)oxy)pyrrolidin-1-yl)-N-(3-(2-((1,5-dimethyl-1H-pyrazol-3-yl)amino)-5-methylpyrimidin-4-yl)-6-(dimethylamino)-1H-indol-7-yl)acetamide 4) 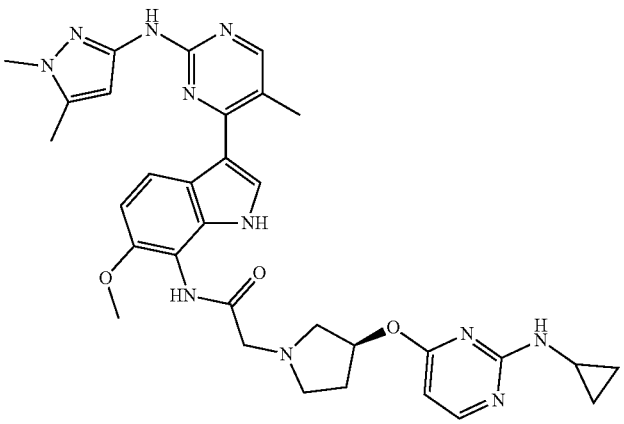 [SMILES: COc1ccc2c(-c3nc(Nc4cc(C)n(C)n4)ncc3C)c[nH]c2c1NC(=O)CN1CC[C@H](Oc2ccnc(NC3CC3)n2)C1]

(S)-2-(3-((2-(cyclopropylamino)pyrimidin-4-yl)oxy)pyrrolidin-1-yl)-N-(3-(2-((1,5-dimethyl-1H-pyrazol-3-yl)amino)-5-methylpyrimidin-4-yl)-6-methoxy-1H-indol-7-yl)acetamide -continued 5) 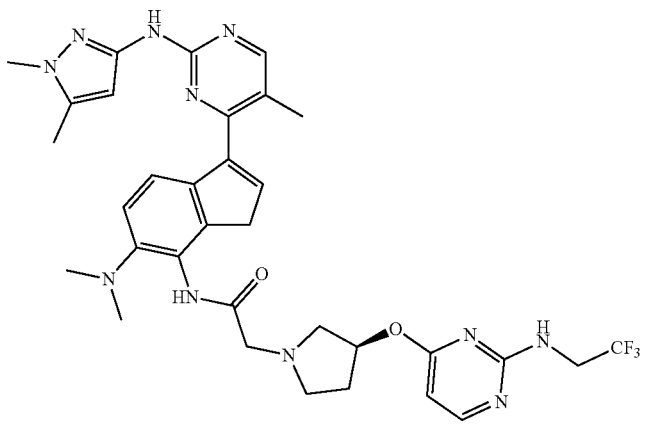 [SMILES: Cc1cnc(Nc2cc(C)n(C)n2)nc1C1=CCc2c1ccc(N(C)C)c2NC(=O)CN1CC[C@H](Oc2ccnc(NCC(F)(F)F)n2)C1]

(S)-N-(3-(2-((1,5-dimethyl-1H-pyrazol-3-yl)amino)-5-methylpyrimidin-4-yl)-6-(dimethylamino)-1H-inden-7-yl)-2-(3-((2-((2,2,2-trifluoroethyl)amino)pyrimidin-4-yl)oxy)pyrrolidin-1-yl)acetamide 6) 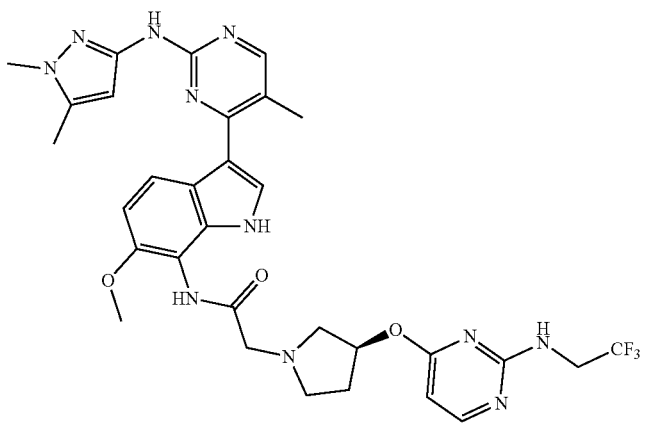 [SMILES: COc1ccc2c(-c3nc(Nc4cc(C)n(C)n4)ncc3C)c[nH]c2c1NC(=O)CN1CC[C@H](Oc2ccnc(NCC(F)(F)F)n2)C1]

(S)-N-(3-(2-((1,5-dimethyl-1H-pyrazol-3-yl)amino)-5-methylpyrimidin-4-yl)-6-methoxy-1H-indol-7-yl)-2-(3-((2-((2,2,2-trifluoroethyl)amino)pyrimidin-4-yl)oxy)pyrrolidin-1-yl)acetamide 7) 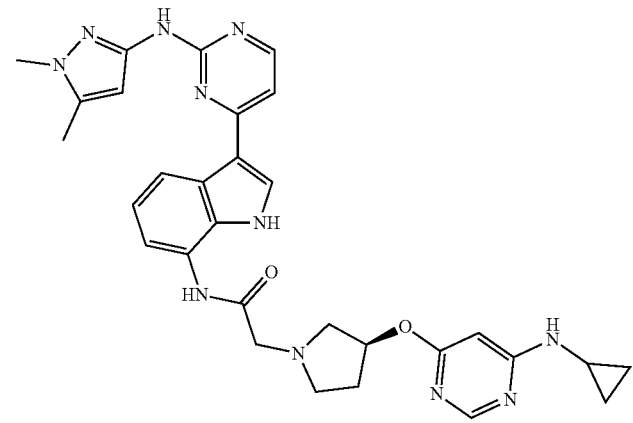 [SMILES: Cc1cc(Nc2nccc(-c3c[nH]c4c(NC(=O)CN5CC[C@H](Oc6cc(NC7CC7)ncn6)C5)cccc34)n2)nn1C]

(S)-2-(3-((6-(cyclopropylamino)pyrimidin-4-yl)oxy)pyrrolidin-1-yl)-N-(3-(2-((1,5-dimethyl-1H-pyrazol-3-yl)amino)pyrimidin-4-yl)-1H-indol-7-yl)acetamide -continued
8) 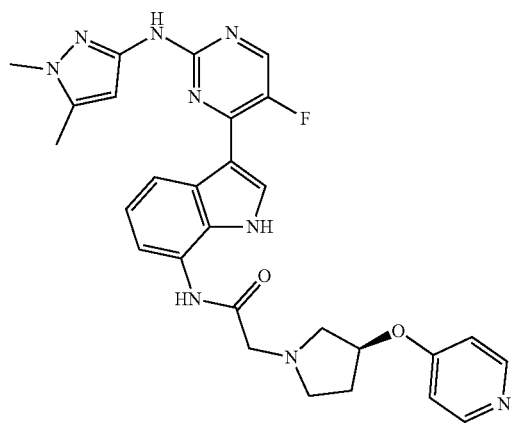 [SMILES: Cc1cc(Nc2ncc(F)c(-c3c[nH]c4c(NC(=O)CN5CC[C@H](Oc6ccncc6)C5)cccc34)n2)nn1C]
(S)-N-(3-(2-((1,5-dimethyl-1H-pyrazol-3-yl)amino)-5-fluoropyrimidin-4-yl)-1H-indol-7-yl)-2-(3-(pyridin-4-yloxy)pyrrolidin-1-yl)acetamide
9) 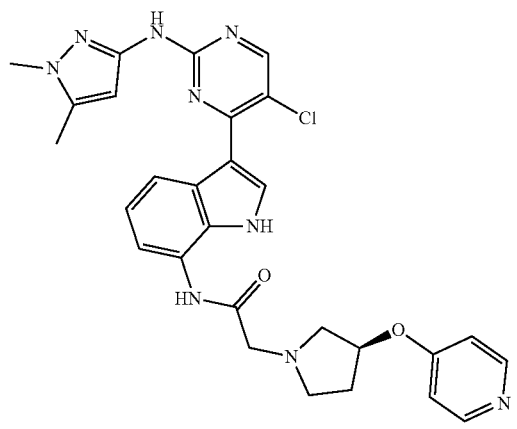 [SMILES: Cc1cc(Nc2ncc(Cl)c(-c3c[nH]c4c(NC(=O)CN5CC[C@H](Oc6ccncc6)C5)cccc34)n2)nn1C]
(S)-N-(3-(5-chloro-2-((1,5-dimethyl-1H-pyrazol-3-yl)amino)pyrimidin-4-yl)-1H-indol-7-yl)-2-(3-(pyridin-4-yloxy)pyrrolidin-1-yl)acetamide
10) 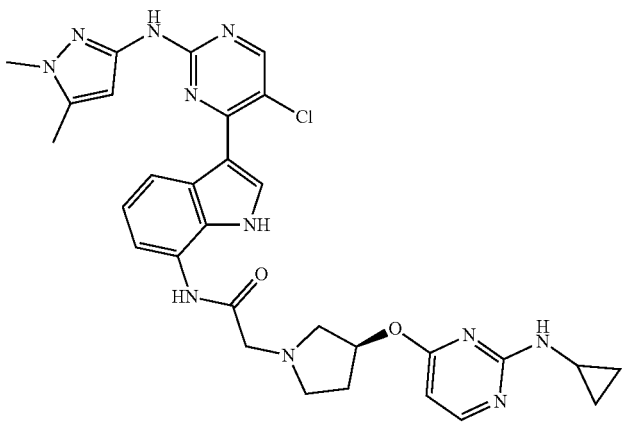 [SMILES: Cc1cc(Nc2ncc(Cl)c(-c3c[nH]c4c(NC(=O)CN5CC[C@H](Oc6ccnc(NC7CC7)n6)C5)cccc34)n2)nn1C]
(S)-N-(3-(5-chloro-2-((1,5-dimethyl-1H-pyrazol-3-yl)amino)pyrimidin-4-yl)-1H-indol-7-yl)-2-(3-((2-(cyclopropylamino)pyrimidin-4-yl)oxy)pyrrolidin-1-yl)acetamide -continued 11) 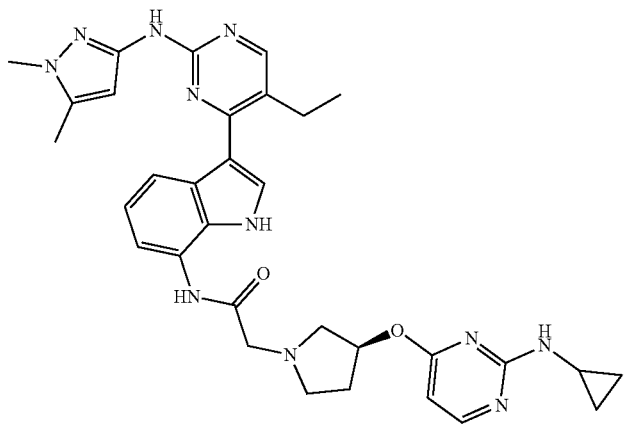 [SMILES: CCc1cnc(Nc2cc(C)n(C)n2)nc1-c1c[nH]c2c(NC(=O)CN3CC[C@H](Oc4ccnc(NC5CC5)n4)C3)cccc12]

(S)-2-(3-((2-(cyclopropylamino)pyrimidin-4-yl)oxy)pyrrolidin-1-yl)-N-(3-(2-((1,5-dimethyl-1H-pyrazol-3-yl)amino)-5-ethylpyrimidin-4-yl)-1H-indol-7-yl)acetamide 12) 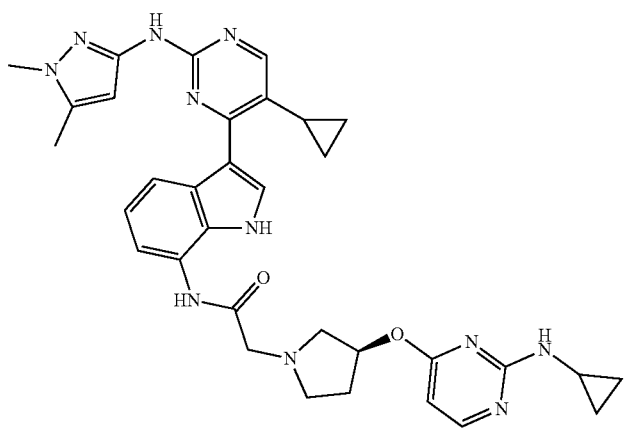 [SMILES: Cc1cc(Nc2ncc(C3CC3)c(-c3c[nH]c4c(NC(=O)CN5CC[C@H](Oc6ccnc(NC7CC7)n6)C5)cccc34)n2)nn1C]

(S)-N-(3-(5-cyclopropyl-2-((1,5-dimethyl-1H-pyrazol-3-yl)amino)pyrimidin-4-yl)-1H-indol-7-yl)-2-(3-((2-(cyclopropylamino)pyrimidin-4-yl)oxy)pyrrolidin-1-yl)acetamide 13) 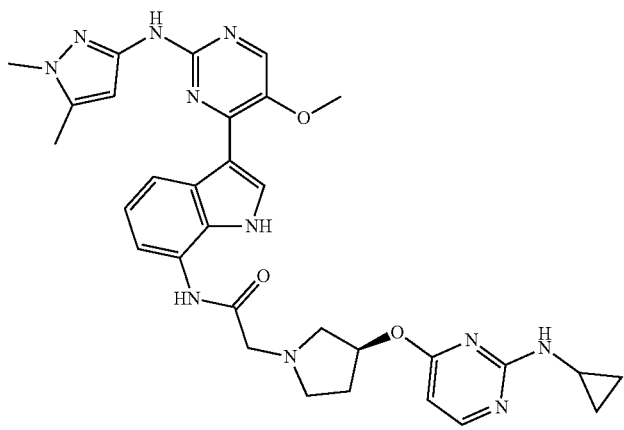 [SMILES: COc1cnc(Nc2cc(C)n(C)n2)nc1-c1c[nH]c2c(NC(=O)CN3CC[C@H](Oc4ccnc(NC5CC5)n4)C3)cccc12]

(S)-2-(3-((2-(cyclopropylamino)pyrimidin-4-yl)oxy)pyrrolidin-1-yl)-N-(3-(2-((1,5-dimethyl-1H-pyrazol-3-yl)amino)-5-methoxypyrimidin-4-yl)-1H-indol-7-yl)acetamide -continued 14) 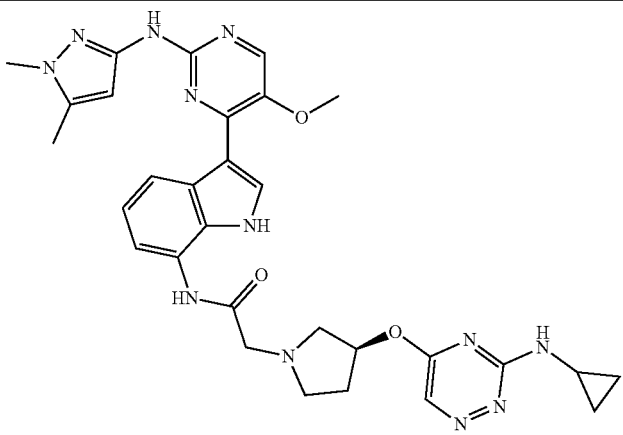

(S)-2-(3-((3-(cyclopropylamino)-1,2,4-triazin-5-yl)oxy)pyrrolidin-1-yl)-N-(3-(2-((1,5-dimethyl-1H-pyrazol-3-yl)amino)-5-methoxypyrimidin-4-yl)-1H-indol-7-yl)acetamide 15) 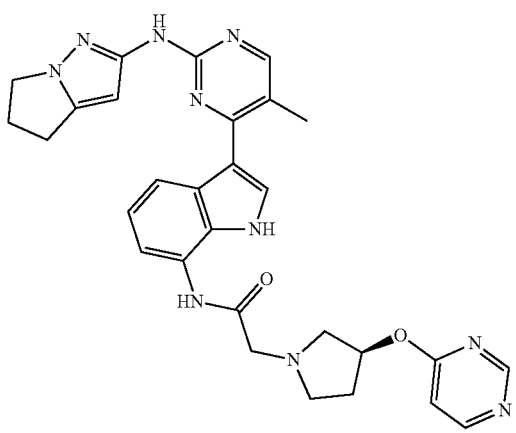 [SMILES: Cc1cnc(Nc2cc3n(n2)CCC3)nc1-c1c[nH]c2c(NC(=O)CN3CC[C@H](Oc4ccncn4)C3)cccc12]

(S)-N-(3-(2-((5,6-dihydro-4H-pyrrolo[1,2-b]pyrazol-2-yl)amino)-5-methylpyrimidin-4-yl)-1H-indol-7-yl)-2-(3-(pyrimidin-4-yloxy)pyrrolidin-1-yl)acetamide 16) 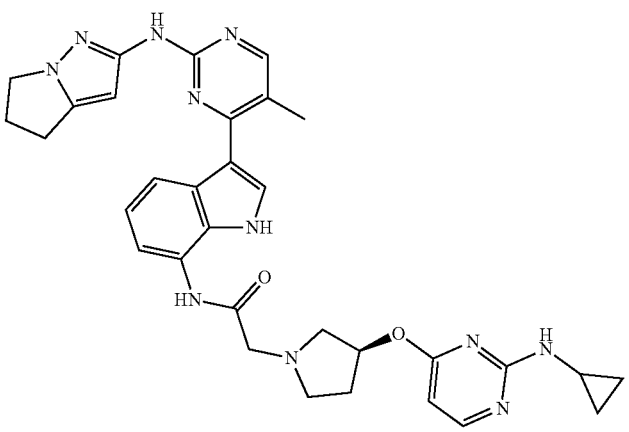 [SMILES: Cc1cnc(Nc2cc3n(n2)CCC3)nc1-c1c[nH]c2c(NC(=O)CN3CC[C@H](Oc4ccnc(NC5CC5)n4)C3)cccc12]

(S)-2-(3-((2-(cyclopropylamino)pyrimidin-4-yl)oxy)pyrrolidin-1-yl)-N-(3-(2-((5,6-dihydro-4H-pyrrolo[1,2-b]pyrazol-2-yl)amino)-5-methylpyrimidin-4-yl)-1H-indol-7-yl)acetamide

| | | |
|---|---|---|
| 17 | 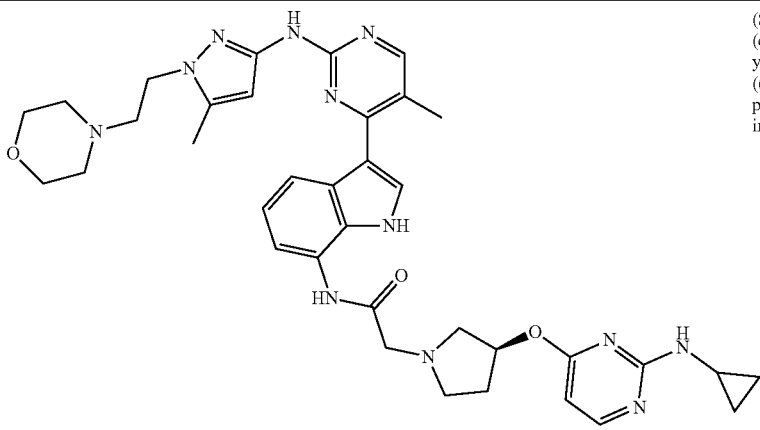 | (S)-2-(3-((2-(cyclopropylamino)pyrimidin-4-yl)oxy)pyrrolidin-1-yl)-N-(3-(5-methyl-2-((5-methyl-1-(2-morpholinoethyl)-1H-pyrazol-3-yl)amino)pyrimidin-4-yl)-1H-indol-7-yl)acetamide |
| 18) | 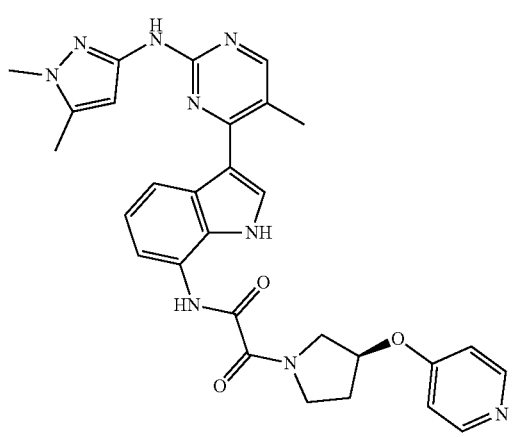 [SMILES: Cc1cnc(Nc2cc(C)n(C)n2)nc1-c1c[nH]c2c(NC(=O)C(=O)N3CC[C@H](Oc4ccncc4)C3)cccc12] | (S)-N-(3-(2-((1,5-dimethyl-1H-pyrazol-3-yl)amino)-5-methylpyrimidin-4-yl)-1H-indol-7-yl)-2-oxo-2-(3-(pyridin-4-yloxy)pyrrolidin-1-yl)acetamide |
| 19) | 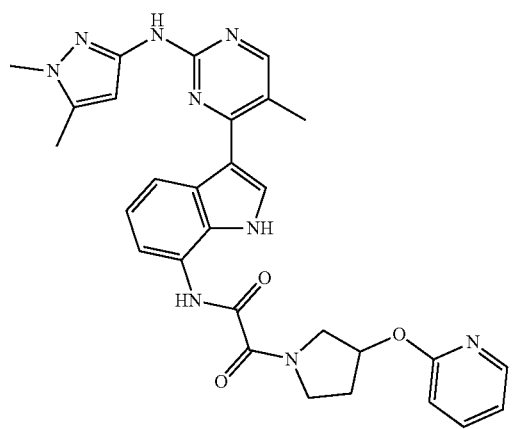 [SMILES: Cc1cnc(Nc2cc(C)n(C)n2)nc1-c1c[nH]c2c(NC(=O)C(=O)N3CCC(Oc4ccccn4)C3)cccc12] | N-(3-(2-((1,5-dimethyl-1H-pyrazol-3-yl)amino)-5-methylpyrimidin-4-yl)-1H-indol-7-yl)-2-oxo-2-(3-(pyridin-2-yloxy)pyrrolidin-1-yl)acetamide |

-continued
20) 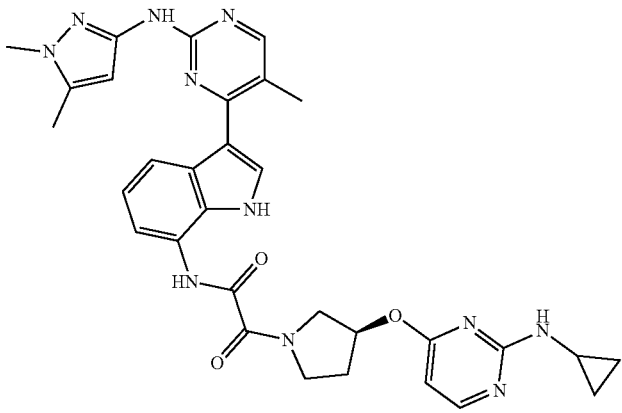 [SMILES: Cc1cnc(Nc2cc(C)n(C)n2)nc1-c1c[nH]c2c(NC(=O)C(=O)N3CC[C@H](Oc4ccnc(NC5CC5)n4)C3)cccc12]
(S)-2-(3-((2-(cyclopropylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)-2-oxoacetamide
21) 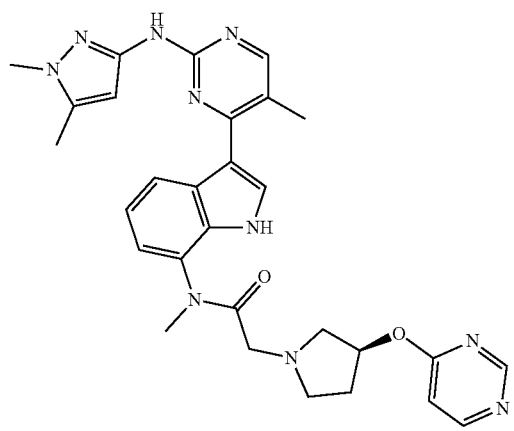 [SMILES: Cc1cnc(Nc2cc(C)n(C)n2)nc1-c1c[nH]c2c(N(C)C(=O)CN3CC[C@H](Oc4ccncn4)C3)cccc12]
(S)-N-(3-(2-((1,5-dimethyl-1H-pyrazol-3-yl)amino)-5-methylpyrimidin-4-yl)-1H-indol-7-yl)-N-methyl-2-(3-(pyrimidin-4-yloxy)pyrrolidin-1-yl)acetamide
22) 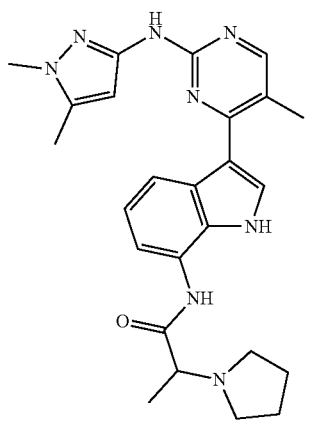
N-(3-(2-((1,5-dimethyl-1H-pyrazol-3-yl)amino)-5-methylpyrimidin-4-yl)-1H-indol-7-yl)-2-(pyrrolidin-1-yl)propanamide 23) 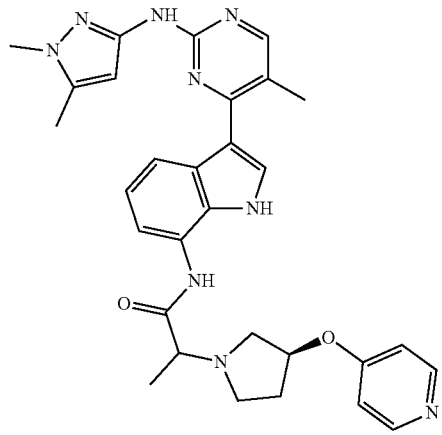 [SMILES: Cc1cnc(Nc2cc(C)n(C)n2)nc1-c1c[nH]c2c(NC(=O)C(C)N3CC[C@H](Oc4ccncc4)C3)cccc12] N-(3-(2-((1,5-dimethyl-1H-pyrazol-3-yl)amino)-5-methylpyrimidin-4-yl)-1H-indol-7-yl)-2-((S)-3-(pyridin-4-yloxy)pyrrolidin-1-yl)propanamide
24) 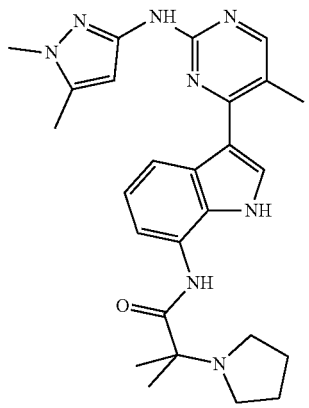 N-(3-(2-((1,5-dimethyl-1H-pyrazol-3-yl)amino)-5-methylpyrimidin-4-yl)-1H-indol-7-yl)-2-methyl-2-(pyrrolidin-1-yl)propanamide
25) 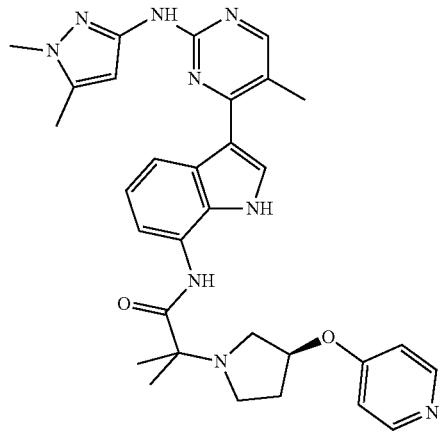 [SMILES: Cc1cnc(Nc2cc(C)n(C)n2)nc1-c1c[nH]c2c(NC(=O)C(C)(C)N3CC[C@H](Oc4ccncc4)C3)cccc12] (S)-N-(3-(2-((1,5-dimethyl-1H-pyrazol-3-yl)amino)-5-methylpyrimidin-4-yl)-1H-indol-7-yl)-2-methyl-2-(3-(pyridin-4-yloxy)pyrrolidin-1-yl)propanamide

| | | |
|---|---|---|
| 26) | 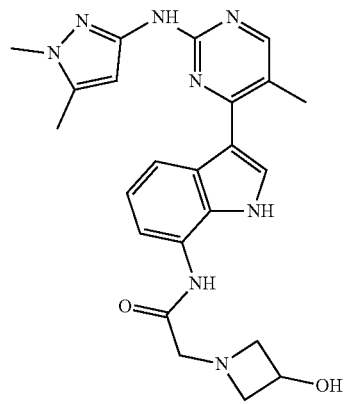 [SMILES: Cc1cnc(Nc2cc(C)n(C)n2)nc1-c1c[nH]c2c(NC(=O)CN3CC(O)C3)cccc12] | N-(3-(2-((1,5-dimethyl-1H-pyrazol-3-yl)amino)-5-methylpyrimidin-4-yl)-1H-indol-7-yl)-2-(3-hydroxyazetidin-1-yl)acetamide |
| 27) | 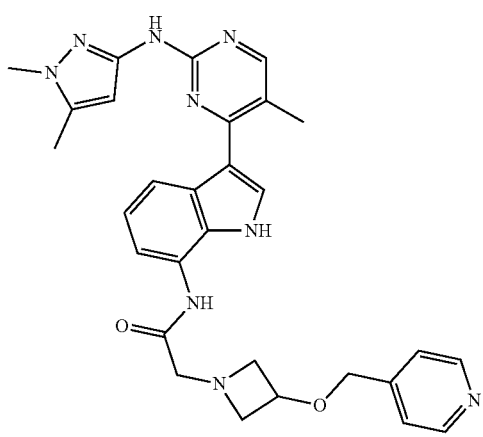 [SMILES: Cc1cnc(Nc2cc(C)n(C)n2)nc1-c1c[nH]c2c(NC(=O)CN3CC(OCc4ccncc4)C3)cccc12] | N-(3-(2-((1,5-dimethyl-1H-pyrazol-3-yl)amino)-5-methylpyrimidin-4-yl)-1H-indol-7-yl)-2-(3-(pyridin-4-ylmethoxy)azetidin-1-yl)acetamide |
| 28) | 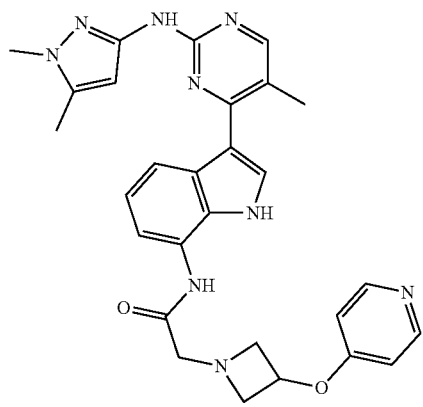 [SMILES: Cc1cnc(Nc2cc(C)n(C)n2)nc1-c1c[nH]c2c(NC(=O)CN3CC(Oc4ccncc4)C3)cccc12] | N-(3-(2-((1,5-dimethyl-1H-pyrazol-3-yl)amino)-5-methylpyrimidin-4-yl)-1H-indol-7-yl)-2-(3-(pyridin-4-yloxy)azetidin-1-yl)acetamide |
| 29) | 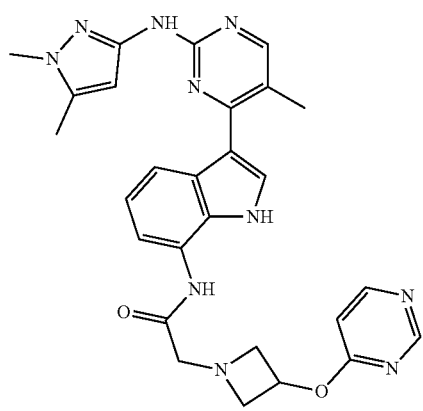 [SMILES: Cc1cnc(Nc2cc(C)n(C)n2)nc1-c1c[nH]c2c(NC(=O)CN3CC(Oc4ccncn4)C3)cccc12] | N-(3-(2-((1,5-dimethyl-1H-pyrazol-3-yl)amino)-5-methylpyrimidin-4-yl)-1H-indol-7-yl)-2-(3-(pyrimidin-4-yloxy)azetidin-1-yl)acetamide |

| | | |
|---|---|---|
| 30) | 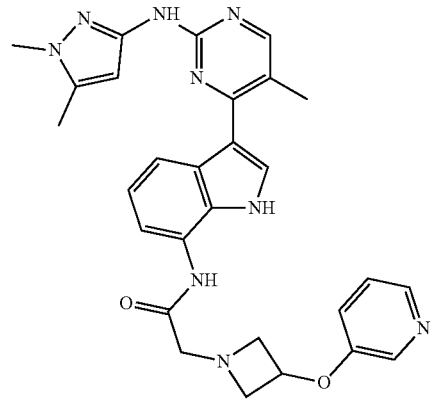 [SMILES: Cc1cnc(Nc2cc(C)n(C)n2)nc1-c1c[nH]c2c(NC(=O)CN3CC(Oc4cccnc4)C3)cccc12] | N-(3-(2-((1,5-dimethyl-1H-pyrazol-3-yl)amino)-5-methylpyrimidin-4-yl)-1H-indol-7-yl)-2-(3-(pyridin-3-yloxy)azetidin-1-yl)acetamide |
| 31) | 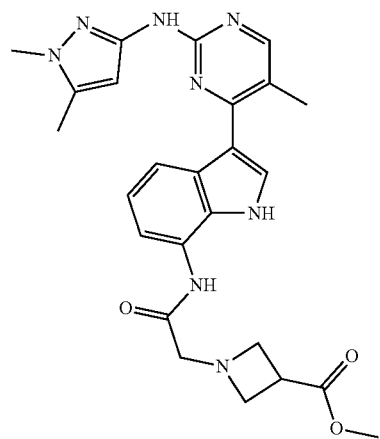 | methyl 1-(2-((3-(2-((1,5-dimethyl-1H-pyrazol-3-yl)amino)-5-methylpyrimidin-4-yl)-1H-indol-7-yl)amino)-2-oxoethyl)azetidine-3-carboxylate |
| 32) | 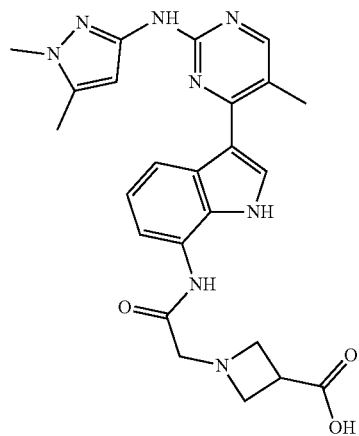 [SMILES: Cc1cnc(Nc2cc(C)n(C)n2)nc1-c1c[nH]c2c(NC(=O)CN3CC(C(=O)O)C3)cccc12] | 1-(2-((3-(2-((1,5-dimethyl-1H-pyrazol-3-yl)amino)-5-methylpyrimidin-4-yl)-1H-indol-7-yl)amino)-2-oxoethyl)azetidine-3-carboxylic acid |

-continued
33) 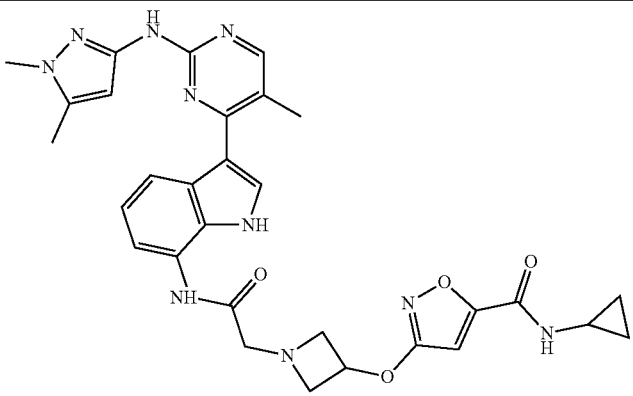
N-cyclopropyl-3-((1-(2-((3-(2-((1,5-dimethyl-1H-pyrazol-3-yl)amino)-5-methylpyrimidin-4-yl)-1H-indol-7-yl)amino)-2-oxoethyl)azetidin-3-yl)oxy)isoxazole-5-carboxamide
34) 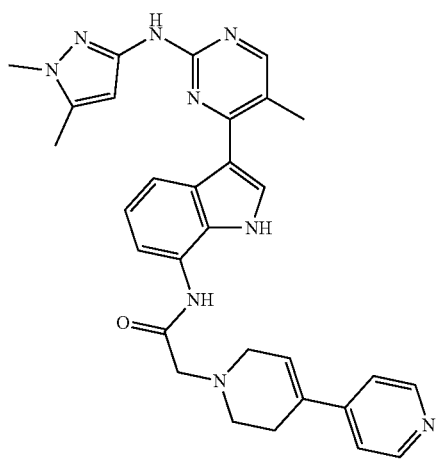 [SMILES: Cc1cnc(Nc2cc(C)n(C)n2)nc1-c1c[nH]c2c(NC(=O)CN3CC=C(c4ccncc4)CC3)cccc12]
2-(5,6-dihydro-[4,4'-bipyridin]-1(2H)-yl)-N-(3-(2-((1,5-dimethyl-1H-pyrazol-3-yl)amino)-5-methylpyrimidin-4-yl)-1H-indol-7-yl)acetamide
35) 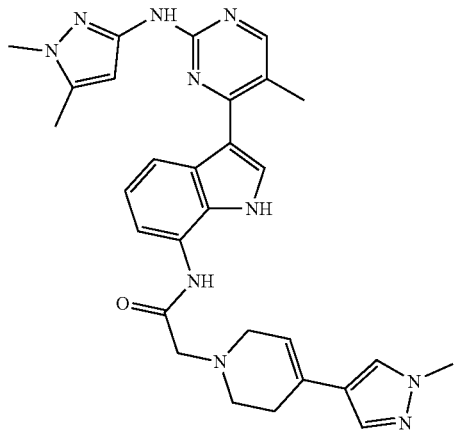
N-(3-(2-((1,5-dimethyl-1H-pyrazol-3-yl)amino)-5-methylpyrimidin-4-yl)-1H-indol-7-yl)-2-(4-(1-methyl-1H-pyrazol-4-yl)-5,6-dihydropyridin-1(2H)-yl)acetamide -continued
36) 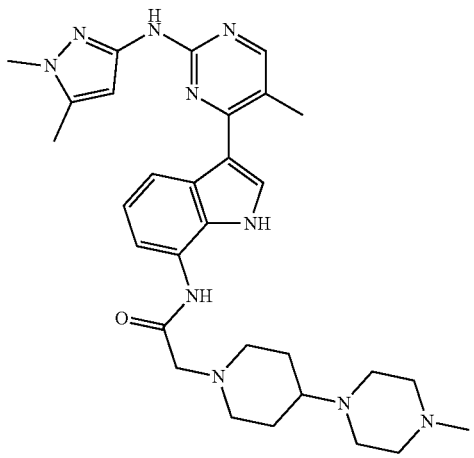 N-(3-(2-((1,5-dimethyl-1H-pyrazol-3-yl)amino)-5-methylpyrimidin-4-yl)-1H-indol-7-yl)-2-(4-(4-methylpiperazin-1-yl)piperidin-1-yl)acetamide
37) 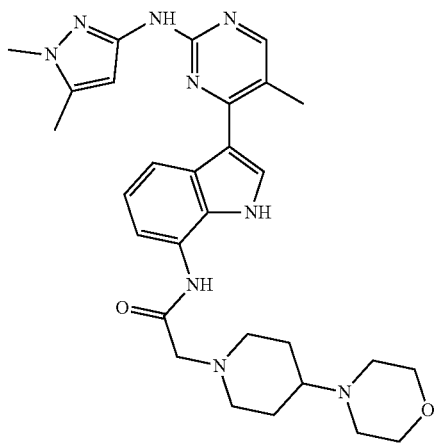 [SMILES: Cc1cnc(Nc2cc(C)n(C)n2)nc1-c1c[nH]c2c(NC(=O)CN3CCC(N4CCOCC4)CC3)cccc12] N-(3-(2-((1,5-dimethyl-1H-pyrazol-3-yl)amino)-5-methylpyrimidin-4-yl)-1H-indol-7-yl)-2-(4-morpholinopiperidin-1-yl)acetamide
38) 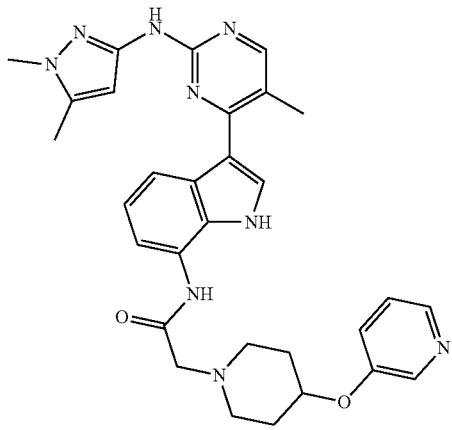 [SMILES: Cc1cnc(Nc2cc(C)n(C)n2)nc1-c1c[nH]c2c(NC(=O)CN3CCC(Oc4cccnc4)CC3)cccc12] N-(3-(2-((1,5-dimethyl-1H-pyrazol-3-yl)amino)-5-methylpyrimidin-4-yl)-1H-indol-7-yl)-2-(4-(pyridin-3-yloxy)piperidin-1-yl)acetamide 39) 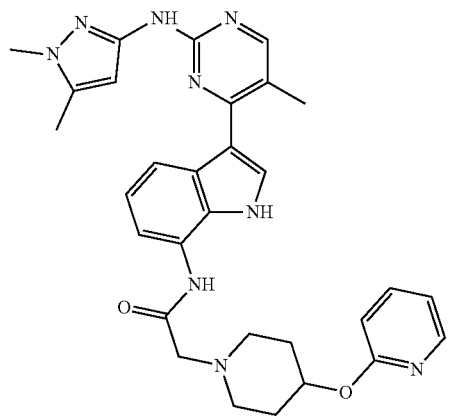 [SMILES: Cc1cnc(Nc2cc(C)n(C)n2)nc1-c1c[nH]c2c(NC(=O)CN3CCC(Oc4ccccn4)CC3)cccc12]
N-(3-(2-((1,5-dimethyl-1H-pyrazol-3-yl)amino)-5-methylpyrimidin-4-yl)-1H-indol-7-yl)-2-(4-(pyridin-2-yloxy)piperidin-1-yl)acetamide
40) 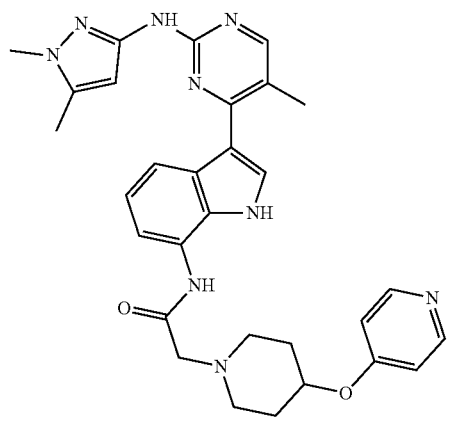 [SMILES: Cc1cnc(Nc2cc(C)n(C)n2)nc1-c1c[nH]c2c(NC(=O)CN3CCC(Oc4ccncc4)CC3)cccc12]
N-(3-(2-((1,5-dimethyl-1H-pyrazol-3-yl)amino)-5-methylpyrimidin-4-yl)-1H-indol-7-yl)-2-(4-(pyridin-4-yloxy)piperidin-1-yl)acetamide
41) 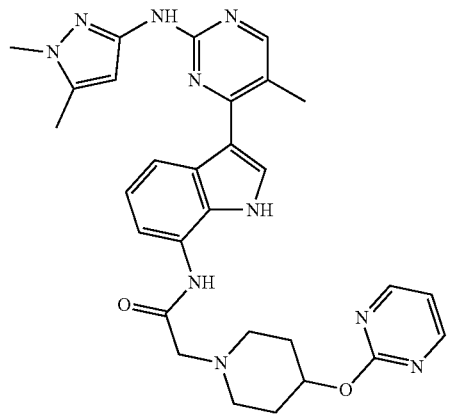 [SMILES: Cc1cnc(Nc2cc(C)n(C)n2)nc1-c1c[nH]c2c(NC(=O)CN3CCC(Oc4ncccn4)CC3)cccc12]
N-(3-(2-((1,5-dimethyl-1H-pyrazol-3-yl)amino)-5-methylpyrimidin-4-yl)-1H-indol-7-yl)-2-(4-(pyrimidin-2-yloxy)piperidin-1-yl)acetamide

| | | |
|---|---|---|
| 42) | 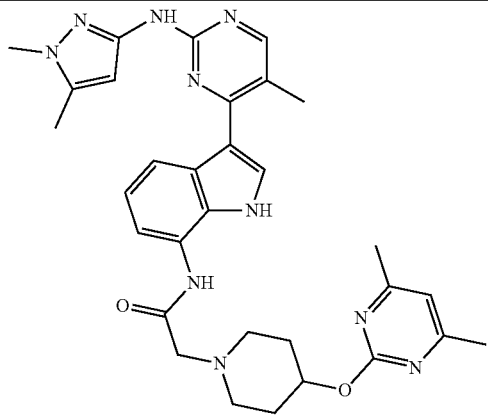 | N-(3-(2-((1,5-dimethyl-1H-pyrazol-3-yl)amino)-5-methylpyrimidin-4-yl)-1H-indol-7-yl)-2-(4-((4,6-dimethylpyrimidin-2-yl)oxy)piperidin-1-yl)acetamide |
| 43) | 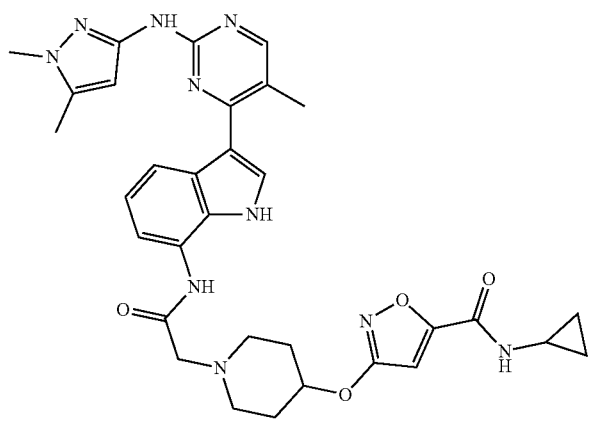 [SMILES: Cc1cnc(Nc2cc(C)n(C)n2)nc1-c1c[nH]c2c(NC(=O)CN3CCC(Oc4cc(C(=O)NC5CC5)on4)CC3)cccc12] | N-cyclopropyl-3-((1-(2-((3-(2-((1,5-dimethyl-1H-pyrazol-3-yl)amino)-5-methylpyrimidin-4-yl)-1H-indol-7-yl)amino)-2-oxoethyl)piperidin-4-yl)oxy)isoxazole-5-carboxamide |
| 44) | 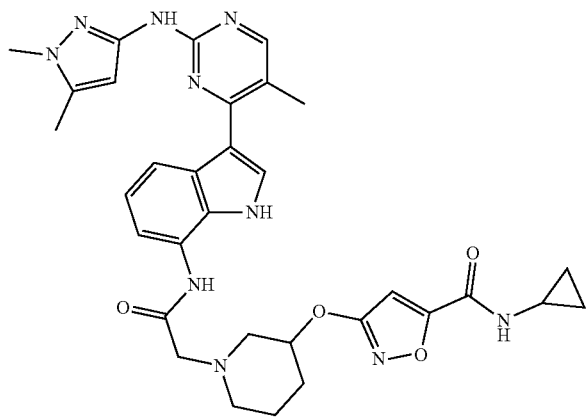 [SMILES: Cc1cnc(Nc2cc(C)n(C)n2)nc1-c1c[nH]c2c(NC(=O)CN3CCCC(Oc4cc(C(=O)NC5CC5)on4)C3)cccc12] | N-cyclopropyl-3-((1-(2-((3-(2-((1,5-dimethyl-1H-pyrazol-3-yl)amino)-5-methylpyrimidin-4-yl)-1H-indol-7-yl)amino)-2-oxoethyl)piperidin-3-yl)oxy)isoxazole-5-carboxamide |
| 45) | 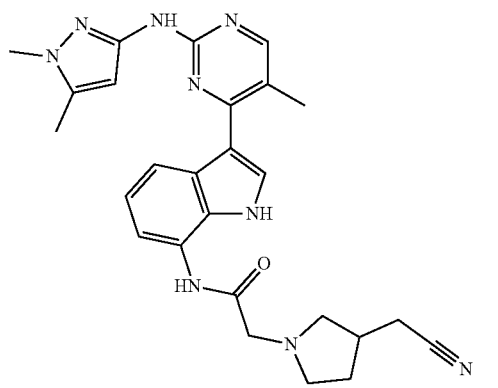 [SMILES: Cc1cnc(Nc2cc(C)n(C)n2)nc1-c1c[nH]c2c(NC(=O)CN3CCC(CC#N)C3)cccc12] | 2-(3-(cyanomethyl)pyrrolidin-1-yl)-N-(3-(2-((1,5-dimethyl-1H-pyrazol-3-yl)amino)-5-methylpyrimidin-4-yl)-1H-indol-7-yl)acetamide |

-continued
46) 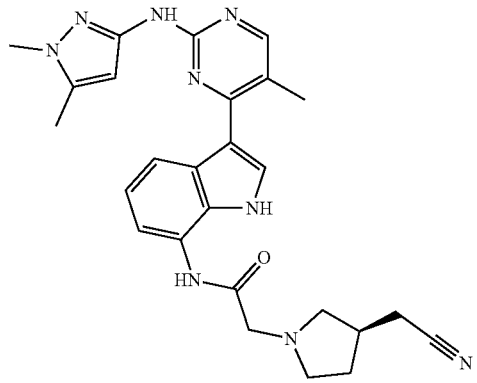 [SMILES: Cc1cnc(Nc2cc(C)n(C)n2)nc1-c1c[nH]c2c(NC(=O)CN3CC[C@H](CC#N)C3)cccc12]
(R)-2-(3-(cyanomethyl)pyrrolidin-1-yl)-N-(3-(2-((1,5-dimethyl-1H-pyrazol-3-yl)amino)-5-methylpyrimidin-4-yl)-1H-indol-7-yl)acetamide
47) 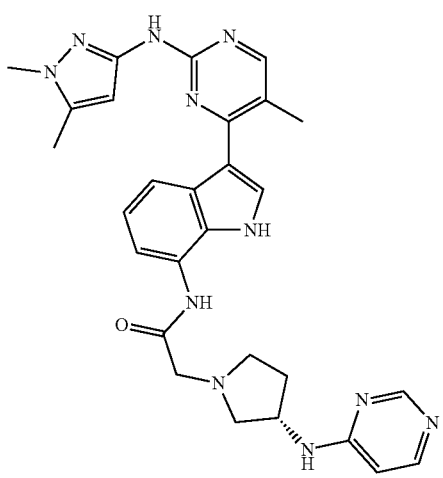 [SMILES: Cc1cnc(Nc2cc(C)n(C)n2)nc1-c1c[nH]c2c(NC(=O)CN3CC[C@H](Nc4ccncn4)C3)cccc12]
(S)-N-(3-(2-((1,5-dimethyl-1H-pyrazol-3-yl)amino)-5-methylpyrimidin-4-yl)-1H-indol-7-yl)-2-(3-(pyrimidin-4-ylamino)pyrrolidin-1-yl)acetamide
48) 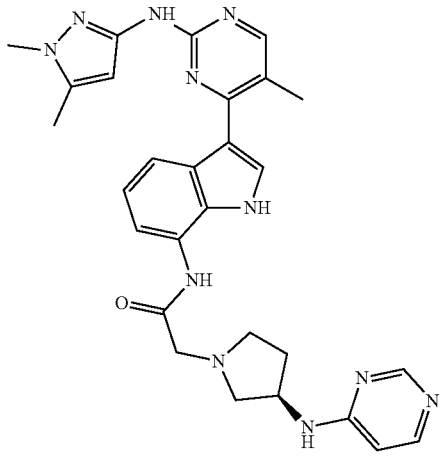 [SMILES: Cc1cnc(Nc2cc(C)n(C)n2)nc1-c1c[nH]c2c(NC(=O)CN3CC[C@@H](Nc4ccncn4)C3)cccc12]
(R)-N-(3-(2-((1,5-dimethyl-1H-pyrazol-3-yl)amino)-5-methylpyrimidin-4-yl)-1H-indol-7-yl)-2-(3-(pyrimidin-4-ylamino)pyrrolidin-1-yl)acetamide -continued
49) 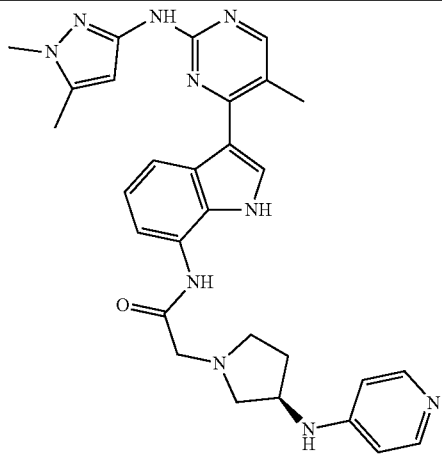
(R)-N-(3-(2-((1,5-dimethyl-1H-pyrazol-3-yl)amino)-5-methylpyrimidin-4-yl)-1H-indol-7-yl)-2-(3-(pyridin-4-ylamino)pyrrolidin-1-yl)acetamide
50) 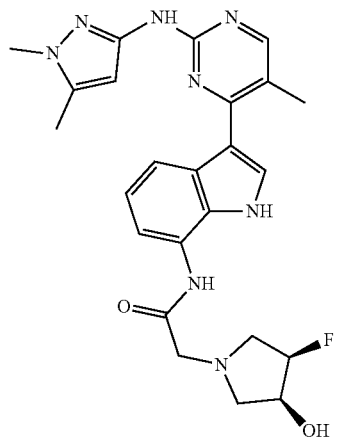 [SMILES: Cc1cnc(Nc2cc(C)n(C)n2)nc1-c1c[nH]c2c(NC(=O)CN3C[C@@H](F)[C@@H](O)C3)cccc12]
N-(3-(2-((1,5-dimethyl-1H-pyrazol-3-yl)amino)-5-methylpyrimidin-4-yl)-1H-indol-7-yl)-2-((3R,4S)-3-fluoro-4-hydroxypyrrolidin-1-yl)acetamide
51) 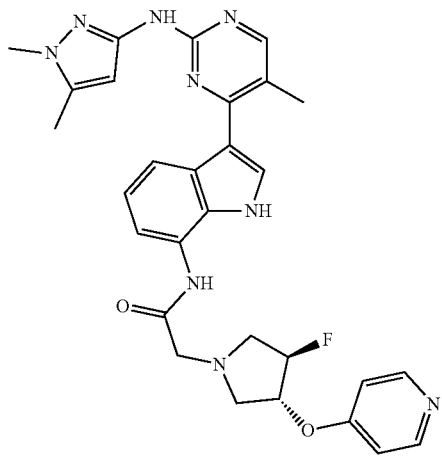 [SMILES: Cc1cnc(Nc2cc(C)n(C)n2)nc1-c1c[nH]c2c(NC(=O)CN3C[C@@H](F)[C@H](Oc4ccncc4)C3)cccc12]
N-(3-(2-((1,5-dimethyl-1H-pyrazol-3-yl)amino)-5-methylpyrimidin-4-yl)-1H-indol-7-yl)-2-((3R,4R)-3-fluoro-4-(pyridin-4-yloxy)pyrrolidin-1-yl)acetamide

| | | |
|---|---|---|
| 52) | 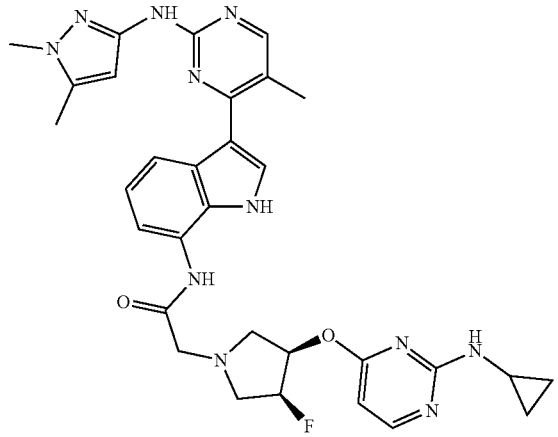 [SMILES: Cc1cnc(Nc2cc(C)n(C)n2)nc1-c1c[nH]c2c(NC(=O)CN3C[C@H](F)[C@H](Oc4ccnc(NC5CC5)n4)C3)cccc12] | 2-((3R,4S)-3-((2-(cyclopropylamino)pyrimidin-4-yl)oxy)-4-fluoropyrrolidin-1-yl)-N-(3-(2-((1,5-dimethyl-1H-pyrazol-3-yl)amino)-5-methylpyrimidin-4-yl)-1H-indol-7-yl)acetamide |
| 53) | 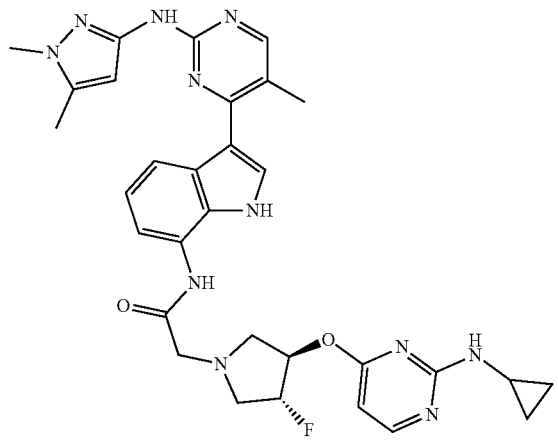 [SMILES: Cc1cnc(Nc2cc(C)n(C)n2)nc1-c1c[nH]c2c(NC(=O)CN3C[C@@H](F)[C@H](Oc4ccnc(NC5CC5)n4)C3)cccc12] | 2-((3R,4R)-3-((2-(cyclopropylamino)pyrimidin-4-yl)oxy)-4-fluoropyrrolidin-1-yl)-N-(3-(2-((1,5-dimethyl-1H-pyrazol-3-yl)amino)-5-methylpyrimidin-4-yl)-1H-indol-7-yl)acetamide |
| 54) | 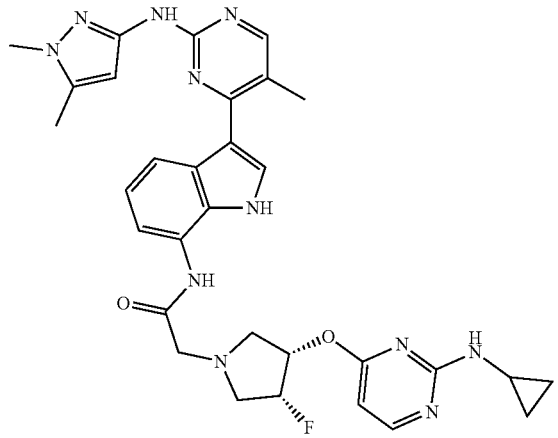 [SMILES: Cc1cnc(Nc2cc(C)n(C)n2)nc1-c1c[nH]c2c(NC(=O)CN3C[C@@H](F)[C@@H](Oc4ccnc(NC5CC5)n4)C3)cccc12] | 2-((3S,4R)-3-((2-(cyclopropylamino)pyrimidin-4-yl)oxy)-4-fluoropyrrolidin-1-yl)-N-(3-(2-((1,5-dimethyl-1H-pyrazol-3-yl)amino)-5-methylpyrimidin-4-yl)-1H-indol-7-yl)acetamide |

-continued

| | | |
|---|---|---|
| 55) | 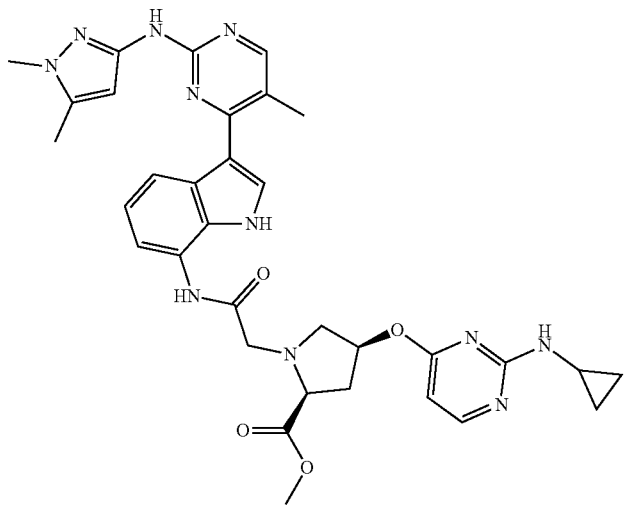 [SMILES: COC(=O)[C@@H]1C[C@H](Oc2ccnc(NC3CC3)n2)CN1CC(=O)Nc1cccc2c(-c3nc(Nc4cc(C)n(C)n4)ncc3C)c[nH]c12] | methyl (2S,4S)-4-((2-(cyclopropylamino)pyrimidin-4-yl)oxy)-1-(2-((3-(2-((1,5-dimethyl-1H-pyrazol-3-yl)amino)-5-methylpyrimidin-4-yl)-1H-indol-7-yl)amino)-2-oxoethyl)pyrrolidine-2-carboxylate |
| 56) | 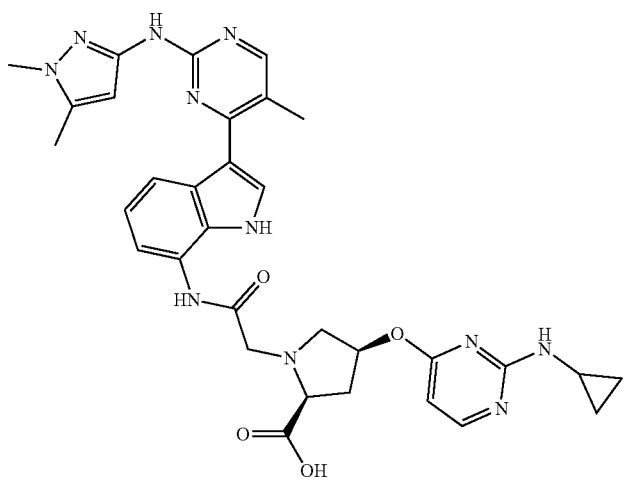 [SMILES: Cc1cnc(Nc2cc(C)n(C)n2)nc1-c1c[nH]c2c(NC(=O)CN3C[C@@H](Oc4ccnc(NC5CC5)n4)C[C@H]3C(=O)O)cccc12] | (2S,4S)-4-((2-(cyclopropylamino)pyrimidin-4-yl)oxy)-1-(2-((3-(2-((1,5-dimethyl-1H-pyrazol-3-yl)amino)-5-methylpyrimidin-4-yl)-1H-indol-7-yl)amino)-2-oxoethyl)pyrrolidine-2-carboxylic acid |
| 57) | 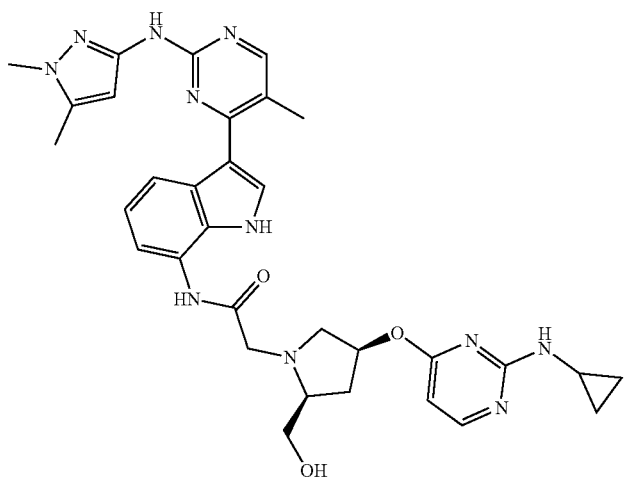 [SMILES: Cc1cnc(Nc2cc(C)n(C)n2)nc1-c1c[nH]c2c(NC(=O)CN3C[C@@H](Oc4ccnc(NC5CC5)n4)C[C@H]3CO)cccc12] | 2-((2S,4S)-4-((2-(cyclopropylamino)pyrimidin-4-yl)oxy)-2-(hydroxymethyl)pyrrolidin-1-yl)-N-(3-(2-((1,5-dimethyl-1H-pyrazol-3-yl)amino)-5-methylpyrimidin-4-yl)-1H-indol-7-yl)acetamide |

-continued

58) 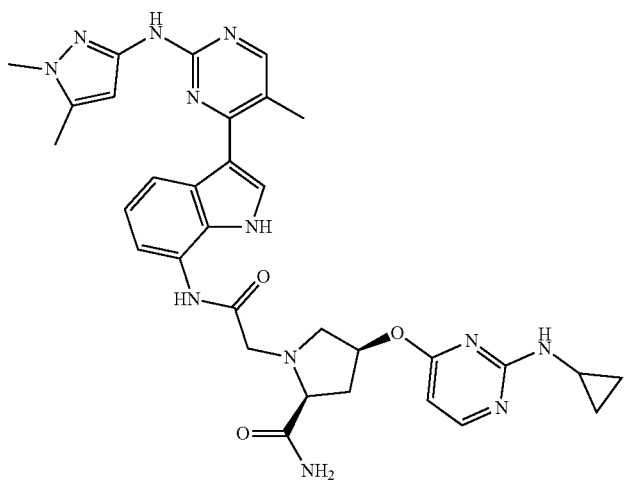 [SMILES: Cc1cnc(Nc2cc(C)n(C)n2)nc1-c1c[nH]c2c(NC(=O)CN3C[C@@H](Oc4ccnc(NC5CC5)n4)C[C@H]3C(N)=O)cccc12]

(2S,4S)-4-((2-(cyclopropylamino)pyrimidin-4-yl)oxy)-1-(2-((3-(2-((1,5-dimethyl-1H-pyrazol-3-yl)amino)-5-methylpyrimidin-4-yl)-1H-indol-7-yl)amino)-2-oxoethyl)pyrrolidine-2-carboxamide 59) 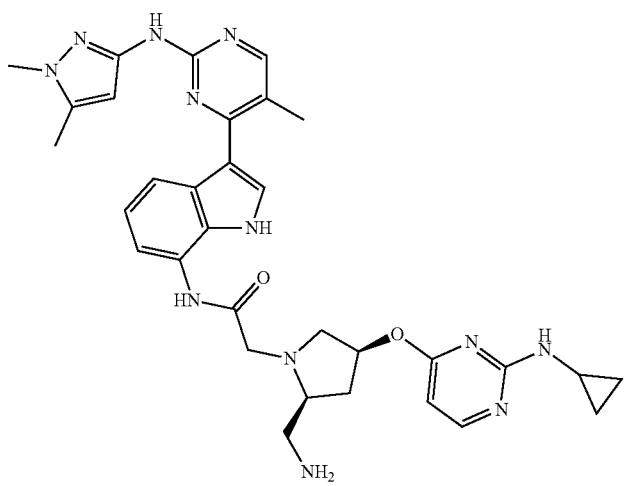 [SMILES: Cc1cnc(Nc2cc(C)n(C)n2)nc1-c1c[nH]c2c(NC(=O)CN3C[C@@H](Oc4ccnc(NC5CC5)n4)C[C@H]3CN)cccc12]

2-((2S,4S)-2-(aminomethyl)-4-((2-(cyclopropylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide 60) 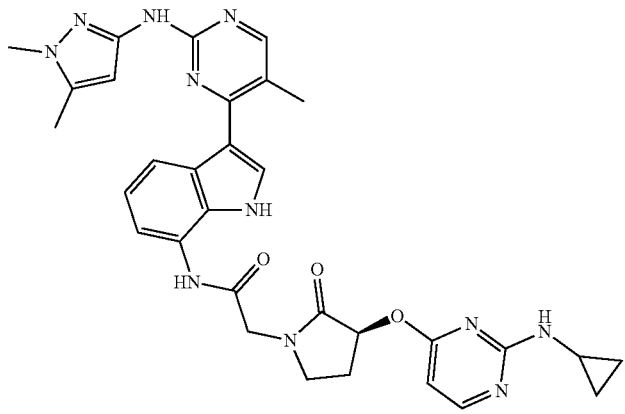 [SMILES: Cc1cnc(Nc2cc(C)n(C)n2)nc1-c1c[nH]c2c(NC(=O)CN3CC[C@H](Oc4ccnc(NC5CC5)n4)C3=O)cccc12]

(S)-2-(3-((2-(cyclopropylamino)pyrimidin-4-yl)oxy)-2-oxopyrrolidin-1-yl)-N-(3-(2-((1,5-dimethyl-1H-pyrazol-3-yl)amino)-5-methylpyrimidin-4-yl)-1H-indol-7-yl)acetamide 61) 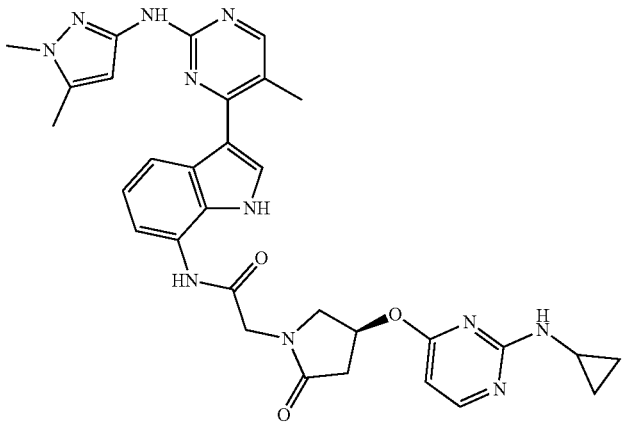 [SMILES: Cc1cnc(Nc2cc(C)n(C)n2)nc1-c1c[nH]c2c(NC(=O)CN3C[C@@H](Oc4ccnc(NC5CC5)n4)CC3=O)cccc12]
(S)-2-(4-((2-(cyclopropylamino)pyrimidin-4-yl)oxy)-2-oxopyrrolidin-1-yl)-N-(3-(2-((1,5-dimethyl-1H-pyrazol-3-yl)amino)-5-methylpyrimidin-4-yl)-1H-indol-7-yl)acetamide
62) 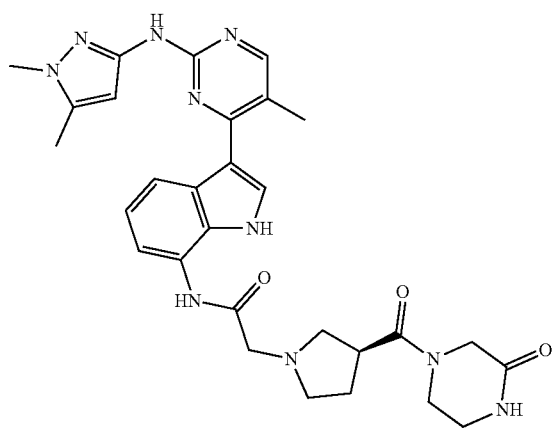 [SMILES: Cc1cnc(Nc2cc(C)n(C)n2)nc1-c1c[nH]c2c(NC(=O)CN3CC[C@H](C(=O)N4CCNC(=O)C4)C3)cccc12]
(S)-N-(3-(2-((1,5-dimethyl-1H-pyrazol-3-yl)amino)-5-methylpyrimidin-4-yl)-1H-indol-7-yl)-2-(3-(3-oxopiperazine-1-carbonyl)pyrrolidin-1-yl)acetamide
63) 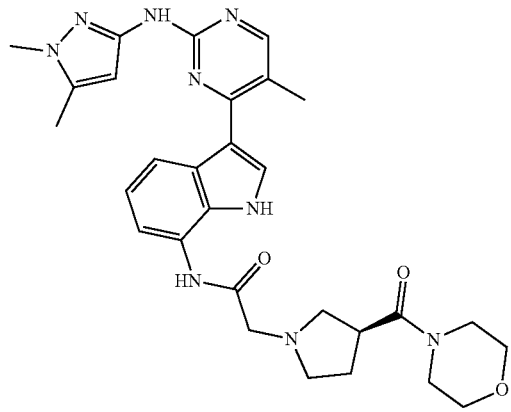 [SMILES: Cc1cnc(Nc2cc(C)n(C)n2)nc1-c1c[nH]c2c(NC(=O)CN3CC[C@H](C(=O)N4CCSCC4)C3)cccc12]
(S)-N-(3-(2-((1,5-dimethyl-1H-pyrazol-3-yl)amino)-5-methylpyrimidin-4-yl)-1H-indol-7-yl)-2-(3-(morpholine-4-carbonyl)pyrrolidin-1-yl)acetamide

| | | |
|---|---|---|
| 64) | 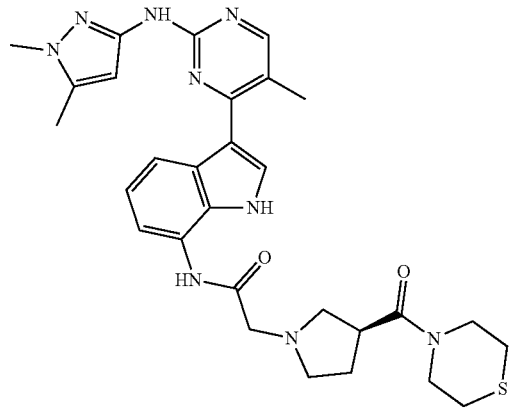 | (S)-N-(3-(2-((1,5-dimethyl-1H-pyrazol-3-yl)amino)-5-methylpyrimidin-4-yl)-1H-indol-7-yl)-2-(3-(thiomorpholine-4-carbonyl)pyrrolidin-1-yl)acetamide |
| 65) | 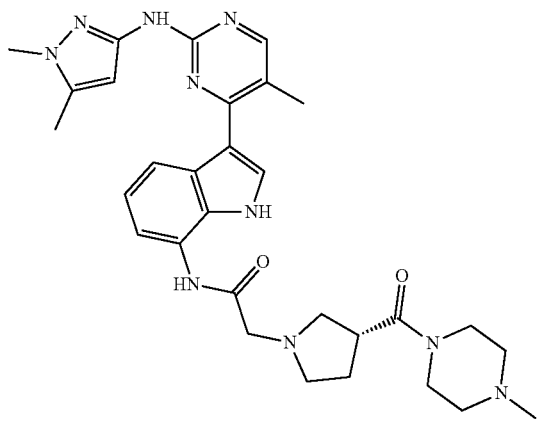 | (R)-N-(3-(2-((1,5-dimethyl-1H-pyrazol-3-yl)amino)-5-methylpyrimidin-4-yl)-1H-indol-7-yl)-2-(3-(4-methylpiperazine-1-carbonyl)pyrrolidin-1-yl)acetamide |
| 66) | 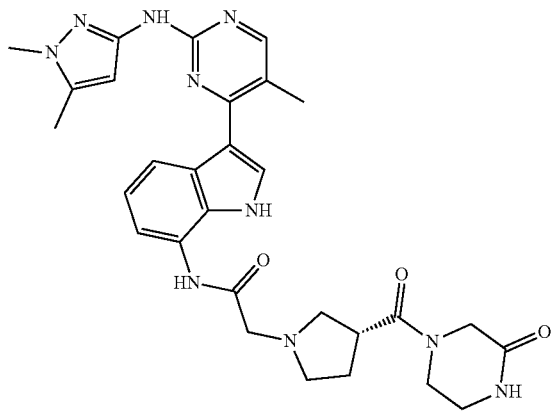 [SMILES: Cc1cnc(Nc2cc(C)n(C)n2)nc1-c1c[nH]c2c(NC(=O)CN3CC[C@@H](C(=O)N4CCNC(=O)C4)C3)cccc12] | (R)-N-(3-(2-((1,5-dimethyl-1H-pyrazol-3-yl)amino)-5-methylpyrimidin-4-yl)-1H-indol-7-yl)-2-(3-(3-oxopiperazine-1-carbonyl)pyrrolidin-1-yl)acetamide |
| 67) | 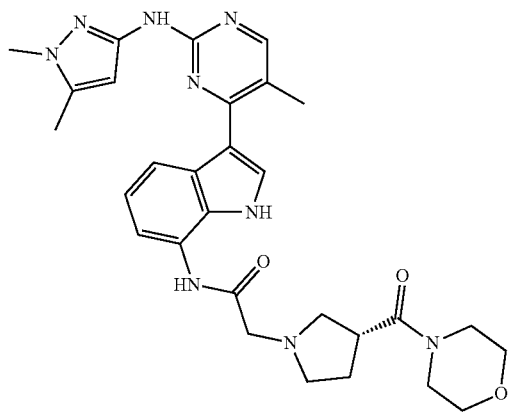 [SMILES: Cc1cnc(Nc2cc(C)n(C)n2)nc1-c1c[nH]c2c(NC(=O)CN3CC[C@@H](C(=O)N4CCOCC4)C3)cccc12] | (R)-N-(3-(2-((1,5-dimethyl-1H-pyrazol-3-yl)amino)-5-methylpyrimidin-4-yl)-1H-indol-7-yl)-2-(3-(morpholine-4-carbonyl)pyrrolidin-1-yl)acetamide |

| | | |
|---|---|---|
| 68) | 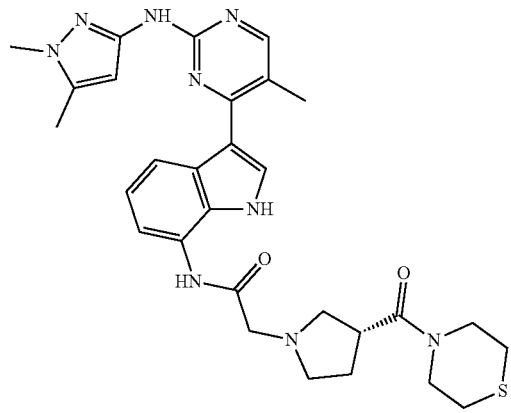 [SMILES: Cc1cnc(Nc2cc(C)n(C)n2)nc1-c1c[nH]c2c(NC(=O)CN3CC[C@@H](C(=O)N4CCSCC4)C3)cccc12] | (R)-N-(3-(2-((1,5-dimethyl-1H-pyrazol-3-yl)amino)-5-methylpyrimidin-4-yl)-1H-indol-7-yl)-2-(3-(thiomorpholine-4-carbonyl)pyrrolidin-1-yl)acetamide |
| 69) | 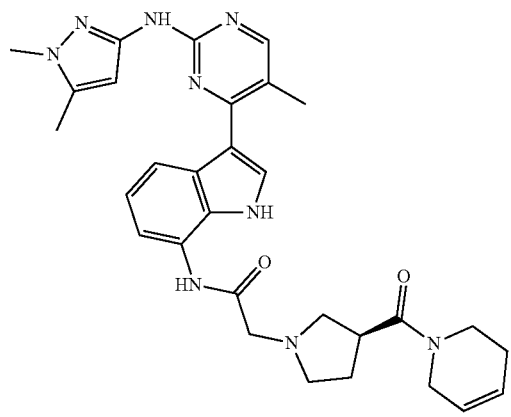 [SMILES: Cc1cnc(Nc2cc(C)n(C)n2)nc1-c1c[nH]c2c(NC(=O)CN3CC[C@H](C(=O)N4CC=CCC4)C3)cccc12] | (S)-N-(3-(2-((1,5-dimethyl-1H-pyrazol-3-yl)amino)-5-methylpyrimidin-4-yl)-1H-indol-7-yl)-2-(3-(1,2,3,6-tetrahydropyridine-1-carbonyl)pyrrolidin-1-yl)acetamide |
| 70) | 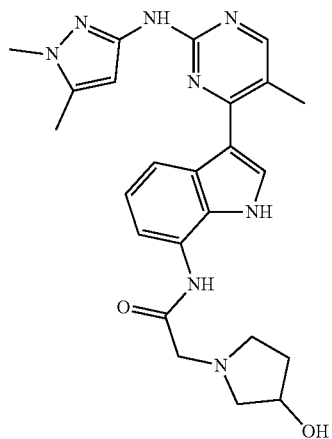 [SMILES: Cc1cnc(Nc2cc(C)n(C)n2)nc1-c1c[nH]c2c(NC(=O)CN3CCC(O)C3)cccc12] | N-(3-(2-((1,5-dimethyl-1H-pyrazol-3-yl)amino)-5-methylpyrimidin-4-yl)-1H-indol-7-yl)-2-(3-hydroxypyrrolidin-1-yl)acetamide |

-continued
71) 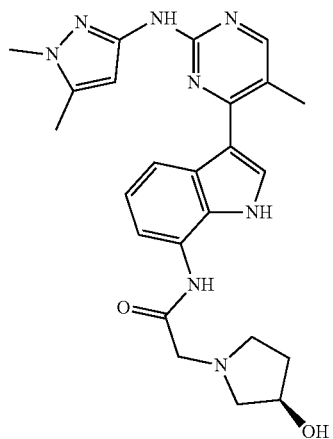 [SMILES: Cc1cnc(Nc2cc(C)n(C)n2)nc1-c1c[nH]c2c(NC(=O)CN3CC[C@@H](O)C3)cccc12] (R)-N-(3-(2-((1,5-dimethyl-1H-pyrazol-3-yl)amino)-5-methylpyrimidin-4-yl)-1H-indol-7-yl)-2-(3-hydroxypyrrolidin-1-yl)acetamide
72) 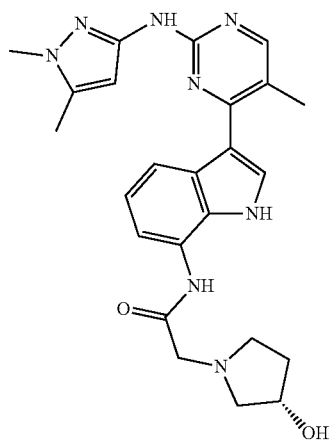 [SMILES: Cc1cnc(Nc2cc(C)n(C)n2)nc1-c1c[nH]c2c(NC(=O)CN3CC[C@H](O)C3)cccc12] (S)-N-(3-(2-((1,5-dimethyl-1H-pyrazol-3-yl)amino)-5-methylpyrimidin-4-yl)-1H-indol-7-yl)-2-(3-hydroxypyrrolidin-1-yl)acetamide
73) 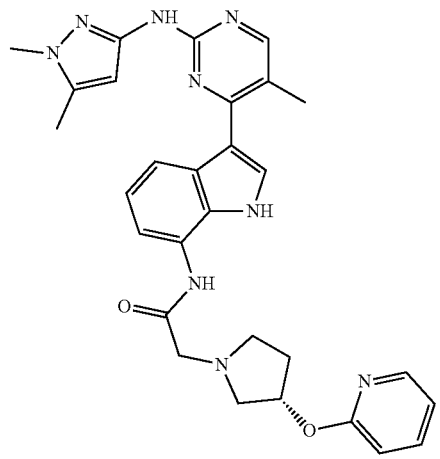 [SMILES: Cc1cnc(Nc2cc(C)n(C)n2)nc1-c1c[nH]c2c(NC(=O)CN3CC[C@H](Oc4ccccn4)C3)cccc12] (S)-N-(3-(2-((1,5-dimethyl-1H-pyrazol-3-yl)amino)-5-methylpyrimidin-4-yl)-1H-indol-7-yl)-2-(3-(pyridin-2-yloxy)pyrrolidin-1-yl)acetamide -continued
| | | |
|---|---|---|
| 74) | 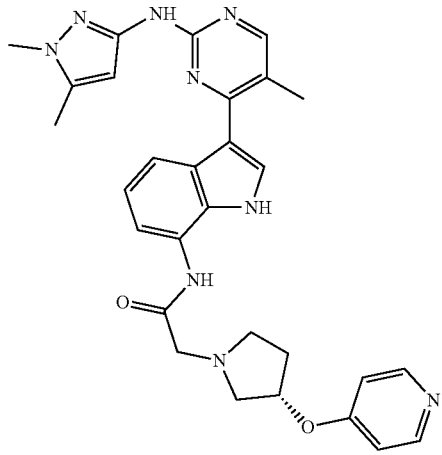 [SMILES: Cc1cnc(Nc2cc(C)n(C)n2)nc1-c1c[nH]c2c(NC(=O)CN3CC[C@H](Oc4ccncc4)C3)cccc12] | (S)-N-(3-(2-((1,5-dimethyl-1H-pyrazol-3-yl)amino)-5-methylpyrimidin-4-yl)-1H-indol-7-yl)-2-(3-(pyridin-4-yloxy)pyrrolidin-1-yl)acetamide |
| 75) | 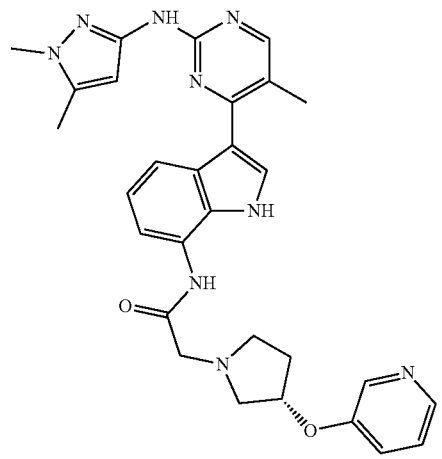 [SMILES: Cc1cnc(Nc2cc(C)n(C)n2)nc1-c1c[nH]c2c(NC(=O)CN3CC[C@H](Oc4cccnc4)C3)cccc12] | (S)-N-(3-(2-((1,5-dimethyl-1H-pyrazol-3-yl)amino)-5-methylpyrimidin-4-yl)-1H-indol-7-yl)-2-(3-(pyridin-3-yloxy)pyrrolidin-1-yl)acetamide |
| 76) | 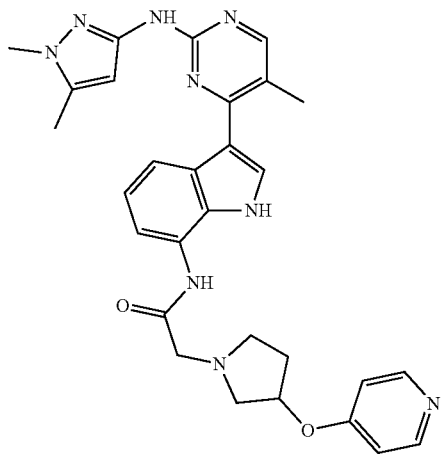 [SMILES: Cc1cnc(Nc2cc(C)n(C)n2)nc1-c1c[nH]c2c(NC(=O)CN3CCC(Oc4ccncc4)C3)cccc12] | N-(3-(2-((1,5-dimethyl-1H-pyrazol-3-yl)amino)-5-methylpyrimidin-4-yl)-1H-indol-7-yl)-2-(3-(pyridin-4-yloxy)pyrrolidin-1-yl)acetamide |

-continued
77) 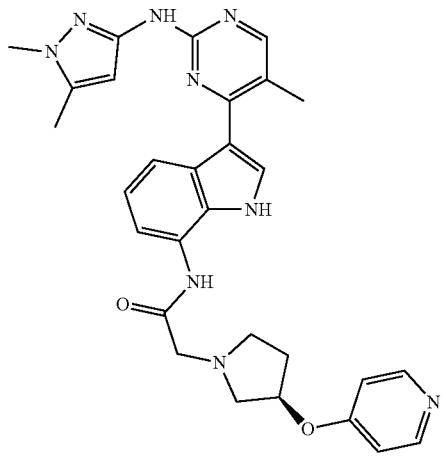 [SMILES: Cc1cnc(Nc2cc(C)n(C)n2)nc1-c1c[nH]c2c(NC(=O)CN3CC[C@@H](Oc4ccncc4)C3)cccc12] (R)-N-(3-(2-((1,5-dimethyl-1H-pyrazol-3-yl)amino)-5-methylpyrimidin-4-yl)-1H-indol-7-yl)-2-(3-(pyridin-4-yloxy)pyrrolidin-1-yl)acetamide
78) 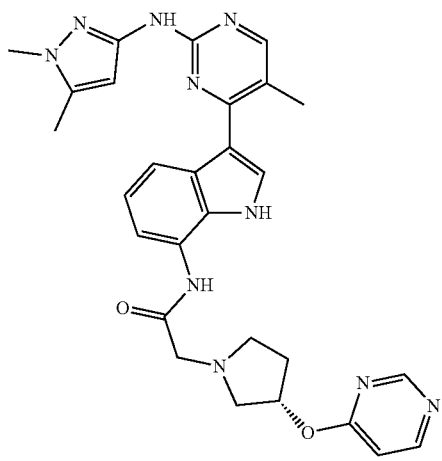 [SMILES: Cc1cnc(Nc2cc(C)n(C)n2)nc1-c1c[nH]c2c(NC(=O)CN3CC[C@H](Oc4ccncn4)C3)cccc12] (S)-N-(3-(2-((1,5-dimethyl-1H-pyrazol-3-yl)amino)-5-methylpyrimidin-4-yl)-1H-indol-7-yl)-2-(3-(pyrimidin-4-yloxy)pyrrolidin-1-yl)acetamide
79) 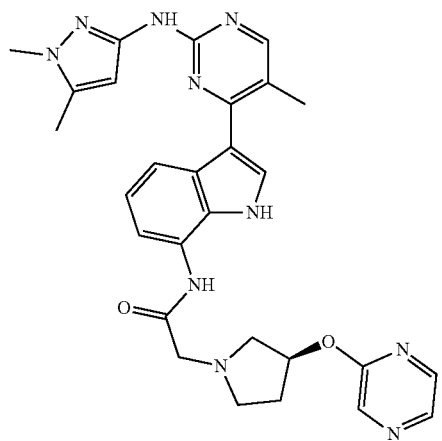 [SMILES: Cc1cnc(Nc2cc(C)n(C)n2)nc1-c1c[nH]c2c(NC(=O)CN3CC[C@H](Oc4cnccn4)C3)cccc12] (S)-N-(3-(2-((1,5-dimethyl-1H-pyrazol-3-yl)amino)-5-methylpyrimidin-4-yl)-1H-indol-7-yl)-2-(3-(pyrazin-2-yloxy)pyrrolidin-1-yl)acetamide

| | | |
|---|---|---|
| 80) | 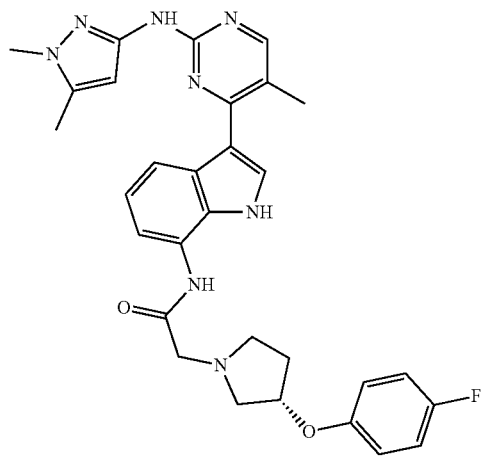 [SMILES: Cc1cnc(Nc2cc(C)n(C)n2)nc1-c1c[nH]c2c(NC(=O)CN3CC[C@H](Oc4ccc(F)cc4)C3)cccc12] | (S)-N-(3-(2-((1,5-dimethyl-1H-pyrazol-3-yl)amino)-5-methylpyrimidin-4-yl)-1H-indol-7-yl)-2-(3-(4-fluorophenoxy)pyrrolidin-1-yl)acetamide |
| 81) | 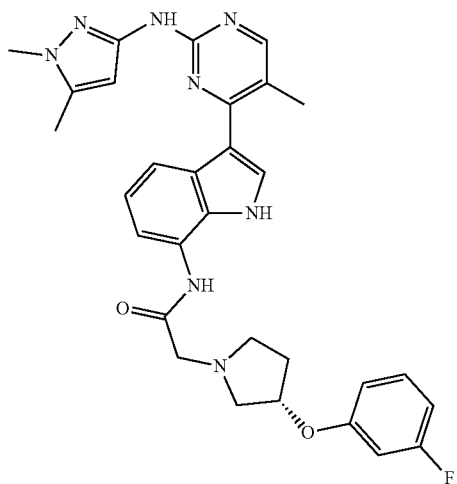 [SMILES: Cc1cnc(Nc2cc(C)n(C)n2)nc1-c1c[nH]c2c(NC(=O)CN3CC[C@H](Oc4cccc(F)c4)C3)cccc12] | (S)-N-(3-(2-((1,5-dimethyl-1H-pyrazol-3-yl)amino)-5-methylpyrimidin-4-yl)-1H-indol-7-yl)-2-(3-(3-fluorophenoxy)pyrrolidin-1-yl)acetamide |
| 82) | 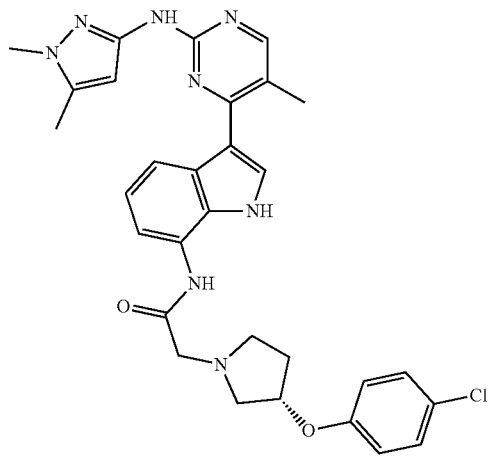 [SMILES: Cc1cnc(Nc2cc(C)n(C)n2)nc1-c1c[nH]c2c(NC(=O)CN3CC[C@H](Oc4ccc(Cl)cc4)C3)cccc12] | (S)-2-(3-(4-chlorophenoxy)pyrrolidin-1-yl)-N-(3-(2-((1,5-dimethyl-1H-pyrazol-3-yl)amino)-5-methylpyrimidin-4-yl)-1H-indol-7-yl)acetamide |

83) 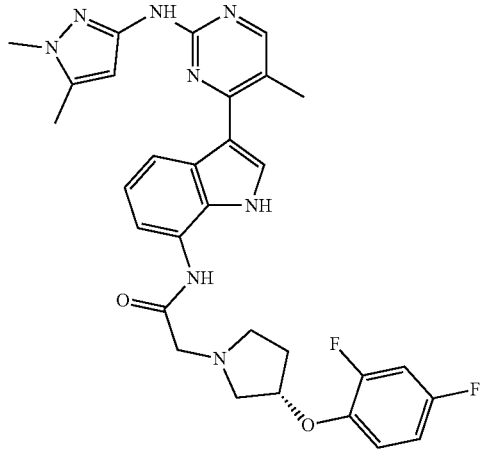 [SMILES: Cc1cnc(Nc2cc(C)n(C)n2)nc1-c1c[nH]c2c(NC(=O)CN3CC[C@H](Oc4ccc(F)cc4F)C3)cccc12]
(S)-2-(3-(2,4-difluorophenoxy)pyrrolidin-1-yl)-N-(3-(2-((1,5-dimethyl-1H-pyrazol-3-yl)amino)-5-methylpyrimidin-4-yl)-1H-indol-7-yl)acetamide
84) 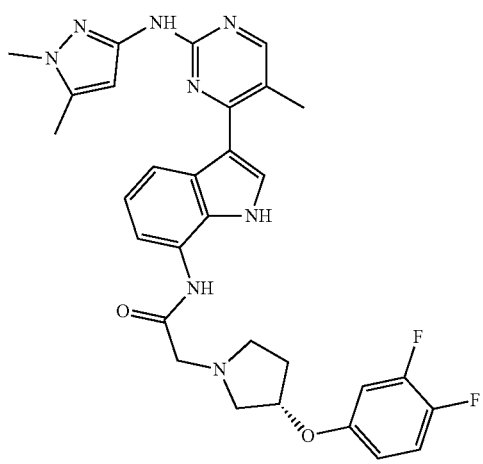 [SMILES: Cc1cnc(Nc2cc(C)n(C)n2)nc1-c1c[nH]c2c(NC(=O)CN3CC[C@H](Oc4ccc(F)c(F)c4)C3)cccc12]
(S)-2-(3-(3,4-difluorophenoxy)pyrrolidin-1-yl)-N-(3-(2-((1,5-dimethyl-1H-pyrazol-3-yl)amino)-5-methylpyrimidin-4-yl)-1H-indol-7-yl)acetamide
85) 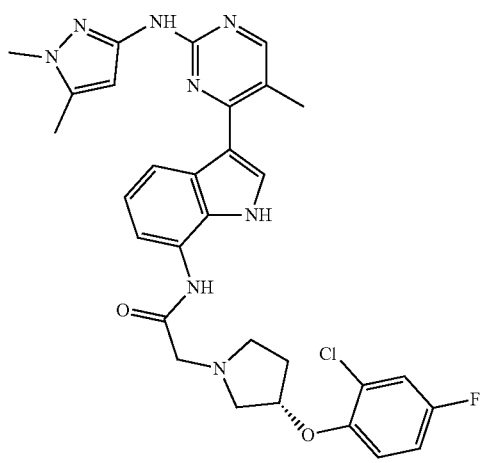 [SMILES: Cc1cnc(Nc2cc(C)n(C)n2)nc1-c1c[nH]c2c(NC(=O)CN3CC[C@H](Oc4ccc(F)cc4Cl)C3)cccc12]
(S)-2-(3-(2-chloro-4-fluorophenoxy)pyrrolidin-1-yl)-N-(3-(2-((1,5-dimethyl-1H-pyrazol-3-yl)amino)-5-methylpyrimidin-4-yl)-1H-indol-7-yl)acetamide

| | | |
|---|---|---|
| 86) | 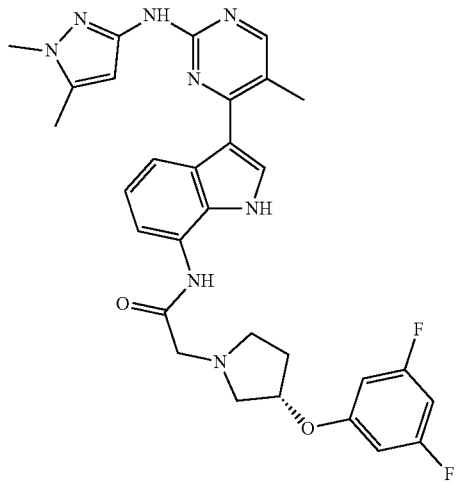 [SMILES: Cc1cnc(Nc2cc(C)n(C)n2)nc1-c1c[nH]c2c(NC(=O)CN3CC[C@H](Oc4cc(F)cc(F)c4)C3)cccc12] | (S)-2-(3-(3,5-difluorophenoxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 87) | 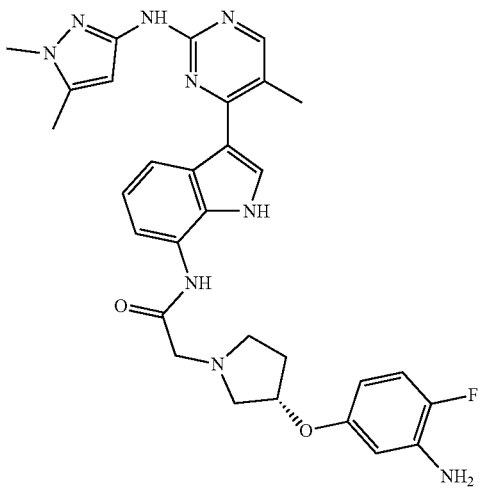 [SMILES: Cc1cnc(Nc2cc(C)n(C)n2)nc1-c1c[nH]c2c(NC(=O)CN3CC[C@H](Oc4ccc(F)c(N)c4)C3)cccc12] | (S)-2-(3-(3-amino-4-fluorophenoxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 88) | 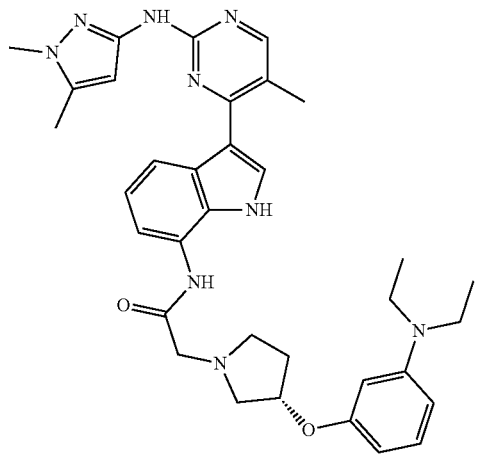 [SMILES: CCN(CC)c1cccc(O[C@H]2CCN(CC(=O)Nc3cccc4c(-c5nc(Nc6cc(C)n(C)n6)ncc5C)c[nH]c34)C2)c1] | (S)-2-(3-(3-(diethylamino)phenoxy)pyrrolidin-1-yl)-N-(3-(2-((1,5-dimethyl-1H-pyrazol-3-yl)amino)-5-methylpyrimidin-4-yl)-1H-indol-7-yl)acetamide |

| | | |
|---|---|---|
| 89) | 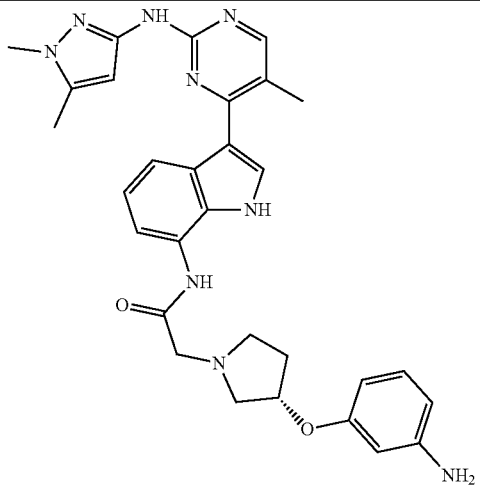 | (S)-2-(3-(3-aminophenoxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 90) | 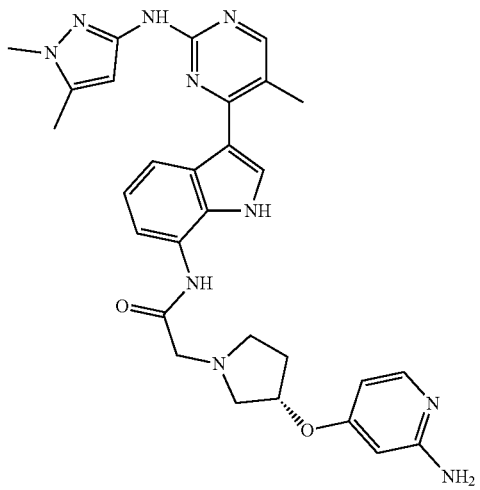 [SMILES: Cc1cnc(Nc2cc(C)n(C)n2)nc1-c1c[nH]c2c(NC(=O)CN3CC[C@H](Oc4ccnc(N)c4)C3)cccc12] | (S)-2-(3-((2-aminopyridin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 91) | 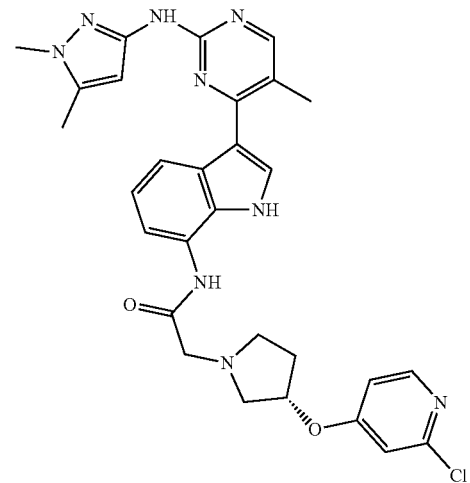 [SMILES: Cc1cnc(Nc2cc(C)n(C)n2)nc1-c1c[nH]c2c(NC(=O)CN3CC[C@H](Oc4ccnc(Cl)c4)C3)cccc12] | (S)-2-(3-((2-chloropyridin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |

| | | |
|---|---|---|
| 92) | 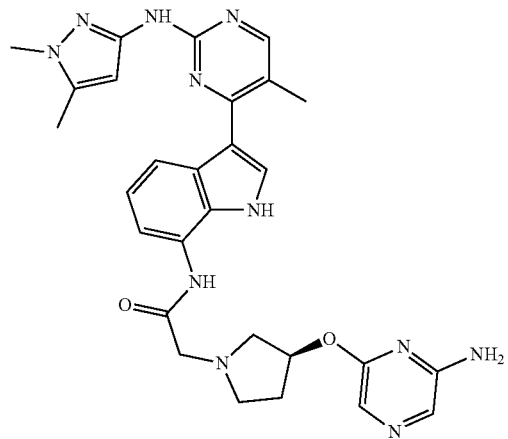 [SMILES: Cc1cnc(Nc2cc(C)n(C)n2)nc1-c1c[nH]c2c(NC(=O)CN3CC[C@H](Oc4cncc(N)n4)C3)cccc12] | (S)-2-(3-((6-aminopyrazin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 93) | 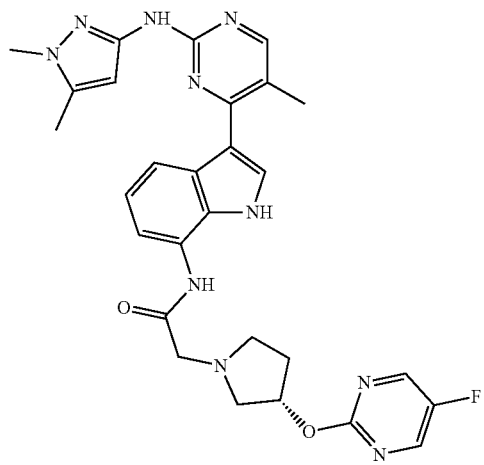 [SMILES: Cc1cnc(Nc2cc(C)n(C)n2)nc1-c1c[nH]c2c(NC(=O)CN3CC[C@H](Oc4ncc(F)cn4)C3)cccc12] | (S)-N-(3-(2-((1,5-dimethyl-1H-pyrazol-3-yl)amino)-5-methylpyrimidin-4-yl)-1H-indol-7-yl)-2-(3-((5-fluoropyrimidin-2-yl)oxy)pyrrolidin-1-yl)acetamide |
| 94) | 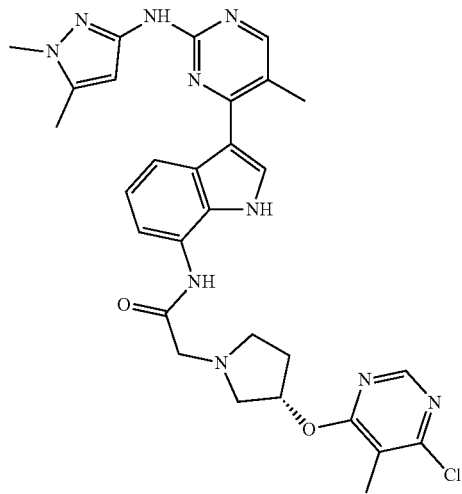 [SMILES: Cc1cnc(Nc2cc(C)n(C)n2)nc1-c1c[nH]c2c(NC(=O)CN3CC[C@H](Oc4ncnc(Cl)c4C)C3)cccc12] | (S)-2-(3-((6-chloro-5-methylpyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |

| | | |
|---|---|---|
| 95) | 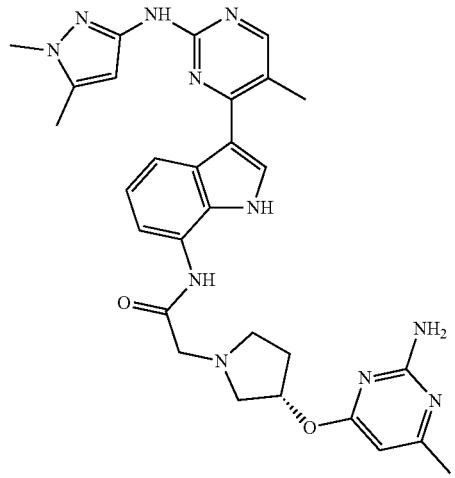 | (S)-2-(3-((2-amino-6-methylpyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 96) | 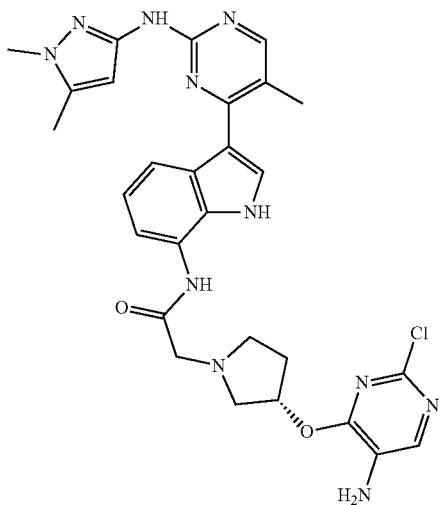 [SMILES: Cc1cnc(Nc2cc(C)n(C)n2)nc1-c1c[nH]c2c(NC(=O)CN3CC[C@H](Oc4nc(Cl)ncc4N)C3)cccc12] | (S)-2-(3-((5-amino-2-chloropyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 97) | 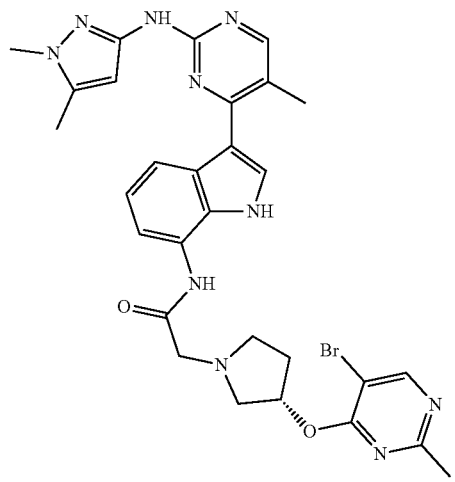 | (S)-2-(3-((5-bromo-2-methylpyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |

| | | |
|---|---|---|
| 98) | 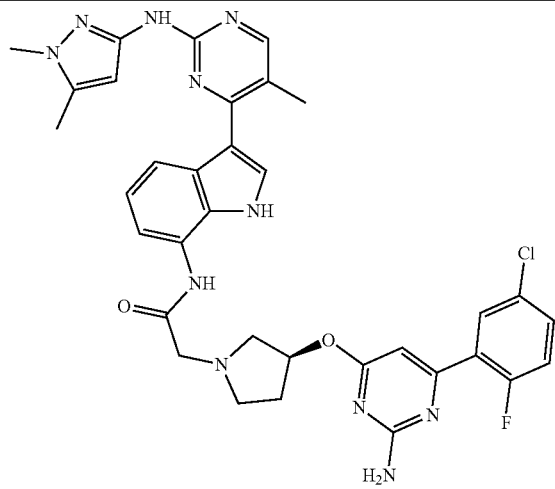 | (S)-2-(3-((2-amino-6-(5-chloro-2-fluorophenyl)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 99) | 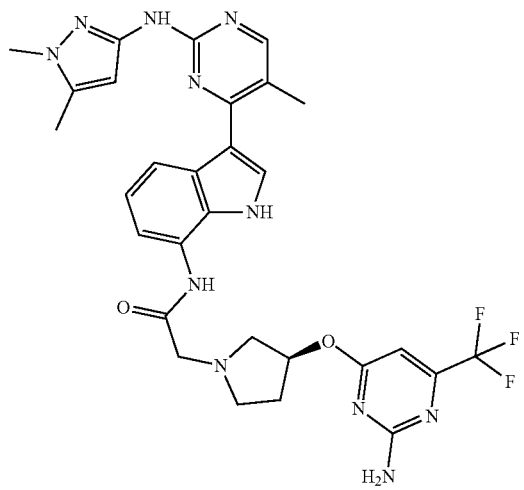 [SMILES: Cc1cnc(Nc2cc(C)n(C)n2)nc1-c1c[nH]c2c(NC(=O)CN3CC[C@H](Oc4cc(C(F)(F)F)nc(N)n4)C3)cccc12] | (S)-2-(3-((2-amino-6-(trifluoromethyl)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 100) | 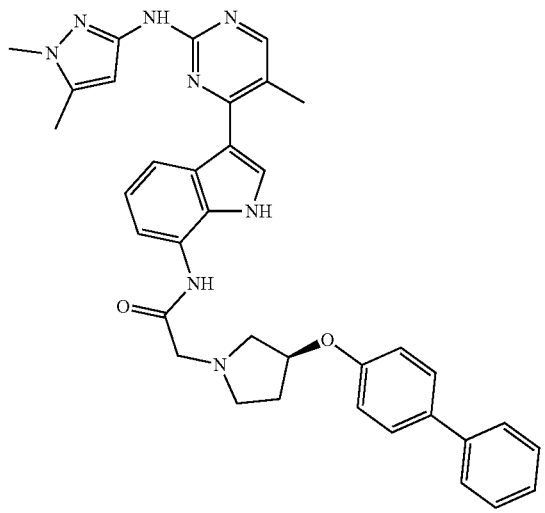 [SMILES: Cc1cnc(Nc2cc(C)n(C)n2)nc1-c1c[nH]c2c(NC(=O)CN3CC[C@H](Oc4ccc(-c5ccccc5)cc4)C3)cccc12] | (S)-2-(3-([1,1'-biphenyl]-4-yloxy)pyrrolidin-1-yl)-N-(3-(2-((1,5-dimethyl-1H-pyrazol-3-yl)amino)-5-methylpyrimidin-4-yl)-1H-indol-7-yl)acetamide |

-continued
101) 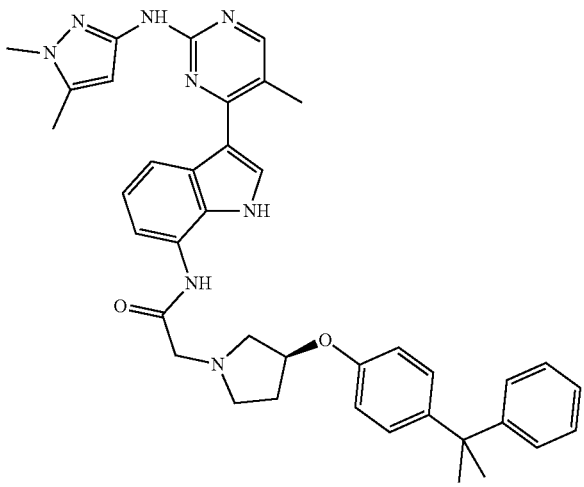 [SMILES: Cc1cnc(Nc2cc(C)n(C)n2)nc1-c1c[nH]c2c(NC(=O)CN3CC[C@H](Oc4ccc(C(C)(C)c5ccccc5)cc4)C3)cccc12]
(S)-N-(3-(2-((1,5-dimethyl-1H-pyrazol-3-yl)amino)-5-methylpyrimidin-4-yl)-1H-indol-7-yl)-2-(3-(4-(2-phenylpropan-2-yl)phenoxy)pyrrolidin-1-yl)acetamide
102) 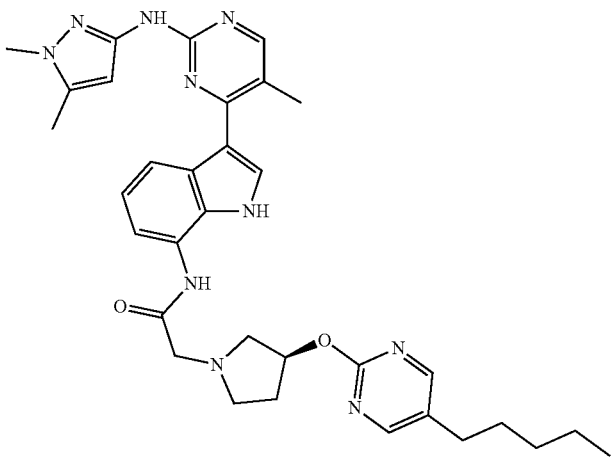 [SMILES: CCCCCc1cnc(O[C@H]2CCN(CC(=O)Nc3cccc4c(-c5nc(Nc6cc(C)n(C)n6)ncc5C)c[nH]c34)C2)nc1]
(S)-N-(3-(2-((1,5-dimethyl-1H-pyrazol-3-yl)amino)-5-methylpyrimidin-4-yl)-1H-indol-7-yl)-2-(3-((5-pentylpyrimidin-2-yl)oxy)pyrrolidin-1-yl)acetamide
103) 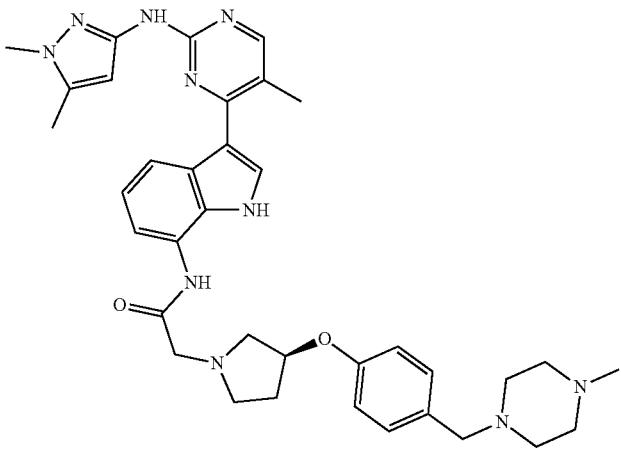
(S)-N-(3-(2-((1,5-dimethyl-1H-pyrazol-3-yl)amino)-5-methylpyrimidin-4-yl)-1H-indol-7-yl)-2-(3-(4-((4-methylpiperazin-1-yl)methyl)phenoxy)pyrrolidin-1-yl)acetamide 104) 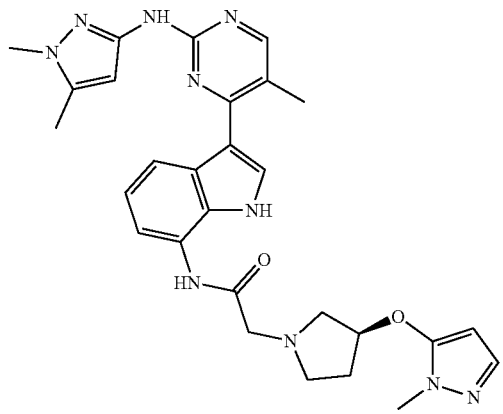 [SMILES: Cc1cnc(Nc2cc(C)n(C)n2)nc1-c1c[nH]c2c(NC(=O)CN3CC[C@H](Oc4ccnn4C)C3)cccc12]
(S)-N-(3-(2-((1,5-dimethyl-1H-pyrazol-3-yl)amino)-5-methylpyrimidin-4-yl)-1H-indol-7-yl)-2-(3-((1-methyl-1H-pyrazol-5-yl)oxy)pyrrolidin-1-yl)acetamide
105) 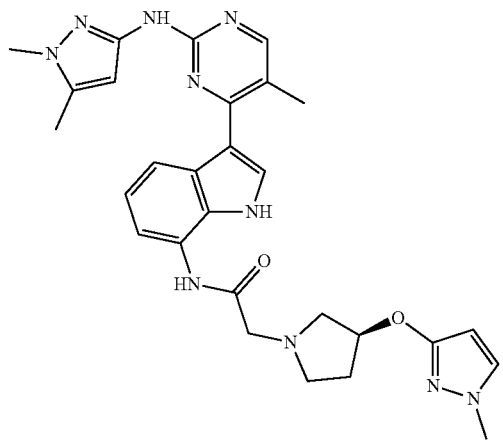 [SMILES: Cc1cnc(Nc2cc(C)n(C)n2)nc1-c1c[nH]c2c(NC(=O)CN3CC[C@H](Oc4ccn(C)n4)C3)cccc12]
(S)-N-(3-(2-((1,5-dimethyl-1H-pyrazol-3-yl)amino)-5-methylpyrimidin-4-yl)-1H-indol-7-yl)-2-(3-((1-methyl-1H-pyrazol-3-yl)oxy)pyrrolidin-1-yl)acetamide
106) 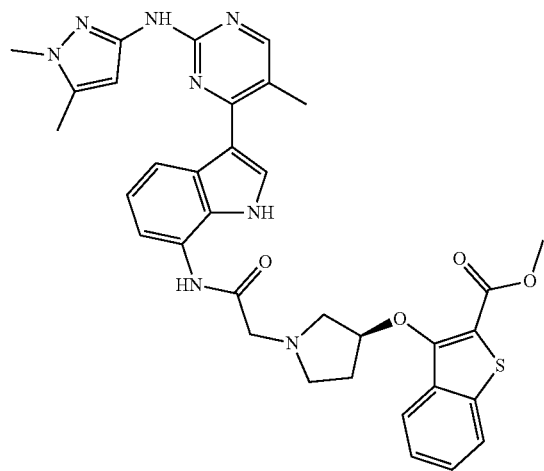
methyl (S)-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)benzo[b]thiophene-2-carboxylate

| | | |
|---|---|---|
| 107) | 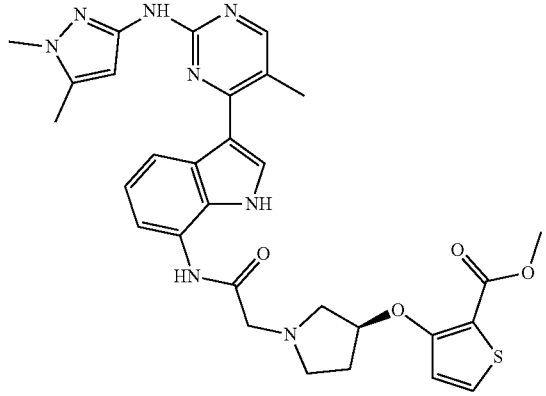 | methyl (S)-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)thiophene-2-carboxylate |
| 108) | 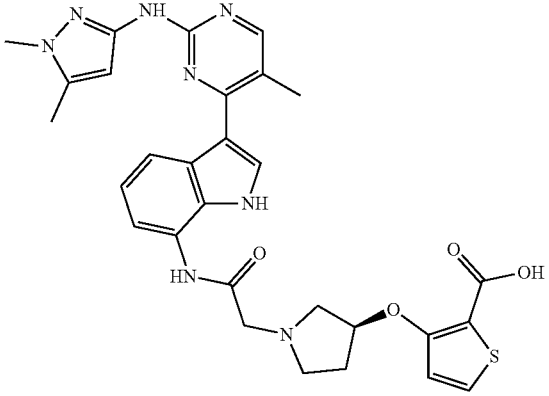 [SMILES: Cc1cnc(Nc2cc(C)n(C)n2)nc1-c1c[nH]c2c(NC(=O)CN3CC[C@H](Oc4ccsc4C(=O)O)C3)cccc12] | (S)-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)thiophene-2-carboxylic acid |
| 109) | 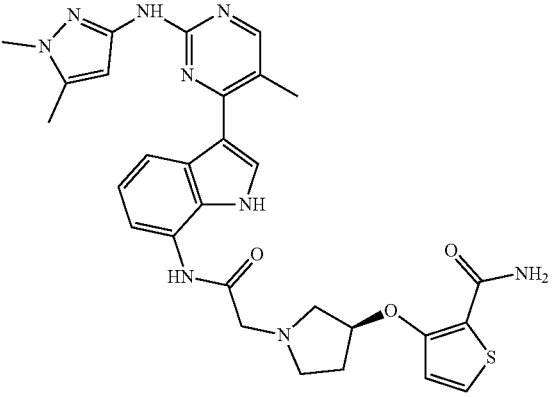 [SMILES: Cc1cnc(Nc2cc(C)n(C)n2)nc1-c1c[nH]c2c(NC(=O)CN3CC[C@H](Oc4ccsc4C(N)=O)C3)cccc12] | (S)-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)thiophene-2-carboxamide |
| 110) | 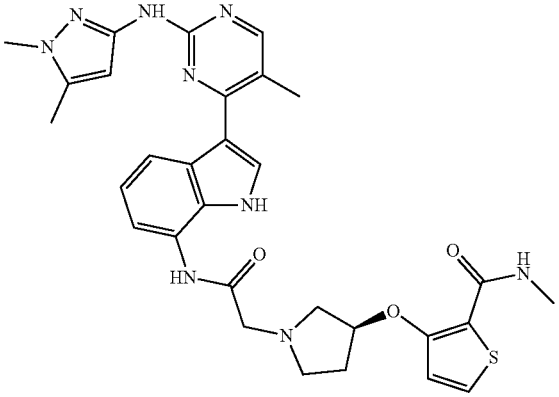 | (S)-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)-N-methylthiophene-2-carboxamide |

| | | |
|---|---|---|
| 111) | 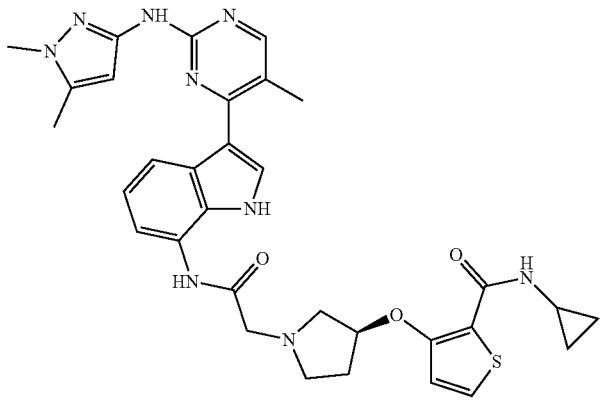 [SMILES: Cc1cnc(Nc2cc(C)n(C)n2)nc1-c1c[nH]c2c(NC(=O)CN3CC[C@H](Oc4ccsc4C(=O)NC4CC4)C3)cccc12] | (S)-N-cyclopropyl-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)thiophene-2-carboxamide |
| 112) | 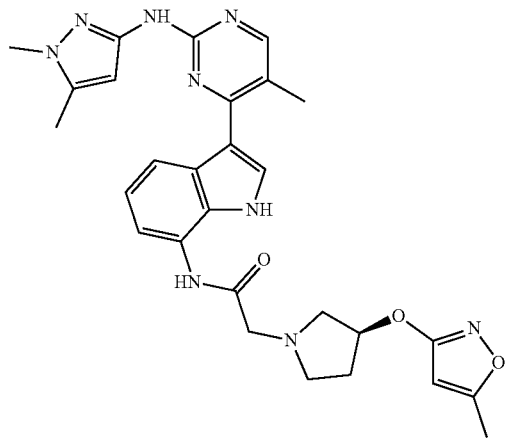 [SMILES: Cc1cc(O[C@H]2CCN(CC(=O)Nc3cccc4c(-c5nc(Nc6cc(C)n(C)n6)ncc5C)c[nH]c34)C2)no1] | (S)-N-(3-(2-((1,5-dimethyl-1H-pyrazol-3-yl)amino)-5-methylpyrimidin-4-yl)-1H-indol-7-yl)-2-(3-((5-methylisoxazol-3-yl)oxy)pyrrolidin-1-yl)acetamide |
| 113) | 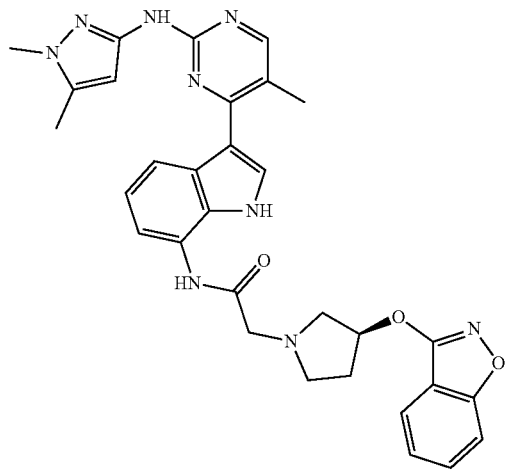 [SMILES: Cc1cnc(Nc2cc(C)n(C)n2)nc1-c1c[nH]c2c(NC(=O)CN3CC[C@H](Oc4noc5ccccc45)C3)cccc12] | (S)-2-(3-(benzo[d]isoxazol-3-yloxy)pyrrolidin-1-yl)-N-(3-(2-((1,5-dimethyl-1H-pyrazol-3-yl)amino)-5-methylpyrimidin-4-yl)-1H-indol-7-yl)acetamide |

114) 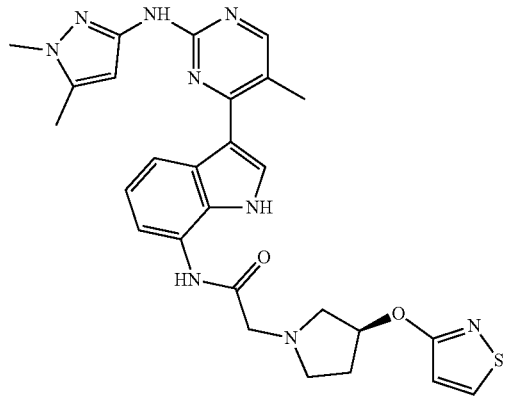 [SMILES: Cc1cnc(Nc2cc(C)n(C)n2)nc1-c1c[nH]c2c(NC(=O)CN3CC[C@H](Oc4ccsn4)C3)cccc12]
(S)-N-(3-(2-((1,5-dimethyl-1H-pyrazol-3-yl)amino)-5-methylpyrimidin-4-yl)-1H-indol-7-yl)-2-(3-(isothiazol-3-yloxy)pyrrolidin-1-yl)acetamide
115) 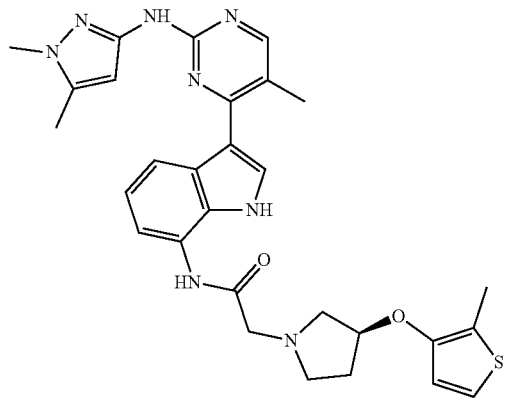 [SMILES: Cc1cnc(Nc2cc(C)n(C)n2)nc1-c1c[nH]c2c(NC(=O)CN3CC[C@H](Oc4ccsc4C)C3)cccc12]
(S)-N-(3-(2-((1,5-dimethyl-1H-pyrazol-3-yl)amino)-5-methylpyrimidin-4-yl)-1H-indol-7-yl)-2-(3-((2-methylthiophen-3-yl)oxy)pyrrolidin-1-yl)acetamide
116) 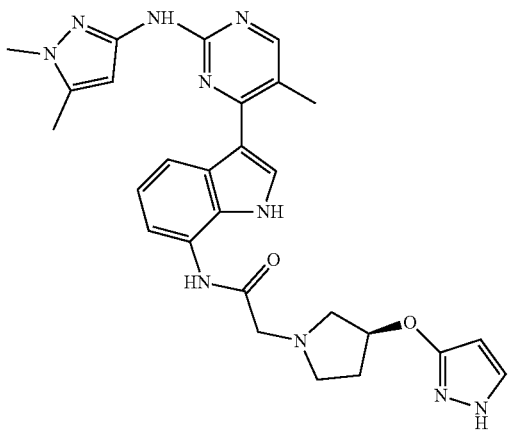 [SMILES: Cc1cnc(Nc2cc(C)n(C)n2)nc1-c1c[nH]c2c(NC(=O)CN3CC[C@H](Oc4cc[nH]n4)C3)cccc12]
(S)-2-(3-((1H-pyrazol-3-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide 117) 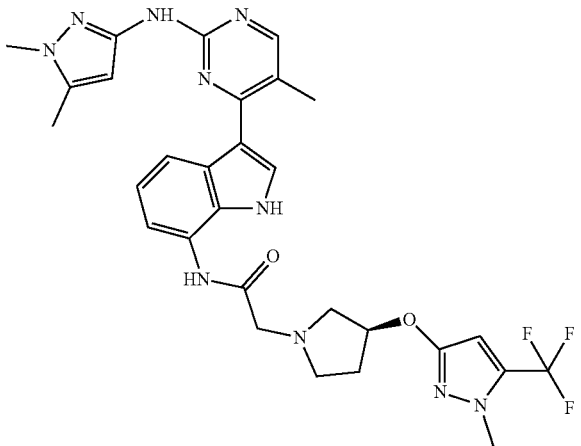 [SMILES: Cc1cnc(Nc2cc(C)n(C)n2)nc1-c1c[nH]c2c(NC(=O)CN3CC[C@H](Oc4cc(C(F)(F)F)n(C)n4)C3)cccc12] (S)-N-(3-(2-((1,5-dimethyl-1H-pyrazol-3-yl)amino)-5-methylpyrimidin-4-yl)-1H-indol-7-yl)-2-(3-((1-methyl-5-(trifluoromethyl)-1H-pyrazol-3-yl)oxy)pyrrolidin-1-yl)acetamide
118) 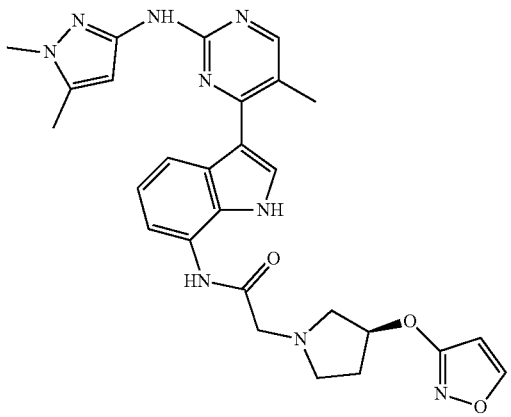 [SMILES: Cc1cnc(Nc2cc(C)n(C)n2)nc1-c1c[nH]c2c(NC(=O)CN3CC[C@H](Oc4ccon4)C3)cccc12] (S)-N-(3-(2-((1,5-dimethyl-1H-pyrazol-3-yl)amino)-5-methylpyrimidin-4-yl)-1H-indol-7-yl)-2-(3-(isoxazol-3-yloxy)pyrrolidin-1-yl)acetamide
119) 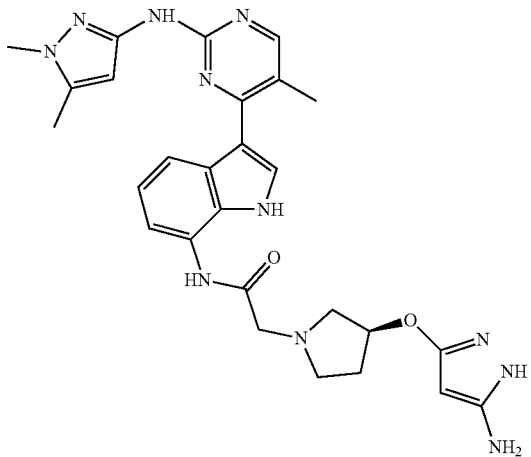 [SMILES: Cc1cnc(Nc2cc(C)n(C)n2)nc1-c1c[nH]c2c(NC(=O)CN3CC[C@H](OC(=N)C=C(N)N)C3)cccc12] (S)-2-(3-((5-amino-1H-pyrazol-3-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

| | | |
|---|---|---|
| 120) | 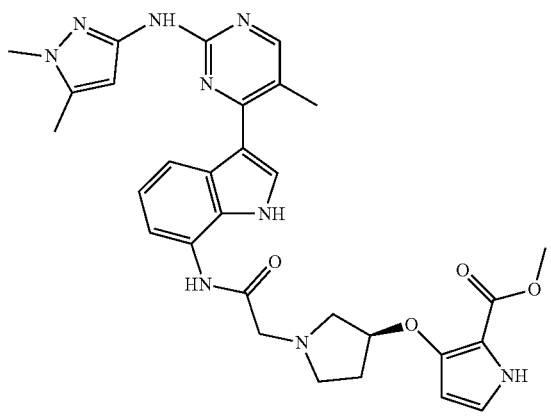 | methyl (S)-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)-1H-pyrrole-2-carboxylate |
| 121) | 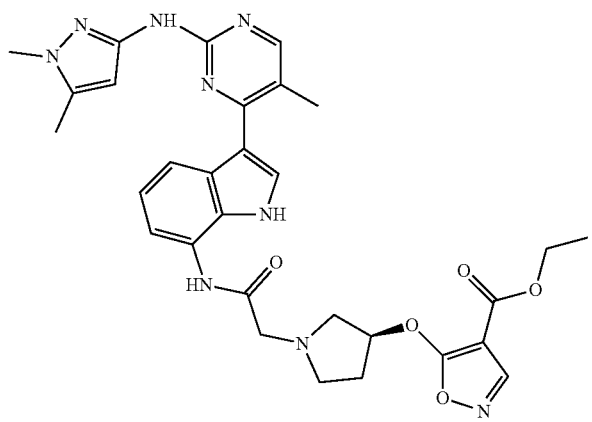 [SMILES: CCOC(=O)c1cnoc1O[C@H]1CCN(CC(=O)Nc2cccc3c(-c4nc(Nc5cc(C)n(C)n5)ncc4C)c[nH]c23)C1] | ethyl (S)-5-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)isoxazole-4-carboxylate |
| 122) | 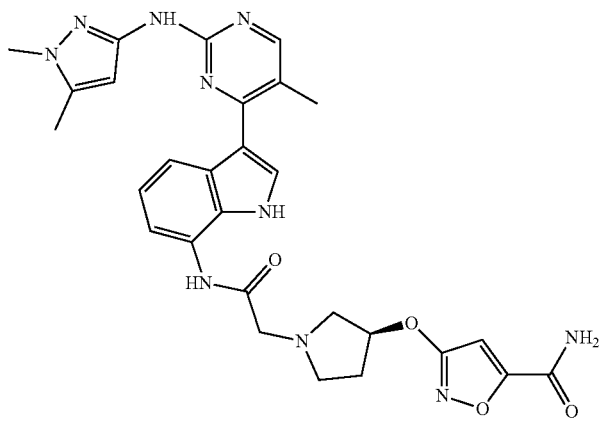 [SMILES: Cc1cnc(Nc2cc(C)n(C)n2)nc1-c1c[nH]c2c(NC(=O)CN3CC[C@H](Oc4cc(C(N)=O)on4)C3)cccc12] | (S)-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)isoxazole-5-carboxamide |

| | | |
|---|---|---|
| 123) | 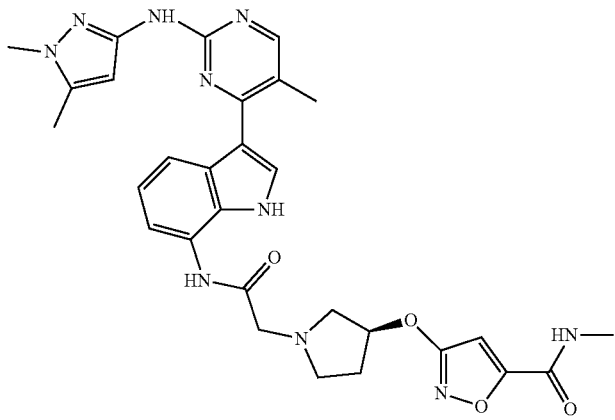 | (S)-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)-N-methylisoxazole-5-carboxamide |
| 124) | 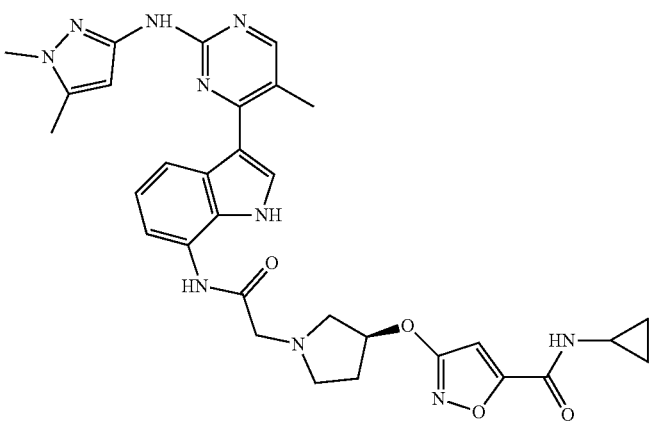 [SMILES: Cc1cnc(Nc2cc(C)n(C)n2)nc1-c1c[nH]c2c(NC(=O)CN3CC[C@H](Oc4cc(C(=O)NC5CC5)on4)C3)cccc12] | (S)-N-cyclopropyl-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)isoxazole-5-carboxamide |
| 125) | 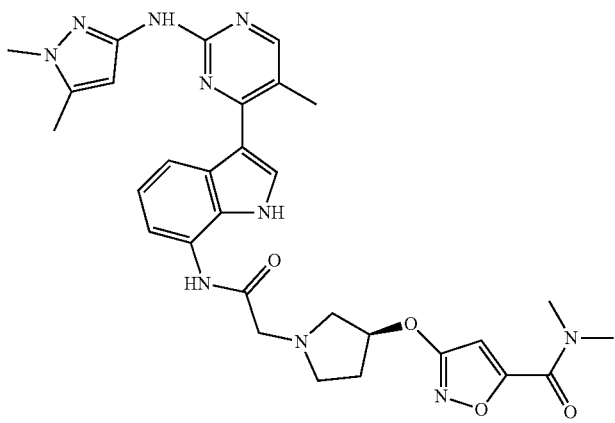 | (S)-3-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)-N,N-dimethylisoxazole-5-carboxamide |

-continued

126) 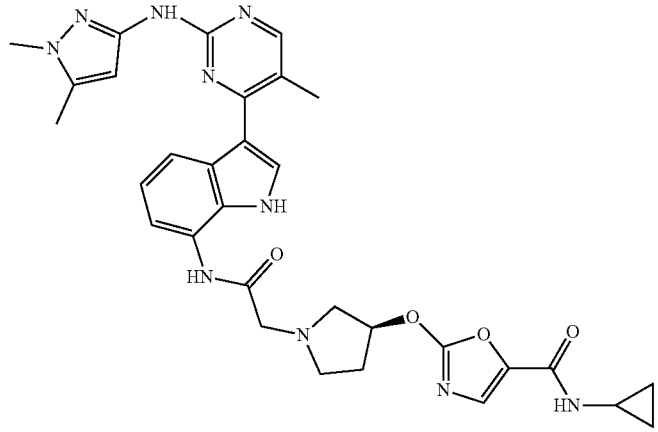 [SMILES: Cc1cnc(Nc2cc(C)n(C)n2)nc1-c1c[nH]c2c(NC(=O)CN3CC[C@H](Oc4ncc(C(=O)NC5CC5)o4)C3)cccc12]

(S)-N-cyclopropyl-2-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)oxazole-5-carboxamide 127) 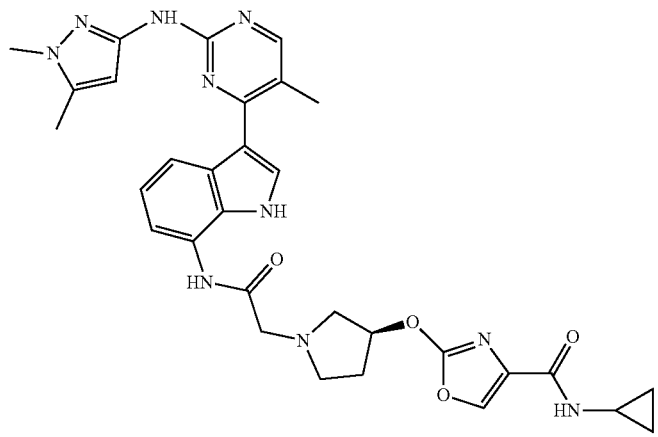 [SMILES: Cc1cnc(Nc2cc(C)n(C)n2)nc1-c1c[nH]c2c(NC(=O)CN3CC[C@H](Oc4nc(C(=O)NC5CC5)co4)C3)cccc12]

(S)-N-cyclopropyl-2-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)oxazole-4-carboxamide 128) 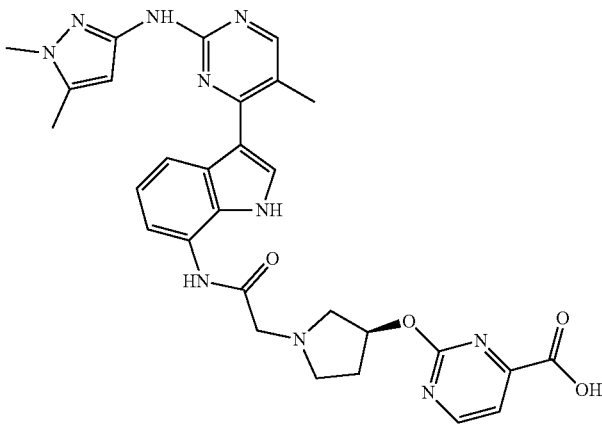 [SMILES: Cc1cnc(Nc2cc(C)n(C)n2)nc1-c1c[nH]c2c(NC(=O)CN3CC[C@H](Oc4nccc(C(=O)O)n4)C3)cccc12]

(S)-2-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)pyrimidine-4-carboxylic acid 129) 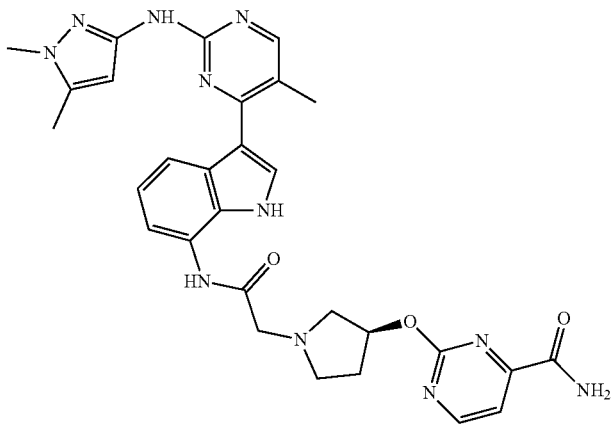 [SMILES: Cc1cnc(Nc2cc(C)n(C)n2)nc1-c1c[nH]c2c(NC(=O)CN3CC[C@H](Oc4nccc(C(N)=O)n4)C3)cccc12]
(S)-2-((1-(2-((3-(2-(((1,5-dimethyl-1H-pyrazol-3-yl)amino)-5-methylpyrimidin-4-yl)-1H-indol-7-yl)amino)-2-oxoethyl)pyrrolidin-3-yl)oxy)pyrimidine-4-carboxamide 130) 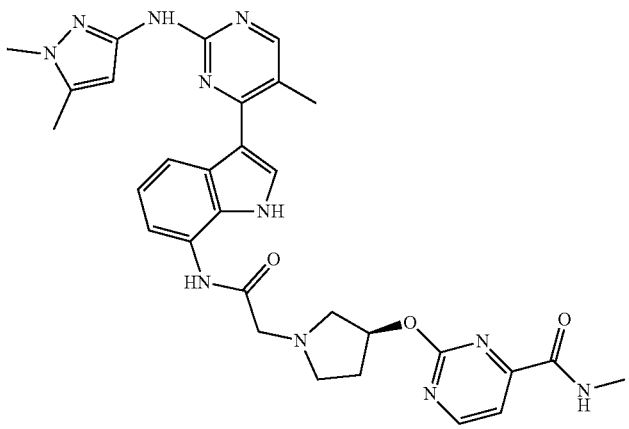
(S)-2-((1-(2-((3-(2-(((1,5-dimethyl-1H-pyrazol-3-yl)amino)-5-methylpyrimidin-4-yl)-1H-indol-7-yl)amino)-2-oxoethyl)pyrrolidin-3-yl)oxy)-N-methylpyrimidine-4-carboxamide 131) 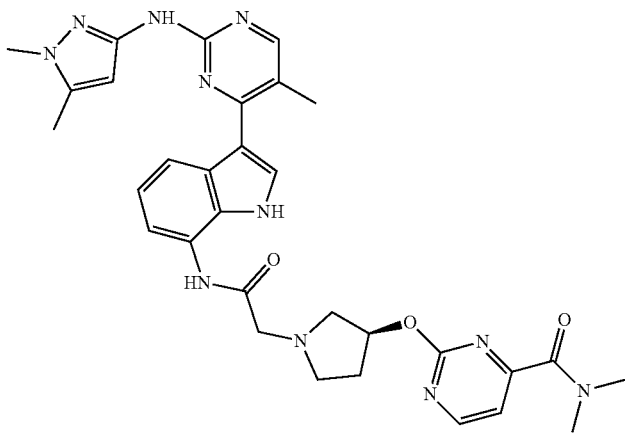
(S)-2-((1-(2-((3-(2-(((1,5-dimethyl-1H-pyrazol-3-yl)amino)-5-methylpyrimidin-4-yl)-1H-indol-7-yl)amino)-2-oxoethyl)pyrrolidin-3-yl)oxy)-N,N-dimethylpyrimidine-4-carboxamide 132) 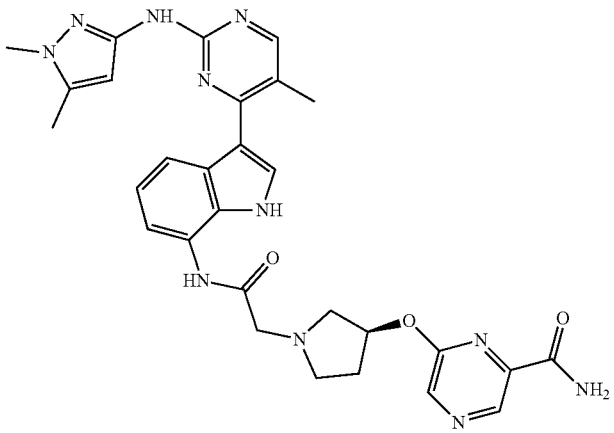 [SMILES: Cc1cnc(Nc2cc(C)n(C)n2)nc1-c1c[nH]c2c(NC(=O)CN3CC[C@H](Oc4cncc(C(N)=O)n4)C3)cccc12]
(S)-6-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)pyrazine-2-carboxamide
133) 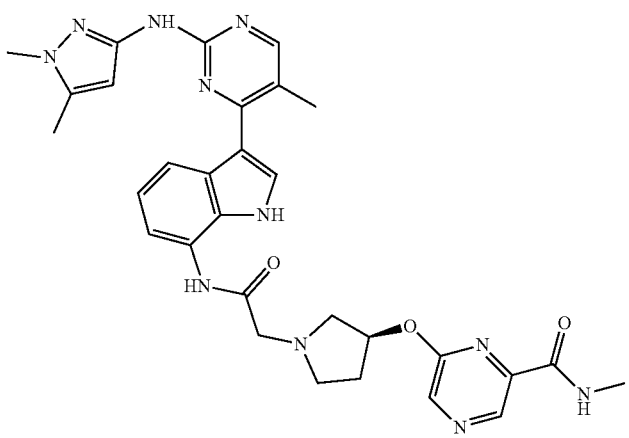
(S)-6-((1-(2-((3-(2-((1,5-dimethyl-1H-pyrazol-3-yl)amino)-5-methylpyrimidin-4-yl)-1H-indol-7-yl)amino)-2-oxoethyl)pyrrolidin-3-yl)oxy)-N-methylpyrazine-2-carboxamide
134) 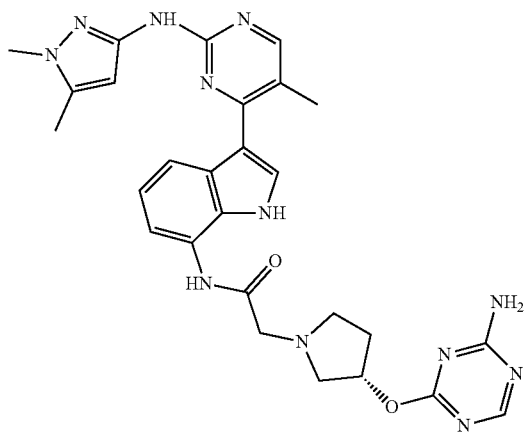 [SMILES: Cc1cnc(Nc2cc(C)n(C)n2)nc1-c1c[nH]c2c(NC(=O)CN3CC[C@H](Oc4ncnc(N)n4)C3)cccc12]
(S)-2-(3-((4-amino-1,3,5-triazin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide -continued
135) 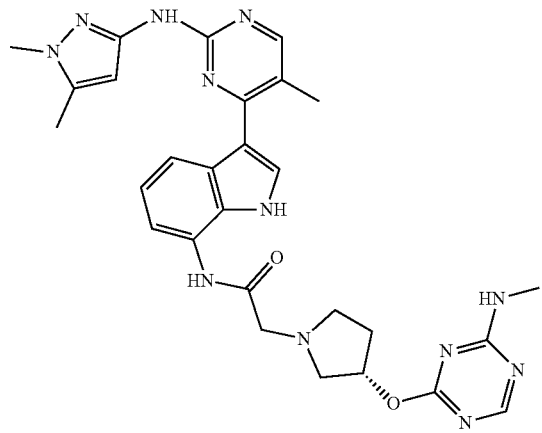 (S)-N-(3-(2-((1,5-dimethyl-1H-pyrazol-3-yl)amino)-5-methylpyrimidin-4-yl)-1H-indol-7-yl)-2-(3-((4-(methylamino)-1,3,5-triazin-2-yl)oxy)pyrrolidin-1-yl)acetamide
136) 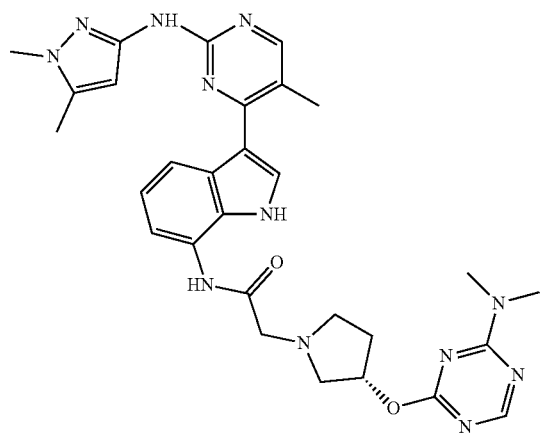 (S)-N-(3-(2-((1,5-dimethyl-1H-pyrazol-3-yl)amino)-5-methylpyrimidin-4-yl)-1H-indol-7-yl)-2-(3-((4-(dimethylamino)-1,3,5-triazin-2-yl)oxy)pyrrolidin-1-yl)acetamide
137) 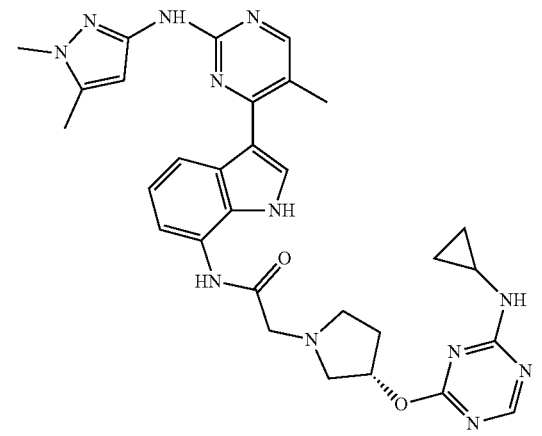 [SMILES: Cc1cnc(Nc2cc(C)n(C)n2)nc1-c1c[nH]c2c(NC(=O)CN3CC[C@H](Oc4ncnc(NC5CC5)n4)C3)cccc12] (S)-2-(3-((4-(cyclopropylamino)-1,3,5-triazin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide 138) 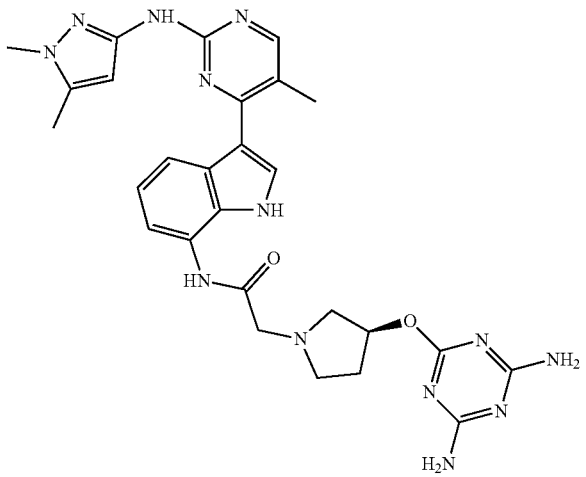 [SMILES: Cc1cnc(Nc2cc(C)n(C)n2)nc1-c1c[nH]c2c(NC(=O)CN3CC[C@H](Oc4nc(N)nc(N)n4)C3)cccc12]
(S)-2-(3-((4,6-diamino-1,3,5-triazin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide
139) 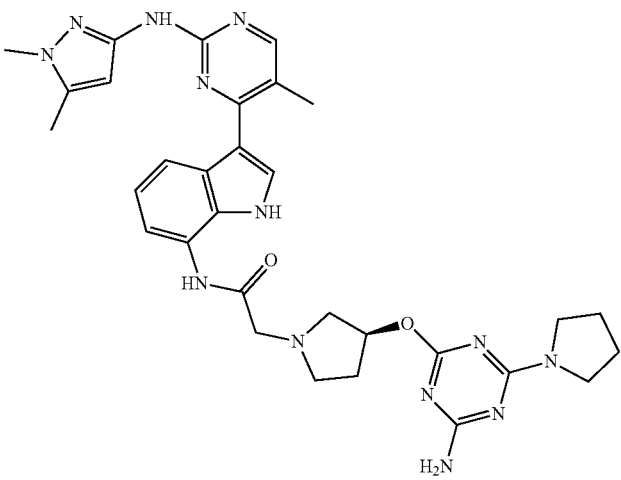 [SMILES: Cc1cnc(Nc2cc(C)n(C)n2)nc1-c1c[nH]c2c(NC(=O)CN3CC[C@H](Oc4nc(N)nc(N5CCCC5)n4)C3)cccc12]
(S)-2-(3-((4-amino-6-(pyrrolidin-1-yl)-1,3,5-triazin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide
140) 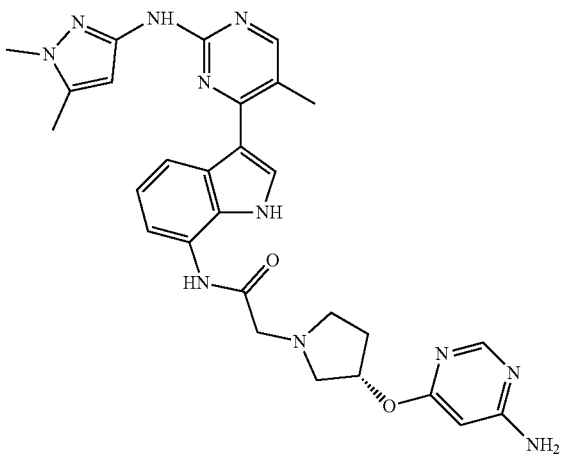 [SMILES: Cc1cnc(Nc2cc(C)n(C)n2)nc1-c1c[nH]c2c(NC(=O)CN3CC[C@H](Oc4cc(N)ncn4)C3)cccc12]
(S)-2-(3-((6-aminopyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

| | | |
|---|---|---|
| 141) | 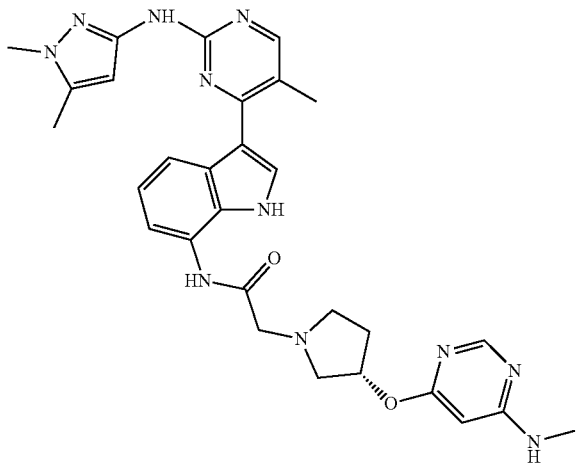 | (S)-N-(3-(2-((1,5-dimethyl-1H-pyrazol-3-yl)amino)-5-methylpyrimidin-4-yl)-1H-indol-7-yl)-2-(3-((6-(methylamino)pyrimidin-4-yl)oxy)pyrrolidin-1-yl)acetamide |
| 142) | 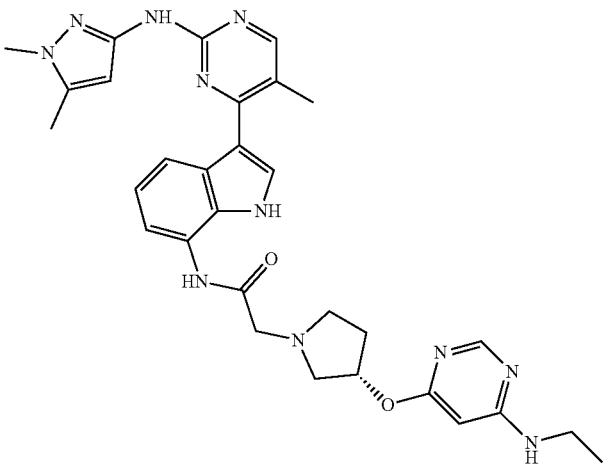 [SMILES: CCNc1cc(O[C@H]2CCN(CC(=O)Nc3cccc4c(-c5nc(Nc6cc(C)n(C)n6)ncc5C)c[nH]c34)C2)ncn1] | (S)-N-(3-(2-((1,5-dimethyl-1H-pyrazol-3-yl)amino)-5-methylpyrimidin-4-yl)-1H-indol-7-yl)-2-(3-((6-(ethylamino)pyrimidin-4-yl)oxy)pyrrolidin-1-yl)acetamide |
| 143) | 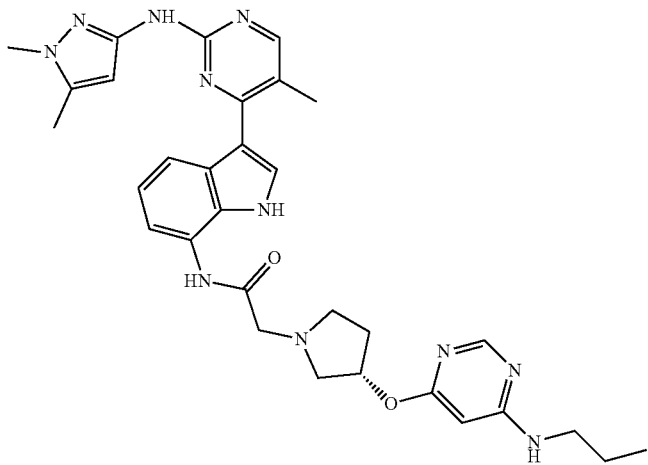 [SMILES: CCCNc1cc(O[C@H]2CCN(CC(=O)Nc3cccc4c(-c5nc(Nc6cc(C)n(C)n6)ncc5C)c[nH]c34)C2)ncn1] | (S)-N-(3-(2-((1,5-dimethyl-1H-pyrazol-3-yl)amino)-5-methylpyrimidin-4-yl)-1H-indol-7-yl)-2-(3-((6-(propylamino)pyrimidin-4-yl)oxy)pyrrolidin-1-yl)acetamide |

144) 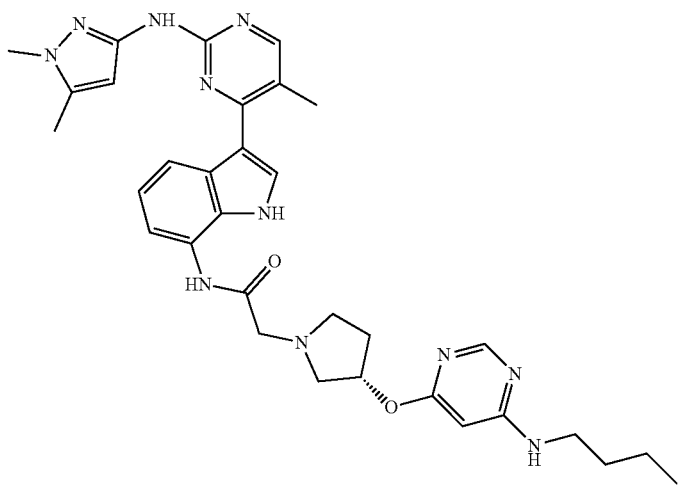 [SMILES: CCCCNc1cc(O[C@H]2CCN(CC(=O)Nc3cccc4c(-c5nc(Nc6cc(C)n(C)n6)ncc5C)c[nH]c34)C2)ncn1] (S)-2-(3-((6-(butylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide 145) 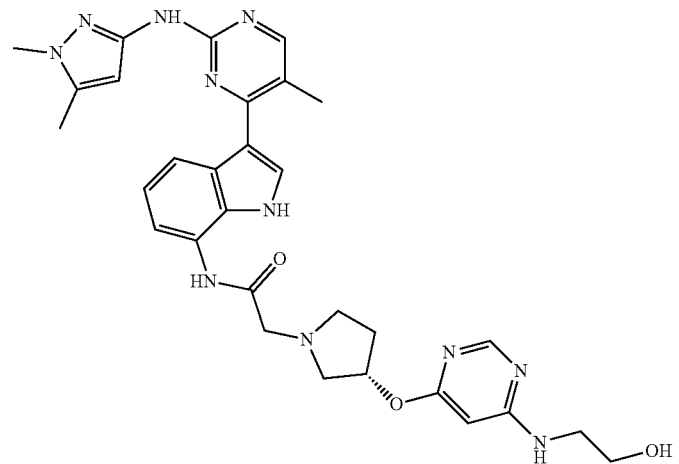 [SMILES: Cc1cnc(Nc2cc(C)n(C)n2)nc1-c1c[nH]c2c(NC(=O)CN3CC[C@H](Oc4cc(NCCO)ncn4)C3)cccc12] (S)-N-(3-(2-((1,5-dimethyl-1H-pyrazol-3-yl)amino)-5-methylpyrimidin-4-yl)-1H-indol-7-yl)-2-(3-((6-((2-hydroxyethyl)amino)pyrimidin-4-yl)oxy)pyrrolidin-1-yl)acetamide 146) 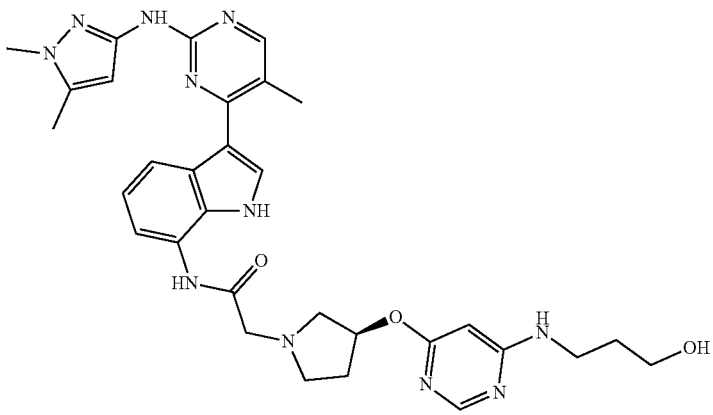 [SMILES: Cc1cnc(Nc2cc(C)n(C)n2)nc1-c1c[nH]c2c(NC(=O)CN3CC[C@H](Oc4cc(NCCCO)ncn4)C3)cccc12] (S)-N-(3-(2-((1,5-dimethyl-1H-pyrazol-3-yl)amino)-5-methylpyrimidin-4-yl)-1H-indol-7-yl)-2-(3-((6-((3-hydroxypropyl)amino)pyrimidin-4-yl)oxy)pyrrolidin-1-yl)acetamide 147) 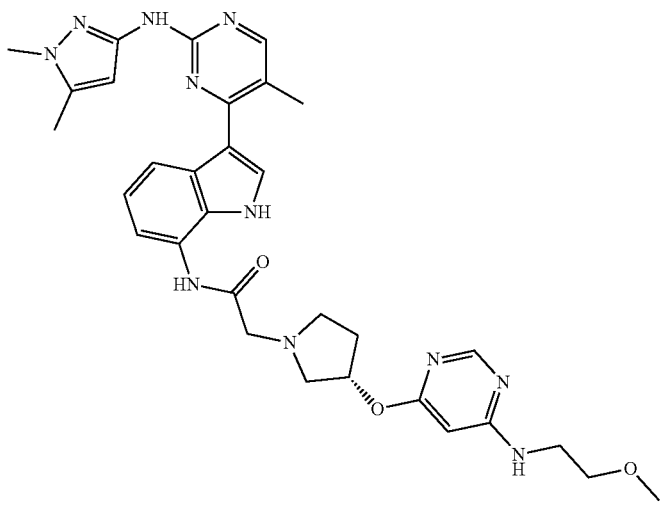

(S)-N-(3-(2-((1,5-dimethyl-1H-pyrazol-3-yl)amino)-5-methylpyrimidin-4-yl)-1H-indol-7-yl)-2-(3-((6-((2-methoxyethyl)amino)pyrimidin-4-yl)oxy)pyrrolidin-1-yl)acetamide 148) 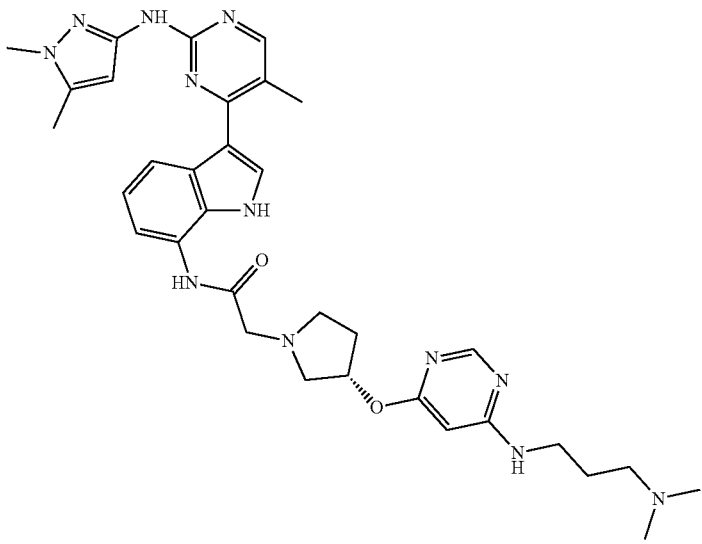

(S)-N-(3-(2-((1,5-dimethyl-1H-pyrazol-3-yl)amino)-5-methylpyrimidin-4-yl)-1H-indol-7-yl)-2-(3-((6-((3-(dimethylamino)propyl)amino)pyrimidin-4-yl)oxy)pyrrolidin-1-yl)acetamide 149) 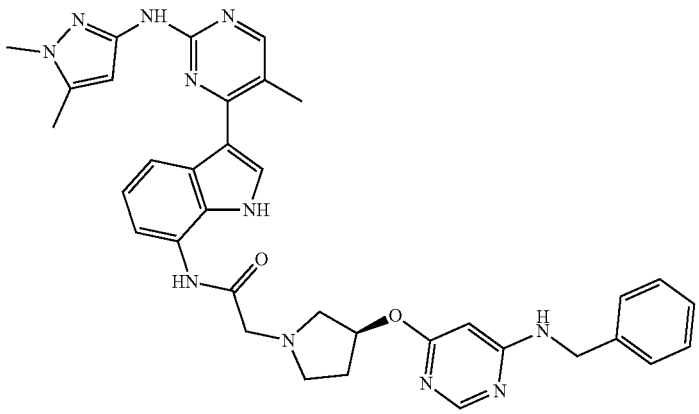 [SMILES: Cc1cnc(Nc2cc(C)n(C)n2)nc1-c1c[nH]c2c(NC(=O)CN3CC[C@H](Oc4cc(NCc5ccccc5)ncn4)C3)cccc12]

(S)-2-(3-((6-(benzylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

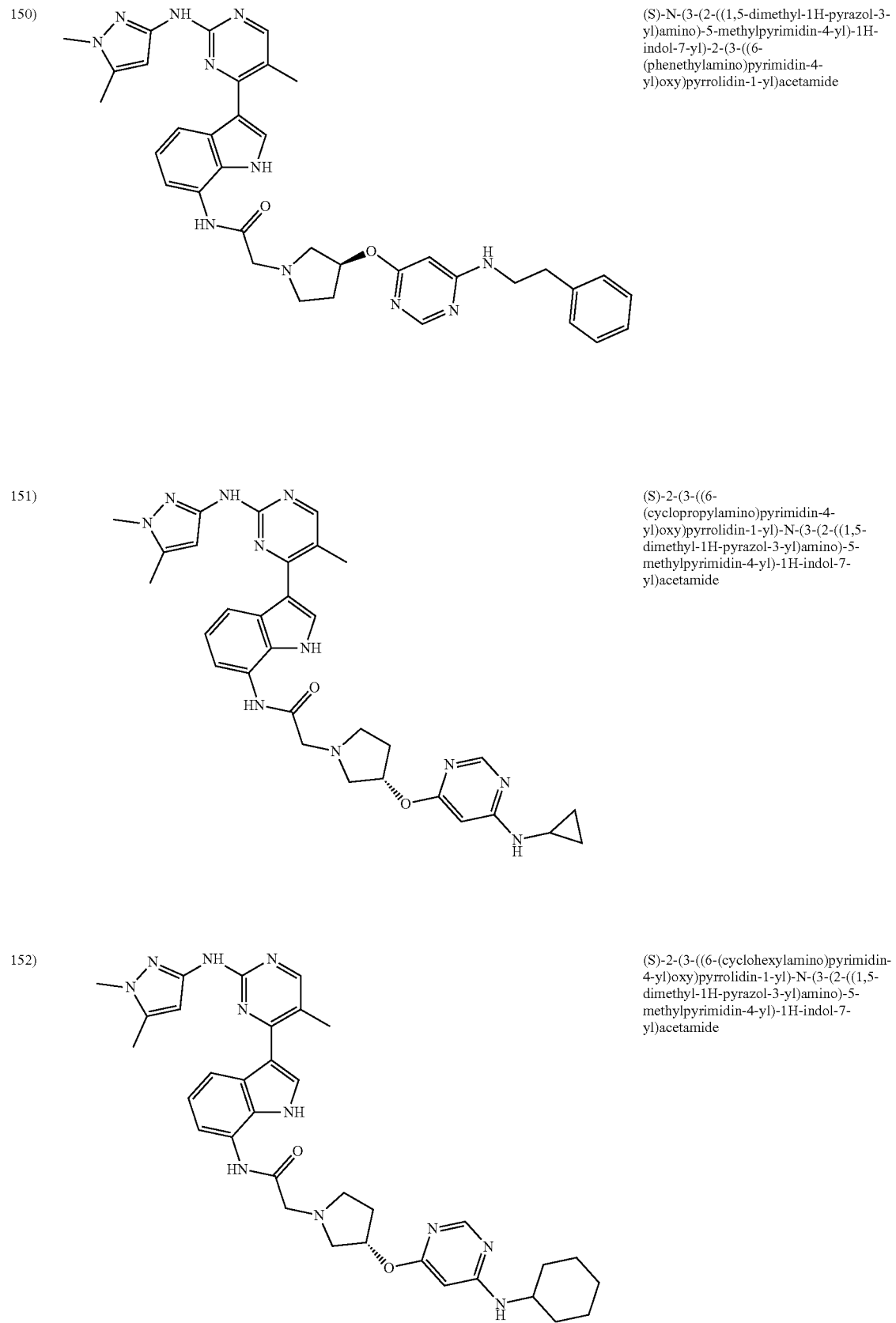

150) (S)-N-(3-(2-((1,5-dimethyl-1H-pyrazol-3-yl)amino)-5-methylpyrimidin-4-yl)-1H-indol-7-yl)-2-(3-((6-(phenethylamino)pyrimidin-4-yl)oxy)pyrrolidin-1-yl)acetamide 151) (S)-2-(3-((6-(cyclopropylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide 152) (S)-2-(3-((6-(cyclohexylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide -continued 153) 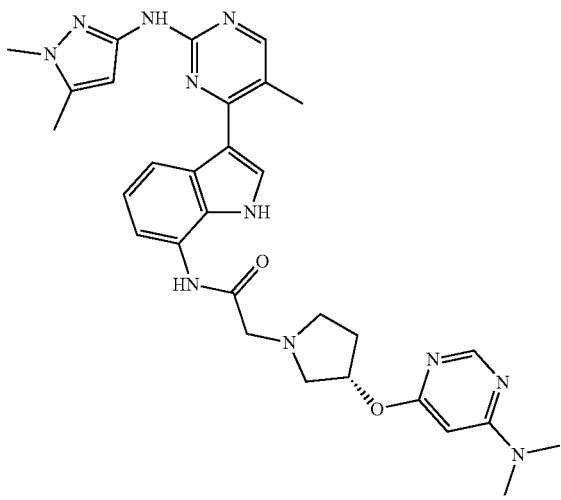

(S)-N-(3-(2-((1,5-dimethyl-1H-pyrazol-3-yl)amino)-5-methylpyrimidin-4-yl)-1H-indol-7-yl)-2-(3-((6-(dimethylamino)pyrimidin-4-yl)oxy)pyrrolidin-1-yl)acetamide 154) 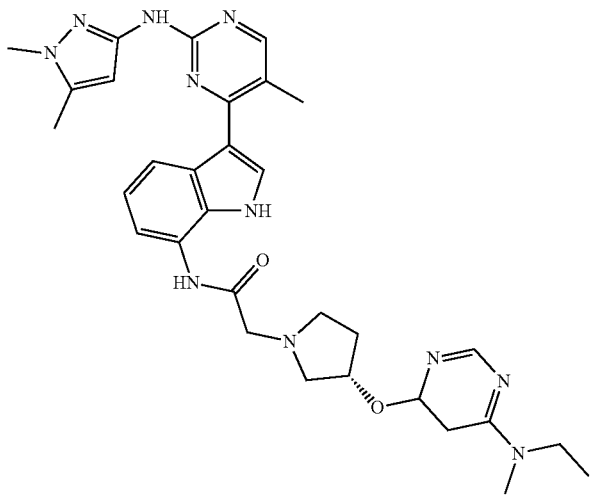 [SMILES: CCN(C)C1=NC=NC(O[C@H]2CCN(CC(=O)Nc3cccc4c(-c5nc(Nc6cc(C)n(C)n6)ncc5C)c[nH]c34)C2)C1]

(S)-N-(3-(2-((1,5-dimethyl-1H-pyrazol-3-yl)amino)-5-methylpyrimidin-4-yl)-1H-indol-7-yl)-2-(3-((6-(ethyl(methyl)amino)pyrimidin-4-yl)oxy)pyrrolidin-1-yl)acetamide 155) 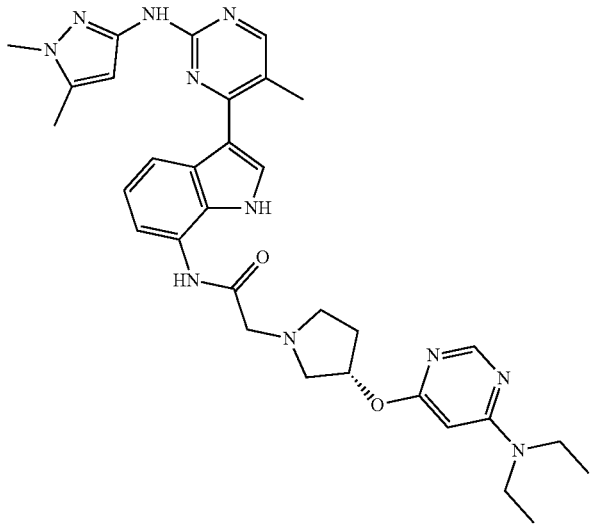 [SMILES: CCN(CC)c1cc(O[C@H]2CCN(CC(=O)Nc3cccc4c(-c5nc(Nc6cc(C)n(C)n6)ncc5C)c[nH]c34)C2)ncn1]

(S)-2-(3-((6-(diethylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide -continued 156) 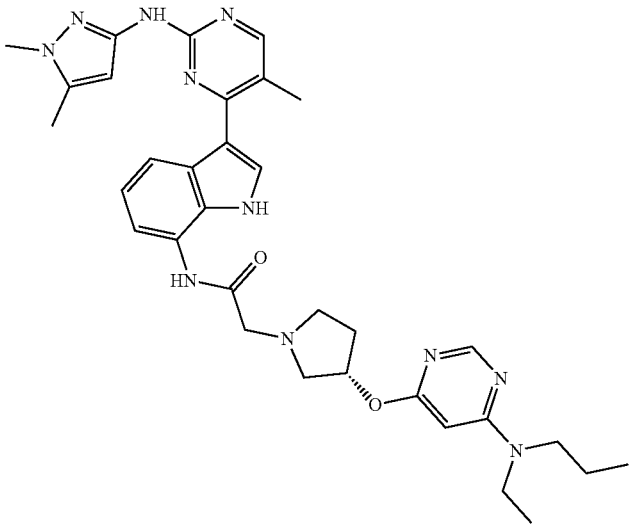 [SMILES: CCCN(CC)c1cc(O[C@H]2CCN(CC(=O)Nc3cccc4c(-c5nc(Nc6cc(C)n(C)n6)ncc5C)c[nH]c34)C2)ncn1] (S)-N-(3-(2-((1,5-dimethyl-1H-pyrazol-3-yl)amino)-5-methylpyrimidin-4-yl)-1H-indol-7-yl)-2-(3-((6-(ethyl(propyl)amino)pyrimidin-4-yl)oxy)pyrrolidin-1-yl)acetamide 157) 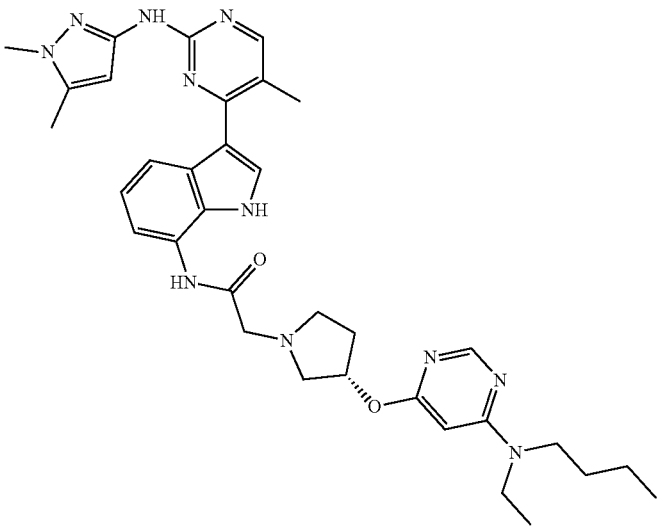 [SMILES: CCCCN(CC)c1cc(O[C@H]2CCN(CC(=O)Nc3cccc4c(-c5nc(Nc6cc(C)n(C)n6)ncc5C)c[nH]c34)C2)ncn1] (S)-2-(3-((6-(butyl(ethyl)amino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide 158) 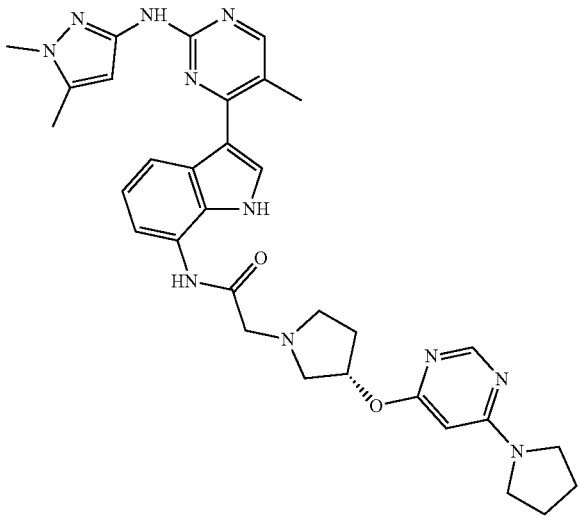 [SMILES: Cc1cnc(Nc2cc(C)n(C)n2)nc1-c1c[nH]c2c(NC(=O)CN3CC[C@H](Oc4cc(N5CCCC5)ncn4)C3)cccc12] (S)-N-(3-(2-((1,5-dimethyl-1H-pyrazol-3-yl)amino)-5-methylpyrimidin-4-yl)-1H-indol-7-yl)-2-(3-((6-(pyrrolidin-1-yl)pyrimidin-4-yl)oxy)pyrrolidin-1-yl)acetamide 159) 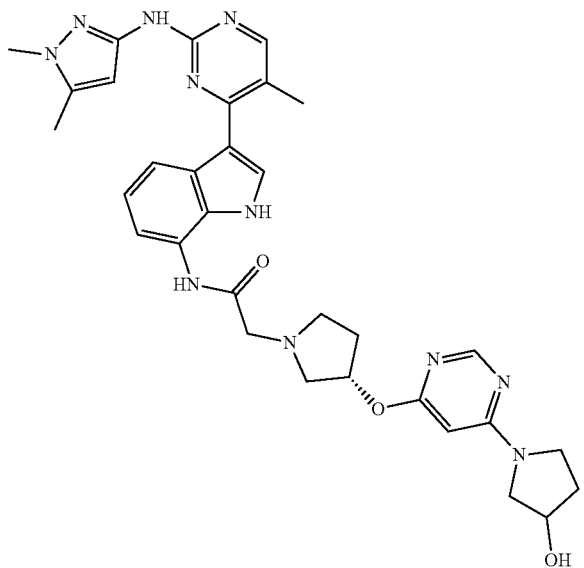
N-(3-(2-((1,5-dimethyl-1H-pyrazol-3-yl)amino)-5-methylpyrimidin-4-yl)-1H-indol-7-yl)-2-((3S)-3-((6-(3-hydroxypyrrolidin-1-yl)pyrimidin-4-yl)oxy)pyrrolidin-1-yl)acetamide
160) 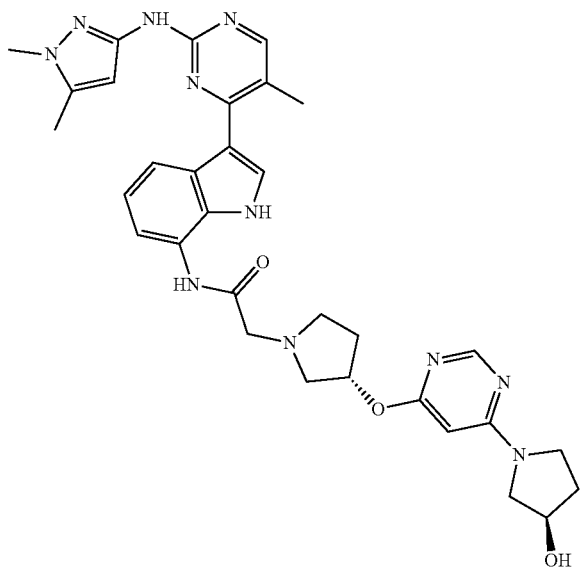 [SMILES: Cc1cnc(Nc2cc(C)n(C)n2)nc1-c1c[nH]c2c(NC(=O)CN3CC[C@H](Oc4cc(N5CC[C@@H](O)C5)ncn4)C3)cccc12]
N-(3-(2-((1,5-dimethyl-1H-pyrazol-3-yl)amino)-5-methylpyrimidin-4-yl)-1H-indol-7-yl)-2-((S)-3-((6-((R)-3-hydroxypyrrolidin-1-yl)pyrimidin-4-yl)oxy)pyrrolidin-1-yl)acetamide 161) 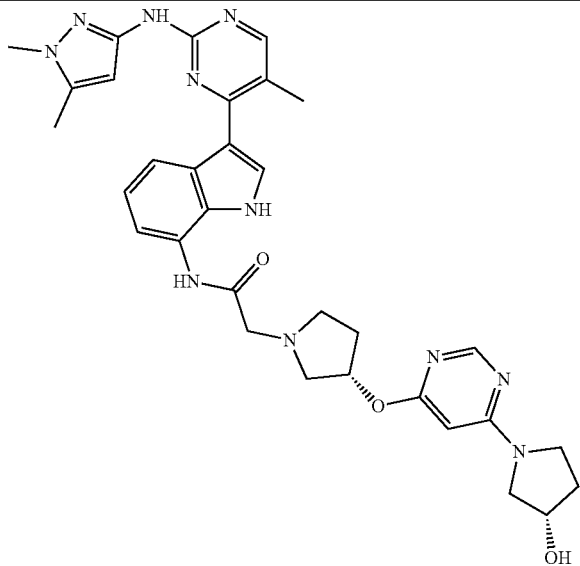 N-(3-(2-((1,5-dimethyl-1H-pyrazol-3-yl)amino)-5-methylpyrimidin-4-yl)-1H-indol-7-yl)-2-((S)-3-((6-((S)-3-hydroxypyrrolidin-1-yl)pyrimidin-4-yl)oxy)pyrrolidin-1-yl)acetamide 162) 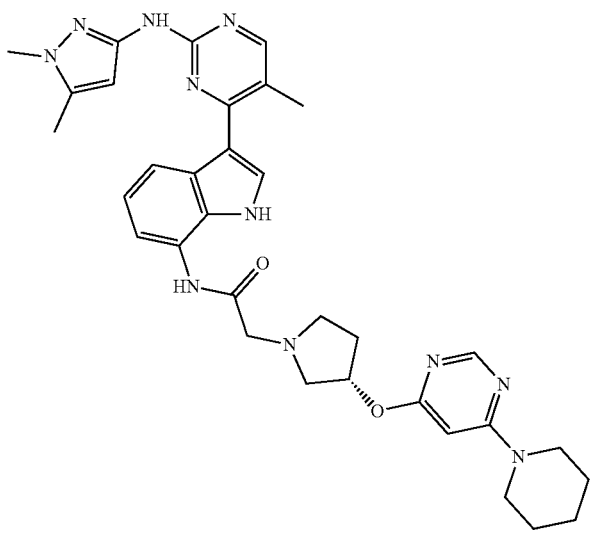 [SMILES: Cc1cnc(Nc2cc(C)n(C)n2)nc1-c1c[nH]c2c(NC(=O)CN3CC[C@H](Oc4cc(N5CCCCC5)ncn4)C3)cccc12] (S)-N-(3-(2-((1,5-dimethyl-1H-pyrazol-3-yl)amino)-5-methylpyrimidin-4-yl)-1H-indol-7-yl)-2-(3-((6-(piperidin-1-yl)pyrimidin-4-yl)oxy)pyrrolidin-1-yl)acetamide 163) 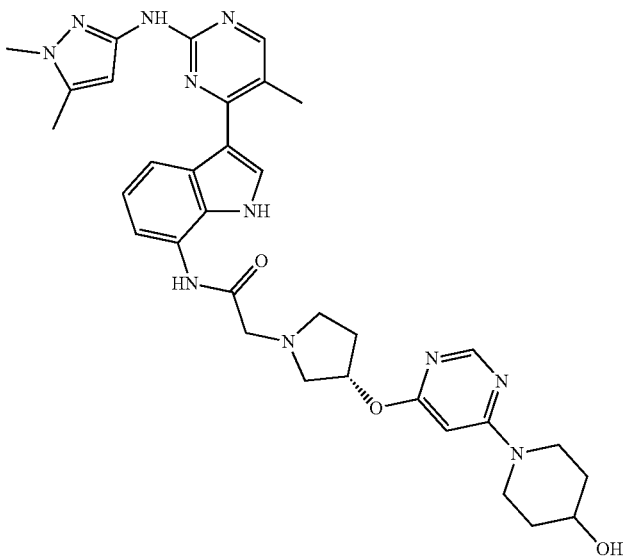 [SMILES: Cc1cnc(Nc2cc(C)n(C)n2)nc1-c1c[nH]c2c(NC(=O)CN3CC[C@H](Oc4cc(N5CCC(O)CC5)ncn4)C3)cccc12] (S)-N-(3-(2-((1,5-dimethyl-1H-pyrazol-3-yl)amino)-5-methylpyrimidin-4-yl)-1H-indol-7-yl)-2-(3-((6-(4-hydroxypiperidin-1-yl)pyrimidin-4-yl)oxy)pyrrolidin-1-yl)acetamide 164) 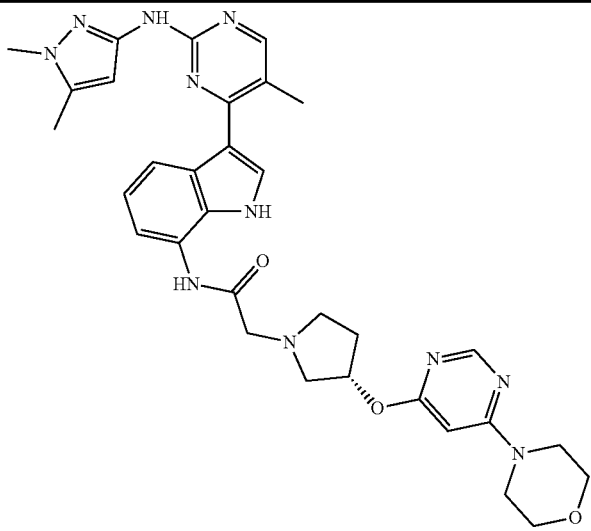
(S)-N-(3-(2-((1,5-dimethyl-1H-pyrazol-3-yl)amino)-5-methylpyrimidin-4-yl)-1H-indol-7-yl)-2-(3-((6-morpholinopyrimidin-4-yl)oxy)pyrrolidin-1-yl)acetamide
165) 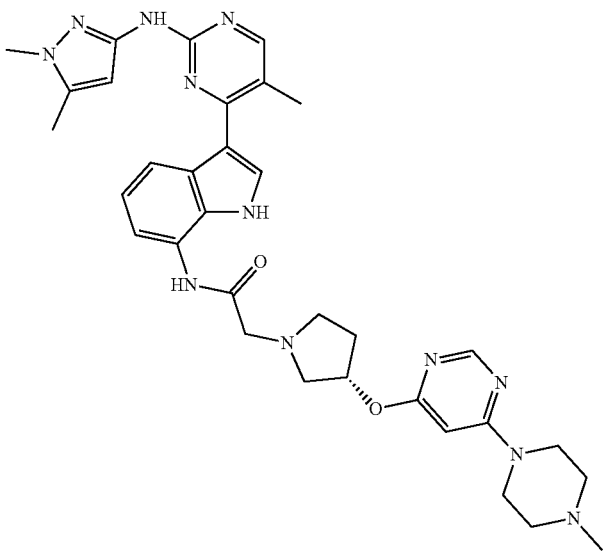
(S)-N-(3-(2-((1,5-dimethyl-1H-pyrazol-3-yl)amino)-5-methylpyrimidin-4-yl)-1H-indol-7-yl)-2-(3-((6-(4-methylpiperazin-1-yl)pyrimidin-4-yl)oxy)pyrrolidin-1-yl)acetamide
166) 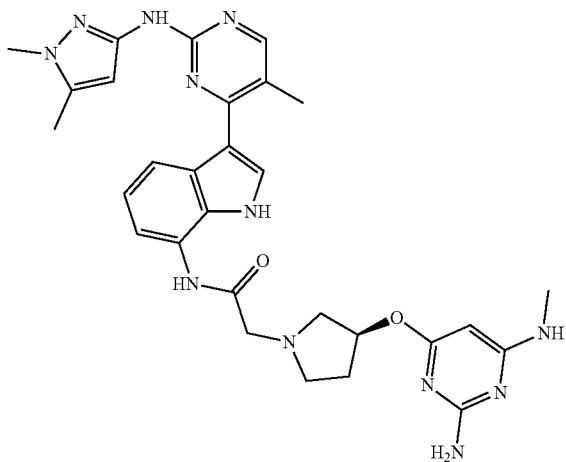
(S)-2-(3-((2-amino-6-(methylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide 167) 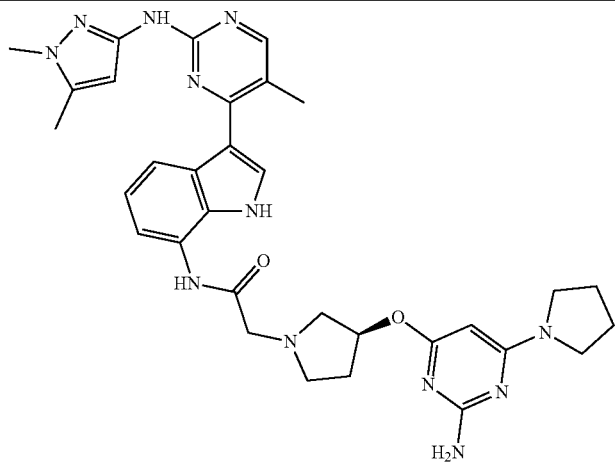
(S)-2-(3-((2-amino-6-(pyrrolidin-1-yl)pyrimidin-4-yl)oxy)pyrrolidin-1-yl)-N-(3-(2-(((1,5-dimethyl-1H-pyrazol-3-yl)amino)-5-methylpyrimidin-4-yl)-1H-indol-7-yl)acetamide
168) 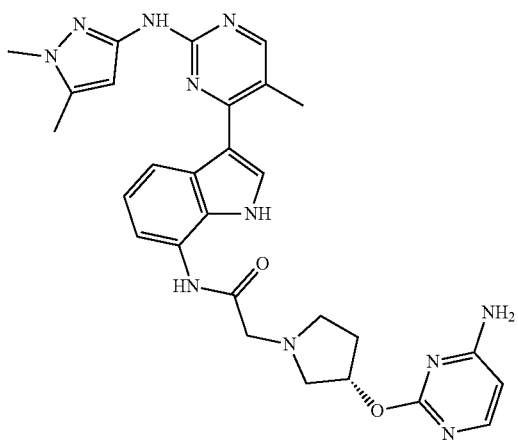 [SMILES: Cc1cnc(Nc2cc(C)n(C)n2)nc1-c1c[nH]c2c(NC(=O)CN3CC[C@H](Oc4nccc(N)n4)C3)cccc12]
(S)-2-(3-((4-aminopyrimidin-2-yl)oxy)pyrrolidin-1-yl)-N-(3-(2-(((1,5-dimethyl-1H-pyrazol-3-yl)amino)-5-methylpyrimidin-4-yl)-1H-indol-7-yl)acetamide
169) 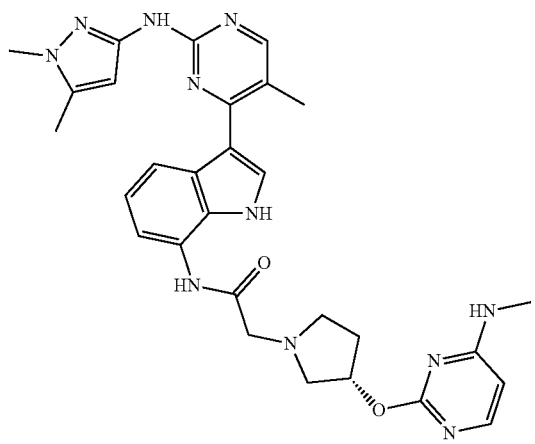
(S)-N-(3-(2-(((1,5-dimethyl-1H-pyrazol-3-yl)amino)-5-methylpyrimidin-4-yl)-1H-indol-7-yl)-2-(3-((4-(methylamino)pyrimidin-2-yl)oxy)pyrrolidin-1-yl)acetamide

| | | |
|---|---|---|
| 170) | 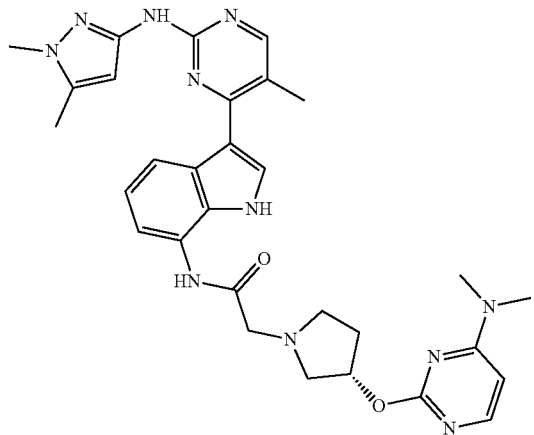 | (S)-N-(3-(2-((1,5-dimethyl-1H-pyrazol-3-yl)amino)-5-methylpyrimidin-4-yl)-1H-indol-7-yl)-2-(3-((4-(dimethylamino)pyrimidin-2-yl)oxy)pyrrolidin-1-yl)acetamide |
| 171) | 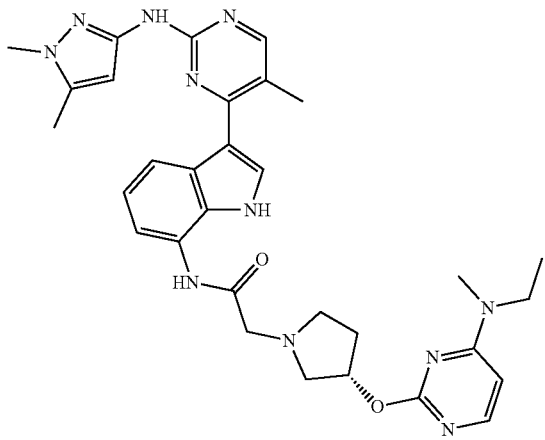 [SMILES: CCN(C)c1ccnc(O[C@H]2CCN(CC(=O)Nc3cccc4c(-c5nc(Nc6cc(C)n(C)n6)ncc5C)c[nH]c34)C2)n1] | (S)-N-(3-(2-((1,5-dimethyl-1H-pyrazol-3-yl)amino)-5-methylpyrimidin-4-yl)-1H-indol-7-yl)-2-(3-((4-(ethyl(methyl)amino)pyrimidin-2-yl)oxy)pyrrolidin-1-yl)acetamide |
| 172) | 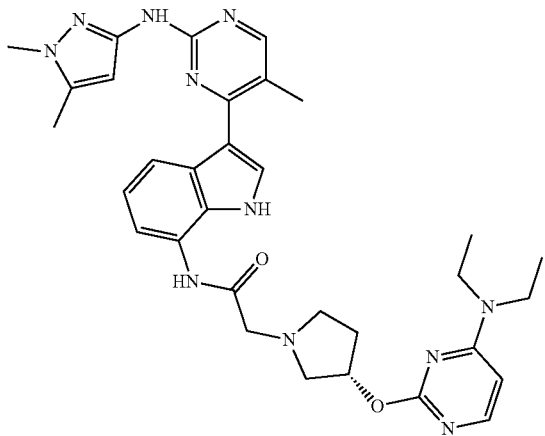 [SMILES: CCN(CC)c1ccnc(O[C@H]2CCN(CC(=O)Nc3cccc4c(-c5nc(Nc6cc(C)n(C)n6)ncc5C)c[nH]c34)C2)n1] | (S)-2-(3-((4-(diethylamino)pyrimidin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |

-continued

173) 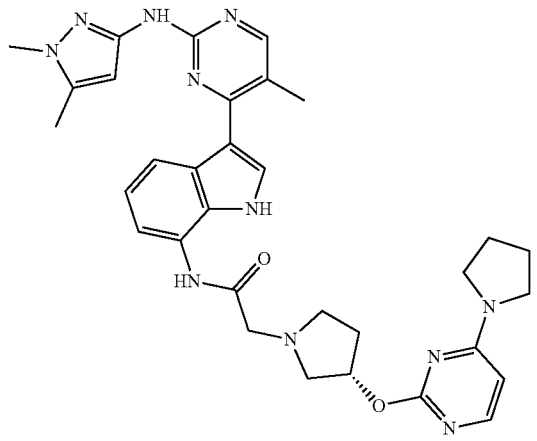 [SMILES: Cc1cnc(Nc2cc(C)n(C)n2)nc1-c1c[nH]c2c(NC(=O)CN3CC[C@H](Oc4nccc(N5CCCC5)n4)C3)cccc12]

(S)-N-(3-(2-((1,5-dimethyl-1H-pyrazol-3-yl)amino)-5-methylpyrimidin-4-yl)-1H-indol-7-yl)-2-(3-((4-(pyrrolidin-1-yl)pyrimidin-2-yl)oxy)pyrrolidin-1-yl)acetamide 174) 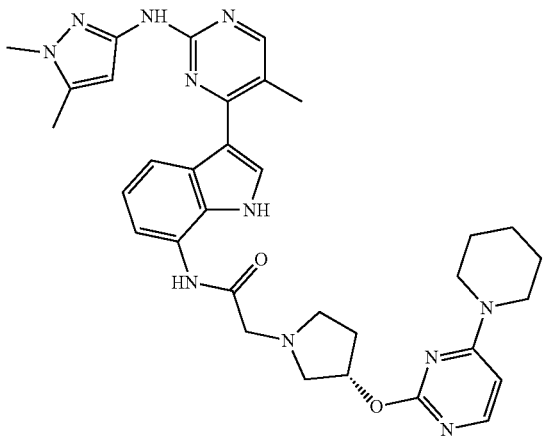 [SMILES: Cc1cnc(Nc2cc(C)n(C)n2)nc1-c1c[nH]c2c(NC(=O)CN3CC[C@H](Oc4nccc(N5CCCCC5)n4)C3)cccc12]

(S)-N-(3-(2-((1,5-dimethyl-1H-pyrazol-3-yl)amino)-5-methylpyrimidin-4-yl)-1H-indol-7-yl)-2-(3-((4-(piperidin-1-yl)pyrimidin-2-yl)oxy)pyrrolidin-1-yl)acetamide 175) 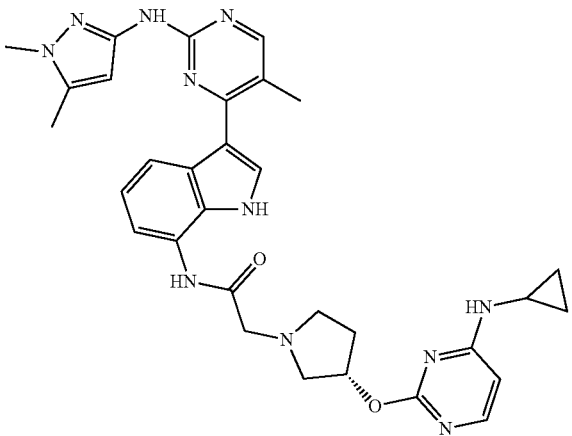 [SMILES: Cc1cnc(Nc2cc(C)n(C)n2)nc1-c1c[nH]c2c(NC(=O)CN3CC[C@H](Oc4nccc(NC5CC5)n4)C3)cccc12]

(S)-2-(3-((4-(cyclopropylamino)pyrimidin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

| | | |
|---|---|---|
| 176) | 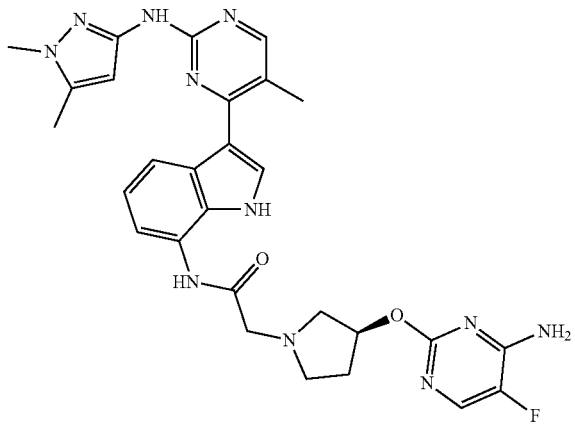 [SMILES: Cc1cnc(Nc2cc(C)n(C)n2)nc1-c1c[nH]c2c(NC(=O)CN3CC[C@H](Oc4ncc(F)c(N)n4)C3)cccc12] | (S)-2-(3-((4-amino-5-fluoropyrimidin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 177) | 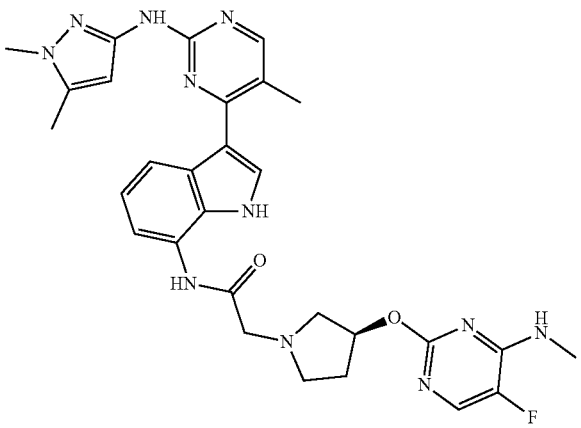 | (S)-N-(3-(2-((1,5-dimethyl-1H-pyrazol-3-yl)amino)-5-methylpyrimidin-4-yl)-1H-indol-7-yl)-2-(3-((5-fluoro-4-(methylamino)pyrimidin-2-yl)oxy)pyrrolidin-1-yl)acetamide |
| 178) | 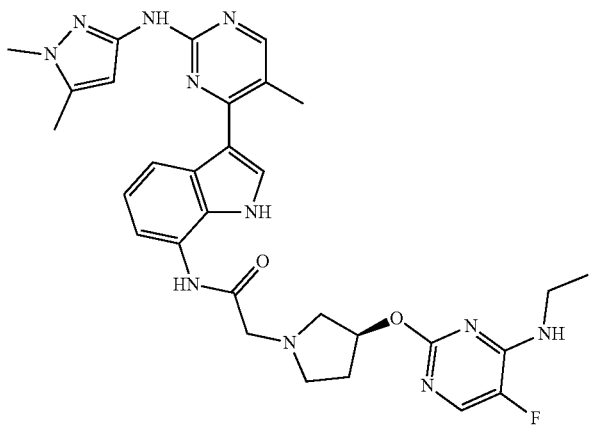 [SMILES: CCNc1nc(O[C@H]2CCN(CC(=O)Nc3cccc4c(-c5nc(Nc6cc(C)n(C)n6)ncc5C)c[nH]c34)C2)ncc1F] | (S)-N-(3-(2-((1,5-dimethyl-1H-pyrazol-3-yl)amino)-5-methylpyrimidin-4-yl)-1H-indol-7-yl)-2-(3-((4-(ethylamino)-5-fluoropyrimidin-2-yl)oxy)pyrrolidin-1-yl)acetamide |

| | | |
|---|---|---|
| 179) | 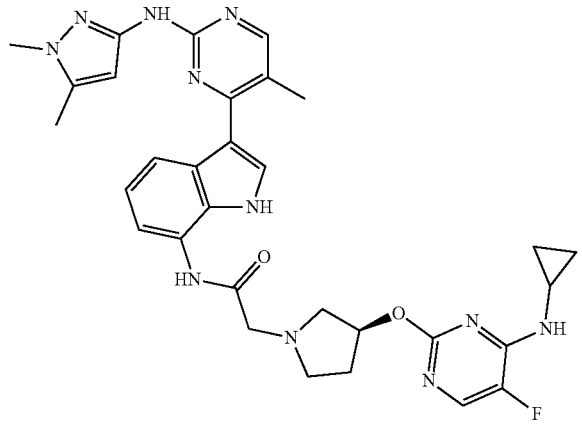 [SMILES: Cc1cnc(Nc2cc(C)n(C)n2)nc1-c1c[nH]c2c(NC(=O)CN3CC[C@H](Oc4ncc(F)c(NC5CC5)n4)C3)cccc12] | (S)-2-(3-((4-(cyclopropylamino)-5-fluoropyrimidin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 180) | 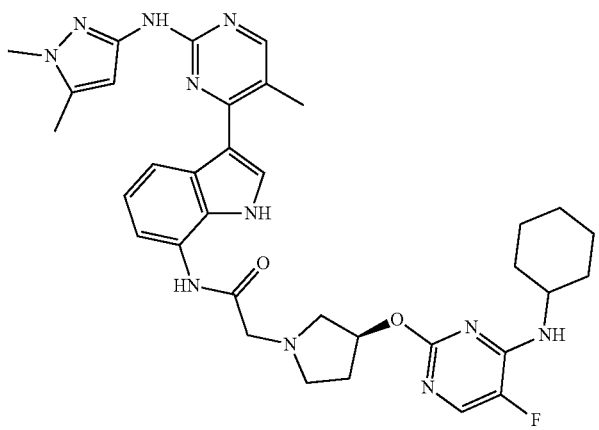 [SMILES: Cc1cnc(Nc2cc(C)n(C)n2)nc1-c1c[nH]c2c(NC(=O)CN3CC[C@H](Oc4ncc(F)c(NC5CCCCC5)n4)C3)cccc12] | (S)-2-(3-((4-(cyclohexylamino)-5-fluoropyrimidin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 181) | 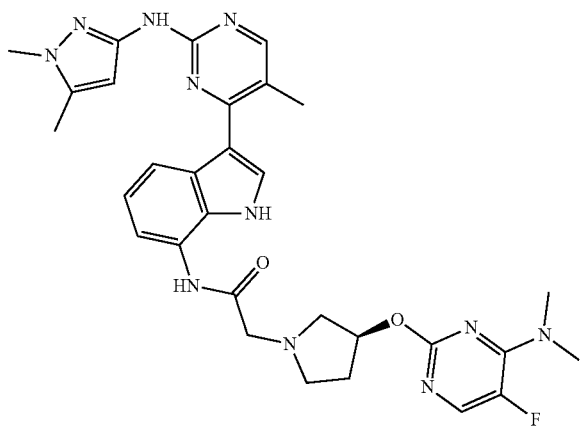 | (S)-N-(3-(2-((1,5-dimethyl-1H-pyrazol-3-yl)amino)-5-methylpyrimidin-4-yl)-1H-indol-7-yl)-2-(3-((4-(dimethylamino)-5-fluoropyrimidin-2-yl)oxy)pyrrolidin-1-yl)acetamide |

-continued

182) 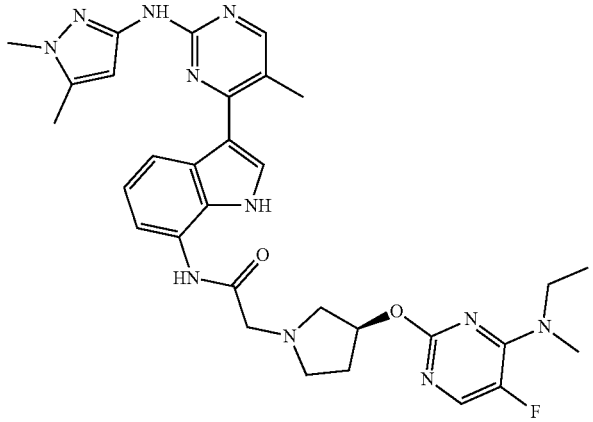 [SMILES: CCN(C)c1nc(O[C@H]2CCN(CC(=O)Nc3cccc4c(-c5nc(Nc6cc(C)n(C)n6)ncc5C)c[nH]c34)C2)ncc1F]

(S)-N-(3-(2-((1,5-dimethyl-1H-pyrazol-3-yl)amino)-5-methylpyrimidin-4-yl)-1H-indol-7-yl)-2-(3-((4-(ethyl(methyl)amino)-5-fluoropyrimidin-2-yl)oxy)pyrrolidin-1-yl)acetamide 183) 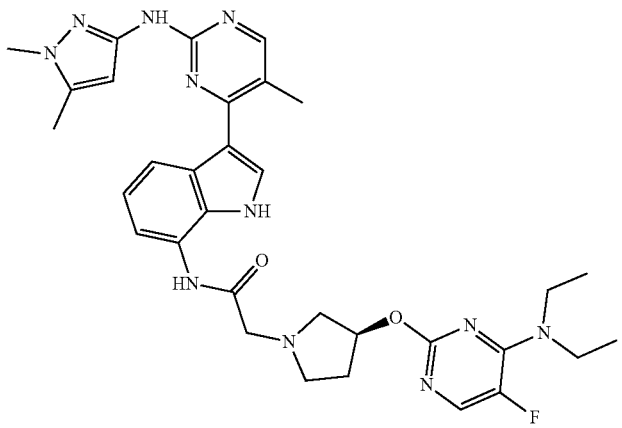 [SMILES: CCN(CC)c1nc(O[C@H]2CCN(CC(=O)Nc3cccc4c(-c5nc(Nc6cc(C)n(C)n6)ncc5C)c[nH]c34)C2)ncc1F]

(S)-2-(3-((4-(diethylamino)-5-fluoropyrimidin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide 184) 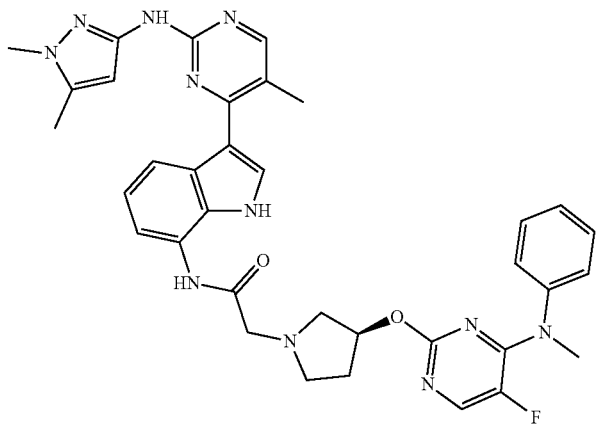 [SMILES: Cc1cnc(Nc2cc(C)n(C)n2)nc1-c1c[nH]c2c(NC(=O)CN3CC[C@H](Oc4ncc(F)c(N(C)c5ccccc5)n4)C3)cccc12]

(S)-N-(3-(2-((1,5-dimethyl-1H-pyrazol-3-yl)amino)-5-methylpyrimidin-4-yl)-1H-indol-7-yl)-2-(3-((5-fluoro-4-(methyl(phenyl)amino)pyrimidin-2-yl)oxy)pyrrolidin-1-yl)acetamide 185) 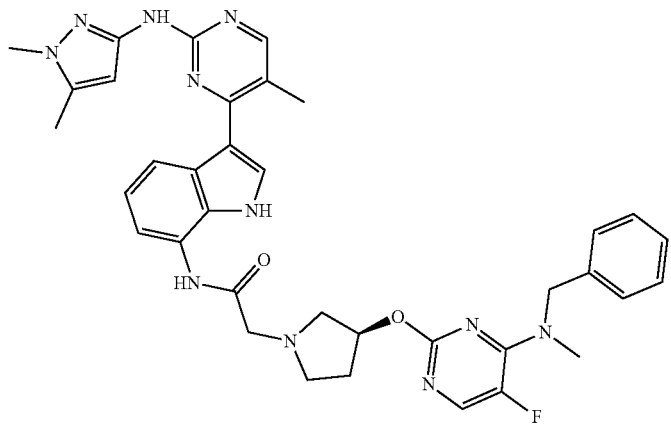 [SMILES: Cc1cnc(Nc2cc(C)n(C)n2)nc1-c1c[nH]c2c(NC(=O)CN3CC[C@H](Oc4ncc(F)c(N(C)Cc5ccccc5)n4)C3)cccc12]

(S)-2-(3-((4-(benzyl(methyl)amino)-5-fluoropyrimidin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide 186) 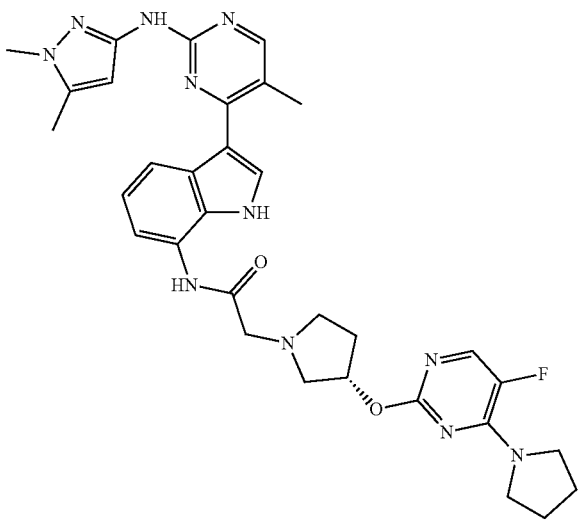 [SMILES: Cc1cnc(Nc2cc(C)n(C)n2)nc1-c1c[nH]c2c(NC(=O)CN3CC[C@H](Oc4ncc(F)c(N5CCCC5)n4)C3)cccc12]

(S)-N-(3-(2-((1,5-dimethyl-1H-pyrazol-3-yl)amino)-5-methylpyrimidin-4-yl)-1H-indol-7-yl)-2-(3-((5-fluoro-4-(pyrrolidin-1-yl)pyrimidin-2-yl)oxy)pyrrolidin-1-yl)acetamide 187) 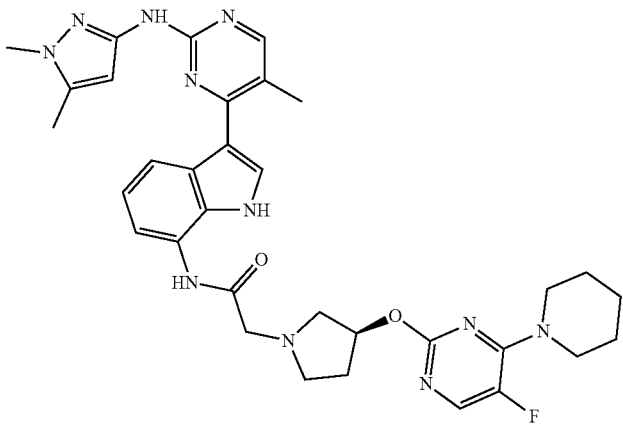 [SMILES: Cc1cnc(Nc2cc(C)n(C)n2)nc1-c1c[nH]c2c(NC(=O)CN3CC[C@H](Oc4ncc(F)c(N5CCCCC5)n4)C3)cccc12]

(S)-N-(3-(2-((1,5-dimethyl-1H-pyrazol-3-yl)amino)-5-methylpyrimidin-4-yl)-1H-indol-7-yl)-2-(3-((5-fluoro-4-(piperidin-1-yl)pyrimidin-2-yl)oxy)pyrrolidin-1-yl)acetamide 188) 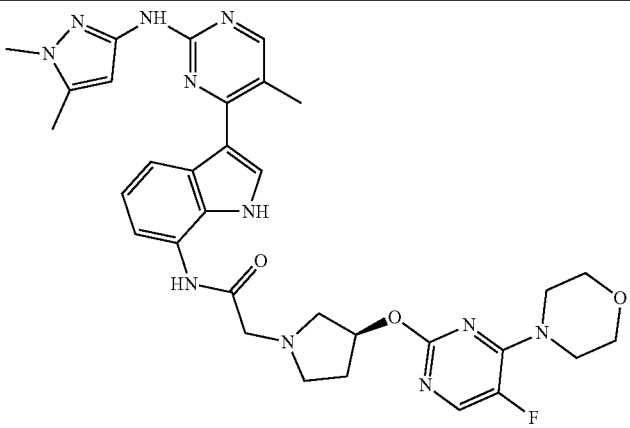

(S)-N-(3-(2-((1,5-dimethyl-1H-pyrazol-3-yl)amino)-5-methylpyrimidin-4-yl)-1H-indol-7-yl)-2-(3-((5-fluoro-4-morpholinopyrimidin-2-yl)oxy)pyrrolidin-1-yl)acetamide 189) 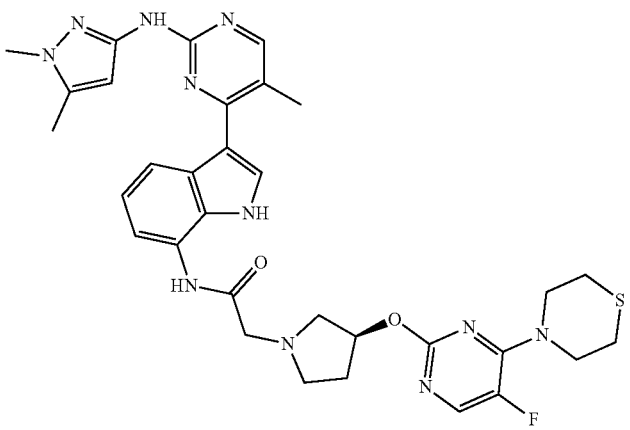 [SMILES: Cc1cnc(Nc2cc(C)n(C)n2)nc1-c1c[nH]c2c(NC(=O)CN3CC[C@H](Oc4ncc(F)c(N5CCSCC5)n4)C3)cccc12]

(S)-N-(3-(2-((1,5-dimethyl-1H-pyrazol-3-yl)amino)-5-methylpyrimidin-4-yl)-1H-indol-7-yl)-2-(3-((5-fluoro-4-thiomorpholinopyrimidin-2-yl)oxy)pyrrolidin-1-yl)acetamide 190) 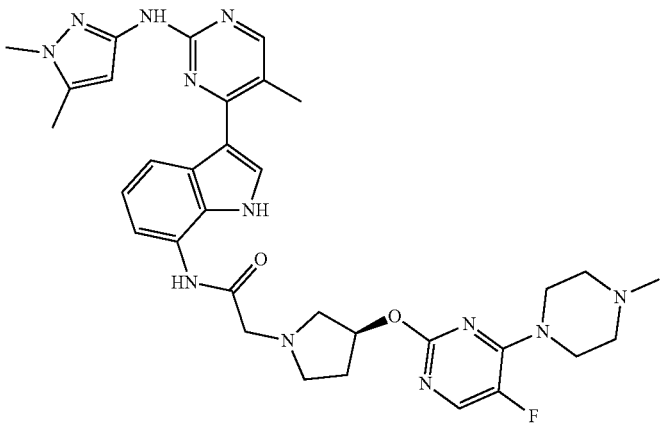

(S)-N-(3-(2-((1,5-dimethyl-1H-pyrazol-3-yl)amino)-5-methylpyrimidin-4-yl)-1H-indol-7-yl)-2-(3-((5-fluoro-4-(4-methylpiperazin-1-yl)pyrimidin-2-yl)oxy)pyrrolidin-1-yl)acetamide 191) 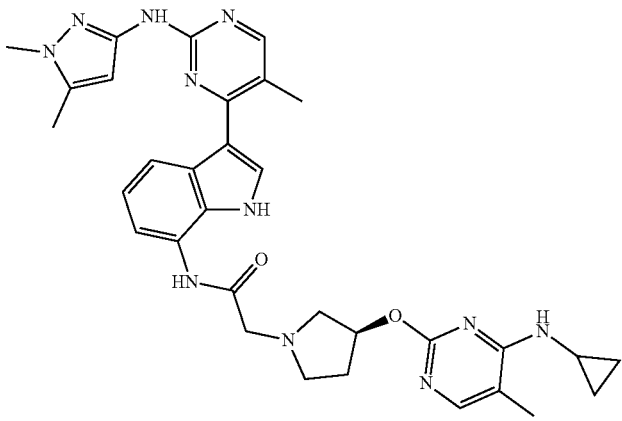 [SMILES: Cc1cnc(O[C@H]2CCN(CC(=O)Nc3cccc4c(-c5nc(Nc6cc(C)n(C)n6)ncc5C)c[nH]c34)C2)nc1NC1CC1]
(S)-2-(3-((4-(cyclopropylamino)-5-methylpyrimidin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide
192) 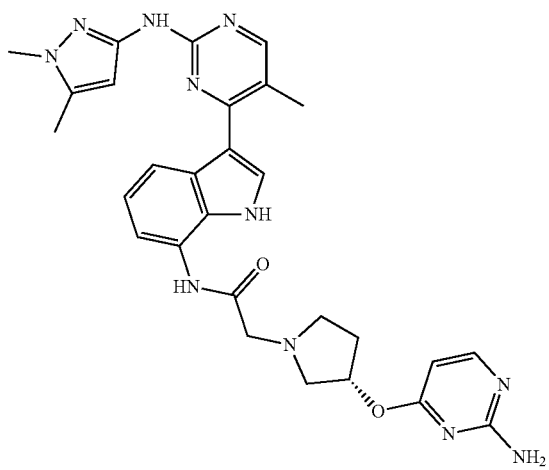 [SMILES: Cc1cnc(Nc2cc(C)n(C)n2)nc1-c1c[nH]c2c(NC(=O)CN3CC[C@H](Oc4ccnc(N)n4)C3)cccc12]
(S)-2-(3-((2-aminopyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide
193) 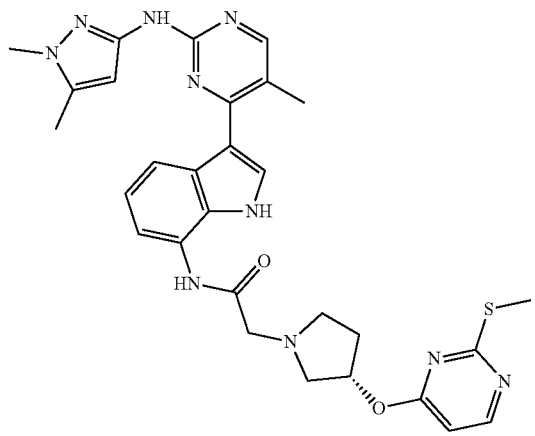
(S)-N-(3-(2-((1,5-dimethyl-1H-pyrazol-3-yl)amino)-5-methylpyrimidin-4-yl)-1H-indol-7-yl)-2-(3-((2-(methylthio)pyrimidin-4-yl)oxy)pyrrolidin-1-yl)acetamide

| | | |
|---|---|---|
| 194) | 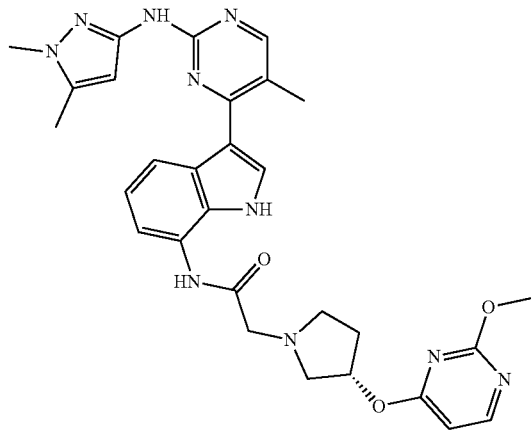 | (S)-N-(3-(2-((1,5-dimethyl-1H-pyrazol-3-yl)amino)-5-methylpyrimidin-4-yl)-1H-indol-7-yl)-2-(3-((2-methoxypyrimidin-4-yl)oxy)pyrrolidin-1-yl)acetamide |
| 195) | 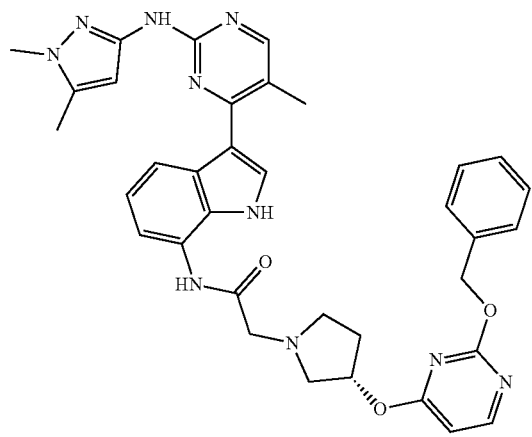 [SMILES: Cc1cnc(Nc2cc(C)n(C)n2)nc1-c1c[nH]c2c(NC(=O)CN3CC[C@H](Oc4ccnc(OCc5ccccc5)n4)C3)cccc12] | (S)-2-(3-((2-(benzyloxy)pyrimidin-4-yl)oxy)pyrrolidin-1-yl)-N-(3-(2-(((1,5-dimethyl-1H-pyrazol-3-yl)amino)-5-methylpyrimidin-4-yl)-1H-indol-7-yl)acetamide |
| 196) | 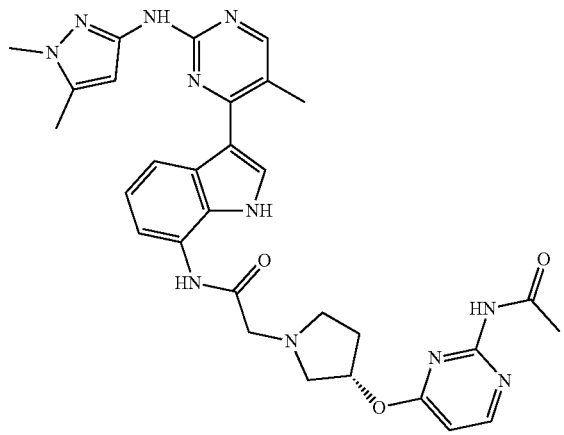 [SMILES: CC(=O)Nc1nccc(O[C@H]2CCN(CC(=O)Nc3cccc4c(-c5nc(Nc6cc(C)n(C)n6)ncc5C)c[nH]c34)C2)n1] | (S)-2-(3-((2-acetamidopyrimidin-4-yl)oxy)pyrrolidin-1-yl)-N-(3-(2-(((1,5-dimethyl-1H-pyrazol-3-yl)amino)-5-methylpyrimidin-4-yl)-1H-indol-7-yl)acetamide |

197) 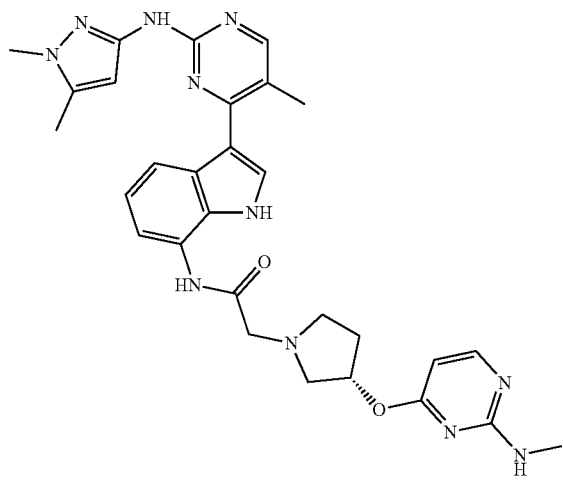 (S)-N-(3-(2-((1,5-dimethyl-1H-pyrazol-3-yl)amino)-5-methylpyrimidin-4-yl)-1H-indol-7-yl)-2-(3-((2-(methylamino)pyrimidin-4-yl)oxy)pyrrolidin-1-yl)acetamide 198) 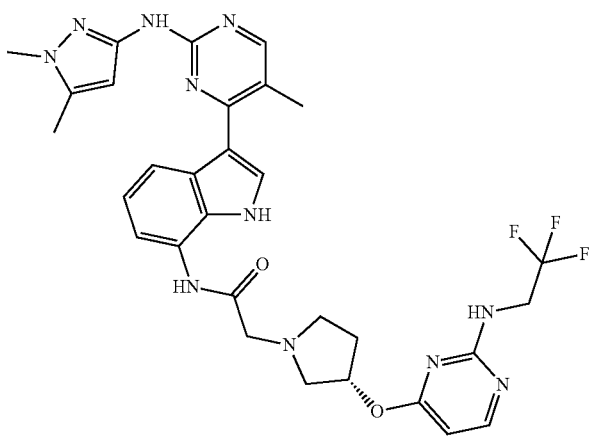 [SMILES: Cc1cnc(Nc2cc(C)n(C)n2)nc1-c1c[nH]c2c(NC(=O)CN3CC[C@H](Oc4ccnc(NCC(F)(F)F)n4)C3)cccc12] (S)-N-(3-(2-((1,5-dimethyl-1H-pyrazol-3-yl)amino)-5-methylpyrimidin-4-yl)-1H-indol-7-yl)-2-(3-((2-((2,2,2-trifluoroethyl)amino)pyrimidin-4-yl)oxy)pyrrolidin-1-yl)acetamide 199) 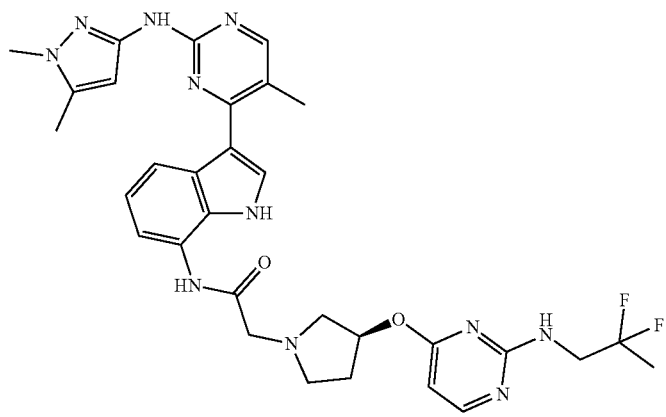 [SMILES: Cc1cnc(Nc2cc(C)n(C)n2)nc1-c1c[nH]c2c(NC(=O)CN3CC[C@H](Oc4ccnc(NCC(C)(F)F)n4)C3)cccc12] (S)-2-(3-((2-((2,2-difluoropropyl)amino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

| | | |
|---|---|---|
| 200) | 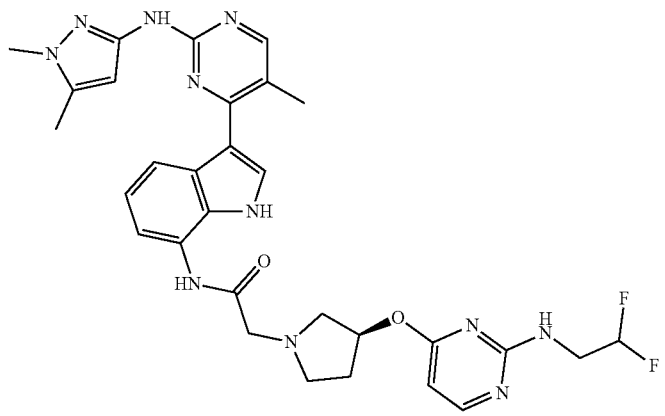 [SMILES: Cc1cnc(Nc2cc(C)n(C)n2)nc1-c1c[nH]c2c(NC(=O)CN3CC[C@H](Oc4ccnc(NCC(F)F)n4)C3)cccc12] | (S)-2-(3-((2-((2,2-difluoroethyl)amino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 201) | 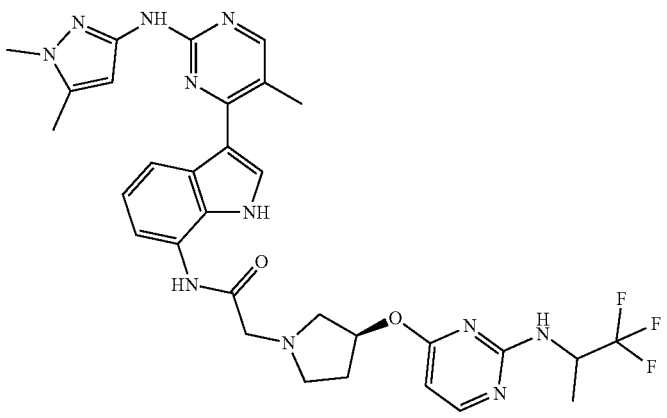 [SMILES: Cc1cnc(Nc2cc(C)n(C)n2)nc1-c1c[nH]c2c(NC(=O)CN3CC[C@H](Oc4ccnc(NC(C)C(F)(F)F)n4)C3)cccc12] | N-(3-(2-((1,5-dimethyl-1H-pyrazol-3-yl)amino)-5-methylpyrimidin-4-yl)-1H-indol-7-yl)-2-((3S)-3-((2-((1,1,1-trifluoropropan-2-yl)amino)pyrimidin-4-yl)oxy)pyrrolidin-1-yl)acetamide |
| 202) | 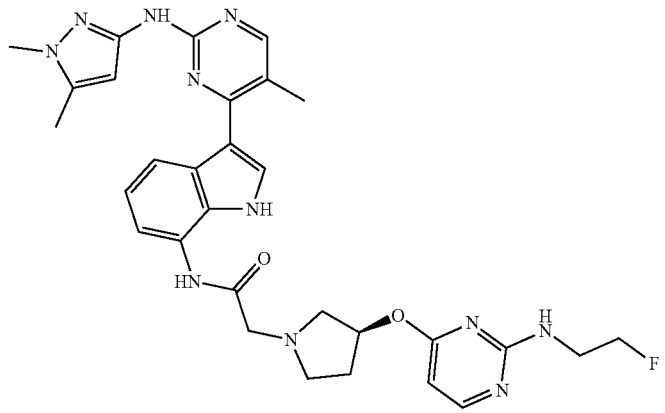 [SMILES: Cc1cnc(Nc2cc(C)n(C)n2)nc1-c1c[nH]c2c(NC(=O)CN3CC[C@H](Oc4ccnc(NCCF)n4)C3)cccc12] | (S)-N-(3-(2-((1,5-dimethyl-1H-pyrazol-3-yl)amino)-5-methylpyrimidin-4-yl)-1H-indol-7-yl)-2-(3-((2-((2-fluoroethyl)amino)pyrimidin-4-yl)oxy)pyrrolidin-1-yl)acetamide |

-continued
203) 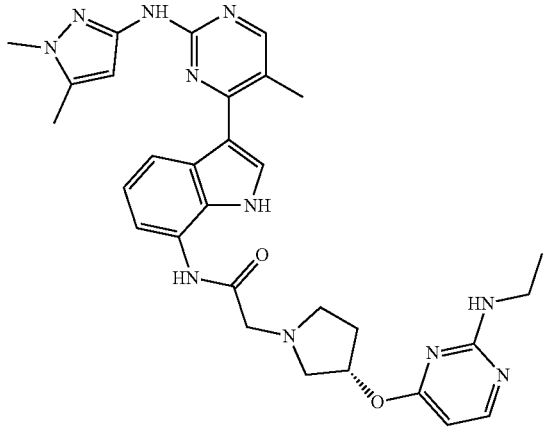 [SMILES: CCNc1nccc(O[C@H]2CCN(CC(=O)Nc3cccc4c(-c5nc(Nc6cc(C)n(C)n6)ncc5C)c[nH]c34)C2)n1]
(S)-N-(3-(2-((1,5-dimethyl-1H-pyrazol-3-yl)amino)-5-methylpyrimidin-4-yl)-1H-indol-7-yl)-2-(3-((2-(ethylamino)pyrimidin-4-yl)oxy)pyrrolidin-1-yl)acetamide
204) 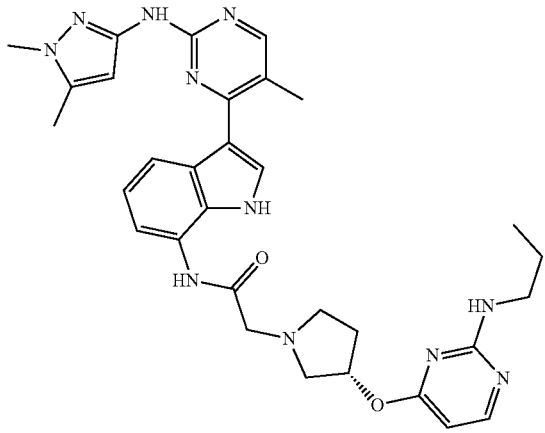 [SMILES: CCCNc1nccc(O[C@H]2CCN(CC(=O)Nc3cccc4c(-c5nc(Nc6cc(C)n(C)n6)ncc5C)c[nH]c34)C2)n1]
(S)-N-(3-(2-((1,5-dimethyl-1H-pyrazol-3-yl)amino)-5-methylpyrimidin-4-yl)-1H-indol-7-yl)-2-(3-((2-(propylamino)pyrimidin-4-yl)oxy)pyrrolidin-1-yl)acetamide
205) 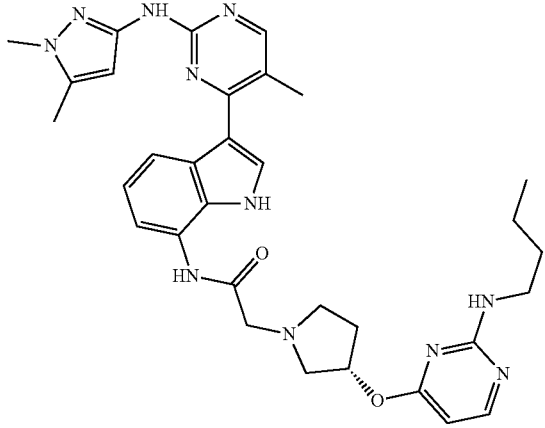 [SMILES: CCCCNc1nccc(O[C@H]2CCN(CC(=O)Nc3cccc4c(-c5nc(Nc6cc(C)n(C)n6)ncc5C)c[nH]c34)C2)n1]
(S)-2-(3-((2-(butylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

| | | |
|---|---|---|
| 206) | 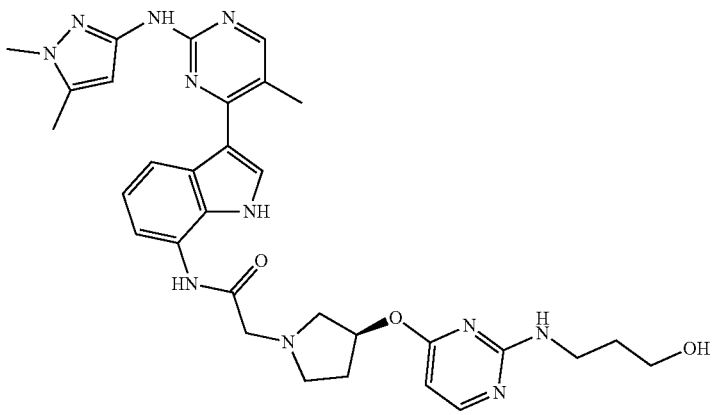 [SMILES: Cc1cnc(Nc2cc(C)n(C)n2)nc1-c1c[nH]c2c(NC(=O)CN3CC[C@H](Oc4ccnc(NCCCO)n4)C3)cccc12] | (S)-N-(3-(2-((1,5-dimethyl-1H-pyrazol-3-yl)amino)-5-methylpyrimidin-4-yl)-1H-indol-7-yl)-2-(3-((2-((3-hydroxypropyl)amino)pyrimidin-4-yl)oxy)pyrrolidin-1-yl)acetamide |
| 207) | 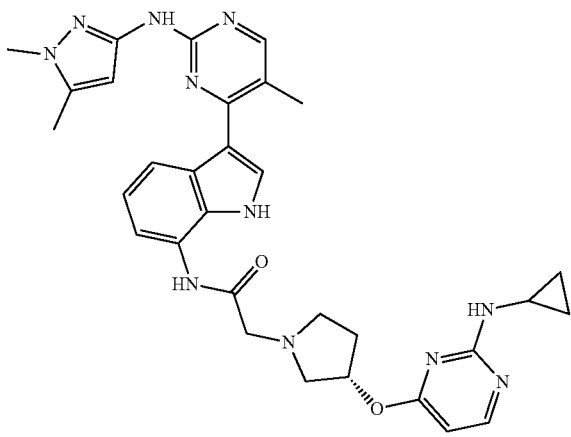 [SMILES: Cc1cnc(Nc2cc(C)n(C)n2)nc1-c1c[nH]c2c(NC(=O)CN3CC[C@H](Oc4ccnc(NC5CC5)n4)C3)cccc12] | (S)-2-(3-((2-(cyclopropylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 208) | 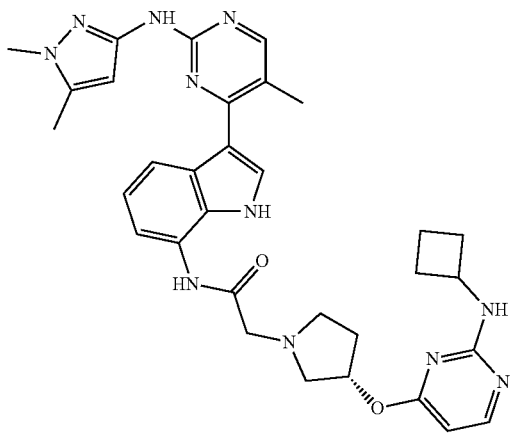 [SMILES: Cc1cnc(Nc2cc(C)n(C)n2)nc1-c1c[nH]c2c(NC(=O)CN3CC[C@H](Oc4ccnc(NC5CCC5)n4)C3)cccc12] | (S)-2-(3-((2-(cyclobutylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |

| | | |
|---|---|---|
| 209) | 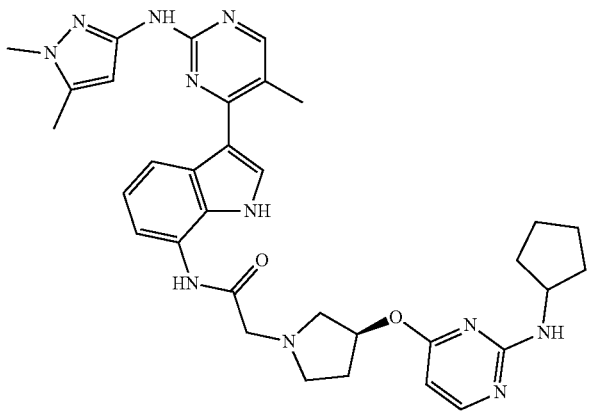 [SMILES: Cc1cnc(Nc2cc(C)n(C)n2)nc1-c1c[nH]c2c(NC(=O)CN3CC[C@H](Oc4ccnc(NC5CCCC5)n4)C3)cccc12] | (S)-2-(3-((2-(cyclopentylamino)pyrimidin-4-yl)oxy)pyrrolidin-1-yl)-N-(3-(2-(((1,5-dimethyl-1H-pyrazol-3-yl)amino)-5-methylpyrimidin-4-yl)-1H-indol-7-yl)acetamide |
| 210) | 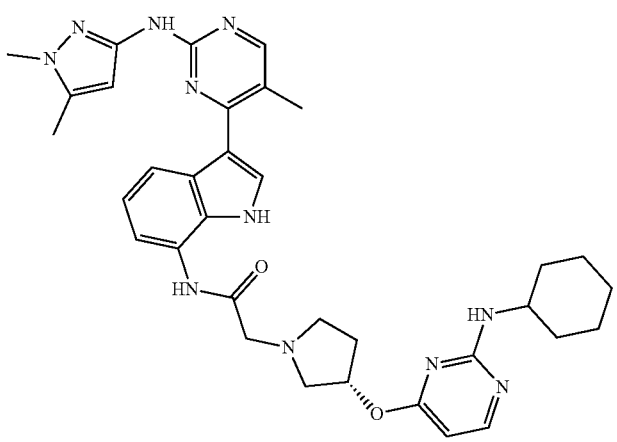 [SMILES: Cc1cnc(Nc2cc(C)n(C)n2)nc1-c1c[nH]c2c(NC(=O)CN3CC[C@H](Oc4ccnc(NC5CCCCC5)n4)C3)cccc12] | (S)-2-(3-((2-(cyclohexylamino)pyrimidin-4-yl)oxy)pyrrolidin-1-yl)-N-(3-(2-(((1,5-dimethyl-1H-pyrazol-3-yl)amino)-5-methylpyrimidin-4-yl)-1H-indol-7-yl)acetamide |
| 211) | 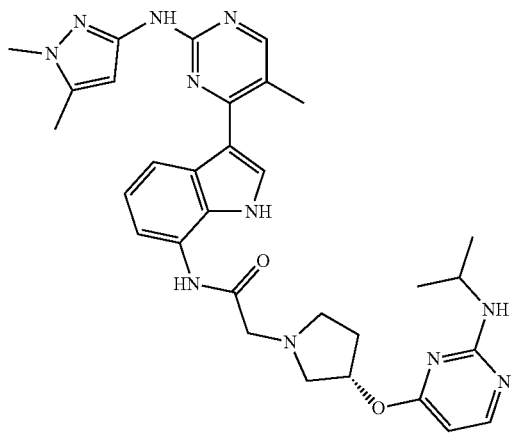 [SMILES: Cc1cnc(Nc2cc(C)n(C)n2)nc1-c1c[nH]c2c(NC(=O)CN3CC[C@H](Oc4ccnc(NC(C)C)n4)C3)cccc12] | (S)-N-(3-(2-(((1,5-dimethyl-1H-pyrazol-3-yl)amino)-5-methylpyrimidin-4-yl)-1H-indol-7-yl)-2-(3-((2-(isopropylamino)pyrimidin-4-yl)oxy)pyrrolidin-1-yl)acetamide |

212) 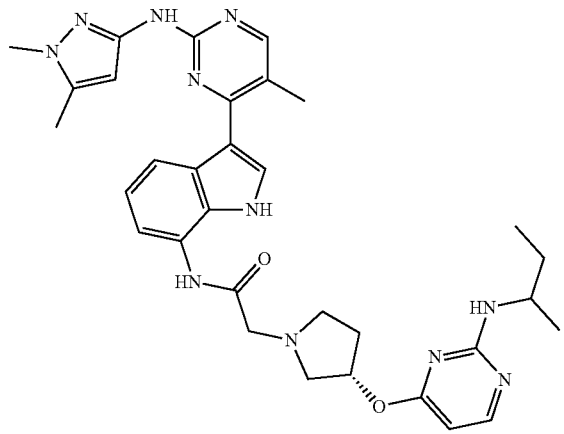 [SMILES: CCC(C)Nc1nccc(O[C@H]2CCN(CC(=O)Nc3cccc4c(-c5nc(Nc6cc(C)n(C)n6)ncc5C)c[nH]c34)C2)n1]

2-((3S)-3-((2-(sec-butylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide 213) 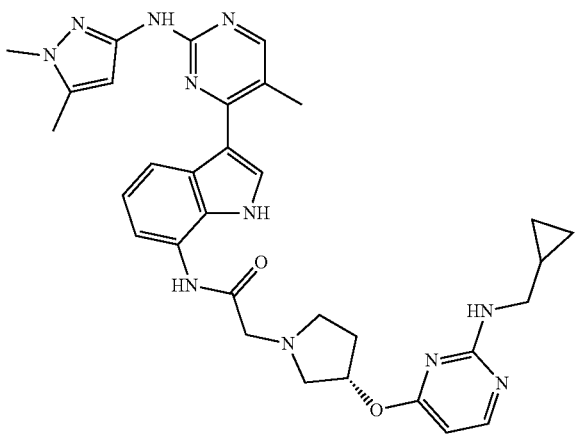 [SMILES: Cc1cnc(Nc2cc(C)n(C)n2)nc1-c1c[nH]c2c(NC(=O)CN3CC[C@H](Oc4ccnc(NCC5CC5)n4)C3)cccc12]

(S)-2-(3-((2-((cyclopropylmethyl)amino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide 214) 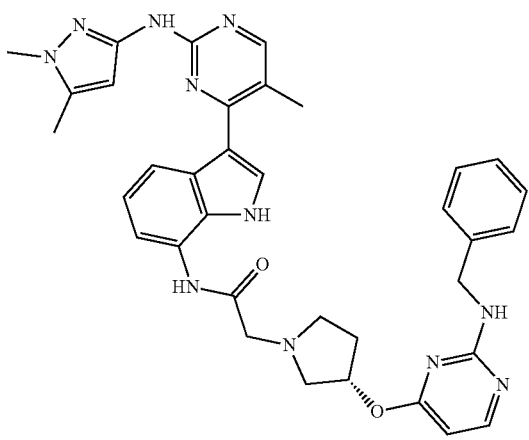 [SMILES: Cc1cnc(Nc2cc(C)n(C)n2)nc1-c1c[nH]c2c(NC(=O)CN3CC[C@H](Oc4ccnc(NCc5ccccc5)n4)C3)cccc12]

(S)-2-(3-((2-(benzylamino)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide

| | | |
|---|---|---|
| 215) | 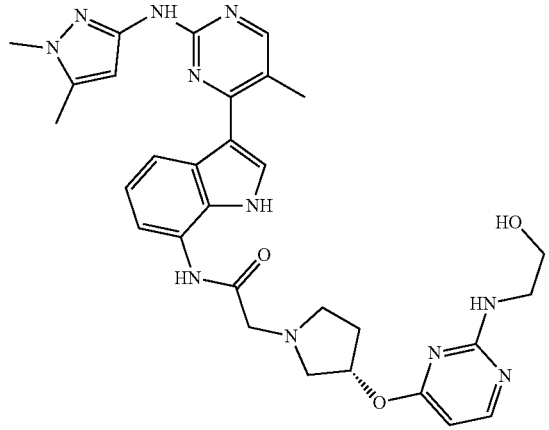 [SMILES: Cc1cnc(Nc2cc(C)n(C)n2)nc1-c1c[nH]c2c(NC(=O)CN3CC[C@H](Oc4ccnc(NCCO)n4)C3)cccc12] | (S)-N-(3-(2-((1,5-dimethyl-1H-pyrazol-3-yl)amino)-5-methylpyrimidin-4-yl)-1H-indol-7-yl)-2-(3-((2-((2-hydroxyethyl)amino)pyrimidin-4-yl)oxy)pyrrolidin-1-yl)acetamide |
| 216) | 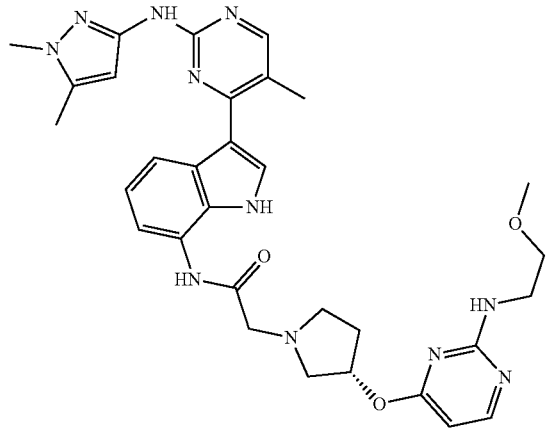 [SMILES: COCCNc1nccc(O[C@H]2CCN(CC(=O)Nc3cccc4c(-c5nc(Nc6cc(C)n(C)n6)ncc5C)c[nH]c34)C2)n1] | (S)-N-(3-(2-((1,5-dimethyl-1H-pyrazol-3-yl)amino)-5-methylpyrimidin-4-yl)-1H-indol-7-yl)-2-(3-((2-((2-methoxyethyl)amino)pyrimidin-4-yl)oxy)pyrrolidin-1-yl)acetamide |
| 217) | 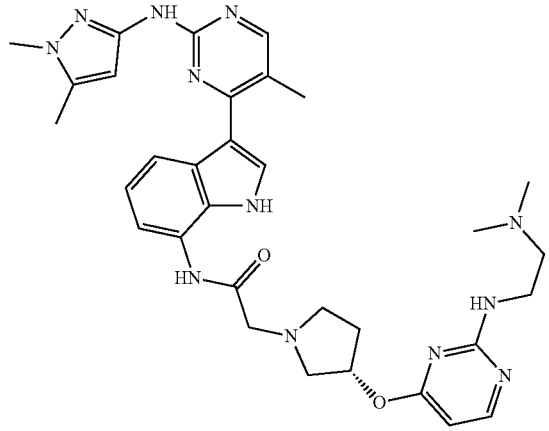 [SMILES: Cc1cnc(Nc2cc(C)n(C)n2)nc1-c1c[nH]c2c(NC(=O)CN3CC[C@H](Oc4ccnc(NCCN(C)C)n4)C3)cccc12] | (S)-N-(3-(2-((1,5-dimethyl-1H-pyrazol-3-yl)amino)-5-methylpyrimidin-4-yl)-1H-indol-7-yl)-2-(3-((2-((2-(dimethylamino)ethyl)amino)pyrimidin-4-yl)oxy)pyrrolidin-1-yl)acetamide |

| | | |
|---|---|---|
| 218) | 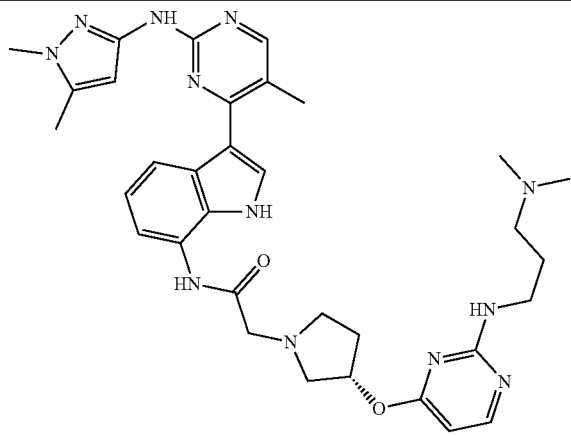 | (S)-N-(3-(2-((1,5-dimethyl-1H-pyrazol-3-yl)amino)-5-methylpyrimidin-4-yl)-1H-indol-7-yl)-2-(3-((2-((3-(dimethylamino)propyl)amino)pyrimidin-4-yl)oxy)pyrrolidin-1-yl)acetamide |
| 219) | 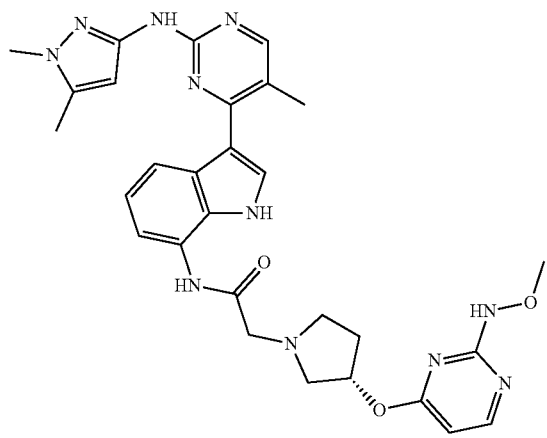 | (S)-N-(3-(2-((1,5-dimethyl-1H-pyrazol-3-yl)amino)-5-methylpyrimidin-4-yl)-1H-indol-7-yl)-2-(3-((2-(methoxyamino)pyrimidin-4-yl)oxy)pyrrolidin-1-yl)acetamide |
| 220) | 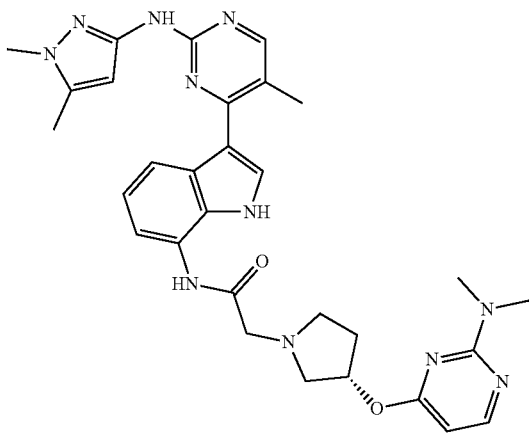 | (S)-N-(3-(2-((1,5-dimethyl-1H-pyrazol-3-yl)amino)-5-methylpyrimidin-4-yl)-1H-indol-7-yl)-2-(3-((2-(dimethylamino)pyrimidin-4-yl)oxy)pyrrolidin-1-yl)acetamide |

| | | |
|---|---|---|
| 221) | 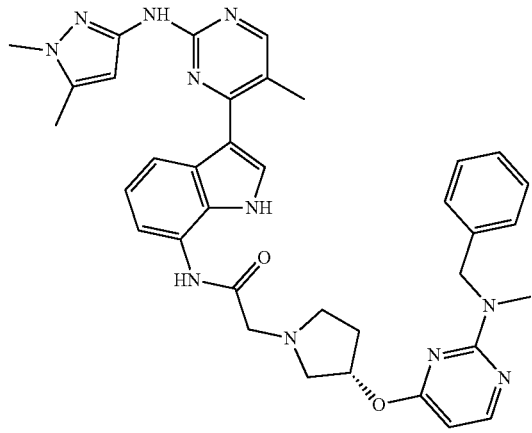 | (S)-2-(3-((2-(benzyl(methyl)amino)pyrimidin-4-yl)oxy)pyrrolidin-1-yl)-N-(3-(2-(((1,5-dimethyl-1H-pyrazol-3-yl)amino)-5-methylpyrimidin-4-yl)-1H-indol-7-yl)acetamide |
| 222) | 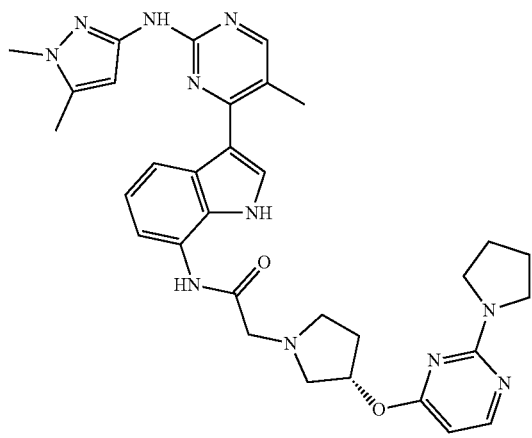 [SMILES: Cc1cnc(Nc2cc(C)n(C)n2)nc1-c1c[nH]c2c(NC(=O)CN3CC[C@H](Oc4ccnc(N5CCCC5)n4)C3)cccc12] | (S)-N-(3-(2-(((1,5-dimethyl-1H-pyrazol-3-yl)amino)-5-methylpyrimidin-4-yl)-1H-indol-7-yl)-2-(3-((2-(pyrrolidin-1-yl)pyrimidin-4-yl)oxy)pyrrolidin-1-yl)acetamide |
| 223) | 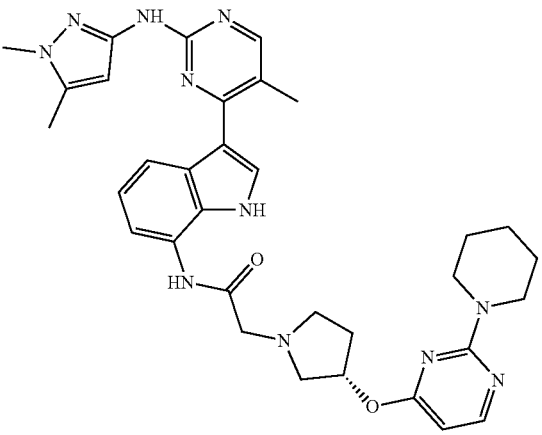 | (S)-N-(3-(2-(((1,5-dimethyl-1H-pyrazol-3-yl)amino)-5-methylpyrimidin-4-yl)-1H-indol-7-yl)-2-(3-((2-(piperidin-1-yl)pyrimidin-4-yl)oxy)pyrrolidin-1-yl)acetamide. |

| | | |
|---|---|---|
| 224) | 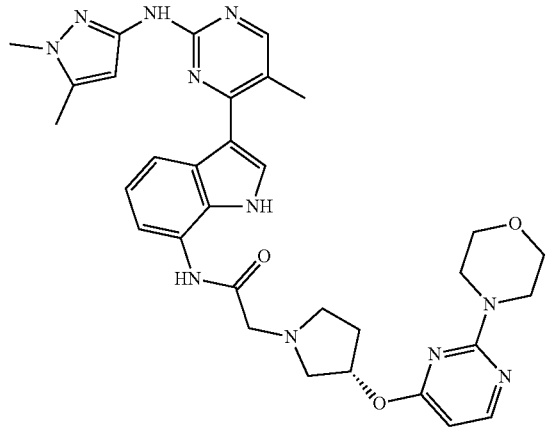 [SMILES: Cc1cnc(Nc2cc(C)n(C)n2)nc1-c1c[nH]c2c(NC(=O)CN3CC[C@H](Oc4ccnc(N5CCOCC5)n4)C3)cccc12] | (S)-N-(3-(2-((1,5-dimethyl-1H-pyrazol-3-yl)amino)-5-methylpyrimidin-4-yl)-1H-indol-7-yl)-2-(3-((2-morpholinopyrimidin-4-yl)oxy)pyrrolidin-1-yl)acetamide |
| 225) | 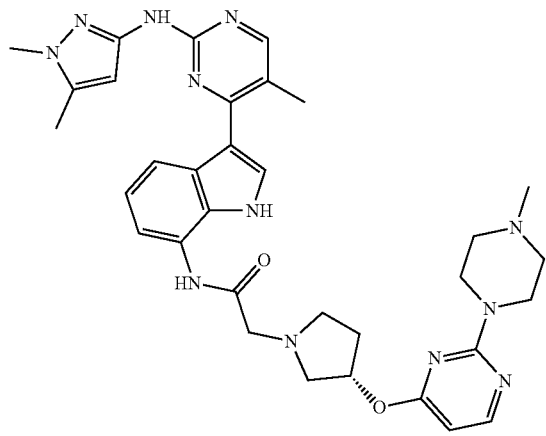 [SMILES: Cc1cnc(Nc2cc(C)n(C)n2)nc1-c1c[nH]c2c(NC(=O)CN3CC[C@H](Oc4ccnc(N5CCN(C)CC5)n4)C3)cccc12] | (S)-N-(3-(2-((1,5-dimethyl-1H-pyrazol-3-yl)amino)-5-methylpyrimidin-4-yl)-1H-indol-7-yl)-2-(3-((2-(4-methylpiperazin-1-yl)pyrimidin-4-yl)oxy)pyrrolidin-1-yl)acetamide |
| 226) | 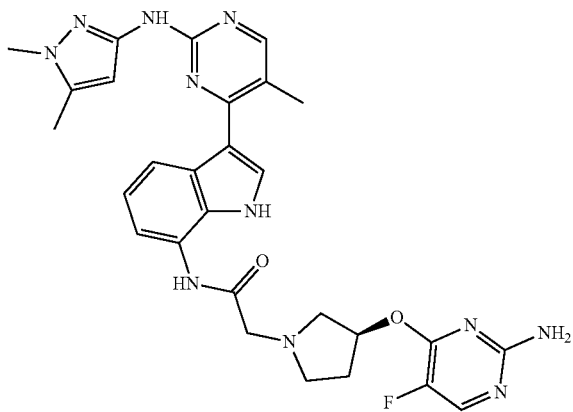 [SMILES: Cc1cnc(Nc2cc(C)n(C)n2)nc1-c1c[nH]c2c(NC(=O)CN3CC[C@H](Oc4nc(N)ncc4F)C3)cccc12] | (S)-2-(3-((2-amino-5-fluoropyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |

| | | |
|---|---|---|
| 227) | 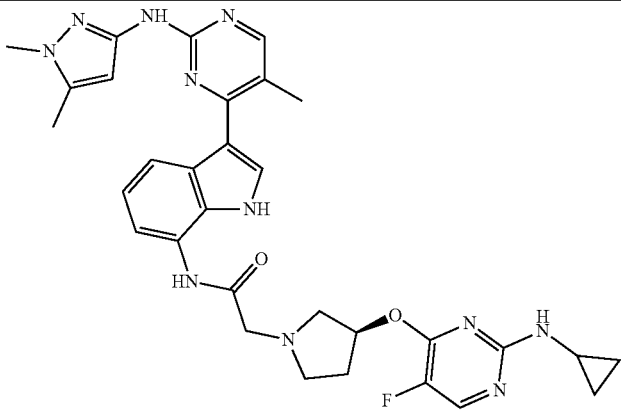 | (S)-2-(3-((2-(cyclopropylamino)-5-fluoropyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 228) | 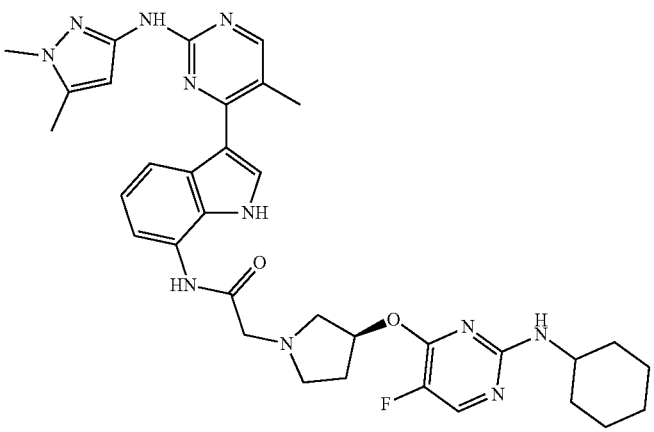 [SMILES: Cc1cnc(Nc2cc(C)n(C)n2)nc1-c1c[nH]c2c(NC(=O)CN3CC[C@H](Oc4nc(NC5CCCCC5)ncc4F)C3)cccc12] | (S)-2-(3-((2-(cyclohexylamino)-5-fluoropyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 229) | 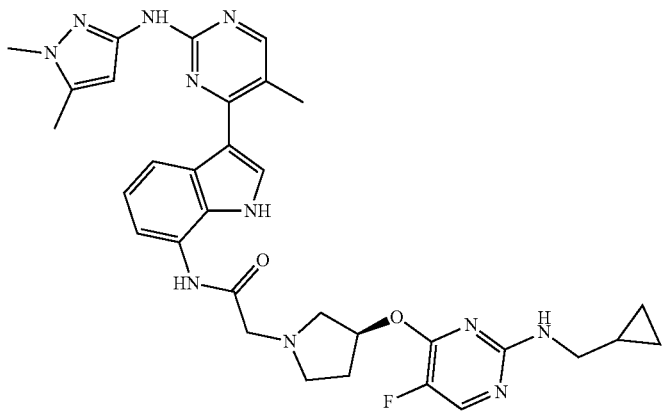 [SMILES: Cc1cnc(Nc2cc(C)n(C)n2)nc1-c1c[nH]c2c(NC(=O)CN3CC[C@H](Oc4nc(NCC5CC5)ncc4F)C3)cccc12] | (S)-2-(3-((2-((cyclopropylmethyl)amino)-5-fluoropyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 230) | 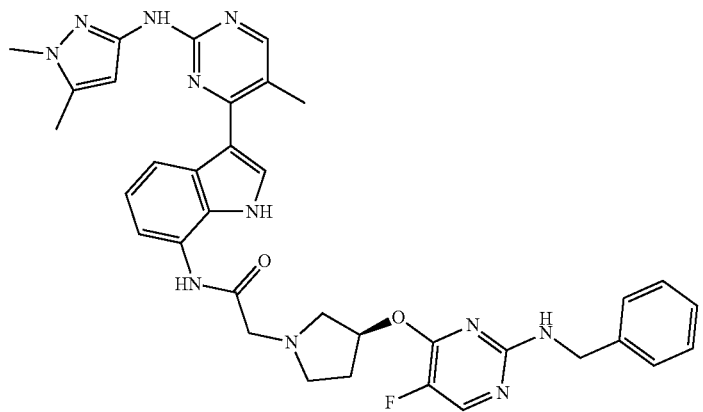 [SMILES: Cc1cnc(Nc2cc(C)n(C)n2)nc1-c1c[nH]c2c(NC(=O)CN3CC[C@H](Oc4nc(NCc5ccccc5)ncc4F)C3)cccc12] | (S)-2-(3-((2-(benzylamino)-5-fluoropyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |

231) 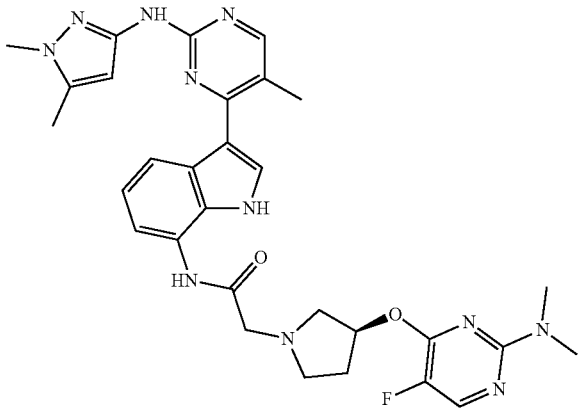

(S)-N-(3-(2-((1,5-dimethyl-1H-pyrazol-3-yl)amino)-5-methylpyrimidin-4-yl)-1H-indol-7-yl)-2-(3-((2-(dimethylamino)-5-fluoropyrimidin-4-yl)oxy)pyrrolidin-1-yl)acetamide 232) 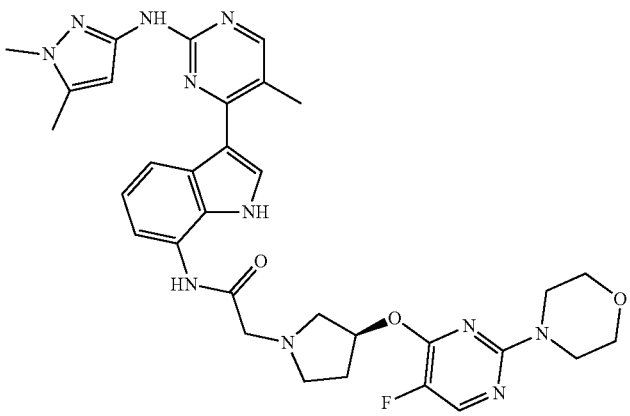 [SMILES: Cc1cnc(Nc2cc(C)n(C)n2)nc1-c1c[nH]c2c(NC(=O)CN3CC[C@H](Oc4nc(N5CCOCC5)ncc4F)C3)cccc12]

(S)-N-(3-(2-((1,5-dimethyl-1H-pyrazol-3-yl)amino)-5-methylpyrimidin-4-yl)-1H-indol-7-yl)-2-(3-((5-fluoro-2-morpholinopyrimidin-4-yl)oxy)pyrrolidin-1-yl)acetamide 233) 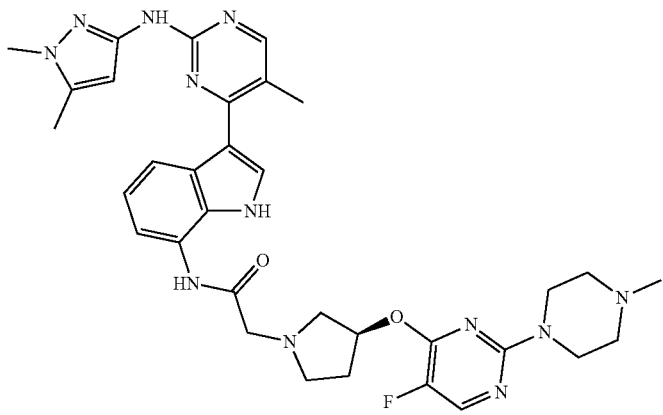

(S)-N-(3-(2-((1,5-dimethyl-1H-pyrazol-3-yl)amino)-5-methylpyrimidin-4-yl)-1H-indol-7-yl)-2-(3-((5-fluoro-2-(4-methylpiperazin-1-yl)pyrimidin-4-yl)oxy)pyrrolidin-1-yl)acetamide

| | | |
|---|---|---|
| 234) | 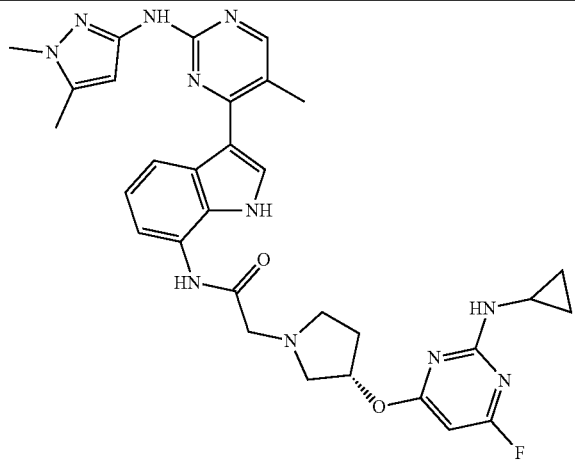 | (S)-2-(3-((2-(cyclopropylamino)-6-fluoropyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 235) | 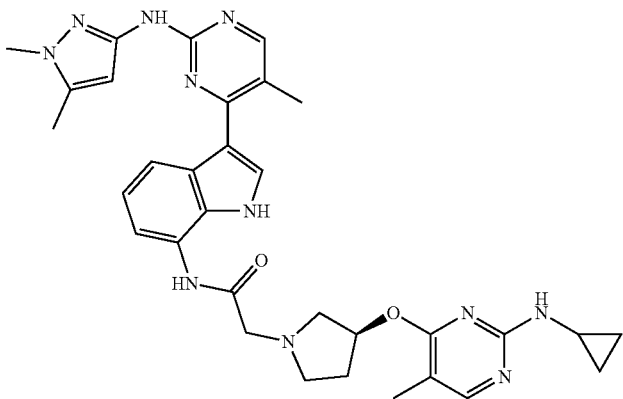 [SMILES: Cc1cnc(NC2CC2)nc1O[C@H]1CCN(CC(=O)Nc2cccc3c(-c4nc(Nc5cc(C)n(C)n5)ncc4C)c[nH]c23)C1] | (S)-2-(3-((2-(cyclopropylamino)-5-methylpyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 236) | 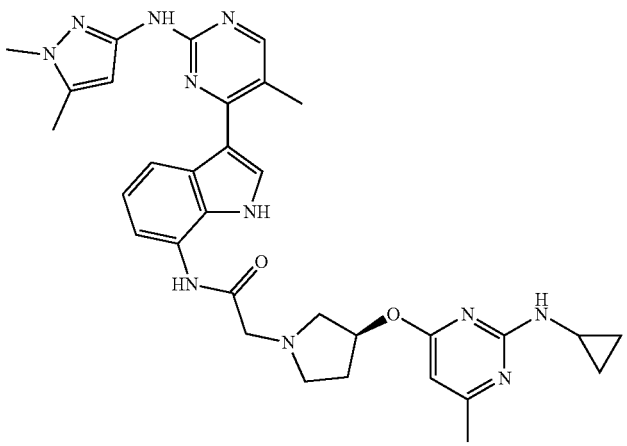 [SMILES: Cc1cc(O[C@H]2CCN(CC(=O)Nc3cccc4c(-c5nc(Nc6cc(C)n(C)n6)ncc5C)c[nH]c34)C2)nc(NC2CC2)n1] | (S)-2-(3-((2-(cyclopropylamino)-6-methylpyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |

| | | |
|---|---|---|
| 237) | 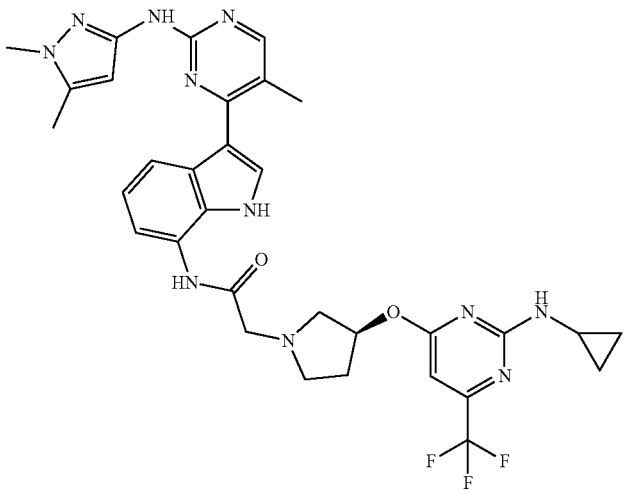 [SMILES: Cc1cnc(Nc2cc(C)n(C)n2)nc1-c1c[nH]c2c(NC(=O)CN3CC[C@H](Oc4cc(C(F)(F)F)nc(NC5CC5)n4)C3)cccc12] | (S)-2-(3-((2-(cyclopropylamino)-6-(trifluoromethyl)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 238) | 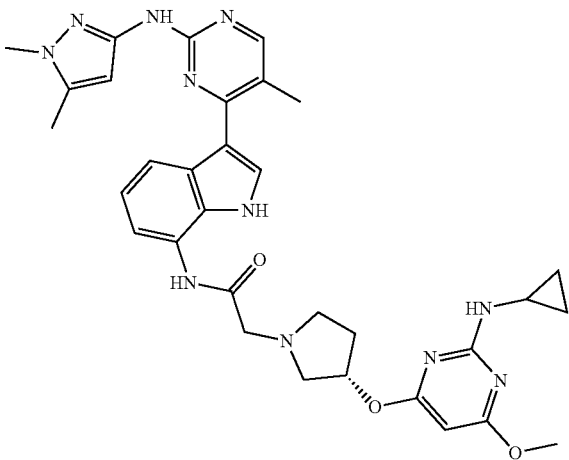 [SMILES: COc1cc(O[C@H]2CCN(CC(=O)Nc3cccc4c(-c5nc(Nc6cc(C)n(C)n6)ncc5C)c[nH]c34)C2)nc(NC2CC2)n1] | (S)-2-(3-((2-(cyclopropylamino)-6-methoxypyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide |
| 239) | 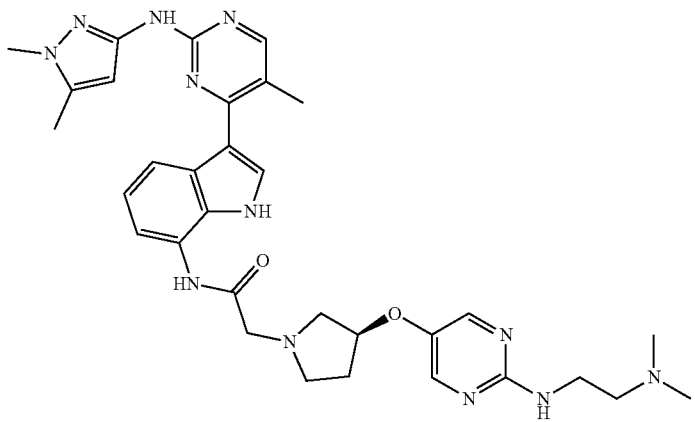 | (S)-N-(3-(2-((1,5-dimethyl-1H-pyrazol-3-yl)amino)-5-methylpyrimidin-4-yl)-1H-indol-7-yl)-2-(3-((2-((2-(dimethylamino)ethyl)amino)pyrimidin-5-yl)oxy)pyrrolidin-1-yl)acetamide |

240) 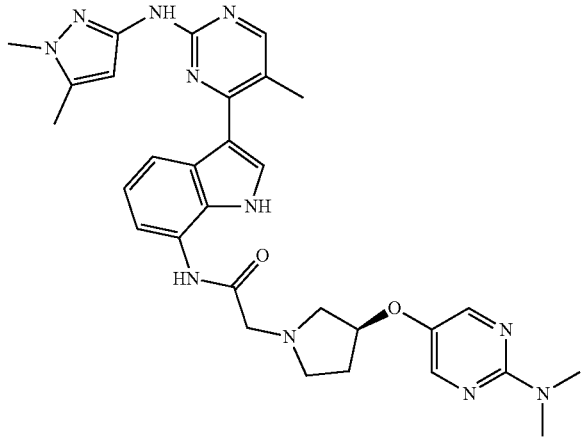
(S)-N-(3-(2-((1,5-dimethyl-1H-pyrazol-3-yl)amino)-5-methylpyrimidin-4-yl)-1H-indol-7-yl)-2-(3-((2-(dimethylamino)pyrimidin-5-yl)oxy)pyrrolidin-1-yl)acetamide
241) 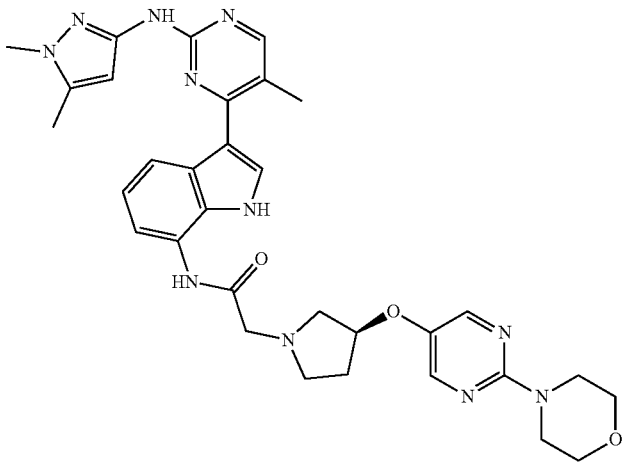 [SMILES: Cc1cnc(Nc2cc(C)n(C)n2)nc1-c1c[nH]c2c(NC(=O)CN3CC[C@H](Oc4cnc(N5CCOCC5)nc4)C3)cccc12]
(S)-N-(3-(2-((1,5-dimethyl-1H-pyrazol-3-yl)amino)-5-methylpyrimidin-4-yl)-1H-indol-7-yl)-2-(3-((2-morpholinopyrimidin-5-yl)oxy)pyrrolidin-1-yl)acetamide
242) 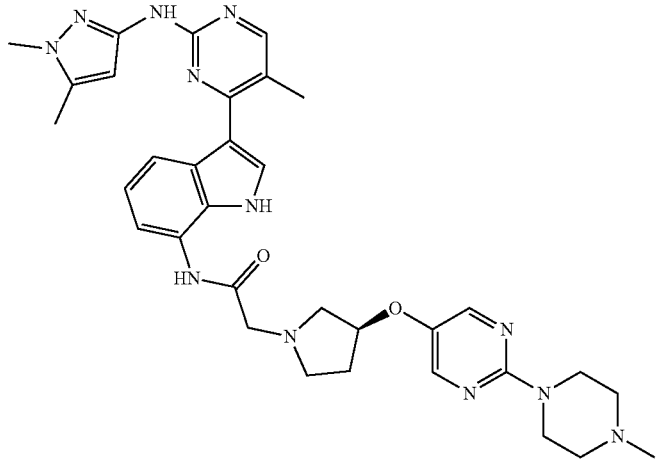
(S)-N-(3-(2-((1,5-dimethyl-1H-pyrazol-3-yl)amino)-5-methylpyrimidin-4-yl)-1H-indol-7-yl)-2-(3-((2-(4-methylpiperazin-1-yl)pyrimidin-5-yl)oxy)pyrrolidin-1-yl)acetamide 243) 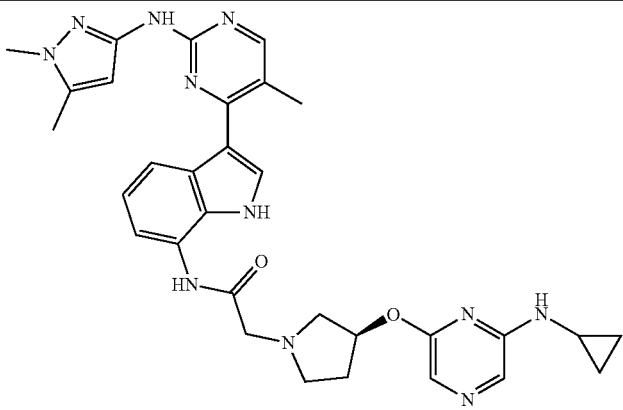 (S)-2-(3-((6-(cyclopropylamino)pyrazin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide 244) 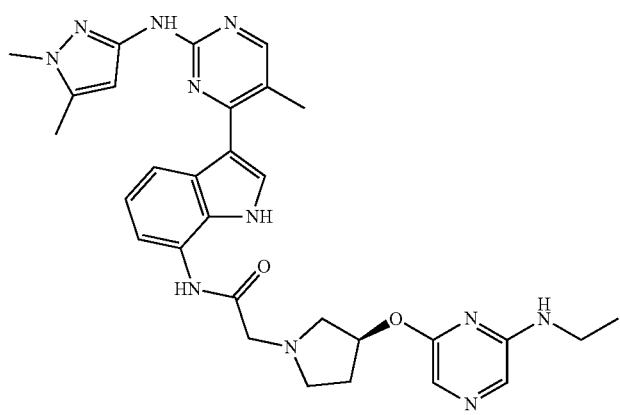 [SMILES: CCNc1cncc(O[C@H]2CCN(CC(=O)Nc3cccc4c(-c5nc(Nc6cc(C)n(C)n6)ncc5C)c[nH]c34)C2)n1] (S)-N-(3-(2-((1,5-dimethyl-1H-pyrazol-3-yl)amino)-5-methylpyrimidin-4-yl)-1H-indol-7-yl)-2-(3-((6-(ethylamino)pyrazin-2-yl)oxy)pyrrolidin-1-yl)acetamide 245) 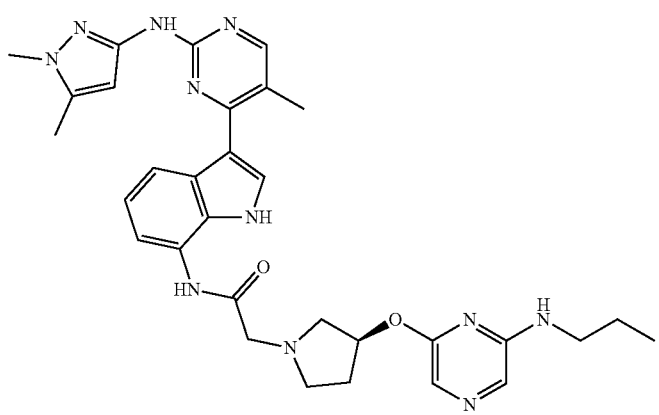 [SMILES: CCCNc1cncc(O[C@H]2CCN(CC(=O)Nc3cccc4c(-c5nc(Nc6cc(C)n(C)n6)ncc5C)c[nH]c34)C2)n1] (S)-N-(3-(2-((1,5-dimethyl-1H-pyrazol-3-yl)amino)-5-methylpyrimidin-4-yl)-1H-indol-7-yl)-2-(3-((6-(propylamino)pyrazin-2-yl)oxy)pyrrolidin-1-yl)acetamide 246) 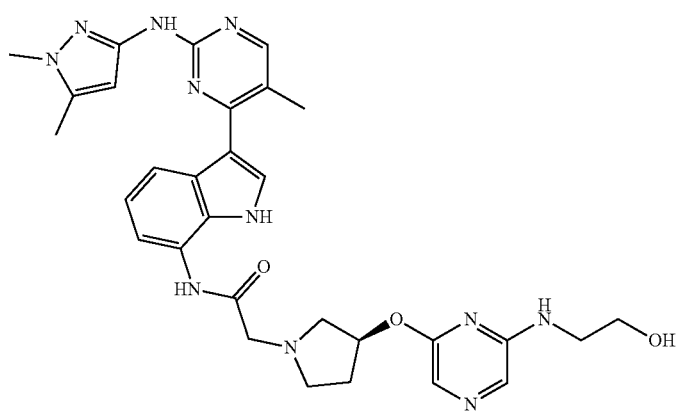 [SMILES: Cc1cnc(Nc2cc(C)n(C)n2)nc1-c1c[nH]c2c(NC(=O)CN3CC[C@H](Oc4cncc(NCCO)n4)C3)cccc12] (S)-N-(3-(2-((1,5-dimethyl-1H-pyrazol-3-yl)amino)-5-methylpyrimidin-4-yl)-1H-indol-7-yl)-2-(3-((6-((2-hydroxyethyl)amino)pyrazin-2-yl)oxy)pyrrolidin-1-yl)acetamide 247) 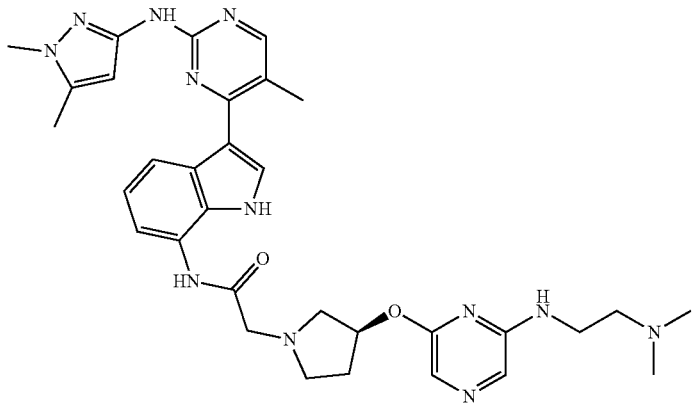 (S)-N-(3-(2-((1,5-dimethyl-1H-pyrazol-3-yl)amino)-5-methylpyrimidin-4-yl)-1H-indol-7-yl)-2-(3-((6-((2-(dimethylamino)ethyl)amino)pyrazin-2-yl)oxy)pyrrolidin-1-yl)acetamide 248) 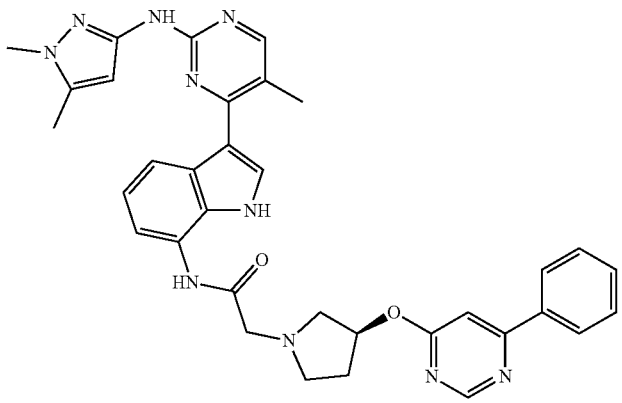 [SMILES: Cc1cnc(Nc2cc(C)n(C)n2)nc1-c1c[nH]c2c(NC(=O)CN3CC[C@H](Oc4cc(-c5ccccc5)ncn4)C3)cccc12] (S)-N-(3-(2-((1,5-dimethyl-1H-pyrazol-3-yl)amino)-5-methylpyrimidin-4-yl)-1H-indol-7-yl)-2-(3-((6-phenylpyrimidin-4-yl)oxy)pyrrolidin-1-yl)acetamide 249) 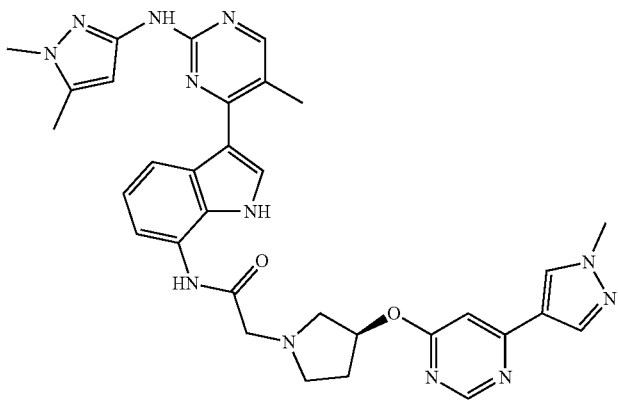 [SMILES: Cc1cnc(Nc2cc(C)n(C)n2)nc1-c1c[nH]c2c(NC(=O)CN3CC[C@H](Oc4cc(-c5cnn(C)c5)ncn4)C3)cccc12] (S)-N-(3-(2-((1,5-dimethyl-1H-pyrazol-3-yl)amino)-5-methylpyrimidin-4-yl)-1H-indol-7-yl)-2-(3-((6-(1-methyl-1H-pyrazol-4-yl)pyrimidin-4-yl)oxy)pyrrolidin-1-yl)acetamide 250) 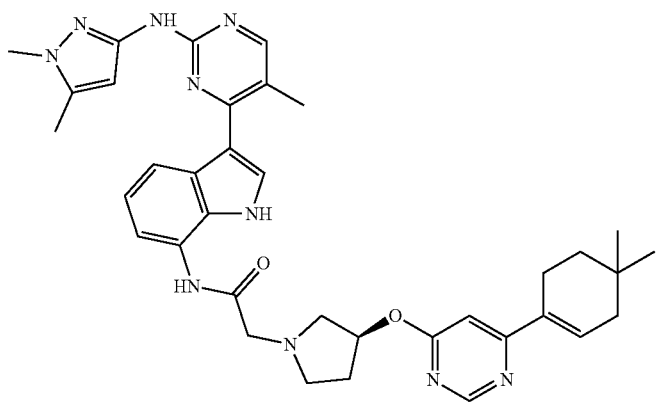 (S)-N-(3-(2-((1,5-dimethyl-1H-pyrazol-3-yl)amino)-5-methylpyrimidin-4-yl)-1H-indol-7-yl)-2-(3-((6-(4,4-dimethylcyclohex-1-en-1-yl)pyrimidin-4-yl)oxy)pyrrolidin-1-yl)acetamide 251) 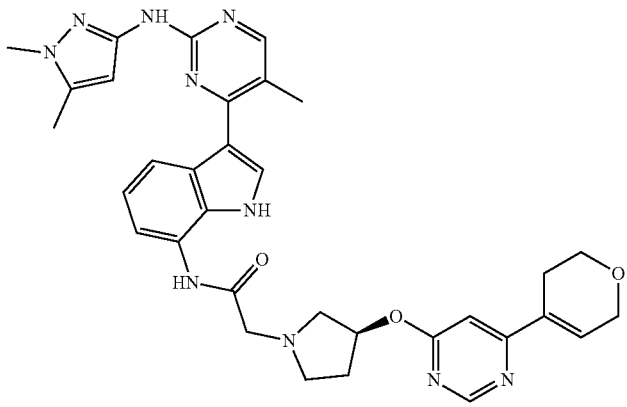 [SMILES: Cc1cnc(Nc2cc(C)n(C)n2)nc1-c1c[nH]c2c(NC(=O)CN3CC[C@H](Oc4cc(C5=CCOCC5)ncn4)C3)cccc12] (S)-2-(3-((6-(3,6-dihydro-2H-pyran-4-yl)pyrimidin-4-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide 252) 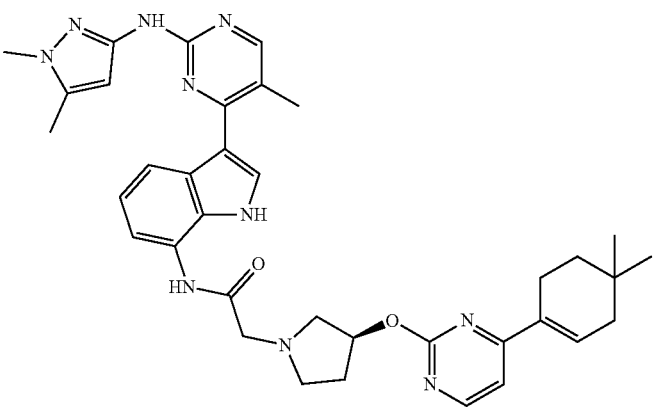 (S)-N-(3-(2-((1,5-dimethyl-1H-pyrazol-3-yl)amino)-5-methylpyrimidin-4-yl)-1H-indol-7-yl)-2-(3-((4-(4,4-dimethylcyclohex-1-en-1-yl)pyrimidin-2-yl)oxy)pyrrolidin-1-yl)acetamide 253) 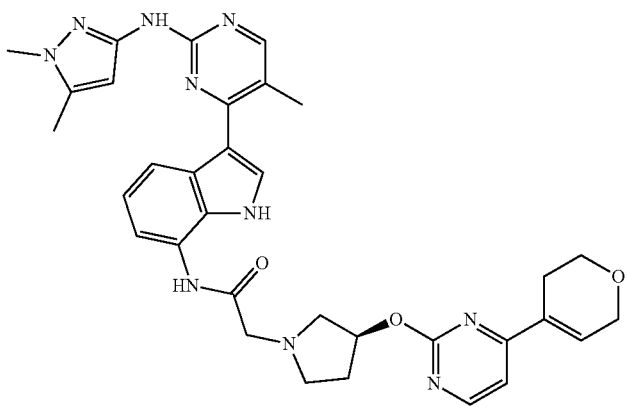 [SMILES: Cc1cnc(Nc2cc(C)n(C)n2)nc1-c1c[nH]c2c(NC(=O)CN3CC[C@H](Oc4nccc(C5=CCOCC5)n4)C3)cccc12] (S)-2-(3-((4-(3,6-dihydro-2H-pyran-4-yl)pyrimidin-2-yl)oxy)pyrrolidin-1-yl)-N-(3-(2-((1,5-dimethyl-1H-pyrazol-3-yl)amino)-5-methylpyrimidin-4-yl)-1H-indol-7-yl)acetamide 254) 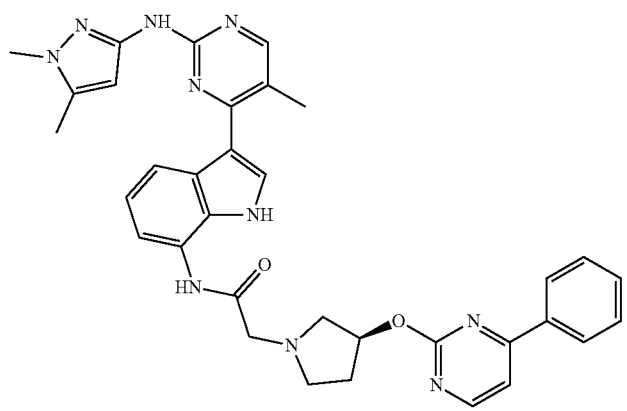 [SMILES: Cc1cnc(Nc2cc(C)n(C)n2)nc1-c1c[nH]c2c(NC(=O)CN3CC[C@H](Oc4nccc(-c5ccccc5)n4)C3)cccc12] (S)-N-(3-(2-((1,5-dimethyl-1H-pyrazol-3-yl)amino)-5-methylpyrimidin-4-yl)-1H-indol-7-yl)-2-(3-((4-phenylpyrimidin-2-yl)oxy)pyrrolidin-1-yl)acetamide

| | | |
|---|---|---|
| 255) | 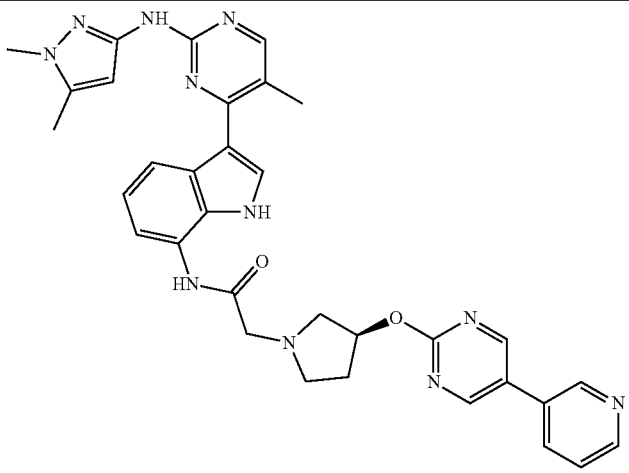 | (S)-N-(3-(2-((1,5-dimethyl-1H-pyrazol-3-yl)amino)-5-methylpyrimidin-4-yl)-1H-indol-7-yl)-2-(3-((5-(pyridin-3-yl)pyrimidin-2-yl)oxy)pyrrolidin-1-yl)acetamide |
| 256) | 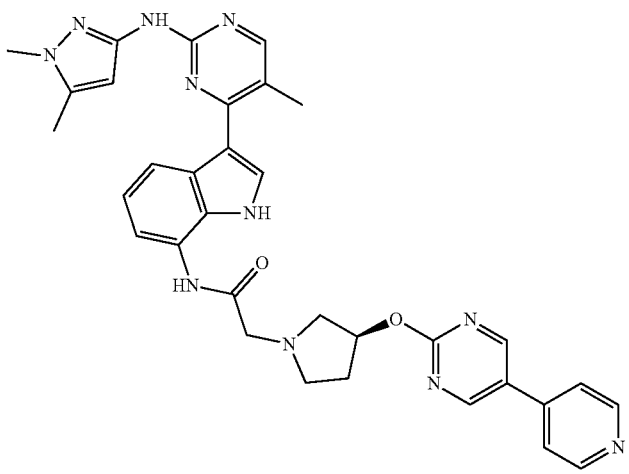 [SMILES: Cc1cnc(Nc2cc(C)n(C)n2)nc1-c1c[nH]c2c(NC(=O)CN3CC[C@H](Oc4ncc(-c5ccncc5)cn4)C3)cccc12] | (S)-N-(3-(2-((1,5-dimethyl-1H-pyrazol-3-yl)amino)-5-methylpyrimidin-4-yl)-1H-indol-7-yl)-2-(3-((5-(pyridin-4-yl)pyrimidin-2-yl)oxy)pyrrolidin-1-yl)acetamide |
| 257) | 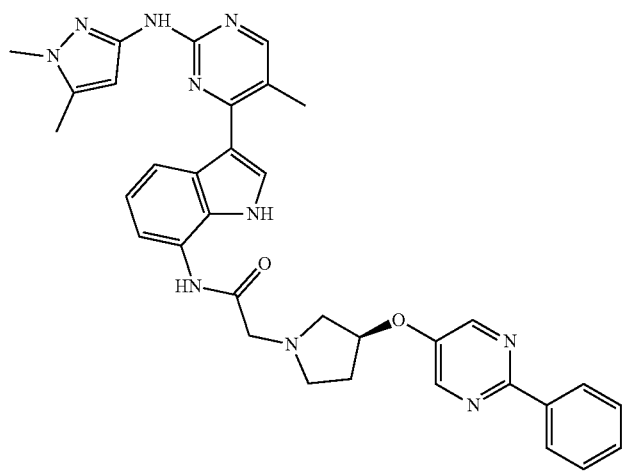 [SMILES: Cc1cnc(Nc2cc(C)n(C)n2)nc1-c1c[nH]c2c(NC(=O)CN3CC[C@H](Oc4cnc(-c5ccccc5)nc4)C3)cccc12] | (S)-N-(3-(2-((1,5-dimethyl-1H-pyrazol-3-yl)amino)-5-methylpyrimidin-4-yl)-1H-indol-7-yl)-2-(3-((2-phenylpyrimidin-5-yl)oxy)pyrrolidin-1-yl)acetamide |

-continued
258) 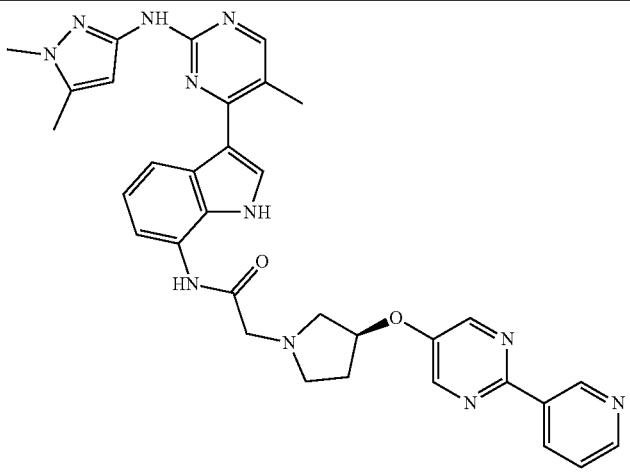 (S)-N-(3-(2-((1,5-dimethyl-1H-pyrazol-3-yl)amino)-5-methylpyrimidin-4-yl)-1H-indol-7-yl)-2-(3-((2-(pyridin-3-yl)pyrimidin-5-yl)oxy)pyrrolidin-1-yl)acetamide
259) 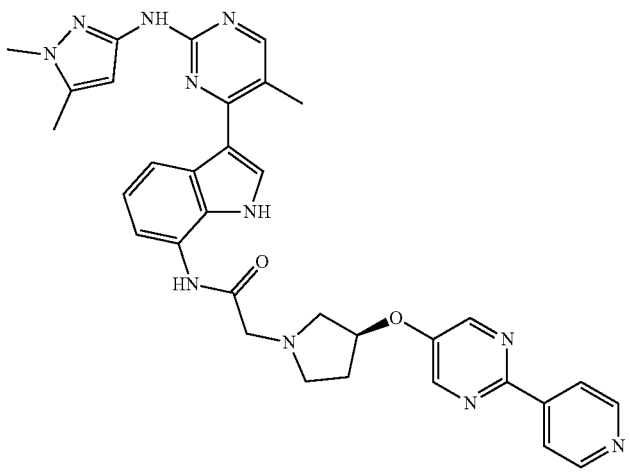 [SMILES: Cc1cnc(Nc2cc(C)n(C)n2)nc1-c1c[nH]c2c(NC(=O)CN3CC[C@H](Oc4cnc(-c5ccncc5)nc4)C3)cccc12] (S)-N-(3-(2-((1,5-dimethyl-1H-pyrazol-3-yl)amino)-5-methylpyrimidin-4-yl)-1H-indol-7-yl)-2-(3-((2-(pyridin-4-yl)pyrimidin-5-yl)oxy)pyrrolidin-1-yl)acetamide
260) 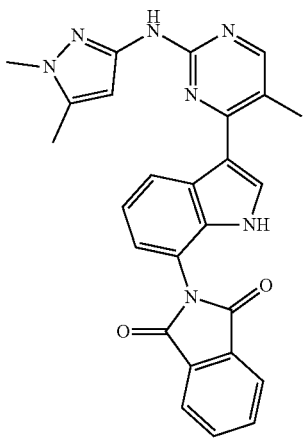 2-(3-(2-((1,5-dimethyl-1H-pyrazol-3-yl)amino)-5-methylpyrimidin-4-yl)-1H-indol-7-yl)isoindoline-1,3-dione -continued
261) 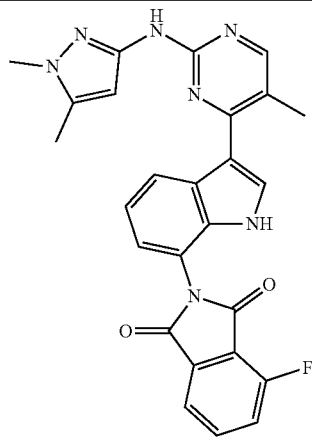
2-(3-(2-((1,5-dimethyl-1H-pyrazol-3-yl)amino)-5-methylpyrimidin-4-yl)-1H-indol-7-yl)-4-fluoroisoindoline-1,3-dione
262) 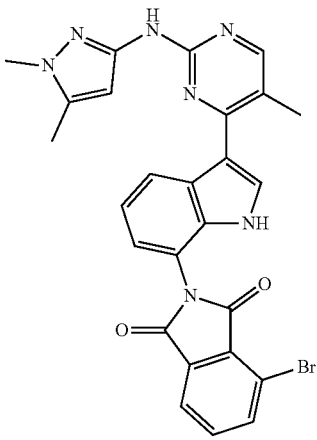 [SMILES: Cc1cnc(Nc2cc(C)n(C)n2)nc1-c1c[nH]c2c(N3C(=O)c4cccc(Br)c4C3=O)cccc12]
4-bromo-2-(3-(2-((1,5-dimethyl-1H-pyrazol-3-yl)amino)-5-methylpyrimidin-4-yl)-1H-indol-7-yl)isoindoline-1,3-dione
263) 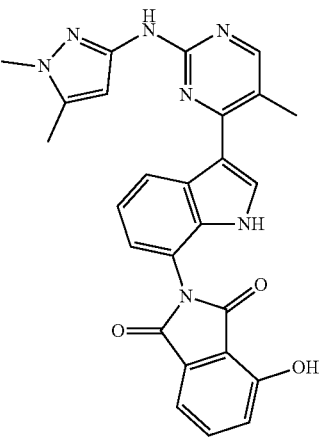 [SMILES: Cc1cnc(Nc2cc(C)n(C)n2)nc1-c1c[nH]c2c(N3C(=O)c4cccc(O)c4C3=O)cccc12]
2-(3-(2-((1,5-dimethyl-1H-pyrazol-3-yl)amino)-5-methylpyrimidin-4-yl)-1H-indol-7-yl)-4-hydroxyisoindoline-1,3-dione 264) 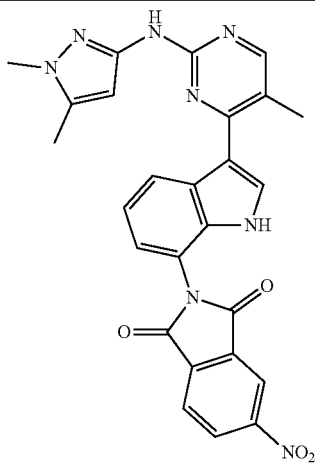 2-(3-(2-((1,5-dimethyl-1H-pyrazol-3-yl)amino)-5-methylpyrimidin-4-yl)-1H-indol-7-yl)-5-nitroisoindoline-1,3-dione
265) 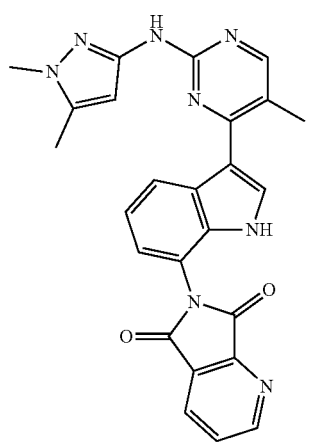 6-(3-(2-((1,5-dimethyl-1H-pyrazol-3-yl)amino)-5-methylpyrimidin-4-yl)-1H-indol-7-yl)-5H-pyrrolo[3,4-b]pyridine-5,7(6H)-dione
266) 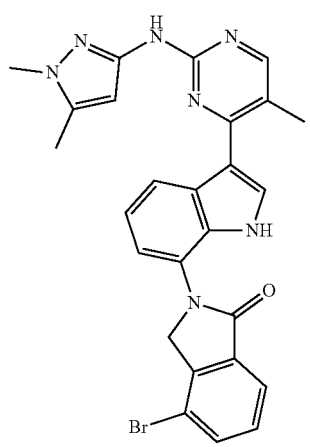 4-bromo-2-(3-(2-((1,5-dimethyl-1H-pyrazol-3-yl)amino)-5-methylpyrimidin-4-yl)-1H-indol-7-yl)isoindolin-1-one 267) 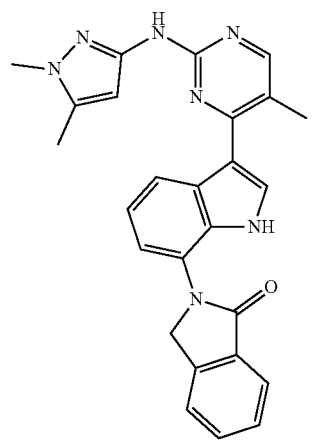
2-(3-(2-((1,5-dimethyl-1H-pyrazol-3-yl)amino)-5-methylpyrimidin-4-yl)-1H-indol-7-yl)isoindolin-1-one
268) 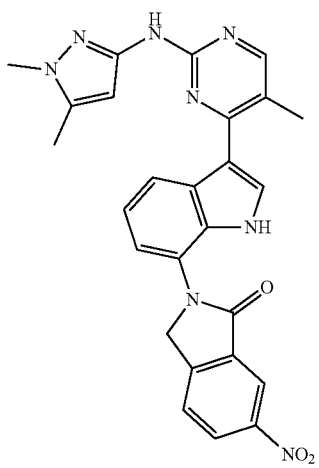
2-(3-(2-((1,5-dimethyl-1H-pyrazol-3-yl)amino)-5-methylpyrimidin-4-yl)-1H-indol-7-yl)-6-nitroisoindolin-1-one
269) 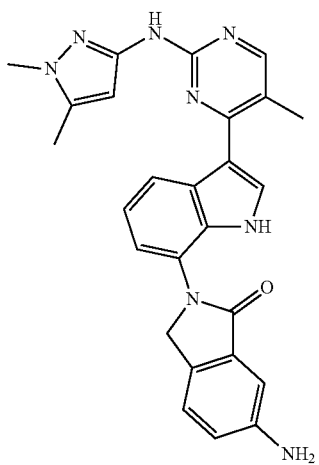
6-amino-2-(3-(2-((1,5-dimethyl-1H-pyrazol-3-yl)amino)-5-methylpyrimidin-4-yl)-1H-indol-7-yl)isoindolin-1-one

| | | |
|---|---|---|
| 270) | 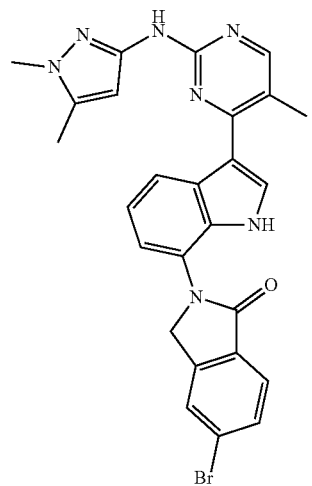 | 5-bromo-2-(3-(2-((1,5-dimethyl-1H-pyrazol-3-yl)amino)-5-methylpyrimidin-4-yl)-1H-indol-7-yl)isoindolin-1-one |
| 271) | 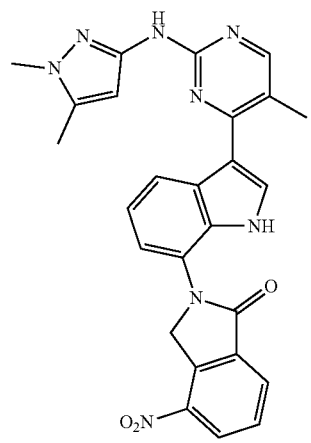 | 2-(3-(2-((1,5-dimethyl-1H-pyrazol-3-yl)amino)-5-methylpyrimidin-4-yl)-1H-indol-7-yl)-4-nitroisoindolin-1-one |
| 272) | 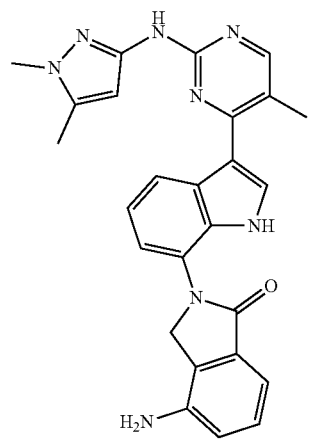 | 4-amino-2-(3-(2-((1,5-dimethyl-1H-pyrazol-3-yl)amino)-5-methylpyrimidin-4-yl)-1H-indol-7-yl)isoindolin-1-one |

273) 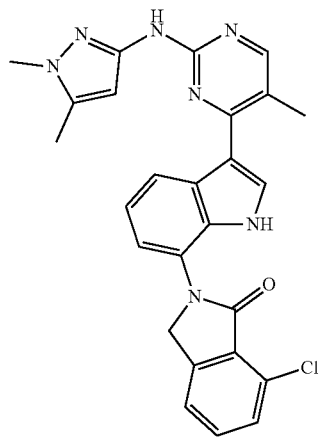 [SMILES: Cc1cnc(Nc2cc(C)n(C)n2)nc1-c1c[nH]c2c(N3Cc4cccc(Cl)c4C3=O)cccc12] 7-chloro-2-(3-(2-((1,5-dimethyl-1H-pyrazol-3-yl)amino)-5-methylpyrimidin-4-yl)-1H-indol-7-yl)isoindolin-1-one
274) 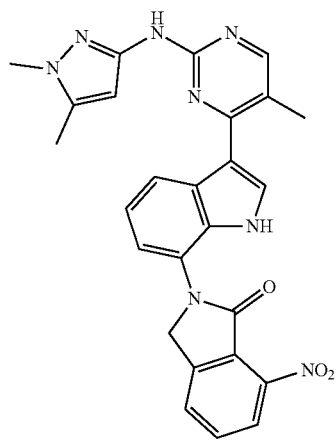 [SMILES: Cc1cnc(Nc2cc(C)n(C)n2)nc1-c1c[nH]c2c(N3Cc4cccc([N+](=O)[O-])c4C3=O)cccc12] 2-(3-(2-((1,5-dimethyl-1H-pyrazol-3-yl)amino)-5-methylpyrimidin-4-yl)-1H-indol-7-yl)-7-nitroisoindolin-1-one
275) 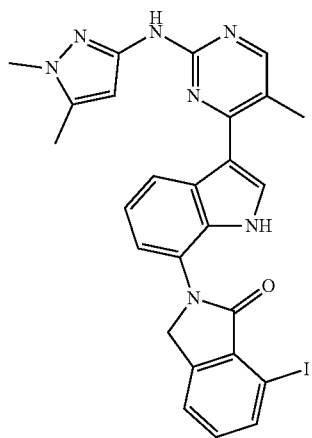 [SMILES: Cc1cnc(Nc2cc(C)n(C)n2)nc1-c1c[nH]c2c(N3Cc4cccc(I)c4C3=O)cccc12] 2-(3-(2-((1,5-dimethyl-1H-pyrazol-3-yl)amino)-5-methylpyrimidin-4-yl)-1H-indol-7-yl)-7-iodoisoindolin-1-one

| 276) | 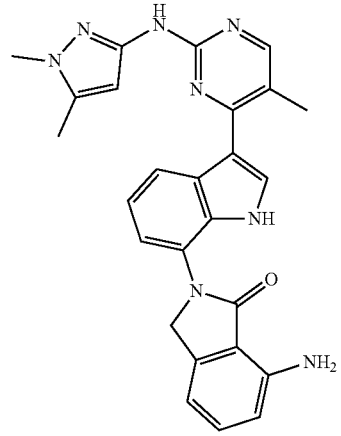 | 7-amino-2-(3-(2-((1,5-dimethyl-1H-pyrazol-3-yl)amino)-5-methylpyrimidin-4-yl)-1H-indol-7-yl)isoindolin-1-one |
| 277) | 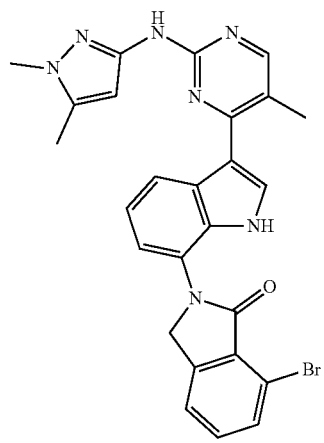 [SMILES: Cc1cnc(Nc2cc(C)n(C)n2)nc1-c1c[nH]c2c(N3Cc4cccc(Br)c4C3=O)cccc12] | 7-bromo-2-(3-(2-((1,5-dimethyl-1H-pyrazol-3-yl)amino)-5-methylpyrimidin-4-yl)-1H-indol-7-yl)isoindolin-1-one |
| 278) | 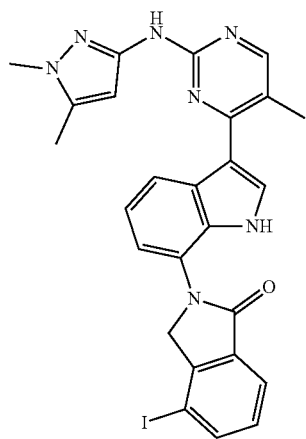 | 2-(3-(2-((1,5-dimethyl-1H-pyrazol-3-yl)amino)-5-methylpyrimidin-4-yl)-1H-indol-7-yl)-4-iodoisoindolin-1-one |

279) 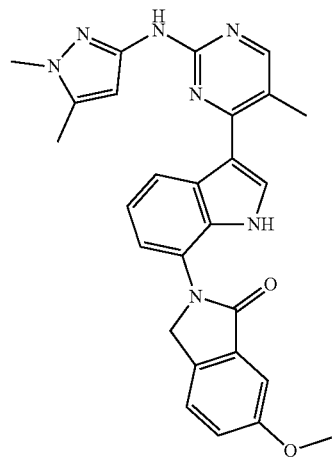
2-(3-(2-((1,5-dimethyl-1H-pyrazol-3-yl)amino)-5-methylpyrimidin-4-yl)-1H-indol-7-yl)-6-methoxyisoindolin-1-one
280) 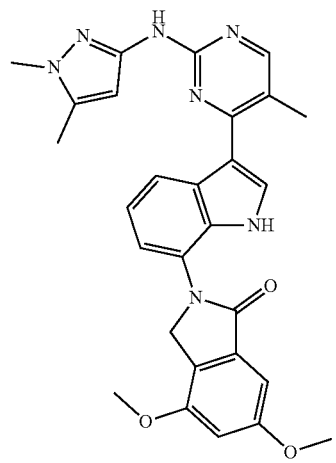
2-(3-(2-((1,5-dimethyl-1H-pyrazol-3-yl)amino)-5-methylpyrimidin-4-yl)-1H-indol-7-yl)-4,6-dimethoxyisoindolin-1-one
281) 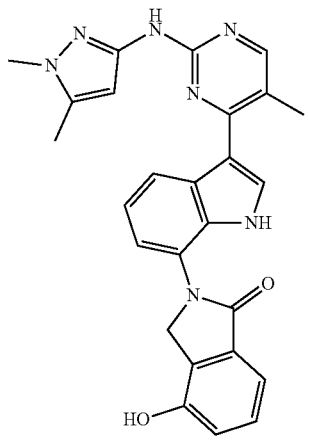
2-(3-(2-((1,5-dimethyl-1H-pyrazol-3-yl)amino)-5-methylpyrimidin-4-yl)-1H-indol-7-yl)-4-hydroxyisoindolin-1-one

| | | |
|---|---|---|
| 282) | 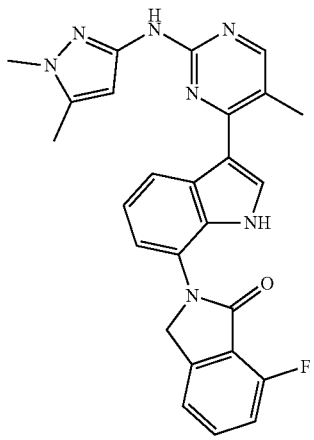 [SMILES: Cc1cnc(Nc2cc(C)n(C)n2)nc1-c1c[nH]c2c(N3Cc4cccc(F)c4C3=O)cccc12] | 2-(3-(2-((1,5-dimethyl-1H-pyrazol-3-yl)amino)-5-methylpyrimidin-4-yl)-1H-indol-7-yl)-7-fluoroisoindolin-1-one |
| 283) | 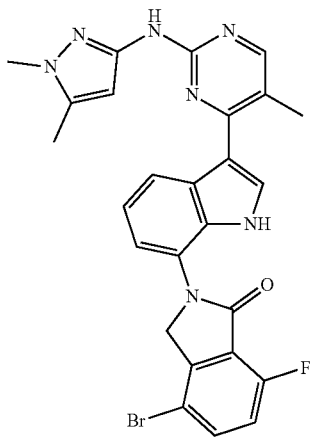 [SMILES: Cc1cnc(Nc2cc(C)n(C)n2)nc1-c1c[nH]c2c(N3Cc4c(Br)ccc(F)c4C3=O)cccc12] | 4-bromo-2-(3-(2-((1,5-dimethyl-1H-pyrazol-3-yl)amino)-5-methylpyrimidin-4-yl)-1H-indol-7-yl)-7-fluoroisoindolin-1-one |
| 284) | 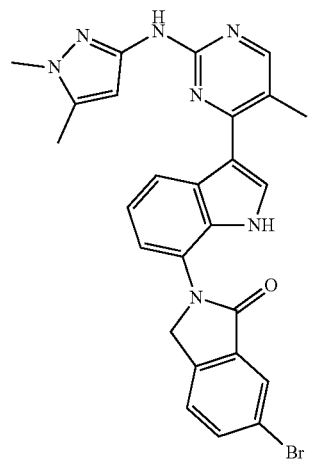 | 6-bromo-2-(3-(2-((1,5-dimethyl-1H-pyrazol-3-yl)amino)-5-methylpyrimidin-4-yl)-1H-indol-7-yl)isoindolin-1-one |

| | | |
|---|---|---|
| 285) | 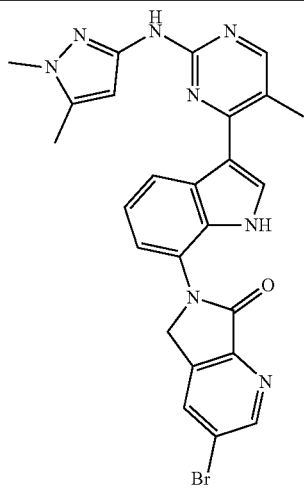 | 3-bromo-6-(3-(2-((1,5-dimethyl-1H-pyrazol-3-yl)amino)-5-methylpyrimidin-4-yl)-1H-indol-7-yl)-5,6-dihydro-7H-pyrrolo[3,4-b]pyridin-7-one |
| 286) | 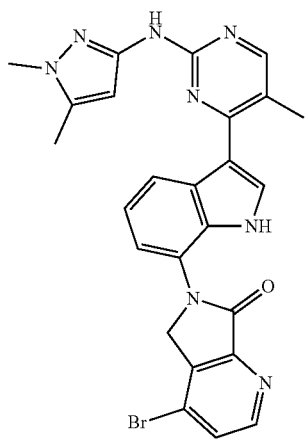 | 4-bromo-6-(3-(2-((1,5-dimethyl-1H-pyrazol-3-yl)amino)-5-methylpyrimidin-4-yl)-1H-indol-7-yl)-5,6-dihydro-7H-pyrrolo[3,4-b]pyridin-7-one |
| 287) | 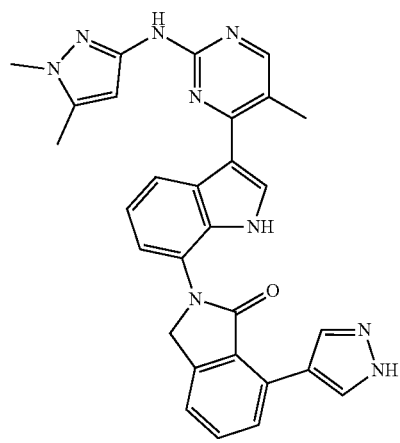 [SMILES: Cc1cnc(Nc2cc(C)n(C)n2)nc1-c1c[nH]c2c(N3Cc4cccc(-c5cn[nH]c5)c4C3=O)cccc12] | 6-(3-(2-((1,5-dimethyl-1H-pyrazol-3-yl)amino)-5-methylpyrimidin-4-yl)-1H-indol-7-yl)-3-methyl-5,6-dihydro-7H-pyrrolo[3,4-b]pyridin-7-one |

288) 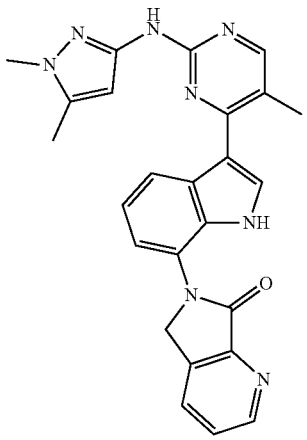
6-(3-(2-((1,5-dimethyl-1H-pyrazol-3-yl)amino)-5-methylpyrimidin-4-yl)-1H-indol-7-yl)-5,6-dihydro-7H-pyrrolo[3,4-b]pyridin-7-one
289) 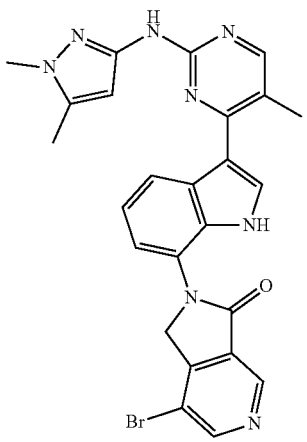
7-bromo-2-(3-(2-((1,5-dimethyl-1H-pyrazol-3-yl)amino)-5-methylpyrimidin-4-yl)-1H-indol-7-yl)-1,2-dihydro-3H-pyrrolo[3,4-c]pyridin-3-one
290) 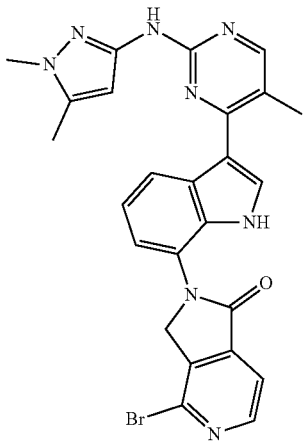
4-bromo-2-(3-(2-((1,5-dimethyl-1H-pyrazol-3-yl)amino)-5-methylpyrimidin-4-yl)-1H-indol-7-yl)-2,3-dihydro-1H-pyrrolo[3,4-c]pyridin-1-one

| | | |
|---|---|---|
| 291) | 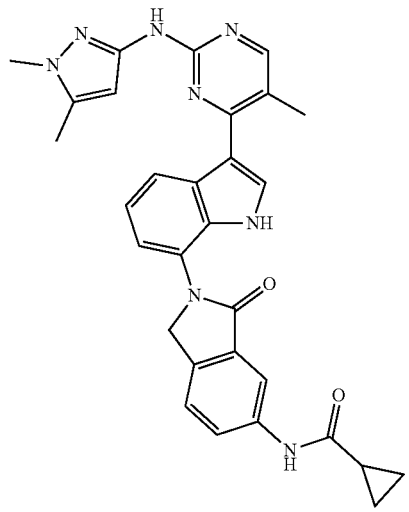 [SMILES: Cc1cnc(Nc2cc(C)n(C)n2)nc1-c1c[nH]c2c(N3Cc4ccc(NC(=O)C5CC5)cc4C3=O)cccc12] | N-(2-(3-(2-((1,5-dimethyl-1H-pyrazol-3-yl)amino)-5-methylpyrimidin-4-yl)-1H-indol-7-yl)-3-oxoisoindolin-5-yl)cyclopropanecarboxamide |
| 292) | 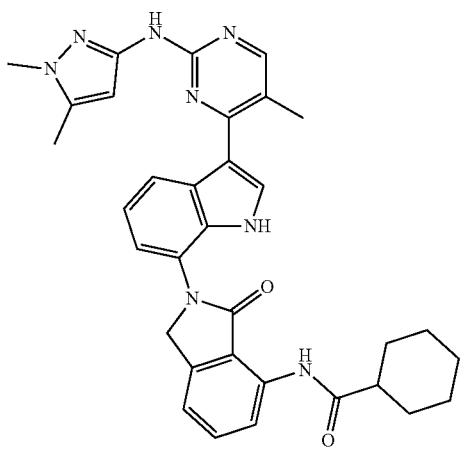 [SMILES: Cc1cnc(Nc2cc(C)n(C)n2)nc1-c1c[nH]c2c(N3Cc4cccc(NC(=O)C5CCCCC5)c4C3=O)cccc12] | N-(2-(3-(2-((1,5-dimethyl-1H-pyrazol-3-yl)amino)-5-methylpyrimidin-4-yl)-1H-indol-7-yl)-3-oxoisoindolin-4-yl)cyclohexanecarboxamide |
| 293) | 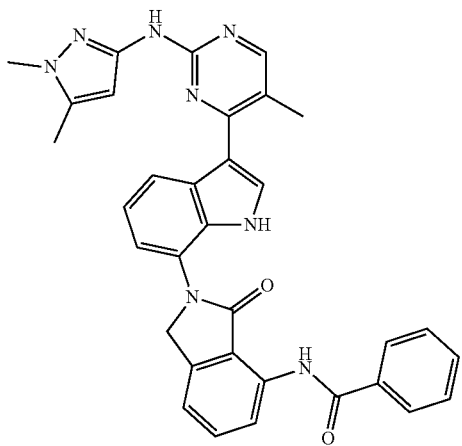 [SMILES: Cc1cnc(Nc2cc(C)n(C)n2)nc1-c1c[nH]c2c(N3Cc4cccc(NC(=O)c5ccccc5)c4C3=O)cccc12] | N-(2-(3-(2-((1,5-dimethyl-1H-pyrazol-3-yl)amino)-5-methylpyrimidin-4-yl)-1H-indol-7-yl)-3-oxoisoindolin-4-yl)benzamide |

-continued
294) 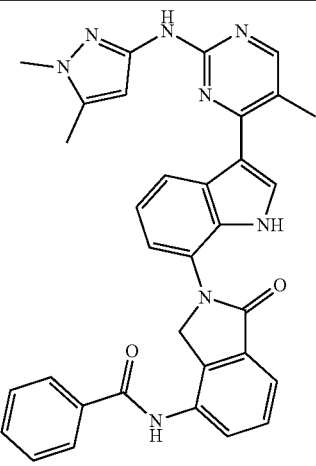
N-(2-(3-(2-((1,5-dimethyl-1H-pyrazol-3-yl)amino)-5-methylpyrimidin-4-yl)-1H-indol-7-yl)-1-oxoisoindolin-4-yl)benzamide
295) 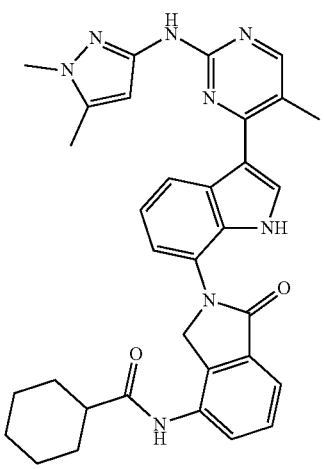 [SMILES: Cc1cnc(Nc2cc(C)n(C)n2)nc1-c1c[nH]c2c(N3Cc4c(NC(=O)C5CCCCC5)cccc4C3=O)cccc12]
N-(2-(3-(2-((1,5-dimethyl-1H-pyrazol-3-yl)amino)-5-methylpyrimidin-4-yl)-1H-indol-7-yl)-1-oxoisoindolin-4-yl)cyclohexanecarboxamide
296) 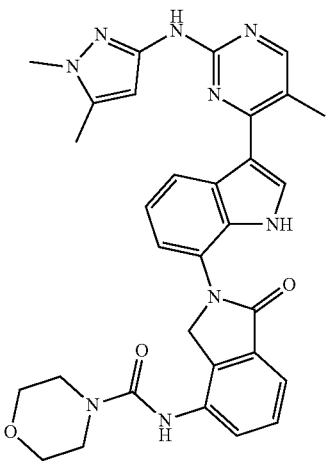 [SMILES: Cc1cnc(Nc2cc(C)n(C)n2)nc1-c1c[nH]c2c(N3Cc4c(NC(=O)N5CCOCC5)cccc4C3=O)cccc12]
N-(2-(3-(2-((1,5-dimethyl-1H-pyrazol-3-yl)amino)-5-methylpyrimidin-4-yl)-1H-indol-7-yl)-1-oxoisoindolin-4-yl)morpholine-4-carboxamide

| | | |
|---|---|---|
| 297) | 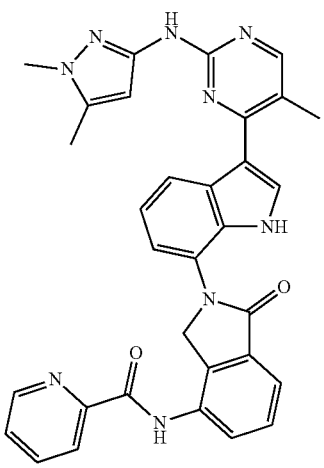 [SMILES: Cc1cnc(Nc2cc(C)n(C)n2)nc1-c1c[nH]c2c(N3Cc4c(NC(=O)c5ccccn5)cccc4C3=O)cccc12] | N-(2-(3-(2-((1,5-dimethyl-1H-pyrazol-3-yl)amino)-5-methylpyrimidin-4-yl)-1H-indol-7-yl)-1-oxoisoindolin-4-yl)picolinamide |
| 298) | 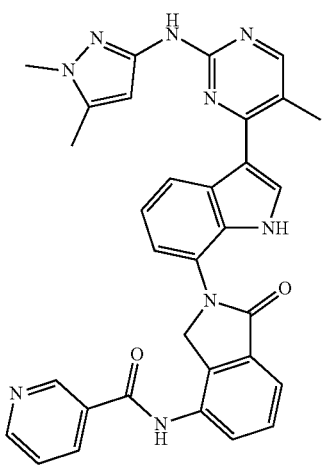 [SMILES: Cc1cnc(Nc2cc(C)n(C)n2)nc1-c1c[nH]c2c(N3Cc4c(NC(=O)c5cccnc5)cccc4C3=O)cccc12] | N-(2-(3-(2-((1,5-dimethyl-1H-pyrazol-3-yl)amino)-5-methylpyrimidin-4-yl)-1H-indol-7-yl)-1-oxoisoindolin-4-yl)nicotinamide |
| 299) | 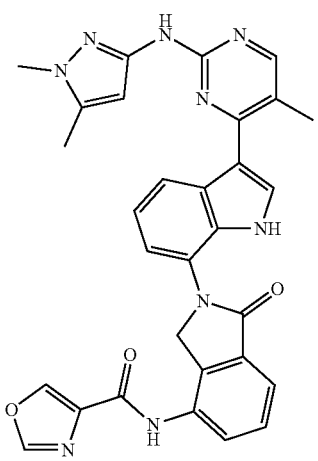 [SMILES: Cc1cnc(Nc2cc(C)n(C)n2)nc1-c1c[nH]c2c(N3Cc4c(NC(=O)c5cocn5)cccc4C3=O)cccc12] | N-(2-(3-(2-((1,5-dimethyl-1H-pyrazol-3-yl)amino)-5-methylpyrimidin-4-yl)-1H-indol-7-yl)-1-oxoisoindolin-4-yl)oxazole-4-carboxamide |

| | | |
|---|---|---|
| 300) | 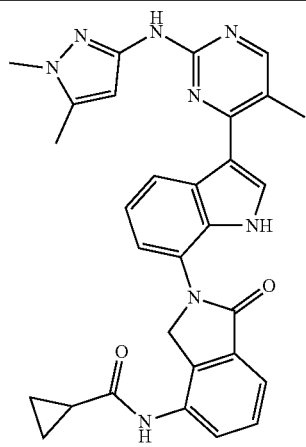 | N-(2-(3-(2-((1,5-dimethyl-1H-pyrazol-3-yl)amino)-5-methylpyrimidin-4-yl)-1H-indol-7-yl)-1-oxoisoindolin-4-yl)cyclopropanecarboxamide |
| 301) | 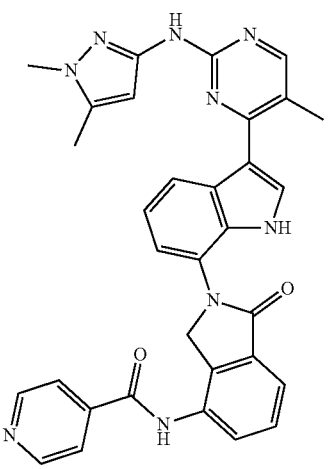 [SMILES: Cc1cnc(Nc2cc(C)n(C)n2)nc1-c1c[nH]c2c(N3Cc4c(NC(=O)c5ccncc5)cccc4C3=O)cccc12] | N-(2-(3-(2-((1,5-dimethyl-1H-pyrazol-3-yl)amino)-5-methylpyrimidin-4-yl)-1H-indol-7-yl)-1-oxoisoindolin-4-yl)isonicotinamide |
| 302) | 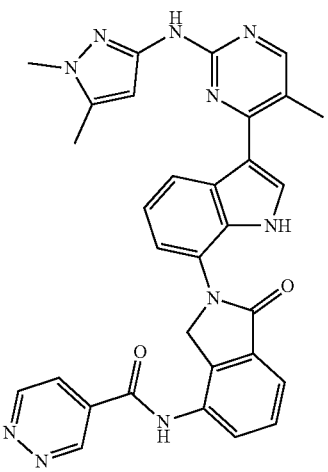 [SMILES: Cc1cnc(Nc2cc(C)n(C)n2)nc1-c1c[nH]c2c(N3Cc4c(NC(=O)c5ccnnc5)cccc4C3=O)cccc12] | N-(2-(3-(2-((1,5-dimethyl-1H-pyrazol-3-yl)amino)-5-methylpyrimidin-4-yl)-1H-indol-7-yl)-1-oxoisoindolin-4-yl)pyridazine-4-carboxamide |

303) 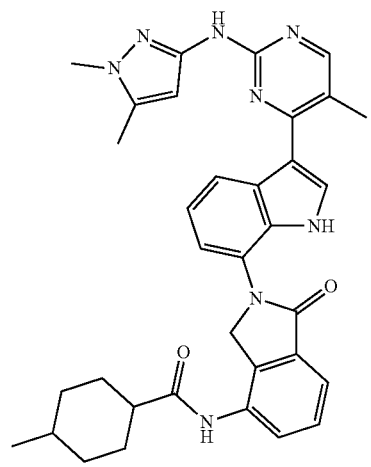 N-(2-(3-(2-((1,5-dimethyl-1H-pyrazol-3-yl)amino)-5-methylpyrimidin-4-yl)-1H-indol-7-yl)-1-oxoisoindolin-4-yl)-4-methylcyclohexane-1-carboxamide
304) 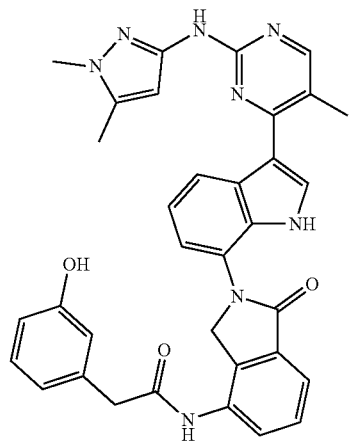 [SMILES: Cc1cnc(Nc2cc(C)n(C)n2)nc1-c1c[nH]c2c(N3Cc4c(NC(=O)Cc5cccc(O)c5)cccc4C3=O)cccc12] N-(2-(3-(2-((1,5-dimethyl-1H-pyrazol-3-yl)amino)-5-methylpyrimidin-4-yl)-1H-indol-7-yl)-1-oxoisoindolin-4-yl)-2-(3-hydroxyphenyl)acetamide
305) 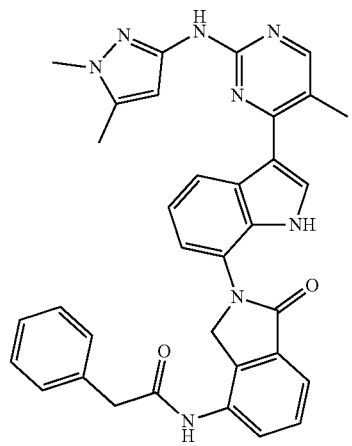 [SMILES: Cc1cnc(Nc2cc(C)n(C)n2)nc1-c1c[nH]c2c(N3Cc4c(NC(=O)Cc5ccccc5)cccc4C3=O)cccc12] N-(2-(3-(2-((1,5-dimethyl-1H-pyrazol-3-yl)amino)-5-methylpyrimidin-4-yl)-1H-indol-7-yl)-1-oxoisoindolin-4-yl)-2-phenylacetamide

| | | |
|---|---|---|
| 306) | 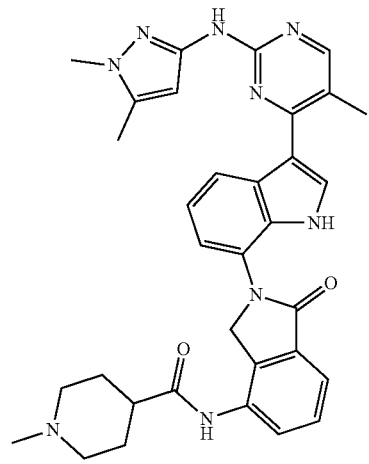 | N-(2-(3-(2-((1,5-dimethyl-1H-pyrazol-3-yl)amino)-5-methylpyrimidin-4-yl)-1H-indol-7-yl)-1-oxoisoindolin-4-yl)-1-methylpiperidine-4-carboxamide |
| 307) | 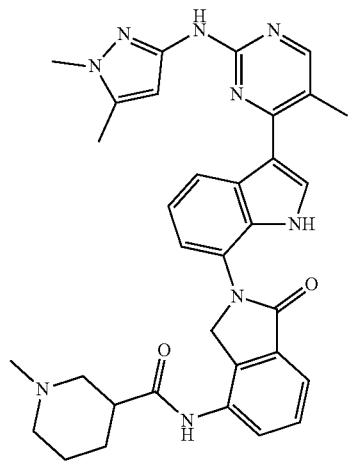 | N-(2-(3-(2-((1,5-dimethyl-1H-pyrazol-3-yl)amino)-5-methylpyrimidin-4-yl)-1H-indol-7-yl)-1-oxoisoindolin-4-yl)-1-methylpiperidine-3-carboxamide |
| 308) | 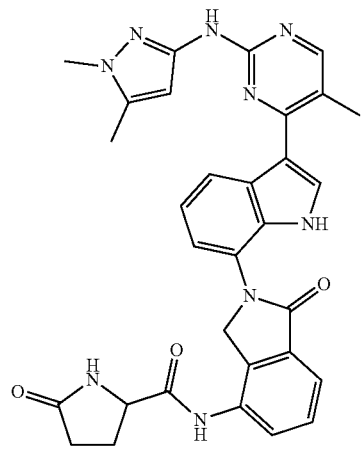 | N-(2-(3-(2-((1,5-dimethyl-1H-pyrazol-3-yl)amino)-5-methylpyrimidin-4-yl)-1H-indol-7-yl)-1-oxoisoindolin-4-yl)-5-oxopyrrolidine-2-carboxamide |

| | | |
|---|---|---|
| 309) | 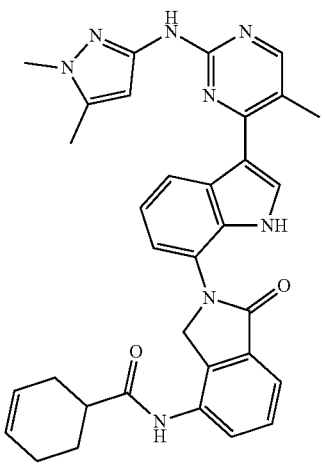 [SMILES: Cc1cnc(Nc2cc(C)n(C)n2)nc1-c1c[nH]c2c(N3Cc4c(NC(=O)C5CC=CCC5)cccc4C3=O)cccc12] | N-(2-(3-(2-((1,5-dimethyl-1H-pyrazol-3-yl)amino)-5-methylpyrimidin-4-yl)-1H-indol-7-yl)-1-oxoisoindolin-4-yl)cyclohex-3-ene-1-carboxamide |
| 310) | 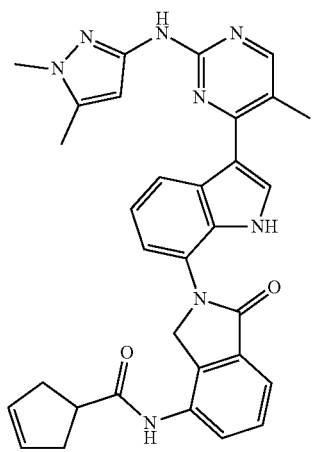 [SMILES: Cc1cnc(Nc2cc(C)n(C)n2)nc1-c1c[nH]c2c(N3Cc4c(NC(=O)C5CC=CC5)cccc4C3=O)cccc12] | N-(2-(3-(2-((1,5-dimethyl-1H-pyrazol-3-yl)amino)-5-methylpyrimidin-4-yl)-1H-indol-7-yl)-1-oxoisoindolin-4-yl)cyclopent-3-ene-1-carboxamide |
| 311) | 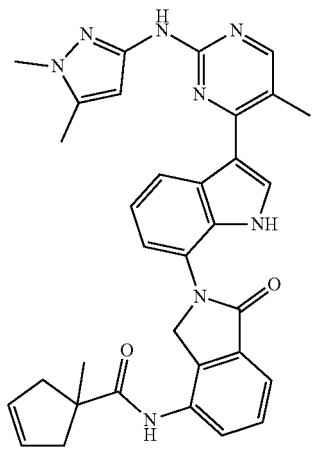 [SMILES: Cc1cnc(Nc2cc(C)n(C)n2)nc1-c1c[nH]c2c(N3Cc4c(NC(=O)C5(C)CC=CC5)cccc4C3=O)cccc12] | N-(2-(3-(2-((1,5-dimethyl-1H-pyrazol-3-yl)amino)-5-methylpyrimidin-4-yl)-1H-indol-7-yl)-1-oxoisoindolin-4-yl)-1-methylcyclopent-3-ene-1-carboxamide |

| | | |
|---|---|---|
| 312) | 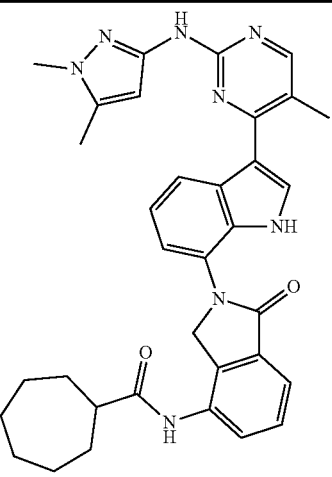 | N-(2-(3-(2-((1,5-dimethyl-1H-pyrazol-3-yl)amino)-5-methylpyrimidin-4-yl)-1H-indol-7-yl)-1-oxoisoindolin-4-yl)cycloheptanecarboxamide |
| 313) | 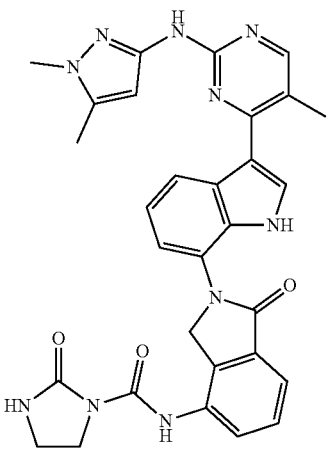 [SMILES: Cc1cnc(Nc2cc(C)n(C)n2)nc1-c1c[nH]c2c(N3Cc4c(NC(=O)N5CCNC5=O)cccc4C3=O)cccc12] | N-(2-(3-(2-((1,5-dimethyl-1H-pyrazol-3-yl)amino)-5-methylpyrimidin-4-yl)-1H-indol-7-yl)-1-oxoisoindolin-4-yl)-2-oxoimidazolidine-1-carboxamide |
| 314) | 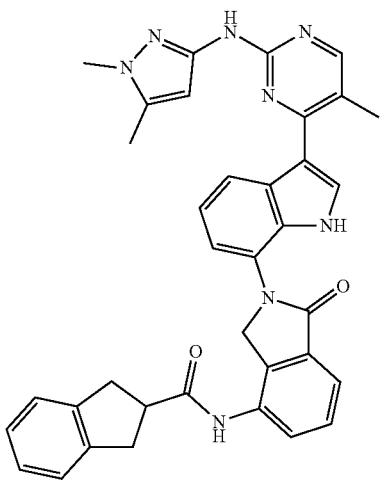 [SMILES: Cc1cnc(Nc2cc(C)n(C)n2)nc1-c1c[nH]c2c(N3Cc4c(NC(=O)C5Cc6ccccc6C5)cccc4C3=O)cccc12] | N-(2-(3-(2-((1,5-dimethyl-1H-pyrazol-3-yl)amino)-5-methylpyrimidin-4-yl)-1H-indol-7-yl)-1-oxoisoindolin-4-yl)-2,3-dihydro-1H-indene-2-carboxamide |

315) 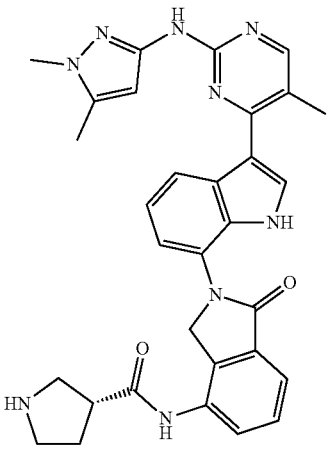 [SMILES: Cc1cnc(Nc2cc(C)n(C)n2)nc1-c1c[nH]c2c(N3Cc4c(NC(=O)[C@@H]5CCNC5)cccc4C3=O)cccc12]
(R)-N-(2-(3-(2-((1,5-dimethyl-1H-pyrazol-3-yl)amino)-5-methylpyrimidin-4-yl)-1H-indol-7-yl)-1-oxoisoindolin-4-yl)pyrrolidine-3-carboxamide
316) 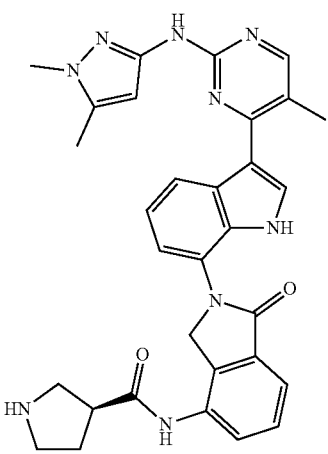 [SMILES: Cc1cnc(Nc2cc(C)n(C)n2)nc1-c1c[nH]c2c(N3Cc4c(NC(=O)[C@H]5CCNC5)cccc4C3=O)cccc12]
(S)-N-(2-(3-(2-((1,5-dimethyl-1H-pyrazol-3-yl)amino)-5-methylpyrimidin-4-yl)-1H-indol-7-yl)-1-oxoisoindolin-4-yl)pyrrolidine-3-carboxamide
317) 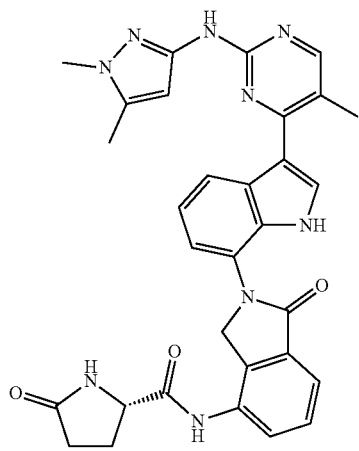 [SMILES: Cc1cnc(Nc2cc(C)n(C)n2)nc1-c1c[nH]c2c(N3Cc4c(NC(=O)[C@@H]5CCC(=O)N5)cccc4C3=O)cccc12]
(S)-N-(2-(3-(2-((1,5-dimethyl-1H-pyrazol-3-yl)amino)-5-methylpyrimidin-4-yl)-1H-indol-7-yl)-1-oxoisoindolin-4-yl)-5-oxopyrrolidine-2-carboxamide

| | | |
|---|---|---|
| 318) | 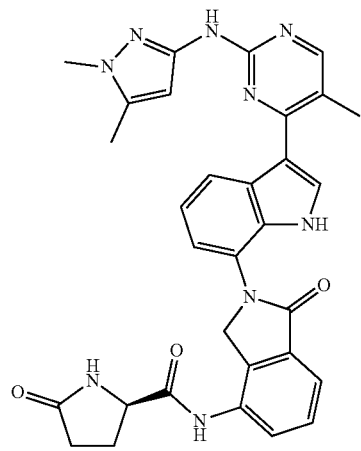 [SMILES: Cc1cnc(Nc2cc(C)n(C)n2)nc1-c1c[nH]c2c(N3Cc4c(NC(=O)[C@H]5CCC(=O)N5)cccc4C3=O)cccc12] | (R)-N-(2-(3-(2-((1,5-dimethyl-1H-pyrazol-3-yl)amino)-5-methylpyrimidin-4-yl)-1H-indol-7-yl)-1-oxoisoindolin-4-yl)-5-oxopyrrolidine-2-carboxamide |
| 319) | 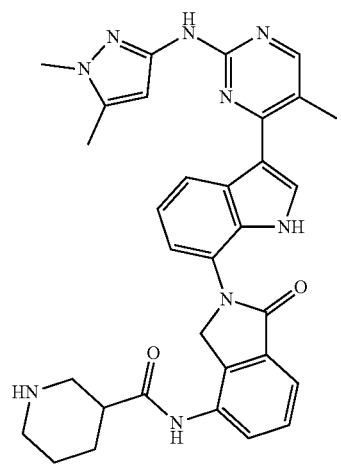 [SMILES: Cc1cnc(Nc2cc(C)n(C)n2)nc1-c1c[nH]c2c(N3Cc4c(NC(=O)C5CCCNC5)cccc4C3=O)cccc12] | N-(2-(3-(2-((1,5-dimethyl-1H-pyrazol-3-yl)amino)-5-methylpyrimidin-4-yl)-1H-indol-7-yl)-1-oxoisoindolin-4-yl)piperidine-3-carboxamide |
| 320) | 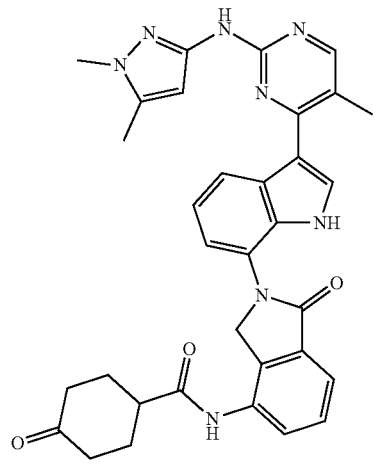 [SMILES: Cc1cnc(Nc2cc(C)n(C)n2)nc1-c1c[nH]c2c(N3Cc4c(NC(=O)C5CCC(=O)CC5)cccc4C3=O)cccc12] | N-(2-(3-(2-((1,5-dimethyl-1H-pyrazol-3-yl)amino)-5-methylpyrimidin-4-yl)-1H-indol-7-yl)-1-oxoisoindolin-4-yl)-4-oxocyclohexane-1-carboxamide |

| | | |
|---|---|---|
| 321) | 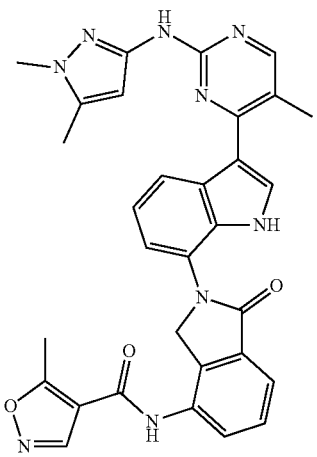 [SMILES: Cc1cnc(Nc2cc(C)n(C)n2)nc1-c1c[nH]c2c(N3Cc4c(NC(=O)c5cnoc5C)cccc4C3=O)cccc12] | N-(2-(3-(2-((1,5-dimethyl-1H-pyrazol-3-yl)amino)-5-methylpyrimidin-4-yl)-1H-indol-7-yl)-1-oxoisoindolin-4-yl)-5-methylisoxazole-4-carboxamide |
| 322) | 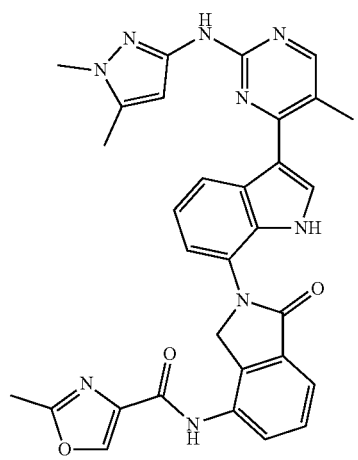 | N-(2-(3-(2-((1,5-dimethyl-1H-pyrazol-3-yl)amino)-5-methylpyrimidin-4-yl)-1H-indol-7-yl)-1-oxoisoindolin-4-yl)-2-methyloxazole-4-carboxamide |
| 323) | 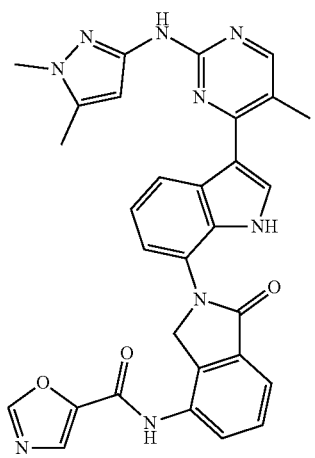 [SMILES: Cc1cnc(Nc2cc(C)n(C)n2)nc1-c1c[nH]c2c(N3Cc4c(NC(=O)c5cnco5)cccc4C3=O)cccc12] | N-(2-(3-(2-((1,5-dimethyl-1H-pyrazol-3-yl)amino)-5-methylpyrimidin-4-yl)-1H-indol-7-yl)-1-oxoisoindolin-4-yl)oxazole-5-carboxamide |

| | | |
|---|---|---|
| 324) | 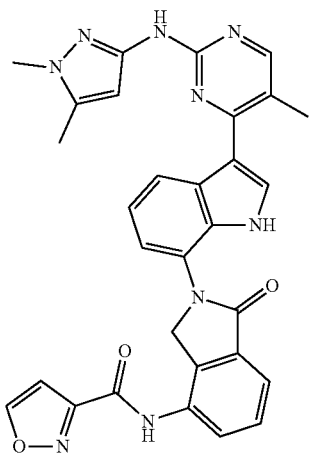 [SMILES: Cc1cnc(Nc2cc(C)n(C)n2)nc1-c1c[nH]c2c(N3Cc4c(NC(=O)c5ccon5)cccc4C3=O)cccc12] | N-(2-(3-(2-((1,5-dimethyl-1H-pyrazol-3-yl)amino)-5-methylpyrimidin-4-yl)-1H-indol-7-yl)-1-oxoisoindolin-4-yl)isoxazole-3-carboxamide |
| 325) | 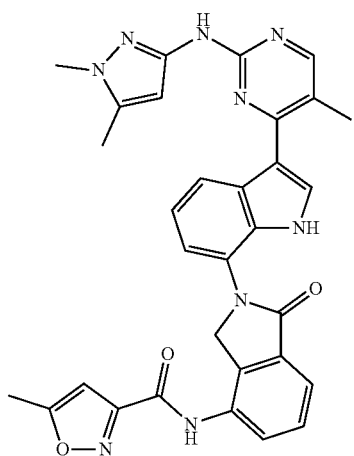 | N-(2-(3-(2-((1,5-dimethyl-1H-pyrazol-3-yl)amino)-5-methylpyrimidin-4-yl)-1H-indol-7-yl)-1-oxoisoindolin-4-yl)-5-methylisoxazole-3-carboxamide |
| 326) | 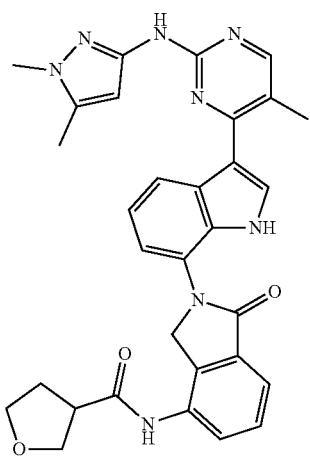 [SMILES: Cc1cnc(Nc2cc(C)n(C)n2)nc1-c1c[nH]c2c(N3Cc4c(NC(=O)C5CCOC5)cccc4C3=O)cccc12] | N-(2-(3-(2-((1,5-dimethyl-1H-pyrazol-3-yl)amino)-5-methylpyrimidin-4-yl)-1H-indol-7-yl)-1-oxoisoindolin-4-yl)tetrahydrofuran-3-carboxamide |

-continued
327) 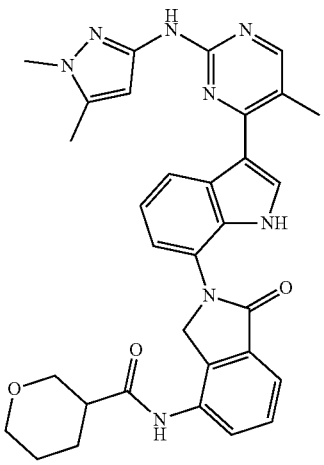 [SMILES: Cc1cnc(Nc2cc(C)n(C)n2)nc1-c1c[nH]c2c(N3Cc4c(NC(=O)C5CCCOC5)cccc4C3=O)cccc12] N-(2-(3-(2-((1,5-dimethyl-1H-pyrazol-3-yl)amino)-5-methylpyrimidin-4-yl)-1H-indol-7-yl)-1-oxoisoindolin-4-yl)tetrahydro-2H-pyran-3-carboxamide
328) 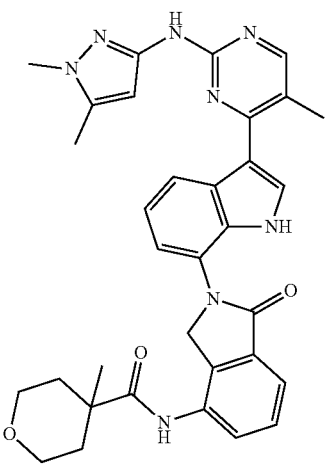 [SMILES: Cc1cnc(Nc2cc(C)n(C)n2)nc1-c1c[nH]c2c(N3Cc4c(NC(=O)C5(C)CCOCC5)cccc4C3=O)cccc12] N-(2-(3-(2-((1,5-dimethyl-1H-pyrazol-3-yl)amino)-5-methylpyrimidin-4-yl)-1H-indol-7-yl)-1-oxoisoindolin-4-yl)-4-methyltetrahydro-2H-pyran-4-carboxamide
329) 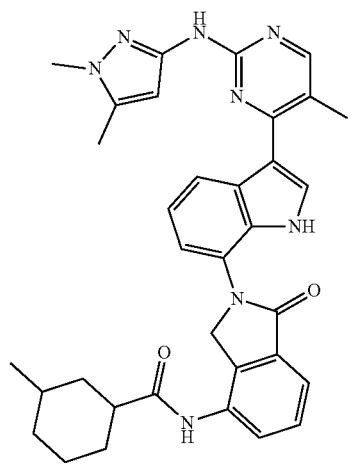 N-(2-(3-(2-((1,5-dimethyl-1H-pyrazol-3-yl)amino)-5-methylpyrimidin-4-yl)-1H-indol-7-yl)-1-oxoisoindolin-4-yl)-3-methylcyclohexane-1-carboxamide 330) 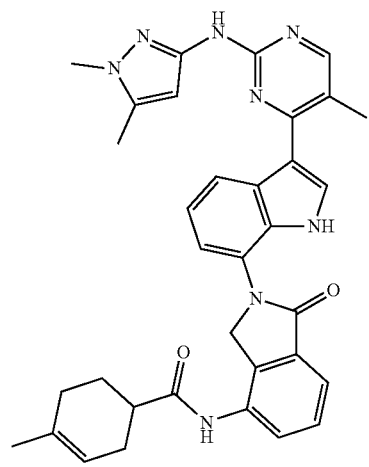
N-(2-(3-(2-((1,5-dimethyl-1H-pyrazol-3-yl)amino)-5-methylpyrimidin-4-yl)-1H-indol-7-yl)-1-oxoisoindolin-4-yl)-4-methylcyclohex-3-ene-1-carboxamide
331) 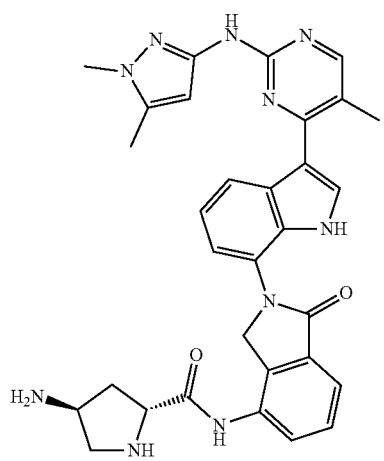 [SMILES: Cc1cnc(Nc2cc(C)n(C)n2)nc1-c1c[nH]c2c(N3Cc4c(NC(=O)[C@H]5C[C@H](N)CN5)cccc4C3=O)cccc12]
(2R,4S)-4-amino-N-(2-(3-(2-((1,5-dimethyl-1H-pyrazol-3-yl)amino)-5-methylpyrimidin-4-yl)-1H-indol-7-yl)-1-oxoisoindolin-4-yl)pyrrolidine-2-carboxamide
332) 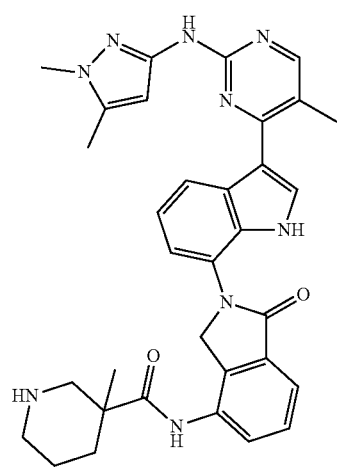 [SMILES: Cc1cnc(Nc2cc(C)n(C)n2)nc1-c1c[nH]c2c(N3Cc4c(NC(=O)C5(C)CCCNC5)cccc4C3=O)cccc12]
N-(2-(3-(2-((1,5-dimethyl-1H-pyrazol-3-yl)amino)-5-methylpyrimidin-4-yl)-1H-indol-7-yl)-1-oxoisoindolin-4-yl)-3-methylpiperidine-3-carboxamide 333) 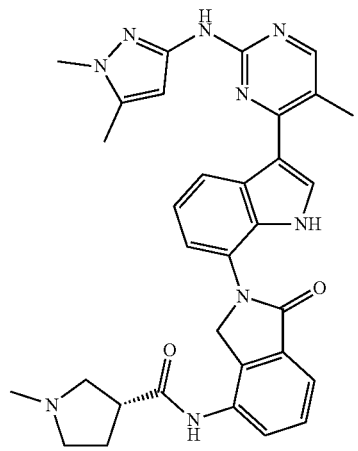
(R)-N-(2-(3-(2-((1,5-dimethyl-1H-pyrazol-3-yl)amino)-5-methylpyrimidin-4-yl)-1H-indol-7-yl)-1-oxoisoindolin-4-yl)-1-methylpyrrolidine-3-carboxamide
334) 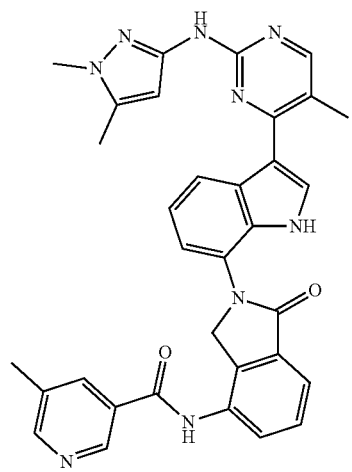
N-(2-(3-(2-((1,5-dimethyl-1H-pyrazol-3-yl)amino)-5-methylpyrimidin-4-yl)-1H-indol-7-yl)-1-oxoisoindolin-4-yl)-5-methylnicotinamide
335) 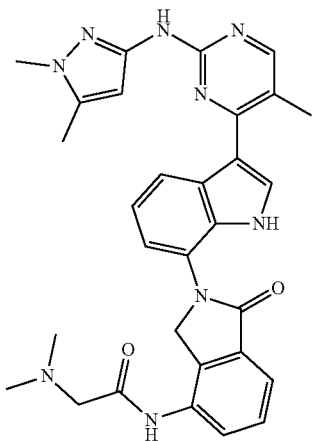
N-(2-(3-(2-((1,5-dimethyl-1H-pyrazol-3-yl)amino)-5-methylpyrimidin-4-yl)-1H-indol-7-yl)-1-oxoisoindolin-4-yl)-2-(dimethylamino)acetamide -continued
336) 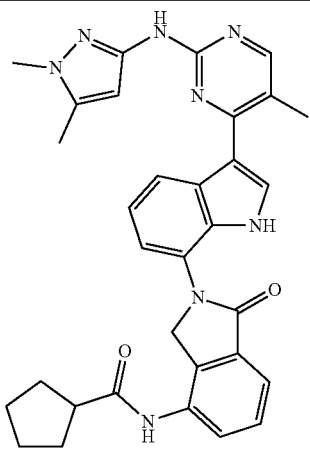
N-(2-(3-(2-((1,5-dimethyl-1H-pyrazol-3-yl)amino)-5-methylpyrimidin-4-yl)-1H-indol-7-yl)-1-oxoisoindolin-4-yl)cyclopentanecarboxamide
337) 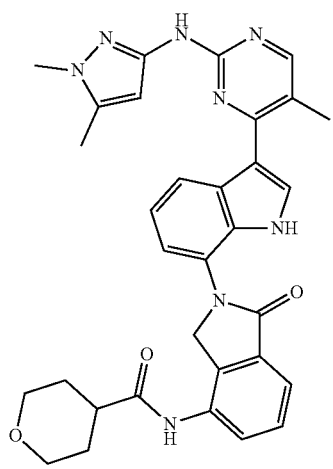 [SMILES: Cc1cnc(Nc2cc(C)n(C)n2)nc1-c1c[nH]c2c(N3Cc4c(NC(=O)C5CCOCC5)cccc4C3=O)cccc12]
N-(2-(3-(2-((1,5-dimethyl-1H-pyrazol-3-yl)amino)-5-methylpyrimidin-4-yl)-1H-indol-7-yl)-1-oxoisoindolin-4-yl)tetrahydro-2H-pyran-4-carboxamide
338) 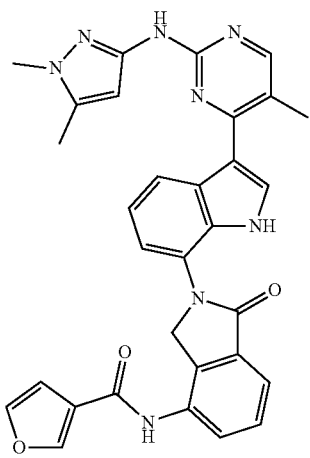 [SMILES: Cc1cnc(Nc2cc(C)n(C)n2)nc1-c1c[nH]c2c(N3Cc4c(NC(=O)c5ccoc5)cccc4C3=O)cccc12]
N-(2-(3-(2-((1,5-dimethyl-1H-pyrazol-3-yl)amino)-5-methylpyrimidin-4-yl)-1H-indol-7-yl)-1-oxoisoindolin-4-yl)furan-3-carboxamide 339) 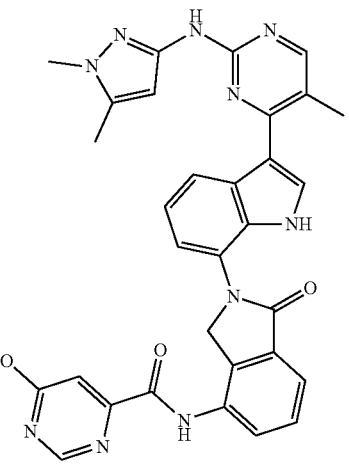
N-(2-(3-(2-((1,5-dimethyl-1H-pyrazol-3-yl)amino)-5-methylpyrimidin-4-yl)-1H-indol-7-yl)-1-oxoisoindolin-4-yl)-6-hydroxypyrimidine-4-carboxamide
340) 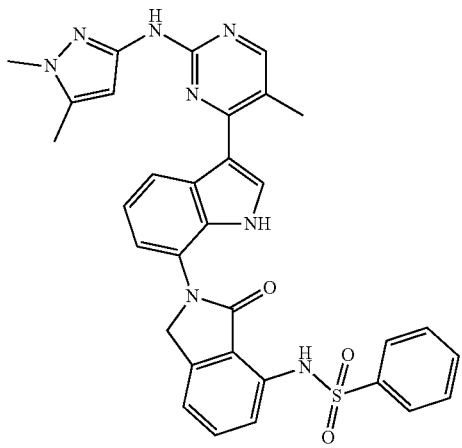 [SMILES: Cc1cnc(Nc2cc(C)n(C)n2)nc1-c1c[nH]c2c(N3Cc4cccc(NS(=O)(=O)c5ccccc5)c4C3=O)cccc12]
N-(2-(3-(2-((1,5-dimethyl-1H-pyrazol-3-yl)amino)-5-methylpyrimidin-4-yl)-1H-indol-7-yl)-3-oxoisoindolin-4-yl)benzenesulfonamide
341) 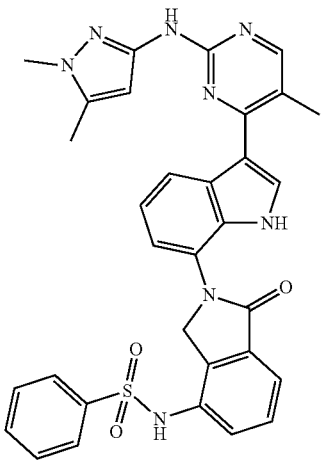 [SMILES: Cc1cnc(Nc2cc(C)n(C)n2)nc1-c1c[nH]c2c(N3Cc4c(NS(=O)(=O)c5ccccc5)cccc4C3=O)cccc12]
N-(2-(3-(2-((1,5-dimethyl-1H-pyrazol-3-yl)amino)-5-methylpyrimidin-4-yl)-1H-indol-7-yl)-1-oxoisoindolin-4-yl)benzenesulfonamide 342) 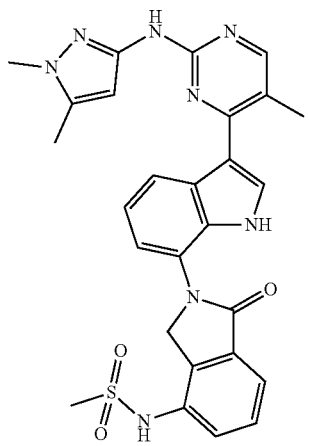 N-(2-(3-(2-((1,5-dimethyl-1H-pyrazol-3-yl)amino)-5-methylpyrimidin-4-yl)-1H-indol-7-yl)-1-oxoisoindolin-4-yl)methanesulfonamide
343) 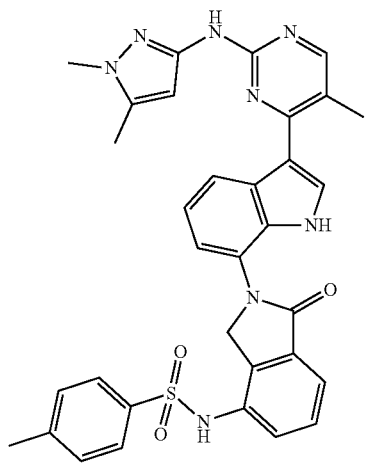 N-(2-(3-(2-((1,5-dimethyl-1H-pyrazol-3-yl)amino)-5-methylpyrimidin-4-yl)-1H-indol-7-yl)-1-oxoisoindolin-4-yl)-4-methylbenzenesulfonamide
344) 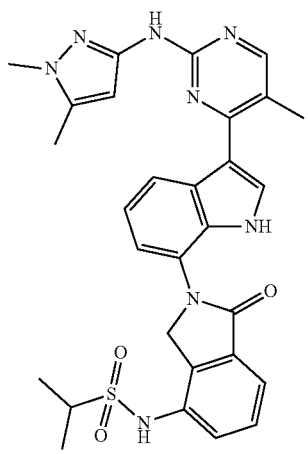 N-(2-(3-(2-((1,5-dimethyl-1H-pyrazol-3-yl)amino)-5-methylpyrimidin-4-yl)-1H-indol-7-yl)-1-oxoisoindolin-4-yl)propane-2-sulfonamide -continued
345) 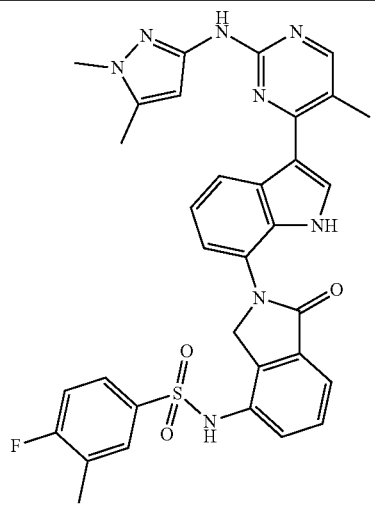
N-(2-(3-(2-((1,5-dimethyl-1H-pyrazol-3-yl)amino)-5-methylpyrimidin-4-yl)-1H-indol-7-yl)-1-oxoisoindolin-4-yl)-4-fluoro-3-methylbenzenesulfonamide
346) 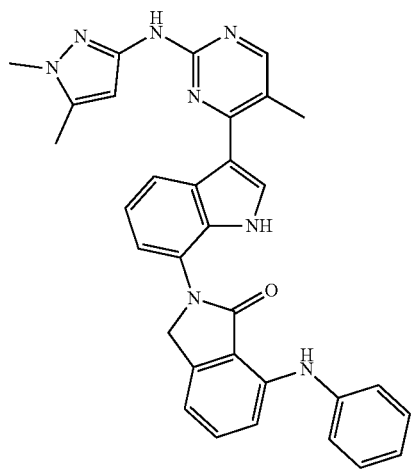 [SMILES: Cc1cnc(Nc2cc(C)n(C)n2)nc1-c1c[nH]c2c(N3Cc4cccc(Nc5ccccc5)c4C3=O)cccc12]
2-(3-(2-((1,5-dimethyl-1H-pyrazol-3-yl)amino)-5-methylpyrimidin-4-yl)-1H-indol-7-yl)-7-(phenylamino)isoindolin-1-one
347) 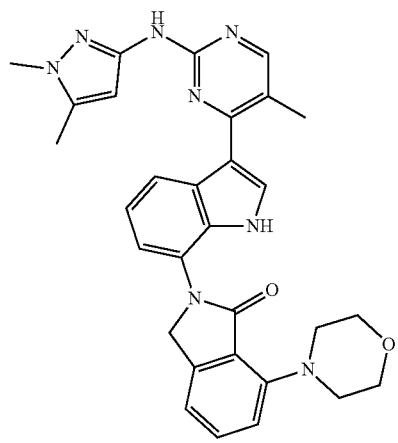 [SMILES: Cc1cnc(Nc2cc(C)n(C)n2)nc1-c1c[nH]c2c(N3Cc4cccc(N5CCOCC5)c4C3=O)cccc12]
2-(3-(2-((1,5-dimethyl-1H-pyrazol-3-yl)amino)-5-methylpyrimidin-4-yl)-1H-indol-7-yl)-7-morpholinoisoindolin-1-one

| | | |
|---|---|---|
| 348) | 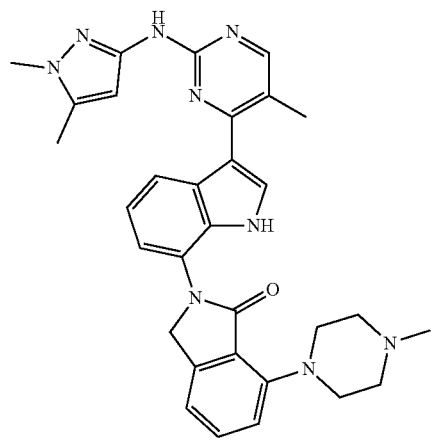 | 2-(3-(2-((1,5-dimethyl-1H-pyrazol-3-yl)amino)-5-methylpyrimidin-4-yl)-1H-indol-7-yl)-7-(4-methylpiperazin-1-yl)isoindolin-1-one |
| 349) | 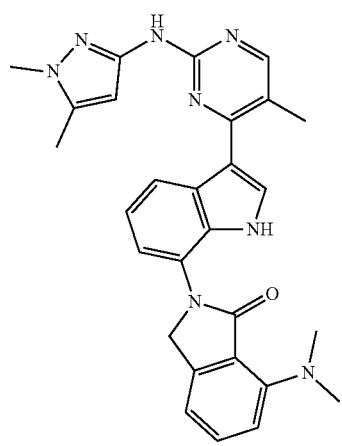 | 2-(3-(2-((1,5-dimethyl-1H-pyrazol-3-yl)amino)-5-methylpyrimidin-4-yl)-1H-indol-7-yl)-7-(dimethylamino)isoindolin-1-one |
| 350) | 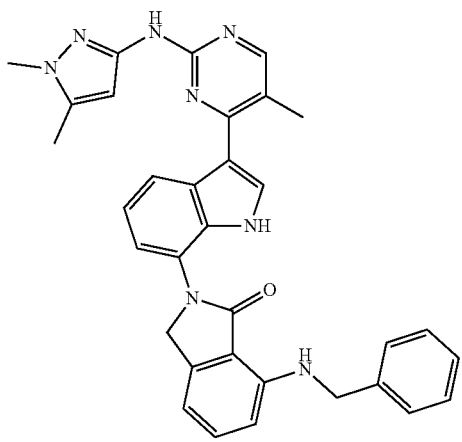 [SMILES: Cc1cnc(Nc2cc(C)n(C)n2)nc1-c1c[nH]c2c(N3Cc4cccc(NCc5ccccc5)c4C3=O)cccc12] | 7-(benzylamino)-2-(3-(2-((1,5-dimethyl-1H-pyrazol-3-yl)amino)-5-methylpyrimidin-4-yl)-1H-indol-7-yl)isoindolin-1-one |

| | | |
|---|---|---|
| 351) | 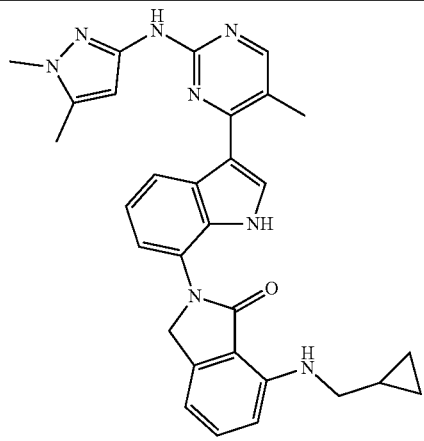 | 7-((cyclopropylmethyl)amino)-2-(3-(2-((1,5-dimethyl-1H-pyrazol-3-yl)amino)-5-methylpyrimidin-4-yl)-1H-indol-7-yl)isoindolin-1-one |
| 352) | 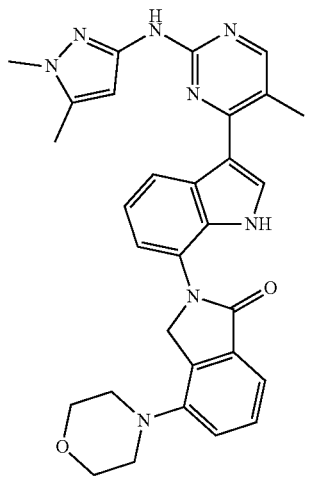 | 2-(3-(2-((1,5-dimethyl-1H-pyrazol-3-yl)amino)-5-methylpyrimidin-4-yl)-1H-indol-7-yl)-4-morpholinoisoindolin-1-one |
| 353) | 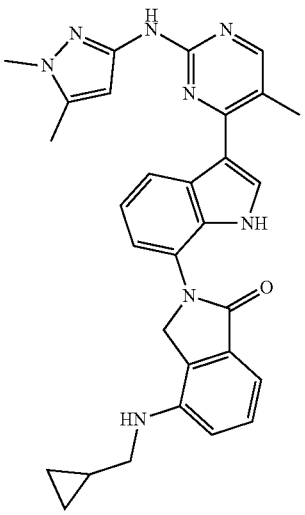 | 4-((cyclopropylmethyl)amino)-2-(3-(2-((1,5-dimethyl-1H-pyrazol-3-yl)amino)-5-methylpyrimidin-4-yl)-1H-indol-7-yl)isoindolin-1-one |

-continued
354) 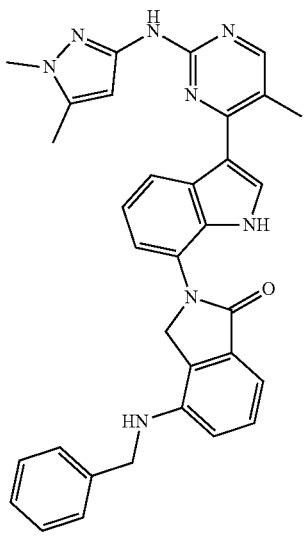 4-(benzylamino)-2-(3-(2-((1,5-dimethyl-1H-pyrazol-3-yl)amino)-5-methylpyrimidin-4-yl)-1H-indol-7-yl)isoindolin-1-one
355) 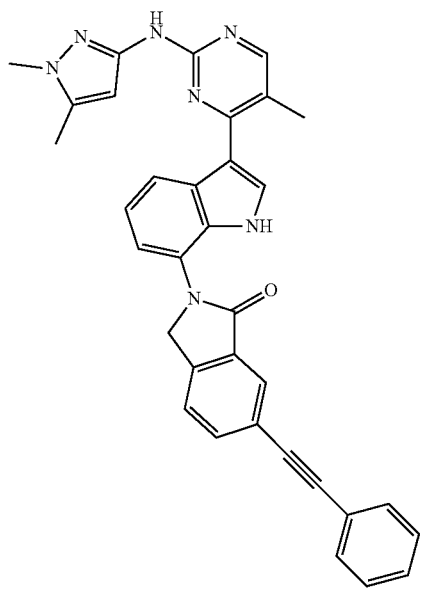 [SMILES: Cc1cnc(Nc2cc(C)n(C)n2)nc1-c1c[nH]c2c(N3Cc4ccc(C#Cc5ccccc5)cc4C3=O)cccc12] 2-(3-(2-((1,5-dimethyl-1H-pyrazol-3-yl)amino)-5-methylpyrimidin-4-yl)-1H-indol-7-yl)-6-(phenylethynyl)isoindolin-1-one
356) 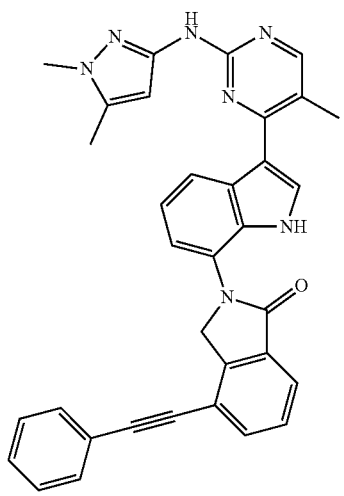 [SMILES: Cc1cnc(Nc2cc(C)n(C)n2)nc1-c1c[nH]c2c(N3Cc4c(C#Cc5ccccc5)cccc4C3=O)cccc12] 2-(3-(2-((1,5-dimethyl-1H-pyrazol-3-yl)amino)-5-methylpyrimidin-4-yl)-1H-indol-7-yl)-4-(phenylethynyl)isoindolin-1-one

| | | |
|---|---|---|
| 357) | 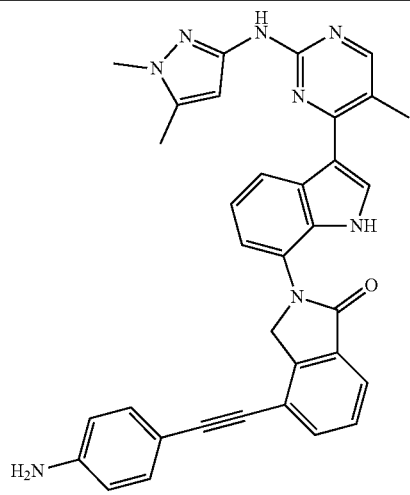 | 4-((4-aminophenyl)ethynyl)-2-(3-(2-((1,5-dimethyl-1H-pyrazol-3-yl)amino)-5-methylpyrimidin-4-yl)-1H-indol-7-yl)isoindolin-1-one |
| 358) | 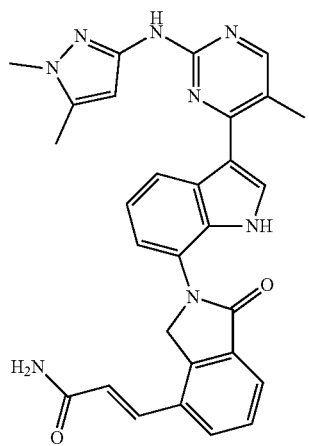 | (E)-3-(2-(3-(2-((1,5-dimethyl-1H-pyrazol-3-yl)amino)-5-methylpyrimidin-4-yl)-1H-indol-7-yl)-1-oxoisoindolin-4-yl)acrylamide |
| 359) | 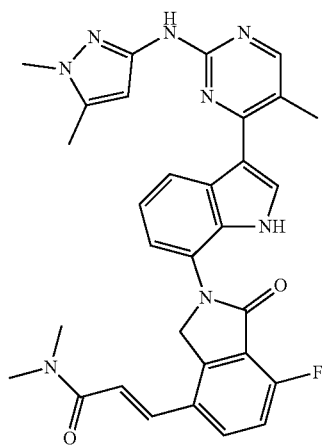 | (E)-3-(2-(3-(2-((1,5-dimethyl-1H-pyrazol-3-yl)amino)-5-methylpyrimidin-4-yl)-1H-indol-7-yl)-7-fluoro-1-oxoisoindolin-4-yl)-N,N-dimethylacrylamide |

360) 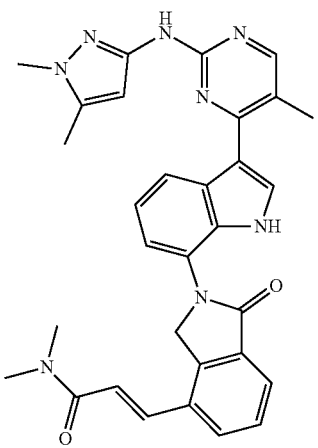
(E)-3-(2-(3-(2-((1,5-dimethyl-1H-pyrazol-3-yl)amino)-5-methylpyrimidin-4-yl)-1H-indol-7-yl)-1-oxoisoindolin-4-yl)-N,N-dimethylacrylamide
361) 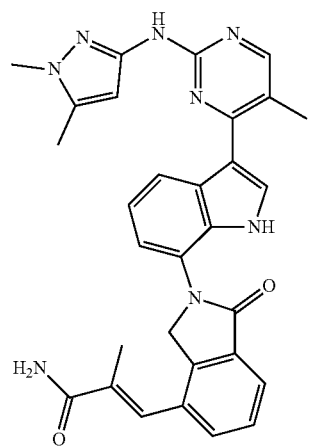
(E)-3-(2-(3-(2-((1,5-dimethyl-1H-pyrazol-3-yl)amino)-5-methylpyrimidin-4-yl)-1H-indol-7-yl)-1-oxoisoindolin-4-yl)-2-methylacrylamide
362) 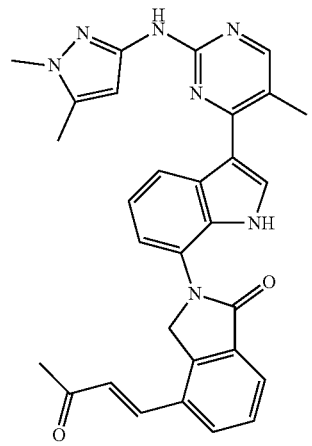
(E)-2-(3-(2-((1,5-dimethyl-1H-pyrazol-3-yl)amino)-5-methylpyrimidin-4-yl)-1H-indol-7-yl)-4-(3-oxobut-1-en-1-yl)isoindolin-1-one

| | | |
|---|---|---|
| 363) | 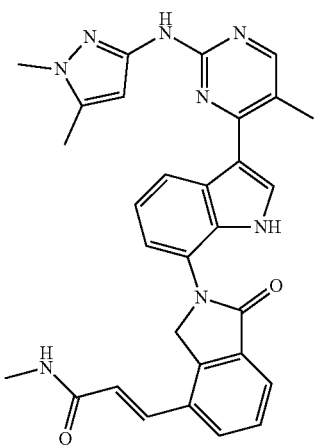 | (E)-3-(2-(3-(2-((1,5-dimethyl-1H-pyrazol-3-yl)amino)-5-methylpyrimidin-4-yl)-1H-indol-7-yl)-1-oxoisoindolin-4-yl)-N-methylacrylamide |
| 364) | 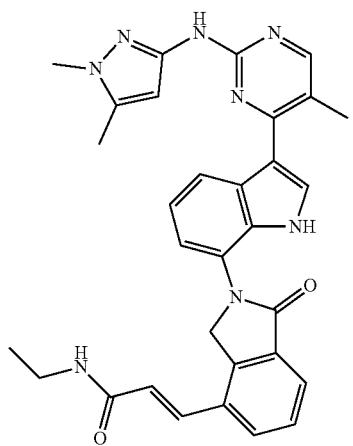 [SMILES: CCNC(=O)/C=C/c1cccc2c1CN(c1cccc3c(-c4nc(Nc5cc(C)n(C)n5)ncc4C)c[nH]c13)C2=O] | (E)-3-(2-(3-(2-((1,5-dimethyl-1H-pyrazol-3-yl)amino)-5-methylpyrimidin-4-yl)-1H-indol-7-yl)-1-oxoisoindolin-4-yl)-N-ethylacrylamide |
| 365) | 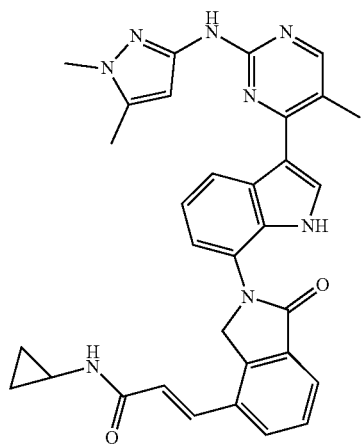 [SMILES: Cc1cnc(Nc2cc(C)n(C)n2)nc1-c1c[nH]c2c(N3Cc4c(/C=C/C(=O)NC5CC5)cccc4C3=O)cccc12] | (E)-N-cyclopropyl-3-(2-(3-(2-((1,5-dimethyl-1H-pyrazol-3-yl)amino)-5-methylpyrimidin-4-yl)-1H-indol-7-yl)-1-oxoisoindolin-4-yl)acrylamide |

-continued
366) 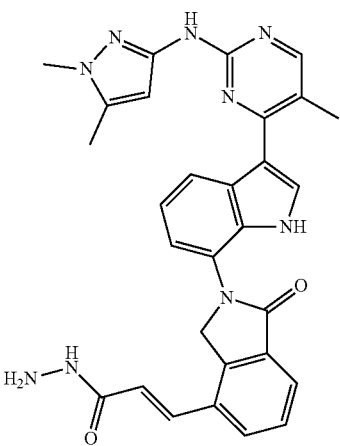 [SMILES: Cc1cnc(Nc2cc(C)n(C)n2)nc1-c1c[nH]c2c(N3Cc4c(/C=C/C(=O)NN)cccc4C3=O)cccc12] (E)-3-(2-(3-(2-((1,5-dimethyl-1H-pyrazol-3-yl)amino)-5-methylpyrimidin-4-yl)-1H-indol-7-yl)-1-oxoisoindolin-4-yl)acrylohydrazide
367) 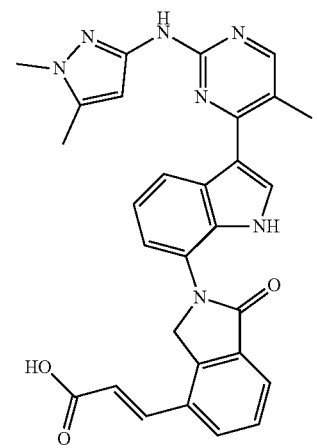 (E)-3-(2-(3-(2-((1,5-dimethyl-1H-pyrazol-3-yl)amino)-5-methylpyrimidin-4-yl)-1H-indol-7-yl)-1-oxoisoindolin-4-yl)acrylic acid
368) 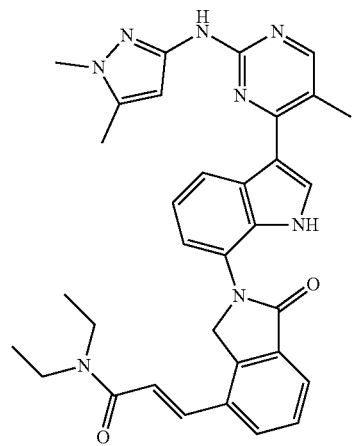 [SMILES: CCN(CC)C(=O)/C=C/c1cccc2c1CN(c1cccc3c(-c4nc(Nc5cc(C)n(C)n5)ncc4C)c[nH]c13)C2=O] (E)-3-(2-(3-(2-((1,5-dimethyl-1H-pyrazol-3-yl)amino)-5-methylpyrimidin-4-yl)-1H-indol-7-yl)-1-oxoisoindolin-4-yl)-N,N-diethylacrylamide

| | | |
|---|---|---|
| 369) | 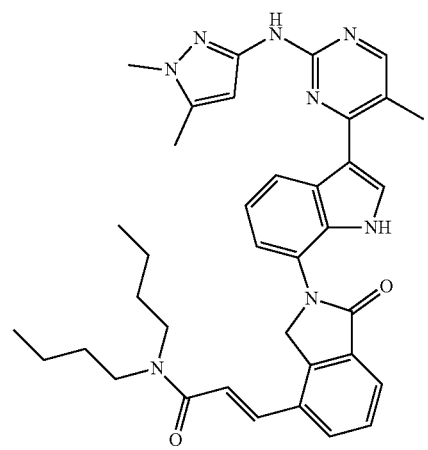 [SMILES: CCCCN(CCCC)C(=O)/C=C/c1cccc2c1CN(c1cccc3c(-c4nc(Nc5cc(C)n(C)n5)ncc4C)c[nH]c13)C2=O] | (E)-N,N-dibutyl-3-(2-(3-(2-((1,5-dimethyl-1H-pyrazol-3-yl)amino)-5-methylpyrimidin-4-yl)-1H-indol-7-yl)-1-oxoisoindolin-4-yl)acrylamide |
| 370) | 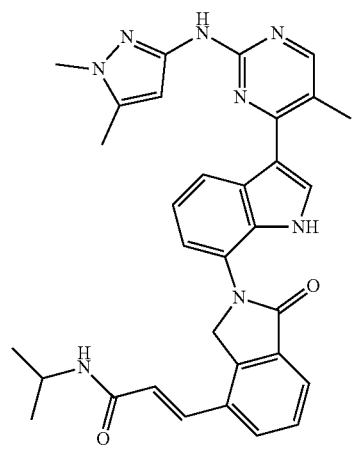 [SMILES: Cc1cnc(Nc2cc(C)n(C)n2)nc1-c1c[nH]c2c(N3Cc4c(/C=C/C(=O)NC(C)C)cccc4C3=O)cccc12] | (E)-3-(2-(3-(2-((1,5-dimethyl-1H-pyrazol-3-yl)amino)-5-methylpyrimidin-4-yl)-1H-indol-7-yl)-1-oxoisoindolin-4-yl)-N-isopropylacrylamide |
| 371) | 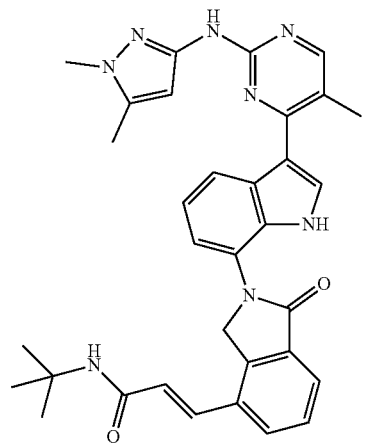 [SMILES: Cc1cnc(Nc2cc(C)n(C)n2)nc1-c1c[nH]c2c(N3Cc4c(/C=C/C(=O)NC(C)(C)C)cccc4C3=O)cccc12] | (E)-N-(tert-butyl)-3-(2-(3-(2-((1,5-dimethyl-1H-pyrazol-3-yl)amino)-5-methylpyrimidin-4-yl)-1H-indol-7-yl)-1-oxoisoindolin-4-yl)acrylamide |

372) 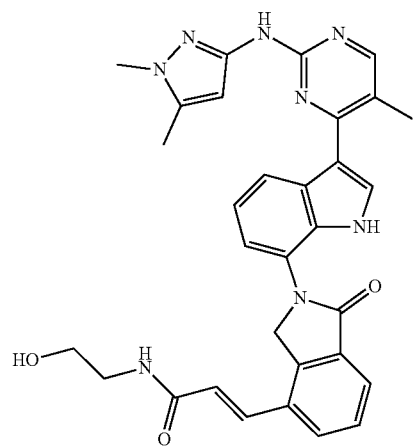 [SMILES: Cc1cnc(Nc2cc(C)n(C)n2)nc1-c1c[nH]c2c(N3Cc4c(/C=C/C(=O)NCCO)cccc4C3=O)cccc12]
(E)-3-(2-(3-(2-((1,5-dimethyl-1H-pyrazol-3-yl)amino)-5-methylpyrimidin-4-yl)-1H-indol-7-yl)-1-oxoisoindolin-4-yl)-N-(2-hydroxyethyl)acrylamide
373) 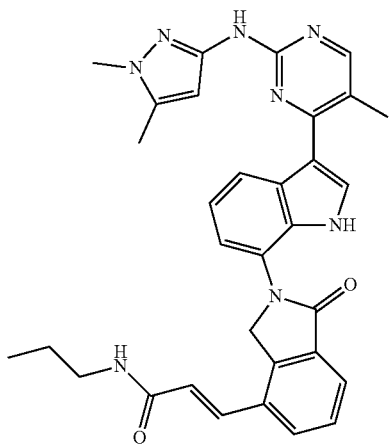 [SMILES: CCCNC(=O)/C=C/c1cccc2c1CN(c1cccc3c(-c4nc(Nc5cc(C)n(C)n5)ncc4C)c[nH]c13)C2=O]
(E)-3-(2-(3-(2-((1,5-dimethyl-1H-pyrazol-3-yl)amino)-5-methylpyrimidin-4-yl)-1H-indol-7-yl)-1-oxoisoindolin-4-yl)-N-propylacrylamide
374) 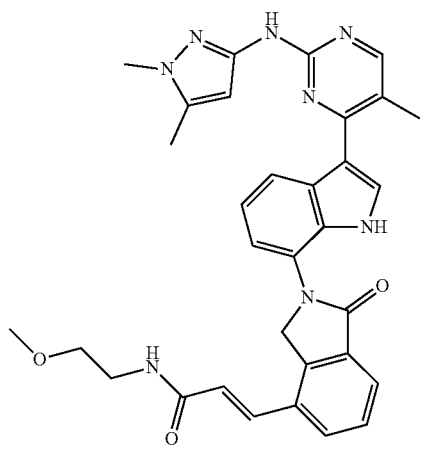
(E)-3-(2-(3-(2-((1,5-dimethyl-1H-pyrazol-3-yl)amino)-5-methylpyrimidin-4-yl)-1H-indol-7-yl)-1-oxoisoindolin-4-yl)-N-(2-methoxyethyl)acrylamide

| | | |
|---|---|---|
| 375) | 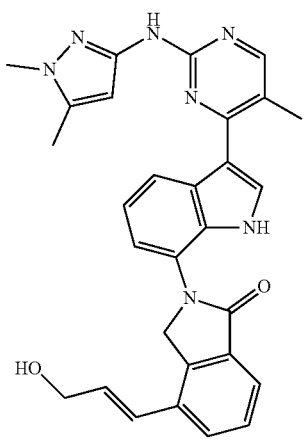 | (E)-2-(3-(2-((1,5-dimethyl-1H-pyrazol-3-yl)amino)-5-methylpyrimidin-4-yl)-1H-indol-7-yl)-4-(3-hydroxyprop-1-en-1-yl)isoindolin-1-one |
| 376) | 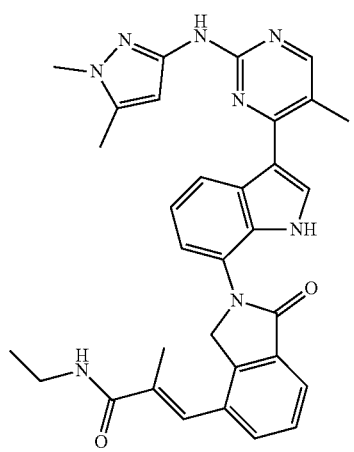 [SMILES: CCNC(=O)/C(C)=C/c1cccc2c1CN(c1cccc3c(-c4nc(Nc5cc(C)n(C)n5)ncc4C)c[nH]c13)C2=O] | (E)-3-(2-(3-(2-((1,5-dimethyl-1H-pyrazol-3-yl)amino)-5-methylpyrimidin-4-yl)-1H-indol-7-yl)-1-oxoisoindolin-4-yl)-N-ethyl-2-methylacrylamide |
| 377) | 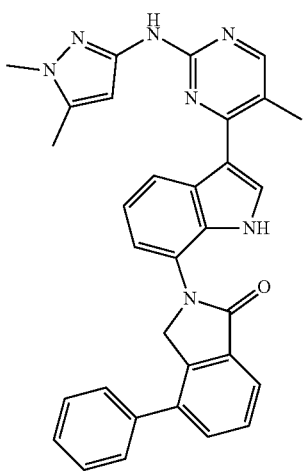 | 2-(3-(2-((1,5-dimethyl-1H-pyrazol-3-yl)amino)-5-methylpyrimidin-4-yl)-1H-indol-7-yl)-4-phenylisoindolin-1-one |

378) 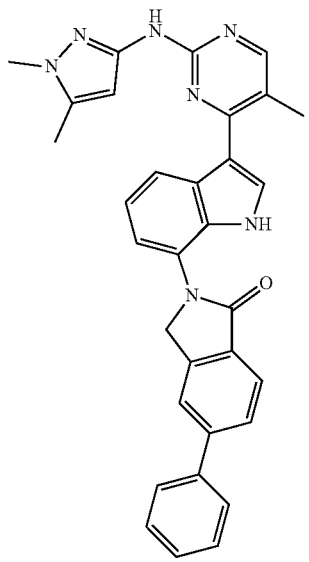
2-(3-(2-((1,5-dimethyl-1H-pyrazol-3-yl)amino)-5-methylpyrimidin-4-yl)-1H-indol-7-yl)-5-phenylisoindolin-1-one
379) 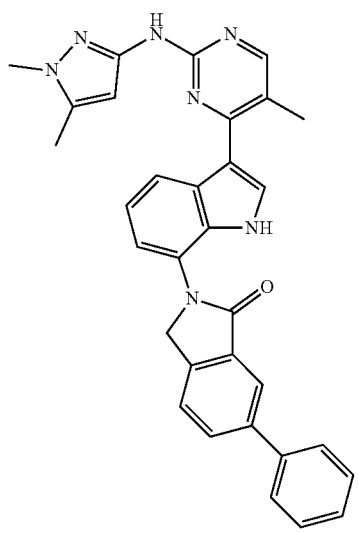 [SMILES: Cc1cnc(Nc2cc(C)n(C)n2)nc1-c1c[nH]c2c(N3Cc4ccc(-c5ccccc5)cc4C3=O)cccc12]
2-(3-(2-((1,5-dimethyl-1H-pyrazol-3-yl)amino)-5-methylpyrimidin-4-yl)-1H-indol-7-yl)-6-phenylisoindolin-1-one
380) 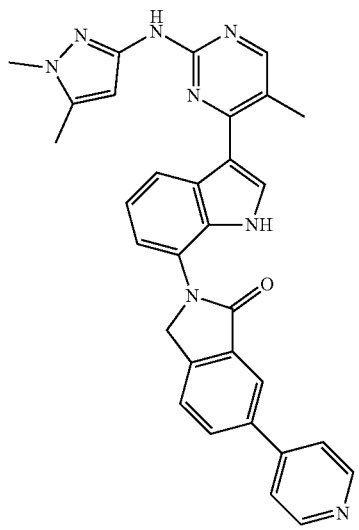 [SMILES: Cc1cnc(Nc2cc(C)n(C)n2)nc1-c1c[nH]c2c(N3Cc4ccc(-c5ccncc5)cc4C3=O)cccc12]
2-(3-(2-((1,5-dimethyl-1H-pyrazol-3-yl)amino)-5-methylpyrimidin-4-yl)-1H-indol-7-yl)-6-(pyridin-4-yl)isoindolin-1-one -continued
381) 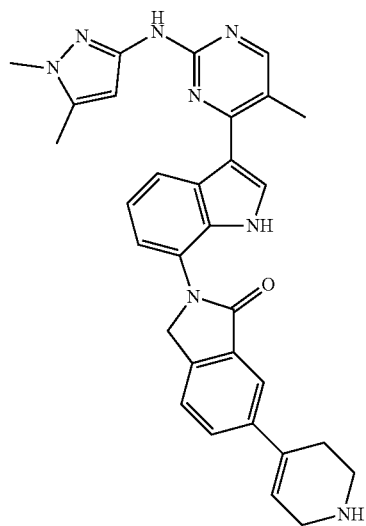 [SMILES: Cc1cnc(Nc2cc(C)n(C)n2)nc1-c1c[nH]c2c(N3Cc4ccc(C5=CCNCC5)cc4C3=O)cccc12]
2-(3-(2-((1,5-dimethyl-1H-pyrazol-3-yl)amino)-5-methylpyrimidin-4-yl)-1H-indol-7-yl)-6-(1,2,3,6-tetrahydropyridin-4-yl)isoindolin-1-one
382) 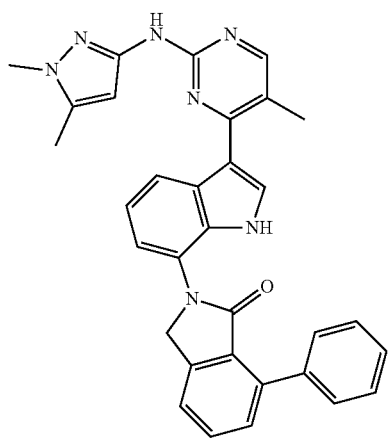 [SMILES: Cc1cnc(Nc2cc(C)n(C)n2)nc1-c1c[nH]c2c(N3Cc4cccc(-c5ccccc5)c4C3=O)cccc12]
2-(3-(2-((1,5-dimethyl-1H-pyrazol-3-yl)amino)-5-methylpyrimidin-4-yl)-1H-indol-7-yl)-7-phenylisoindolin-1-one
383) 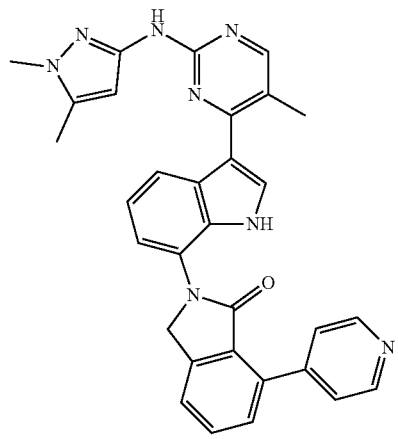 [SMILES: Cc1cnc(Nc2cc(C)n(C)n2)nc1-c1c[nH]c2c(N3Cc4cccc(-c5ccncc5)c4C3=O)cccc12]
2-(3-(2-((1,5-dimethyl-1H-pyrazol-3-yl)amino)-5-methylpyrimidin-4-yl)-1H-indol-7-yl)-7-(pyridin-4-yl)isoindolin-1-one 384) 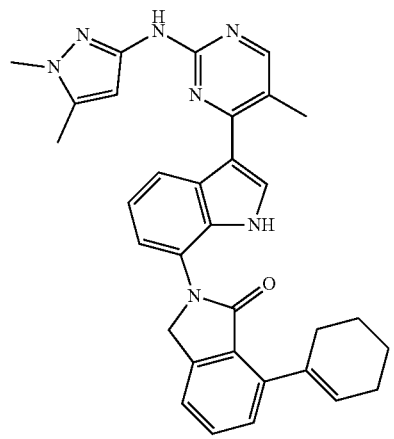 [SMILES: Cc1cnc(Nc2cc(C)n(C)n2)nc1-c1c[nH]c2c(N3Cc4cccc(C5=CCCCC5)c4C3=O)cccc12]
7-(cyclohex-1-en-1-yl)-2-(3-(2-((1,5-dimethyl-1H-pyrazol-3-yl)amino)-5-methylpyrimidin-4-yl)-1H-indol-7-yl)isoindolin-1-one
385) 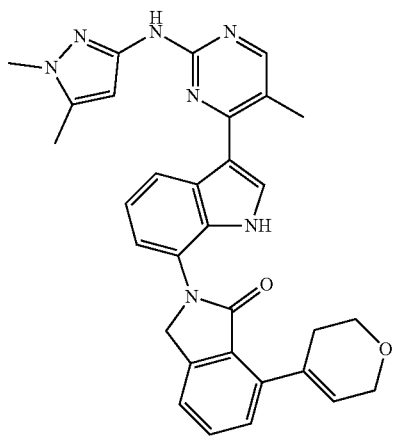 [SMILES: Cc1cnc(Nc2cc(C)n(C)n2)nc1-c1c[nH]c2c(N3Cc4cccc(C5=CCOCC5)c4C3=O)cccc12]
7-(3,6-dihydro-2H-pyran-4-yl)-2-(3-(2-((1,5-dimethyl-1H-pyrazol-3-yl)amino)-5-methylpyrimidin-4-yl)-1H-indol-7-yl)isoindolin-1-one
386) 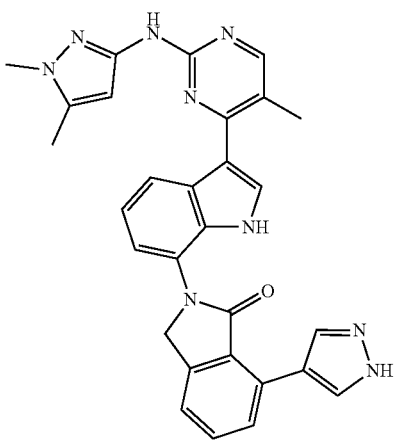 [SMILES: Cc1cnc(Nc2cc(C)n(C)n2)nc1-c1c[nH]c2c(N3Cc4cccc(-c5cn[nH]c5)c4C3=O)cccc12]
2-(3-(2-((1,5-dimethyl-1H-pyrazol-3-yl)amino)-5-methylpyrimidin-4-yl)-1H-indol-7-yl)-7-(1H-pyrazol-4-yl)isoindolin-1-one 387) 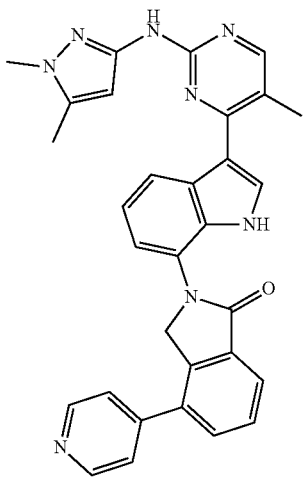
2-(3-(2-((1,5-dimethyl-1H-pyrazol-3-yl)amino)-5-methylpyrimidin-4-yl)-1H-indol-7-yl)-4-(pyridin-4-yl)isoindolin-1-one
388) 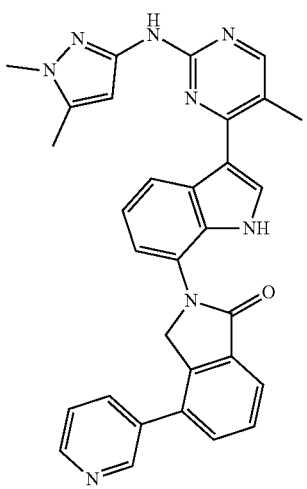
2-(3-(2-((1,5-dimethyl-1H-pyrazol-3-yl)amino)-5-methylpyrimidin-4-yl)-1H-indol-7-yl)-4-(pyridin-3-yl)isoindolin-1-one
389) 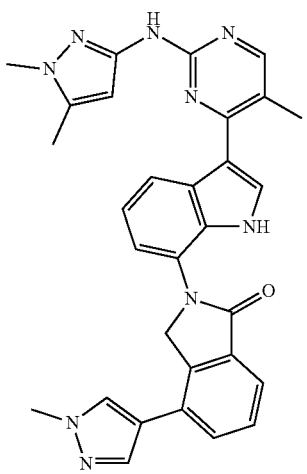
2-(3-(2-((1,5-dimethyl-1H-pyrazol-3-yl)amino)-5-methylpyrimidin-4-yl)-1H-indol-7-yl)-4-(1-methyl-1H-pyrazol-4-yl)isoindolin-1-one -continued
390) 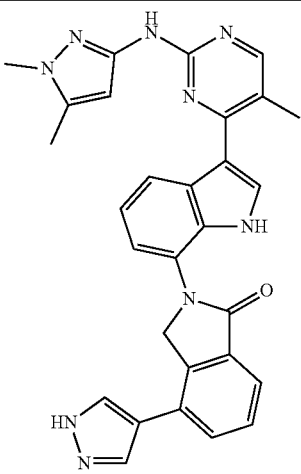
2-(3-(2-((1,5-dimethyl-1H-pyrazol-3-yl)amino)-5-methylpyrimidin-4-yl)-1H-indol-7-yl)-4-(1H-pyrazol-4-yl)isoindolin-1-one
391) 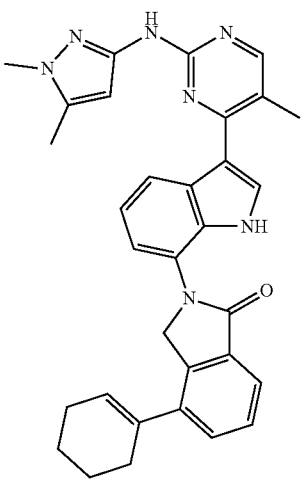
4-(cyclohex-1-en-1-yl)-2-(3-(2-((1,5-dimethyl-1H-pyrazol-3-yl)amino)-5-methylpyrimidin-4-yl)-1H-indol-7-yl)isoindolin-1-one
392) 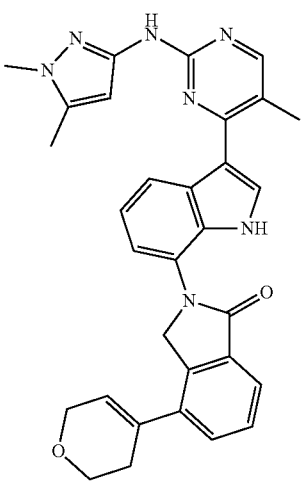
4-(3,6-dihydro-2H-pyran-4-yl)-2-(3-(2-((1,5-dimethyl-1H-pyrazol-3-yl)amino)-5-methylpyrimidin-4-yl)-1H-indol-7-yl)isoindolin-1-one

| | | |
|---|---|---|
| 393) | 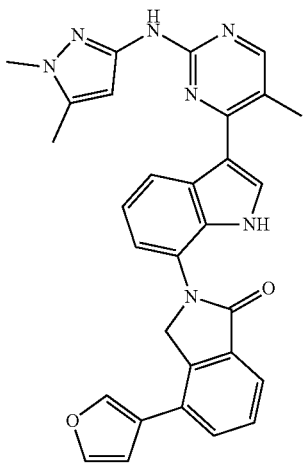 | 2-(3-(2-((1,5-dimethyl-1H-pyrazol-3-yl)amino)-5-methylpyrimidin-4-yl)-1H-indol-7-yl)-4-(furan-3-yl)isoindolin-1-one |
| 394) | 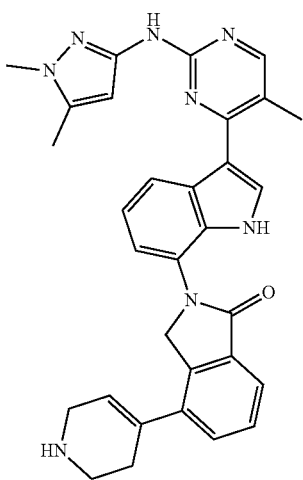 | 2-(3-(2-((1,5-dimethyl-1H-pyrazol-3-yl)amino)-5-methylpyrimidin-4-yl)-1H-indol-7-yl)-4-(1,2,3,6-tetrahydropyridin-4-yl)isoindolin-1-one |
| 395) | 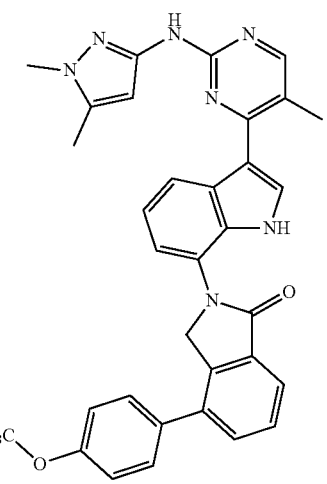 | 2-(3-(2-((1,5-dimethyl-1H-pyrazol-3-yl)amino)-5-methylpyrimidin-4-yl)-1H-indol-7-yl)-4-(4-(trifluoromethoxy)phenyl)isoindolin-1-one |

396) 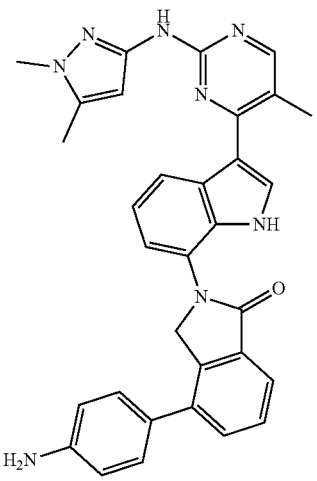
4-(4-aminophenyl)-2-(3-(2-((1,5-dimethyl-1H-pyrazol-3-yl)amino)-5-methylpyrimidin-4-yl)-1H-indol-7-yl)isoindolin-1-one
397) 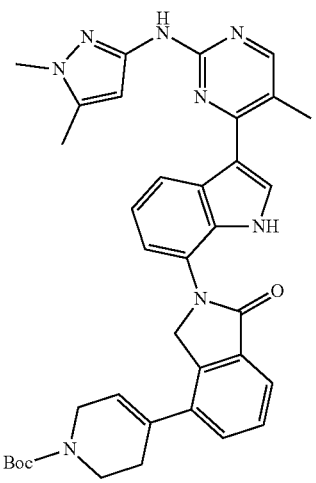
tert-butyl 4-(2-(3-(2-((1,5-dimethyl-1H-pyrazol-3-yl)amino)-5-methylpyrimidin-4-yl)-1H-indol-7-yl)-1-oxoisoindolin-4-yl)-5,6-dihydropyridine-1(2H)-carboxylate
398) 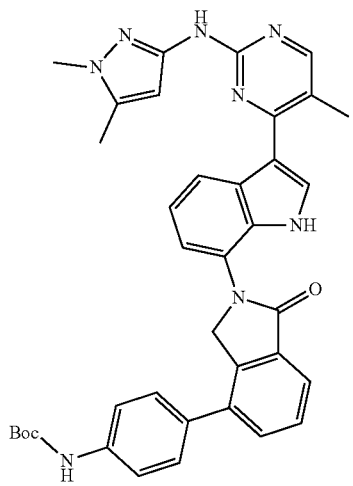 [SMILES: Cc1cnc(Nc2cc(C)n(C)n2)nc1-c1c[nH]c2c(N3Cc4c(cccc4-c4ccc(NC(=O)OC(C)(C)C)cc4)C3=O)cccc12]
tert-butyl (4-(2-(3-(2-((1,5-dimethyl-1H-pyrazol-3-yl)amino)-5-methylpyrimidin-4-yl)-1H-indol-7-yl)-1-oxoisoindolin-4-yl)phenyl)carbamate

| | | |
|---|---|---|
| 399) | 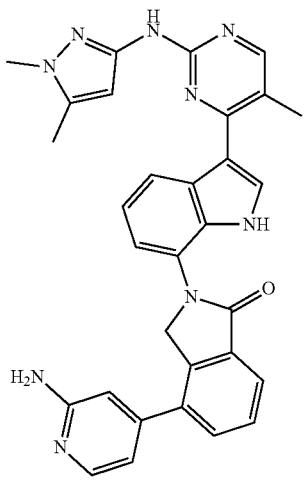 | 4-(2-aminopyridin-4-yl)-2-(3-(2-((1,5-dimethyl-1H-pyrazol-3-yl)amino)-5-methylpyrimidin-4-yl)-1H-indol-7-yl)isoindolin-1-one |
| 400) | 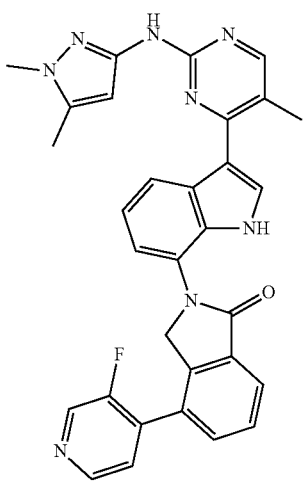 | 2-(3-(2-((1,5-dimethyl-1H-pyrazol-3-yl)amino)-5-methylpyrimidin-4-yl)-1H-indol-7-yl)-4-(3-fluoropyridin-4-yl)isoindolin-1-one |
| 401) | 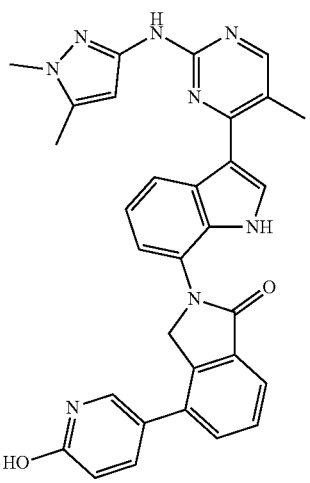 | 2-(3-(2-((1,5-dimethyl-1H-pyrazol-3-yl)amino)-5-methylpyrimidin-4-yl)-1H-indol-7-yl)-4-(6-hydroxypyridin-3-yl)isoindolin-1-one |

-continued
| | | |
|---|---|---|
| 402) | 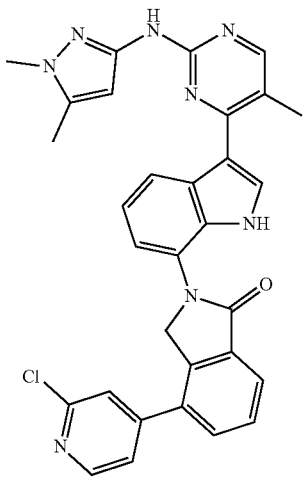 | 4-(2-chloropyridin-4-yl)-2-(3-(2-((1,5-dimethyl-1H-pyrazol-3-yl)amino)-5-methylpyrimidin-4-yl)-1H-indol-7-yl)isoindolin-1-one |
| 403) | 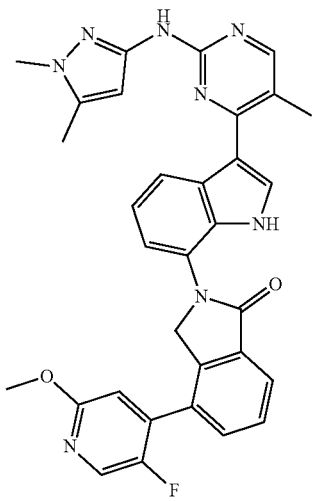 | 2-(3-(2-((1,5-dimethyl-1H-pyrazol-3-yl)amino)-5-methylpyrimidin-4-yl)-1H-indol-7-yl)-4-(5-fluoro-2-methoxypyridin-4-yl)isoindolin-1-one |
| 404) | 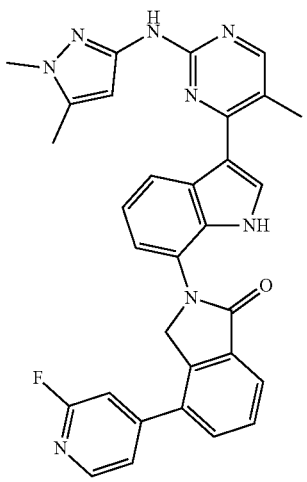 | 2-(3-(2-((1,5-dimethyl-1H-pyrazol-3-yl)amino)-5-methylpyrimidin-4-yl)-1H-indol-7-yl)-4-(2-fluoropyridin-4-yl)isoindolin-1-one |

| | | |
|---|---|---|
| 405) | 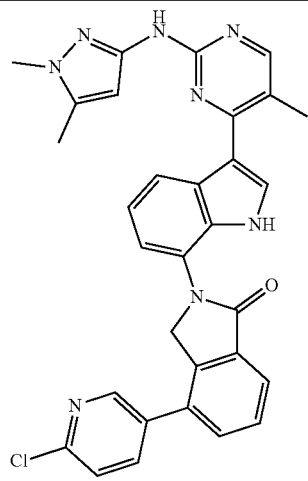 | 4-(6-chloropyridin-3-yl)-2-(3-(2-((1,5-dimethyl-1H-pyrazol-3-yl)amino)-5-methylpyrimidin-4-yl)-1H-indol-7-yl)isoindolin-1-one |
| 406) | 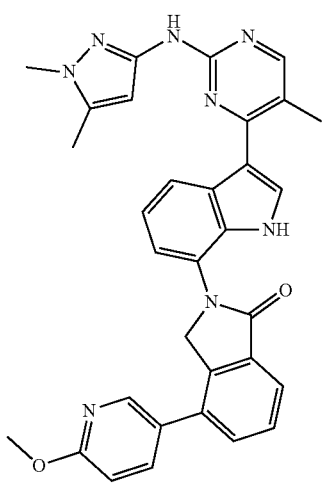 | 2-(3-(2-((1,5-dimethyl-1H-pyrazol-3-yl)amino)-5-methylpyrimidin-4-yl)-1H-indol-7-yl)-4-(6-methoxypyridin-3-yl)isoindolin-1-one |
| 407) | 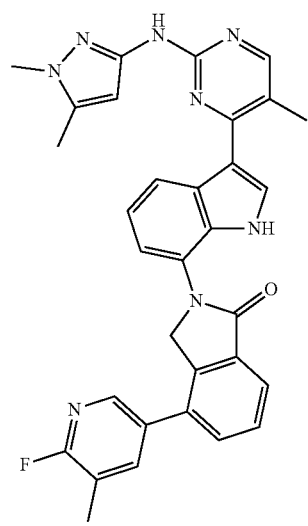 | 2-(3-(2-((1,5-dimethyl-1H-pyrazol-3-yl)amino)-5-methylpyrimidin-4-yl)-1H-indol-7-yl)-4-(6-fluoro-5-methylpyridin-3-yl)isoindolin-1-one |

| | | |
|---|---|---|
| 408) | 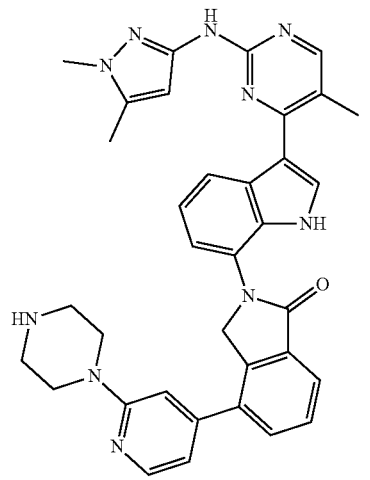 [SMILES: Cc1cnc(Nc2cc(C)n(C)n2)nc1-c1c[nH]c2c(N3Cc4c(cccc4-c4ccnc(N5CCNCC5)c4)C3=O)cccc12] | 2-(3-(2-((1,5-dimethyl-1H-pyrazol-3-yl)amino)-5-methylpyrimidin-4-yl)-1H-indol-7-yl)-4-(2-(piperazin-1-yl)pyridin-4-yl)isoindolin-1-one |
| 409) | 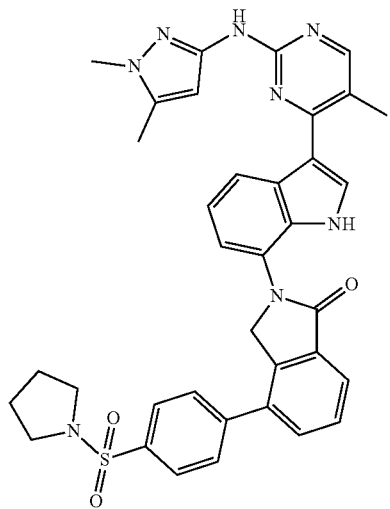 [SMILES: Cc1cnc(Nc2cc(C)n(C)n2)nc1-c1c[nH]c2c(N3Cc4c(cccc4-c4ccc(S(=O)(=O)N5CCCC5)cc4)C3=O)cccc12] | 2-(3-(2-((1,5-dimethyl-1H-pyrazol-3-yl)amino)-5-methylpyrimidin-4-yl)-1H-indol-7-yl)-4-(4-(pyrrolidin-1-ylsulfonyl)phenyl)isoindolin-1-one |
| 410) | 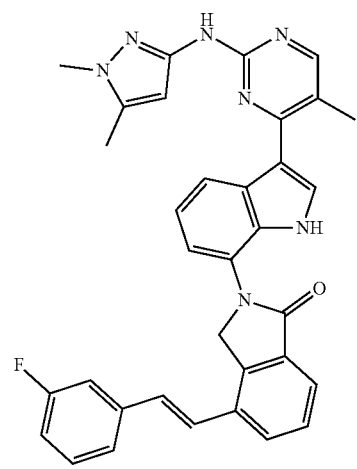 [SMILES: Cc1cnc(Nc2cc(C)n(C)n2)nc1-c1c[nH]c2c(N3Cc4c(/C=C/c5cccc(F)c5)cccc4C3=O)cccc12] | (E)-2-(3-(2-((1,5-dimethyl-1H-pyrazol-3-yl)amino)-5-methylpyrimidin-4-yl)-1H-indol-7-yl)-4-(3-fluorostyryl)isoindolin-1-one |

| | | |
|---|---|---|
| 411) | 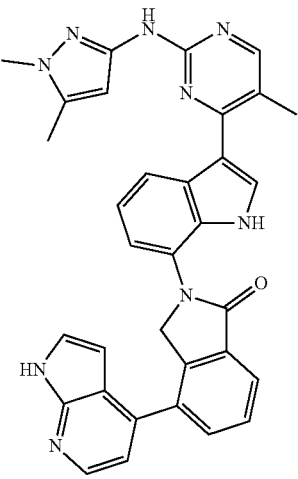 | 2-(3-(2-((1,5-dimethyl-1H-pyrazol-3-yl)amino)-5-methylpyrimidin-4-yl)-1H-indol-7-yl)-4-(1H-pyrrolo[2,3-b]pyridin-4-yl)isoindolin-1-one |
| 412) | 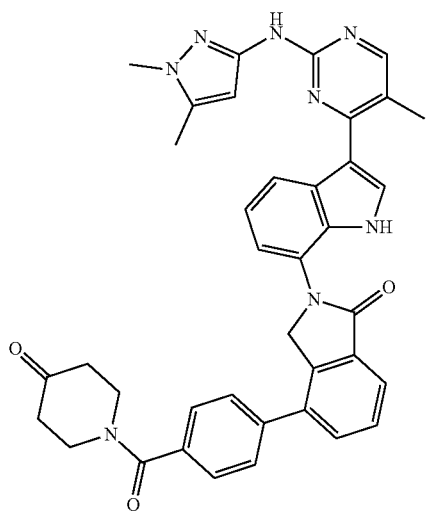 [SMILES: Cc1cnc(Nc2cc(C)n(C)n2)nc1-c1c[nH]c2c(N3Cc4c(cccc4-c4ccc(C(=O)N5CCC(=O)CC5)cc4)C3=O)cccc12] | 2-(3-(2-((1,5-dimethyl-1H-pyrazol-3-yl)amino)-5-methylpyrimidin-4-yl)-1H-indol-7-yl)-4-(4-(4-oxopiperidine-1-carbonyl)phenyl)isoindolin-1-one |
| 413) | 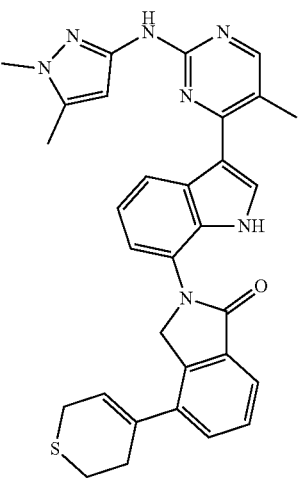 | 4-(3,6-dihydro-2H-thiopyran-4-yl)-2-(3-(2-((1,5-dimethyl-1H-pyrazol-3-yl)amino)-5-methylpyrimidin-4-yl)-1H-indol-7-yl)isoindolin-1-one |

414) 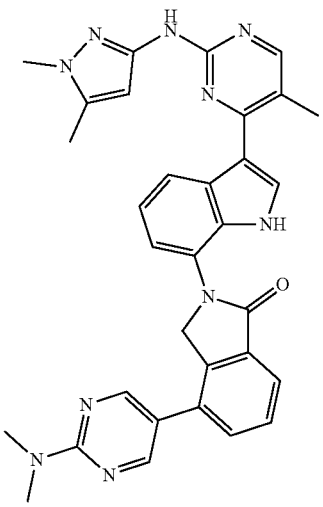
2-(3-(2-((1,5-dimethyl-1H-pyrazol-3-yl)amino)-5-methylpyrimidin-4-yl)-1H-indol-7-yl)-4-(2-(dimethylamino)pyrimidin-5-yl)isoindolin-1-one
415) 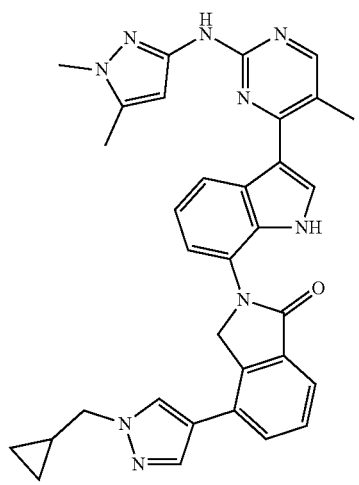 [SMILES: Cc1cnc(Nc2cc(C)n(C)n2)nc1-c1c[nH]c2c(N3Cc4c(cccc4-c4cnn(CC5CC5)c4)C3=O)cccc12]
4-(1-(cyclopropylmethyl)-1H-pyrazol-4-yl)-2-(3-(2-((1,5-dimethyl-1H-pyrazol-3-yl)amino)-5-methylpyrimidin-4-yl)-1H-indol-7-yl)isoindolin-1-one
416) 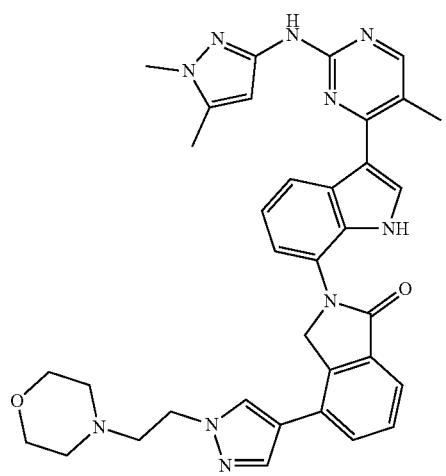 [SMILES: Cc1cnc(Nc2cc(C)n(C)n2)nc1-c1c[nH]c2c(N3Cc4c(cccc4-c4cnn(CCN5CCOCC5)c4)C3=O)cccc12]
2-(3-(2-((1,5-dimethyl-1H-pyrazol-3-yl)amino)-5-methylpyrimidin-4-yl)-1H-indol-7-yl)-4-(1-(2-morpholinoethyl)-1H-pyrazol-4-yl)isoindolin-1-one

| | | |
|---|---|---|
| 417) | 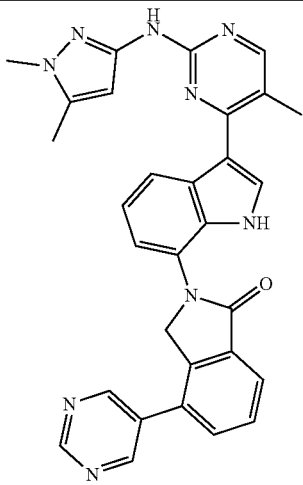 | 2-(3-(2-((1,5-dimethyl-1H-pyrazol-3-yl)amino)-5-methylpyrimidin-4-yl)-1H-indol-7-yl)-4-(pyrimidin-5-yl)isoindolin-1-one |
| 418) | 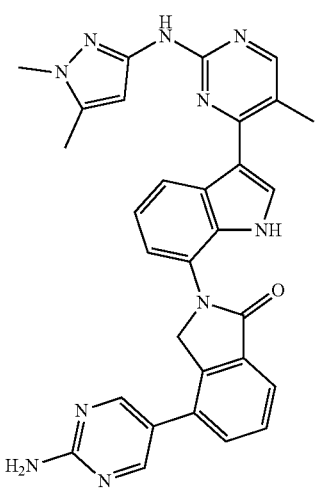 | 4-(2-aminopyrimidin-5-yl)-2-(3-(2-((1,5-dimethyl-1H-pyrazol-3-yl)amino)-5-methylpyrimidin-4-yl)-1H-indol-7-yl)isoindolin-1-one |
| 419) | 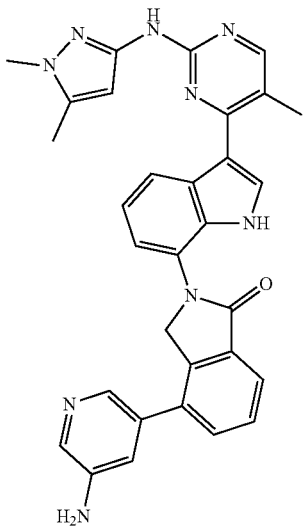 | 4-(5-aminopyridin-3-yl)-2-(3-(2-((1,5-dimethyl-1H-pyrazol-3-yl)amino)-5-methylpyrimidin-4-yl)-1H-indol-7-yl)isoindolin-1-one |

| | | |
|---|---|---|
| 420) | 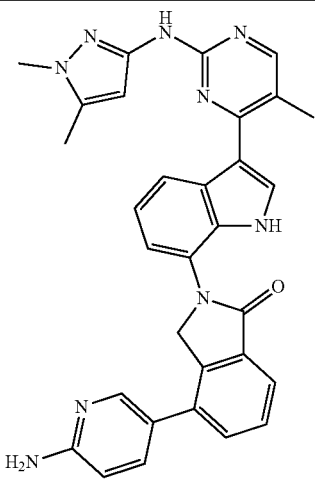 | 4-(6-aminopyridin-3-yl)-2-(3-(2-((1,5-dimethyl-1H-pyrazol-3-yl)amino)-5-methylpyrimidin-4-yl)-1H-indol-7-yl)isoindolin-1-one |
| 421) | 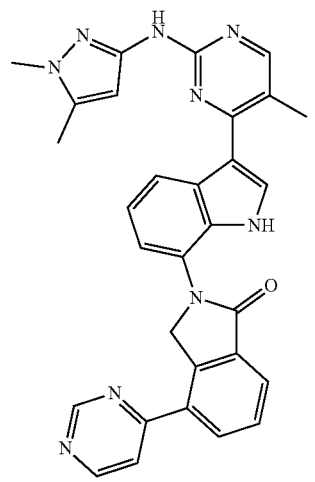 | 2-(3-(2-((1,5-dimethyl-1H-pyrazol-3-yl)amino)-5-methylpyrimidin-4-yl)-1H-indol-7-yl)-4-(pyrimidin-4-yl)isoindolin-1-one |
| 422) | 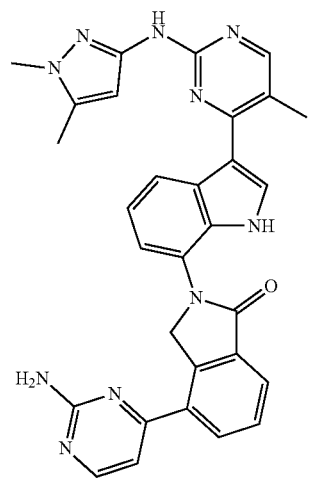 | 4-(2-aminopyrimidin-4-yl)-2-(3-(2-((1,5-dimethyl-1H-pyrazol-3-yl)amino)-5-methylpyrimidin-4-yl)-1H-indol-7-yl)isoindolin-1-one |

423) 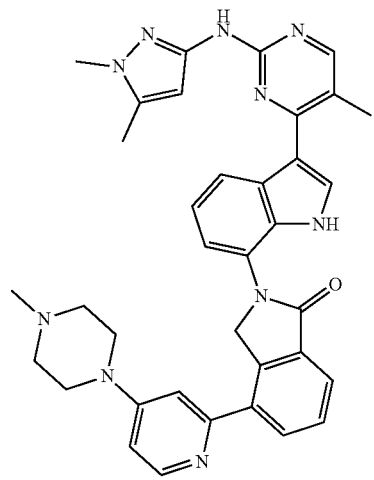
2-(3-(2-((1,5-dimethyl-1H-pyrazol-3-yl)amino)-5-methylpyrimidin-4-yl)-1H-indol-7-yl)-4-(4-(4-methylpiperazin-1-yl)pyridin-2-yl)isoindolin-1-one
424) 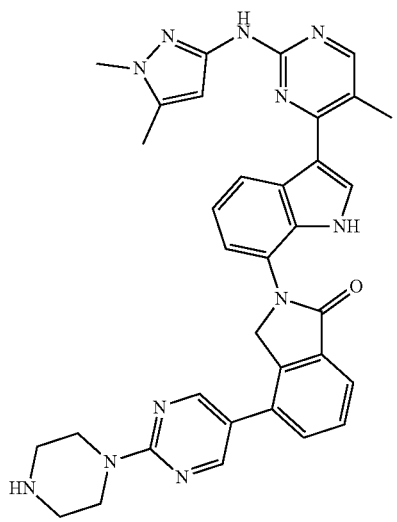 [SMILES: Cc1cnc(Nc2cc(C)n(C)n2)nc1-c1c[nH]c2c(N3Cc4c(cccc4-c4cnc(N5CCNCC5)nc4)C3=O)cccc12]
2-(3-(2-((1,5-dimethyl-1H-pyrazol-3-yl)amino)-5-methylpyrimidin-4-yl)-1H-indol-7-yl)-4-(2-(piperazin-1-yl)pyrimidin-5-yl)isoindolin-1-one
425) 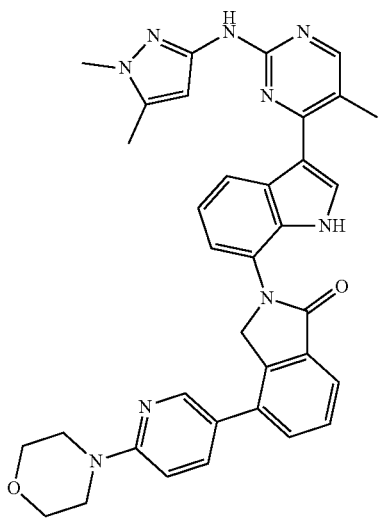 [SMILES: Cc1cnc(Nc2cc(C)n(C)n2)nc1-c1c[nH]c2c(N3Cc4c(cccc4-c4ccc(N5CCOCC5)nc4)C3=O)cccc12]
2-(3-(2-((1,5-dimethyl-1H-pyrazol-3-yl)amino)-5-methylpyrimidin-4-yl)-1H-indol-7-yl)-4-(6-morpholinopyridin-3-yl)isoindolin-1-one

| | | |
|---|---|---|
| 426) | 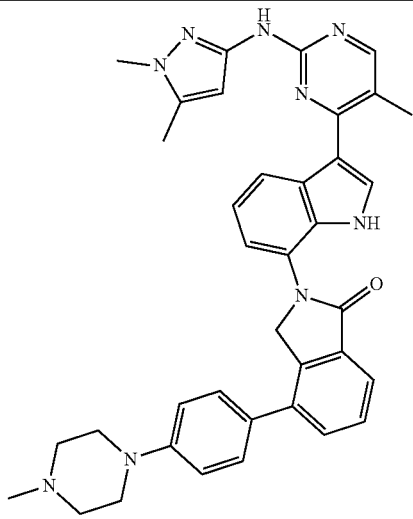 | 2-(3-(2-((1,5-dimethyl-1H-pyrazol-3-yl)amino)-5-methylpyrimidin-4-yl)-1H-indol-7-yl)-4-(4-(4-methylpiperazin-1-yl)phenyl)isoindolin-1-one |
| 427) | 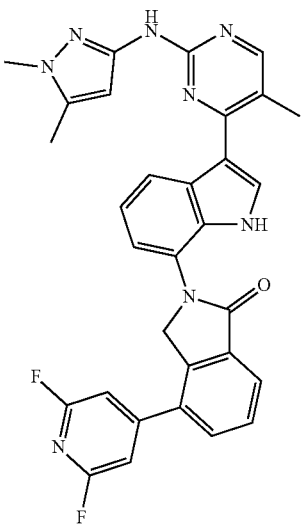 | 4-(2,6-difluoropyridin-4-yl)-2-(3-(2-((1,5-dimethyl-1H-pyrazol-3-yl)amino)-5-methylpyrimidin-4-yl)-1H-indol-7-yl)isoindolin-1-one |
| 428) | 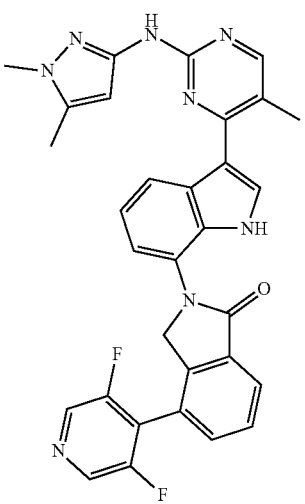 | 4-(3,5-difluoropyridin-4-yl)-2-(3-(2-((1,5-dimethyl-1H-pyrazol-3-yl)amino)-5-methylpyrimidin-4-yl)-1H-indol-7-yl)isoindolin-1-one |

| | | |
|---|---|---|
| 429) | 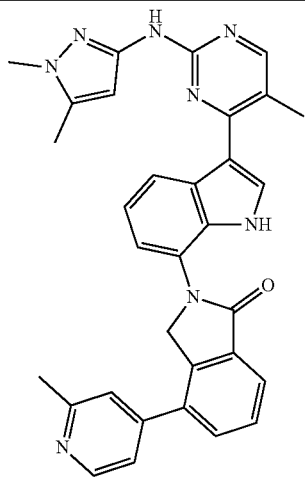 | 2-(3-(2-((1,5-dimethyl-1H-pyrazol-3-yl)amino)-5-methylpyrimidin-4-yl)-1H-indol-7-yl)-4-(2-methylpyridin-4-yl)isoindolin-1-one |
| 430) | 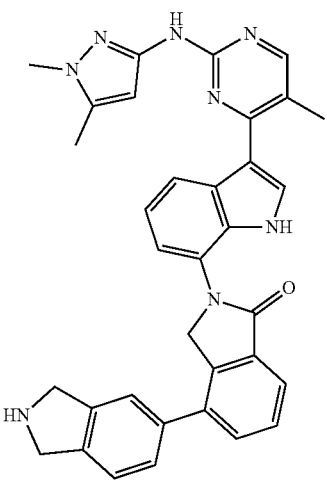 [SMILES: Cc1cnc(Nc2cc(C)n(C)n2)nc1-c1c[nH]c2c(N3Cc4c(cccc4-c4ccc5c(c4)CNC5)C3=O)cccc12] | 2-(3-(2-((1,5-dimethyl-1H-pyrazol-3-yl)amino)-5-methylpyrimidin-4-yl)-1H-indol-7-yl)-[4,5'-biisoindolin]-1-one |
| 431) | 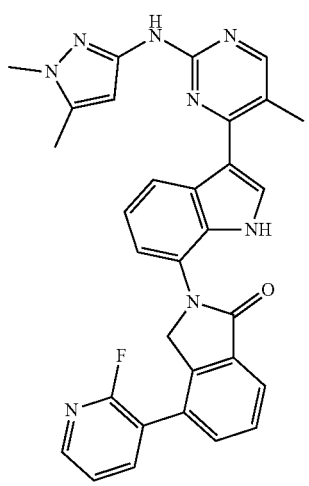 | 2-(3-(2-((1,5-dimethyl-1H-pyrazol-3-yl)amino)-5-methylpyrimidin-4-yl)-1H-indol-7-yl)-4-(2-fluoropyridin-3-yl)isoindolin-1-one |

-continued
| | | |
|---|---|---|
| 432) | 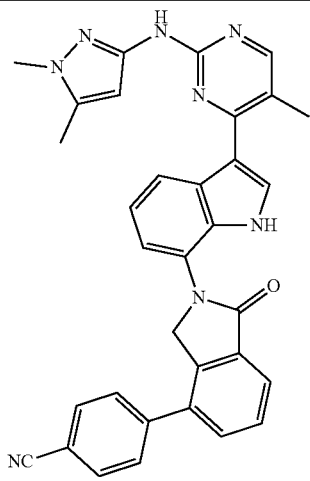 | 4-(2-(3-(2-((1,5-dimethyl-1H-pyrazol-3-yl)amino)-5-methylpyrimidin-4-yl)-1H-indol-7-yl)-1-oxoisoindolin-4-yl)benzonitrile |
| 433) | 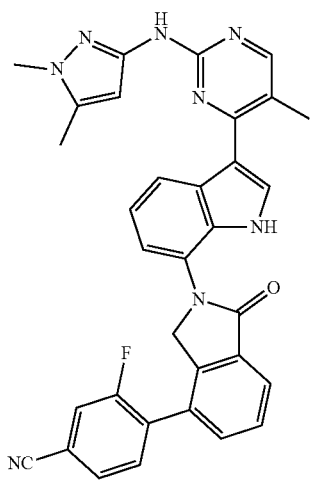 | 4-(2-(3-(2-((1,5-dimethyl-1H-pyrazol-3-yl)amino)-5-methylpyrimidin-4-yl)-1H-indol-7-yl)-1-oxoisoindolin-4-yl)-3-fluorobenzonitrile |
| 434) | 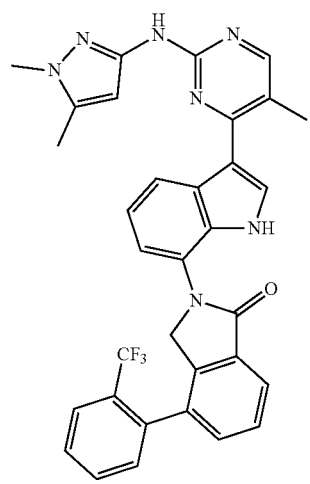 | 2-(3-(2-((1,5-dimethyl-1H-pyrazol-3-yl)amino)-5-methylpyrimidin-4-yl)-1H-indol-7-yl)-4-(2-(trifluoromethyl)phenyl)isoindolin-1-one |

| | | |
|---|---|---|
| 435) | 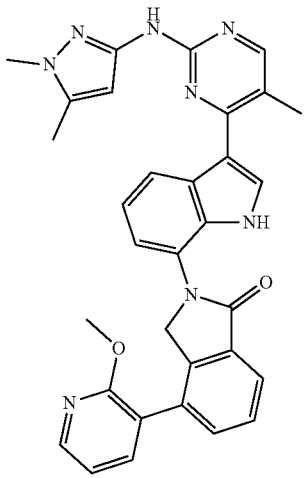 | 2-(3-(2-((1,5-dimethyl-1H-pyrazol-3-yl)amino)-5-methylpyrimidin-4-yl)-1H-indol-7-yl)-4-(2-methoxypyridin-3-yl)isoindolin-1-one |
| 436) | 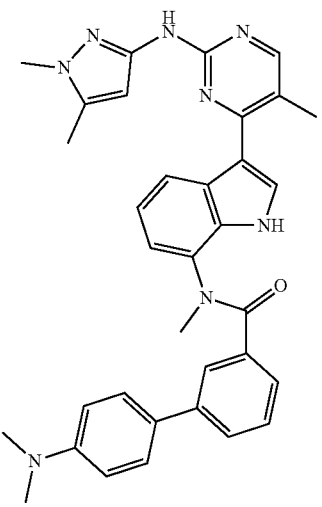 | 2-(3-(2-((1,5-dimethyl-1H-pyrazol-3-yl)amino)-5-methylpyrimidin-4-yl)-1H-indol-7-yl)-4-(4-(dimethylamino)phenyl)isoindolin-1-one |
| 437) | 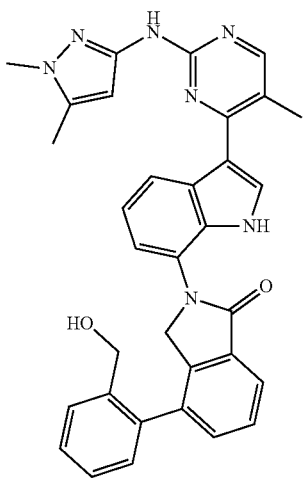 | 2-(3-(2-((1,5-dimethyl-1H-pyrazol-3-yl)amino)-5-methylpyrimidin-4-yl)-1H-indol-7-yl)-4-(2-(hydroxymethyl)phenyl)isoindolin-1-one |

| | | |
|---|---|---|
| 438) | 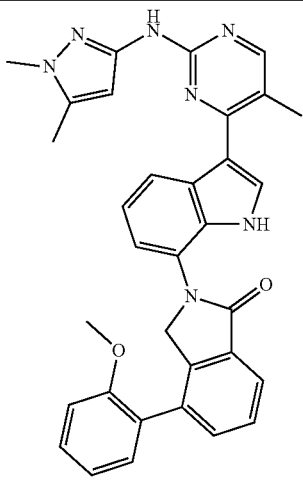 | 2-(3-(2-((1,5-dimethyl-1H-pyrazol-3-yl)amino)-5-methylpyrimidin-4-yl)-1H-indol-7-yl)-4-(2-methoxyphenyl)isoindolin-1-one |
| 439) | 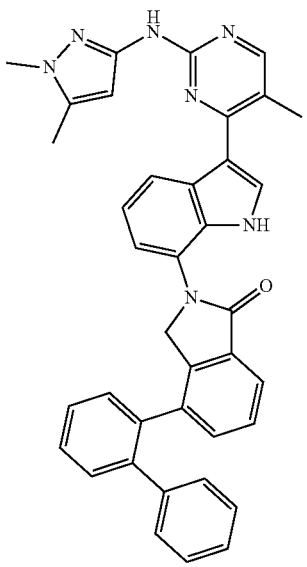 | 4-([1,1'-biphenyl]-2-yl)-2-(3-(2-((1,5-dimethyl-1H-pyrazol-3-yl)amino)-5-methylpyrimidin-4-yl)-1H-indol-7-yl)isoindolin-1-one |
| 440) | 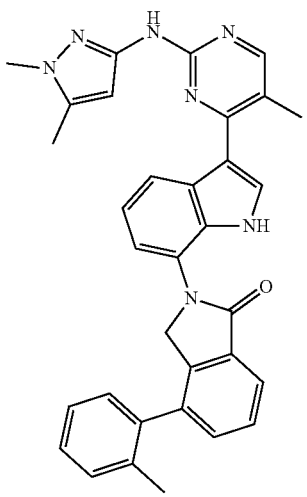 | 2-(3-(2-((1,5-dimethyl-1H-pyrazol-3-yl)amino)-5-methylpyrimidin-4-yl)-1H-indol-7-yl)-4-(o-tolyl)isoindolin-1-one |

-continued
441) 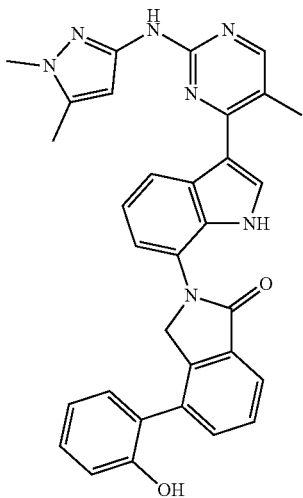
2-(3-(2-((1,5-dimethyl-1H-pyrazol-3-yl)amino)-5-methylpyrimidin-4-yl)-1H-indol-7-yl)-4-(2-hydroxyphenyl)isoindolin-1-one
442) 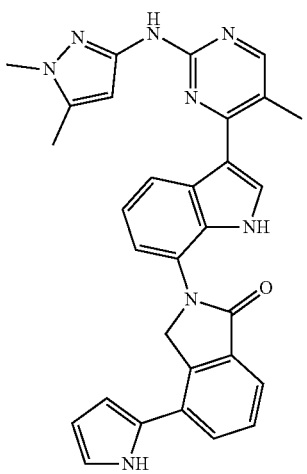
2-(3-(2-((1,5-dimethyl-1H-pyrazol-3-yl)amino)-5-methylpyrimidin-4-yl)-1H-indol-7-yl)-4-(1H-pyrrol-2-yl)isoindolin-1-one
443) 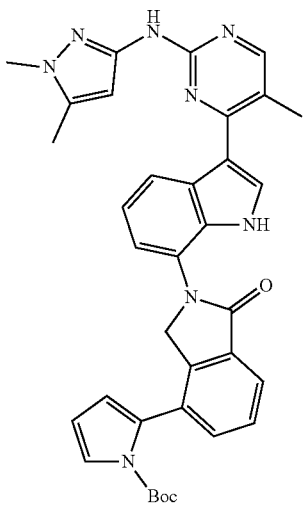
tert-butyl 2-(2-(3-(2-((1,5-dimethyl-1H-pyrazol-3-yl)amino)-5-methylpyrimidin-4-yl)-1H-indol-7-yl)-1-oxoisoindolin-4-yl)-1H-pyrrole-1-carboxylate

| | | |
|---|---|---|
| 444) | 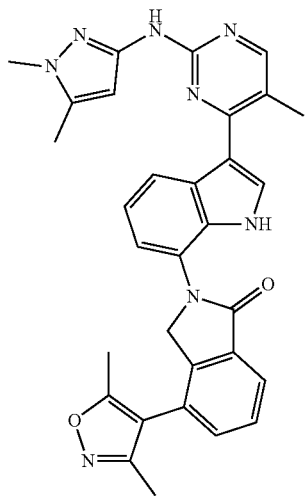 | 2-(3-(2-((1,5-dimethyl-1H-pyrazol-3-yl)amino)-5-methylpyrimidin-4-yl)-1H-indol-7-yl)-4-(3,5-dimethylisoxazol-4-yl)isoindolin-1-one |
| 445) | 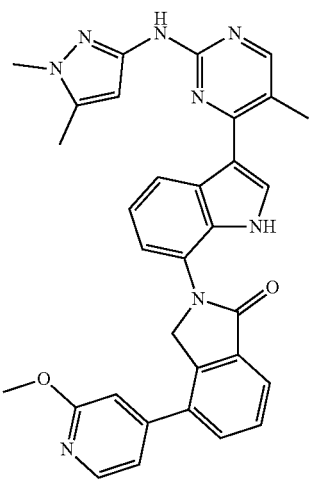 | 2-(3-(2-((1,5-dimethyl-1H-pyrazol-3-yl)amino)-5-methylpyrimidin-4-yl)-1H-indol-7-yl)-4-(2-methoxypyridin-4-yl)isoindolin-1-one |
| 446) | 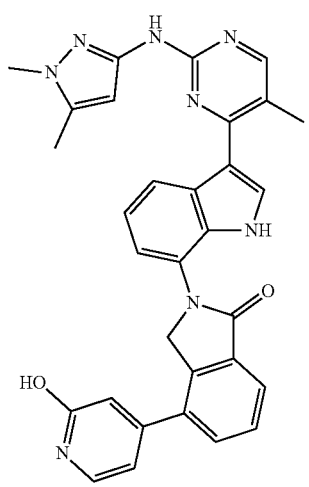 | 2-(3-(2-((1,5-dimethyl-1H-pyrazol-3-yl)amino)-5-methylpyrimidin-4-yl)-1H-indol-7-yl)-4-(2-hydroxypyridin-4-yl)isoindolin-1-one |

447) 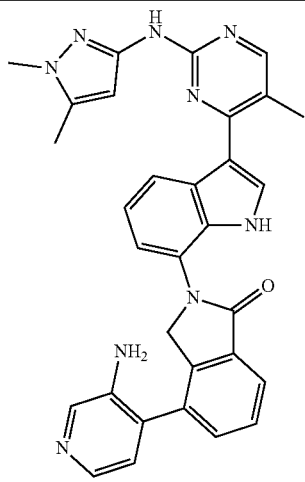 4-(3-aminopyridin-4-yl)-2-(3-(2-((1,5-dimethyl-1H-pyrazol-3-yl)amino)-5-methylpyrimidin-4-yl)-1H-indol-7-yl)isoindolin-1-one
448) 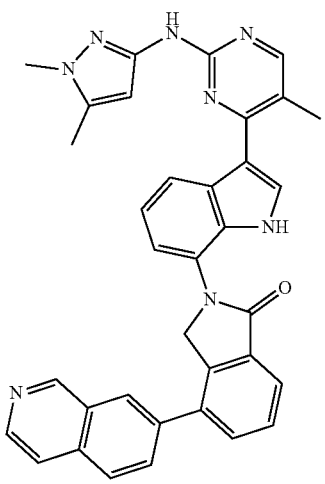 [SMILES: Cc1cnc(Nc2cc(C)n(C)n2)nc1-c1c[nH]c2c(N3Cc4c(cccc4-c4ccc5ccncc5c4)C3=O)cccc12] 2-(3-(2-((1,5-dimethyl-1H-pyrazol-3-yl)amino)-5-methylpyrimidin-4-yl)-1H-indol-7-yl)-4-(isoquinolin-7-yl)isoindolin-1-one
449) 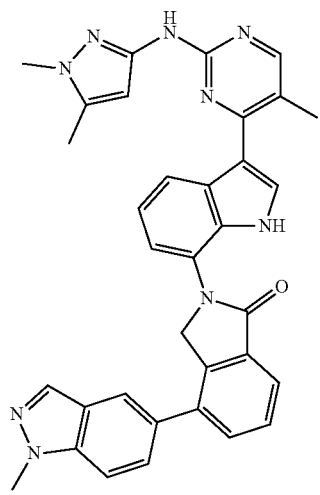 2-(3-(2-((1,5-dimethyl-1H-pyrazol-3-yl)amino)-5-methylpyrimidin-4-yl)-1H-indol-7-yl)-4-(1-methyl-1H-indazol-5-yl)isoindolin-1-one

| | | |
|---|---|---|
| 450) | 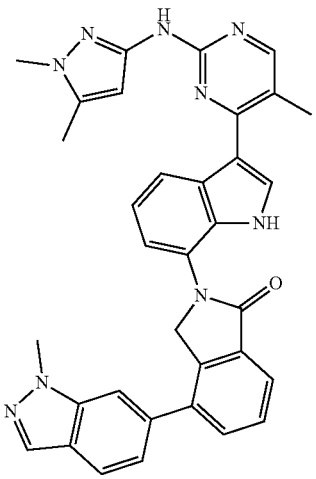 [SMILES: Cc1cnc(Nc2cc(C)n(C)n2)nc1-c1c[nH]c2c(N3Cc4c(cccc4-c4ccc5cnn(C)c5c4)C3=O)cccc12] | 2-(3-(2-((1,5-dimethyl-1H-pyrazol-3-yl)amino)-5-methylpyrimidin-4-yl)-1H-indol-7-yl)-4-(1-methyl-1H-indazol-6-yl)isoindolin-1-one |
| 451) | 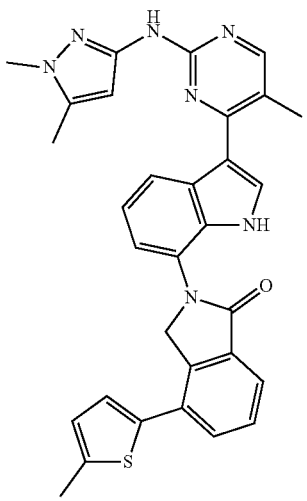 | 2-(3-(2-((1,5-dimethyl-1H-pyrazol-3-yl)amino)-5-methylpyrimidin-4-yl)-1H-indol-7-yl)-4-(5-methylthiophen-2-yl)isoindolin-1-one |
| 452) | 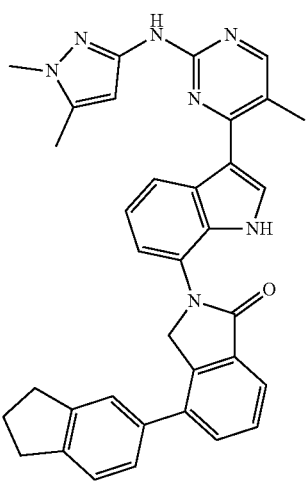 [SMILES: Cc1cnc(Nc2cc(C)n(C)n2)nc1-c1c[nH]c2c(N3Cc4c(cccc4-c4ccc5c(c4)CCC5)C3=O)cccc12] | 4-(2,3-dihydro-1H-inden-5-yl)-2-(3-(2-((1,5-dimethyl-1H-pyrazol-3-yl)amino)-5-methylpyrimidin-4-yl)-1H-indol-7-yl)isoindolin-1-one |

| | | |
|---|---|---|
| 453) | 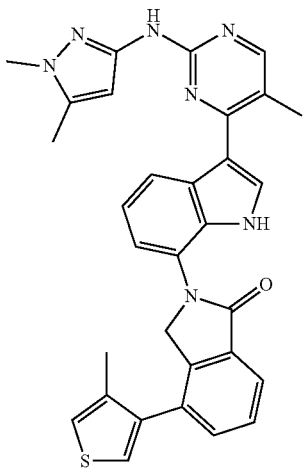 | 2-(3-(2-((1,5-dimethyl-1H-pyrazol-3-yl)amino)-5-methylpyrimidin-4-yl)-1H-indol-7-yl)-4-(4-methylthiophen-3-yl)isoindolin-1-one |
| 454) | 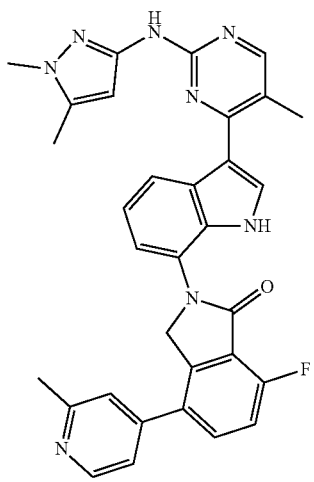 | 2-(3-(2-((1,5-dimethyl-1H-pyrazol-3-yl)amino)-5-methylpyrimidin-4-yl)-1H-indol-7-yl)-7-fluoro-4-(2-methylpyridin-4-yl)isoindolin-1-one |
| 455) | 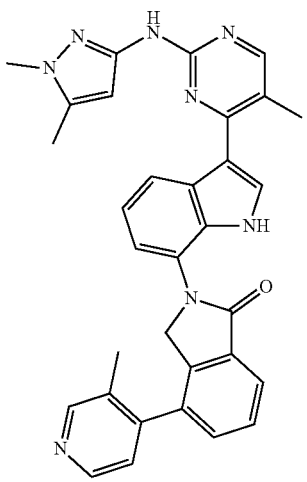 | 2-(3-(2-((1,5-dimethyl-1H-pyrazol-3-yl)amino)-5-methylpyrimidin-4-yl)-1H-indol-7-yl)-4-(3-methylpyridin-4-yl)isoindolin-1-one |

| | | |
|---|---|---|
| 456) | 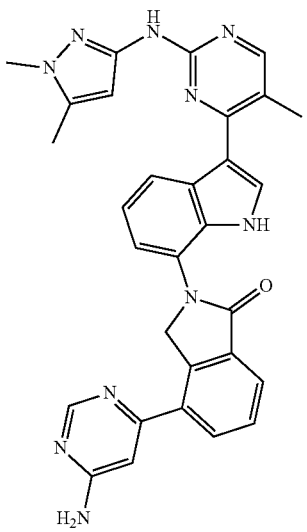 | 4-(6-aminopyrimidin-4-yl)-2-(3-(2-((1,5-dimethyl-1H-pyrazol-3-yl)amino)-5-methylpyrimidin-4-yl)-1H-indol-7-yl)isoindolin-1-one |
| 457) | 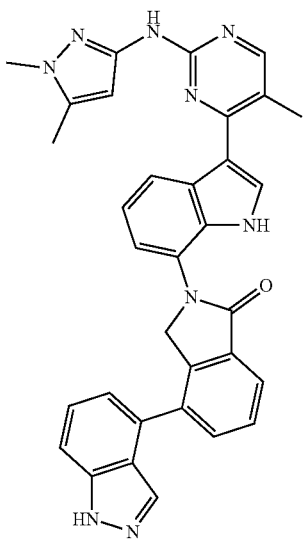 | 2-(3-(2-((1,5-dimethyl-1H-pyrazol-3-yl)amino)-5-methylpyrimidin-4-yl)-1H-indol-7-yl)-4-(1H-indazol-4-yl)isoindolin-1-one |
| 458) | 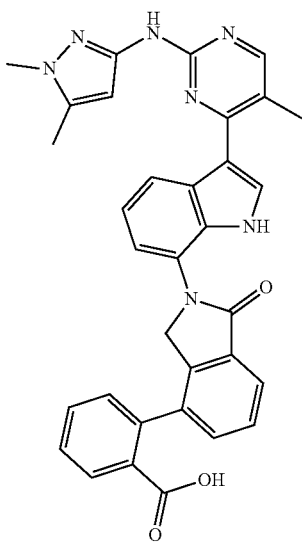 | 2-(2-(3-(2-((1,5-dimethyl-1H-pyrazol-3-yl)amino)-5-methylpyrimidin-4-yl)-1H-indol-7-yl)-1-oxoisoindolin-4-yl)benzoic acid |

| | | |
|---|---|---|
| 460) | 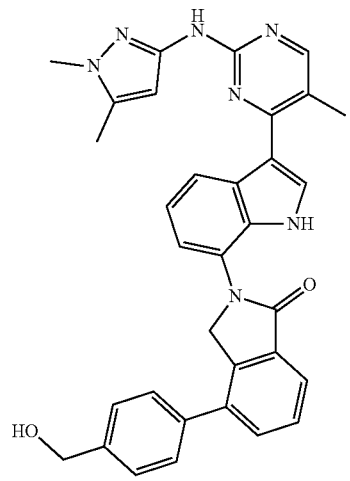 [SMILES: Cc1cnc(Nc2cc(C)n(C)n2)nc1-c1c[nH]c2c(N3Cc4c(cccc4-c4ccc(CO)cc4)C3=O)cccc12] | 2-(3-(2-((1,5-dimethyl-1H-pyrazol-3-yl)amino)-5-methylpyrimidin-4-yl)-1H-indol-7-yl)-4-(4-(hydroxymethyl)phenyl)isoindolin-1-one |
| 461) | 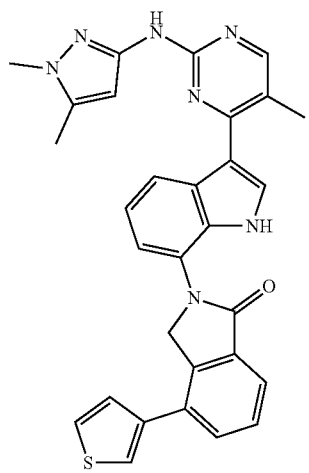 | 2-(3-(2-((1,5-dimethyl-1H-pyrazol-3-yl)amino)-5-methylpyrimidin-4-yl)-1H-indol-7-yl)-4-(thiophen-3-yl)isoindolin-1-one |
| 462) | 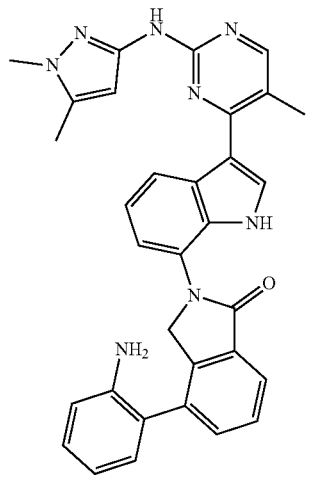 | 4-(2-aminophenyl)-2-(3-(2-((1,5-dimethyl-1H-pyrazol-3-yl)amino)-5-methylpyrimidin-4-yl)-1H-indol-7-yl)isoindolin-1-one |

| | | |
|---|---|---|
| 463) | 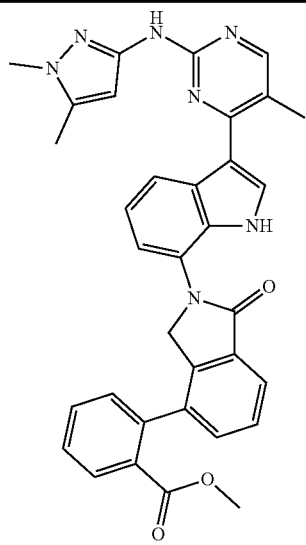 | methyl 2-(2-(3-(2-((1,5-dimethyl-1H-pyrazol-3-yl)amino)-5-methylpyrimidin-4-yl)-1H-indol-7-yl)-1-oxoisoindolin-4-yl)benzoate |
| 464) | 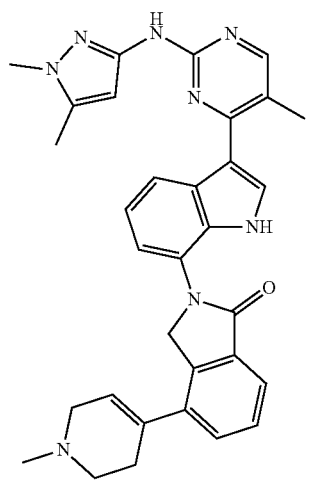 | 2-(3-(2-((1,5-dimethyl-1H-pyrazol-3-yl)amino)-5-methylpyrimidin-4-yl)-1H-indol-7-yl)-4-(1-methyl-1,2,3,6-tetrahydropyridin-4-yl)isoindolin-1-one |
| 465) | 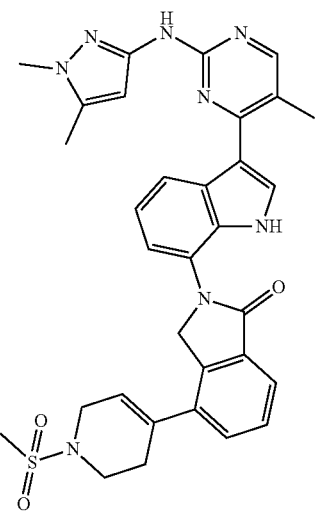 | 2-(3-(2-((1,5-dimethyl-1H-pyrazol-3-yl)amino)-5-methylpyrimidin-4-yl)-1H-indol-7-yl)-4-(1-(methylsulfonyl)-1,2,3,6-tetrahydropyridin-4-yl)isoindolin-1-one |

| | | |
|---|---|---|
| 466) | 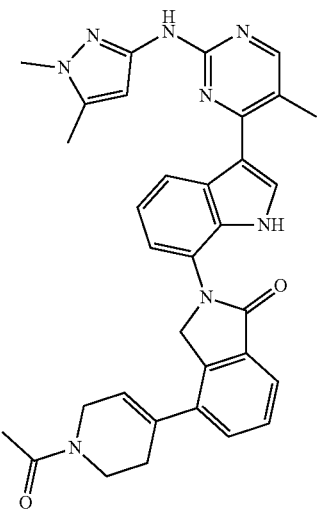 [SMILES: CC(=O)N1CC=C(c2cccc3c2CN(c2cccc4c(-c5nc(Nc6cc(C)n(C)n6)ncc5C)c[nH]c24)C3=O)CC1] | 4-(1-acetyl-1,2,3,6-tetrahydropyridin-4-yl)-2-(3-(2-((1,5-dimethyl-1H-pyrazol-3-yl)amino)-5-methylpyrimidin-4-yl)-1H-indol-7-yl)isoindolin-1-one |
| 467) | 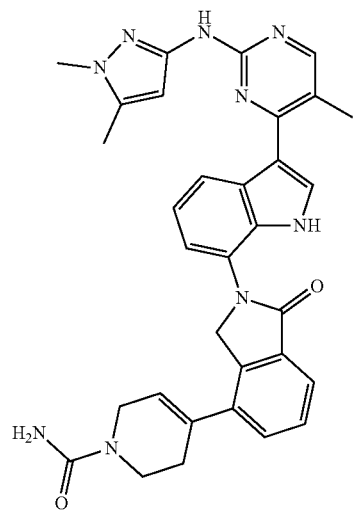 [SMILES: Cc1cnc(Nc2cc(C)n(C)n2)nc1-c1c[nH]c2c(N3Cc4c(cccc4C4=CCN(C(N)=O)CC4)C3=O)cccc12] | 4-(2-(3-(2-((1,5-dimethyl-1H-pyrazol-3-yl)amino)-5-methylpyrimidin-4-yl)-1H-indol-7-yl)-1-oxoisoindolin-4-yl)-5,6-dihydropyridine-1(2H)-carboxamide |
| 468) | 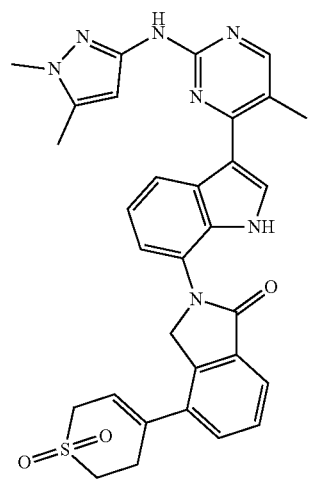 | 2-(3-(2-((1,5-dimethyl-1H-pyrazol-3-yl)amino)-5-methylpyrimidin-4-yl)-1H-indol-7-yl)-4-(1,1-dioxido-3,6-dihydro-2H-thiopyran-4-yl)isoindolin-1-one |

| | | |
|---|---|---|
| 469) | 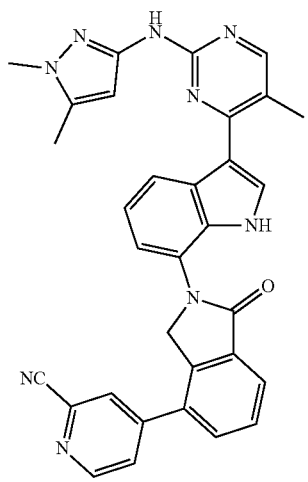 | 4-(2-(3-(2-((1,5-dimethyl-1H-pyrazol-3-yl)amino)-5-methylpyrimidin-4-yl)-1H-indol-7-yl)-1-oxoisoindolin-4-yl)picolinonitrile |
| 470) | 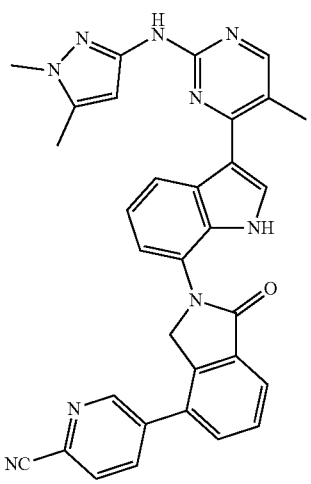 | 5-(2-(3-(2-((1,5-dimethyl-1H-pyrazol-3-yl)amino)-5-methylpyrimidin-4-yl)-1H-indol-7-yl)-1-oxoisoindolin-4-yl)picolinonitrile |
| 471) | 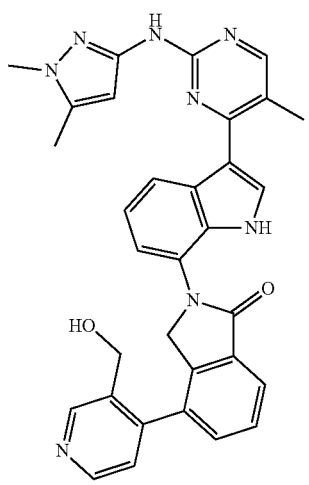 | 2-(3-(2-((1,5-dimethyl-1H-pyrazol-3-yl)amino)-5-methylpyrimidin-4-yl)-1H-indol-7-yl)-4-(3-(hydroxymethyl)pyridin-4-yl)isoindolin-1-one |

| | | |
|---|---|---|
| 472) | 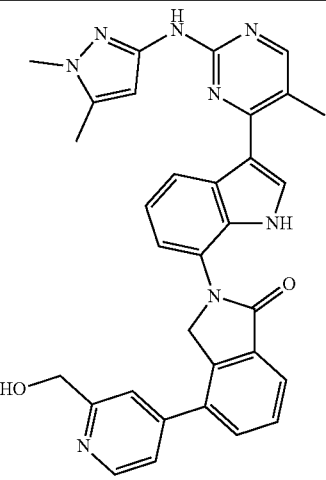 | 2-(3-(2-((1,5-dimethyl-1H-pyrazol-3-yl)amino)-5-methylpyrimidin-4-yl)-1H-indol-7-yl)-4-(2-(hydroxymethyl)pyridin-4-yl)isoindolin-1-one |
| 473) | 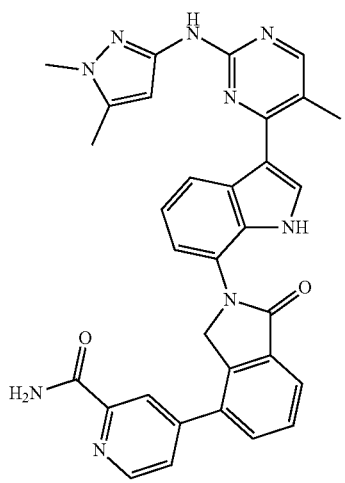 [SMILES: Cc1cnc(Nc2cc(C)n(C)n2)nc1-c1c[nH]c2c(N3Cc4c(cccc4-c4ccnc(C(N)=O)c4)C3=O)cccc12] | 4-(2-(3-(2-((1,5-dimethyl-1H-pyrazol-3-yl)amino)-5-methylpyrimidin-4-yl)-1H-indol-7-yl)-1-oxoisoindolin-4-yl)picolinamide |
| 474) | 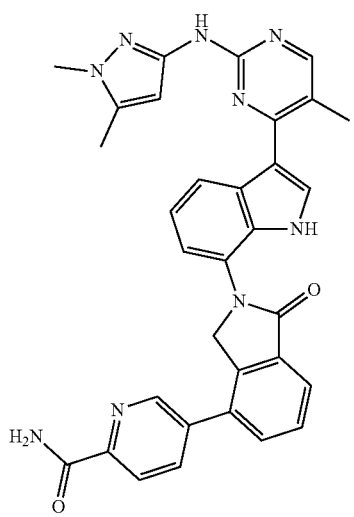 [SMILES: Cc1cnc(Nc2cc(C)n(C)n2)nc1-c1c[nH]c2c(N3Cc4c(cccc4-c4ccc(C(N)=O)nc4)C3=O)cccc12] | 5-(2-(3-(2-((1,5-dimethyl-1H-pyrazol-3-yl)amino)-5-methylpyrimidin-4-yl)-1H-indol-7-yl)-1-oxoisoindolin-4-yl)picolinamide |

| | | |
|---|---|---|
| 475) | 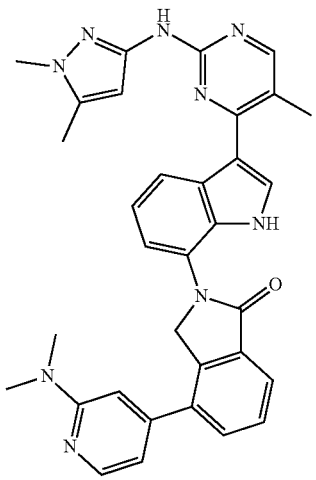 | 2-(3-(2-((1,5-dimethyl-1H-pyrazol-3-yl)amino)-5-methylpyrimidin-4-yl)-1H-indol-7-yl)-4-(2-(dimethylamino)pyridin-4-yl)isoindolin-1-one |
| 476) | 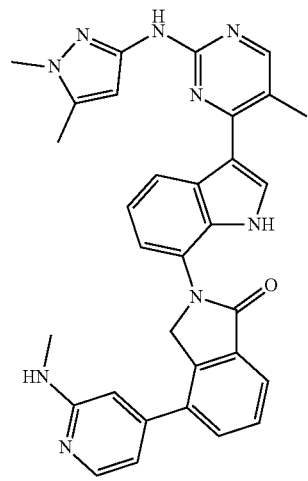 | 2-(3-(2-((1,5-dimethyl-1H-pyrazol-3-yl)amino)-5-methylpyrimidin-4-yl)-1H-indol-7-yl)-4-(2-(methylamino)pyridin-4-yl)isoindolin-1-one |
| 477) | 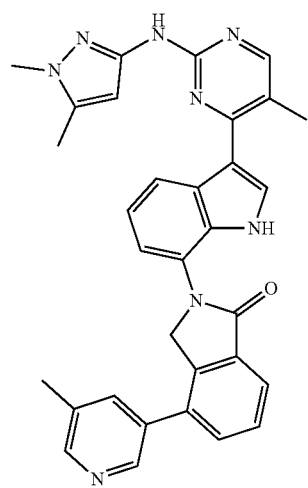 | 2-(3-(2-((1,5-dimethyl-1H-pyrazol-3-yl)amino)-5-methylpyrimidin-4-yl)-1H-indol-7-yl)-4-(5-methylpyridin-3-yl)isoindolin-1-one |

-continued
| | | |
|---|---|---|
| 478) | 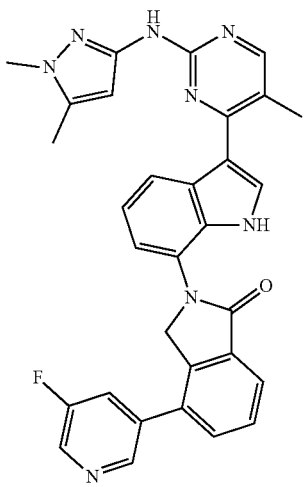 | 2-(3-(2-((1,5-dimethyl-1H-pyrazol-3-yl)amino)-5-methylpyrimidin-4-yl)-1H-indol-7-yl)-4-(5-fluoropyridin-3-yl)isoindolin-1-one |
| 479) | 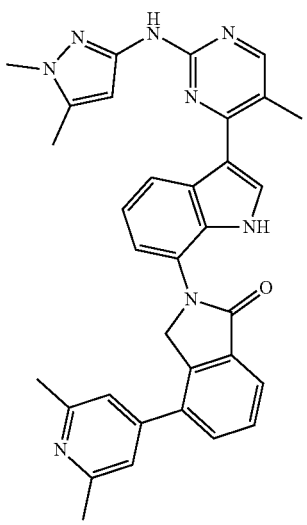 | 2-(3-(2-((1,5-dimethyl-1H-pyrazol-3-yl)amino)-5-methylpyrimidin-4-yl)-1H-indol-7-yl)-4-(2,6-dimethylpyridin-4-yl)isoindolin-1-one |
| 480) | 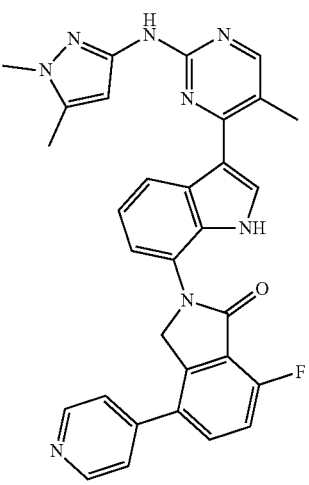 [SMILES: Cc1cnc(Nc2cc(C)n(C)n2)nc1-c1c[nH]c2c(N3Cc4c(-c5ccncc5)ccc(F)c4C3=O)cccc12] | 2-(3-(2-((1,5-dimethyl-1H-pyrazol-3-yl)amino)-5-methylpyrimidin-4-yl)-1H-indol-7-yl)-7-fluoro-4-(pyridin-4-yl)isoindolin-1-one |

| | | |
|---|---|---|
| 481) | 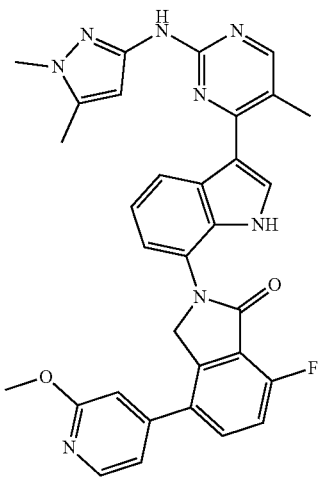 [SMILES: COc1cc(-c2ccc(F)c3c2CN(c2cccc4c(-c5nc(Nc6cc(C)n(C)n6)ncc5C)c[nH]c24)C3=O)ccn1] | 2-(3-(2-((1,5-dimethyl-1H-pyrazol-3-yl)amino)-5-methylpyrimidin-4-yl)-1H-indol-7-yl)-7-fluoro-4-(2-methoxypyridin-4-yl)isoindolin-1-one |
| 482) | 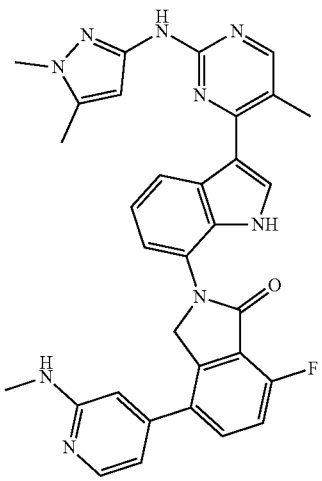 [SMILES: CNc1cc(-c2ccc(F)c3c2CN(c2cccc4c(-c5nc(Nc6cc(C)n(C)n6)ncc5C)c[nH]c24)C3=O)ccn1] | 2-(3-(2-((1,5-dimethyl-1H-pyrazol-3-yl)amino)-5-methylpyrimidin-4-yl)-1H-indol-7-yl)-7-fluoro-4-(2-(methylamino)pyridin-4-yl)isoindolin-1-one |
| 483) | 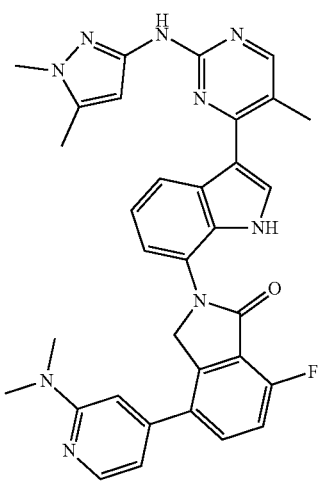 [SMILES: Cc1cnc(Nc2cc(C)n(C)n2)nc1-c1c[nH]c2c(N3Cc4c(-c5ccnc(N(C)C)c5)ccc(F)c4C3=O)cccc12] | 2-(3-(2-((1,5-dimethyl-1H-pyrazol-3-yl)amino)-5-methylpyrimidin-4-yl)-1H-indol-7-yl)-4-(2-(dimethylamino)pyridin-4-yl)-7-fluoroisoindolin-1-one |

| | | |
|---|---|---|
| 484) | 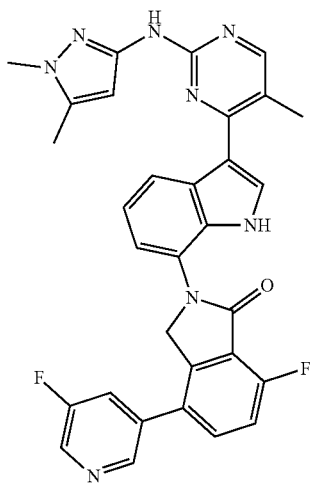 | 2-(3-(2-((1,5-dimethyl-1H-pyrazol-3-yl)amino)-5-methylpyrimidin-4-yl)-1H-indol-7-yl)-7-fluoro-4-(5-fluoropyridin-3-yl)isoindolin-1-one |
| 485) | 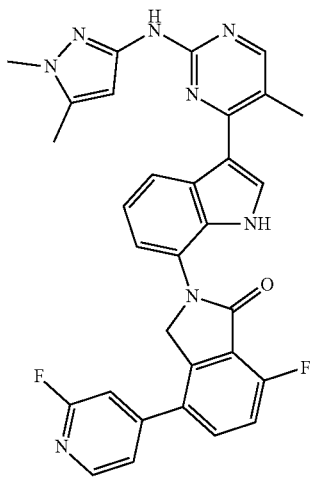 [SMILES: Cc1cnc(Nc2cc(C)n(C)n2)nc1-c1c[nH]c2c(N3Cc4c(-c5ccnc(F)c5)ccc(F)c4C3=O)cccc12] | 2-(3-(2-((1,5-dimethyl-1H-pyrazol-3-yl)amino)-5-methylpyrimidin-4-yl)-1H-indol-7-yl)-7-fluoro-4-(2-fluoropyridin-4-yl)isoindolin-1-one |
| 486) | 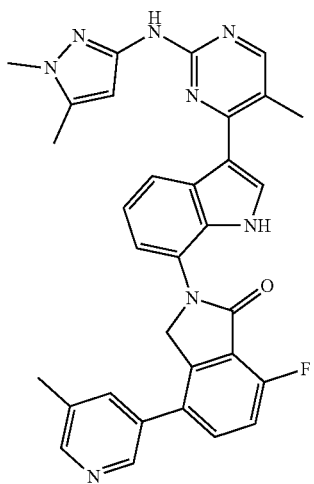 [SMILES: Cc1cncc(-c2ccc(F)c3c2CN(c2cccc4c(-c5nc(Nc6cc(C)n(C)n6)ncc5C)c[nH]c24)C3=O)c1] | 2-(3-(2-((1,5-dimethyl-1H-pyrazol-3-yl)amino)-5-methylpyrimidin-4-yl)-1H-indol-7-yl)-7-fluoro-4-(5-methylpyridin-3-yl)isoindolin-1-one |

487) 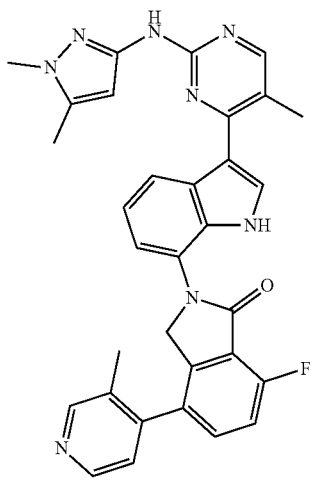 [SMILES: Cc1cnccc1-c1ccc(F)c2c1CN(c1cccc3c(-c4nc(Nc5cc(C)n(C)n5)ncc4C)c[nH]c13)C2=O]
2-(3-(2-((1,5-dimethyl-1H-pyrazol-3-yl)amino)-5-methylpyrimidin-4-yl)-1H-indol-7-yl)-7-fluoro-4-(3-methylpyridin-4-yl)isoindolin-1-one
488) 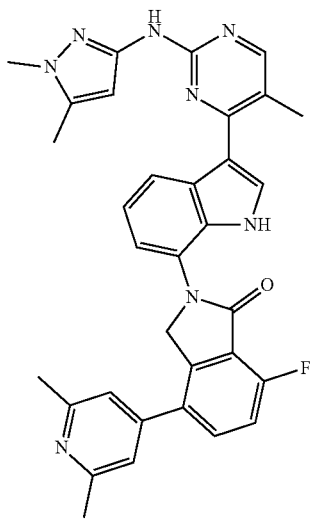 [SMILES: Cc1cc(-c2ccc(F)c3c2CN(c2cccc4c(-c5nc(Nc6cc(C)n(C)n6)ncc5C)c[nH]c24)C3=O)cc(C)n1]
2-(3-(2-((1,5-dimethyl-1H-pyrazol-3-yl)amino)-5-methylpyrimidin-4-yl)-1H-indol-7-yl)-4-(2,6-dimethylpyridin-4-yl)-7-fluoroisoindolin-1-one
489) 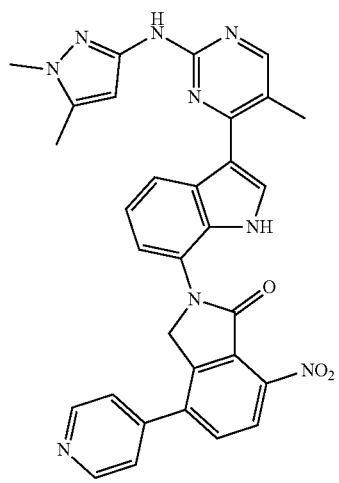 [SMILES: Cc1cnc(Nc2cc(C)n(C)n2)nc1-c1c[nH]c2c(N3Cc4c(-c5ccncc5)ccc([N+](=O)[O-])c4C3=O)cccc12]
2-(3-(2-((1,5-dimethyl-1H-pyrazol-3-yl)amino)-5-methylpyrimidin-4-yl)-1H-indol-7-yl)-7-nitro-4-(pyridin-4-yl)isoindolin-1-one 490) 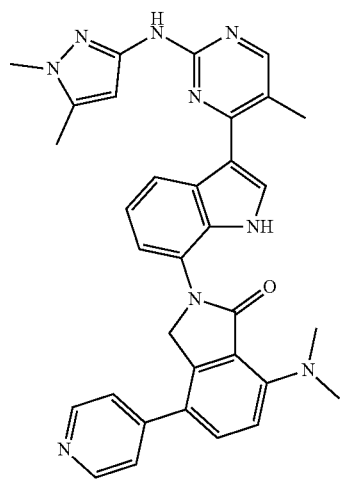 2-(3-(2-((1,5-dimethyl-1H-pyrazol-3-yl)amino)-5-methylpyrimidin-4-yl)-1H-indol-7-yl)-7-(dimethylamino)-4-(pyridin-4-yl)isoindolin-1-one
491) 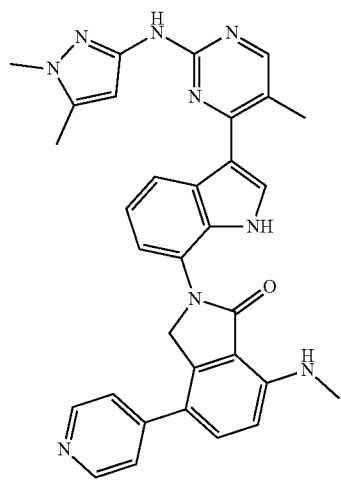 2-(3-(2-((1,5-dimethyl-1H-pyrazol-3-yl)amino)-5-methylpyrimidin-4-yl)-1H-indol-7-yl)-7-(methylamino)-4-(pyridin-4-yl)isoindolin-1-one
492) 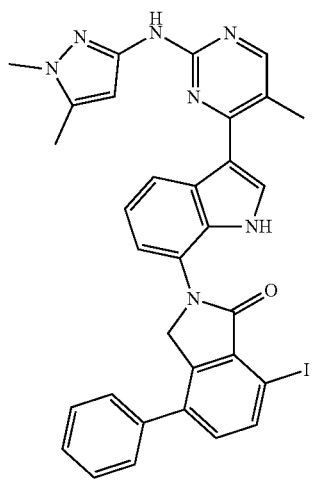 [SMILES: Cc1cnc(Nc2cc(C)n(C)n2)nc1-c1c[nH]c2c(N3Cc4c(-c5ccccc5)ccc(I)c4C3=O)cccc12] 2-(3-(2-((1,5-dimethyl-1H-pyrazol-3-yl)amino)-5-methylpyrimidin-4-yl)-1H-indol-7-yl)-7-iodo-4-phenylisoindolin-1-one 493) 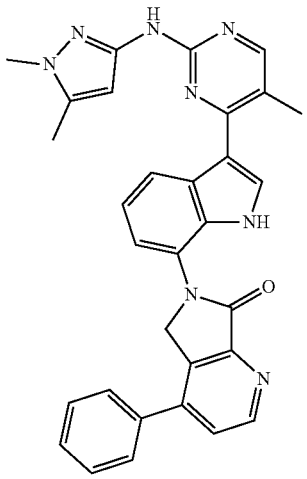
6-(3-(2-((1,5-dimethyl-1H-pyrazol-3-yl)amino)-5-methylpyrimidin-4-yl)-1H-indol-7-yl)-4-phenyl-5,6-dihydro-7H-pyrrolo[3,4-b]pyridin-7-one
494) 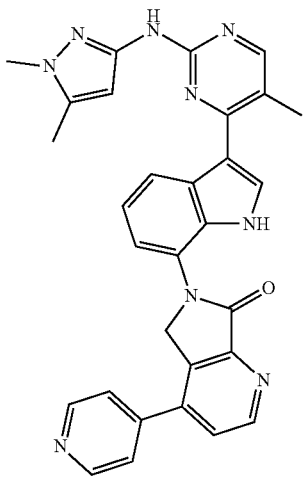
6-(3-(2-((1,5-dimethyl-1H-pyrazol-3-yl)amino)-5-methylpyrimidin-4-yl)-1H-indol-7-yl)-4-(pyridin-4-yl)-5,6-dihydro-7H-pyrrolo[3,4-b]pyridin-7-one
495) 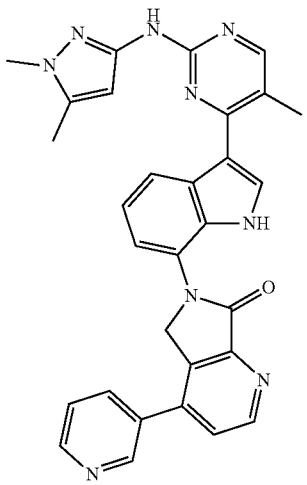
6-(3-(2-((1,5-dimethyl-1H-pyrazol-3-yl)amino)-5-methylpyrimidin-4-yl)-1H-indol-7-yl)-4-(pyridin-3-yl)-5,6-dihydro-7H-pyrrolo[3,4-b]pyridin-7-one

| | | |
|---|---|---|
| 496) | 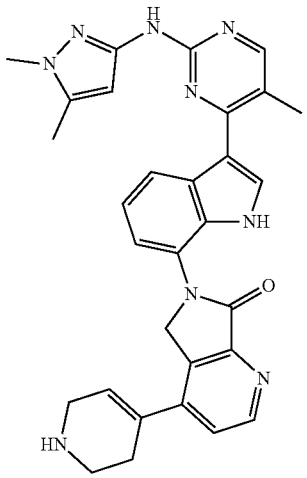 | 6-(3-(2-((1,5-dimethyl-1H-pyrazol-3-yl)amino)-5-methylpyrimidin-4-yl)-1H-indol-7-yl)-4-(1,2,3,6-tetrahydropyridin-4-yl)-5,6-dihydro-7H-pyrrolo[3,4-b]pyridin-7-one |
| 497) | 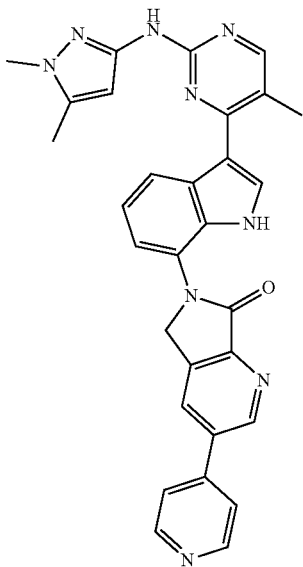 | 6-(3-(2-((1,5-dimethyl-1H-pyrazol-3-yl)amino)-5-methylpyrimidin-4-yl)-1H-indol-7-yl)-3-(pyridin-4-yl)-5,6-dihydro-7H-pyrrolo[3,4-b]pyridin-7-one |
| 498) | 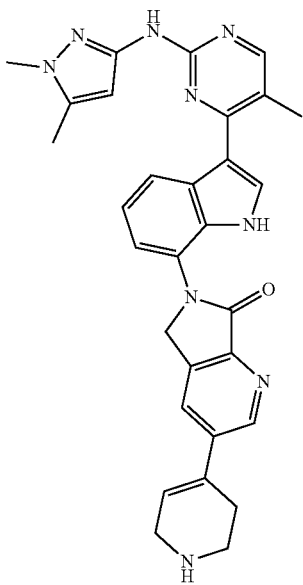 | 6-(3-(2-((1,5-dimethyl-1H-pyrazol-3-yl)amino)-5-methylpyrimidin-4-yl)-1H-indol-7-yl)-3-(1,2,3,6-tetrahydropyridin-4-yl)-5,6-dihydro-7H-pyrrolo[3,4-b]pyridin-7-one |

| | | |
|---|---|---|
| 499) | 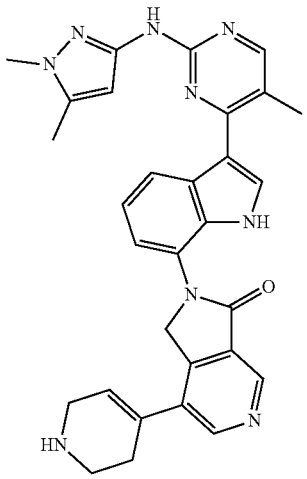 | 2-(3-(2-((1,5-dimethyl-1H-pyrazol-3-yl)amino)-5-methylpyrimidin-4-yl)-1H-indol-7-yl)-7-(1,2,3,6-tetrahydropyridin-4-yl)-1,2-dihydro-3H-pyrrolo[3,4-c]pyridin-3-one |
| 500) | 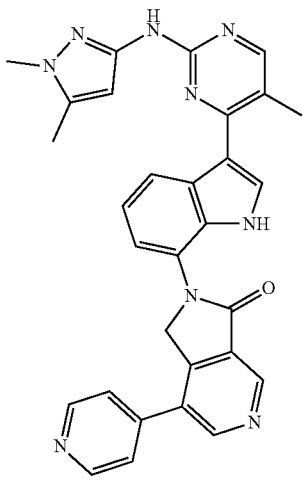 | 2-(3-(2-((1,5-dimethyl-1H-pyrazol-3-yl)amino)-5-methylpyrimidin-4-yl)-1H-indol-7-yl)-7-(pyridin-4-yl)-1,2-dihydro-3H-pyrrolo[3,4-c]pyridin-3-one |
| 501) | 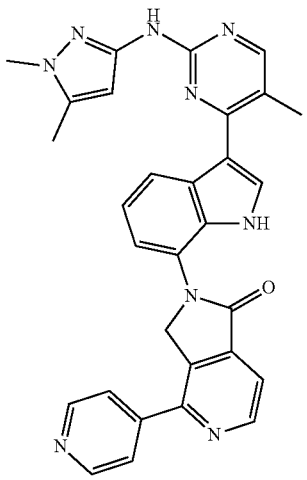 | 2-(3-(2-((1,5-dimethyl-1H-pyrazol-3-yl)amino)-5-methylpyrimidin-4-yl)-1H-indol-7-yl)-4-(pyridin-4-yl)-2,3-dihydro-1H-pyrrolo[3,4-c]pyridin-1-one |

502) 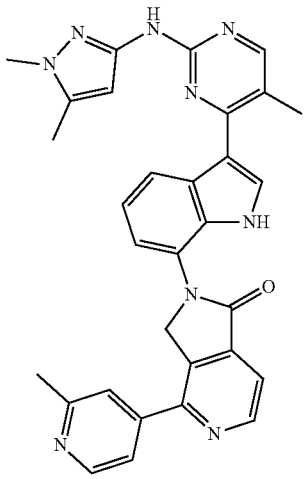
2-(3-(2-((1,5-dimethyl-1H-pyrazol-3-yl)amino)-5-methylpyrimidin-4-yl)-1H-indol-7-yl)-4-(2-methylpyridin-4-yl)-2,3-dihydro-1H-pyrrolo[3,4-c]pyridin-1-one
503) 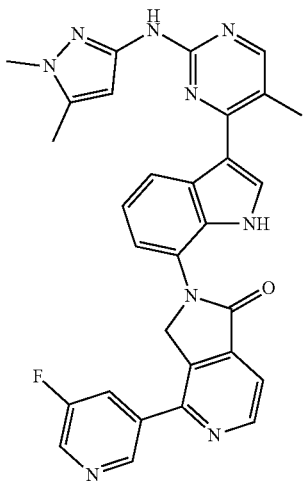
2-(3-(2-((1,5-dimethyl-1H-pyrazol-3-yl)amino)-5-methylpyrimidin-4-yl)-1H-indol-7-yl)-4-(5-fluoropyridin-3-yl)-2,3-dihydro-1H-pyrrolo[3,4-c]pyridin-1-one
504) 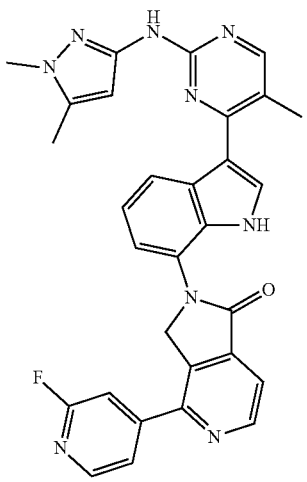
2-(3-(2-((1,5-dimethyl-1H-pyrazol-3-yl)amino)-5-methylpyrimidin-4-yl)-1H-indol-7-yl)-4-(2-fluoropyridin-4-yl)-2,3-dihydro-1H-pyrrolo[3,4-c]pyridin-1-one -continued 505) 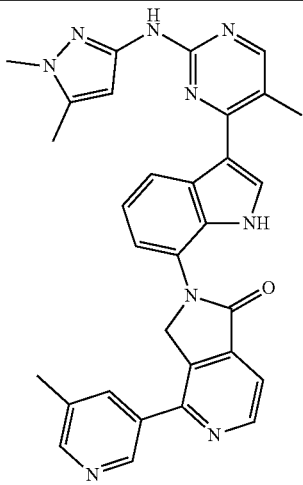

2-(3-(2-((1,5-dimethyl-1H-pyrazol-3-yl)amino)-5-methylpyrimidin-4-yl)-1H-indol-7-yl)-4-(5-methylpyridin-3-yl)-2,3-dihydro-1H-pyrrolo[3,4-c]pyridin-1-one 506) 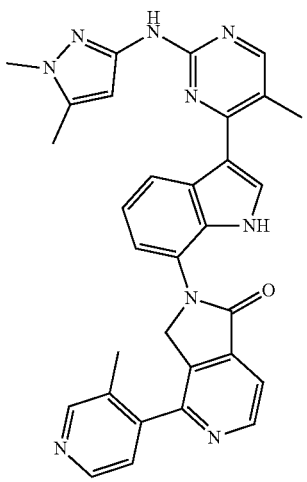

2-(3-(2-((1,5-dimethyl-1H-pyrazol-3-yl)amino)-5-methylpyrimidin-4-yl)-1H-indol-7-yl)-4-(3-methylpyridin-4-yl)-2,3-dihydro-1H-pyrrolo[3,4-c]pyridin-1-one 7. A pharmaceutical composition for treating GCN2 activation-related diseases, comprising the compound, the stereoisomer thereof, the pharmaceutically acceptable salt thereof, or the solvate thereof according to claim 6 as an active ingredient.

* * * * *